US009140715B2

(12) United States Patent
Wilson et al.

(10) Patent No.: US 9,140,715 B2
(45) Date of Patent: Sep. 22, 2015

(54) SYSTEM AND METHOD FOR CONTROLLING THERMAL CYCLER MODULES

(71) Applicant: Beckman Coulter, Inc., Brea, CA (US)

(72) Inventors: Brian D. Wilson, Chaska, MN (US); Matthew S. Davis, Indianapolis, IN (US); Alan N. Johnson, Chaska, MN (US); Garrick A. Maurer, Carmel, IN (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/747,952

(22) Filed: Jan. 23, 2013

(65) Prior Publication Data
US 2013/0143199 A1 Jun. 6, 2013

Related U.S. Application Data

(63) Continuation of application No. PCT/US2011/045107, filed on Jul. 22, 2011.

(60) Provisional application No. 61/367,343, filed on Jul. 23, 2010.

(51) Int. Cl.
| | | |
|---|---|---|
| C12P 19/34 | (2006.01) | |
| G01N 35/04 | (2006.01) | |
| G01N 35/10 | (2006.01) | |
| G01N 35/00 | (2006.01) | |
| B01L 3/00 | (2006.01) | |
| B01L 7/00 | (2006.01) | |
| C12Q 3/00 | (2006.01) | |

(Continued)

(52) U.S. Cl.
CPC ............... *G01N 35/04* (2013.01); *B01L 3/021* (2013.01); *B01L 3/5085* (2013.01); *B01L 3/50825* (2013.01); *B01L 3/50851* (2013.01); *B01L 3/52* (2013.01); *B01L 3/545* (2013.01); *B01L 7/52* (2013.01); *C12M 41/12* (2013.01); *C12P 19/34* (2013.01); *C12Q 1/68* (2013.01); *C12Q 1/686* (2013.01); *C12Q 3/00* (2013.01); *G01F 23/24* (2013.01); *G01F 23/26* (2013.01); *G01N 1/31* (2013.01); *G01N 1/38* (2013.01); *G01N 35/0092* (2013.01); *G01N 35/0098* (2013.01); *G01N 35/00732* (2013.01); *G01N 35/1002* (2013.01); *G01N 35/1011* (2013.01); *G01N 35/1016* (2013.01); *G01N 35/1081* (2013.01); *G05B 13/02* (2013.01); *G06F 19/10* (2013.01); *B01L 3/0275* (2013.01); *B01L 2200/025* (2013.01); *B01L 2200/0642* (2013.01); *B01L 2200/0668* (2013.01); *B01L 2200/12* (2013.01); *B01L 2200/147* (2013.01); *B01L 2300/021* (2013.01); *B01L 2300/022* (2013.01); *B01L 2300/024* (2013.01); *B01L 2300/042* (2013.01); *B01L 2300/044* (2013.01); *B01L 2300/045* (2013.01); *B01L 2300/046* (2013.01); *B01L 2300/0654* (2013.01); *B01L 2300/0851* (2013.01); *B01L 2300/123* (2013.01); *B01L 2300/1822* (2013.01); *B01L 2300/1827* (2013.01); *B01L 2400/043* (2013.01); *G01N 2035/00435* (2013.01); *G01N 2035/00752* (2013.01); *G01N 2035/00851* (2013.01); *G01N 2035/0413* (2013.01); *G01N 2035/0415* (2013.01); *G01N 2035/0436* (2013.01); *G01N 2035/0465* (2013.01); *G01N 2035/0475* (2013.01); *G01N 2035/1013* (2013.01); *G01N 2035/1025* (2013.01); *G01N 2035/1048* (2013.01); *G01N 2035/1051* (2013.01); *G01N 2035/1076* (2013.01)

(58) Field of Classification Search
CPC ......................................................... C12P 19/34
USPC ......................................................... 435/91.2
See application file for complete search history.

(56) References Cited

U.S. PATENT DOCUMENTS

| | | | |
|---|---|---|---|
| 3,158,765 A | 11/1964 | Prolgreen | |
| 3,622,279 A | 11/1971 | Moran | |

(Continued)

FOREIGN PATENT DOCUMENTS

| | | | |
|---|---|---|---|
| CA | 1 282 692 A1 | 4/1991 | |
| CN | 1127887 A | 7/1996 | |

(Continued)

OTHER PUBLICATIONS

Abe et al., "Quantitation of Hepatitis B Virus Genomic DNA by Real-Time Detection PCR," J. Clin. Microbiol., 1999, 37(9):2899-2903, American Society for Microbiology, Washington D.C., USA.

(Continued)

*Primary Examiner* — Ardin Marschel
(74) *Attorney, Agent, or Firm* — Kilpatrick Townsend & Stockton LLP

(57) ABSTRACT

Systems and methods for processing and analyzing samples are disclosed. The system may process samples, such as biological fluids, using assay cartridges which can be processed at different processing locations. In some cases, the system can be used for PCR processing. The different processing locations may include a preparation location where samples can be prepared and an analysis location where samples can be analyzed. To assist with the preparation of samples, the system may also include a number of processing stations which may include processing lanes. During the analysis of samples, in some cases, thermal cycler modules and an appropriate optical detection system can be used to detect the presence or absence of certain nucleic acid sequences in the samples. The system can be used to accurately and rapidly process samples.

24 Claims, 86 Drawing Sheets

(51) Int. Cl.
  *G05B 13/02* (2006.01)
  *G01F 23/24* (2006.01)
  *G01F 23/26* (2006.01)
  *G06F 19/10* (2011.01)
  *C12M 1/34* (2006.01)
  *C12Q 1/68* (2006.01)
  *G01N 1/38* (2006.01)
  *G01N 1/31* (2006.01)
  *B01L 3/02* (2006.01)

(56) References Cited

U.S. PATENT DOCUMENTS

| | | |
|---|---|---|
| 3,937,322 A | 2/1976 | Cohen |
| 4,052,161 A | 10/1977 | Atwood et al. |
| 4,101,070 A | 7/1978 | Hoare et al. |
| 4,119,381 A | 10/1978 | Muka et al. |
| 4,250,266 A | 2/1981 | Wade |
| 4,401,189 A | 8/1983 | Majewski |
| 4,486,539 A | 12/1984 | Ranki et al. |
| 4,501,495 A | 2/1985 | Faulkner et al. |
| 4,530,056 A | 7/1985 | MacKinnon et al. |
| 4,593,238 A | 6/1986 | Yamamoto |
| 4,593,239 A | 6/1986 | Yamamoto |
| 4,673,657 A | 6/1987 | Christian |
| 4,674,640 A | 6/1987 | Asa et al. |
| 4,676,952 A | 6/1987 | Edelmann et al. |
| 4,683,195 A | 7/1987 | Mullis et al. |
| 4,683,202 A | 7/1987 | Mullis |
| 4,751,177 A | 6/1988 | Stabinsky |
| 4,780,817 A | 10/1988 | Lofgren |
| 4,800,159 A | 1/1989 | Mullis et al. |
| 4,851,330 A | 7/1989 | Kohne |
| 4,865,986 A | 9/1989 | Coy et al. |
| 4,943,415 A | 7/1990 | Przybylowicz et al. |
| 4,947,094 A | 8/1990 | Dyer et al. |
| 4,950,613 A | 8/1990 | Arnold, Jr. et al. |
| 5,055,393 A | 10/1991 | Kwoh et al. |
| 5,055,408 A | 10/1991 | Higo et al. |
| 5,075,853 A | 12/1991 | Luke, Jr. |
| 5,118,191 A | 6/1992 | Hopkins |
| 5,147,529 A | 9/1992 | Lee et al. |
| 5,154,888 A | 10/1992 | Zander et al. |
| 5,158,895 A | 10/1992 | Ashihara et al. |
| 5,168,766 A | 12/1992 | Stoffel |
| 5,179,329 A | 1/1993 | Nishikawa et al. |
| 5,185,439 A | 2/1993 | Arnold, Jr. et al. |
| 5,186,827 A | 2/1993 | Liberti et al. |
| 5,190,136 A | 3/1993 | Greecksch et al. |
| 5,196,168 A | 3/1993 | Muszak et al. |
| 5,205,393 A | 4/1993 | Malow et al. |
| 5,229,297 A | 7/1993 | Schnipelsky et al. |
| 5,234,665 A | 8/1993 | Ohta et al. |
| 5,244,055 A | 9/1993 | Shimizu |
| 5,283,174 A | 2/1994 | Arnold et al. |
| 5,283,739 A | 2/1994 | Summerville et al. |
| 5,288,463 A | 2/1994 | Chemelli |
| 5,330,916 A | 7/1994 | Williams et al. |
| 5,350,564 A | 9/1994 | Mazza et al. |
| 5,351,801 A | 10/1994 | Markin et al. |
| 5,362,291 A | 11/1994 | Williamson, IV |
| 5,366,896 A | 11/1994 | Margrey et al. |
| 5,374,395 A | 12/1994 | Robinson et al. |
| 5,375,898 A | 12/1994 | Ohmori et al. |
| 5,380,487 A | 1/1995 | Choperena et al. |
| 5,388,682 A | 2/1995 | Dudley |
| 5,389,339 A | 2/1995 | Petschek et al. |
| 5,397,709 A | 3/1995 | Berndt |
| 5,399,491 A | 3/1995 | Kacian et al. |
| 5,403,711 A | 4/1995 | Walder et al. |
| 5,411,876 A | 5/1995 | Bloch et al. |
| 5,415,839 A | 5/1995 | Zaun et al. |
| 5,422,271 A | 6/1995 | Chen et al. |
| 5,427,930 A | 6/1995 | Birkenmeyer et al. |
| 5,437,990 A | 8/1995 | Burg et al. |
| 5,443,791 A | 8/1995 | Cathcart et al. |
| 5,447,687 A | 9/1995 | Lewis et al. |
| 5,449,602 A | 9/1995 | Royer et al. |
| 5,462,881 A | 10/1995 | Perlman |
| 5,466,574 A | 11/1995 | Liberti et al. |
| 5,480,784 A | 1/1996 | Kacian et al. |
| 5,482,834 A | 1/1996 | Gillespie |
| 5,504,345 A | 4/1996 | Bartunek et al. |
| 5,514,550 A | 5/1996 | Findlay et al. |
| 5,525,300 A | 6/1996 | Danssaert et al. |
| 5,527,673 A | 6/1996 | Reinhartz et al. |
| 5,536,649 A | 7/1996 | Fraiser et al. |
| 5,538,849 A | 7/1996 | Uematsu et al. |
| 5,554,516 A | 9/1996 | Kacian et al. |
| 5,563,037 A | 10/1996 | Sutherland et al. |
| 5,578,270 A | 11/1996 | Reichler et al. |
| 5,582,796 A | 12/1996 | Carey et al. |
| 5,585,242 A | 12/1996 | Bourma et al. |
| 5,585,481 A | 12/1996 | Arnold, Jr. et al. |
| 5,587,128 A | 12/1996 | Wilding et al. |
| 5,589,333 A | 12/1996 | Bagasra et al. |
| 5,602,042 A | 2/1997 | Farber |
| 5,604,130 A | 2/1997 | Warner et al. |
| 5,612,200 A | 3/1997 | Dattagupta et al. |
| 5,612,525 A | 3/1997 | Apter et al. |
| 5,623,415 A | 4/1997 | O'Bryan et al. |
| 5,628,962 A | 5/1997 | Kanbara et al. |
| 5,637,275 A | 6/1997 | Carey et al. |
| 5,639,599 A | 6/1997 | Ryder et al. |
| 5,639,604 A | 6/1997 | Arnold et al. |
| 5,641,658 A | 6/1997 | Adams et al. |
| 5,648,727 A | 7/1997 | Tyberg et al. |
| 5,652,489 A | 7/1997 | Kawakami |
| 5,653,940 A | 8/1997 | Carey et al. |
| 5,656,493 A | 8/1997 | Mullis et al. |
| 5,665,554 A | 9/1997 | Reeve et al. |
| 5,679,553 A | 10/1997 | Van Gemen et al. |
| 5,686,272 A | 11/1997 | Marshall et al. |
| 5,688,643 A | 11/1997 | Oka et al. |
| 5,702,950 A | 12/1997 | Tajima |
| 5,705,062 A | 1/1998 | Knobel |
| 5,714,380 A | 2/1998 | Neri et al. |
| 5,720,923 A | 2/1998 | Haff et al. |
| 5,723,591 A | 3/1998 | Livak et al. |
| 5,730,938 A | 3/1998 | Carbonari et al. |
| 5,735,587 A | 4/1998 | Malin et al. |
| 5,741,708 A | 4/1998 | Carey et al. |
| 5,746,978 A | 5/1998 | Bienhaus et al. |
| 5,750,338 A | 5/1998 | Collins et al. |
| 5,773,268 A | 6/1998 | Korenberg et al. |
| 5,779,981 A | 7/1998 | Danssaert et al. |
| 5,786,182 A | 7/1998 | Catanzariti et al. |
| 5,795,547 A | 8/1998 | Moser et al. |
| 5,798,263 A | 8/1998 | Wood et al. |
| 5,814,008 A | 9/1998 | Chen et al. |
| 5,814,276 A | 9/1998 | Riggs |
| 5,814,961 A | 9/1998 | Imahashi |
| 5,827,653 A | 10/1998 | Sammes et al. |
| 5,846,489 A | 12/1998 | Bienhaus et al. |
| 5,846,491 A | 12/1998 | Choperena et al. |
| 5,846,726 A | 12/1998 | Nadeau et al. |
| 5,857,955 A | 1/1999 | Phillips et al. |
| 5,866,336 A | 2/1999 | Nazarenko et al. |
| 5,881,781 A | 3/1999 | Bishop |
| 5,882,903 A | 3/1999 | Andrevski et al. |
| 5,895,631 A | 4/1999 | Tajima et al. |
| 5,897,783 A | 4/1999 | Howe et al. |
| 5,914,230 A | 6/1999 | Liu et al. |
| 5,919,622 A | 7/1999 | Macho et al. |
| 5,922,591 A | 7/1999 | Anderson et al. |
| 5,925,517 A | 7/1999 | Tyagi et al. |
| 5,928,907 A | 7/1999 | Woudenberg |
| 5,948,673 A | 9/1999 | Cottingham et al. |
| 5,966,309 A | 10/1999 | O'Bryan et al. |
| 5,972,693 A | 10/1999 | Rothberg et al. |
| 5,994,056 A | 11/1999 | Higuchi et al. |
| 6,011,508 A | 1/2000 | Perreault et al. |
| 6,033,574 A | 3/2000 | Siddiqi |
| 6,033,880 A | 3/2000 | Haff et al. |

(56) References Cited

U.S. PATENT DOCUMENTS

| | | |
|---|---|---|
| 6,043,880 A | 3/2000 | Andrews et al. |
| 6,049,745 A | 4/2000 | Douglas et al. |
| 6,056,106 A | 5/2000 | van Dyke, Jr. et al. |
| 6,060,022 A | 5/2000 | Pang et al. |
| 6,063,340 A | 5/2000 | Lewis et al. |
| 6,068,978 A | 5/2000 | Zaun et al. |
| 6,071,395 A | 6/2000 | Lange |
| 6,096,561 A | 8/2000 | Tayi |
| 6,100,079 A | 8/2000 | Tajima |
| 6,110,676 A | 8/2000 | Coull et al. |
| 6,110,678 A | 8/2000 | Weisburg et al. |
| 6,117,398 A | 9/2000 | Bienhaus et al. |
| 6,129,428 A | 10/2000 | Helwig et al. |
| 6,150,097 A | 11/2000 | Tyagi et al. |
| 6,165,778 A | 12/2000 | Kedar |
| 6,171,780 B1 | 1/2001 | Pham et al. |
| 6,212,448 B1 | 4/2001 | Xydis |
| 6,277,332 B1 | 8/2001 | Sucholeiki |
| 6,296,809 B1 * | 10/2001 | Richards et al. .......... 422/64 |
| 6,300,068 B1 | 10/2001 | Burg et al. |
| 6,300,138 B1 | 10/2001 | Gleason et al. |
| 6,306,658 B1 | 10/2001 | Turner et al. |
| 6,333,008 B1 | 12/2001 | Leistner et al. |
| 6,335,166 B1 | 1/2002 | Ammann et al. |
| 6,353,774 B1 | 3/2002 | Goldenberg et al. |
| 6,368,872 B1 | 4/2002 | Juranas |
| 6,370,452 B1 | 4/2002 | Pfister |
| 6,374,989 B1 | 4/2002 | van Dyke, Jr. et al. |
| 6,377,888 B1 | 4/2002 | Olch |
| 6,429,016 B1 | 8/2002 | McNeil |
| 6,436,349 B1 | 8/2002 | Carey et al. |
| 6,444,171 B1 | 9/2002 | Sakazume et al. |
| RE37,891 E | 10/2002 | Collins et al. |
| 6,458,324 B1 | 10/2002 | Schinzel |
| 6,520,313 B1 | 2/2003 | Kaarakainen et al. |
| 6,548,026 B1 | 4/2003 | Dales et al. |
| 6,586,234 B1 | 7/2003 | Burg et al. |
| 6,586,255 B1 | 7/2003 | Hubert et al. |
| 6,597,450 B1 | 7/2003 | Andrews et al. |
| 6,599,476 B1 | 7/2003 | Watson et al. |
| 6,605,213 B1 | 8/2003 | Ammann et al. |
| 6,629,028 B2 | 9/2003 | Paromtchik et al. |
| 6,633,785 B1 | 10/2003 | Kasahara et al. |
| 6,692,708 B2 | 2/2004 | Chandler, Jr. |
| 6,764,649 B2 | 7/2004 | Ammann |
| 6,770,883 B2 | 8/2004 | McNeal et al. |
| 6,818,183 B2 | 11/2004 | Hajduk et al. |
| 6,890,742 B2 | 5/2005 | Ammann et al. |
| 6,919,058 B2 | 7/2005 | Andersson et al. |
| 6,919,175 B1 | 7/2005 | Bienhaus et al. |
| 6,941,200 B2 | 9/2005 | Sonoyama et al. |
| 6,993,176 B2 | 1/2006 | Yamagishi et al. |
| 7,033,820 B2 | 4/2006 | Ammann et al. |
| 7,045,358 B2 | 5/2006 | Chandler, Jr. |
| 7,071,006 B2 | 7/2006 | Tajima et al. |
| 7,078,698 B2 | 7/2006 | Itoh |
| 7,118,892 B2 | 10/2006 | Ammann et al. |
| 7,135,145 B2 | 11/2006 | Ammann et al. |
| 7,174,836 B2 | 2/2007 | Marino et al. |
| 7,267,795 B2 | 9/2007 | Ammann et al. |
| 7,269,480 B2 | 9/2007 | Hashimoto et al. |
| 7,273,749 B1 | 9/2007 | Wittwer et al. |
| 7,288,229 B2 | 10/2007 | Turner et al. |
| 7,362,258 B2 | 4/2008 | Kawabe et al. |
| 7,419,830 B2 | 9/2008 | Canos et al. |
| 7,463,948 B2 | 12/2008 | Orita |
| 7,473,897 B2 | 1/2009 | Braendle et al. |
| 7,482,143 B2 | 1/2009 | Ammann et al. |
| 7,499,581 B2 | 3/2009 | Tribble et al. |
| 7,524,652 B2 | 4/2009 | Ammann et al. |
| 7,560,255 B2 | 7/2009 | Ammann et al. |
| 7,560,256 B2 | 7/2009 | Ammann et al. |
| 7,666,681 B2 | 2/2010 | Ammann et al. |
| 7,688,448 B2 | 3/2010 | Bamberg et al. |
| 7,771,659 B2 | 8/2010 | Ziegler |
| 8,074,578 B2 | 12/2011 | Thornton |
| 8,192,992 B2 | 6/2012 | Ammann et al. |
| 2002/0025064 A1 | 2/2002 | Itoh |
| 2002/0028489 A1 | 3/2002 | Ammann et al. |
| 2002/0031768 A1 | 3/2002 | McMillan et al. |
| 2002/0077239 A1 | 6/2002 | Evans, III et al. |
| 2002/0086417 A1 | 7/2002 | Chen |
| 2002/0098117 A1 | 7/2002 | Ammann et al. |
| 2002/0123156 A1 | 9/2002 | Tajima |
| 2002/0137194 A1 | 9/2002 | Ammann et al. |
| 2002/0137197 A1 | 9/2002 | Ammann et al. |
| 2002/0147515 A1 | 10/2002 | Fava et al. |
| 2003/0026736 A1 | 2/2003 | Hajduk et al. |
| 2003/0027206 A1 | 2/2003 | Ammann et al. |
| 2003/0054542 A1 | 3/2003 | Burns et al. |
| 2003/0129614 A1 | 7/2003 | Parameswaran et al. |
| 2003/0190755 A1 | 10/2003 | Turner et al. |
| 2003/0213313 A1 | 11/2003 | Katagi |
| 2003/0223916 A1 | 12/2003 | Testrut et al. |
| 2004/0029260 A1 | 2/2004 | Hansen et al. |
| 2004/0076983 A1 | 4/2004 | Karlsen |
| 2004/0087426 A1 | 5/2004 | Lattanzi |
| 2004/0115796 A1 | 6/2004 | Burns |
| 2004/0158355 A1 | 8/2004 | Holmqvist et al. |
| 2004/0184959 A1 | 9/2004 | Itoh |
| 2004/0206419 A1 | 10/2004 | Ganz et al. |
| 2004/0213651 A1 | 10/2004 | Malin |
| 2005/0130198 A1 | 6/2005 | Ammann et al. |
| 2005/0158212 A1 | 7/2005 | Yavilevich |
| 2005/0163354 A1 | 7/2005 | Ziegler |
| 2005/0207937 A1 | 9/2005 | Itoh |
| 2005/0220670 A1 | 10/2005 | Palmieri et al. |
| 2005/0233370 A1 | 10/2005 | Ammann et al. |
| 2005/0239127 A1 | 10/2005 | Ammann et al. |
| 2005/0266489 A1 | 12/2005 | Ammann et al. |
| 2006/0003373 A1 | 1/2006 | Ammann et al. |
| 2006/0014295 A1 | 1/2006 | Ziegler |
| 2006/0020370 A1 | 1/2006 | Abramson |
| 2006/0148063 A1 | 7/2006 | Fauzi et al. |
| 2006/0228268 A1 | 10/2006 | Heimberg et al. |
| 2007/0044676 A1 | 3/2007 | Clark et al. |
| 2007/0059209 A1 | 3/2007 | Pang et al. |
| 2007/0100498 A1 | 5/2007 | Matsumoto et al. |
| 2007/0110634 A1 | 5/2007 | Heimberg et al. |
| 2007/0134131 A1 | 6/2007 | Watson et al. |
| 2007/0179690 A1 | 8/2007 | Stewart |
| 2007/0184548 A1 | 8/2007 | Tan et al. |
| 2007/0193859 A1 | 8/2007 | Kyuyoku et al. |
| 2007/0196237 A1 | 8/2007 | Neuzil et al. |
| 2007/0208440 A1 | 9/2007 | Bliss et al. |
| 2007/0225901 A1 | 9/2007 | Yamaguchi |
| 2007/0225906 A1 | 9/2007 | Ikeda |
| 2008/0014181 A1 | 1/2008 | Ariff et al. |
| 2008/0015470 A1 | 1/2008 | Sarstedt |
| 2008/0056958 A1 | 3/2008 | Vijay et al. |
| 2008/0069730 A1 | 3/2008 | Itoh |
| 2008/0138249 A1 | 6/2008 | Itoh |
| 2008/0167817 A1 | 7/2008 | Hessler et al. |
| 2008/0241837 A1 | 10/2008 | Ammann et al. |
| 2008/0255683 A1 | 10/2008 | Takahashi et al. |
| 2008/0268528 A1 | 10/2008 | Ammann et al. |
| 2008/0274511 A1 | 11/2008 | Tan et al. |
| 2008/0297769 A1 | 12/2008 | Bamberg et al. |
| 2009/0029352 A1 | 1/2009 | Ammann et al. |
| 2009/0029871 A1 | 1/2009 | Ammann et al. |
| 2009/0029877 A1 | 1/2009 | Ammann et al. |
| 2009/0030551 A1 | 1/2009 | Hein et al. |
| 2009/0035185 A1 | 2/2009 | Tsujimura et al. |
| 2009/0042281 A1 | 2/2009 | Chang et al. |
| 2009/0047179 A1 | 2/2009 | Ping et al. |
| 2009/0117620 A1 | 5/2009 | Fritchie et al. |
| 2009/0318276 A1 | 12/2009 | Miler |
| 2009/0324032 A1 | 12/2009 | Chen |
| 2010/0018330 A1 | 1/2010 | Marty et al. |
| 2010/0115887 A1 | 5/2010 | Schroeder et al. |
| 2010/0129789 A1 | 5/2010 | Self et al. |
| 2010/0141756 A1 | 6/2010 | Grote et al. |
| 2010/0261595 A1 | 10/2010 | Schaefer et al. |
| 2010/0291619 A1 | 11/2010 | Robinson et al. |

(56) References Cited

U.S. PATENT DOCUMENTS

| | | | |
|---|---|---|---|
| 2011/0065193 A1 | 3/2011 | Kitagawa et al. | |
| 2011/0226584 A1 | 9/2011 | Ek | |
| 2012/0129673 A1 | 5/2012 | Fukugaki et al. | |

FOREIGN PATENT DOCUMENTS

| | | |
|---|---|---|
| CN | 1164894 A | 11/1997 |
| CN | 1212019 A | 3/1999 |
| CN | 1212021 A | 3/1999 |
| CN | 1245218 A | 2/2000 |
| CN | 1281462 A | 1/2001 |
| CN | 1498186 A | 5/2004 |
| CN | 1662431 A | 8/2005 |
| CN | 1974781 A | 6/2007 |
| CN | 101541429 A | 9/2009 |
| EP | 0 287 005 A2 | 10/1988 |
| EP | 0 324 616 A2 | 7/1989 |
| EP | 0 328 829 A2 | 8/1989 |
| EP | 0 410 645 A2 | 1/1991 |
| EP | 0 479 448 A2 | 4/1992 |
| EP | 0 502 589 A2 | 9/1992 |
| EP | 0 502 638 A2 | 9/1992 |
| EP | 0 542 422 A1 | 5/1993 |
| EP | 0 574 267 A2 | 12/1993 |
| EP | 0 574 267 A3 | 12/1993 |
| EP | 0 622 457 A1 | 2/1994 |
| EP | 0 600 130 A2 | 6/1994 |
| EP | 0 687 501 B1 | 12/1995 |
| EP | 0 656 864 B1 | 3/1996 |
| EP | 0 727 665 A2 | 8/1996 |
| EP | 0 763 739 A1 | 3/1997 |
| EP | 0 806 665 A1 | 11/1997 |
| EP | 0 819 941 A2 | 1/1998 |
| EP | 0 875 584 A2 | 4/1998 |
| EP | 0 843 176 A1 | 5/1998 |
| EP | 0 680 883 B1 | 12/1998 |
| EP | 0 889 328 A | 7/1999 |
| EP | 0 953 838 A1 | 11/1999 |
| EP | 0 640 828 B1 | 5/2000 |
| EP | 1 069 942 B1 | 1/2001 |
| EP | 1 075 328 B1 | 2/2001 |
| EP | 0 875 584 A3 | 5/2001 |
| EP | 0 752 971 B1 | 6/2001 |
| EP | 1 205 756 A2 | 5/2002 |
| EP | 1 248 170 B1 | 10/2002 |
| EP | 1 273 919 A1 | 1/2003 |
| EP | 0 687 502 B1 | 3/2003 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 024 355 B1 | 3/2008 |
| EP | 0 885 958 B1 | 6/2008 |
| EP | 1 138 784 B1 | 10/2008 |
| EP | 1 623 764 B1 | 2/2009 |
| EP | 1 614 470 B1 | 3/2009 |
| EP | 1 721 671 B1 | 10/2009 |
| EP | 1 731 222 B1 | 3/2010 |
| EP | 2 295 144 A | 3/2011 |
| EP | 2 316 570 A2 | 5/2011 |
| EP | 2 316 571 A2 | 5/2011 |
| EP | 2 316 572 A2 | 5/2011 |
| EP | 2 148 205 B1 | 1/2013 |
| GB | 2 101 514 A | 1/1983 |
| GB | 2 203 243 A | 10/1988 |
| JP | 62-148858 A | 7/1987 |
| JP | 64-053167 A | 3/1989 |
| JP | 01-211500 A1 | 8/1989 |
| JP | 02-025754 A2 | 1/1990 |
| JP | 05-184397 A | 7/1993 |
| JP | 05-219933 A | 8/1993 |
| JP | 05-281239 A | 10/1993 |
| JP | 06-011512 A | 1/1994 |
| JP | 06-197797 A | 7/1994 |
| JP | 06-327476 A | 11/1994 |
| JP | 07-049346 A | 2/1995 |
| JP | 07-75544 A | 3/1995 |
| JP | 07-191042 A | 7/1995 |
| JP | 07-213586 A | 8/1995 |
| JP | 07-107999 B2 | 11/1995 |
| JP | 07-301637 A | 11/1995 |
| JP | 07-333230 A | 12/1995 |
| JP | 08-9957 A | 1/1996 |
| JP | 08-035971 A | 2/1996 |
| JP | 08-62224 A | 3/1996 |
| JP | 08-211071 A | 8/1996 |
| JP | 08-285857 A | 11/1996 |
| JP | 08-286749 A | 11/1996 |
| JP | 08-320274 A | 12/1996 |
| JP | 09-021805 A | 1/1997 |
| JP | 09-080056 A | 3/1997 |
| JP | 09-089902 A | 4/1997 |
| JP | 09-89907 A | 4/1997 |
| JP | 09-121899 A | 5/1997 |
| JP | 09-329602 A | 12/1997 |
| JP | 10-504389 A | 1/1998 |
| JP | 10-062426 A | 3/1998 |
| JP | 11-503315 A | 3/1999 |
| JP | 2000-500331 A | 1/2000 |
| JP | 3007571 B2 | 2/2000 |
| JP | 2001-503730 A | 3/2001 |
| JP | 2002-296286 A | 10/2002 |
| JP | 2006-317330 A | 11/2006 |
| JP | 2007-249632 A | 9/2007 |
| JP | 2008-032652 A2 | 2/2008 |
| JP | 4511034 A | 5/2010 |
| JP | 4662580 A | 3/2011 |
| WO | 88/01302 A1 | 2/1988 |
| WO | 88/10315 A1 | 12/1988 |
| WO | 89/02476 A1 | 3/1989 |
| WO | 90/06042 A2 | 6/1990 |
| WO | 90/08840 A1 | 8/1990 |
| WO | 91/15768 A1 | 10/1991 |
| WO | 91/16675 A1 | 10/1991 |
| WO | 93/07292 A1 | 4/1993 |
| WO | 93/25912 A2 | 12/1993 |
| WO | 93/25912 A3 | 12/1993 |
| WO | 93/25913 A1 | 12/1993 |
| WO | 95/08774 A2 | 3/1995 |
| WO | 95/11454 A1 | 4/1995 |
| WO | 95/21382 A2 | 8/1995 |
| WO | 95/30139 A1 | 11/1995 |
| WO | 95/35390 A1 | 12/1995 |
| WO | 96/29602 A1 | 9/1996 |
| WO | 96/31781 A1 | 10/1996 |
| WO | 96/40990 A1 | 12/1996 |
| WO | 97/03348 A1 | 1/1997 |
| WO | 97/05492 A1 | 2/1997 |
| WO | 97/16561 A1 | 5/1997 |
| WO | 97/22882 A1 | 6/1997 |
| WO | 97/31105 A1 | 8/1997 |
| WO | 97/34908 A1 | 9/1997 |
| WO | 97/46707 A2 | 12/1997 |
| WO | 98/18008 A1 | 4/1998 |
| WO | 99/25476 A2 | 5/1999 |
| WO | 99/28724 A1 | 6/1999 |
| WO | 99/57561 A2 | 11/1999 |
| WO | 00/08472 A2 | 2/2000 |
| WO | 00/08472 A3 | 2/2000 |
| WO | 00/15481 A1 | 3/2000 |
| WO | 00/38046 A1 | 6/2000 |
| WO | 00/67547 A2 | 11/2000 |
| WO | 0144510 A2 | 6/2001 |
| WO | 03/097808 A2 | 11/2003 |
| WO | 2004/013640 A1 | 2/2004 |
| WO | 2006/021052 A1 | 3/2006 |
| WO | 2006/068470 A1 | 6/2006 |
| WO | 2007/094744 A1 | 8/2007 |
| WO | 2008/030914 A2 | 3/2008 |
| WO | 2008/043393 A1 | 4/2008 |
| WO | 2008/057375 A2 | 5/2008 |
| WO | 2008/067847 A1 | 6/2008 |
| WO | 2009/068555 A1 | 6/2009 |

(56) References Cited

FOREIGN PATENT DOCUMENTS

| | | |
|---|---|---|
| WO | 2009/097263 A1 | 8/2009 |
| WO | 2009/150632 A2 | 12/2009 |
| WO | 2009/150632 A3 | 12/2009 |
| WO | 2010/017528 A2 | 2/2010 |
| WO | 2010/080340 A1 | 7/2010 |
| WO | 2010/081606 A1 | 7/2010 |
| WO | 2011/013701 A1 | 2/2011 |
| WO | 2011/028166 A1 | 3/2011 |
| WO | 2012/090795 A1 | 7/2012 |

OTHER PUBLICATIONS

ABI Prism® 373 DNA Sequencer With XL Upgrade—User's Manual, Mar. 2001, TOC-iii-TOC-v & 6-11-6-16, Applied Biosystems, USA.
Abravaya, "Strategies to Avoid Amplicon Contamination," in Nucleic Acid Amplification Technologies: Application to Disease Diagnosis, 1997, pp. 125-133, Eaton Pub. Co., Natick, USA.
Akane, "Identification of the heme compound copurified with deoxyribonucleic acid (DNA) from bloodstains, a major inhibitor of polymerase chain reaction (PCR) amplification", J. Forensic Sci., 1994, 39:362-72, Blackwell Pub., USA.
Akduman et al., "Evaluation of a Strand Displacement Amplification Assay (BD ProbeTec-SDA) for Detection of *Neisseria gonorrhoeae* in Urine Specimens," J. Clin. Microbiol., 2002, 40(1):281-282, American Society for Microbiology, Washington D.C., USA.
Amplification Technical Bulletin, "Comparison of TMA with PCR and LCR Amplification Methods," undated, Gen-Probe Incorporated, San Diego, USA, 1 page.
Analog Device; "±5 g to ±5 g, Low Noise, Low Power, Single/Dual Axis / MEMS® Accelerometers,"; http://hibp.ecse.rpi.edu/~connor.education/EISpecs/ADXL150_250_0.pdf;; Jan. 1, 1998; pp. 1-15.
Anderson et al., "Microfluidic Biochemical Analysis System," Transducers, International Conference on Solib-Slate Sensors and Actuators, Jun. 16-19, 1997, p. 477-480, IEEE Electron Devices Society, Piscataway, USA.
Armstrong et al., 1996, "Automated high throughput RT-PCR," Laboratory Robotics and Automation 8:311-315, VCH Publishers, USA.
Astle, "Standards in Robotics and Instrucmentation," Society Updates, Working Group Updates, and Conference Highlights, J. Biomol. Screen., 1996, 1(4):161-172, Sage Publications, USA.
Bailey et al., "Robotic Nucleic Acid Isolation Using a Magnetic Bead Resin and an Automated Liquid Handler for Biological Agent Simulants,", JALA, Dec. 2003, 8:113-120.
Bassam. "Nucleic Acid Sequence Detection Systems: Revolutionary Automation For Monitoring and Reporting PCR Products" Australasian Biotechnology, 1996, 6:285-294, Australian Biotechnology Association, Australia.
Belgrader et al., "Automated DNA Purification and Amplification from Blood-Stained Cards Using a Robotic Workstation," Short Technical Reports, Biotechniques, 1995, 19(9):426-432, Informa Healthcare USA, Inc., UK.
Belgrader et al., "Automated Polymerase Chain Reaction Product Sample Preparation for Capillary Electrophoresis Analysis," J. Chromatogr. B Biomed. Appl., 1996, 683:109-114, Elsevier Science, Amsterdam, Netherlands.
Belgrader et al., "Automated Sample Processing Using Robotics for Genetic Typing of Short Tandem Repeat Polymorphisms by Capillary Electrophoresis," Laboratory Robotics and Automation, 1997, 9:3-7, Wiley & Sons Inc., USA.
Borst et al., "False-Positive Results and Contamination in Nucleic Acid Amplification Assays: Suggestions for a Prevent and Destroy Strategy," Eur. J. Clin. Microbiol. Infect Dis., 2004, 23:289-299, Springer-Verlag, Berlin, Germany.
Boyd et al., "Robotics and the changing face of the clinical laboratory," Clin. Chem., 1996, 42(12):1901-1910, Washington DC American Association for Clinical Chemistry, USA.
Brochure, "Amplified Mycobacteria Direct Tests," undated, Gen-Probe Incorporated, San Diego, USA, 6 pages.

Brochure, "Introducing the Amplified Mycobacterium Tuberculosis Direct (MTD) Test from Gen-Probe," Oct. 1996, Gen-Probe Incorporated, San Diego, USA, 2 pages.
Brochure, "The Future of Amplification Technology has Arrived," Oct. 1995, Gen-Probe Incorporated, San Diego, USA, 4 pages.
Buhlmann et al., "An Open Software Environment to Optimize the Productivity of Robotized Laboratories," J. Chromatogra. Sci., 1994, 32:243-248, Preston Technical Abstracts, Niles, USA.
Bush et al., "Detection of human immunodeficiency virus type 1 RNA in plasma samples from high-risk pediatric patients by using the self-sustained sequence replication reaction," J. Clin. Microbiol., 1992, 30(2):281-286, American Society for Microbiology, Washington D.C., USA.
Butler et al., "Forensic DNA typing by capillary electrophoresis using the ABI Prism 310 and 3100 genetic analyzers for STR analysis," Electrophoresis, 2004, 25:1397-1412, Wiley-VCH Verlag GmbH & Co. KGaA, Germany.
Caprari, G. et al.; "The autonomous Micro Robot "Alice": a platform for scientific and commercial applications"; *Proceedings of the 1998 International Symposium on Micromechatronics and Human Science*, Nagoya, Japan; Nov. 25-28, 1998; pp. 1-5.
Carlson et al., "Laboratory Detection of *Chlamydia trachomatis*, *Neisseria gonorrhoeae*, and Other Sexually-Transmitted Agents," 97th General Meeting of the American Society for Microbiology, C-308, May 4-8, 1997, Miami Beach, USA.
Carrino et al., "Nucleic Acid Amplification Methods," J. Micorbiol. Methods, 1995, 23:3-20.
Check, "Real-time PCR for the rest of us," CAP Today, Jun. 2006, College of American Pathologists, Skokie, IL, USA, 6 pages.
Chemistry Guide, "Automated DNA Sequencing," PE Applied Biosystems, 1998, pp. I-4~I-6, The Perkin-Elmer Corporation.
Cimino et al., "Post-PCR sterilization: a method to control carryover contamination for the polymerase chain reaction," Nucleic Acids Res., 1991, 19(1):99-107, Oxford University Press, Oxford, United Kingdom.
Clewley, "Automation of the Polymerase Chain Reaction Part 2. Extraction—the Foundation for Success," Communicable Disease and Public Health, Jun. 1999, 2(2):147-148, Public Health Laboratory Service in association with the Scottish Centre for Infection and Environmental Health, London, United Kingdom.
Corkan et al., "Experiment Manager Software for an Automated Chemistry Workstation, Including a Scheduler for Parallel Experimentation," Chemometrics and Intelligent Laboratory Systems: Laboratory Information Management, 1992, 17:47-74, Elsevier Science Publishers, Amsterdam, Netherlands.
Corrected Request for Inter Partes Reexamination of U.S. Patent No. 7,482,143, filed on Sep. 14, 2012, 121 pages.
Crotchfelt et al., "Detection of *Chlamydia trachomatis* by the Gen-Probe Amplified *Chlamydia trachomatis* Assay (AMP CT) in Urine Specimens from Men and Women and Endocervical Specimens from Women," J. Clin. Microbiol., Feb. 1998, 36(2):391-394, American Society for Microbiology, Washington D.C., USA.
Davis et al., "Amplification of DNA Using the Polymerase Chain Reaction," in Basic Methods in Molecular Biology, 2nd ed., 1994, p. 121, Appleton & Lange, Norwalk, USA.
Diamandis, "Automation of molecular diagnostics," Clinical Chemistry, 1996, 42:7-8, American Association for Clinical Chemistry, USA.
DiDomenico et al., "COBAS AMPLICOR™: fully automated RNA and DNA amplification and detection system for routine diagnostic PCR," Clin. Chem., 1996, 42(12):1915-1923, Washington DC American Association for Clinical Chemistry, USA.
Dieffenbach et al., "Setting Up a PCR Laboratory," Genome Rsearch, PCR Methods and Applications, 1993, 3:s2-s7, Cold Spring Harbor Laboratory, Cold Spring Harbor, USA.
Dragon, "Handling Reagents in the PCR Laboratory," Genome Research, PCR Methods and Applications, 1993, 3:s8-s9, Cold Spring Harbor Laboratory, Cold Spring Harbor, USA.
Dynal®, Technical Handbook. Molecular Biology, First Edition. "Dynabeads®biomagnetic separation system," 1992, 4 pages, Dynal AS, Norway.
Erlich, "PCR Technology," in Encyclopedia of Molecular Biology and Molecular Medicine: Mass Spectrometry High Speed DNA

(56) References Cited

OTHER PUBLICATIONS

Fragment Sizing to Plasma Lipoproteins, vol. 4, 1996, p. 337, VCH Verlagsgesellschaft mbH, Weinheim, Germany.
Espy et al., "Dependence of polymerase chain reaction product inactivation protocols on amplicon length and sequence composition," J. Clin. Microbiol., 1993, 31(9):2361-2365, American Society for Microbiology, Washington D.C., USA.
Farrell, Jr., "RT PCR" in RNA Method: A Laboratory Guide for Isolation and Characterization, 1998, 2nd ed., Chapter 15, pp. 296-307, Academic Press, San Diego, California, USA.
Feinberg, "A Technique for Radiolabeling DNA Restriction Endonuclease Fragments to High Specific Activity", Analytical Biochemistry, 1983, 132:6-13, Academic Press, USA.
Findlay et al., "Automated Closed-Vessel System for in Vitro Diagnostics Based on Polymerase Chain Reaction," Clin. Chem., 1993, 39(9):1927-1933, American Association for Clinical Chemistry, Washington, D.C., USA.
Fiore et al., "The Abbott IMx automated benchtop immunochemistry analyzer system," Clin. Chem., 1988, 34 (9):1726-32, American Association for Clinical Chemistry, Washington D.C., USA.
Flexlink®; "TX45E puck handling (mx. 250g),"; located at http://www.flexlink.com/en/offering/conveyor-systems/pallet-and-puck-handling/x45e.jsp; last visited on Jul. 20, 2013; 2 pages.
Friendenberg et al., "Developing a fully automated instrument for molecular diagnostic assays," IVD Technology, 2005, 11(6), 6 pages, A Canon Communications, Los Angeles, USA.
Furrows et al., "'Good laboratory practice' in diagnostic laboratories using nucleic acid amplification methods," Clin. Microbiol. Infect., 2001, 7(5):227-229, Blackwell Science, Oxford, United Kingdom.
Gelmini et al., "Quantitative polymerase chain reaction-based homogeneous assay with fluorogenic probes to measure c-erbB-2 oncogene amplification," Clin. Chem., 1997, 43(5):752-758, American Association for Clinical Chemistry, Washington D.C., USA.
Gerber et al., "Differential Transcriptional Regulation of the Two Vascular Endothelial Growth Factor Receptor Genes," J. Biol. Chem., 1997, 272(38):23659-23667, The American Society for Biochemistry and Molecular Biology, Baltimore, USA.
Gibson et al., "A homogenous method for genotyping with fluorescence polarization," Clin. Chem., 1997, 43(8):1336-1341, American Association for Clinical Chemistry, Washington D.C., USA.
Gibson et al., "A novel method for real time quantitative RT-PCR," Genome Methods, 1996, 6:995-1001, Cold Spring Harbor Laboratory Press, Cold Spring Harbor, USA.
Giesendorf et al., "Molecular beacons: a new approach for semiautomated mutation analysis," Clin. Chem., 1998, 44(3):482-486, American Association for Clinical Chemistry, Washington D.C., USA.
Gilgen et al., "Hydroxyquinoline overcomes PCR inhibition by UV-damaged mineral oil," Nucleic Acids Res., 1995, 23(19):4001-4002, Oxford University Press, Oxford, United Kingdom.
Ginocchio, "Life Beyond PCR: Alternative Target Amplification Technologies for the Diagnosis of Infectious Diseases, Part II," Clinical Microbiology Newsletter, 2004, 26(17):129-136, Elsevier Science, New York, USA.
Godfrey-Faussett, "Molecular Diagnosis of Tuberculosis: The Need for New Diagnostic Tools," Thorax, 1995, 50(7):709-711, British Medical Association, London, United Kingdom.
Greenstein, "Preparing and Using M13-Derived Vectors," Current Protocols in Molecular Biology, published 1990, §1.151 and 1.15.4, J. Wiley and Sons, USA.
Haas, "Clinical Instrumentation (General Chemistry and Immunoassay Analyzers)," Anal. Chem., 1993, 65(12):444R-449R, American Chemical Society, Washington D.C., USA.
Haglund et al., "Polymerase Chain Reaction," in Forensic Taphonomy: the Postmortem Fate of Human Remains, 1997, p. 114-115, CRC Press LLC, Boca Raton, USA.
Hartley et al., "Dealing with Contamination: Enzymatic Control of Carryover Contamination in PCR," Genome Research, PCR Methods and Applications, 1993, 3:s10-s14, Cold Spring Harbor Laboratory, Cold Spring Harbor, USA.

Hawker, "Laboratory Automation: Total and Subtotal," Clin. Lab. Med., 2007, 27:749-770, Elsevier Health Sciences Division, Philadelphia, USA.
Hawkes et al., "Asymptomatic carriage of *Haemophilus ducreyi* confirmed by the polymerase chain reaction," J. Genitourin. Med., 1995, 71:224-227.
Hawkins et al., "A Magnetic Attraction to High-Throughput Genomics," Science, 1997, 276:1887 & 1889 (p. 1888 omitted—advertisement only), Washington, DC: American Association for the Advancement of Science, USA.
Hedrum et al., "Immunomagnetic Recovery of *Chlamydia trachomatis* from Urine with Subsequent Colorimetric DNA Detection," PCR Methods Appl., 1992, 2:167-171, Cold Spring Harbor Laboratory Press, Cold Spring Harbor, USA.
Heid et al., "Real Time Quantitative PCR," Genome Research, 1996, 6:986-994, Cold Spring Harbor Laboratory Press, Cold Spring Harbor, USA.
Hellyer et al., "Letter to the Editor: Specificity of IS6110-Based Amplification Assays for *Mycobacterium tuberculosis* Complex," J. Clin. Microbiol., 1997, 35(3):799-801, American Society for Microbiology, Washington D.C., USA.
Herring et al., "ELISA Automation: A Biomek 1000 to Biomek 2000 Comparison of Clinical ELISAs", Application Information, 1995, Beckman Industries, Inc., USA.
Herrmann et al., "General Aspects of Sample Preparation," in Ancient DNA: Recovery and Analysis of Genetic Material from Paleontological, Archaeological, Museum, Medical, and Forensic Specimens, 1994, pp. 63-64, Springer-Verlag, New York City, USA.
Hicks et al., "Beckman/Sagian "Core" Molecular Biology System,", T-1845A, Beckman Instruments, Inc., 1997, 4 pages.
Higuchi et al., "Simultaneous Amplification and Detection of Specific DNA Sequences," Bio/Technology, 1992, 10:413-417, Nature Publishing Company, New York, USA.
Hildebrandt et al., Development of an Automated Sample Preparation Method for HCV, J. Microbiol. Methods, 1997, 30:235-253, Abstract 17, 1 page, Elsevier Biomedical, Amsterdam, Netherlands.
Hill, "Gen-Probe Transcription-Mediated Amplification: System Principles," Jan. 1996, Gen-Probe Incorporated, San Diego, USA, 4 pages.
Hill, "How Full Automation of Molecular Diagnostic Testing Can Increase Accuracy, Lab Efficiency, Cost Savings," Issue Stories, Jul. 2004, 3 pages, Clinical Lab Products, Los Angeles, USA.
Hill, "Molecular diagnostic testing for infectious diseases using TMA technology," Expert Rev. Mol. Diagn., 2001, 1 (4):445-455, Future Drugs Ltd., London, United Kingdom.
Hill, "Molecular Diagnostic Tests for Sexually Transmitted Infections in Women," in Infectious Diseases in Obstetrics and Gynecology, 2008, 6th ed., pp. 612-623, Informa plc, St. Helier, Jersey.
Hill, "Molecular Diagnostics for Infectious Diseases," J. Clin. Ligand Assay, 1996, 19(1):43-52, Clinical Ligand Assay Society, Wayne, Michigan, USA.
Hoad et al., "Virus Genome Detection by the PCR," in Practical Molecular Virology: Viral Vectors for Gene Expression, 1991, pp. 75-76, Humana Press, Totowa, USA.
Holland et al., "Detection of specific polymerase chain reaction product by utilizing the 5'→3' exonuclease activity of *Thermus aquaticus* DNA polymerase," Biochemistry, 1991, 88:7276-7280, Proc. Natl. Acad. Sci. USA, Washington D.C., USA.
International Search Report and Written Opinion mailed on Feb. 15, 2013 for PCT Application No. PCT/US2012/063923, 12 pages.
International Search Report and Written Opinion mailed on Feb. 15, 2013 for PCT Application No. PCT/US2012/063914, 9 pages.
International Search Report and Written Opinion mailed on Jun. 12, 2013 for PCT Patent Application No. PCT/US2012/063888, 18 pages.
International Search Report and Written Opinion mailed on Mar. 19, 2013 for PCT Application No. PCT/US2012/063929, 13 pages.
International Search Report and Written Opinion mailed on Dec. 7, 2012 for PCT Patent Application No. PCT/US2011/045107, 18 pages.
International Search Report and Written Opinion mailed on Oct. 4, 2013 for PCT Patent Application No. PCT/US2012/063931, 24 pages.

(56) References Cited

OTHER PUBLICATIONS

International Search Report and Written Opinion mailed on Sep. 30, 2013 for PCT Patent Application No. PCT/US2012/063930, 37 pages.
Invitation to Pay Additional Fees mailed on Mar. 1, 2013 for PCT Patent Application No. PCT/US2012/063918, 6 pages.
Invitation to Pay Additional Fees mailed on Mar. 19, 2013 for PCT Patent Application No. PCT/US2012/063930, 8 pages.
Invitation to Pay Additional Fees mailed on Mar. 25, 2013 for PCT Patent Application No. PCT/US2012/063931, 8 pages.
Invitation to Pay Additional Fees mailed on Mar. 6, 2013 for PCT Patent Application No. PCT/US2012/063888, 6 pages.
Invitrogen; Manual, "Dynabeads® DNA Direct™ Blood" Cat. No. 631.02 "For the isolation of PCR-ready genomic DNA from blood" Rev. o. 006, Invitrogen *Dynal® Invitrogen Bead Separations*, 2007.
Jaklevic, "Automation of High-Throughput PCR Assays," Laboratory Robotics and Automation, 8(5):277-286, John Wiley & Sons Inc., USA.
Jaton et al., "Development of polymerase chain reaction assays for detection of *Listeria monocytogenes* in clinical cerebrospinal fluid samples," J. Clin. Microbiol., 1992, 30(8):1931-1936, American Society for Microbiology, Washington D.C., USA.
Jungkind et al., "Evaluation of Automated COBAS AMPLICOR PCR System for Detection of Several Infectious Agents and Its Impact on Laboratory Management," J. Clin. Microbiol., 1996, 34(11):2778-2783, American Society for Microbiology, Washington, D.C., USA.
Kalinina et al., "Nanoliter scale PCR with TagMan detection," Nucleic Acids Res., 1997, 25(10):1999-2004, Oxford University Press, Oxford, United Kingdom.
Kapperud et al., "Detection of Pathogenic *Yersinia enterocolitica* in Foods and Water by Immunomagnetic Separation, Nested Polymerase Chain Reactions, and Colorimetric Detection of Amplified DNA," Appl. Environ. Microbiol., 1993, 59(9):2938-2944, American Society for Microbiology, Washington, D.C., USA.
Kendrew et al., "Polymerase Chain Reaction," in the Encyclopedia of Molecular Biology, 1994, pp. 864-865, Blackwell Science Ltd., Cambridge, USA.
Khalil "Automation and Use of Robotics in Nucleic Acid Amplification Assays," in Nucleic Acid Amplification Technologies: Application to Disease Diagnosis, 1997, p. 151-164, Eaton Pub. Co., Natick, USA.
Kolk et al., "Development of Individual and Multiplex Assays for the Detection of HIV and HCV," 13th Annual Clinical Virology Symposium and Annual Meeting of the Pan American Society for Clinical Virology, M7, Apr. 27-30, 1997, Clearwater Beach, USA.
Kolmodin et al., "Basic Principles and Routine Practice," in PCR Cloning Protocols From Molecular Cloning to Genetic Engineering, 1997, pp. 3-5, Humana Press, Totowa, USA.
Kost, G. J. *Handbook of Clinical Automation, Robotics, and Optimization*; Chapters 1, 10, and 12-14; 1996 by John Wiley & Sons, Inc.; 189 pages total.
Kretz et al., "Cycle sequencing," PCR Methods and Applications, 1994, 3:S107-S112, Cold Spring Harbor Laboratory, Cold Spring Harbor Press, USA.
Krieg, "Quantification of RNA by Competitive RT PCR," in a Laboratory Guide to RNA, 1996, p. 210, Wiliey-Liss, New York City, USA.
Kwok et al., "Avoiding False Positive with PCR," Nature, 1989, 339:237-238, Nature Publishing Group, Basingstoke, USA.
Landry, "False-Positive Polymerase Chain Reaction Results in the Diagnosis of Herpes Simplex Encephalitis," J. Infect. Dis., 1995, 172(6):1641-1642, University of Chicago Press, Chicago, USA.
Lay et al., "Real-time fluorescence genotyping of factor V Leiden during rapid-cycle PCR," Clin. Chem., 1997, 43(12):2262-2267, American Association for Clinical Chemistry, Washington D.C., USA.
Lee et al., "Direct Identification of *Vibrio vulnificus* in Clinical Specimens by Nested PCR," J. Clin. Microbial., 1998, 36 (10):2887-2892, American Society for Microbiology, Washington D.C., USA.

Lee et al., "Nucleic Acid Amplification Technologies: Application to Disease Diagnosis," BioTechniques Books, 1997, pp. 1-286, Eaton Publishing, Massachusetts, USA.
Leone et al., "Molecular beacon probes combined with amplification by NASBA enable homogeneous, real-time detection of RNA," Nucleic Acids Res., 1998, 26(9): 2150-2155, Oxford University Press, Oxford, United Kingdom.
Lisby, "Application of Nucleic Acid Amplification in Clinical Microbiology," in Methods in Molecular Biology: PCR in Bioanalysis, 1998, pp. 1-29, Humana Press, Totowa, USA.
Livak et al., "Oligonucleotides with Fluorescent Dyes at Opposite Ends Provide a Quenched Probe System Useful for Detecting PCR Product and Nucleic Acid Hybridization," PCR Methods and Applications, 1995, 4:357-362, Cold Spring Harbor Laboratory Press, Cold Spring Harbor, New York, USA.
Lo et al., "Quantitative Analysis of Fetal DNA in Maternal Plasma ad Serum: Implications for Noninvasive Prenatal Diagnosis," 1998, Am. J. Hum. Genet., 62:768-775, American Society of Human Genetics, Baltimore, USA.
Lo, "Setting Up a PCR Laboratory," in Methods in Molecular Medicine: Clinical.Applications of PCR, 1998, pp. 12-17, Humana Press, Totowa, USA.
Longo, "Use of uracil DNA glycosylase to control carry-over contamination in polymerase chain reactions" Gene, 1990, 93: 125-128, Elsevier/North-Holland, Amsterdam.
Mabilat et al., "Routine Identification of *Mycobacterium tuberculosis* Complex Isolates by Automated Hybridization," J. Clin. Microbiol., 1994, 32(11):2702-2705, American Society for Microbiology, Washington, D.C., USA.
Magnemotion; "MagneMover™ LITE,"; located at http://www.magnemotion.com/industrial-automation/magmoverlite.cfm; last visited on Jul. 20, 2013; 3 pages.
Mangiapan, "Sequence capture-PCR improves detection of mycobacterial DNA in clinical specimens" J Clin Microbiol., 1996, 34: 1209-1215, American Society for Microbiology, USA.
Martin et al., "PCR and Its Modifications for the Detection of Infectious Disease," Nucleic Acid Amplification Technologies: Application to Disease Diagnosis, 1997, p. 79-100, Eaton Pub. Co., Massachusetts, USA.
McCreedy et al., "Laboratory Design and Work Flow," Diagnostic Molecular Microbiology Principles and Applications, 1993, p. 149-159, Mayo Foundation, Rochester, USA.
Meng et al., "Turbo PCR—An Integrated Robotic System for Continuously Setting Up and Running Multiple PCR Reactions," DOE Human Genome Program Contractor-Grantee Workshop IV, Nov. 13-17, 1994, Santa Fe, New Mexico, 1 page.
Mercier et al., "Direct PCR from whole blood, without DNA extraction," Nucleic Acids Res., 1990, 18(19):5908, Oxford University Press, Oxford, United Kingdom.
Merel et al., "Completely Automated Extraction of DNA from Whole Blood," Clin. Chem., 1996, 42(8):1285-1286, American Association for Clinical Chemistry, USA.
Merel et al., "Perspectives on Molecular Diagnostics Automation," JALA, 2005, 10:342-350, Association for Laboratory Automation, Charlottesville, USA.
Meyers, "PCR Technology," Molecular Biology and Biotechnology: A Comprehensive Desk Reference, 1995, pp. 642-646, VCH Publishers Inc., New York City, USA.
Mischiati et al., "Use of an Automated Laboratory Workstation for Isloation of Genomic DNA Suitable for PCR and Allele-Specific Hybridization," BioTechniques, 1993, 15(1):146-151, Eaton Pub. Co., Natick, USA.
Mondada, Francesco et al.; "The e-Puck, a Robot Designed for Education in Engineering", *Proceedings of the 9th Conference on Autonomous Robot Systems and Competitions*, Castelo Branco, Portugal; May 7, 2009; vol. 1; Issue 1; pp. 59-65.
Mullis, "Eine Nachtfahrt und die Polymerase-Kettenreaktion," Spektrum der Wissenschaft, 1950, pp. 60-67, Germany.
Muramatsu et al., "Molecular Cell Biology Dictionary," 1997, Tokyo Kagaku Dojin Publisher, Tokyo, Japan, English Translation, 10 pages.

(56) References Cited

OTHER PUBLICATIONS

Nace, "Automation in Molecular Diagnostics: A Pleasant Surprise," Advance for Medical Laboratory Professionals, 2006, 14(11):64, Merion Publications, King of Prussia, PA, USA.

Nazarenko et al., "A closed tube format for amplification and detection of DNA based on energy transfer," Nucleic Acids Res., 1997, 25(12):2516-2521, Oxford University Press, Oxford, United Kingdom.

Neumaier et al., "Fundamentals of Quality Assessment of Molecular Amplification Methods in Clinical Diagnostics," Clin. Chem., 1998, 44(1):12-26, American Society for Clinical Chemistry, Washington D.C., USA.

Newton et al., "Instrumentation, Reagents and Consumables," PCR, 1996, 2nd ed., Chpt. 2, pp. 9-28, Bios Scientific, UK.

Nickerson et al., "Automated DNA Diagnostics Using an ELISA-based Oligonucleotide Ligation Assay," Proc. Natl. Acad. Sci. USA, 1990, 87:8923-8927, National Academy of Sciences, Washington, D.C., USA.

Niederhauser et al., "Direct Detection of *Listeria monocytogenes* Using Paramagnetic Bead DNA Extraction and Enzymatic DNA Amplificaiton,", Molecular and Cellular Probes, 1994, 8:223-228.

Noordhoek et al., "Reliability of Nucleic Acid Amplification for Detection of *Mycobacterium tuberculosis*: an International Collaborative Quality Control Study Among 30 Laboratories," J. Clin. Microbiol., 1996, 34(10):2522-2524, American Society for Microbiology, Washington D.C., USA.

Obata et al., "Development of a Novel Method for Operating Magnetic Particles, Magtration Technology, and Its Use for Automating Nucleic Acid Purification," J. Biosci. Bioeng., 2001, 91(5):500-503, Elsevier Science, Amsterdam, Netherlands.

Oehlenschlager et al., "Detection of HIV-1 RNA by nucleic acid sequence-based amplification combined with fluorescence correlation spectroscopy," Biochemistry, 1996, 93:12811-12816, Proc. Natl. Acad. Sci. USA, Washington D.C., USA.

Olive, "Q-Beta Replicase Assays for the Clinical Detection of Infectious Agents," in Nucleic Acid Amplification Technologies: Application to Disease Diagnosis, 1997, p. 110, Eaton Pub. Co., Natick, USA.

Olsvik et al., "Magnetic Separation Techniques in Diagnostic Microbiology," Clin. Microbiol. Rev., 1994, 7(1):43-54, American Society for Microbiology, Washington, D.C., USA.

Oste, "Polymerase Chain Reaction," Product Application FOCUS, BioTechniques, 1988, 6(2):162-167, Informa Healthcare USA, Inc., UK.

Package Insert, "APTIMA® Assay for *Neisseria gonorrhoeae*," IN0148-01-REG, Rev. 1, Nov. 2004, Gen-Probe Incorporated, San Diego, USA, 20 pages.

Package Insert, "APTIMA® HCV RNA Qualitative Assay," 500237 Rev. B, Jul. 2006, Gen-Probe Incorporated, San Diego, USA, 18 pages.

Package Insert, "Gen-Probe® Amplified *Mycobacterium tuberculosis* Direct Test," IN0006 Rev. A, Feb. 24, 1994, Gen-Probe Incorporated, San Diego, USA, 14 pages.

Package Insert, "Gen-Probe® Amplified™ *Chlamydia trachomatis* Assay," IN0012 Rev. A, Jan. 6, 1997, Gen-Probe Incorporated, San Diego, USA, 17 pages.

Package Insert, "Gen-Probe® Amplified™ *Chlamydia trachomatis* Swab Specimen Preparation Kit," In0016 Rev. A, Jan. 6, 1997, Gen-Probe Incorporated, San Diego, USA, 3 pages.

Package Insert, "Gen-Probe® Amplified™ *Chlamydia trachomatis* Urine Specimen Preparation Kit," IN0017 Rev. A, Nov. 11, 1996, Gen-Probe Incorporated, San Diego, USA, 3 pages.

Package Insert, "Gen-Probe® APTIMA® Combo 2 Assay," IN0037 Rev. A, Jun. 6, 2001, Gen-Probe Incorporated, San Diego, USA, 28 pages.

Package Insert, "Gen-Probe® APTIMA Combo 2® Assay," 501011 Rev. A, Jan. 2007, Gen-Probe Incorporated, San Diego, USA, 44 pages.

Package Insert, "Gen-Probe® APTIMA® Assay for *Chlamydia trachomatis*," IN0147-01, Rev. B, Apr. 2005, Gen-Probe Incorporated, San Diego, USA, 24 pages.

Package Insert, "Procleix® HIV-1/HCV Assay," IN0076-01-FDA, Rev. 3, Jun. 2004, Gen-Probe Incorporated, San Diego, USA, 28 pages.

Package Insert, "Procleix® HIV-1/HCV Assay," IN0076-02-FDA, Rev. 1, Jan. 2005, Gen-Probe Incorporated, San Diego, USA, 32 pages.

Package Insert, "Procleix® Ultrio™ Assay," IN0167EN, Rev. 1, Aug. 2004, Gen-Probe Incorporated, San Diego, USA, 44 pages.

Package Insert, "Procleix® WNV Assay," IN0155, Rev. 1, Apr. 2004, Gen-Probe Incorporated, San Diego, USA, 15 pages.

Paillard et al., "Direct nucleic acid diagnostic tests for bacterial infectious diseases: *Streptococcal pharyngitis*, pulmonary tuberculosis, vaginitis, chlamydial and gonococcal infections," MLO, Jan. 2004, pp. 10-15, Medical Laboratory Observer, NP Communications, LLC, Monroe Township, USA.

Panaccio et al., "PCR based diagnosis in the presence of 8% (v/v) blood," Nucleic Acids Res., 1991, 19(5):1151, Oxford University Press, Oxford, United Kingdom.

Patel et al., "Death from Inappropriate Therapy for Lyme Disease," Clin. Infect. Dis., 2000, 31:1107-1109, The University of Chicago Press, Chicago, USA.

Patterson et al., "Random and continuous-access immunoassays with chemiluminescent detection by Access automated analyzer," Clin. Chem., 1994, 40(11):2042-2045, American Association for Clinical Chemistry, Washington D.C., USA.

Pauwels et al., "Automated techniques in biotechnology," Current Opinion in Biotechnology, 1995, 6:111-117, Current Biology Ltd., London, United Kingdom.

Pawlotsky, "Measuring Hepatitis C Viremia in Clinical Samples: Can We Trust the Assays?" J. Hepatol., 1997, 26(1):1-4, Viral Hepatitis Foundation Bangladesh, Dhaka, Bangladesh.

Persing, "Diagnostic molecular microbiology. Current challenges and future directions," Diagn. Microbiol. Infect. Dis., 1993, 16(2):159-163, Elsevier Biomedical, New York, USA.

Petrik et al., "Human Hepatic Glyceraldehyde-3-phosphate dehydrogenase Binds to the poly(U) tract of the 3' Non-Coding Region of Hepatitis C Virus Genomic RNA," J. General Virology, 1999, 80:3109-3113.

Request for Inter Partes Reexamination of U.S. Patent No. 7,524,652, filed on Sep. 15, 2012, 134 pages.

Riggio et al., "Identification by PCR of *Helicobacter pylori* in subgingival plaque of adult periodontitis patients," J. Med. Microbiol., 1999, 48:317-322, The Pathological Society of Great Britain and Ireland.

Rosenblum et al., "New dye-labeled terminators for improved DNA sequencing patterns," Nucleic Acids Res., 1997, 25(22):4500-4504, Oxford University Press, UK.

Rudi et al., "Rapid, Universal Method to Isolate PCR-Ready DNA Using Magnetic Beads," BioTechniques, 1997, 22(3):506-511, Informa Healthcare USA, Inc., UK.

Rudi, et al., "Detection of Toxin-Producing Cyanobacteria by Use of Paramagnetic Beads for Cell Concentration and DNA Purification," 1998, Appl. Environ. Microbiol., 64(1):34-37, Am. Society of Microbiol., USA.

Schepetiuk et al., "Detection of *Chlamydia trachomatis* in Urine Samples by Nucleic Acid Tests: Comparison with Culture and Enzyme Immunoassay of Genital Swab Specimens," J. Clin Micorbiol., Dec. 1997, 35(12):3355-3357.

Skeggs, "An automatic method for colorimetric analysis," Am. J. Clin. Pathol., 1957, 28:311-322, American Society of Clinical Pathologists, Chicago, USA.

Smith et al., "Abbott AxSYM random and continuous access immunoassay system for improved workflow in the clinical laboratory," Clin. Chem., 1993, 39(10):2063-2069, American Association for Clinical Chemistry, Washington D. C., USA.

Smith et al., "Detection of *Mycobacterium tuberculosis* Directly from Sputum by Using a Prototype Automated Q-Beta Replicase Assay," J. Clin. Microbiol., 1997, 35(6):1477-1483, American Society for Microbiology, Washington, D.C., USA.

(56) References Cited

OTHER PUBLICATIONS

Smith et al., "Performance of an Automated Q-Beta Replicase Amplification Assay For *Mycobacterium tuberculosis* in a Clinical Trial," J. Clin. Microbiol., 1997, 35(6):1484-1491, Am. Society for Microbiology, USA.
Stanley et al., "A Survey of More Than 90 Commercially Available Luminometers and Imaging Devices for Low-Light Measurements of Chemiluminescence and Bioluminescence, Including Instruments for Manual, Automatic and Specialized Operation, for HPLC, LC, GLC and Microtitre Plates. Part 2: Photographs," J. Biolumin. Chemilumin., 1992, 7:157-169, John Wiley & Sons, Ltd., Chichester, Sussex, England.
Stanley, "Commercially Available Luminometers and Imaging Devices for Low-Light Level Measurements and Kits and Reagents Utilizing Bioluminescence or Chemiluminescence: Survey Update 3," J. Biolumin. Chemilumin., 1994, 9:123-125, John Wiley & Sons, Ltd., UK.
Stone et al., "Detection of rRNA from four respiratory pathogens using an automated Qβ replicase assay," Mol. Cell. Probes, 1996, 10:359-370, Academic Press Limited, San Diego, California, USA.
Suryanarayana et al., "Plasma SIV RNA Viral Load Determination by Real-Time Quantification of Product Generation in Reverse Transcriptase-Polymerase Chain Reaction," AIDS Res. Hum. Retroviruses, 1998, 14(2):183-189, Mary Ann Liebert, Inc., USA.
Sutton et al., "Hands Free Polymerase Chain Reaction," International Symposium on Laboratory Automation and Robotics, Oct. 17-20, 1993, p. 326-336, Boston, USA.
Sutton et al., "PCR Has Outgrown Appropriate Automated Instrumentation But Help is on the Way," Today's Chemist at Work, 1995, p. 42-48, American Chemical Society, Washington, D.C., USA.
Taos Inc. "TCS230 Programmable Color to Light-to-Frequency Converter," www.http?pdfl.alldatasheet.com/datasheet-pdf/view/96470/ETC/TCS230.html; Jan. 31, 2003, pp. 1-8.
Techne PHC-3 Thermal Cycler—Techni, Jun. 2009, Pegasus Scientific Inc., USA.
Tjian, "Purification and comparative properties of the delta and sigma subunits of RNA polymerase from *Bacillus subtilis*" Eur. J. Biochem., 1977, 74:149, Blackwell Science Ltd. on behalf of the Federation of European Biochemical Societies, UK.
Tyagi et al., "Extremely sensitive, background-free gene detection using binary proves and QB Replicase," Biochemistry, 1996, 93:5395-5400, Proc. Natl. Acad. Sci. USA, Washington D.C., USA.
Tyagi et al., "Molecular Beacons: Probes that Fluoresce upon Hybridization," Nature Biotechnology, 1996, 14:303-308, Nature Publishing Company, New York, USA.
Uckun et al., "Clinical Significance of MLL-AF4 Fusion Transcript Expression in the Absence of a Cytogenetically Detectable t(4;11)(q21;q23) Chromosomal Translocation," Blood, 1998, 92(3):810-821, American Society of Hematology, Washington D.C., USA.
Van Gemen, B. at al.; "The One-tube Quantitative HIV-1 RNA NASBA: Precision, and Application,"; 1995; *PCR Methods Appl.*; vol. 4; pp. 177-184.
Victor et al., "Laboratory Experience and Guidelines for Avoiding False Positive Polymerase Chain Reaction Results," Eur. J. Clin. Chem. Clin. Biochem., 1993, 31(8):531-535, Walter de Gruyter & Co., Berlin, Germany.
Voss et al., "Direct genomic fluorescent on-line sequencing and analysis using in vitro amplification of DNA," Nucl. Acids Res., 1989, 17(7):2517-2527, IRL Press, USA.
Walker et al., "Detection of *Mycobacterium tuberculosis* DNA with thermophilic strand displacement amplification and fluorescence polarization," Clin. Chem., 1996, 42(10):1604-1608, American Association for Clinical Chemistry, Washington D.C., USA.
Walker et al., "Strand displacement amplification (SDA) and transient-state fluorescence polarization detection of *Mycobacterium tuberculosis* DNA," Clin. Chem., 1996, 42(1):9-13, American Association for Clinical Chemistry, Washington D.C., USA.
Walter et al., "Fluorescence correlation analysis of probe diffusion simplifies quantitative pathogen detection by PCR," Proc. Natl. Acad. Sci. USA, 1996, 93:12805-12810, National Academy of Sciences, Washington D.C., USA.
Whelan et al., "The Role of Nucleic Acid Amplification and Detection in the Clinical Microbiology Laboratory," Annu. Rev. Microbiol., 1996, 50:349-373, Annual Reviews, Palo Alto, USA.
Wilke et al., "Automation of Polymerase Chain Reaction Tests Reduction of Human Errors Leading to Contamination," Diagn. Microbiol. Infect. Dis., 1995, 21:181-185, Elsevier Sciences, New York City, USA.
Wilke et al., "Automation of Polymerase Chain Reaction Tests to Achieve Acceptable Contamination Rates," Clin. Chem., 1995, 41(4):622-623, American Association for Clinical Chemistry, Washington, D.C., USA.
Wittwer et al., "The LightCycler: a microvolume multisample fluorimeter with rapid temperature control," BioTechniques, 1997, 22:176-181, Informa Healthcare USA, Inc., London, United Kingdom.
Yourno et al., "A method for nested PCR with single closed reaction tubes," PCR Methods Appl., 1992, 2(1):60-65, Cold Spring Harbor Laboratory Press, Cold Spring Harbor, New York, USA.
Genprobe; "Test Procedure Guide. Amplified *Mycobacterium tuberculosis* Direct (MTD) Test,"; 2000, 1 page.
International Search Report and Written Opinion mailed on Nov. 6, 2013 for PCT Patent Application No. PCT/US2012/063918, 22 pages.
ABI Product Catalogue, 1993-1994, "DNA Sequencing Reagents," p. 146, Applied Biosystems, USA.
Anonymous, "GeneAmp optical reaction plate," Nature, 1998, 391(8):210, Nature Publishing Group, USA.
Asper et al., "Laboratory Mechanization and Automation," in Laboratory Organization Automation, 1991, pp. 271-275, Walter deGruyter, USA.
Bieche et al., "Novel Approach to Quantitative Polymerase Chain Reaction Using Real-Time Detection: Application to the Detection of Gene Amplification in Breast Cancer," Int. J. Cancer, 1998, 78:661-666, Wiley-Liss, Inc., USA.
Billyard, et al., "Early detection of HIV-1 RNA from sero-conversion panels using Gen-Probe's transcription-mediated amplification," The San Diego Conference Nucleic Acid Technology: The Cutting Edge of Discovery, Nov. 6-8, 1997, Clin. Chem., 1997, 43(11):2221, Am. Assoc. for Clin. Chem., USA.
Burg et al., "Real-time fluorescence detection of RNA amplified by Q beta replicase," Anal. Biochem., 1995, 230(2):263-272, Academic Press, Orlando, Florida, USA.
Chemistry Guide, "ABI PRISM DNA Sequencing," 1995, pp. 1-3-1-6, The Perkin-Elmer Corporation, USA.
Civitello et al., "A simple protocol for the automation of DNA cycle sequencing reactions and polymerase chain reactions," DNA Sequence—J. DNA Sequencing and Mapping, 1992, 3:17-23, Harwood Academic Publishers GmbH, UK.
Dangler, ed., Nucleic Acid Analysis: Principles and BioApplications, 1996, pp. 1-3, 19, 68-75, 106-109, 116, 117, 144, 145, 157, 162 & 163, Wiley-Liss, Inc., USA.
Educational Guide, "New Directions in Molecular Diagnostic Testing," pp. 1-12, Rev. A, 2000, Gen-Probe Incorporated, San Diego, USA.
Felder, "Automation of Preanalytical Processing and Mobile Robotics," in Handbook of Clinical Automation, Robotics, and Optimization, 1996, pp. 252-256, John Wiley & Sons, Inc., USA.
Hawkins et al., "Thermal Cycle DNA Sequence Setup Using a Modified Lab Workstation," LRA, 1995, 7:117-122, VCH Publishers, New York City, USA.
Higuchi et al., "Kinetic PCR Analysis: Real-time Monitoring of DNA Amplification Reactions," Bio/Technology, 1993, 11(9):1026-30, Nature Publishing Group, New York, USA.
Hill et al., "The Polymerase Chain Reaction in Molecular and Microbiology," Biotechnol. Genet. Eng. Rev., 1992, 10:343-377, Taylor & Francis, UK.

(56) References Cited

OTHER PUBLICATIONS

Holmberg et al., "Automatic Preparation of DNA Templates for Sequencing on the ABI Catalyst Robotic Workstation," Automated DNA Sequencing and Analysis, 1994, Academic Press Inc., San Diego, USA.
Hunkapiller, "Advances in DNA sequencing technology," Curr. Opin. Genet. Dev., 1991, 1:88-92, Elsevier, UK.
Jakobsen et al., "Direct mRNA Isolation Using Magnetic Oligo (dT) Beads: A Protocol for All Types of Cell Cultures, Animal and Plant Tissues," in Advances in Biomagnetic Separation, 1994, pp. 61-71, Eaton Publishing, USA.
Kasper, "Automated Instrumentation (Generic)," in Clinical Laboratory Instrumentation and Automation: Principles, Applications, and Selection, 1994, pp. 184-205, W.B. Saunders Company, USA.
Kaufman et al., "Direct Sequencing by PCR," in Handbook of Molecular and Cellular Methods in Biology and Medicine, 1995, pp. 233-235, CRC Press, USA.
Krieg, ed., "Quantitation of RNA Transcripts Using RT-PCR," in a Laboratory Guide to RNA: Isolation, Analysis, and Synthesis, 1996, pp. 176-190, John Wiley & Sons, Inc., USA.
Little et al., "Recent Advances in Robotic Automation of Microplate Assays," Lab. Info. Mgmt., 1994, 26:89-99, Elsevier Science, Amsterdam, Netherlands.
Lundeberg et al., "Solid-Phase Technology: Magnetic Beads to Improve Nucleic Acid Detection and Analysis," Biotechnol. Annu. Rev., 1995, 1:373-401, Elsevier Science, Amsterdam, Netherlands.
Mahan et al., "An Automated System for Infectious Disease Diagnosis with Q-Beta Replicase Amplification," in New Horizons in Gene Amplification Technologies: Proceedings of a CHI Meeting, 1994, Cambridge, USA, 25 pages.
McDonough et al., High Throughput Assay for the Simultaneous or Separate Detection of Human Immunodeficiency Virus (HIV) and Hepatitis Type C Virus (HCV), Infusionsther. Transfusionsmed, 1998, 25:164-169, Karger GmbH, Germany.
Mertes et al., Automatische genetische Analytik, 1997, forward and pp. 68, 69, 73 & 74, Wiley-VCH, Germany; German Language Reference.
Mizutani et al., "Magnetic Separation in Molecular Studies of Human Leukemia,"in Advances in Biomagnetic Separation, 1994, p. 127-133, Eaton Publishing, USA.
Muller et al., "Evaluation des klinish-chemischen Analysensystems Technicon DAX 72," Lab. Med., 1992, 16:210-218, Am. Soc. for Clinical Pathology, USA, with English Summary.
Olsvik et al., "Magnetic Separation in Laboratory Diagnosis of Infectious Diseases," in Advances in Biomagnetic Separation, 1994, pp. 149-158, Eaton Publishing, USA.
Olympus Corporation, "Olympus News Release: Automated Chemistry Analyser AU1000," 1997, http://www.olympus-global.com/en/news/1997a/nr970421au1000e.jsp, downloaded Jun. 17, 2013, USA, 3 pages.
Overbergh et al., "Quantification of Murine Cytokine mRNAs Using Real Time Quantitative Reverse Transcriptase PCR," Cytokine, 1999, 11(4):305-312, Academic Press, USA.
Petrik et al., "High throughput PCR detection of HCV based on semiautomated multisample RNA capture," J. Virol. Methods, 1997, 64:147-159, Elsevier/North-Holland Biomedical Press, Amsterdam, Netherlands.
Piatek et al., "Molecular beacon sequence analysis for detecting drug resistance in *Mycobacterium tuberculosis*," Nature Biotechnology, 1998, 16:359-363, Nature America Publishing, New York, USA.
Shah et al., "Novel, Ultrasensitive, Q-Beta Replicase-Amplified Hybridization Assay for Detection of *Chlamydia trachomatis*," J. Clin. Microbiol., 1994, 32(11):2718-2724, American Society for Microbiology, USA.
Slatko, "Thermal Cycle Dideoxy DNA Sequencing," in Protocols for Gene Analysis (Methods in Molecular Biology), 1994, vol. 31, pp. 35-45, Humana Press Inc., USA.
Sloan et al., "Screening Yeast Artificial Chromosome Libraries with Robot-Aided Automation," GATA, 1993, 10(6):128-143, Elsevier Science Publishing Co., Inc., USA.

Truchaud et al., "Liquid-Phase Reactions Started by Rehydrating Lyophilized Reagents in a Centrifugal Analyzer," Clin. Chem., 1985, 31(9):1506-1508, Am. Assoc. for Clin. Chem., USA.
Tyagi et al., "Multicolor molecular beacons for allele discrimination," Nat. Biotechnol., 1998, 16:49-53, Nature Publishing Group, USA.
Vonderschmitt, ed., "Robots in the Clinical Laboratory," in Laboratory Automation Organization, 1991, pp. 576-577, Walter deGruyter, USA.
Ward, ed., "Improving Laboratory Efficiency Through Workflow Analysis", in Clinical Laboratory Instrumentation and Automation: Principles, Applications, and Selection, 1994, pp. 453 & 457, W.B. Saunders Company, USA.
Webster's New World Dictionary, Third college Edition, 1988: Definition of Incubate, Incubator.
Yohda et al., "Development of a Novel Laboratory Automation System for Molecular Biology," Kaguku-Koguku Symposium, 1998, p. 17-20.
Abbott Molecular; "m2000 System," located at http://www.abbottmolecular.com/us/products/instrumentation-automationlrealtimepcr/m2000-svstems.html; 2013; 3 pages.
Adams, C. et al.; "13. Direct Detection of HBV genomic DNA in plasma using transcription mediated amplification (TMA),"; Clinical Chemistry; 1997; vol. 43, No. 11; p. 2215.
Albadalejo, J. et al.; "Multicenter evaluation of the COBAS AMPLICOR HCV assay, an integrated PCR system for rapid detection of hepatitis C virus RNA in the diagnostics laboratory,"; J Clin Microbiol; Apr. 1998; pp. 862-865.
Alphey, L.; "Chain Termination (Sanger Dideoxy) Method,"; Chapter 3, section 1.; DNA Sequencing; 1997; pp. 15-19.
Altwegg, M.; "General problems associated with diagnostic applications of amplification methods,"; J Microbiol Methods; 1995; vol. 23; pp. 21-30.
American Association for Laboratory Accreditation; "Product Information,"; Medical Laboratory Observer 29.8; Aug. 2007; 63 pages.
American Red Cross; "Infectious Disease Testing,"; located at htt[:// redcrossblood.org/hospitals/infectious-disease-testing; last visited May 9, 2013; 3 pages.
Anonymous, "COBAS AmpliPrep/COBAS TaqMan HIV-1 Test, Summary of Safety and Effectiveness,"; 2007, pp. 1-20.
Anonymous, "Emerging Technologies Are Diagnostics Not Ready for the Genetic Revolution?"; Jan. 1, 1997; 9 pages.
Anonymous.; "CEO Interview: Henry Nordhoff—Gen Probe, Inc. (GPRO),"; The Wall Street Transcript Corporation; Oct. 25, 2004; 8 pages.
Anonymous; "BioMerieux Exercises Second Option to License RNA Technology from Gen-Probe;"; PR Newswire; Dec. 21, 2005; 4 pages.
Anonymous; "Blood banks push expanded effort on pathogen reduction,"; Biomedical Business & Technology; Jun. 5, 2008; 5 pages.
Anonymous; "Blood Safety; TIGRIS Instrument System to Be Used for Clinical Testing,"; Hepatitis Weekly; Oct. 21, 2002; 3 pages.
Anonymous; "Captains of the life sciences industries; Frost & Sullivan presents in-depth interviews with 'Movers and Shakers,'"; Business Wire; Jan. 20, 2004; 4 pages.
Anonymous; "Cepheid at NASDAQ OMX International Investor Program—Final,"; Fair Disclosure Wire; Dec. 4, 2012; 9 pages.
Anonymous; "Detection (HIV, Hepatitis); High Throughput Nucleic Acid Amplification Assay Systems in Feasible: [2],"; Hepatitis Weekly; Jan. 10, 2008; 3 pages.
Anonymous; "Diagnostics; Study finds demand for effective prognosis spurs uptake of molecular diagnostics,"; Medical letter on the CDC & FDA; Oct. 31, 2004; 4 pages.
Anonymous; "Event Brief on Q1 2005 Gen-Probe Earnings Conference Call—Final,"; Fair Disclosure Wire; May 4, 2005; 11 pages.
Anonymous; "Gen-Probe at William Blair & Company Healthcare Conference—Final,"; Fair Disclosure Wire; Jun. 10, 2009; 10 pages.
Anonymous; "Gen-Probe Incorporated; Gen-Probe Incorporated presents its most recent news and research developments,"; Science Letter; Apr. 24, 2007; 4 pages.
Anonymous; "Gen-Probe Incorporated; Recent findings from Gen-Probe incorporated provide an update on new developments,"; Life Science Weekly; Jun. 26, 2007; 4 pages.

(56) References Cited

OTHER PUBLICATIONS

Anonymous; "Gen-Probe issues update on regulatory process for blood screening assay; FDA clearance for standalone Aptima assay,"; ESPICOM Pharmaceutical and Medical Device News; Jan. 30, 2007; 3 pages.

Anonymous; "Gen-Probe Receives FDA Approval for STD Testing on the TIGRIS® DTS™ System, First Fully Automated, Amplified Molecular Diagnostic Testing Instrument; —Innovative System Designed to Improve Workflow and Increase Productivity for Clinical Laboratories,"; PR Newswire; Dec. 29, 2003; 6 pages.

Anonymous; "Gen-Probe Reports Strong Financial Results for First Quarter 2004, Raises Full-Year Guidance,"; PR Newswire; May 3, 2004; 12 pages.

Anonymous; "Gen-Probe Responds to FDA Questions to TIGRIS(R) / West Nile Virus Regulatory Application,"; PR Newswire; Sep. 20, 2006; 4 pages.

Anonymous; "Gen-Probe, Chiron submit Biologics License Application to FDA for WNV assay for blood screening,"; Transplant News 15.3; Feb. 14, 2005; 3 pages.

Anonymous; "Industry News (Joint Venture); Strategic Alliance Formed to Further Improve Blood Safety,"; Blood Weekly; Jul. 27, 1998; 3 pages.

Anonymous; "Novartis; Officials at Novartis announce latest new and research developments,"; Parhma Business Week; Sep. 3, 2007; 5 pages.

Anonymous; "Q2 2009 Gen-Probe Earnings Conference Call—Final,"; Fair Disclosure Wire; Jul. 30, 2009; 17 pages.

Anonymous; "Q3 2009 Gen-Probe Earnings Conference Call—Final,"; Fair Disclosure Wire; Oct. 29, 2009; 16 pages.

Anonymous; "Study: Novartis' Tigris efficient at screening blood,"; Medical Device Daily; Oct. 27, 2010; 3 pages.

Anonymous; "Testing With Proclelx(R) West Nile Virus Assay Initiated on Proclelx(R) TIGRIS(R) System Under IND,"; PR Newswire; Sep. 1, 2004; 5 pages.

Anonymous; "US FDA: FDA Approves First Fully Automated Test to Screen for West Nile Virus in Blood and Tissue Donors,"; M2 Presswire; Mar. 5, 2008; 3 pages.

Anonymous; "Chiron Signs Contract with South African National Blood Service,"; Business Wire; Apr. 14, 2005; 4 pages.

Applied Biosystems; "ABI Prism® 373 DNA Sequencer With XL Upgrade—User's Manual,"; Applied Biosystems, USA; Mar. 2001, 395 pages.

Arnal, C. et al.; "Simplified reverse transcription polymerase chain reaction procedure with detection by microplate hybridization for routine screening of hepatitis A virus,"; Can J Micorbio; Mar. 1998; vol. 44; No. 3; pp. 298-302.

Asfahl, C.R.; "Robot Implementation,"; Chapter 8; Robots and Manufacturing Automation; 1985; pp. 213-231.

Aslanzadeh, J.; "Preventing PCR Amplification Carryover Contamination in a Clinical Laboratory,"; Annal Clin Lab Sci; 2004; vol. 34, No. 4; pp. 389-396.

Ausina, V. et al. "Evaluation of the Semiautomated Abbott L Cx *Mycobacterium tuberculosis* Assay for Direct Detection of *Mycobacterium tuberculosis* Assay for Direct Detection of *Mycobacterium tuberculosis* in Respiratory Specimens,"; J Clin. Micorbiol; Aug. 1997; pp. 1996-2002.

Bankowski, M.T.; "Standardization of Molecular Amplification Testing in the Clinical Microbiology Laboratory,"; Clinical Microbiology Newsletter; Dec. 15, 2000; pp. 185-190.

Batt, C. "Symposium: Molecular Probes—Theory and Application. Molecular Diagnostics for Dairy-Borne Pathogens,"; Journal of Dairy Science; Jan. 1997; 80(1):220-229.

Beckman Coulter, Inc.; "Automated Sample Preparation for Forensic DNA Typing. Biomek 2000,"; 2002; 3 pages.

Beggs, M.L. et al.; Characterization of *Mycobacterium tuberculosis* Complex Direct Repeat Sequence for Use in Cycling Probe Reaction.; J Clin Microbiol; Dec. 1996; pp. 2985-2989.

Berson, S. et al.; "Quantitative Aspects of the Reaction Between Insulin and Insulin-Binding Antibody,"; J Clin Invest; 1959; pp. 1996-2016.

Boothroyd, G. et al.; "Design of Assembly Machines,"; Chapter 9; Automatic Assembly; 1982; pp. 275-297.

Bortlin, S. et al. "Quantitative RT-PCR combined with time-resolved fluorometry for determination of BCR-ABL mRNA,"; Clinical Chemistry; 1996; vol. 24; pp. 1924-1929.

Boyd et al., "False-positive polymerase chain reaction results for human papillomavirus in lichen planus,"; J Am Acad Dermatol; 1996; Vo. 35; pp. 42-46.

Bustin, S.A.; "Absolute quantification of mRNA using real-time reverse transcription polymerase chain reaction assays,"; J Molec Encodrin; 2000; pp. 169-193.

Carlotti, A. et al. "Rapid identification and fingerprinting of *Candida krusei* by PCR-based amplification of the Species-Specific Repetitive Polymorphic Sequence CKRS-1,"; J Clin Microbiol; Jun. 1997; pp. 1337-134.

Chan et al.; "AIA-12000 Immunoassay System," Chapter 10; Immunoassay Automation: An Updated Guide to Systems; 1996; pp. 96-115.

Chan et al.; "Automation of Immunoassay," Chapter 2; Immunoassay Automation; A Practical Guide; 1992; p. 17.

Chan et al.; "Technical Evaluation,"; Chapter 4; Immunoassay Automation: A Practical Guide; 1992; p. 39.

Chan, "Summary of Automated Immunoassay Systems," Chapter 2; Immunoassay Automation: An Updated Guide to Systems; 1996; pp. 9-12.

Chan, D.W.; "Immunoassay Automation: From Concept to System Performance,"; Chapter 16; Handbook of Clinical Automation, Robotics and Optimization; 1996; pp. 419-441.

Cherian, T. et al.; "PCR-Enzyme Immunoassay for Detection of *Streptococcus pneumoniae* DNA in Cerebrospinal Fluid Samples from Patients with Culture-Negative Meningitis,"; J Clin Micorbiol; Dec. 1998; pp. 3605-3608.

Chernesky, M.; "Head to Head Comparison of Second Generation Nucleic Acid Amplification Tests for *Chlamydia trachomatis* and *Neisseria gonorrhoeae* on Femal Urines and Self Collected Vaginal Swabs,"; J Clin Micorbiol; Apr. 2, 2014; 21 pages.

Chernesky, M.A. et al. "APTIMA transcription-mediated amplification assays for *Chlamydia trachomatis* and *Neisseria gonorrhoeae*,"; Expert Rev Mol Diagn; 2006; pp. 519-525.

Chu et al.; "Synthesis of an amplifiable reporter RNA for bioassays,"; Nucleic Acids Res.; 1986; 14(4):5591-5603.

Clewley, "Automation of the Polymerase Chain Reaction Part 1. Prospects and Problems," Communicable Disease and Public Health, Mar. 1999, 2(1):71-72.

Clewley, "Automation of the Polymerase Chain Reaction Part 3. Amplification—The heart of the process," Communicable Disease and Public Health, Sep. 1999, 2(3):223-224.

Cohen, M.S. et al.; "Acute HIV-1 Infection,"; New England Journal Medicine; May 19, 2011; pp. 1943-1954.

Compton, J.; "Nucleic acid sequence-based amplification,"; Nature; Mar. 7, 1991; vol. 35; pp. 91-92.

Davidson College; "Transcription Mediated Amplification (TMA) (isothermal reaction in one tube),"; located at http://www.bio.davidson.edu/Courses/Bio111/TMA/TMA_Method.html; 2008; last visited Jun. 24, 2013; 7 pages.

Davies, P.O. et al.; "The role of polymerase chain reaction and ligase chain reaction for the detection of *Chlamydia trachomatis*,"; Int J of STD and AIDS; 1997; pp. 731-738.

De Vos, D. et al.; "Direct detection and Identification of *Pseudomonas aeruginosa* in clinical samples such as skin biopsy specimens and expectorations by multiplex PCR based on two outer membrane lipoprotein genes, optI and orL,"; J Clin Microbiol; Jun. 1997; pp. 1295-1299.

Denis, M. et al.; "Development of a semiquantitative PCT assay using internal standard and colorimetric detection on microwell plate for pseudorabies virus,"; Mol Cel Probes; 1997; pp. 439-448.

Dilulio, R.; "Yesterday's future, tomorrow's past: recent developments in infectious-disease testing affect today's reality,"; Clinical Lab Products; Feb. 2006; 7 pages.

Doern, C.D. ; "Integration of Technology Into Clinical Practice,"; Clin Lab Med; 2013; vol. 33; pp. 705-729.

Dorf, R.C.; "Applications of Robots,"; Chapter 8; Robotics and Automated Manufacturing; 1983; pp. 117-147.

(56) References Cited

OTHER PUBLICATIONS

Einsele, H. et al. "Detection and identification of fungal pathogens in blood by using molecular probes,"; J Clin Microbiol; Jun. 1997; pp. 1353-1360.
Elsayed, S. et al.; "Development and Validation of a Molecular Beacon Probe-Based Real-Time Polymerase Chain Reaction Assay for Rapid Detection of Methicillin Resistance in *Staphylococcus aureus*,"; Arch Pathol Lab Med; Jul. 2003; vol. 217; pp. 845-849.
Fahy et al.; "Self-Sustained Sequence Replication (3SR): An Isothermal Transcription-based amplification system alternative to PCR," Genome Res; 1991; 1:25-33.
FDC Reports, Inc.; "Medical Devices, Diagnostics & Instrumentation, The Gray Sheet,"; May 30, 1994; 4 pages.
Ferrero, D.V. et al.; "Analytical Sensitivity Comparison of *Chlamydia trachomatis* (CT) Nucleic Acid Amplification Assays,"; Poster 2002 European IUSTI; 2002; 1 page.
Garduno, F. et al.; "46. Early detection of HIV-1 RNA from seroconversion panels using Gen-Probes transcription-mediated amplification,"; Clinical Chemistry; 1997; vol. 43; No. 11; p. 2221.
Gen-Probe, "About Us,"; Hologic, Gen-Probe Incorporated; 2012; 2 pages.
Gen-Probe; "510(k) Substantial Equivalence Determination Decision Summary Device Only Template,"; 2003; 9 pages.
Gen-Probe; "APTIMA® HPV Assay,"; 502170 Rev A.; 2011; 47 pages.
Gen-Probe; "Gen-Probe Receives FDA Biologics License Approval in United,"; Feb. 28, 2002; 2 pages.
Gen-Probe; "Gen-Probe Reports Strong Financial Results for Fourth Quarter and Full Year 2005,"; Feb. 15, 2006; 8 pages.
Gen-Probe; "Press Release. Gen-Probe Received FDA Clearance to Run Standalone APTIMA(R) Tests for Chlamydia and Gonorrhea on the TIGRIS(R) System,"; Oct. 18, 2006; located at http://www.gen-probe.com/news/PressReleaseText.asp?compid=135117 &releaseID=918229; 2 pages.
Gen-Probe; "Procleix WNV Assay, for in Vitro Diagnostic Use 5000 Test Kit,"; 500630 Rev. A.; 2007; 34 pages.
Gen-Probe; "The Power of TIGRIS," Brochure; 2006; 2 pages.
Gen-Probe; "TIGRIS DTS™ System Operator's Manual,"; 2005; 260 pages.
Gen-Probe; "TIGRIS . . . from Gen-Probe,"; 1998; 1 page.
Guitard; "Access Immunoassay System,"; Immunoassay Automation: An Updated Guide to Systems; 1996; Chapter 11; pp. 185-199.
Guiver, M. et al.; "Evaluation of the Applied Biosystems Automated Taqman Polymerase Chain Reaction System for the Detection of Meningococcal DNA,"; FEMS Immuno Med Microbiol; 2000; vol. 28; pp. 173-179.
Hawkins, T.; "DNA Sample Manipulation and Automation," Abstract; DOE Human Genome Program Report, Part 2; 1996; p. 8.
Heman, P.; "Contained Use of GMOs and pathogens,"; Belgian Biosafety Server; Dec. 19, 2007; 4 pages.
Hilali, F. et al.; "Decontamination of Polymerase Chain Reaction Reagents for Detection of Low Concentrations of 16S rRNA genes,"; Molecular Biotech; Jun. 1997; pp. 207-216.
Hill; "Automating nucleic acid amplification tests,"; IVD Technology; 2000; pp. 36-45.
Hines, E.; "PCR based testing,"; Food Quality; Mar./Apr. 2000; pp. 22-28.
Hood, L.; Construction of a genome-wide characterized clone resource for genome sequencing, Abstract; DOE Human Genome Program Report, Part 2; 1996; p. 8.
Horton, B.; "GeneAmp optical reaction plate,"; Nature; Jan. 1998; vol. 391; p. 210.
Ikegame, S. et al.; Clinical Evaluation of COBAS TagMan PCT for the detection of *Mycobacterium tuberculosis* and *M. avium* Complex,; Tuberculosis Research and Treatment; 2012; vol. 2012; 5 pages.
Innis, M.A. et al. "DNA sequencing with *Thermus aquaticus* DNA polymerase and direct sequencing of polymerase chain reaction-amplified DNA,"; Proc. Natl. Acad. Sci. USA; Dec. 1988; vol. 85; pp. 9436-9440.

Invitrogen; "Dynal MPC-96B,"; Product Sheet; Invitrogen; 2008; 2 pages.
Jago, T. et al.; "Evaluation of the Gen-Prone APTIMA Combo 2 (CTNG) Assay and the TIGRIS DRS Automated Workstation for the Detection of CT and NG rRNA from Liquid Cytology Specimens,"; Journal Molecular Diagnostics; AMP Abstracts; Nov. 2006; p. 643.
Khalil, O.S.; "Review. Instrumentation Methods and Automation in Nucleic Acid Assays,"; CMB2; Nov.-Dec. 1995; pp. 669-681.
Kaul, K. et al.; "Amplification of Residual DNA Sequences in Sterile Bronchoscopes Leading to False-Positive PCR Results,"; J Clin Microbiol; Aug. 1996; pp. 1949-1951.
Kenzelmann, M. et al.; "Pitfalls of PCR: Cross-Reactivity with Joyride *E. coli* Nucleic Acid,"; BioTechniques; 1997; pp. 204-206.
Krafft, A.E. et al. "Optimization of the Isolation and Amplification of RNA From Formalin-fixed, Paraffin-embedded Tissue: The Armed Forces Institute of Pathology Experience and Literature Review,"; Molecular Diagnosis; 1997; vol. 2; No. 3; pp. 217-230.
Lau, G.; "Gen-Probe Inc. San Diego, California; Medical Test Supplier Speeds Up Treatments,"; Investor's Business Daily; Dec. 2002; 4 pages.
Le, H. et al. "Capillary electrophoresis: New Technology for DNA Diagnostics,"; Pathology; 1998; vol. 30; pp. 304-308.
Legler, T.J.; "High-throughput extraction, amplification, and detection (HEAD) of HCV-RNA in individual blood donations," Journal Clin Virology; 1999; pp. 95-103.
Leone, G. et al.; "Direct detection of potato leafroll virus in potato tubers by immunocapture and the isothermal nucleic acid amplification method NASBA,"; Journal of Virological Methods; 1997; vol. 66; pp. 19-27.
Levett, P.N. et al.; "Evaluation of Three Automated Nucleic Acid Amplification Systems for Detection of *Chlamydia trachomatis* and *Neisseria gonorrhoeae* in First-Void Urine Specimens,"; J Clin Micorbiol; Jun. 2008; pp. 2109-2111.
Lichtinghagen, R. et al. "A competitive polymerase chain reaction assay for reliable identification of *Bordetella pertussis* in nasopharyngeal swabs,"; Eur J Clin Chem Clin Biochem; 1995; pp. 87-93.
Life Technologies; "DynaMag-96 Side Skirted, DynaMag-96 Side, DynaMag-96 bottom,"; product manaul; 2012; 2 pages.
Merel, P.; "Nucleic Acid Extraction Automation in Molecular Diagnostic. Part 1,"; Biomedical Innovation Platform (PTIB),; 2011; 125 pages.
Merel, P.; "Nucleic Acid Extraction Automation in Molecular Diagnostic. Part 2,"; Biomedical Innovation Platform (PTIB),; 2011; 107 pages.
Merel, P.; "Nucleic Acid Extraction Automation in Molecular Diagnostic. Part 3,"; Biomedical Innovation Platform (PTIB),; 2011; 107 pages.
Meyers, R.A.; "2.2. Potential Problems,"; Encyclopedia of Molecular Biology and Molecular Medicine; vol. 4; 1996; p. 337.
Miffin, T.E. et al.; "Robotic automation performs a nested RT-PCT analysis for HCV without introducing sample contamination,"; Clinica Chimica Acta; 2000; vol. 290; pp. 199-211.
Mitchell, P.S. et al.; "Laboratory diagnosis of central nervous system infections with herpes simplex virus by PCR performed with cerebrospinal fluid specimens,"; J Clin Microbiol; Nov. 1997; pp. 2873-2877.
Mora-Bruges, J. et al.; "Evaluation of Ciba Corning ACS:180 Automated Immunoassay System,"; Clin. Chem. 19954; vol. 40; Issue 3; pp. 407-410.
Morosini et al.; "Multicenter Evaluation of the Bayer BAD System,"; Eur. J. Clin. Chem. Clin. Biochem.; 1993; 31:875-896.
Morris; "Rapid Revers Transcription-PCR Detection of Hepatitis C Virus RNA in Serum by Using the TaqMan Fluorogenic Detection System," Journal Clin Micorbio; Dec. 1996; pp. 2933-2936.
Mullis, K.; "Specific Enzymatic Amplification of DNA in Vitro: The Polymerase Chain Reaction."; 1996; Cold Spring Harbor Symposium on Quantitative Biology; pp. 263-273.
Nadeau, J.G. et al.; "Real-Time, Sequence-Specific Detection of Nucleic Acids during Strand Displacement Amplification,"; Analytical Biochemistry; 1999; pp. 177-187.
Newton et al.: "Setting up a PCR Laboratory," PCT Essential Data; 1995; Chapter 2; pp. 6-9.

(56) References Cited

OTHER PUBLICATIONS

Newton et al.; "Contamination Avoidance,"; PCR Essential Data; 1995; Chapter 9; pp. 87-92 and 202-203.
Newton et al.; "Instruments,"; PCR Essential Data;1995; chapter 3; pp. 12-37.
O'Brien et al.; "The Magic Lite System and Acridimium Ester-Based Immunoassays," Immunoassay Automation: A Practical Guide; 1992; Chapter 18; pp. 221-244.
O'Meara, D. et al.; "Cooperative Oligonucleotides Mediating Direct Capture of Hepatitis C Virus in RNA from Serum,"; J Clin Microbiol; Sep. 1998; pp. 2454-2459.
Package Insert, "Gen-Probe® APTIMA Combo 2® Assay," 502446 Rev. A, May 2012, Gen-Probe Incorporated, San Diego, USA, 41 pages.
Painter; "AxSYM Immunoassay System," Immunoassay Automation: An Updated Guide to Systems; 1996; Chapter 3; pp. 13-22.
Pelloux, H. et al.; "A second European collaborative study on polymerase chain reaction for *Toxoplasma gondii*, involving 15 teams,"; FEMS Microbiology Letters; 1998; pp. 231-237.
Pritchard, C.G. et al.; "Amplified detection of viral nucleic acid at subattomole levels using Q beta replicase;"; Ann Biol Clin; 1990; pp. 492-497.
Ratnam, S. et al.; "Workflow and Maintenance Characteristics of Five Automated Laboratory Instruments for the Diagnosis of Sexually Transmitted Infections,"; J Clin Micorbiol; 2014; pp. 1-22.
Reichelderfer, P.S. et al.; "Quality Assurance and Use of PCR in Clinical Trials,"; PCR Methods and Applications; Manual Supplement; 1995; pp. S141-S149.
Robertson, J.M. et al.; "An Introduction to PCR Primer Design and Optimization of Amplification Reactions,"; Chapter 13; Methods in Molecular Biology; 1998; vol. 98; pp. 121-154.
Robinson, C. et al.; "28. Technology Development for the Human Genome Project"; Genome Sequencing Technologies and Resources Abstracts; 1999; 33 pages.
Roche; "COBAS® AmpliPrep Instrument,"; located at http://molecularroche.com/instruments/Pages/COBASAmpliPrepinstrument.aspx; May 9, 2013; 3 pages.
Roche; "COBAS®AmpliPrep/COBAS® TaqMan® HIV-1 Test, v2.0,"; located at.htt:/ /molecular. roche.com/assays/Pages/COBASAmpliPrepCOBASTagManHIV-1 Testv20.aspx; May 24, 2013; 3 pages.
Roche; "PCR Applications Manual,"; 3rd Edition; 2006; 340 pages.
Roche; "Timeline of PCR and Roche,"; located at http://molecular.roche.com/About/PCR/Pages/PCRTimeline.aspx; May 9, 2013; 8 pages.
Roka Bioscience; "Atlas Listeria Detection Assay,"; Catalog # PRT-00255; 2013; 2 pages.
Rotbart, H. et al.; "Diagnosis of Enterovirus Infection by Polymerase Chain Reaction of Multiple Specimen Types,:" Pediatric Infectious Disease Journal; Apr. 1997; pp. 409-411.
Rundell, M.; "Veris molecular diagnostic system sample-to-sample crossover contamination study," Abstract; 25th ECCMID; May 2014; 1 page.
Sanders, S. et al.; "Novel method for detection of small amounts of RNA based on the semi-nested polymerase chain reaction,"; J Clin Pathol Mol Pathol; 1997; vol. 50; pp. 105-107.
Sandin, R.L.; "Molecular Biology of Infectious Diseases,"; Clinical Laboratory Medicine, Second Edition; 2002; pp. 203-210.
Saulnier, P. et al.; "Single-Step polymerase chain reaction for combined gene detection and epidemiological typing in three bacterial models,"; FEMS Microbiol Letters; 1997; pp. 311-316.
Schmidt, B.L.; "PCR in Laboratory Diagnosis of Human *Borrelia burgdorgeri* Infections,"; Clin Microbiol Review; Jan. 1997; p. 185-201.
Shoemaker et al.; "OPUS MAGNUM Automated Immunoassay System,"; Immunoassay Automation: An Updated Guide to Systems; 1996; Chapter 4; pp. 29-49.
Smit, M.L. et al.; "Automated extraction and amplification of DNA from whole blood using a robotic workstation and an integrated thermocylcer,"; Biotech and Applied Biochem; 2000; pp. 121-125.

Smith, M.; "Chiron at UBS Global Life Sciences Conference—Final."; Fair Disclosure Wire; Sep. 27, 2005; 7 pages.
Solomon, M. et al.; "14. The simultaneous detection and differentiation of *Chlamydia trachomatis* and *Neisseria gonorrhoaea* using transcription mediated amplification,": Clinical Chemistry; 1997; vol. 43, No. 11; p. 2215.
Sooknanan, R. et al. "Nucleic acid sequence-based amplification,"; Chapter 12; Molecular Methods for Virus Detection; 1995; pp. 261-285.
Speechly, D.; "Celera Genomics Analyst Meeting—Final,"; Fair Disclosure Wire; Jun. 22, 2006; 35 pages.
Stramer, S.L. et al. "Nucleic acid testing to detect HBV infection in blood donors,"; New England J Med; 2011; pp. 236-247.
Trademarks Journal; "TIGRIS,"; Trademarks Journal; Mar. 17, 2004; vol. 51; No. 2577; p. 1.
Turner, W.C.; "18.4 Systems Engineering,"; Introduction to Industrial and Systems Engineering; Third Edition; 1993; pp. 440-443, 474-475.
US Department Health and Human Services; "Guidance for Industry and Food and Drug Administration Staff. Establishing the Performance Characteristics of in vitro Diagnostic Device for the Detection or Detection and Differentiation of Human Papillomaviruses,"; Sep. 9, 2009; 30 pages.
US Department of Commerce; "II. Summary of Nominee's Contribution / Achievement,"; 2005; pp. 4-8.
US Food and Drug Administration; "Vaccines, Blood & Biologics. Mar. 2, 2007 Approval Letter—Procleix WNV Assay,"; located at http://www.fda.gov/BiologicsBloodVaccines/BloodBloodProducts/ApprovedProducts/LicensedProductsBLAs/Blood-DonorScreeningLinfectiousDisease/ucm090250.htm, Mar. 2, 2007; 3 pages.
Uyttendaele, M. et al. "Identification of *Campylobacter jejuni*, *Campylobacter coli* and *Campylobacter lari* by the nucleic acid amplification system NASBA," Journal Applied Bacteriology; 1994; vol. 77; pp. 694-701.
Van Gemen, B. at al.; "One-tube Quantitative HIV-1 RNA NASBA:"; PCR Primer, A Laboratory Manual; 1995; pp. 667-677.
Van Gemen, B. et al.; "Transcription based nucleic acid amplification methods like NASBA and 3SR applied to viral diagnosis,"; Reviews in Medical Virology; 1995; vol. 5; pp. 205-211.
Van Schie, R.C.A.A. et al.; "Semiautomated Clone Verification by Real-Time PCR Using Molecular Beacons,"; BioTechniques; Dec. 2000; Vo. 29; pp. 1296-1308.
Vaneechoutte, M.; "The possibilities and limitations of nucleic acid amplification technology in diagnostic microbiology;" J. Med Microbiol; 1997; pp. 188-194.
Vernet, G.; "Molecular diagnostics in virology,"; J Clin Virol; 2004; vol. 31; pp. 239-247.
Vet, J.M. et al.; "Multiplex detection of four pathogenic retroviruses using molecular beacons,"; Proc Natl Acad Sci USA; May 1999; pp. 6394-6399.
Walker; G.T. et al.; "Isothermal in vitro amplification of DNA by a restriction enzyme/DNA polymerase system,"; Proc Natl Acad Sci USA; Jan. 1992; vol. 89; pp. 392-396.
Watts, M. et al.; "Event Brief of Q4 2011 Gen-Probe Incorporated Earnings Conference Call—Final,"; Fair Disclosure Wire; Feb. 13, 2012; 13 pages.
Watzka, M. et al.; "An optimized protocol for mRNA quantification using nested competitive RT-PCR,"; Biochem and BioPhys Research; 1997; 813-817.
Widojoatmodjo, M. et al.; "Nucleic acid sequence-based amplification (NASBA) detection of medically important *Candida* species," Journal Microbio Methods; 1999; vol. 38; pp. 81-90.
Yacoo, J. "BD Announces FDA 510(k) Clearance of BD Probtec™ Qx Amplified Assays for the Detection of *Chlamydia trachomatis* and *Neisseria gonorrhoeae*,"; BD Worldwide; Mar. 23, 2009; 2 pages.
Chinese Office Action mailed on Jul. 30, 2014 for CN Patent Application No. 201310390095.8, with English Translation, 12 pages.
Chinese Office Action mailed on Apr. 14, 2015 for CN Patent Application No. 201310390095.8, with English Translation, 7 pages.

\* cited by examiner

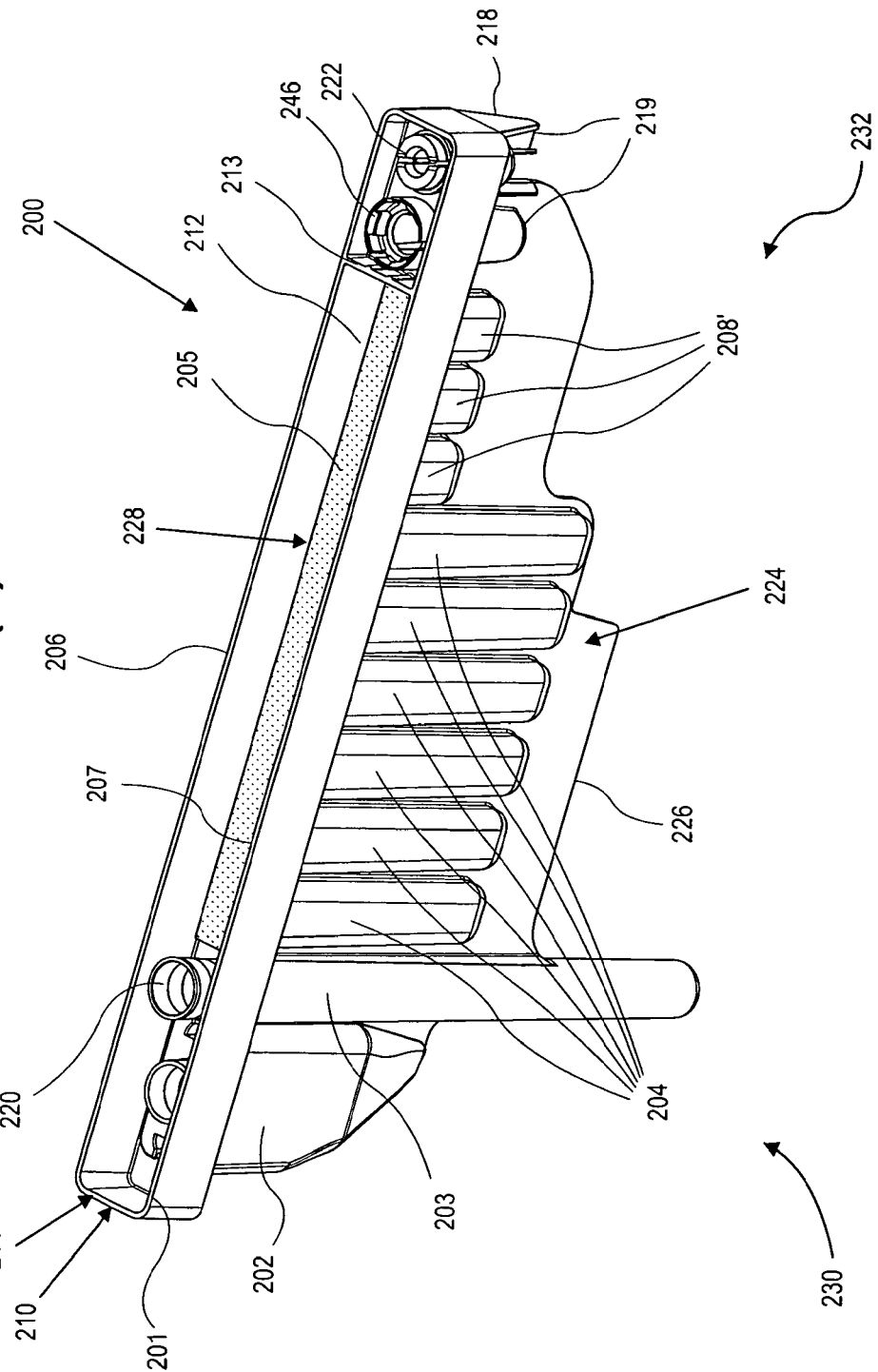

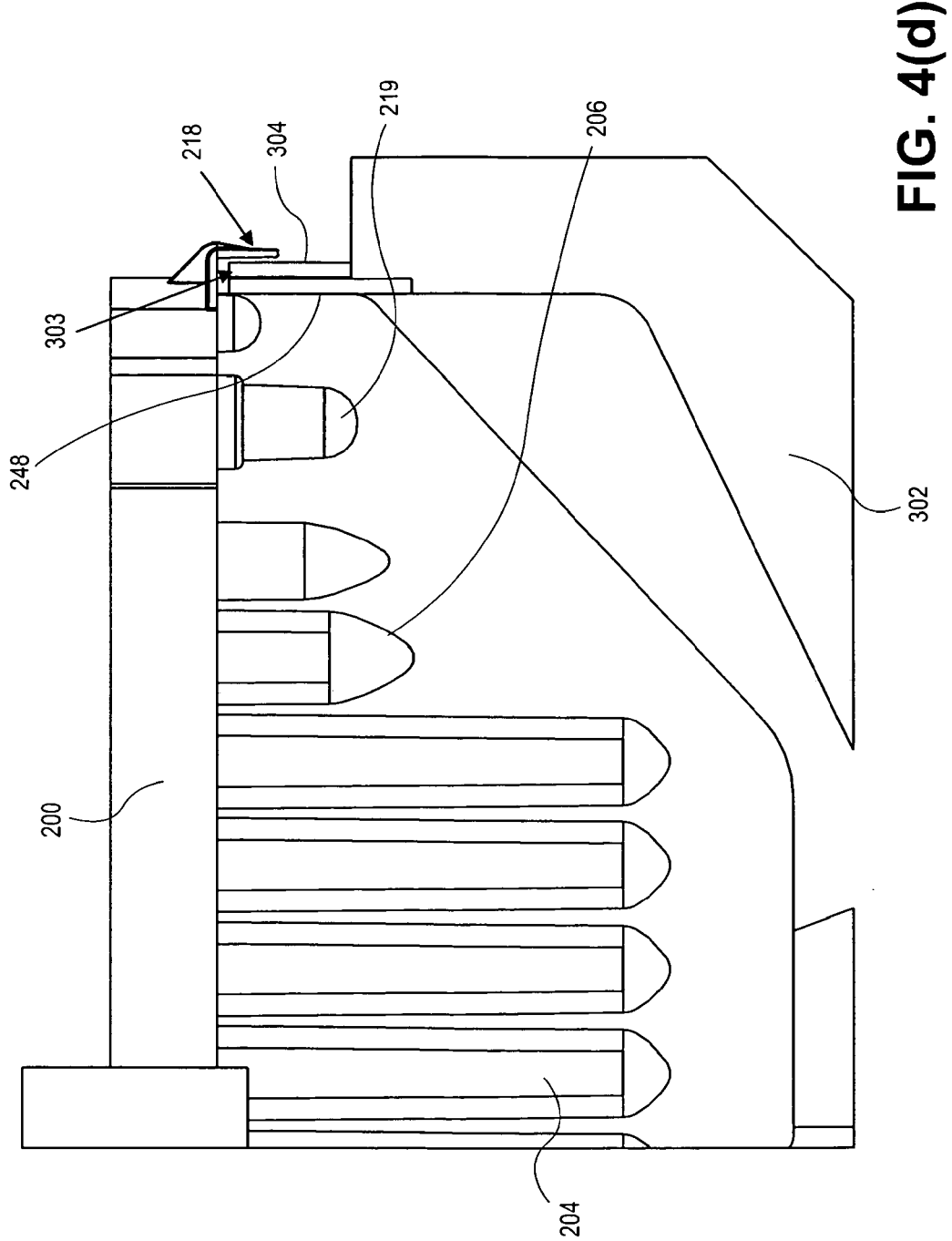

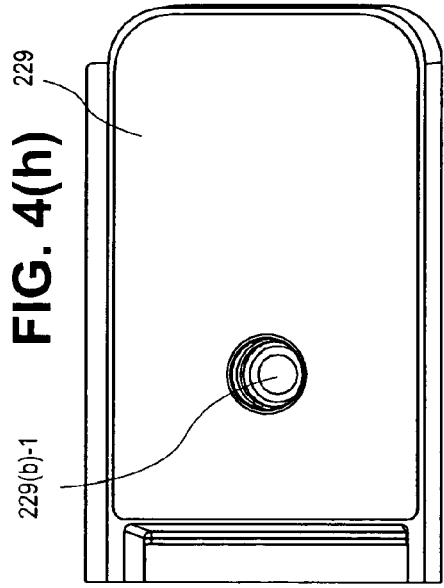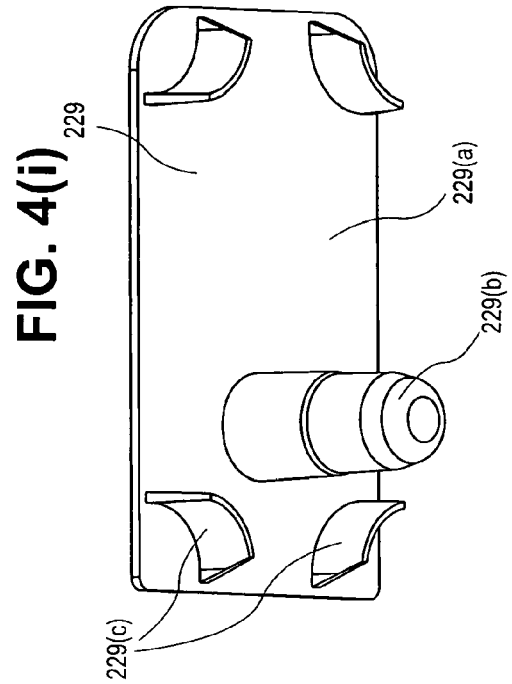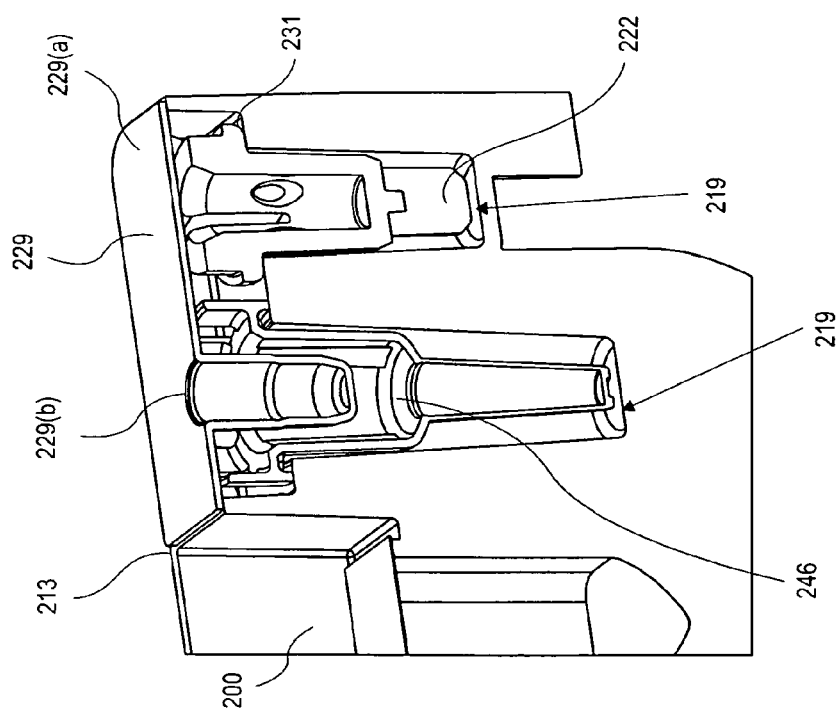

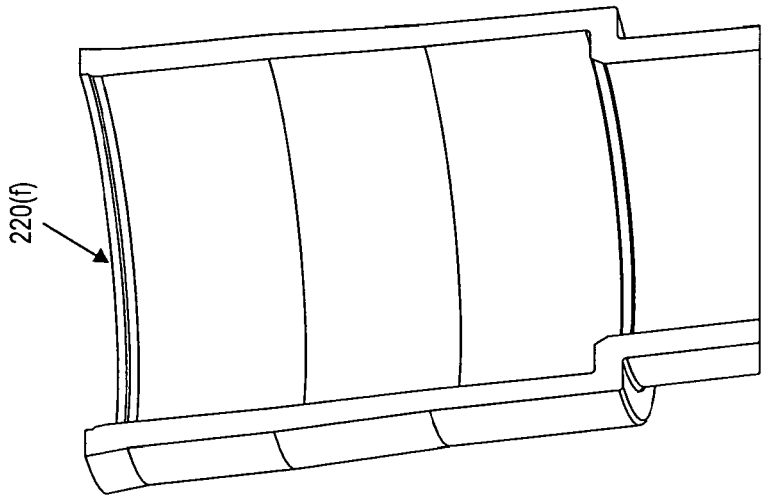
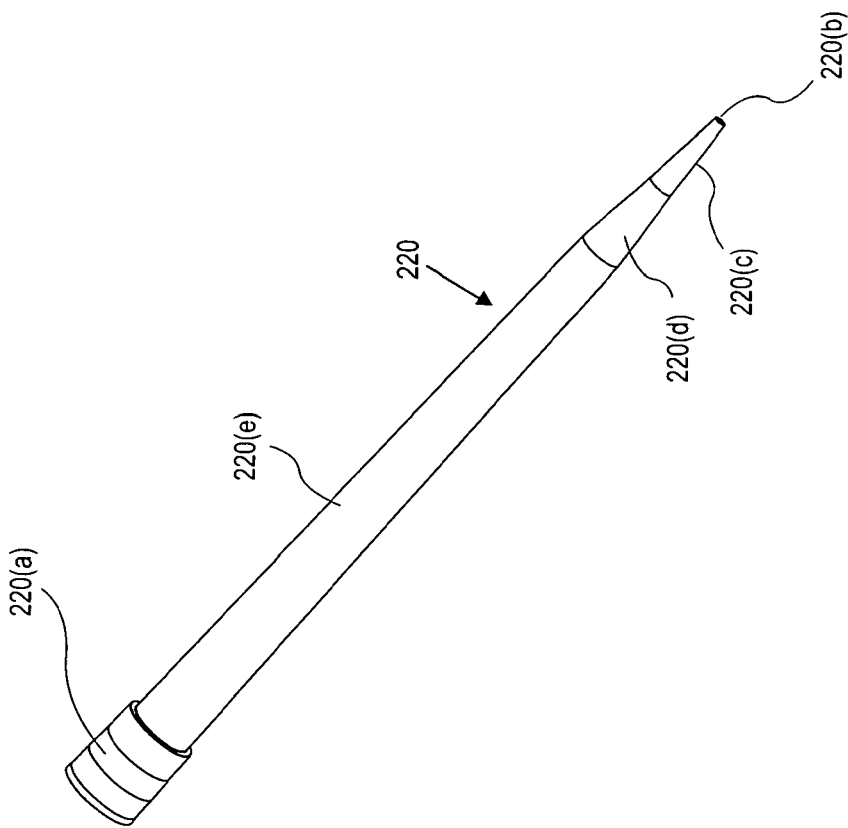
FIG. 6(b)
FIG. 6(a)

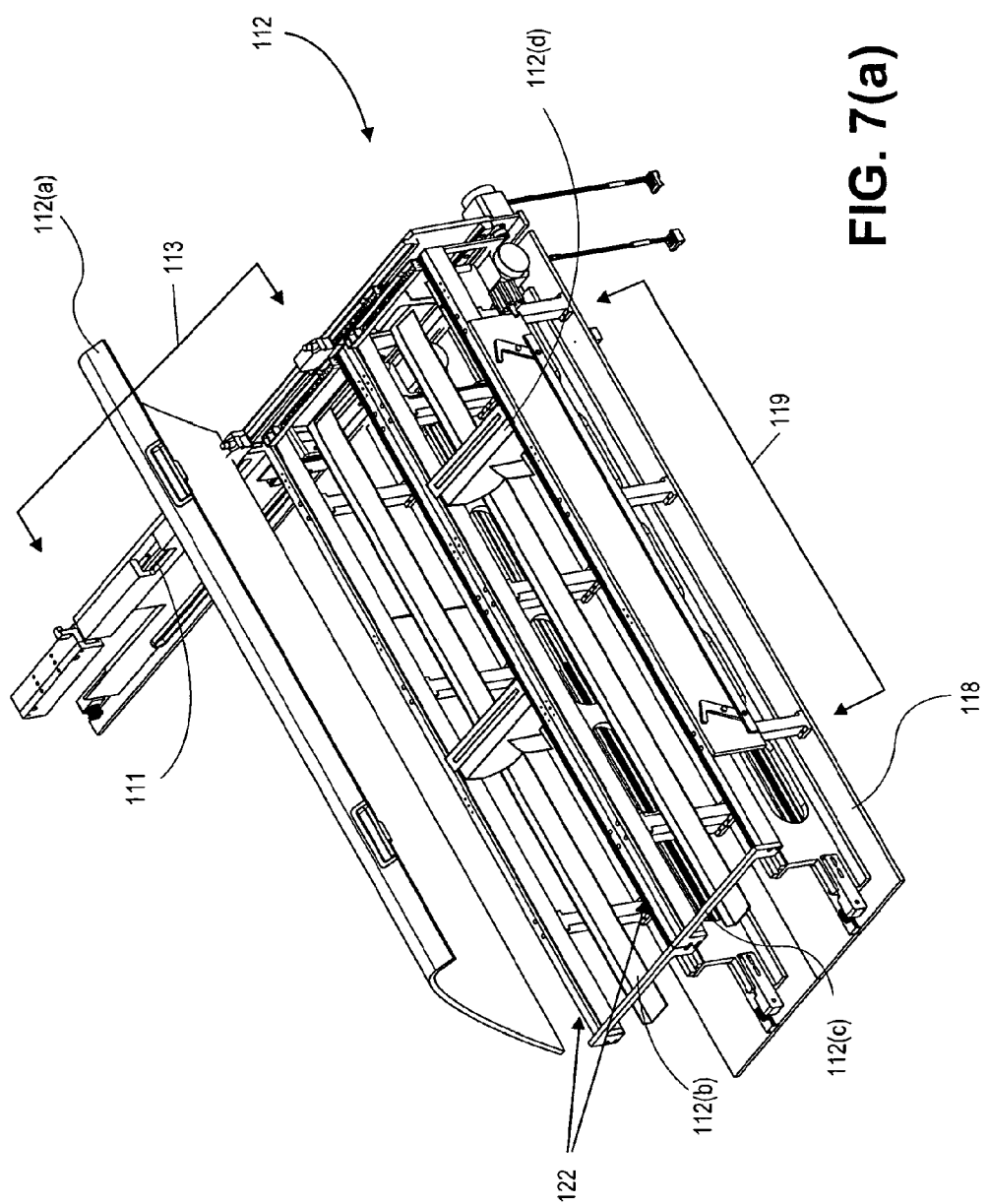

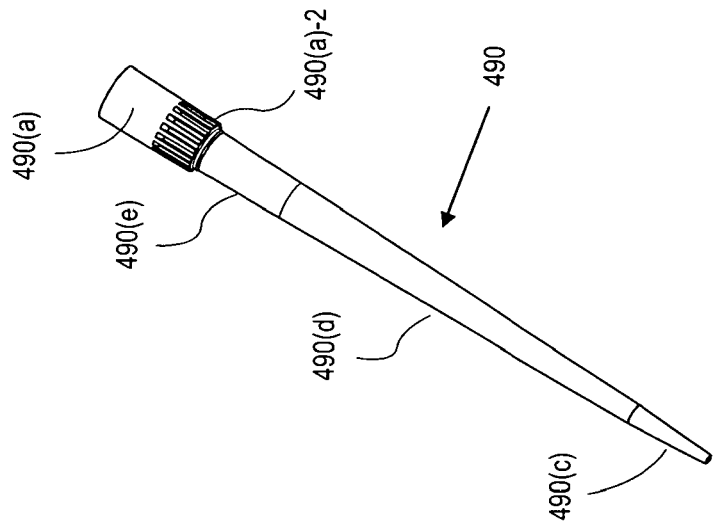
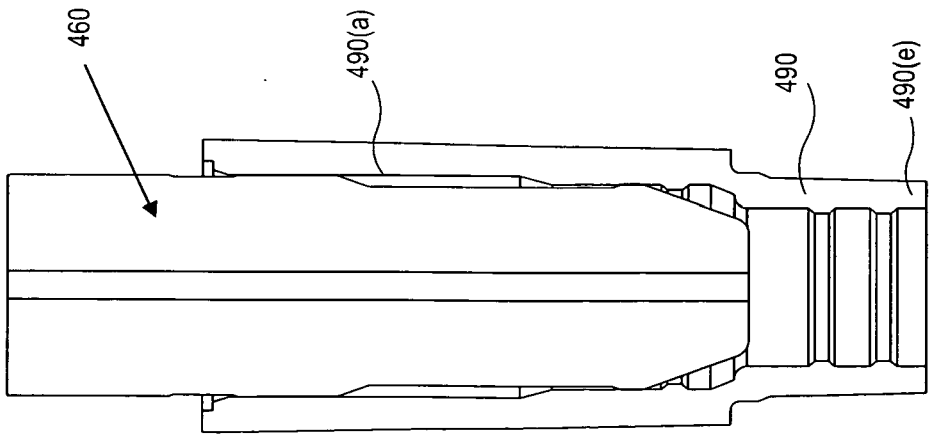
FIG. 12(b)
FIG. 12(a)

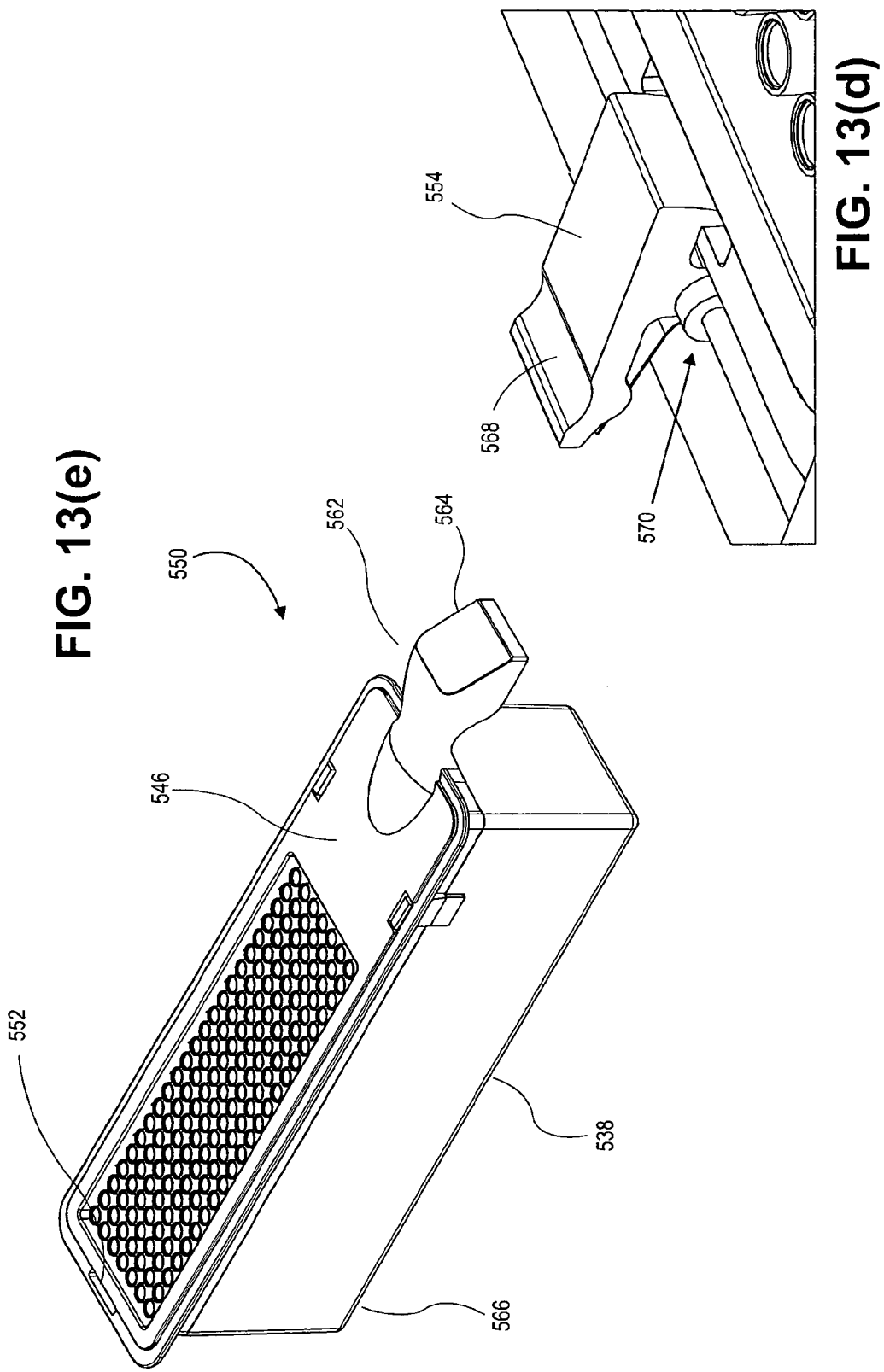

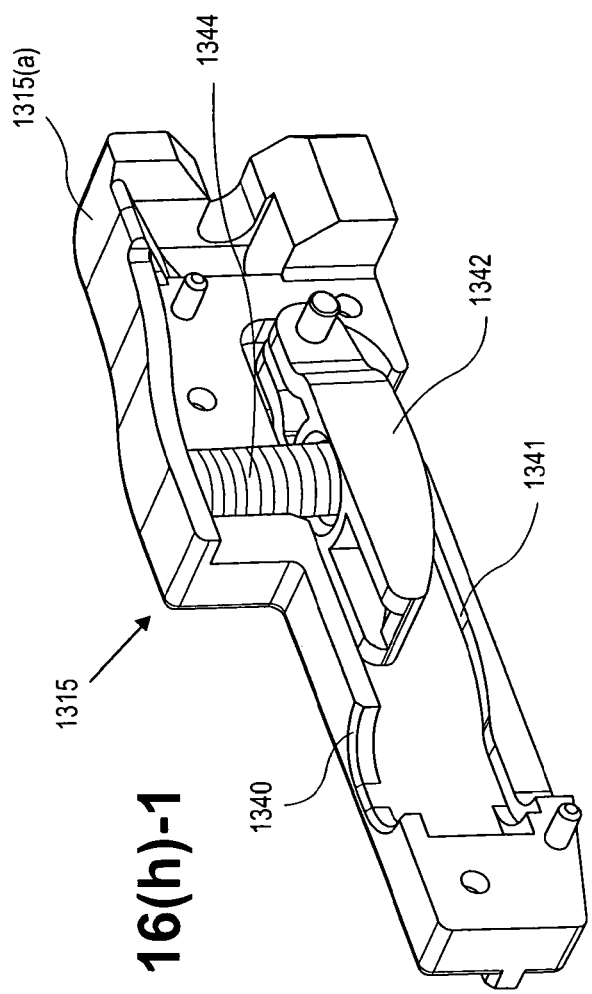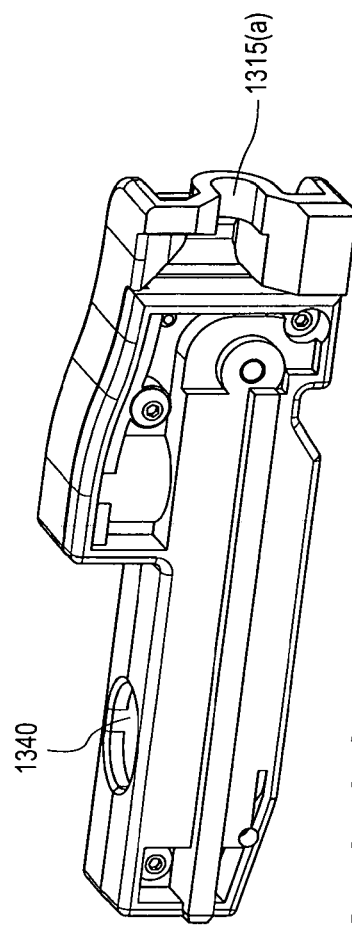
FIG. 16(h)-1
FIG. 16(h)-2

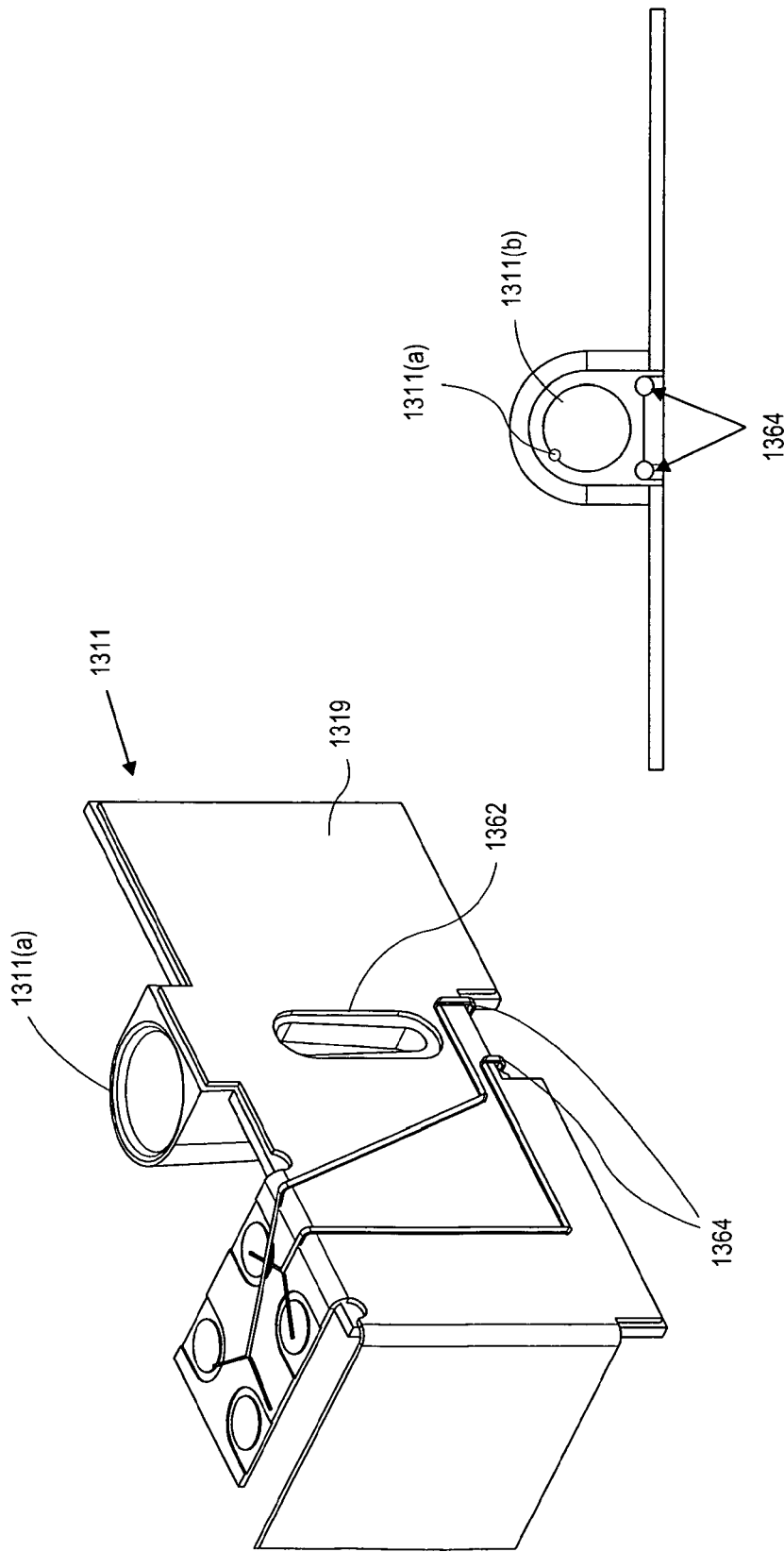

SYSTEM AND METHOD FOR CONTROLLING THERMAL CYCLER MODULES

CROSS-REFERENCE TO RELATED APPLICATIONS

This application is a continuation of PCT Application No. PCT/US2011/045107 filed Jul. 22, 2011 which claims priority to U.S. provisional application 61/367,343, filed on Jul. 23, 2010, the disclosures of which are hereby incorporated by reference in their entirety for all purposes.

BACKGROUND

Many nucleic acid sequences have clinical relevance. For example, nucleic acid sequences associated with infectious organisms provide indications of the presence of an infection by the organism. Nucleic acid sequences not normally expressed in a patient sample may indicate activation of pathways associated with a disease or other conditions. Still other nucleic acid sequences may indicate differences in a patient's likely response to proposed therapies.

Determination of clinically relevant nucleic acids generally depends on controlled amplification of specific nucleic acid sequences and detection of the amplification products. Amplification improves analytical sensitivity by generating sufficient copies of nucleic acids found in the sample for ready determination. Amplification may also improve analytical specificity by selectively generating only those nucleic acids of clinical interest. A problem with amplification-based determinations, particularly when amplification generates large numbers of copies of a target nucleic acid sequence, is the possibility that some of these copies from one sample might contaminate other samples to produce apparently elevated results where none of the target nucleic acid sequence was originally present in the sample.

Other sources of contamination could affect nucleic acid determinations. Carryover between samples can contribute contaminating material. An amplification mixture may receive contaminating materials from environmental sources transferred on surfaces or by laboratory technicians or by aerosols. In some cases, unintended transfers of reagents, such as inappropriate amplification primers, may contaminate mixtures and cause erroneous results. Amplification mixtures may also retain interfering substances originally present in the sample through incomplete purification of target nucleic acids. Thus, there is a need for automation of nucleic acid analysis that avoids transfer and retention of contaminating material from a variety of sources.

Clinical laboratory workflow is a consequence of medical care delivery and varies between institutions. A clinic or large group practice may generate patient specimens throughout the course of a day at a relatively constant rate. In contrast, a clinical reference laboratory may receive all of its specimens in one or two deliveries and a large hospital may generate specimens through a large blood draw in the morning supplemented by an irregular stream of samples throughout the day. Most nucleic acid analysis specimens arrive at a clinical laboratory in a sequence unrelated to the type of requested assay. In some cases, selected specimens may be of high priority with immediate or critical treatment decisions dependent on the outcome. Other specimens may be of more routine priority. Non-specimen samples such as laboratory controls may be interspersed among the clinical specimens according to individual laboratory practice. In some cases, exhaustion of reagents or of particular lots of reagents may dictate the insertion of controls and calibration samples irrespective of other samples in queue.

Thus, there is a need for an analytical system having flexible and adjustable operating capabilities to match the unpredictable demand of clinical laboratories.

Nucleic acid analysis determines multiple analytes from diverse source organisms using a mix of specimen types. These inputs drive diverse processing requirements. For example, RNA and DNA have different chemical properties and stabilities; their preparation may use different processing regimens, different enzymes, and different thermal conditions. Both the base sequence and the length of target analytes affect binding energy, and hence processing. The length and sequence of complementary oligonucleotides used for amplification further affect amplification conditions.

Different source organisms for analytical targets may require different steps to release or isolate the nucleic acid sequences. For example, release of DNA sequences from gram positive bacteria might use elevated temperatures not used for release of DNA sequences from relatively labile white blood cells.

Thus, there is a need for an analytical system able to freely intermix a variety of processing protocols, each composed of a variety of processing steps. Technologies exist that attempt to address some of the issues described above.

Russel/Higuchi in U.S. Pat. No. 5,994,056, *Homogeneous Methods for Nucleic Acid Amplification and Detection*, described improved methods for nucleic acid detection using methods such as the polymerase chain reaction (PCR). Higuchi described methods for simultaneous amplification and detection to enhance the speed and accuracy of prior methods. The methods provide means for monitoring the increase in product DNA during an amplification reaction. According to the description, amplified nucleic acids are detected without opening the reaction vessel once the amplification reaction is initiated and without any additional handling or manipulative steps subsequent to the reaction.

K. Rudi et al. described a *Rapid, Universal Method to Isolate PCR-Ready DNA Using Magnetic Beads in Bio Techniques* 22(3) 506-511, March 1997. Rudi et al. described application of a magnetic bead-based kit for rapid DNA isolation (Dynabeads® DNA DIRECT™; Dynal A.S.) to diverse organisms and tissues to produce a general approach for the purification of PCR-ready DNA. DNA suitable for PCR was prepared in less than 30 minutes.

Systems that automate nucleic acid analysis have a long history. Integrated platforms demonstrated the entire range of automated analytical and preparative steps, including isolation of nucleic acid, amplification of the isolated material, and detection of the amplification products.

For example, Bienhaus et al. in U.S. Pat. No. 5,746,978, Device for Treating Nucleic Acids from a Sample, described a single device to link treatment steps that separate nucleic acids from other sample components with steps for amplification of the nucleic acids. The device included reaction chambers for individual treatment steps with the outlet of one chamber attached to inlet of another. A conventional pipetting instrument transferred both the nucleic acid-containing sample liquid and all possibly necessary reagents from sample and reagent storage containers into the device. Bienhaus et al. described magnetic separation, amplification by PCR or NASBA, and using a hybridization probe complementary to the PCR amplificate in a detection reaction measured using an ES analyzer (manufactured by Boehringer Mannheim).

P. Belgrader, et al. described *Automated DNA Purification and Amplification from Blood-Stained Cards Using a Robotic Workstation* in *BioTechniques* 19(3) 427-432 1995. Belgrader et al. introduced a prototype which could perform coupled DNA purification and amplification that required no user participation once the process was initiated. The method was implemented into a high throughput automated system using a Biomek® 1000 robotic workstation (Beckman Instruments) using phenol and isopropanol to purify DNA on blood-stained cards. The Biomek® 1000 performed DNA purification and amplification using an HCU (Biomek® on-board heater-cooler unit) as a thermal cycler. Belgrader et al. described that the next objective was to integrate a detection step for a completely automated DNA typing system.

Patrick Merel et al. described *Completely Automated Extraction of DNA from Whole Blood* in *Clinical Chemistry* 42, No. 8, p 1285-6 1996. Merel et al. disclosed using the Biomek® 2000 (Beckman Instruments) and DNA DIRECT™ (Dynal France S.A.) in combination to fully automate the DNA extraction procedure using magnetic particle separation. Merel et al. used several different PCR protocols to evaluate the quantity and quality of the DNA obtained. Merel et al. routinely used the described materials for a 10-min automated DNA extraction procedure, a 10-min automated PCR setup step for 96 tubes, PCR for 80 min, and a simple electrophoresis analysis of 15 min.

Ammann et al. U.S. Pat. No. 6,335,166 Automated Process for Isolating and Amplifying a Target Nucleic Acid Sequence described an automated analyzer including multiple stations, or modules, in which discrete aspects of the assay are performed on fluid samples contained in reaction receptacles. The analyzer includes stations for automatically preparing a specimen sample, incubating the sample at prescribed temperatures for prescribed periods, preforming an analyte isolation procedure, and ascertaining the presence of a target analyte. An automated receptacle transporting system moves the reaction receptacles from one station to the next. Ammann also describes a method for performing an automated diagnostic assay includes an automated process for isolating and amplifying a target analyte. The process is performed by automatically moving each of a plurality of reaction receptacles containing a solid support material and a fluid sample between stations for incubating the contents of the reaction receptacle and for separating the target analyte bound to the solid support from the fluid sample. An amplification reagent is added to the separated analyte after the analyte separation step and before a final incubation step.

Even though such automated systems have been available, further improvements are desirable. In particular, multiple sources of contamination continues to risk erroneous results. Further, complexities of multi-step processes needed for complete nucleic acid analysis can produce processing bottlenecks and degrade repeatability, limiting answer reporting turnaround and processing flexibility. Limited answer reporting turnaround may increase the time to institute proper clinical treatment. Lack of processing flexibility limits support for variations in assay protocols for a broad and expandable test menu. Lack of processing flexibility may also force laboratories to sequence or batch samples and reagents in a manner at odds with clinical need.

Embodiments of the invention address these and other problems, individually and collectively.

SUMMARY

Embodiments of the invention are directed to systems, methods, and devices associated with the processing of samples, which may contain DNA or RNA. Embodiments of the invention include a fully-automated, random access system for determining specific nucleic acid sequences.

One embodiment of the invention is directed to a system for processing a sample. The system comprises a preparation location suitable for processing the sample in an assay cartridge including a first compartment and a second compartment. The system also includes a first pipettor configured to transfer liquids from the first compartment to the second compartment of the assay cartridge. The system further comprises a materials storage location that is distinct from the preparation location. It also comprises a second pipettor disposed to travel between the materials storage location and the preparation location. The system also comprises a controller configured to direct the first pipettor to transfer a first reagent from the first compartment to the second compartment of the assay cartridge, and to direct the second pipettor to transfer a second reagent from the materials storage location to the second compartment.

Another embodiment of the invention is directed to a method comprising providing an assay cartridge comprising a first compartment and a second compartment with a cartridge guide, transferring a first reagent from a first compartment to a second compartment in an assay cartridge using a first pipettor at a preparation location, and transferring a second reagent from a reagent pack in a reagent storage unit to the second compartment using a second pipettor.

Another embodiment of the invention is directed to a sensor system comprising a mandrel and a sensing circuit. The sensing circuit is configured to determine a characteristic of the mandrel or of an extension element on the mandrel. The sensing circuit comprises one or more sensor channels, coupled to a processor configured to determine the characteristic of the extension element based on the error signal.

Another embodiment of the invention is directed to a system for processing a sample. The system comprises a first pipettor, a second pipettor, and a controller operatively coupled to the first pipettor and to the second pipettor. The controller is configured to direct the first pipettor to transfer a fluid from a first compartment in an assay cartridge or from a reagent pack in a reagent storage unit to a reaction vessel in the assay cartridge, and to direct the second pipettor to remove the reaction vessel from the assay cartridge.

Another embodiment of the invention is directed to a method comprising: providing an assay cartridge comprising a first compartment and a second compartment with a cartridge guide, transferring a first reagent from a first compartment or from a reagent pack in a reagent storage unit to a reaction vessel in an assay cartridge using a first pipettor, and removing the reaction vessel from the assay cartridge using the second pipettor.

Another embodiment of the invention is directed to a sensor system configured to determine at least two properties associated with a mandrel. The sensor system comprises a sensing circuit comprising a processor and a mandrel. The sensing circuit is configured to generate a first signal and a second signal, each of the first signal and the second signal relating to at least one of resistance, capacitance, and inductance of the mandrel. The processor is further configured to compare the first signal to a first stored reference value to determine contact of an extension element with a liquid. The processor is further configured to compare the second signal to a second stored reference value to determine one of the presence of an extension element on the mandrel, the fill level of the extension element, or the proximity of the mandrel to a conductive target.

Another embodiment of the invention is directed to a system, which can be for determining the presence of a nucleic acid in a sample. The system may comprise a cartridge loading unit to accept a plurality of assay cartridges. The cartridge loading unit can include a storage location to support the plurality of assay cartridges, a loading lane coupled to the storage location, and a loading transport coupled to the storage location and to the loading lane and configured to move an assay cartridge from the storage location to the loading lane. The system can also include a plurality of processing lanes to process an assay cartridge, each processing lane configured to operate on an assay cartridge, a shuttle to move the assay cartridge among the loading lane and the plurality of processing lanes. The shuttle can be positionable in alignment with the loading lane and in alignment with each of the plurality of processing lanes. A controller can be operatively coupled to the loading transport, to the shuttle, and to the plurality of processing lanes.

Another embodiment of the invention is directed to a method comprising loading a plurality of assay cartridges into a storage location in a cartridge loading unit, wherein each assay cartridge includes a reaction well and a reagent well containing a reagent. The method also includes moving an assay cartridge of the plurality of assay cartridges to a loading lane using a loading transport, moving the assay cartridge to a shuttle, and moving the assay cartridge to one of a plurality of processing lanes. Each processing lane can be configured to process the assay cartridge using a different process.

Another embodiment of the invention is directed to a system comprising a first processing lane, a second processing lane, a third processing lane, and a transfer shuttle operatively coupled to the first, second, and third processing lanes. The system further comprises a controller operatively coupled to each of the first, second and third processing lanes and the transfer shuttle. The controller can be configured to execute a first protocol and a second protocol. The controller in executing the first protocol directs the transfer shuttle to move a first assay cartridge from the first processing lane to the second processing lane. The controller in executing the second protocol directs the transfer shuttle to move a second assay cartridge from the first processing lane to the third processing lane without moving the assay cartridge to the second processing lane.

Another embodiment of the invention is directed to a method comprising: executing a first protocol by a controller, wherein in the first protocol, the controller directs a transfer shuttle to move a first assay cartridge from the first processing lane to the second processing lane; and executing a second protocol by the controller, wherein in the second protocol, the controller directs the transfer shuttle to move a second assay cartridge from the first processing lane to the third processing lane without moving the assay cartridge to the second processing lane.

Another embodiment of the invention is directed to a system comprising a preparation location for processing samples, a reaction vessel for containing the processed sample, an analysis location for characterizing the processed sample, and a transport device for transferring the reaction vessel between the preparation location and the analysis location. The system may also comprise a plurality of non-identical processing lanes in the preparation location, the processing lanes configured to perform different processing functions, and a plurality of identical analytical units in the analysis location.

Another embodiment of the invention is directed to a method comprising loading a sample into a system, and loading an assay cartridge into a preparation location. The assay cartridge includes a reaction well and a compartment. A reaction vessel is in the compartment. The method also includes extracting the nucleic acid in the reaction well, transferring the extracted nucleic acid from the reaction well to the reaction vessel, moving the reaction vessel to a thermal cycler module, and detecting the nucleic acid in the thermal cycler module.

Another embodiment of the invention is directed to a system for determining the presence of a nucleic acid in a sample, the system comprising a first processing lane configured to perform operations on a sample in an assay cartridge, a transfer shuttle configured to move assay cartridges into and out of the first processing lane, and a controller to direct operation of the system. The controller can be operatively coupled to the first processing lane and to the transfer shuttle, and can be configured to execute a first protocol and a second protocol. The controller, in executing the first protocol, directs the transfer shuttle to move a first assay cartridge into the first processing lane, and after a fixed interval, directs the transfer shuttle to move the first assay cartridge out of the first processing lane, and within the fixed interval directs the first processing lane to execute a first sequence of operations. The controller, in executing the second protocol, directs the transfer shuttle to move a second assay cartridge into the first processing lane, after the fixed interval, directs the transfer shuttle to move the second assay cartridge out of the first processing lane, and directs the first processing lane to execute a second sequence of operations that differs from the first sequence of operations.

Another embodiment of the invention is directed to a method comprising executing a first protocol by a controller, to direct a transfer shuttle to move a first assay cartridge into a first processing lane, after a fixed interval, direct the transfer shuttle to move the first assay cartridge out of the first processing lane, and within the fixed interval direct the first processing lane to execute a first sequence of operations. The method also includes executing a second protocol by the controller, to direct the transfer shuttle to move a second assay cartridge into the first processing lane, after the fixed interval, direct the transfer shuttle to move the second assay cartridge out of the first processing lane, and direct the first processing lane to execute a second sequence of operations that differs from the first sequence of operations.

Another embodiment of the invention can be directed to a pipettor for transferring liquids on an automated instrument, comprising a linear actuator and a piston enclosed within a barrel. The piston comprises a fluid tight seal with the inner wall of the barrel, the piston and the barrel cooperatively configured to allow movement of the piston within the barrel. The pipettor can comprise a compliant coupling interposed between the linear actuator and the piston, the compliant coupling having a first connecting feature affixing the compliant coupling to the linear actuator, a second connecting feature affixing the compliant coupling to the piston, and a compressible member interposed between the first connecting feature and the second connecting feature.

Another embodiment of the invention is directed to an assay cartridge comprising a reaction well including a first sidewall, a second sidewall, a first endwall, a second endwall, and a well floor arranged to receive a reaction mixture. The first sidewall, the second sidewall, the first endwall and the second endwall form an open end. The first endwall includes a first segment and a second segment. The first and second segment are joined by a bend, and at least one of the first segment and second segment is tapered so that the cross section of the reaction well decreases closer to the well floor.

Another embodiment of the invention is directed to a method for mixing the contents of a well. The method comprises directing a pipettor to a first location in an assay cartridge having a well with an endwall comprising a segment, a first sidewall, and a second sidewall, where the segment of the endwall extends towards the center of the well at an angle relative to the vertical axis and has a radius about a mid-plane to create a culvert, the mid-plane being defined by the first sidewall and the second sidewall. The method also includes dispensing a liquid from the pipettor onto the culvert of the well, wherein the radius of the culvert collects the dispensed liquid and directs the dispensed liquid towards the midline of the culvert such that turbulence is induced in the flow of the dispensed liquid.

Another embodiment of the invention is directed to a cartridge loading unit for loading assay cartridges onto an automated system. It includes a presentation lane including a carriage to receive an assay cartridge, the presentation lane configured to transport the assay cartridge into the automated system for processing. It also includes a first loading lane including a cavity to receive a DNA assay cartridge and transfer the DNA assay cartridge to the carriage of the presentation lane. The DNA assay cartridge includes a reaction well and a reagent compartment, the reagent compartment containing a reagent used for DNA extraction from a sample.

Another embodiment of the invention can be directed to an automated analyzer comprising a pipettor, a reagent pack comprising a well containing a reagent, and a reagent storage unit. The reagent storage unit is configured to hold the reagent pack, and includes a cavity containing the reagent pack, a latch arranged about the cavity, the latch configured to secure and align the reagent pack within the cavity, the latch including a releasing feature, a cover disposed over the cavity and latch, the cover including a first aperture and a second aperture, wherein the first aperture aligns over the well of the reagent pack thereby providing the pipettor access to the reagent contained in the well. The second aperture aligns over the releasing feature thereby providing the pipettor access to actuate the releasing feature to unsecure the reagent pack from the latch.

Another embodiment of the invention is directed to a method comprising aligning a consumable pack in a storage unit. The consumable pack comprises consumables that are manipulated using a pipettor. The method also includes securing the consumable pack within the storage unit by engaging a latch having a releasing feature with a mating feature of the consumable pack, and releasing the consumable pack by aligning the pipettor with the releasing feature, moving the pipettor towards the releasing feature, and contacting the releasing feature with the pipettor. This causes the latch to disengage from the mating of the consumable pack.

Another embodiment of the invention is directed to a reagent cartridge comprising a containment section that comprises a horizontally planar containment floor and a containment wall that extends vertically from the periphery of the containment floor, the floor including an access opening of a reagent receptacle. It also includes a gripping handle that is attached to an isolation portion, the isolation portion attached to the containment section and thereby providing a separation between gripping handle and the reagent receptacle, and a memory unit.

Another embodiment of the invention is directed to a system comprising: a movable cartridge carriage configured to engage an assay cartridge. The assay cartridge comprises a well containing a magnetically responsive particle, the well including a wall at an angle relative to the vertical axis. The system also includes a movable magnet trolley, the movable magnet trolley comprising a separation magnet mounted at an angle complementary to the assay cartridge wall angle, and a reversible coupling device configured to reversibly join the movable cartridge carriage and the movable magnet trolley. The separation magnet is aligned in proximity to the assay cartridge wall when the movable cartridge carriage is coupled to the movable magnet trolley.

Another embodiment of the invention is directed to an assay cartridge including a reaction well, a pipette tip, and a reagent well in a linear arrangement, wherein the pipette tip lies between the reaction well and the reagent well; and a processing lane comprising a lane heater, wherein the lane heater comprises a plurality of heating zones that are in thermal communication with the assay cartridge. The first heating zone is juxtaposed with the reaction well and a second heating zone is juxtaposed with the reagent well.

Another embodiment of the invention is directed to a system for processing an assay cartridge. The system comprises a first assay cartridge comprising reagents for processing a first analyte, a second assay cartridge comprising reagents for processing a second analyte, a first processing lane comprising a heating assembly configured to transfer heat to an assay cartridge raise the temperature of an assay cartridge, and a second processing lane comprising a heating assembly configured to transfer heat to an assay cartridge to maintain the temperature of an assay cartridge. The temperature of the first assay cartridge may be raised to a first temperature in the first processing lane and the first temperature maintained in the second processing lane and the second assay cartridge may be raised to a second temperature in the first processing lane and the second temperature maintained in the second processing lane. The first and second temperatures are different.

Another embodiment of the invention can be directed to an assay cartridge comprising an elongated body comprising a distal end and a proximal end, and a plurality of compartments arranged linearly between the distal end and the proximal end. At least one of the compartments is a reaction well. The reaction well comprises first and second sidewalls, and first and second endwalls, and a well floor joining at least the first and second endwalls. The first endwall comprises a plurality of bends.

Another embodiment of the invention is directed to a cartridge loading unit for loading assay cartridges onto an automated system. The cartridge loading unit comprises a rail for supporting an assay cartridge. The assay cartridge comprises a keying feature. The cartridge loading unit also comprises an identification bar, and a baseplate coupled to the rail and identification bar. The identification bar is positioned on the baseplate to mate with the keying structure, thereby permitting the assay cartridge to rest on the rail.

Another embodiment of the invention is directed to a method comprising: placing an assay cartridge in the cartridge loading unit, and mating a keying feature of the assay cartridge with the identification bar. The mating of the keying feature of the assay cartridge with the configuration bar allows the assay cartridge to rest on a rail in the cartridge loading unit in alignment with a pusher. The method also includes propelling the aligned cartridge towards a presentation lane using the pusher.

Another embodiment of the invention is directed to a method comprising: aligning a probe with an aperture in a storage unit that holds consumable packs, inserting the probe through the aperture, and pushing a latch as the probe is inserted through the aperture. This causes the latch to disengage from a latch pocket of a consumable pack held within the storage unit.

Another embodiment of the invention is directed to a system comprising: a slidable cartridge carriage configured to engage an assay cartridge, the cartridge carriage engaging a carriage track; a slidable magnet trolley, the slidable magnet trolley engaging the carriage track and comprising a separation magnet; and a reversible coupling device configured to reversibly couple slidable cartridge carriage and the slidable magnet trolley.

Another embodiment of the invention is directed to a system comprising: an assay cartridge comprising a plurality of compartments; and a lane heater, wherein the lane heater is cooperatively configured with the assay cartridge. The lane heater is in thermal contact with a plurality of the compartments of the assay cartridge when the assay cartridge is engaged with the lane heater.

Another embodiment of the invention is directed to a system comprising a linear track, a pipetting arm coupled to the linear track, and a slide lock manipulator coupled to the linear track and configured to extend away from the linear track and retract towards the linear track.

Another embodiment of the invention is directed to a method comprising: acquiring a reaction vessel with a pipetting arm, opening an analytical unit with a slide lock manipulator, aligning the pipetting arm with the analytical unit; and releasing the reaction vessel from the pipetting arm.

Another embodiment of the invention is directed to a thermal cycler module for performing real time PCR within a PCR reaction vessel. It may comprise a thermal block comprising a receptacle for receiving a PCR reaction vessel, and a slidable lid. The lid overlaps with the thermal block and has an open position and a closed position. It is capable of moving between the open and closed positions. It can also include an excitation optics assembly, the excitation optics assembly configured to pass excitation light to the PCR reaction vessel when the PCR reaction vessel is located in the receptacle, and an emission optics assembly, the emission optics assembly is configured to receive light from the PCR reaction vessel when the PCR reaction vessel is located in the receptacle in the thermal block.

Another embodiment of the invention is directed to a plurality of thermal cycler modules. Each thermal cycler module includes a thermal block having a top surface and a defined receptacle. The receptacle can be tapered to conform to a reaction vessel. Each thermal cycler module also comprises a heater thermally coupled to the thermal block, a temperature sensor thermally coupled to the thermal block, and a temperature controller electrically coupled to the heater and to the temperature sensor and configured to cycle the thermal block between at least two temperatures independently of the other thermal cycler modules. Each thermal cycler module also includes an excitation optics assembly. The excitation optics assembly is configured to pass excitation light to the reaction vessel when the reaction vessel is located in the receptacle in the thermal block. Each thermal cycler module may also include an emission optics assembly, wherein the emission optics assembly is configured to receive light from the reaction vessel when the reaction vessel is located in the receptacle in the thermal block.

Another embodiment of the invention is directed to a method for conducting a PCR reaction process using a thermal cycler module, the thermal cycler module comprising a thermal block, and the thermal block comprising a receptacle configured to receive a PCR reaction vessel, and a slidable lid. The method comprises: inserting the PCR reaction vessel in the receptacle; and sliding the slidable lid from the open position to the closed position.

Another embodiment of the invention is directed to a vessel for real time PCR comprising: a radially symmetrical reaction base, and a plug comprising a handling feature, the handling feature configured to receive a pipette mandrel, wherein the reaction base comprises an upper cylindrical portion that receives the plug and a lower portion, and wherein the lower portion opens into the upper cylindrical portion and comprises a frustum of a conical shape.

Another embodiment of the invention is directed to a system comprising: a plurality of thermal cycler modules, each thermal cycler module including a thermal block having a top surface and a receptacle, the receptacle tapered to conform to a reaction vessel; a heater thermally coupled to the thermal block; a temperature sensor thermally coupled to the thermal block; and, a temperature controller electrically coupled to the heater and to the temperature sensor and configured to cycle the thermal block between at least two temperatures independently of other thermal blocks in other thermal cycler units; an excitation optics assembly, the excitation optics assembly configured to pass excitation light to the reaction vessel when the reaction vessel is located in the receptacle in the thermal block; and an emission optics assembly, the emission optics assembly configured to receive light from the reaction vessel when the reaction vessel is located in the receptacle in the thermal block.

Another embodiment of the invention can be directed to a process for determining a nucleic acid in a sample using a system including a processing area and a thermal cycler, the process comprising the steps of: providing in the processing area a vessel plug with a gripping feature and a vessel base configured to lockably engage with the vessel plug; pipetting an amplification reagent to the vessel base with a pipette tip held on a mandrel; pipetting the nucleic acid to the vessel base; lifting the vessel plug using the mandrel to grip the gripping feature; engaging the vessel plug to the vessel base; and moving the engaged vessel plug and vessel base to the thermal cycler.

Another embodiment of the invention is directed to vessel for real time PCR comprising: a radially symmetrical reaction base, and a plug comprising a handling feature, the handling feature configured to receive a pipette mandrel.

Another embodiment of the invention is directed to a method for operating a thermal cycler module, the method comprising: obtaining a predetermined temperature vs. time profile associated with a selected thermal cycler module in an array of thermal cycler modules, the array of thermal cycler modules comprising the selected thermal cycler module and a set of thermal cycler modules; and controlling, by a processor, the thermal cycler modules in the set of thermal cycler modules so that their performance matches the predetermined temperature vs. time profile, each of the thermal cycler modules in the set of thermal cycler modules being controlled using a source of variation between the thermal cycler modules in the array.

Another embodiment of the invention is directed to a method of driving a first thermal cycler in a predetermined thermal profile ($B(t)$), the first thermal cycler including a thermal block, a heater thermally coupled to the thermal block, and a blower to direct air to the thermal block, the method comprising: determining the rate of change of the thermal block temperature with respect to time ($dB/dt$) as a function of heater output ($h_a$), of blower heat transfer ($k$), and of ambient temperature ($Ta$); measuring the thermal block temperature; measuring the ambient temperature at the thermal cycler; and adjusting one of the heater output and the blower heat transfer according to a modeled relationship of:

$$dB/dt = h_a + k(Ta - B(t)).$$

These and other embodiments of the invention are described in further detail below.

BRIEF DESCRIPTION OF THE DRAWINGS

FIG. 4(a)-2 shows a top perspective view of an assay cartridge according to another embodiment of the invention.

FIG. 4(b) shows a side, cross-sectional view of a reaction well.

FIG. 4(c)-1 shows a top plan view of a reaction well according to one embodiment of the invention.

FIG. 4(c)-2 shows a top plan view of a reaction well according to another embodiment of the invention.

FIG. 4(d) shows an end of the assay cartridge with a support tab, which engages a propelling feature of a cartridge carriage.

FIG. 4(g) shows a cross-sectional, perspective view of a cover on a portion of an assay cartridge.

FIG. 4(h) shows a top plan view of a cover on a portion of an assay cartridge.

FIG. 4(i) shows a bottom perspective view of a cover that can cover a portion of an assay cartridge.

FIG. 6(a) shows a perspective view of a millitip according to an embodiment of the invention.

FIG. 6(b) shows cross-sectional view of a mounting aperture of a millitip.

FIG. 7(a) shows a top perspective view of a cartridge loading unit.

FIG. 10(e) shows a front view of a processing lane heater.

FIG. 12(a) shows a microtip on a pipettor mandrel.

FIG. 12(b) shows a perspective view of a microtip.

FIG. 12(c)-1 shows a perspective view of a microtip with venting features.

FIG. 12(c)-2 shows a side view of another microtip embodiment.

FIG. 13(d) shows an exploded view of a microtip rack.

FIG. 13(e) shows a microtip rack.

FIG. 16(h)-1 shows a partial internal perspective view of internal components of a slidable lid.

FIG. 16(h)-2 shows a side, perspective view of internal components of a slidable lid.

FIG. 16(i)-1 shows a side, cross-sectional view of a slidable lid in a thermal cycler module, where the slidable lid is in a closed position.

FIG. 16(i)-2 shows a side, cross-sectional view of a slidable lid in a thermal cycler module, wherein the slidable lid is in an open position.

FIG. 16(o) shows a side perspective view of a thermal block.

FIG. 16(p) shows a top view of a thermal block.

DETAILED DESCRIPTION

PCR or "Polymerase Chain Reaction" refers to a method used to amplify DNA through repeated cycles of enzymatic replication followed by denaturation of the DNA duplex and formation of new DNA duplexes. Denaturation and renaturation of the DNA duplex may be performed by altering the temperature of the DNA amplification reaction mixture. Real time PCR refers to a PCR process in which a signal that is related to the amount of amplified DNA in the reaction is monitored during the amplification process. This signal is often fluorescence. However, other detection methods are possible. In an exemplary embodiment, a PCR subsystem takes a prepared and sealed reaction vessel and performs a complete real-time polymerase chain reaction analysis, thermal cycling the sample multiple times and reporting the intensity of emitted fluorescent light at each cycle.

A "preparation location" can include any suitable location or combination of locations which can prepare a sample for analysis. Preparation locations can include one or more of a sample presentation unit, a sample pipettor, and various processing lanes.

A "cartridge guide" can include any suitable structure for guiding an assay cartridge. In some cases, it can include a generally linear structure to guide the assay cartridge in a linear path.

An "analysis location" can refer to any suitable location or combination of locations where samples are analyzed.

A "processing location" can be a location where samples are processed. A processing location can be within a preparation location. For example, a processing location can have a plurality of processing lanes that can process a sample.

A "reagent storage unit" may refer to a unit that is configured to store reagents.

A "reagent pack" may include any suitable container that can store a reagent. An example of a reagent pack can include a generally rectangular elongated body formed to include multiple reagent receptacles including one or more large reagent receptacles, and one or more relatively smaller reagent receptacles, as well as features to facilitate handling and automation.

A "processor" may comprise any suitable data processing device that can be used to process data. Such processors may include one or more microprocessor working together to process data and provide instructions.

A "controller" may also be a data processing device that can be used to process data or provide control functions. A controller may include one or more microprocessor, or it could be a general purpose computer in some embodiments.

A. Overall System Layout

Figure 1A:
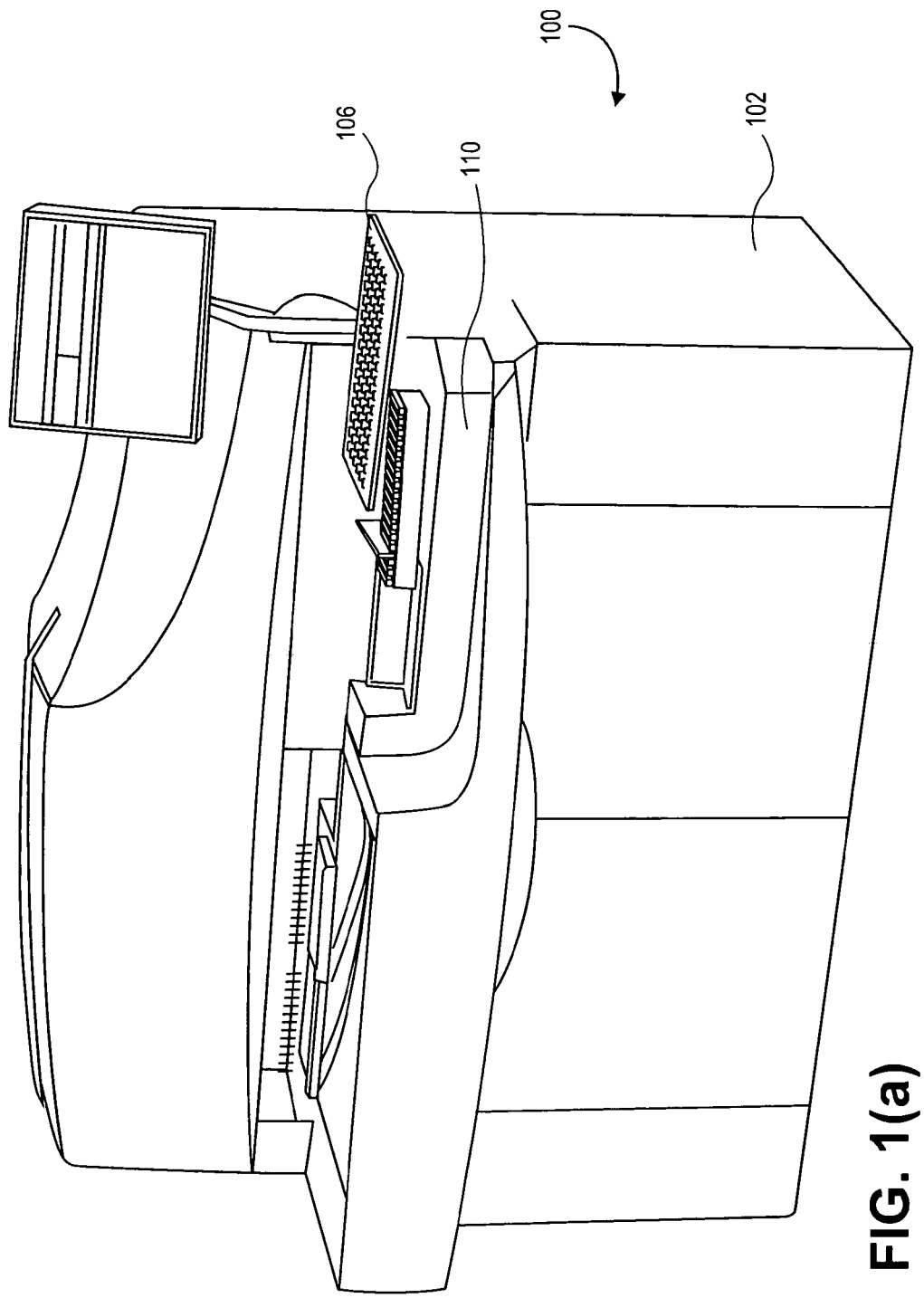
FIG. 1(a) shows a front perspective view of an instrument according to an embodiment of the invention.

An automated instrument for the determination of nucleic acids according to an embodiment of the present invention is shown in FIG. 1(a), designated by reference number 100. As shown in FIG. 1(a), one embodiment of the instrument of the invention includes a generally rectangular housing 102 with sides defining the front, back, left and right sides, top and bottom as illustrated. The automated instrument can be a single, enclosed system, and can include a horizontal working deck that incorporates readily accessible areas 110 for an operator to add samples for analysis and consumables for use in processing the samples. It also includes a data entry device 106 and a display 108. Embodiments of the invention include a fully automated, random access system for determining specific nucleic acid sequences in samples. The system includes consumables incorporating necessary reagents for performance of a variety of assays, reaction sites, and transfer devices. Sufficient storage space for consumables is provided on the system to permit it to run with minimal operator intervention for an extended time.

The system can combine two functions: sample preparation in the form of isolation of nucleic acids from the sample matrix, and detection of specific sequences within these isolated nucleic acids. Towards this end, the system can have at least two distinct functional areas: one including instrumentation to process samples using the consumables and a second including the instrumentation and reagents for nucleic acid amplification and detection. The system also includes holders for samples, containers for wastes, and connections for power and information. These are integrated in a single unit to provide a system that performs major functions of sample handling, nucleic acid isolation, and amplification and detection, plus supporting functions of supply and consumable management, information management, and maintenance. In some embodiments, to support sample throughput while retaining scheduling flexibility, the sample preparation portion of the system processes samples in a sequential fashion as they enter the system while the detection portion of the system performs amplification and detection in parallel.

Combining these functions into a single, highly automated, self contained system provides seamless integration of molecular diagnostics into the workflow of the clinical laboratory. A further purpose is to perform all steps of nucleic acid determination to produce clinically acceptable results without the need for user intervention. The system advantageously allows users to load samples as they become available, and to perform determinations on those samples as dictated by the needs of the patient and their physician, without constraints on sample or analyte order being imposed by the system.

Figures 1, 4A:
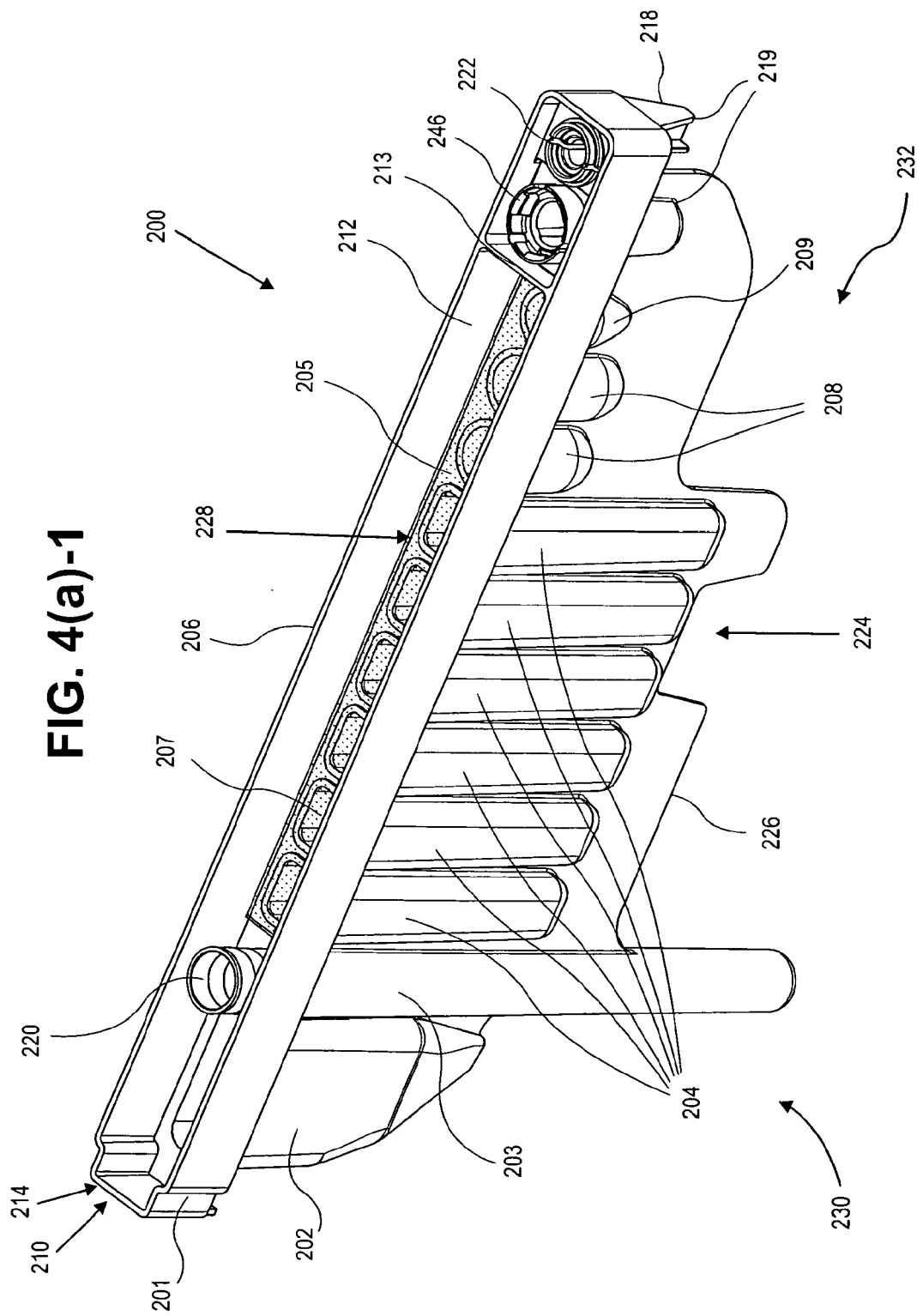
FIG. 4(a)-1 shows a top perspective view of an assay cartridge according to one embodiment of the invention.

FIG. 1(*b*) shows a plan view of the embodiment of FIG. 1(*a*) from above, with some components removed to clarify the basic structural and functional modules. FIG. 1(*b*) also shows three distinct locations including an analysis location 96 where sample analysis can occur, and a preparation location 98 where the sample can be prepared for analysis. FIG. 1(*b*) also shows three distinct locations including an analysis location 96 where sample analysis can occur, a preparation location 98 where the sample can be prepared for analysis, and a material storage location 92 where preparation and analysis materials can be stored. The three illustrated locations can be adjacent to each other.

The system shown in FIG. 1(*b*) can be used to perform a variety of methods, including a method comprising providing an assay cartridge comprising a first compartment and a second compartment with a cartridge guide, transferring a first reagent from a first compartment to a second compartment in an assay cartridge using a first pipettor at a preparation location, and transferring a second reagent from a reagent pack in a reagent storage unit or in a materials storage location to the second compartment using a second pipettor.

The system may include an instrument, which may include a sample presentation unit 110 for loading samples, a sample pipettor 70 for transferring samples, a cartridge loading unit 112 for loading disposable assay cartridges onto the system, a reagent storage unit 10 for storing reagents, a set of processing lanes 116 for processing samples, a transfer shuttle 50 for transferring assay cartridges, an XYZ transport device 40 for transferring materials, a microtip storage unit 20 for storing disposable pipette tips, a collection of thermal cycler modules 30 for amplification, and an optical detector (not shown) for detection of products from the detection reaction. The XYZ transport device 40 may include an XYZ gantry, as well as an XYZ pipettor. The processing lanes may be present in the preparation location 98.

The gantry can perform a number of functions. For example, it can be configured to: position the mandrel to remove the vessel plug from the second compartment; position the mandrel to mate the vessel plug to the vessel base in the first compartment; position the actuator to move the lid from the closed position to the open position; position the mandrel to seat the amplification vessel in the block; and position the actuator to move the lid from the open position to the closed position.

The system can include processing lanes 116 that perform the operational steps needed for nucleic acid extraction and purification from a biological or patient sample. Each processing lane 116 can accommodate an assay cartridge 200. When the system uses a linearly arranged assay cartridge 200 each processing lane may extend linearly relative to the long axis of the assay cartridge. Such processing lanes 116 may reflect the dimensions of the assay cartridge 200, reducing the need to orient the assay cartridge and permitting the system to package multiple processing lanes in a space-efficient parallel manner. In some embodiments, the system includes processing lanes that are physically arranged in an order approximating their order of use in at least some protocols. This advantageously minimizes the distance and time the system needs to transfer assay cartridges between processing lanes. Alternatively, the system may include processing lanes with similar functions grouped together. This advantageously minimizes the time spent performing repetitive functions, such as, for example, washing.

As shown in FIG. 1(*b*) the system may include different types of processing lanes that support functions appropriate to different processing steps. In some embodiments, the system includes replicates of some lane types, allowing processing of multiple assay cartridges 200 in parallel. Examples of processing lane types include a cartridge loading lane 116(*f*), a transfer lane 50, a heated temperature stabilization lane 116(*j*), a wash lane 116(*a*) and 116(*b*), an elution lane 116(*e*), an amplification preparation lane 116(*g*), and a waste lane 116(*c*). In some embodiments, the system includes 13 processing lanes in the following sequence:

| LANE POSITION | LANE TYPE |
|---|---|
| 1 | AMPLIFICATION PREPARATION LANE |
| 2 | CARTRIDGE LOADING LANE |
| 3 | ELUTION LANE |
| 4 | WASTE LANE |
| 5 | HEATED TEMPERATURE STABILIZATION LANE |
| 6 | AMBIENT TEMPERATURE STABILIZATION LANE |
| 7 | AMBIENT TEMPERATURE STABILIZATION LANE |
| 8 | WASH LANE |
| 9 | WASH LANE |
| 10 | WASH LANE |
| 11 | WASH LANE |
| 12 | WASH LANE |
| 13 | WASH LANE |

The first lane position can be near the center of the instrument, with successive lanes numbered toward the right side of the system as viewed from the front. Successive lane positions may be disposed adjacent the preceding lane position. Alternatively, the system may incorporate one or more processing lanes that individually incorporate all of the processing tools needed to perform each processing step.

In some embodiments, the instrument includes an area for connecting to a laboratory automation device 80 for automated delivery of samples from a central location in the laboratory. A conventional instrument framework provides physical and operational support to these modules. The framework provides support components, including electrical power supplies; airflow control components such as fans, blowers, ducts for directing airflow, and air filters; and communications and control components such as displays, one or more control computers, wiring, and other interconnects. The sections below describe each of the basic structural and functional modules in more detail.

Figure 1B:
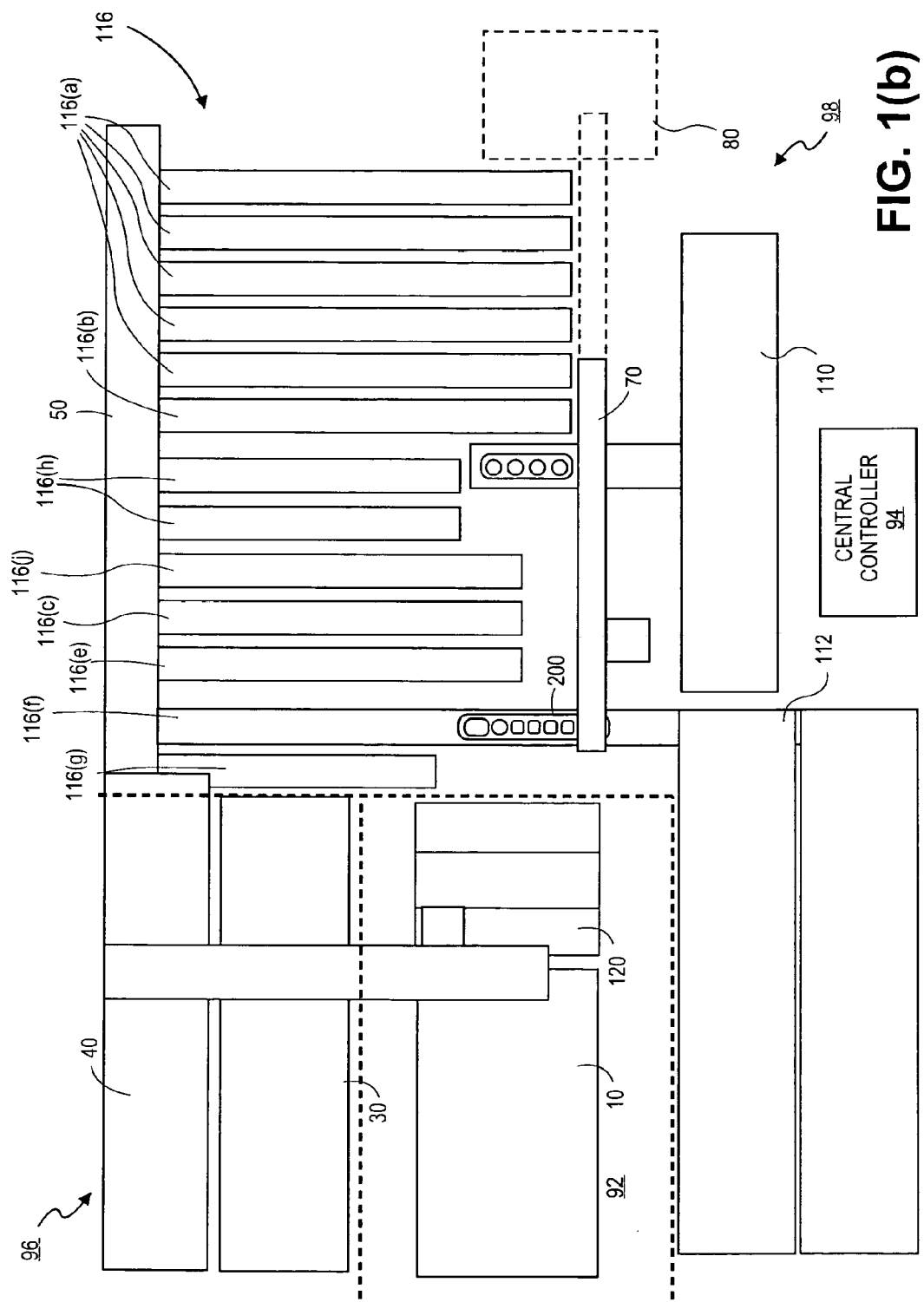
FIG. 1(b) shows a top plan view of the layout of the components of the instrument.
Figure 1C:
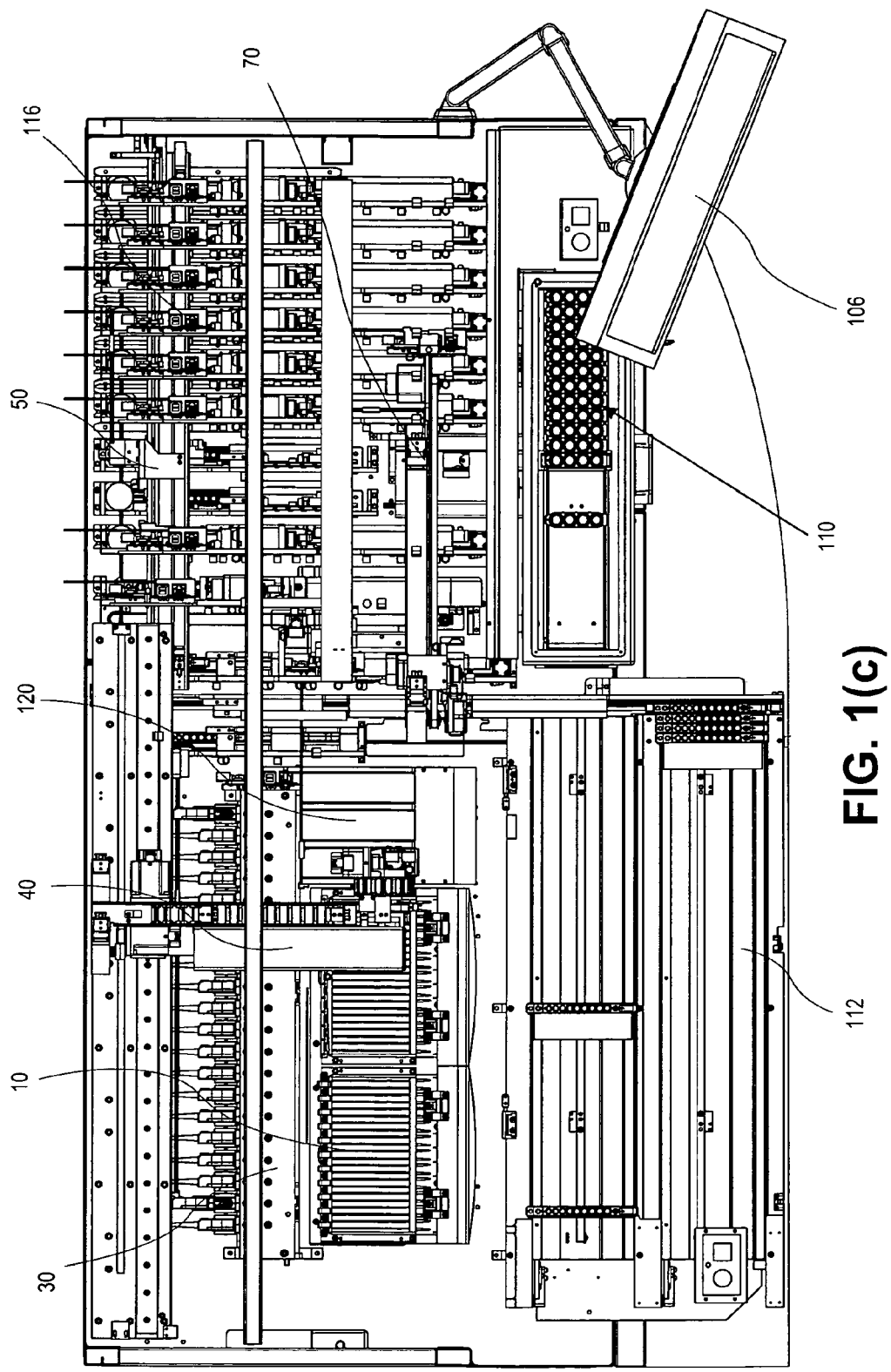
FIG. 1(c) is a top plan view of the instrument.

FIG. 1(c) shows a detailed top view of an embodiment of the instrument, with some components removed for clarity. The components shown in FIGS. 1(a)-1(c) are described in greater detail below.

The system according to an embodiment of the invention can include a preparation location 98 to process a sample. The preparation location 98 can be any suitable location where sample preparation may take place. In some embodiments, the preparation location is found on the right side of the instrument when facing the front.

The preparation location 98 can include a sample presentation unit 110 where samples are loaded onto the system, a set of processing lanes 116 where sample preparation takes place and a sample pipettor 70 for transfer of sample to an assay cartridge for processing. The assay cartridge can be transferred in the system and the preparation location 98 using a cartridge guide (which is described in further detail below). Samples are prepared for amplification in a disposable assay cartridge that includes a first compartment and a second compartment. In some embodiments, the second compartment may be a reaction well, while the first compartment may be a small, medium, or large reagent well. The processing lanes 116 can include features to retain, warm, and guide the assay cartridge, and a first pipettor configured to transfer liquids from at least the first compartment to the second compartment.

The system can also include a reagent storage unit 10 that is configured to store at least one reagent pack. In some cases, the reagent storage unit comprises a plurality of reagent packs for storing reagents for performing a PCR process. In some embodiments of the invention, the reagent storage unit 10 and microtip racks 120 can be in the materials storage location 92. A second pipettor (not shown) can be associated with the XYZ transport device 40 and can be disposed to travel between the reagent storage unit 124 and the materials storage location 92 under the direction of a central controller 94 for the system.

The central controller 94 can direct the operation of any of the components described herein by providing instructions to various sub-controllers within the system. The central controller 94 can include any of the components shown in FIG. 20 (which describes a computer apparatus).

The central controller 94 can be operatively coupled to the first pipettor and to the second pipettor and is configured to direct the first pipettor to transfer a first reagent from the first compartment (e.g., a small, medium, or large reagent well) of the assay cartridge to the second compartment and to direct the second pipettor to transfer a second reagent from the reagent pack to the second compartment (e.g., a reaction well). Suitable examples of first and second reagents (e.g., wash fluids, buffers, etc.) are provided below. The use of a first pipettor and a second pipettor advantageously permits the system to quickly and accurately dispense both large and small volumes to the assay cartridge, by avoiding the risk of inaccuracy due to attempting to transfer small volumes using a large volume pipettor and the risk of inaccuracy due to attempting to deliver large volumes through repeated dispenses using a small volume pipettor. This operational flexibility supports both the processing or relatively large sample volumes and the use of compact reagent packs that store concentrated reagents.

Following the completion of sample preparation, the treated sample, plus additional reagents, is transferred to the detection and amplification portion of the system. The detection and amplification portion of the system may be at an analysis location 96. The analysis location 96 can contain a plurality of analysis or analytical units, such as thermal cyclers, and may be positioned at any suitable location within the system. In some embodiments the analysis location 96 is found on the left side of the system when facing the front. This location maximizes the distance between the preparation portion and the amplification and detection portions of the system. This permits the introduction of barriers to reduce contamination, including but not limited to directed airflow, ultraviolet light, and physical barriers such as partitions or filters, while allowing easy access for servicing. In another embodiment, the detection and amplification portion of the system can be encased within the instrument housing, below the working deck.

In the embodiment shown in FIG. 1(c), amplification and detection are provided by a bank of thermal cycler modules 30. The thermal cycler modules within bank 30 may process samples independently but simultaneously, with each thermal cycler module processing a single sample at a time. Scheduling of processing in the thermal cycler modules in bank 30 may be balanced to equalize the degree of wear between different thermal cyclers. One or more thermal cycler modules may be reserved for use in circumstances where additional modules beyond those necessary for normal operations are needed. Examples of such atypical circumstances include the failure of a thermal cycler module and the processing of an urgent or STAT sample. The number of these thermal cycler modules can vary between different embodiments of the invention, being optimized for the desired throughput of the system.

The need for random access processing and the possibility of contamination between amplification products and samples makes the use of consumables central to system operation. In some embodiments, system consumables include assay cartridges used for storage of selected reagents and isolation and purification of nucleic acids from samples; reaction vessels for amplification and detection; reagent packs for storing selected reagents; millitips for large volume pipetting operations; microtips for small volume pipetting operations; and microtip racks to retain microtips.

Figure 1D:
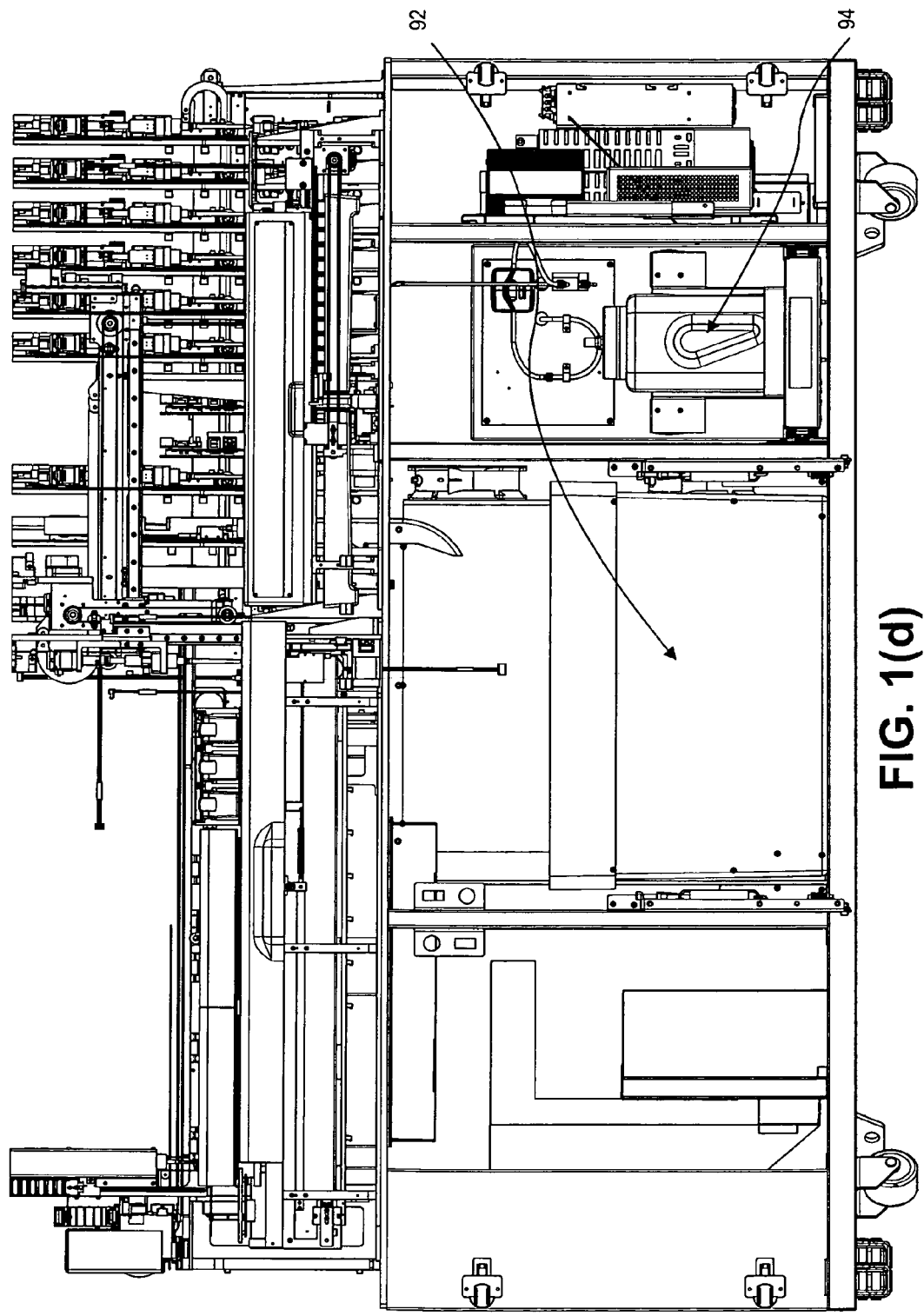
FIG. 1(d) shows a partial front view of the instrument.

As shown in FIG. 1(d), the system provides storage areas for spent consumables. These storage areas may be below the working deck in order to reduce the chances for contamination from stored waste. As described in greater detail below, waste liquids may be stored in a designated liquid waste container 94. Similarly, solid wastes may be temporarily stored on the system in a designated solid waste container 92. Waste containers may be held within enclosed cabinets in the lower portion of the system. These cabinets may be kept at negative pressure in order to prevent aerosols and particulates from the waste containers from reaching the working deck of the system, and may be conveniently accessed in order for the user to empty the waste containers. Waste storage areas may also include mechanisms to inactivate contaminants following inadvertent release, including ultraviolet light sources.

Another embodiment of the invention can be directed to a system comprising a first pipettor and a second pipettor, as well as a controller operatively coupled to the first pipettor and to the second pipettor. The controller is configured to direct the first pipettor to transfer a fluid from a first compartment in an assay cartridge or from a reagent pack in a reagent storage unit to a reaction vessel in the assay cartridge, and to direct the second pipettor to remove the reaction vessel from the assay cartridge. In the system, an assay cartridge comprising a first compartment and a second compartment can be guided with a cartridge guide, and a fluid (such as a processed sample) is transferred from the first compartment (which may be a reaction well) or from a reagent pack in a reagent storage unit to a reaction vessel in an assay cartridge using a first pipettor. The reaction vessel is then removed from the assay cartridge, and then transferred to a thermal cycler module using the second pipettor. The first pipettor can be a millitip pipettor and the second pipettor can be a microtip pipettor. Other suitable details regarding such embodiments of the invention can be found below.

The second pipettor can advantageously have multiple uses including transferring fluids as well as moving reaction vessels within the system. Since separate devices are not needed to perform these and other functions, the system according to embodiments of the invention can be compact and less complex than other types of systems.

Yet another embodiment of the invention is directed to a system, which can be for determining the presence of a nucleic acid in a sample. The system may comprise a cartridge loading unit 112 to accept a plurality of assay cartridges. The cartridge loading unit 112 can include a storage location to support the plurality of assay cartridges, a loading lane coupled to the storage location, and a loading transport coupled to the storage location and to the loading lane and configured to move an assay cartridge from the storage location to the loading lane. The system can also include a plurality of processing lanes (e.g., 116(a), 116(b), 116(c), 116(e), 116(g), etc.) to process an assay cartridge, each processing lane configured to operate on an assay cartridge, and a shuttle 50 to move the assay cartridge among the loading lane and the plurality of processing lanes, the shuttle positionable in alignment with the loading lane 116(f) and in alignment with each of the plurality of processing lanes; and a controller 94 operatively coupled to the loading transport, to the shuttle 50, and to the plurality of processing lanes. As shown in FIG. 1(b), the processing lanes (e.g., 116(a), 116(b), 116(c), 116(e), 116(g), etc.) and the loading lane 116(f) are parallel to each other, and they are all perpendicular to the travel paths of the transfer shuttle 50.

In this embodiment, a method for using the system may comprise loading a plurality of assay cartridges into a storage location in a cartridge loading unit, moving an assay cartridge to a loading lane using a loading transport, moving the assay cartridge to a shuttle, and moving the assay cartridge to one of a plurality of processing lanes, each processing lane configured to process the assay cartridge using a different process.

The particular arrangement of a loading lane and various processing lanes with an assay cartridge transport shuttle provides a number of advantages. In embodiments of the invention, assay cartridges can be provided to a transfer shuttle, which can access various processing lanes as needed for particular protocols. This provides for flexibility in processing, while providing for a compact system.

Yet another embodiment of the invention can be directed to a system comprising a preparation location 98 for processing samples, a reaction vessel for containing the processed sample, an analysis location 96 for characterizing the processed sample, and a transport device for transferring the reaction vessel between the preparation location and the analysis location. An example of a transport device can be the XYZ transport device 40. The system may also comprise a plurality of non-identical processing lanes 116 in the preparation location 98, the processing lanes 116 configured to perform different processing functions, and a plurality of identical analytical units in the analysis location. The analytical units may comprise thermal cycler modules, which are described in further detail below.

This particular system arrangement can provide for flexibility in processing, while providing good throughput.

Yet another embodiment of the invention is directed to a system for determining the presence of a nucleic acid in a sample, the system comprising a first processing lane configured to perform operations on a sample in an assay cartridge, a transfer shuttle 50 configured to move assay cartridges into and out of the first processing lane, and a controller 94 to direct operation of the system. The first processing lane would be any of the described processing lanes 116 shown in FIG. 1(b). The controller 94 can be operatively coupled to the first processing lane and to the transfer shuttle 50, and can be configured to execute a first protocol and a second protocol. The first and second protocols can involve any suitable number or type of processing steps, where the first processing lane is used in both protocols, where the two protocols process different samples in different assay cartridges.

The controller 94, in executing the first protocol, directs the transfer shuttle 50 to move a first assay cartridge into the first processing lane, and after a fixed interval, directs the transfer shuttle to move the first assay cartridge out of the first processing lane, and within the fixed interval directs the first processing lane to execute a first sequence of operations. The fixed interval may comprise any suitable amount of time. The controller 94, in executing the second protocol, directs the transfer shuttle 50 to move a second assay cartridge into the first processing lane, after the fixed interval, directs the transfer shuttle to move the second assay cartridge out of the first processing lane, and directs the first processing lane to execute a second sequence of operations.

The first sequence of operations can be different from the second sequence of operations. The first and second protocols and their sequence of operations may differ in any suitable manner. For example, the first and second protocols may include common processing steps, but may different according to the duration processing or the parameters used for processing. For instance, in some embodiments, two different protocols may have similar processing steps, but the processing steps may differ because they are performed at different temperatures and/or for different periods of time. In another example, two protocols may have similar steps, but they may be performed in different orders. For example, a first protocol may include steps A, B, and C performed in that order. A second protocol may include steps B, A, and C performed in that order. Lastly, in yet another example, different protocols may include different sets of steps. For example, a first protocol may comprise steps A, B, C, and D, while a second protocol may comprise steps B, D, E, F, and G.

B. Sample Presentation Unit

Figure 2A:
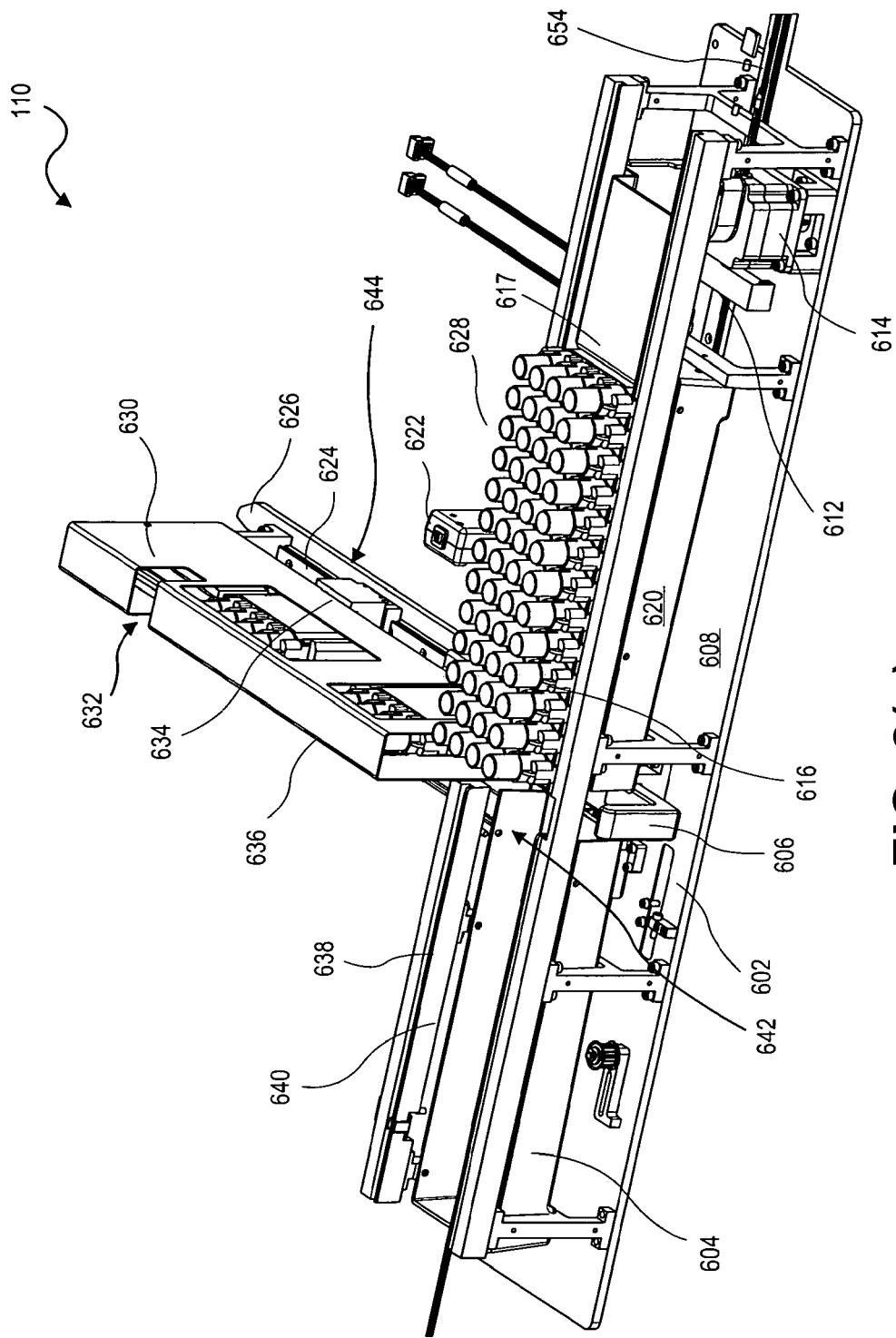
FIG. 2(a) shows a front perspective view of a sample presentation unit according to an embodiment of the invention.

FIG. 2(a) shows a perspective view of an embodiment of the sample presentation unit.

Figure 2B:
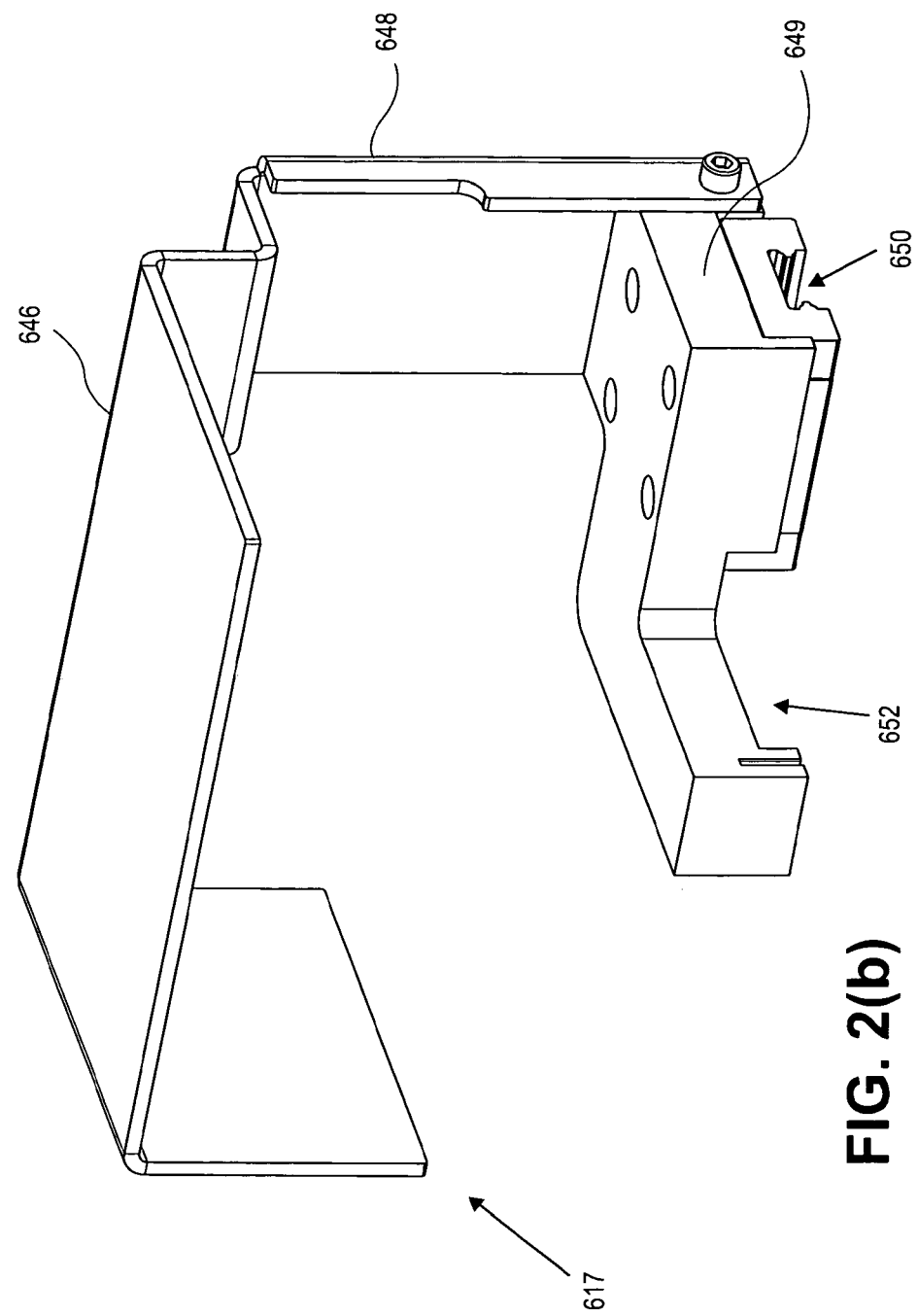
FIG. 2(b) shows a front perspective view of a sample presentation unit pusher cartridge according to an embodiment of the invention.

FIG. 2(b) shows an embodiment of the pusher carriage.

As shown in FIG. 2(a) the sample presentation unit 110 can have multiple functions related to handling of samples to be analyzed on the system. The sample presentation unit 110 may act as a buffer between the user and the instrument, providing a holding area for storage of samples when they are not being actively processed by the instrument. The sample presentation unit 110 may also provide a mechanism for presenting the samples or volumes taken from the samples to processing portions of the instrument. A user may place samples onto the sample presentation unit 110 as they become available in the laboratory; the instrument may subsequently access the loaded samples as its processes require. This buffering mechanism advantageously incorporates the system into the laboratory workflow by integrating the essentially random appearance of samples requiring testing with the system's scheduled timing requirements.

One embodiment of the sample presentation unit 110 processes samples presented in sample holders 616. The sample presentation unit 110 may include, among other components, a sample base 602, an input queue 628, an output queue 640, a presentation carriage 634, and a sample barcode reader 622. The sample presentation unit 110 may include a sample return lane for routing samples from the output queue 640 back to the input queue 628. This arrangement supports secondary testing of specific samples as designated by the system in response to the results of the initial test, also known as reflex testing. Such a secondary test may be a repeat of the initial test (for example, in response to a reported error condition) or a different test. In some embodiments, the sample presentation unit may include a barcode reader for recording sample information prior to placing a sample on the system. Such a barcode reader may be a hand held unit. In an alternative embodiment, the sample presentation unit may have a vertical arrangement, with input and output queues comprised of elevator assemblies that carry samples into the system for analysis and out of the system for removal, respectively.

In some embodiments, the sample presentation unit 110 may accept samples in a variety of containers in the form of sample tubes. Sample tubes may be of several different types that differ by size, by type of sample, or by some other attribute or some combination of attributes. Examples of sample tubes are primary blood collection tubes, swab collection tubes, swab culture tubes, secondary cups and tubes containing samples aliquoted from primary tubes. These samples presented in these sample tubes may include but are not limited to blood, serum, plasma, spinal fluid, saliva, urine, tissue samples, and fecal specimens. Samples may also include purified or partially purified materials generated by processing of specimens prior to presentation to the system. In addition to samples, sample tubes may also contain swabs and other sample collection devices that are utilized in taking surface samples from wounds and other test areas. Such sample tubes may include a barcode or other machine-readable indicia that designates the patient from which the sample originated, sample type, testing to be performed, or other information. This information may be entered into the system via a suitable reader prior to or after loading the sample onto the system, In some embodiments of the invention, the user loads samples onto the system as individual tubes. In other embodiments, the user may load samples onto the system as individual tubes that are held in sample holders 616.

Sample holders 616 may accommodate a plurality of sample tubes. This advantageously reduces user effort by reducing the number of loading and unloading operations required, since each operation may involve multiple samples. The use of sample holders 616 additionally reduces the level of user attention required to operate the system as sample holders 616 may be self-supporting, whereas individual sample tubes typically are not. This is useful to prevent accidental spills, which reduces the chances of contamination and preserves sample integrity. In addition, some samples, such as whole blood tubes treated to separate cells from plasma or serum, may generate erroneous results if tilting or dropping re-mixes the contents.

Sample holders 616 may be any of a variety of forms including disks, rings, sectors, or linear racks. In some embodiments, the sample holders 616 are linear racks with support tabs at either end to maximize packing density. In some embodiments of the invention the sample holders 616 are in the form of linear racks that hold four sample tubes, such as that shown in FIG. 2A. Users can easily manipulate these sample holders 616 with one hand, and specialized centrifuge rotors permit centrifugation of sample tubes while held in such sample holders 616. In an alternative embodiment, sample holders may be loaded into the sample presentation unit while held in a rack that supports multiple sample holders. In yet another embodiment, sample holders may be loaded into the sample presentation unit while held in a device that joins multiple racks together. In another embodiment, the assay cartridge 200 may include a feature that supports a sample tube, thereby also serving as a single position sample tube holder.

The sample base 602 may support and provide connection points for other components of the sample presentation unit 110. In some embodiments, the sample base 602 is an essentially planar surface disposed horizontally beneath the other components of the sample presentation unit 110. The sample base 602 can define the bottom of the sample presentation unit 110. In some embodiments, the sample base 602 is "T-shaped," with a relatively narrow stem 626 joining near the midpoint of and perpendicular to a broader crossbar 608. This stem 626 can support the presentation track 624 and the presentation carriage 634 that rides on the presentation track 624. The stem 626 may project in an inward direction, toward the rear of the system.

The crossbar 608 can support the input queue 628 and the output queue 640. One terminus of the crossbar 608 defines both the entrance point and the entrance direction for sample holders 616 onto the system. The opposite terminus can define the exit point and the exit direction for the sample holders 616.

The input queue 628 can serve as a storage location for one or more sample holders 616 containing samples that have not yet been processed. In some embodiments, the input queue 628 can hold up to 12 (or more) sample holders 616. The input queue 628 can support the sample holders 616 in an ordered arrangement such that the instrument processes the sample holders 616 sequentially, as loaded by the user. This advantageously allows a user to determine the order of processing by simply loading sample holders 616 onto the input queue 628 in the desired order. In some cases, users may load samples of higher priority first. In some embodiments, the input queue 628 may have a temporary holding area and an onload queue that feeds sample holders into the system. This arrangement permits the system to alter the loading sequence of the sample holders by temporarily diverting one or more sample holders from the onload queue into the temporary holding area, reinserting the diverted sample holders into the onload queue at a later time in order to prioritize samples. In an alternative embodiment, the input queue may include a dedicated position for onloading of one or more high priority or STAT samples. In some embodiments, the input queue 628 includes an input support, an input spill tray 620, and a pusher plate 617.

The input support can be a portion of the crossbar 608 of the sample base 602 that extends from near the entrance end of the sample presentation unit 110 to near the junction of the stem 626 and crossbar 608. The input support can include a pair of support rails arranged parallel to one another at a separation distance corresponding to the distance between support tabs disposed at opposite ends of sample holders 616. The support rails can define the boundaries of the active region of the input queue 628 and can connect to the sample base 602. In operation, sample holders 616 can rest on the support rails, and may be free to slide along the support rails with sample holders 616 loaded earlier in the process pushed along the support rails by adjacent sample holders 616 loaded later. In alternative embodiments, sample holders 616 may be moved by resting the sample holders upon a moving belt or a set of drive wheels.

The input spill tray 620 may lie between and beneath the support rails, and serves to control contamination by containing any spills, drips, or leakage from sample tubes. The input spill tray 620 can be an oblong or essentially rectangular structure, and can include a floor with containment walls on two sides and the entrance end. The input spill tray 620 may be open at the top and at the exit end of the input queue 628. In some embodiments, the floor includes a deeper sump region near the entrance end. The floor may slope towards this sump region to provide collection and containment of spilled liquids at one location for easy removal. The input spill tray 620 can be removable, and may rest on other sample presentation components including the sample base 602.

The queue pusher may include a pusher carriage 612 that includes a pusher plate 617 to push against the sample holder 616 closest to the entrance end of the input queue 628, a queue track 654 to guide the movement of the pusher carriage 612, and a queue drive 614 to move the pusher carriage 612 along the queue track 654. The system may include a function whereby the user can signal the system to move the queue pusher away from the terminal sample holder, allowing the user manipulate the sample holder queue to load a sample holder including sample tubes containing STAT or urgent samples at the front of the sample holder queue, for early presentation to the system on reengagement of the queue pusher. In one embodiment, the input queue may include a STAT queue pusher that manipulates that sample holder queue to permit a user to load a sample holder that includes sample tubes containing STAT or urgent samples. In an alternative embodiment, the queue pusher can include grippers that clasp the terminal sample holder, allowing the queue pusher to manipulate the sample holder queue to permit a user to load a sample holder that includes sample tubes containing STAT or urgent samples.

The pusher carriage 612 may include one or more bearings 650 to engage the queue track 654, and a pusher plate 617 to engage the flat side of the last sample holder within the input queue 628, and a bracket 652 to connect the pusher plate 617 to the bearing 650. The pusher plate 617 pushes against the last sample holder in the queue, which in turn pushes successive sample holders 616, if any are present, to move all loaded sample holders 616 toward the exit end of the input queue 628.

Figures 1, 4B, 4C:
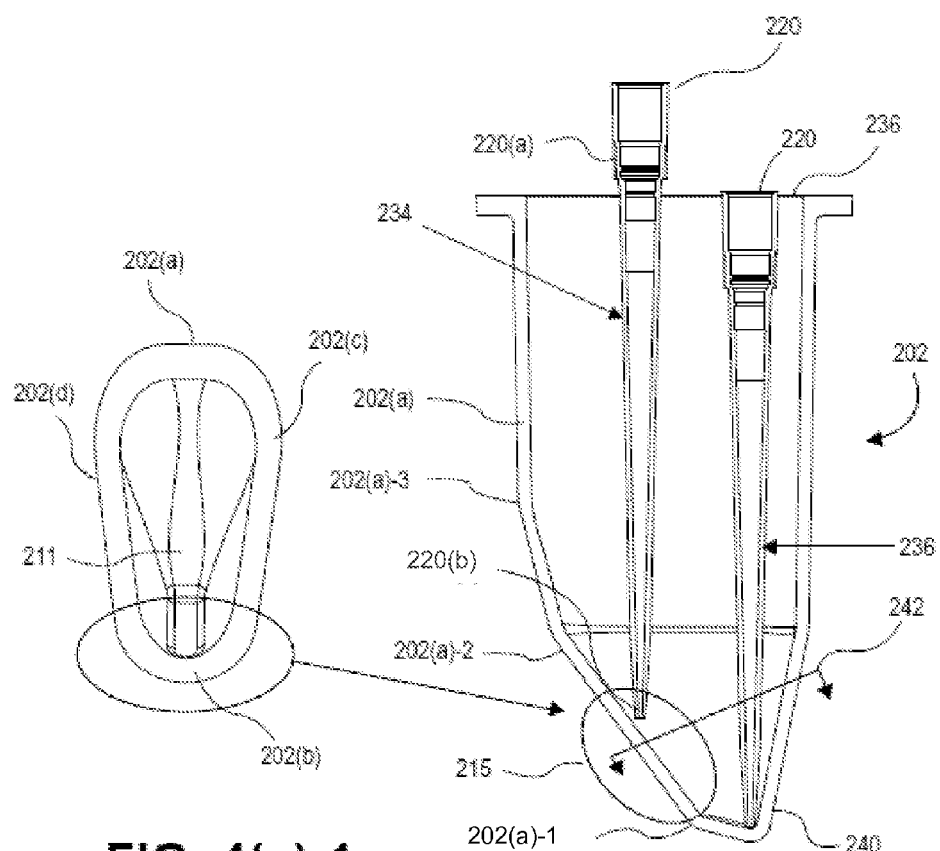
Figures 2, 4C:
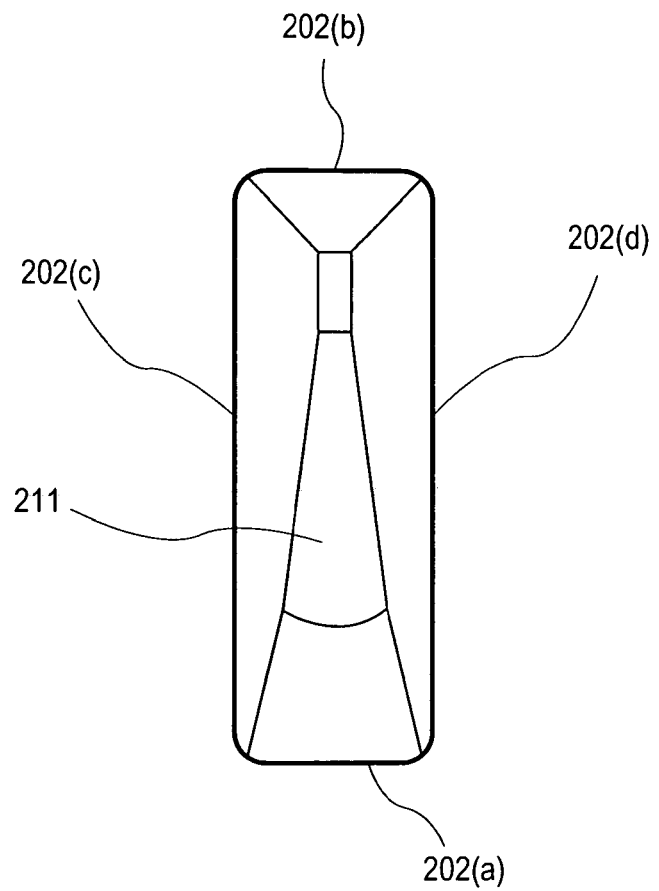

As shown in FIG. 2(*a*) and FIG. 2(*b*), the pusher plate 617 may be a planar sheet oriented vertically within the input spill tray 620, and can extend across most of the width of the input spill tray 620. The bracket 652 may include an upper horizontal member 646, a vertical member 648, and a lower horizontal member 649. The upper horizontal member 646 extends from the pusher plate 617 above the closed end wall of the input spill tray 620. The vertical member 648 extends from an edge of the upper horizontal member 646 to below the level of the input spill tray 620. The lower horizontal member extends from the lower edge of the vertical member 648 toward the queue track 654 and couples to the bearing 650. A portion of the bracket 652 may ride within a gap between the input spill tray 620 and one of the support rails. This arrangement advantageously allows the pusher plate 617 to move within the inner spill tray without requiring an opening in the inner spill tray. An absence of openings in the inner spill tray helps in the containment of spills and reduces possible contamination.

The queue track 654 may extend under the input queue 628 along the crossbar 608 of the sample base 602. The queue track 654 is fixed to the sample base 602 and guides the motion of the pusher carriage 612 along the pusher motion path. The queue track 654 connects to the pusher carriage 612 through complementary bearings 650. In some embodiments, the queue track 654 is a linear guide rail and the bearings 650 are caged ball bearing blocks or caged roller bearing blocks.

The queue drive 614 may move the pusher carriage 612 along the queue track 654 by any of a number of drive methods, including the use of a lead screw and nut, a linear motor, or a pneumatic actuator. In some embodiments, the instrument uses a motor that is attached to the sample base 602 near an end of the queue track 654, and is coupled to a drive pulley. An idler pulley may be attached to the sample base 602, or alternatively to the support rails, near the opposite end of the queue track 654 by an attachment that permits adjustment of the separation between the idler pulley and the drive pulley. A timing belt substantially parallel to the queue track 654 runs from the drive pulley to the idler pulley and couples to the pusher carriage 612. Adjustment of the separation between the idler and drive pulleys permits adjustment of the force applied to the sample holders 616 via the pusher plate 617. Rotation of the motor drives the timing belt and moves the pusher carriage 612 along the queue track 654.

As noted above, in some embodiments of the invention, sample tubes may be transported onto the system through an input queue individually, without the use of a sample holder. In such an embodiment, the input queue can utilize individual pucks that each support one sample tube; such pucks may be impelled using a magnetic drive. Alternatively, individual tubes may be transported using a belt drive or a set of drive wheels. In other embodiments, the input queue may include a storage location for holding individual sample tubes, which are transported onto the system using a pick and place device. Such an embodiment advantageously simplifies prioritization of sample testing by the system by permitting it to select sample tubes independent of order in which they are loaded by the user.

The output queue 640 is a storage location for sample tubes following removal of an aliquot that is utilized for testing purposes. The output queue may also serve as a site for the offloading of sample aliquots that have been processed by the system, for retrieval by the user for further testing. In some embodiments, the output queue 640 supports the sample holders 616 in an ordered arrangement similar to that of the input queue 628. The output queue 640 may include an output support 638 and an output spill tray 604.

The output support 638 extends from near the area where the stem 626 and crossbar 608 of the sample base 602 join to near the exit end of the sample presentation unit 110. The output support 638 may be similar in structure and function to the input support. In some embodiments, the output support 638 includes parallel support rails, one of which may be contiguous with one of the support rails of the input support. In some embodiments, sensors mounted to one of the parallel support rails may indicate when the output queue 640 has reached a predetermined fill level. These sensors may be optical sensors.

The output spill tray 604 may be similar in form to the input spill tray 620 and performs a similar function. However, it is supported by the output support 638. The output spill tray 604 rests within the output support 638 in an approximately reverse orientation to that of the input spill tray 620, with the end vertical wall oriented towards the exit end of the sample presentation unit 110. The sump of the output spill tray 604 may therefore be near the exit end, with the open end of the output spill oriented towards the entrance end. This advantageously creates an open path for sample holders 616 to travel either directly or indirectly from the input queue 628 to the output queue 640. The manufacturing process may employ any of a variety of methods to form the input and output spill trays 604. In some embodiments, the spill trays are vacuum formed plastic.

The input queue 628 and the output queue 640 may be aligned with one another, separated by a gap that is approximately the width of a sample holder. A presentation shuttle 656 can intrude within this gap and extend toward the inboard end of the sample base 602.

The presentation shuttle 656 transports sample holders 616 along a sample motion path that extends over several operative positions. This sample motion path may be oriented transverse to the path of the sample pipettor 700. Operative positions may include a transfer position 642, a sample identification position 644, and an aspiration position 632. The sample identification position 644 may be disposed between the transfer position 642 and the aspiration position 632.

The transfer position 642 can be disposed within the aforementioned gap between the input queue 628 and the output queue 640. The aspiration position 632 can be disposed near the inboard end of the sample motion path, where the sample motion path intersects the path of the sample pipettor. The sample identification position 644 may be disposed between the transfer position 642 and the aspiration position 632 and is aligned with a sample reader 622.

The presentation shuttle 656 may include a presentation carriage 634 to engage the sample holder 616, a presentation track 624 to guide motion of the presentation carriage 634, a presentation drive to move the presentation carriage 634 along the presentation track 624, an aspiration channel 630 to support the sample holder during aspiration, a sample gate 606 to prevent unintended movement of sample holders 616, and a faring 636 to protect the sample holders 616 and reduce contamination.

The presentation carriage 634 engages a controlled surface of a sample holder in order to move the sample holder within the cartridge guide. In some embodiments, the controlled surface is an essentially vertical edge of the sample holder that is disposed inward of one of the support tabs. In some embodiments, the presentation carriage 634 is a narrow "U-shaped" body that includes a pair of vertical members and a connecting base member. The base member may include one or more bearings (not shown) to connect the presentation carriage 634 to the presentation track 624. The vertical members may rise from either end of the base member and terminate in short vertical protrusions that engage the support tabs of the sample holders 616. The U-shaped body may have a width approximating that of a sample holder. When positioned within the transfer position 642 between the input queue 628 and the output queue 640, the presentation carriage 634 effectively joins the input support to the output support 638 as one continuous path. The gaps between the presentation carriage 634 and the input support between the presentation carriage 634 and the output support 638 may be narrower than the width of a sample holder. As a result, when the presentation carriage 634 is within this transfer position 642, motion of the sample pusher (617) may propel a sample holder smoothly from the input queue 628 to the presentation carriage 634 while simultaneously propelling a different sample holder held within the presentation carriage 634 to the output queue 640. Cooperative motion between the sample pusher and the presentation carriage 634 serves to load and unload sample holders 616 onto the presentation carriage 634 and may also serve to transfer sample holders 616 directly from the input queue 628 to the output queue 640 without intervening movement along a sample motion path associated with processing and analysis of the sample. In an alternative embodiment, the output queue may have a dedicated drive mechanism for offloading sample racks from the transfer position.

The presentation track 624 may extend along the stem 626 of the sample base 602 and defines the sample motion path. The presentation track 624 may be fixed to the stem 626 of the sample base 602, and guides motion of the presentation carriage 634 along the sample motion path. The presentation track 624 may connect to the presentation carriage 634 through complementary bearings 650. In some embodiments, the presentation track 624 is a linear guide rail and the bearings are caged ball bearing blocks or caged roller bearing blocks.

The presentation drive moves the presentation carriage 634 along the presentation track 624, and may do so by any of a number of drive methods. Such drive methods include but are not limited to a lead screw and nut, a linear motor, or a pneumatic actuator. In some embodiments, the instrument uses a motor attached to the sample base 602 near one end of the presentation track 624 and coupled to a drive pulley. An idler pulley may be attached to the sample base 602 near the opposite end of the presentation track 624, by an attachment that allows adjustment of the separation between idler pulley and drive pulley. A timing belt substantially parallel to the presentation track 624 may run from the drive pulley to the idler pulley couple to the presentation carriage 634. The tension of this timing belt may be altered by adjusting the separation between the idler pulley and the drive pulley. Rotation of the motor drives the timing belt and impels the presentation carriage 634 along the presentation track 624.

In some embodiments, the aspiration channel 630 may be a rectangular tunnel. The length of the aspiration channel 630 can approximate the length of a sample holder with a width slightly greater than the width of the sample holder. The aspiration channel 630 lies along the sample motion path and may extend beyond the aspiration position 632. An opening in the upper surface of the aspiration channel 630 at the aspiration position 632 gives access to the sample pipettor (not shown in FIG. 2(a)). This arrangement of the aspiration channel 630 advantageously supports a sample holder in a defined position that is consistent for each sample tube in the sample holder and necessary for accurate pipetting.

The aspiration channel 630 may include one or more sample springs to impel a sample holder that is within the aspiration channel 630 against an internal aspect of the aspiration channel 630 in order to better control lateral and vertical position. Sample springs may be strips of a relatively stiff but elastic material, such as spring steel, mounted to an aspiration channel 630 wall. Alternatively, sample springs mounted within the presentation lane at the aspiration position may be used to stabilize lateral and vertical position of the assay cartridge without an aspiration channel.

The sample gate 606 may be a generally "L-shaped" member approximately the same width as the presentation carriage 634, and may have a rounded free end. The opposite arm of the L may mount to the sample base 602 near the transfer position 642. The mounting may connect the member to the sample base 602 through a pivot near the end of the arm. This pivot may include a spring. When the presentation carriage 634 is outside of the transfer position 642, the sample gate 606 pivots to occupy at least a portion of the transfer area, thereby preventing movement of a sample holder into the transfer area. The presentation carriage 634, upon returning to the transfer position 642, impacts the rounded free end of the sample gate 606 to push the sample gate 606 out of the transfer position 642. This arrangement advantageously allows loading of the input queue 628 while the presentation carriage 634 is engaged in sample transfer operations. This has the beneficial effect of further decoupling scheduled instrument operations from user action, freeing the user to load and unload samples without concern for instrument timing.

In some embodiments, the shape of the sample gate 606 can be an approximately rectangular shape, oriented with the long axis vertical. A large crescent-shaped section can be removed that extends from the top right corner to the middle of the lower short edge. It may be characterized as a modified "C," rather than an "L" shape as shown in FIG. 2(*a*).

In some embodiments, a protective faring 636 may cover the sample motion path to prevent contamination of the sample tubes. The faring 636 may be a plastic or sheet metal shield formed to extend above and on the sides of sample holders 616 as they pass along the sample motion path. The faring 636 may include openings to allow access to the sample pipettor and to the sample reader 622.

The sample presentation unit 110 may also have of a sample reader 622 to identify individual sample tubes as they enter the system by reading a unique sample identification associated with each sample tubes. Sample identification typically includes a form of machine readable information, such as a barcode or other graphical code. Well-established practice surrounds use of such codes in clinical laboratories.

In some embodiments, the sample reader 622 is an image-based or scanning barcode reader positioned along the sample motion path at the sample identification position 644. The sample reader 622 is oriented so that the scanner has a view of any sample identification labels affixed to sample tubes or sample holders 616 as the sample holders 616 are transported on the presentation shuttle 656. The sample reader 622 may connect to the instrument controller in order to pass sample identification information to the instrument controller. The instrument controller, in turn, may query off-board computer systems or an on-board database to determine which assay or assays are to be performed on the identified sample.

The sample presentation unit 110 may include a sample cover. The sample cover controls user access to the input queue 628 and the output queue 640, and may also serve to reduce contamination and sample evaporation. The sample cover may include a mechanized latch and at least one control switch. The sample cover may be at least partly transparent in order to allow users to gauge the extent of work in progress and occupancy of the input and output queues 640.

The sample presentation unit 110 may also include one or more covers. In one embodiment, the sample presentation unit 110 may have a hinged or sliding cover to protect the sample tubes. Further, the cover could be latched when the sample presentation unit 110 is in operation.

In some embodiments, the sample cover is a substantially flat lid hinged to the inboard edges of the input queue 628 and the output queue 640. The sample cover may be disposed in either an open or a closed position. When the sample cover is closed, the instrument operates normally and users may not access the sample presentation unit 110. When the sample cover is open, the instrument may continue to process assays, but does not transfer any sample holders 616 into or out of either queue. In some embodiments, the sample cover extends across the entirety of the input queue 628 and the output queue 640. In other embodiments, a fixed top may cover parts of the input queue 628 and the output queue 640 close to the transfer position 642, and the sample cover in the open position reveals only a limited portion of the queues.

The mechanized latch may include an actuator mounted to the sample base 602, one or more latching hooks mounted to the outboard support rails, and a linkage connecting the actuator to the latching hooks. The actuator may be any of a number of linear or rotary actuators, including as solenoids, linear motors, stepping motors, or pneumatic actuators. The latching hooks may align with catches incorporated into the sample cover when the sample cover is in the closed position. The purpose of the mechanized latch is to prevent the user from accessing to the sample presentation unit 110 while the sample holders 616 are in motion. In operation, the user requests access by activating a control switch. The control switch may be implemented utilizing a user interface displayed on a system monitor. The system may respond by completing any sample holder transfers in progress, reversing the sample pusher to provide room to add new sample holders 616, cutting power to mechanisms in the input queue 628, and releasing the mechanized latch. The user may then open the sample cover in order to load, unload, or reorganize sample holders 616. Operations may resume on closing the sample cover.

In an alternative embodiment, the input queue, the output queue or both the input and output queues may support sample holders in a radial or circular arrangement. An example of such a circular arrangement is a turntable. In another embodiment a single radial or circular queue may serve as a combined input and output queue, storing both samples that have been accessed by the system and unaccessed samples.

In some embodiments, a feature has been added to support the use of secure covered tubes during pipetting. These tubes can have a valve assemblies that serve to protect sample tube contents, which are typically pushed open by the pipette tip during a pipetting operation. These tubes may also have a cap, below which can be a circumferential ridge that is affixed to the exterior wall of the tube. There can be a tube stabilizer that inserts into the gap between the cap and the circumferential ridge to hold covered tubes in place during pipetting. Yet in some embodiments, a sample tube may have a piercable cover or film to protect sample tube contents. In such an arrangement, the sample presentation unit 110 may utilize a pipette tip as a dedicated piercing tool to penetrate through the piercable cover or film to facilitate accessing the sample contained in the sample tube.

Embodiments of the invention can also include sample holder sensors in the output queue 640 and the input queue 628. The sensors may include a vision system, a barcode reader, etc. Such sensors may also verify that the sample holder is properly oriented. The sample presentation unit may also include features that support the use of sample tubes with closures. Such features include sensors that detect the presence of sample tube caps, and devices for removal or piercing of sample tube caps in order to provide access to sample tube contents by a sample pipettor. In some embodiments, the sample presentation unit includes features that enhance the stability of sample tube contents. Sample tube temperature can be controlled by incorporating one or more temperature controlled zones, which may be set to different temperatures. The sample presentation unit may also include devices, such as infrared sensors, for determining the temperature of the sample tubes held therein. The sample presentation unit can also include devices for mixing the contents of sample tubes, such as rocking mechanisms.

C. Sample Pipettor and Pipette Pumps

Figure 3A:
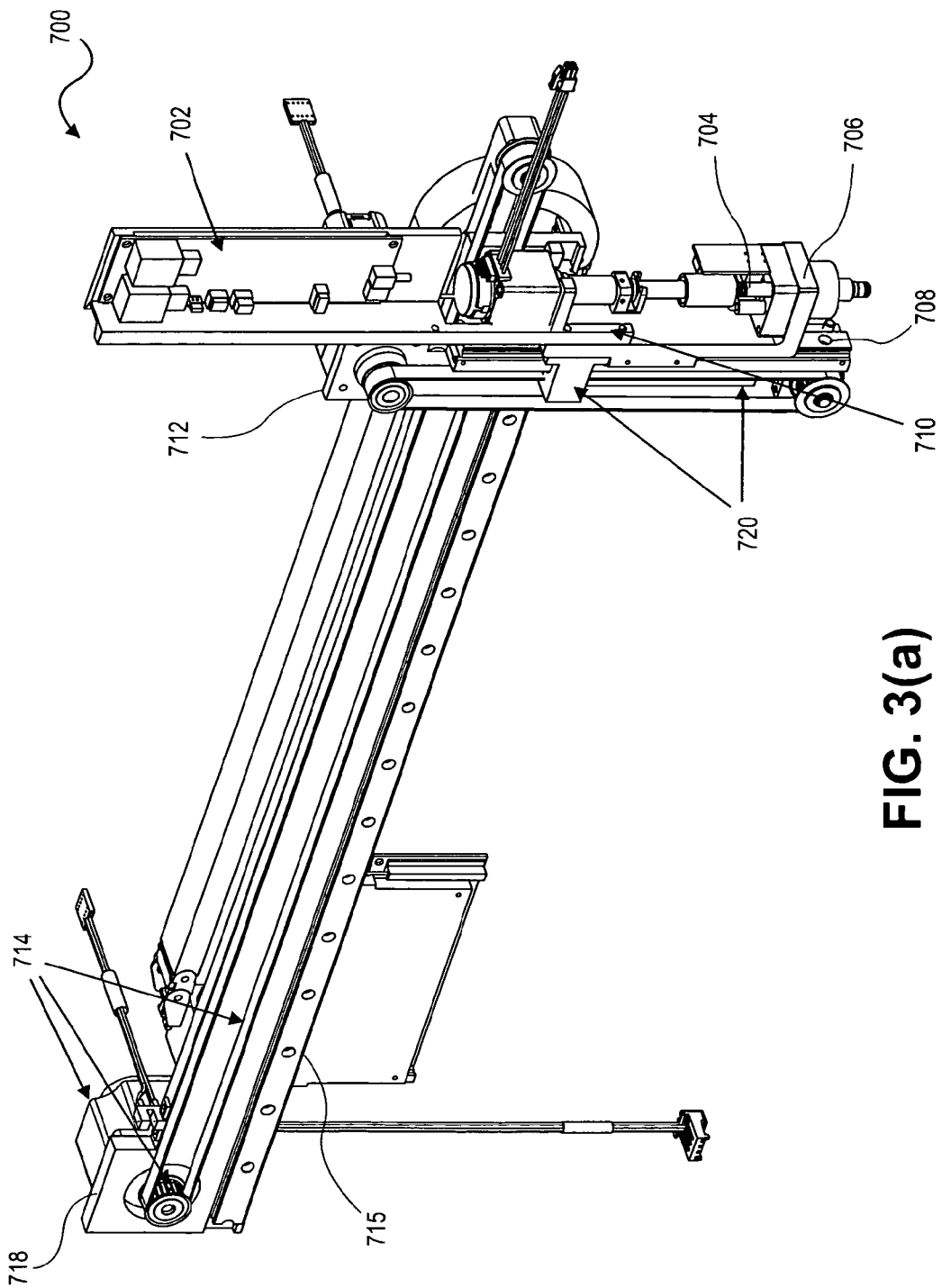
FIG. 3(a) shows a front, perspective view of a sample pipettor according to an embodiment of the invention.

FIG. 3(a) shows a perspective view of a gantry with a pipette pump assembly

Figure 3B:
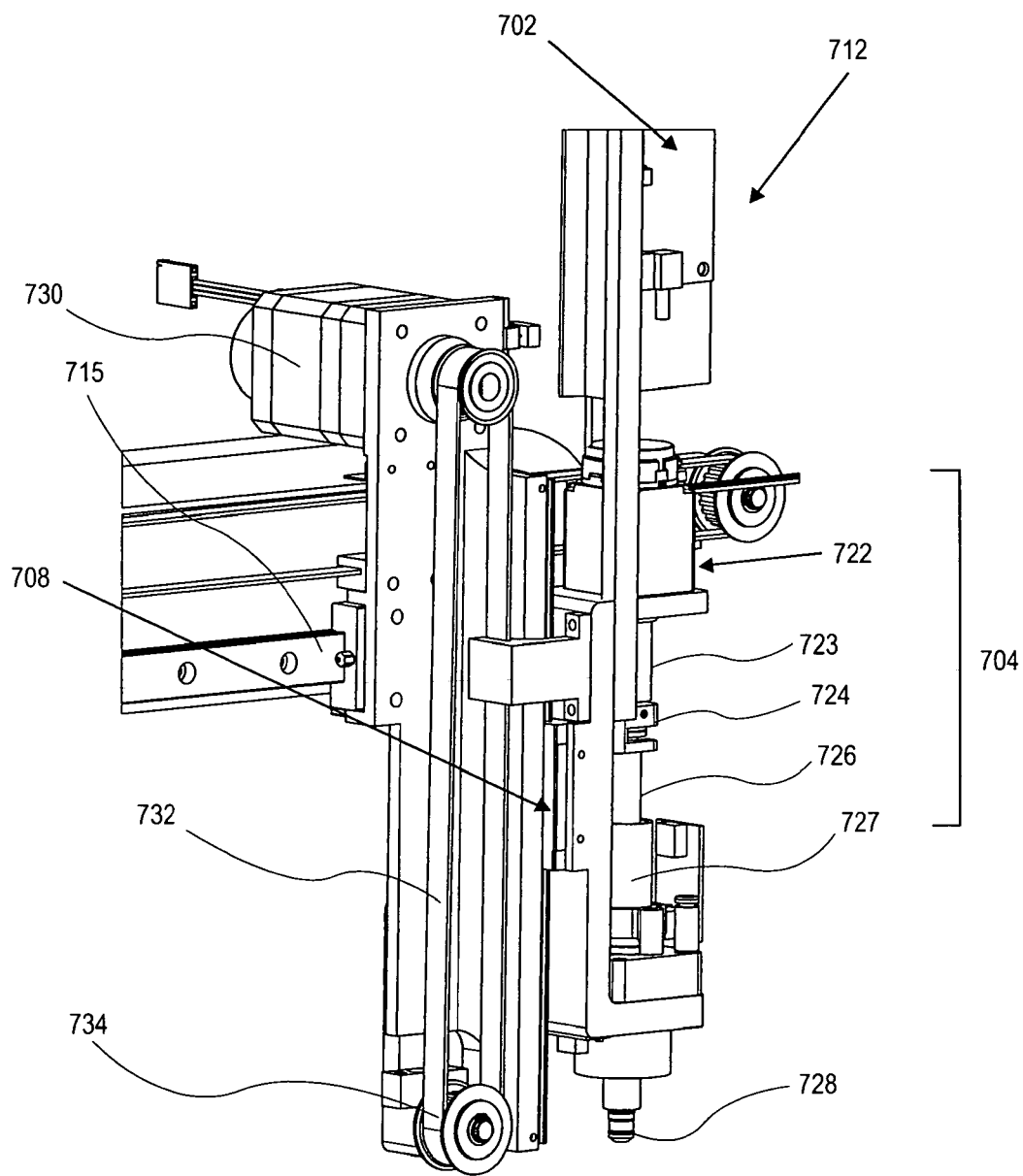
FIG. 3(b) shows a front perspective view of the sample pipettor in more detail.

FIG. 3(b) shows another perspective view of the pipette pump in greater detail.

Figure 3C:
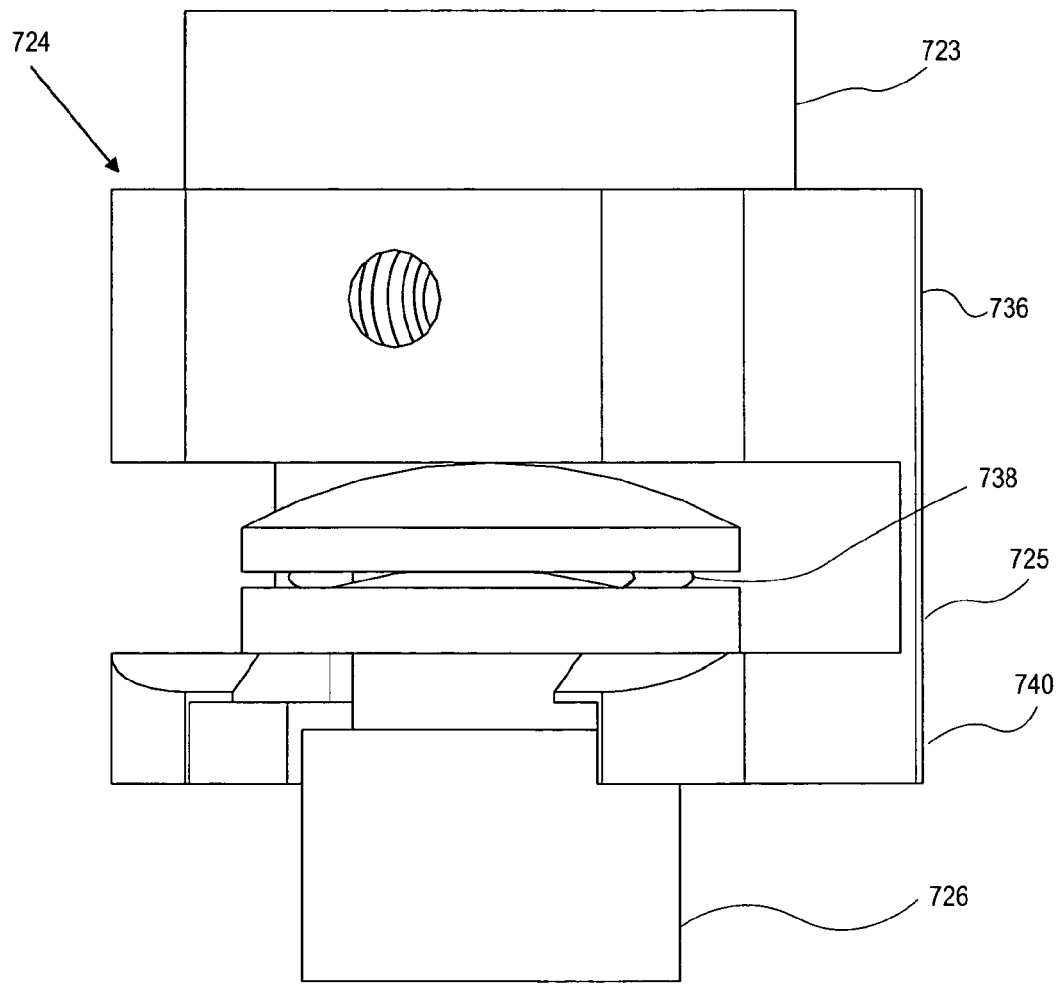
FIG. 3(c) shows a perspective view of a compliant coupling.

FIG. 3(c) shows details of a compliant coupling used in pipette pumps

A pipette pump or pipettor can be used to transfer liquids from one location to another throughout the system. A sample pipettor may transfer liquids that include patient samples stored in sample tubes, which may include serum, plasma, whole blood, urine, feces, cerebrospinal fluid, saliva, tissue suspensions, and wound secretions. Transferred liquids may also include liquid reagents. Such sample tubes may be supplied by a user via placement in the SPU 110 described above. Alternatively, sample tubes may be directed to a sample pipettor by a laboratory automation system 80 or by both the SPU and a laboratory automation system. The sample pipettor can also interact with the reaction vessel plug 222 and piercer 262 (which are described in further detail below).

Pipettors can also include obstruction detectors (not shown) for detection of clots in samples and other obstructions. Obstruction detectors can use a pressure sensor that monitors the pressure profile within the pipettor during pipetting events. Certain pressure profiles may be associated with specific pipettor conditions, including obstructions and the presence of items attached to the pipettor. Items that may be attached to pipettors include pipette tips, reaction vessel plugs 222, and sealed reaction vessels. Obstruction detectors can also detect if a filter is present in a pipette tip, if pipette tips have molding defects.

Pipettors can also have sensing circuits, such as liquid level sensor circuits, that can be used to detect contact with a liquid surface. Liquid level sensors can also be used to determine available sample volume when used in conjunction with encoder information from the elevator motor 730. They can also be used to determine if there is sufficient sample volume to perform a test, and one can be used to verify that the correct sample volume was removed from the tube.

In order to reduce contamination, such pipette pumps typically use disposable pipette tips to contact fluids. A pipette mandrel 728 may act as the point for the attachment of disposable pipette tips to the pipettor. Attachment can be held in place actively by a gripper or held in place passively by friction between the inner surface of the pipette tip and the outer surface of the pipettor mandrel. The pipette mandrel 728 also allows pipette pump assemblies to attach to and subsequently transport other consumables that have appropriate interfaces, such as a reaction vessel plug or a film piercer, between different locations on the system. The sensing circuit noted above and described in greater detail below can be used to detect the presence of disposable pipette tips, and other consumables that have appropriate interfaces, on the pipettor mandrel. Alternatively, pipette pumps with fixed fluid transfer probes may be used for fluid handling, in conjunction with probe washing mechanisms.

A pipette pump according to an embodiment of the invention may be specifically constructed to accurately aspirate and dispense fluids within a defined range of volumes. Different pipette pumps may be of substantially identical design, with specific components having different dimensions in order to accurately aspirate and dispense within different volume ranges. In one embodiment, a millitip pipette pump or pipettor can be constructed to accurately aspirate and dispense fluid volumes ranging from about 50 μL to about 1,200 μL (1.2 mL), and a microtip pipette pump or pipettor can be constructed to accurately aspirate and dispense fluid volumes ranging from about 5 μL to about 200 μL. In some embodiments, the system may utilize dual resolution pipette pumps, which are capable of accurately aspirating and dispensing across a wide range of volumes, in place of one or more conventional pipette pumps. In an alternative embodiment, liquids may be transferred using a pipette pump with a fixed probe or fixed tip, in combination with a wash station for removal of residual liquids following transfer.

One example of a pipette pump assembly is the sample pipettor 700 shown in FIG. 3(a). Reference is also made to certain components in FIGS. 4(a)-4(f). The sample pipettor 700 can be used to transfer aliquots of samples from sample tubes to assay cartridges 200. The sample pipettor 700 may also serve to transfer fluids from well to well within the assay cartridge 200, add reagents to a sample tube prior to transferring an aliquot from a sample tube to an assay cartridge, mix fluids within the assay cartridge 200 (or tubes), puncture holes through a barrier film 205 using a piercer 262, and dispose of a piercer 262. The sample pipettor 700 can be located within the system so that it can access samples in the sample presentation unit 110 at the aspiration position 632 (see FIG. 2(a)) and can reach assay cartridges in the cartridge loading unit at the sample dispense position. In some embodiments, the sample pipettor 700 can access a waste chute to facilitate safe disposal of solid waste, including but not restricted to a piercer 262.

The sample pipettor 700 may include a sample gantry 718, a pipettor carriage 712 that supports a millitip pipettor 704, and a liquid sensor 702. The liquid sensor 702 may be capacitance based, and may detect both proximity and contact with liquids and solids that are conductive. In some embodiments, the sample gantry 718 includes a pipettor carriage 712 that carries a sample elevator 710 and is disposed to reach sample tubes and the cartridge loading lane. The sample elevator 710 raises and lowers the millitip pipettor 704 as required for pipetting, mixing, resuspension, and millitip transfer. Alternatively, the sample gantry 718 may be any suitable structure capable of reaching the sample tube and the reaction well such as a rotary transport, a guided track transport, an XYZ Cartesian transport, or an articulated arm. A liquid sensor 702 may be incorporated into the sample gantry 718, connecting to the millitip pipettor 704 and to extensions thereof. Such extensions include disposable pipette tips, reaction vessel plugs, and film piercers, which may be constructed of conductive materials. The sample gantry 718 positions the millitip pipettor 704 adjacent each operative location, the sample elevator 710 raises and lowers the millitip pipettor 704, and the millitip pipettor 704 aspirates, dispenses, or ejects the millitip.

An embodiment of the pipettor carriage 712 is shown in FIG. 3(b). The pipettor carriage can include a pipettor track 715, and a pipettor drive 714. The pipettor track 715 can be a section of linear guide rail attached to the sample gantry 718 in the direction of travel of the pipettor carriage 712. The pipettor carriage 712 supports the sample elevator 710 and moves along the pipettor track 715 in response to operation of the pipettor drive 714. The pipettor track 715 connects to the pipettor carriage 712 through complementary bearings. In some embodiments, the bearings are caged ball bearing blocks or caged roller bearing blocks. Although shown with a single pipettor carriage 712 in some embodiments, the sample gantry 718, can support multiple pipettor carriages, which may in turn carry pipettors with different volume ranges.

Referring to FIGS. 3(*a*) and 3(*b*), the pipettor drive 714 may move the pipettor carriage 712 along the pipettor track 715 by any of a number of drive methods. Exemplary drive methods include a lead screw and nut, a linear motor, or a pneumatic actuator. In an embodiment shown in FIG. 3(*a*), the instrument uses a motor attached to the sample gantry 718 near one terminus of the pipettor track, the motor being coupled to a drive pulley. An idler pulley may be attached to the sample gantry 718 near the opposite terminus of the pipettor track 715, by an attachment that allows adjustment of the separation distance between idler pulley and drive pulley. A timing belt substantially parallel to the pipettor track may connect the drive pulley to the idler pulley couple to the pipettor carriage 712. The tension of this timing belt may be altered by adjusting the separation between the idler pulley and the drive pulley. Rotation of the motor drives the timing belt and moves the pipettor carriage 712 along the pipettor track 715.

The sample elevator 710 can be a linear transport that includes an elevator track 708, an elevator carriage 706, and an elevator drive 720. The elevator track 708 can be a section of linear guide rail affixed to the sample elevator 710 in the direction of travel of the elevator carriage 706. The sample elevator 710 can move in a vertical direction in order to move the millitip pipettor 704 into position to access sample tubes; the elevator track 708 is similarly disposed.

In one embodiment of the invention, the elevator carriage 706 supports the millitip pipettor 704, and moves along the elevator track 708 in response to operation of the elevator drive 720. The elevator drive 720 may move the elevator carriage 706 along the elevator track 708 by any of a number of drive methods. Exemplary methods include the use of a lead screw and nut, a linear motor, or a pneumatic actuator. In some embodiments, the instrument uses a motor attached to the sample elevator 710 near one end of the elevator track 708 and coupled to a drive pulley. An idler pulley 734 may be attached to the sample elevator 710 near the opposite end of the elevator track 708, by an attachment that allows adjustment of the separation distance between idler pulley 734 and drive pulley. A timing belt 732 substantially parallel to the elevator track 708 runs from the drive pulley to the idler pulley 734 and couples to the elevator carriage 706. The tension of this timing belt 732 may be altered by adjusting the separation between the idler pulley 732 and the drive pulley. Rotation of the motor 730 drives the timing belt 732 and moves the elevator carriage 706 along the elevator track 708, resulting in vertical movement of the pipettor. The elevator motor 730 drives the mandrel 728 into the opening of the disposable tip, forming an air tight seal. The tip is held in place by friction, and detachment may be passive or active.

The sample pipettor 700 may include additional features that support sample handling functions. The sample pipettor 700 can include a reusable film piercing device, configured to pierce the protective film that covers a portion of the assay cartridge 200 in one or more locations in order to provide access to contents. In some embodiments, the sample pipettor 700 includes mixing devices, such as mixing paddles or ultrasonic probes, that can serve to mix the contents of sample tubes or the assay cartridge 200. The sample pipettor may also include areas for the storage of reagent bottles.

As shown in FIG. 3(*b*), the millitip pipettor 704 may include a linear step motor 722 that is connected to linear actuator 723, which is in turn coupled to a piston 726. The piston 726 lies partially within a barrel 727 that serves as a pressure chamber. A seal lies between the piston 726 and an inner wall of the barrel 727. The barrel 727 can be cooperatively configured to allow movement of the piston within the barrel. The pipettor 704 may also comprise a mandrel 728 that is in fluid connection with the barrel 727. Movement of the piston 726 via the linear step motor 722 generates pressure changes within the barrel 727. These pressure changes are communicated to the mandrel 728 and subsequently to a pipette tip affixed to the mandrel 728, resulting in the uptake of fluids into the pipette tip or the dispensing of fluids previously held therein. After use the pipette tip can be removed from the mandrel 728 by a pneumatically pressurized ejector, which applies pressure to an upper surface of the pipette tip. Alternatively, a stripper plate that is driven by the elevator motor 730 may be used to remove the pipette tip. A pipette tip held in place by a gripper may be removed from the mandrel by releasing the gripping device. The force of pipette tip ejection can be controllable; for example, the pressure applied to a mounted pipette tip by an ejector or stripper plate may be varied, This advantageously permits both slow tip ejections that minimize the potential for droplet formation and subsequent contamination and rapid tip ejections that facilitate throughput.

In some embodiments, the connection between the linear step motor 722 and the piston 726 incorporates a compliant coupling 724 that connects these features. The compliant coupling 724 advantageously simplifies replacement of the linear step motor 722, piston 726, housing, and other components of a pipettor, permitting mechanical coupling of the drive and fluid handling components of the device without the need for precise alignment and build tolerances.

FIG. 3(*c*) shows one embodiment of the compliant coupling 724, where the compliant coupling 724 can deform slightly along the axis of the linear step motor 722 and the piston 726 and restricts movement lateral to this axis. The compliant coupling 724 may have an upper plate 736 (which is an example of a first connecting feature) and a lower plate 740 (which is an example of a second connecting feature), these plates being separated by a gap, and connectable by an intermediate member 725. The upper plate 736 can be affixed to the linear step motor 722. In some embodiments, the lower plate 740 has a channel, and the upper portion of the piston 726 narrows to pass through this channel, and then flares to a diameter greater than the width of the channel once within the gap. The lower plate 740 is at least partially disposed around the piston 726. Compliance is provided by a spring mechanism 738 (or other type of compressible member) that lies between the flared portion of the piston 726 and the lower plate 740 of the compliant coupling 724. Compliance may also be provided by a spring mechanism 738 that is located outside of this interface and on periphery of the coupling. In an alternative embodiment, compliance is provided by an elastomeric polymer rather than a spring mechanism 738. This compliance provides the force desired for a firm connection between the linear step motor 722 and the piston 726, which is desirable for accurate fluid dispensing, while reducing the need to build these components to tight tolerances. Additionally, this compliance simplifies replacement of the linear step motor 722 or the piston 726 as it reduces the need for careful alignment of these components. Use of the compliant coupling 724 may not be restricted to the sample millitip pipettor 704, but may be used on pipetting mechanisms throughout the system, or even in systems that are different than the systems described herein.

The millitip pipettor 704 in the sample pipettor 700 may use a millitip disposable pipette tip associated with each assay cartridge 200 to transfer sample from the sample tube to the assay cartridge reaction well 202. This advantageously reduces the possibility of contamination, as a different millitip is used in each sample processing instance. The use of the relatively large volume millitip allows transfer of a large sample volume. In some embodiments, the sample pipettor 700 picks up the millitip carried within an assay cartridge, transfers the sample aliquot to the reaction well 202 of that assay cartridge, mixes the sample with other materials present in the reaction well 202, and then returns the millitip to a storage position of the assay cartridge 200.

In some embodiments, a pipettor used on the system may use a sensing circuit, such as a liquid sensor 702, to detect contact with liquid during pipetting operations. The liquid may be sample held within a sample tube or liquid reagents held within an assay cartridge 200 or a reagent pack. This detection may be combined with information related to the position of the pipettor to determine the height of the liquid. The liquid sensor 702 may incorporate a capacitance-based circuit. Liquid sensing may take place via a conductive pipette tip, such as a millitip or microtip, held on the mandrel 728 of the pipettor. In operation, the pipette tip may be submerged slightly below the liquid surface in order to limit contamination of the exterior. In some embodiments, the pipettor descends during aspiration to maintain the pipette tip at a relatively constant depth below the sample surface. A sensing apparatus is described in further detail below.

D. Assay Cartridge

Assay cartridges can be one-time use consumables, or may be re-usable. There can be many different assay cartridge embodiments. In one embodiment, the assay cartridge comprises an elongated body comprising a distal end and a proximal end, and a plurality of compartments arranged linearly between the distal end and the proximal end, wherein at least one of the compartments is a reaction well. The reaction well comprises first and second sidewalls, and first and second endwalls, and a well floor joining at least the first and second endwalls. The first endwall comprises a plurality of bends, which can form a faceted shape.

The various compartments in the assay cartridge can include DNA reagent compartments for storing reagents for DNA extraction from a sample, or RNA reagent compartments for storing reagents for RNA extraction from a sample.

In a specific embodiment, the assay cartridge comprises a reaction well including a first sidewall, a second sidewall, a first endwall, a second endwall, and a well floor arranged to receive a reaction mixture. The first sidewall, the second sidewall, the first endwall and the second endwall form an open end. The first endwall includes a first segment and a second segment. The first and second segment are joined by a bend, and at least one of the first segment and second segment is tapered so that the cross section of the reaction well decreases closer to the well floor.

FIG. 4(a)-1 shows one embodiment of an assay cartridge 200. The assay cartridge 200 comprises an elongated body 201 formed to include multiple compartments, which may hold fluids (e.g., reagents) and devices (e.g., millitips) needed to perform various analyses. Examples of compartments may include one or more reaction wells 202, one or more millitip holders 203, one or more large reagent wells 204, one or more medium reagent wells 208, and one or more small reagent wells 209. In some embodiments, the assay cartridge 200 can be in the form of a monolithic body, and may be formed of plastic (or any other suitable material). In some cases, a plastic injection molding process can be used to form the assay cartridge 200. Alternatively, the assay cartridge 200 may be constructed by fitting individual components into a rigid framework.

Each assay cartridge may also include a containment region 212, a cover (e.g., a barrier film 205) which is disposed around various compartments, features to facilitate handling and automation (e.g., a detection feature 210), selected reagents, labeling, and removable components that can be used during processing. The assay cartridge 200 can have a proximal end 230 and a distal end 232 at opposite ends of the elongated body 201. The orientation of the compartments defines the top and bottom portions of the assay cartridge 200. In some embodiments, compartments can be open at the top and closed on the bottom and sides.

As shown in FIG. 4(a)-1, compartments within an assay cartridge can align in a single file. This linear layout allows simple linear motion to align each compartment of the assay cartridge with operative locations in linear processing lanes. Alternatively, assay cartridges may take other shapes such as an arc, a multi-row grid, or a circle, among others. The choice of shape for an assay cartridge can depend on the overall system design, such as on the number and sequence of operative locations that need access to the individual compartments within an assay cartridge. The described linear assay cartridge design is advantageous, because it supports compact storage of assay cartridges, compact layout of processing lanes that operate on the assay cartridges, and easy user handling of multiple assay cartridges. It is also relatively simple to manufacture.

In some embodiments, the top ends of compartments within an assay cartridge form openings that align at a common height. In some cases, compartment bottom ends generally do not align because compartments differ in depth and because the compartment bottoms may have different shapes. The common height facilitates use of shared closures to reduce contamination risk at lower cost. It also reduces the effect of assay cartridge tolerance stackup on system alignment, since the system may support assay cartridges during processing from a controlled surface close to the assay cartridge top.

In some embodiments, assay cartridges have a skirted containment region 212 surrounding the openings of each compartment. The containment region 212 can be defined by a first longitudinal wall 206, a second longitudinal wall 207 substantially parallel to the first longitudinal wall 206, a first transverse wall 213, and a second transverse wall 214. Walls 206, 207, 213, and 214 may be referred to as "skirting walls" in some embodiments of the invention. In some embodiments, the assay cartridge 200 may have multiple skirting walls that serve to contain assay well contents that might otherwise be sources of contamination. The first and second transverse walls 213, 214 may be substantially perpendicular to the first and second longitudinal walls 206, 207, such that the containment region 212 is defined by a rectangle in this embodiment. The longitudinal walls 206, 207, and the transverse walls 213, 214 can extend above the upper openings of the various compartments. The transverse walls 213, 214 help to contain any drips or spills that may occur during assay cartridge processing. The transverse walls 213, 214 surround the openings of the compartments to create an extended cavity open at the top and contiguous with the interior of one or more compartments. The containment region 212 may further be defined by a horizontal web 228, which may connect between the compartment openings and the transverse walls 213, 214. The horizontal web 228 forms a floor for the containment region 212 and a support for the compartment walls 206, 207, 213, 214. The bottom surface of the horizontal web 228 can be a controlled surface that the system uses to support each assay cartridge during processing.

Compartments within the assay cartridge can perform a variety of functions. For example, component storage compartments can store removable components such as millitips. Reagent wells can store reagents. A reaction well can provide a reaction site. In addition, some compartments may perform more than one function. For example, reagent wells initially contain reagents used in processing the assay cartridge, and some reagent wells may later hold wastes produced during assay cartridge processing. Used compartments can hold discarded components (microtips, piercer, and vessel cover) in addition to discarded fluids.

Generally, compartments in some embodiments lack common walls to prevent the creeping of liquids between compartments. This has the benefit of reducing the possibility of contamination between compartments. Lack of common wells also supports leak testing of reagent wells during assay cartridge manufacture. In some embodiments, the external profile of each compartment closely tracks the cavity internal profile. That is, the walls can be of relatively constant thickness and can be thin with respect to the size of the compartment. This has the benefit of reducing the amount of material used and hence reduces the manufacturing cost of the assay cartridge. An additional benefit of thin compartment walls and constant thickness is more efficient and consistent heat transfer, which can be desirable for temperature control. Relatively constant cross-sections also contribute to more consistent parts with injection molded assay cartridges. The walls that define each compartment may extend as rims above the horizontal web both to prevent the incursion of fluids dripped or spilled in the containment region, and to act as energy directors to attach closures to the compartments. These rims may also support leak testing of reagent wells during assay cartridge manufacturing. The walls of the compartments may extend slightly above the horizontal web to act as energy directors for attachment of closures. They can also act as heat sealing contacts.

In some embodiment, a vertical web 226 disposed generally along the longitudinal axis of the assay cartridge may connect the compartment walls. The vertical web 226 may extend beyond the compartments to at least partially define the external profile of the assay cartridge 200. This has benefits of conferring rigidity to the assay cartridge, of controlling the fit of assay cartridges in the instrument loading area, and of providing space for labels and other indicia. An additional benefit of the vertical web 226 is to assist in the flow of plastic through the mold during the injection molding process. The vertical web 226 may also provide a location for keying features used to designate cartridge type and prevent insertion into the wrong lane of the cartridge loading unit. It can also be a support for human and machine readable information such as machine readable one and two dimensional barcodes. The assay cartridge 200 may also include other vertical extensions that provide lateral stability and allow it to be free standing.

Component storage compartments within assay cartridges may hold discrete components used in the extraction and purification process or in the amplification process. In some embodiments, one compartment can be a millitip holder 203, which supports a millitip pipette tip 220. Other compartments can include reaction vessel component holders 219, which can hold components of a reaction vessel. Components of a reaction vessel may comprise a vessel base 246 and a vessel plug 222, which can fit within the vessel base 246.

In some embodiments, each storage compartment supports its associated discrete component at a common operating height. The operating height is the height at which the discrete component interacts with instrument tools. In some embodiments, one or more walls 213 extend between at least some of the storage compartments and connect to the longitudinal walls 206, 207 to segregate at least some of the discrete components.

Reagent wells within assay cartridges may be of several types. Among these may be small reagent wells 209 that hold small volumes of reagents, medium reagent wells 208 to hold solid phase microparticles or to contain intermediate volumes of reagents, and large reagent wells 204 that may hold wash fluids, buffers, other reagents, or sample. Reagents stored in reagent wells may be in the form of liquids or particles suspended in liquid. In some embodiments, reagents stored in reagent wells are in the form of lyophilized solids, lyophilized pellets, or dry films adhered to the interior walls of the reagent wells. Some reagent wells may be empty. A barrier film 205 can close the tops of the reagent wells.

Small reagent wells 209 may hold materials used in small amounts. Small reagent wells 209 may be cylindrical with conically tapered bottoms. This shape minimizes dead volume and allows a pipettor to collect all, or nearly all, of the contained reagent. In some embodiments, each assay cartridge 200 has one small reagent well 209 with a fill volume of about 200 microliters (or more) with a headspace allowance of about 7.6 mm (or more). Small reagent wells may also be rectangular with pyramidal bottoms to (a) direct liquid volumes to the bottom of the well and (b) improve conductive heat transfer when a heating element is applied to the external walls. Small reagent wells may also have a rectangular cross-section in some embodiments of the invention. Bottoms may be have a central deepest point, and may be rounded, conical, pyramidal. A benefit of well with a rectangular cross-section is that flat contact areas provide for improved thermal contact/temperature control.

Medium reagent wells 204 hold reagents needed in relatively small volumes or reagents that may need mixing during use. For example, medium reagent wells 204 may hold the solid phase microparticles. In some embodiments, the system stores solid phase microparticles in suspension, but dry storage may extend shelf-life. In either case, solid phase microparticles may require mixing before use either to resuspend microparticles that settle in storage or to disperse a rehydrated suspension. Other medium reagent wells may hold reagents not requiring mixing or another mixture, such as a mixture of sample and a diluent, which the system may form preparatory to transfer into the reaction well. In some embodiments, each assay cartridge 200 has two medium reagent wells, each with a fill volume of about 350 microliters (or more) with a headspace allowance of about 7.6 mm (or more). Medium reagent wells may also have a rectangular cross-section in some embodiments of the invention. Bottoms may be have a central deepest point, and may be rounded, conical, or pyramidal. A benefit of well with a rectangular cross-section is that flat contact areas provide for improved thermal contact/temperature control.

Medium reagent wells 208 may have a rectangular cross-section, with pyramidal bottoms. This conformation advantageously directs liquid volumes to the bottom of the well and improves conductive heat transfer when a heating element is applied to the external walls. In other embodiments, the medium reagent wells can be cylindrical with rounded bottoms, and in some cases with hemispherical bottoms. In some embodiments, the system mixes medium reagent well contents using tip mixing. Tip mixing can include one or more cycles of aspiration and redispense of the contents. For example, the tip could be a millitip and aspiration and redispense of the contents may be performed using the millitip. Tip mixing agitates the contents so that different elements of the fluid interact on a small scale. The pyramidal or hemispherical bottoms of the medium reagent wells 208 support agitation and limited rotation of the redispensed contents with a minimum of uninvolved volume. The redispense process uses the kinetic energy of the redispensed fluid to impel fluid agitation. The medium reagent well 208 has a diameter that is a relatively large fraction of the width of the assay cartridge to reduce the effects of capillary forces on mixing. The medium reagent well 208 has a depth greater than its diameter to better contain any splashing. In some embodiments, the depth of the medium reagent well is at least twice its diameter; the diameter may be at least about 1 mm (e.g., between about 1 and 10 mm) and in some cases at least about 5 mm.

The system may use any of a number of other methods to mix reagent well contents. For example, the system may accelerate the assay cartridge 200 in one or more dimensions to agitate contents, or it may use a pipette tip or other device disposed in the fluid as a mixing tool. Other mixing methods may include magnetic mixing, ultrasound, and rotating paddles or similar devices that are inserted into the wells.

Large reagent wells 204 may hold wash fluids, buffers, other reagents, wastes, or sample. Generally the system uses large reagent wells 204 to accommodate relatively large volumes of reagents or to accommodate reagents that are sufficiently homogeneous as not to require mixing. Even so, the system may mix materials in large reagent wells by, for example, the tip mixing process described above. Large reagent wells 204 can taper to minimize dead volume and hence allow a pipettor to collect all, or nearly all, of the contained reagent. In some embodiments, the taper is at least a two part taper to allow a relatively large volume pipette tip with a shallow taper to reach the bottom of the large reagent well 204. The taper has the added benefit of acting as a draft that eases ejection of the assay cartridge 200 during fabrication. In some embodiments, assay cartridges have seven large reagent wells, each with a fill volume of about 2000 microliters with a headspace allowance of about 7.6 mm. Large reagent wells may also have a rectangular cross-section in some embodiments of the invention. Bottoms may be have a central deepest point, and may be rounded, conical, pyramidal. A benefit of well with a rectangular cross-section is that flat contact areas provide for improved thermal contact/temperature control. The flat exterior walls of the large reagent wells may be used to support labels, barcodes, and other indicia.

A barrier film 205 may seal the reagent wells individually to preserve the reagents and to prevent reagent cross-contamination. In some embodiments, a single barrier film 205 may cover all reagent wells. In another embodiment, the reagent wells of the assay cartridge 200 may have individual seals. The barrier film 205 may be a multilayer composite of polymer and foils, and can include metallic foils. In some embodiments, the barrier film 205 includes at least one foil component that has both a low piercing force and sufficient stiffness to maintain an opening in the barrier film 205 once the piercing device is removed. Additionally, the barrier film 205 may be constructed such that no fragments of the foil component are released from the barrier film upon piercing. A suitable material for the barrier film may be Part No. AB-00559 supplied by Thermo Scientific, Inc. of Epsom, UK. The barrier film 205 can be a continuous piece spanning all of the reagent wells. In operation, a pipette tip pierces the barrier film to access reagent well contents. The manufacturing process may pre-score the barrier film so that any tearing upon piercing occurs in predictable locations. In some embodiments, the manufacturing process laser welds the barrier film to the rims of each reagent well. Alternatively, the manufacturing process may use other attachment methods to fix the barrier film to the reagent wells. Other suitable processes may include heat sealing, ultrasonic welding, induction welding, or adhesive bonding.

FIG. 4(a)-2 shows a top perspective view of another assay cartridge according to another embodiment of the invention. The assay cartridge 200 shown in FIG. 4(a)-2 is similar to the assay cartridge 200 in FIG. 4(a)-1, except that the side walls of the medium reagent wells 208' are substantially flat and the openings of the reagent wells 208' are substantially parallelepipeds (e.g., squares). The side walls of the reagent wells 208' are substantially curved and the openings of the reagent wells 208 and are substantially round in the assay cartridge 200 in FIG. 4(a)-2. The flat side walls of the reagent wells 208' can advantageously be in better thermal contact with a heater compared to the curved side walls of the reagent wells 208 thereby providing better heat transfer to reagents in the reagent wells 208'.

FIG. 4(b) shows a side cross-section view and a top plan view of a reaction well 202 in the assay cartridge 200.

Referring to both FIGS. 4(a) and 4(b), the assay cartridge 200 includes at least one reaction well 202 that contains reaction mixtures during the extraction and purification process. While the system operates on other assay cartridge compartments primarily from the top, the reaction well 202 can also interact with tools such as magnets and heaters through its sides and edges. For this reason, in one embodiment, the reaction well 202 can reside near one end (the proximal end) of the assay cartridge 200. This end positioning advantageously allows tool operation by moving the assay cartridge 200 to place the reaction well 202 close to the tools. The end positioning has the further benefit of reducing the possibility of contamination by avoiding transporting the reaction well under an active pipette tip, except while pipetting to or from the reaction well 202. Placement of reaction well at one end also reduces risk of contamination entering the reaction vessel during mixing activities.

The reaction well 202 has a faceted shape (which may be formed by rectangular segments) designed to contain a relatively large reaction volume, to permit effective mixing of its contents, to permit aspiration with minimal dead volume, to assure good thermal contact with external heaters, and to interact with external magnets at either high or low fill volumes. The reaction well 202 can have a capacity of about 4500 microliters with a headspace allowance of about 7.6 mm. This relatively large capacity supports the processing of sample volumes in the milliliter range. The ability to process large sample volumes reduces sampling error and improves detection of rare sequences that may be present at only a few copies per milliliter of sample. In other embodiments, the reaction well can have a gradual transition design instead of a faceted shape. In some embodiments, the combination of reaction well volume and its faceted shape permits both the processing of large sample volumes and the recovery of small volumes, allowing it to be used for sample concentration and hence detection of rare sequences.

As shown in FIG. 4(c)-1, the reaction well 202 can have a generally rectangular cross-section (in the plane of the horizontal web) with the long axis of the rectangle aligned with the long axis of the assay cartridge 202. The reaction well 202 can be at least wide enough to accommodate the millitip pipette tip 220. The reaction well 202 tapers with depth both from its sidewalls (generally parallel to the assay cartridge axis), which may include first and second sidewalls 202(c), 202(d), and from its endwalls (generally perpendicular to the assay cartridge axis), which may include first and second endwalls 202(a), 202(b). The first and second sidewalls 202 (c), 202(d) have a dual taper with a shallow draft (closer to vertical) for most of the height and a steeper draft (closer to horizontal) near the reaction well floor 240 (shown in FIG. 4(b)). The first and second sidewalls 202(c), 202(d) converge in the steeper draft portion to narrow the reaction well near its floor 240.

In the longitudinal section along the assay cartridge axis, the reaction well 202 can be asymmetric, with a deepest portion aligned relatively close to that endwall 202(b) distal from the assay cartridge proximal end 230 (see FIG. 4(a)-1). As shown in FIG. 4(b), this deepest portion fits a millitip pipette tip 220 so that the millitip 220 can reach the deepest portion without touching the sidewalls when the millitip is in an aspirate position 236 (which can correspond to a second location in some cases). The pipette tip 220 may include a coupling taper 220(a) at one end and a pipetting orifice 220(b) at the other end. The longitudinal section profile of the reaction well can be polygonal, and the bottom can rise in a piecewise linear fashion to join the endwall proximal to the proximal end 230 of the assay cartridge 200. Each successive segment (beginning at reaction well floor 240 and respectively bounded by first bend 202(a)-1, by second bend 202(a)-2, and by third bend 202(a)-3), aligns closer to the vertical. The angles of these successive segments may be obtuse relative to the vertical axis. In one embodiment the angle of the internal surface of the first segment (extending from reaction well floor 240 to bend 202(a)-1) ranges from 100° to 120° relative to the vertical axis, the angle of the internal surface of the second segment ranges from 135° to 155° relative to the vertical axis, and the angle of the internal surface of the third segment ranges from 150° to 170° relative to the vertical axis. The segment extending beyond third bend 202(a)-3 may be approximately parallel to the vertical axis. In another embodiment, the angle of the internal surface of the first segment is about 110° relative to the vertical axis, the angle of the second segment is about 145° relative to the vertical axis, and the angle of the third segment is about 160° relative to the vertical axis. In some embodiments, the reaction well longitudinal section profile along the assay cartridge axis plane includes four linear segments (defined by the first, second, and third bends 202(a)-1, 202(a)-2, 202(a)-3) between the deepest point and the reaction well top at the proximal end. Two linear segments can connect the deepest point and the reaction well top at the distal end. The previously described bends may be rounded transitions that link successive linear segments. However, the transitions that link successive segments may be angular where it is desirable to confine standing liquids.

In embodiments of the invention, a first segment (above bend 202(a)-3) is closer to the open end of the reaction well and has a first taper, the second segment (e.g., below bend 202(a)-2) is farther from the open end and has a second taper. The second taper can be being greater than the first taper so as to decrease the cross-section of the reaction well at a greater rate.

The proximal endwall (i.e., the first endwall 202(a)) tapers towards the proximal end of the end of the assay cartridge and towards the bottom of the reaction well. As proximal endwall 202(a) approaches reaction well floor 240, sidewalls 202(c) and 202(d) converge toward the reaction well mid-line (or mid-plane). The cross-section of the reaction well can decrease towards the well floor 240. The lower segments of proximal endwall 202(a) and converging sidewalls 202(c) and 202(d) may intersect in a smooth curve. The radius of this curve decreases towards reaction well floor 240, thereby forming a segment of a frusto-conical surface defining culvert 211. The smooth walls of culvert 211 serve to funnel fluid towards reaction well floor 240. The culvert 211 directs fluid added from above the culvert toward the reaction well midline so as to engulf and induces turbulence to scour any materials localized on the lower proximal endwall. In some embodiments materials localized on the lower proximal endwall include magnetically responsive particles. The culvert 211 may also enhance mixing of reaction mixtures.

The faceted geometry of the reaction well 202 can permit effective mixing of reaction well contents using a modified tip mixing protocol. The system can mix by aspirating reaction well contents with the millitip 220 in or near the deepest portion of the reaction well 220. The system then redispenses the aspirated material with the millitip 220 nearer the proximal sidewall in a dispense position 234 (which may correspond to a first location in some cases), roiling and mixing the fluid. In some embodiments, the system redispenses the aspirated material with the millitip 220 onto the culvert 211, inducing turbulence while roiling and mixing the liquid. Particulates, such as microparticles, that have been deposited on the culvert may be suspended by such mixing. Such mixing actions may be repeated by re-aspirating the dispensed liquid and re-dispensing it. The system can aspirate from the reaction well using either a millitip or a microtip.

Aspirating with the millitip 220 at or near the deepest point minimizes dead volume. The angled floor of the reaction well 202 in this region prevents formation of a seal between millitip 220 and reaction well floor 240 that might otherwise block the millitip during aspiration. The intersections that define the bends between linear segments of the facets can serve to segregate volumes of liquid from materials localized within the culvert 211.

The culvert 211 also advantageously amplifies the scouring effect of added fluid to wet and resuspend solid phase materials. The narrowing and incurving shape of the culvert directs even small volumes of fluid with increased velocity to help resuspend magnetic materials previously pulled to the culvert's lower portion. The proximal first endwall 202(a) may curve outwards proximally in order to give the culvert an oval cross-section. This acts to contain materials localized against this portion of the proximal endwall in a defined area along the midline, enhancing the scouring action of added fluid and physically isolating such contained materials from small eluent volumes. This is particularly advantageous in the late steps of nucleic acid isolation when a small eluent volume is desirable.

FIG. 4(c)-2 shows a top plan view of another reaction well according to another embodiment. In FIGS. 4(c)-1 and 4(c)-2, like numerals designate like elements. In FIG. 4(c)-2, the culvert 211 is formed by relatively straight side boundaries, whereas the culvert 211 in FIG. 4(c)-1 has curved side boundaries.

In some embodiments, the external profile of the reaction well 202 closely tracks the cavity internal profile. That is, the walls 202(a)-202(d) are of relatively constant thickness and thin with respect to the size of the reaction well 202. In addition to the benefits discussed above, this advantageously improves thermal conduction between external heaters and reaction well contents. Better thermal conduction reduces the time for reaction well contents to reach desired temperatures, decreasing the length of processing and assuring more uniform conditions within the reaction well. More uniform conditions contribute to better repeatability in nucleic acid isolation and hence to more precise answers. Alternatively, the reaction well 202 may have walls of relatively uniform thickness but of reduced thickness in regions of contact with external heaters.

The faceted shape of the reaction well 202 also supports interaction with external magnets at either high or low fill volumes by providing an extended region for magnetic coupling. The extended region may be a facet of the reaction well 202 forming a segment of the proximal first endwall. The external surface of an endwall segment can be disposed at an acute angle with respect to the vertical axis of the reaction well. In some embodiments, the acute angle can be between about 20 degrees and about 70 degrees and in some cases about 35 degrees. This acute angle advantageously allows juxtaposition of either a relatively large magnet or a smaller magnet proximate the facet. Either size magnet so disposed sets up a magnetic field that collects and pellets magnetically responsive microparticles adjacent the interior reaction well first endwall 202(a) in the culvert 211. A smaller magnet can collect the magnetically responsive microparticles along the culvert surface near the bottom of the reaction well 202. A large magnet also collects the magnetically responsive microparticles along the culvert 211 but distributes them over a larger portion of the interior surface. The larger magnet may collect the magnetically responsive microparticles more rapidly, and the system can more readily resuspend the distributed pellet. Both of these attributes reduce processing time. The smaller magnet spatially limits the distribution of magnetically responsive microparticles so that addition of a small volume of fluid reaches essentially all of the smaller pellet. This is advantageous when the subsequent processing step adds only a small volume of fluid. This may occur, for example, immediately prior to elution of the nucleic acid where a minimal elution volume is desirable.

Figure 4F:
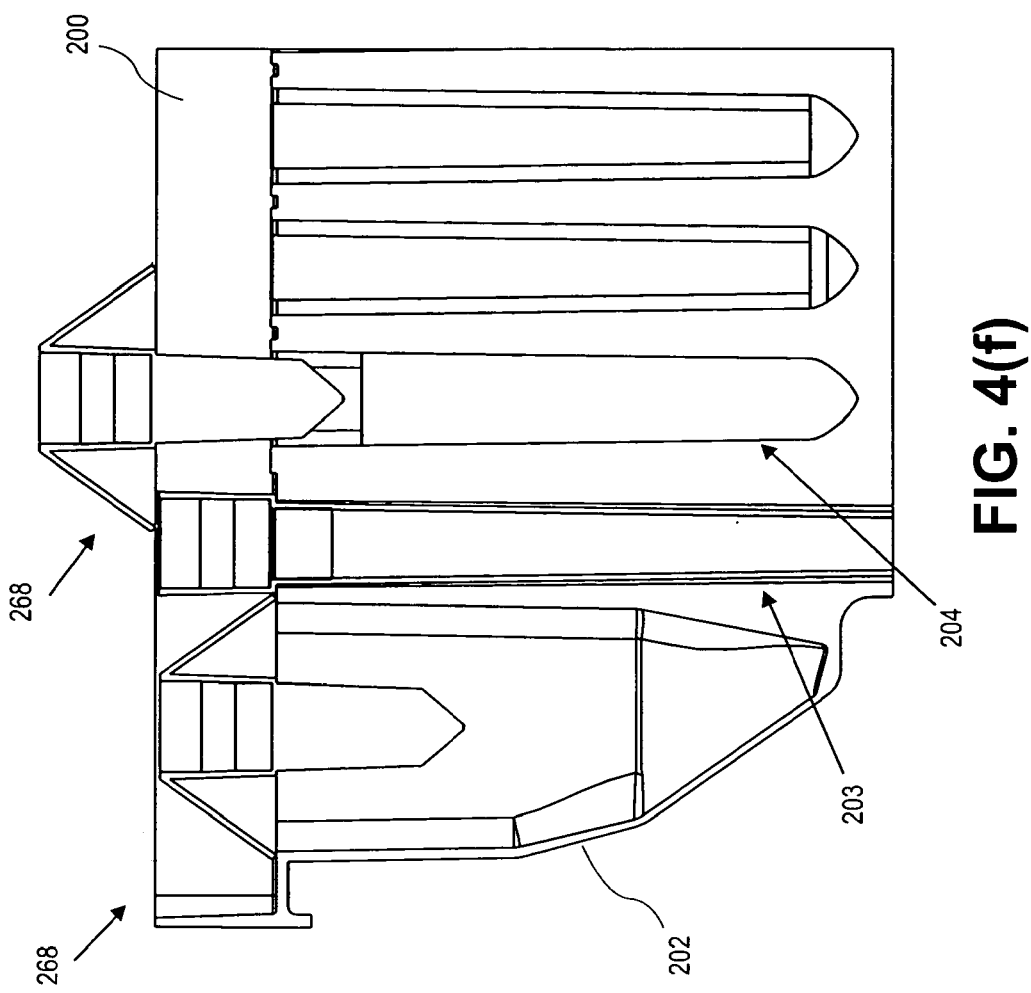
FIG. 4(f) shows a side, cross-sectional view of the film piercer in FIG. 4(d) as it is used with an assay cartridge.
Figure 4E:
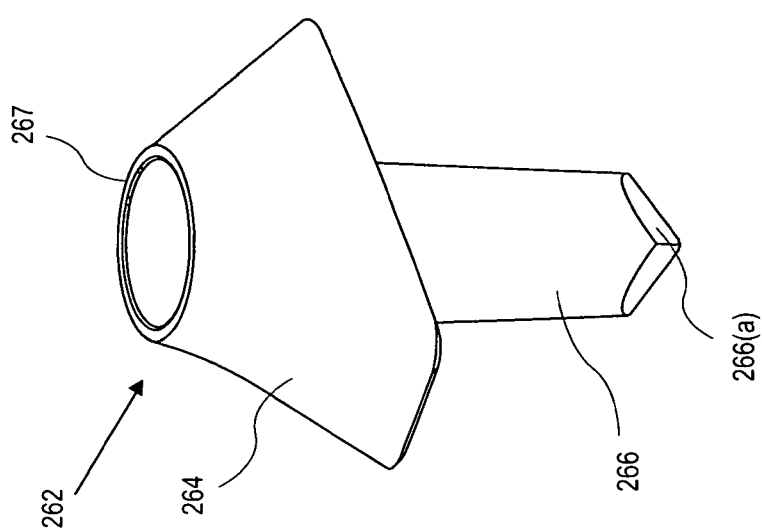
FIG. 4(e) shows a front perspective view of a film piercer according to an embodiment of the invention.
Figure 4J:
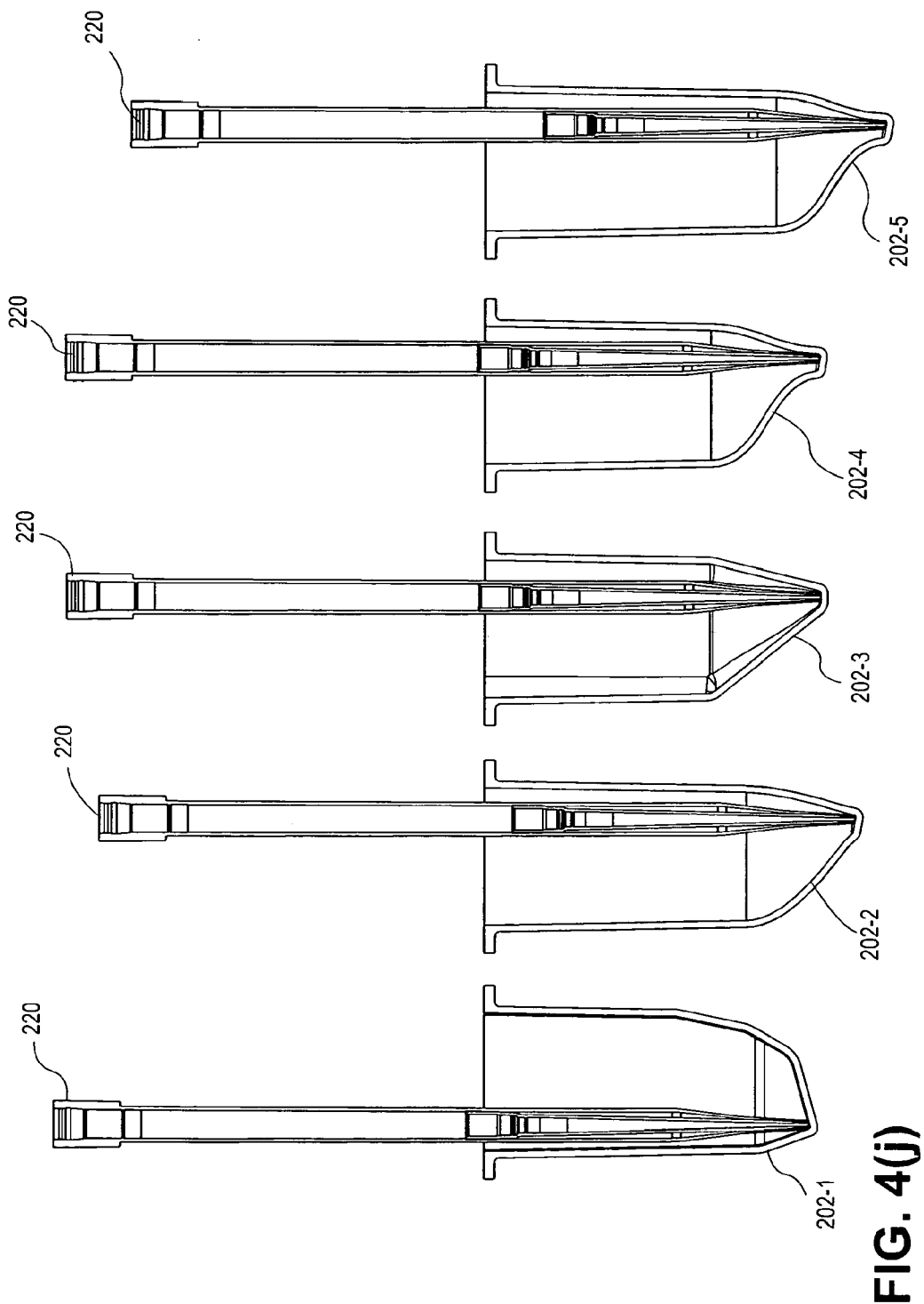
FIG. 4(j) shows a number of side, cross-sectional views of reaction well embodiments. A microtip is shown with each reaction well design.

FIG. 4(j) shows a number of side cross-sectional views of alternative reaction well embodiments 202-1, 202-2, 202-3, 202-4, 202-5. Each design has a different endwall configuration. A millitip 220 is shown with each reaction well design. Reaction well embodiment 202-1 has a configuration that is somewhat similar to the reaction well shown in FIG. 4(b). Reaction well embodiments 202-2, 202-3 have fewer angled portions in the endwall leading to the bottom than the reaction well embodiment 202-1. Reaction well embodiments 202-4, 202-5 show embodiments where endwall portions of the reaction wells are curved. Reaction well embodiment 202-4 is shorter and has less volume than reaction well 202-5.

The assay cartridge 200 may be made of any suitable material. For example, the assay cartridge 200 may comprise of a hydrophobic polymer, such as polypropylene. If this is the case, the interface between aqueous buffers and the assay cartridge can have a high angle of incidence. This high angle of incidence can localize the air/liquid interface of an appropriate volume of buffer along the line defined by an angular intersection between the culvert facet and an adjacent facet. This volume may be between about 1 microliter and about 100 microliters, and in a preferred embodiment is about 25 microliters. The assay cartridge 200 could alternatively comprise polyethylene, fluoropolymers, polystyrene, silicone, and copolymers thereof, and these and other materials could be applied as films or layers over other materials Assay cartridges may include a removable cartridge cover (not shown) to protect contents prior to use. Covers may be made of plastic, paper or cardboard that fit on or near the top of a containment wall of the assay cartridge. The cover advantageously reduces the possibility of contamination during storage and handling. In some embodiments, the user removes the cartridge cover at about the time she loads assay cartridges into the system. Alternatively, assay cartridge packaging may integrate the cartridge cover such that removal of the assay cartridge from the packaging also removes the cartridge cover. The cartridge cover may adhere to the assay cartridge by a snap fit or similar method but in some cases, the cartridge cover forms a "tear-off" strip adhered to the top of the skirting walls. A flexible barrier material such as paper, Tyvek®, or a polymer film can form the body of the tear-off strip. Adhesion of the tear-off strip to the skirting walls may be by any of a variety of techniques such as adhesive bonding or ultrasonic welding, and is in some cases thermal bonding. In use, a user may simply peel the tear-off strip from the assay cartridge. Optionally, the cartridge cover may include preprinted instructions or other information.

Referring to FIG. 4(d), the assay cartridge 200 includes features to facilitate handling and automation. These features include surfaces controlled during manufacture to establish one or more positioning references, support tabs 218 to support the assay cartridge 200 during storage and to position an assay cartridge during processing, a cartridge flange to retain the assay cartridge during withdrawal of a pipette tip, a detection feature (see element 210 in FIG. 4(a)-1) to discriminate adjacent assay cartridges, asymmetric features to prevent inverted loading of assay cartridges, keying features to distinguish types of assay cartridges, and marking elements to transfer information related to assay cartridges.

Controlled surfaces facilitate assay cartridge position by providing reference locations that the manufacturing process holds to tight tolerances. In some embodiments, one controlled surface is the vertically disposed edge of the vertical web at the distal end of the assay cartridge. The bottom surface of the horizontal web may be a controlled surface.

FIG. 4(d) shows an end of the assay cartridge 200 with a support tab 218, which engages a propelling feature 303 of a cartridge carriage.

In embodiments of the invention, a pair of support tabs 218 may support the assay cartridge 200 on the system. Support tabs 218 protrude from either end of the assay cartridge, and each support tab 218 includes a horizontal element and a vertical element. Parallel rails within the system (e.g., within a cartridge loading unit) may retain the assay cartridges by providing support for the horizontal elements from below. The vertical elements extend downward from the horizontal elements. Similar spacing of the vertical elements and of the parallel rails aligns the assay cartridges on the parallel rails. In some embodiments, the vertical elements are further from the assay cartridge midpoint than are the horizontal elements. That is, the horizontal elements extend peripherally from the assay cartridge and terminate in the vertical elements. This has the benefit of preventing a misaligned assay cartridge from falling between the parallel rails.

The support tabs 218 may also position the assay cartridge during processing within the processing lanes. While the system may push or pull assay cartridges from either end, avoidance of tolerance stackup favors pushing or pulling consistently from a single end. Accordingly, assay cartridges may have a more robust support tab at one end to provide greater rigidity for this more demanding use. In some embodiments, this more robust support tab integrates a vertical I-beam structure into the vertical element and connects it to the bottom of the most distal compartment. The support tab 218 on the distal end of the assay cartridge 200 depends from the assay cartridge a small distance distal to the controlled surface defining a gap. Support tabs 218 on the assay cartridge may also be used to support the assay cartridges when held within packaging. The gap between the support tab 218 and the distal surface of the assay cartridge 200 may also be tapered to facilitate transfers of the assay cartridge within the system.

The assay cartridge 200 can also include features to retain the assay cartridge during withdrawal of a pipette tip. Such features may be of particular benefit when the system removes a pipette tip 220 from a reagent well covered by a barrier film 205. Assay cartridge retention features are also useful when using the piercer to penetrate the seal over the compartments. As discussed above, the barrier film 205 may include components that exert friction on a pipette tip 220 as the system withdraws the pipette tip from the reaction well. Without features to retain the assay cartridge 200, the pipette tip 220 may lift the entire assay cartridge 200 from its support, displacing it or causing splashing and subsequent spills when the assay cartridge 200 drops back down to the support. The barrier film 205 may also contain brittle or rigid components, such as foils, that hold the hole in the film open after piercing so as to not interfere with subsequent pipetting operations.

In some embodiments, the assay cartridge 200 includes a cartridge flange disposed on at least one edge of the assay cartridge 200. Such a cartridge flange may be an extension of the horizontal web extending beyond the skirting wall for at least a portion of the length of the assay cartridge. The cartridge flange may protrude at a height slightly lower than the horizontal web to support closer packing of assay cartridges when disposed side by side. In some embodiments, the cartridge flange extends substantially the entire length of the assay cartridge. The system may also or alternatively use some other feature, such as the top of the skirting wall, to retain the assay cartridge. The presence of the cartridge flange also supports manual handling of multiple assay cartridges.

Assay cartridges may include detection features 210 to discriminate adjacent assay cartridges when the instrument stores multiple assay cartridges together. The purpose of such detection features 210 is to permit the instrument to sense the presence of loaded assay cartridges within the loading area. For example, the first and second longitudinal walls 206, 207 can extend around the entirety of the assay cartridge 200 above the horizontal web 228. The first and second longitudinal walls 206, 207 may determine the separation distance between assay cartridges when disposed side by side such that an external sensor responsive to the longitudinal wall at one end of the assay cartridges might not readily distinguish one assay cartridge from another. In some embodiments, the longitudinal wall at the distal end has reduced extent compared to the distance between longitudinal walls along the assay cartridge sides. The distal end portion of the longitudinal wall may include two or more segments, where one segment is disposed at or near the distal end of the assay cartridge and other segments are disposed inward of the distal end. The segments can connect to each other by short transverse segments of longitudinal wall disposed generally parallel to the assay cartridge axis. This segmented geometry retains the complete containment of the longitudinal wall and allows an external sensor placed near the distal end to discriminate the segment disposed near the distal end from the rest of the assay cartridge.

Assay cartridges may include asymmetric features to prevent a user from inadvertently loading assay cartridges backwards, i.e. end-for-end reversed. The system may include features in the assay cartridge loading area complementary to these asymmetric features but not complementary to a reversed assay cartridge. Thus, the assay cartridges may only fit in one orientation in the loading area. Assay cartridge asymmetric features may be a natural consequence of the distribution of differently sized and shaped compartments. For example, the millitip pipette tip has sufficient capacity to transfer the content of a reagent well in a single aspiration, but the millitip diameter can be less than the reagent well diameter in order to reach the reagent well contents. The millitip can therefore be longer than the depth of the reagent well, and the compartment within the assay cartridge that supports the millitip is thus deeper than the reagent well. Since each assay cartridge includes a single millitip pipette tip, and since the millitip may be adjacent the reaction well near the proximal end of the assay cartridge, the assay cartridge may have greater height near its proximal end than near its distal end. Alternatively, the vertical web of the assay cartridge may have an asymmetrical shape.

Assay cartridges may include keying features 224 to distinguish types of assay cartridges during user loading of assay cartridges within the loading area. The purpose of this keying is to avoid inadvertent misloading of different assay cartridge types. The keying prevents assay cartridges of one type from fitting into a portion of the loading area designated for a second type. In some embodiments, the keying features are rectangular cutouts at the bottom of the vertical web. The position of the cutouts along the length of the assay cartridge may be unique for each assay cartridge type.

Assay cartridges may include marking elements to transfer information. Marking may include machine readable information in any of a variety of forms such as a barcodes, dot codes, radio frequency identification tags (RFID) or direct-reading electronic memory. In addition, human readable information such as text or illustrations may also be present. In some embodiments, each assay cartridge includes a barcode on the vertical web and text on the vertical web, on the longitudinal walls, and on the removable cover. The marking may include information about assay cartridge type, manufacturing information, serial numbers, expiration dates, use directions, and similar information.

Assay cartridges can contain at least some reagents used in isolation and purification of nucleic acids. Assay cartridges may also contain some reagents used in amplification and detection. Among the reagents may be wash fluids, buffers, diluents, eluents, microparticles, enzymes, cofactors, or other reagents. In some embodiments, the system first uses materials from reagent wells nearest the reaction well. When removing wastes, the system first deposits waste material in empty wells closest to the reaction well. This advantageously reduces the possibility of contamination, as droplets falling from a pipette tip can only fall into wells that the system has already used.

During processing, assay cartridge compartments contain in-process materials. Although most in-process materials reside in the reaction well, others, such as neat or diluted samples, reconstituted reagents, eluted nucleic acids, wastes, or others, may reside in other compartments at various times during processing. Among the wastes retained may be liquid wastes such as expended reactants and solid wastes such as expended pipette tips. Placement of the millitip holder next to the reaction well reduces the chances of contamination of open reagent wells by the millitip, as it is placed in the millitip holder after processing contents of the reaction well potentially contaminating drips fall into bottom of millitip holder on ejection of the millitip.

In some embodiments, the system uses materials from reagent wells in a sequence that is roughly based on the position of the reagent wells in the assay cartridge. The system may limit transfers (other than tip mixing) to a single aspiration from each reagent well in order to avoid use of material possibly contaminated by an earlier aspiration. The system may first use materials from reagent wells nearest the reaction well. When removing wastes, the system first deposits waste material in empty wells closest to the reaction well. This sequencing of well usage advantageously reduces the possibility of contamination. Any drips falling from the pipettor can only fall in wells that the system has already used.

Prior to loading on the system, assay cartridges may be stored in transport boxes. A transport box retains several assay cartridges in common orientation, grouped for easy grasping of several at a time to load. In some embodiments, transport boxes include a supporting base, labeling, and a clamshell lid to protect the assay cartridges during handling. Storage slots in the supporting base may group assay cartridges as two sets of three to five with a gap in between the sets. Manufacturing processes useful for producing transport boxes include at least plastics thermoforming and plastics injection molding.

Some embodiments of the invention are also directed to a disposable film piercer. As noted above, the assay cartridge 200 has a barrier film 205 that lies over and seals the reagent wells 204, 208, 209 prior to use. The millitip 220 pipette tip can be used to penetrate the film. The millitip 220 can have features incorporated into the tip to equalize the air pressure as it pushes through the barrier film 205. In some instances, this could cause contamination problems. For example, in protocols where the millitip first draws patient sample; some residual sample may be retained on the exterior surface of the millitip and in pressure equalizing features. When the film 205 is subsequently penetrated by the millitip the initial stretching of the film pressurizes the interior of the sealed well. This may generate a small burst of air that exits around the exterior of the millitip on actual penetration, which may atomize such residual sample. It is possible that the patient sample could be spread beyond its intended area. To help solve this problem, some embodiments of the invention can use a separate film piercer.

FIG. 4(e) shows a perspective view of a film piercer 262 according to an embodiment of the invention. As shown, the film piercer 262 comprises a linear piercing element 266 comprising a piercing element end 266(a), which is sharp, and a pipette mandrel interface 267. The pipette mandrel interface 267 can define an aperture that can receive a pipette mandrel. A skirt 264 may be coupled to the piercing element 266. The pipette mandrel interface, piercing element 266, and the skirt 264 may be a single unitary piece. In some embodiments, the piercer 262 may comprise an injection molded plastic material or the like. The skirt 264 of the film piercer 262 can also act as a contamination cover for the reaction well.

The film piercer 262 can include a pyramidal blade, with sharp edges that slice through the film as it is moved vertically. Other possible configurations, such as a square cross-section or overall conical shape with a sharp tip are possible. Suitable materials for the film piercer 262 may be similar to those noted above for the pipette tips, and can include conductive polymers that permit detection by a liquid sensing circuit. It can also include a handling feature, which is configured to interface with a pipetting device that is normally used with the millitip.

FIG. 4(f) shows a film piercer 262 as it is used with an assay cartridge 200. As shown therein, the film piercer 262 can pierce a barrier film, and the piercing element can be sized to fit within a reagent well. The skirt 262 may have bottom lateral dimensions that are larger than the area defining the top of the reaction well. As shown in FIG. 4(f), the skirt 262 may allow the piercer to sit on top of the reaction well. In some embodiments, the film piercer 262 can have features that retain it in the assay cartridge 200 during handling, including mechanical features that provide an interference fit, snap fit, or friction fit. The film piercer 262 may also be retained in the assay cartridge 200 using an adhesive.

In use, the film piercer 262 can be manipulated using a pipette mandrel, which is inserted into the pipette mandrel interface 267. In a preferred embodiment, the sample millitip pipettor 704 is used to manipulate the film piercer 262. Following acquisition by the pipette mandrel, the film piercer is directed downwards at a controlled rate to bring the piercing element 266 into contact with the barrier film 205 that overlies at least one of the reagent wells of the assay cartridge 200. In one embodiment, the barrier film 205 overlaying each reagent well is pierced in one series of operations. In alternative embodiments, the barrier film 205 over a portion of the reagent wells may be pierced in one series operations and the assay cartridge 200 returned following intervening steps for piercing of additional portions of the barrier film 205.

The film piercer 262 may be disposed of by ejecting it in a manner similar to a pipette tip, as described above. In one embodiment, the film piercer 262 is ejected into a position on the assay cartridge 200, and is eventually disposed of on disposal of the spent assay cartridge 200 following sample processing. In another embodiment, the film piercer 262 is disposed of by moving the pipettor carrying the film piercer 262 to a designated waste disposal chute that leads to a solid waste container 92. Such a waste chute may be located within the path of the sample pipettor 700. The film piercer 262 may be ejected into this waste disposal chute by moving a pipette mandrel carrying it through a passive stripping device oriented to direct the film piercer 262 to a waste disposal chute. This advantageously permits slow and gradual removal of the film piercer 262, minimizing the chance of accidental uncontrolled release of this sharp device.

FIG. 4(g) shows a portion of an assay cartridge 200 with a vessel base 246 and a vessel plug 246 disposed within reaction vessel component holders 219. FIG. 4(h) shows a top plan view of a cartridge cover 229 that is on the assay cartridge 200. FIG. 4(i) is a bottom perspective view of the cartridge cover 229. In this embodiment, a cartridge cover 229 is present and may be configured to fit on top of the portion of the assay cartridge 200. The cartridge cover 229 may comprise a cover main portion 229 which may be substantially planar. It may also comprise a cover protrusion 229(a) that fits within the vessel base 246 when it is on the assay cartridge 200. As shown, the cartridge cover 229 may extend to the first transverse wall 213 of the assay cartridge 200 to an end of the assay cartridge 200, while being laterally coextensive with the longitudinal walls of the assay cartridge 200. In some embodiments, a similar cover may be used to protect the reaction well 202 without incorporating the piercing function of the film piercer 262.

Referring to FIG. 4(h), the cover protrusion 229(b) can define a hollow recess 229(b)-1 at the top of the cover 229. The hollow recess 229(b)-1 may serve as a handling feature, which can allow a device, such as a pipettor or other device to manipulate the cover 229.

Referring to FIGS. 4(g) and 4(i), four corner fitting elements 229(c) can be positioned around the cover protrusion 229(b). This corner fitting elements 229(c) can be used to position the cover in a vessel component region 231, which may merge into the reaction vessel component holders 219.

The cartridge cover 229 may be made of any suitable material and may have any suitable configuration. For example, it may include any suitable molded plastic material. It may also include any suitable number of protrusions (e.g., two or more), and may have any suitable lateral and longitudinal dimensions.

The cartridge cover 229 may be advantageously used to cover the vessel base 246 and the vessel plug 246 during processing, so that they are protected from potential sources of contamination.

Embodiments of the invention may also comprise a pre-cut plastic retention film that surrounds the edges of the compartments holding the reaction vessel base and reaction vessel plug, which provides enough friction to hold these items in place during handling while permitting them to be removed easily using a pipettor mandrel.

E. Reaction Vessel

FIG. 5 shows one embodiment of the invention, which can be directed to a reaction vessel 221 for real time PCR. In some embodiments, the reaction vessel 221 can be an amplification vessel, a PCR reaction vessel, or a PCR vessel. The reaction vessel 221 may be sealed or unsealed. Specifically, FIG. 5(a) shows a top perspective view of a reaction vessel 221 according to an embodiment of the invention. FIG. 5(b) shows an exploded view of a reaction vessel according to an embodiment of the invention. FIG. 5(c) shows a perspective, cross-sectional view of a reaction vessel according to an embodiment of the invention.

Figure 5B:
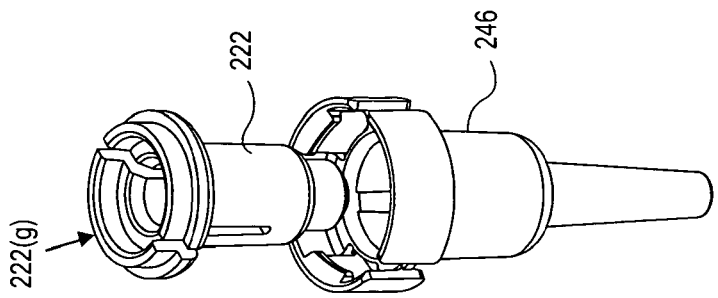
FIG. 5(b) shows an exploded view of a reaction vessel according to an embodiment of the invention.
Figure 5A:
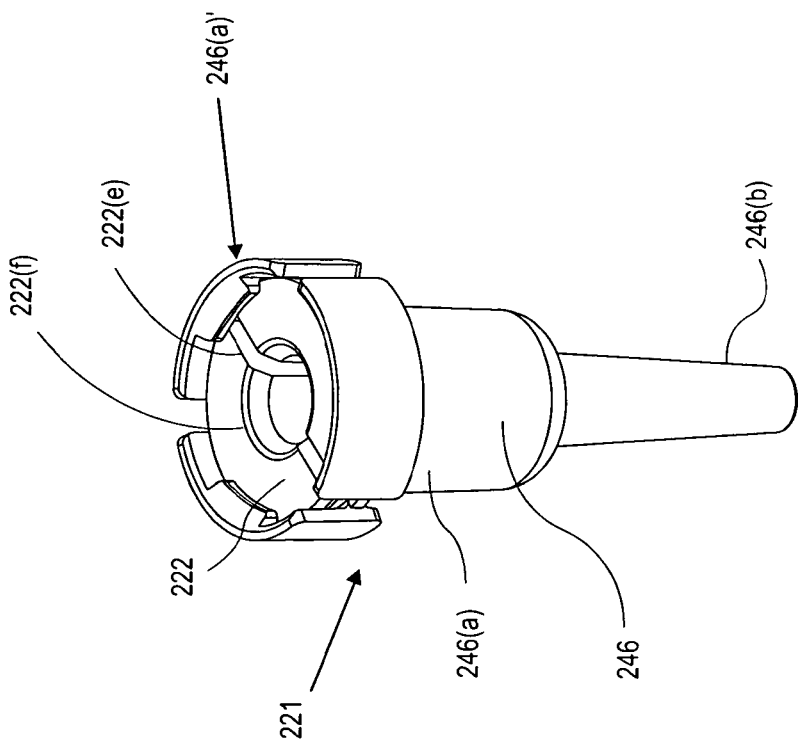
FIG. 5(a) shows a top perspective view of a reaction vessel according to an embodiment of the invention.

As shown in FIG. 5(a), the reaction vessel 221 can be a two-part container used to contain the amplification mixture during nucleic acid amplification and detection. Each part resides in a separate compartment within the assay cartridge (see FIG. 4(a)-1). Alternatively, reaction vessel bases 246 and plugs 222 may be provided in racks similar to the microtip racks 550 described below. The reaction vessel 221 includes a vessel base 246 and a vessel plug 222. The system loads the vessel base 246 with amplification mixture and then seats the vessel plug 222 onto the vessel base 246. The amplification mixture may comprise a mixture of processed sample and enzymes, primers, probes, and other materials needed for nucleic acid amplification. Once the vessel plug is seated, the vessel plug 222 locks to the vessel base 246 and seals the amplification mixture within the assembled reaction vessel 221. The reaction vessel 221 can remain sealed and locked through completion of the assay to reduce the risk of contamination. In an alternative embodiment, the vessel base 246 and the vessel plug 222 may be provided as a single unit, with the two portions joined by a flexible tether.

Figure 5C:
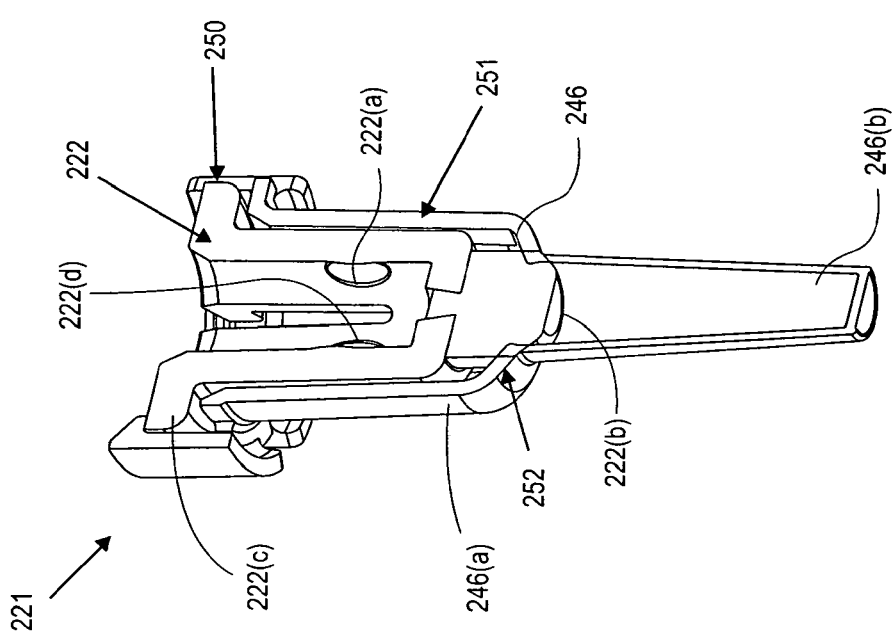
FIG. 5(c) shows a perspective cross-section view of an embodiment of the invention.
Figure 5D:
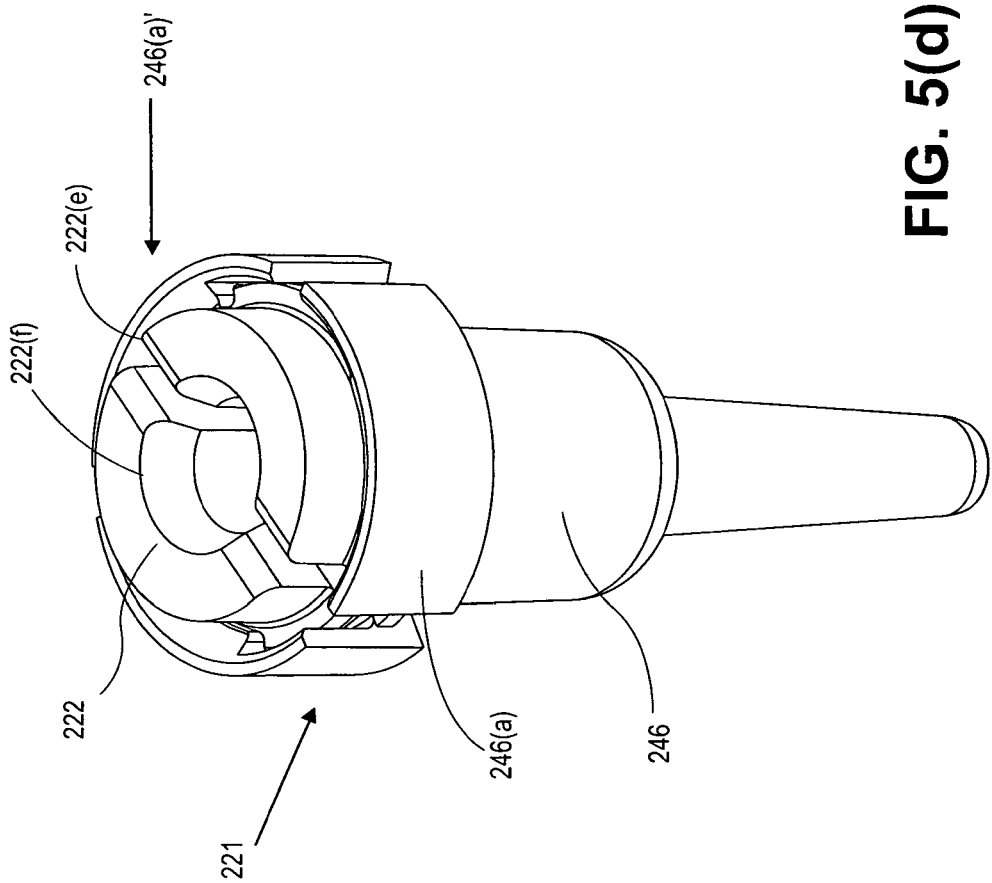
FIG. 5(d) shows a perspective view of a reaction vessel according to another embodiment of the invention.

Referring to FIGS. 5(a), 5(b), and 5(c), the reaction vessel 221 can include a radially symmetrical reaction base 246, and a vessel plug 222. The reaction base 246 can comprise an upper vessel base portion 246(a) that receives the vessel plug 222 and a lower vessel base portion 246(b), which can be a lower portion of the vessel base. The lower vessel base portion 246(b) opens into the upper (cylindrical) vessel base portion 246(a) and comprises a frustum of a conical shape. The terms "lower" and "upper" can refer to the relative positions of the portions of the vessel base, when the vessel base is used in the system. The vessel plug 222 may also include a handling feature 222(f). The handling feature 222(f) can comprise a cylindrical enclosure configured to receive a pipette mandrel (not shown).

The symmetrical nature of the base 246 can allow the system to place the reaction vessel in an arbitrary orientation about the axis of the reservoir region. That is, when a radially symmetric vessel is placed into a complementarily shaped cavity, unlike a vessel with a rectangular cross-section, it does not matter how the vessel is oriented, as long as the primary axes of the reaction vessel and the cavity are aligned.

The reaction vessel 221 may include any suitable number or types of distinct features or materials. For example, the material forming the base 246 and/or plug 222 may include a material that has the following characteristics: a thermal conductivity greater than about 0.1 W/m·K; a Young's modulus of about 1.5 GPa to about 2 GPa; and a frictional coefficient of less than about 0.25. The material may comprise a polymer such as polypropylene and it may have elastomeric properties with a hardness ranging from 20 to 50 durometer (Shore) A, and it may also be conductive. In one embodiment, the polymer has a hardness of about 30 durometer (Shore) A. Suitable materials for the vessel base can be transparent as well as translucent. Other suitable alternative materials for the vessel base may include polyethylene, polystyrene, polyacrylate, polycarbonate, silicone, and copolymers and blends thereof.

The base 246 may also include any suitable geometry or features. For example, in some embodiments, the lower vessel base portion 246(b) of the vessel base 246 has a geometry where the walls (in a cross-sectional view as shown in FIG. 5(c)) form an angle between about 4 degrees and about 8 degrees, or about 6 degrees. Further, the lower vessel base portion 246(b) may include a volume of about 10μ L to about 70μ L, and a terminus of the lower portion 246(b) of the reaction vessel base 246 can have an optical window. A wall thickness of the lower portion 246(b) may be about 0.0005 inches to about 0.02 inches.

In some cases, the upper vessel base portion 246(a) comprises a latching feature 246(a)' that engages the plug 222 on insertion, so that the latching feature 246(a)' irreversibly secures the plug 222. In this example, the latching feature 246(a)' may be the latching portion. The plug 222 can form a seal that is resistant to a pressure of at least about 50 psi when the plug 222 is engaged in the upper vessel base portion 246(a) of the reaction vessel base 246. The latching feature 246(a)' of the upper cylindrical portion can comprise one or a plurality of flexible locking tabs, which may be in the form of ridges, where the flexible locking tabs project downwards and centrally, displace outwards on initial insertion of the plug 222, move centrally on seating of the plug 222 in the reaction vessel base 246, and engage the plug 222 on moving centrally.

The latching feature 246(a)' of the upper cylindrical portion 246 can comprise a circumferential ridge, where it projects centrally. It may also expand radially on initial insertion of the plug 222. It may also contract radially on seating of the plug 222 in the reaction vessel base 246. The circumferential ridge engages the plug on radial contraction of the upper cylindrical portion of the reaction vessel base 246. The latching feature 246(a)' of the upper vessel base portion 246(a) can also comprise a plurality of arcuate ridges, wherein the arcuate ridges project centrally. The upper vessel base portion 246(a) of the reaction vessel base 246 can expand radially on initial insertion of the plug 222, can contract radially on seating of the plug 222(f) in the reaction vessel base 246, and can engage the plug 222 on radial contraction of the upper vessel base portion 246(a) of the reaction vessel 221.

In some embodiments, plug 222 comprises a block of elastomer with a diameter greater than that of the opening of the lower portion of the reaction base. It may also include a handling feature 222(f), which may comprise an inner surface, an outer surface, and a longitudinal groove 222(e). A cylindrical enclosure of the handling feature 222(f) can have an internal diameter of about 0.125 to about 0.4 inches in some embodiments, and the inner surface of the cylindrical enclosure can comprise a plurality of projections 222(d) (such as protrusions), which can be hemispherical.

The vessel base 246 can be further characterized to include a reservoir region and a locking region. The locking region may correspond to the upper vessel base portion 246(a), while the reservoir region may correspond to the lower vessel base portion 246(b). The reservoir region holds the amplification mixture, and the locking region cooperates to lock and retain the vessel plug 222 once seated.

The vessel base 246 may be made of any suitable material. A suitable material for the vessel base 246 is a translucent polymer capable of withstanding the elevated temperatures and pressures of the amplification process and compatible with its chemical conditions. Suitable materials include PD702 polypropylene homopolymer manufactured by LyondellBasell Industries of Rotterdam, The Netherlands.

The reservoir region corresponding to the lower vessel base portion 246(*b*) may include a thin-walled, truncated cone that holds up to about 50 microliters of amplification mixture. In some embodiments, the reservoir region is a frustum of a cone, a shape that serves to improve thermal contact between the reservoir region and a thermal cycler heat block. The conical shape improves thermal contact with a complementarily formed region of the heat block both at the macroscopic scale and at the microscopic scale. At the macroscopic scale, the conical shape reduces tolerance requirements by using a single extended surface for alignment. At the microscopic scale, the conical shape permits simple downward pressure to increase asperity contact over the full surface. Improved thermal contact decreases the response time to temperature changes and hence decreases the length of each thermal cycle. Shorter thermal cycle length may have a beneficial effect on the total time to produce results, as the thermal cycle may repeat many times during each assay.

The reservoir region's conical shape may have a small opening angle. That is, the sides are close to parallel with the axis of the reservoir region. A small opening angle provides a conical volume where each element of volume along the axis is relatively equidistant from the nearest wall. Since the elements of volume along the axis are the most distant from the walls, and since thermal transfer decreases with distance, these elements are the last to reach target temperature. A small opening angle improves temperature uniformities along the axis by assuring that each axial fluid element has about the same thermal distance from the wall as each other axial fluid element. Improved temperature uniformity may directly contribute to assay precision by reducing variations between regions in the amplification mixture. In some embodiments, the opening angle is less than about 15 degrees and in some cases is about 6 degrees.

In some embodiments, a substantially flat bottom surface truncates the conical portion of the reservoir region. The flat bottom portion of the reservoir region can be an optical window that can be used for monitoring or characterizing vessel contents. For example, the flat bottom may be an optical window for excited or emitted light to enter the reaction vessel or for emitted light to leave the reaction vessel 221. In some embodiments, the circumferential edge of the bottom of the reservoir region extends slightly beyond the exterior surface of the flat bottom to recess the bottom surface. The recessed surface may reduce the likelihood of damage to the optical window in handling. Alternatively, the bottom surface may curve to act as the bounding surface of a lens. Such a lens may focus light in a desired pattern within the reaction vessel 221 or may enhance collection of light from within the reaction vessel in embodiments where the optical window collects emitted light from the reaction vessel 221.

The reservoir region can be thin-walled to support intimate thermal contact between the reservoir region contents and external heaters. Like the bottom portion of the reservoir region, the side walls of the reservoir region can also be an optical window that can be used for monitoring or characterizing vessel contents. In some embodiments, the reservoir region wall thickness is as thin as practical based on strength of the materials used, on production process considerations, and on uniform clarity. The wall material can be strong enough to withstand elevated pressures and temperatures during amplification. The wall may soften and deform during amplification, possibly causing it to conform to and adhere to the thermal cycler heat block. The wall material can have sufficient strength such that, once so deformed, the system may detach the reaction vessel from the heat block without rupturing the reaction vessel 221.

As noted above, since the system samples emitted light through the wall of the reservoir region, any portion of the wall in a band at the light sampling height may act as an optical window. The production process controls mold filling to maintain optical uniformity throughout this band. Using injection molded polypropylene, the reservoir region wall thickness can be less than about 0.50 mm and in some cases about 0.10 mm, or less.

In some embodiments, amplification monitoring involves providing excitation light illuminating the amplification mixture and detecting emitted light that the amplification mixture produces in response to the excitation light. At least the vessel base 246 is at least partially transparent or translucent to both excitation light and emitted light in order to allow monitoring of amplification progress. Both excitation and emitted light need to traverse the vessel base wall; the translucent nature of the vessel base 246 wall makes this possible. Any other suitable part of the reaction vessel may also be transparent or translucent.

Additional considerations relevant to wall material selection include chemical compatibility, cleanliness, compliance, and cost. Wall materials can be chemically compatible with reaction conditions. In some embodiments, wall materials have at least some compliance to improve thermal contact when pressed into the thermal cycler. Such compliance may also help in locking the vessel base to the vessel plug. A variety of polymers, including polyolefins, polystyrene, PEEK, fluorocarbon polymers, and other polymers may be suitable. In a preferred embodiment, the wall material is polypropylene. Reaction vessel materials can be free of contaminants that might interfere with amplification or detection reactions. This may be accomplished by using only virgin materials in the manufacture of the reaction vessel, by eliminating unprotected handling of either reaction vessel components or of equipment used in their production, and by treatment of equipment with materials that destroy potential contaminants. In some embodiments, the vessel may comprise a polymer such as PD702, which is a high flow, controlled rheology polypropylene homopolymer resin.

Other embodiments of the invention are directed to the process of making the reaction vessel. In some embodiments, the reaction vessel base is made by injection molding. This is usually performed by injecting the plastic at a position where the thickness of the molded part is greatest and allowing it to flow to where the thickness is least, however, the thin sections may produce high resistance to molten polymer flow in plastics injection molding. Such high flow resistance may contribute to incomplete filling, particularly when parts mix thick and thin sections. The reaction vessel can be formed by injecting the fluid plastic through a gate corresponding to the lower terminus of the vessel, where the walls are thinnest. This avoids problems often seen in conventional injection molding methods, where thin sheets of rapidly cooling plastic fail to blend completely and form partially opaque or mechanically weak areas.

The locking region of the vessel base 246 connects to the reservoir region and is annularly disposed upward and outward of the reservoir opening. In some embodiments, the locking region and the reservoir region form a single integrated part made of a single material in a single forming process. The locking region may include a plug receiving portion 251, a sealing portion 252, and a latching portion 250.

The sealing portion 252 extends upward and outward from the reservoir region, connecting the reservoir region to the plug receiving portion 251 of the locking region. The sealing portion 252 acts as a transition to the larger diameter plug receiving portion 251 and provides a sealing surface for the vessel plug 222 to seal against. The sealing portion 252 may form a conical annulus flaring out from the reservoir region and continuing as the walls of the plug receiving portion. The internal angle of the conical annulus is greater than 90 degrees and in some cases about 120 degrees. In some embodiments, the sealing portion 252 has thicker walls than the reservoir region to resist deformation while sealed. In some cases, the sealing portion walls are about twice the thickness of the reservoir region walls. The sealing portion 252 merges into the reservoir portion in a smooth transition, including a slight overhang so that the diameter of the opening in the sealing portion annulus is smaller than the diameter of the upper portion of the reservoir portion. The overhang can be sufficiently small such that the production process may "bump" the parts from the mold. In some embodiments, the overhang is less than about 0.1 mm and in some cases about 0.06 mm. This overhang advantageously deforms the elastomeric seal of the vessel plug 222 to more tightly seal the reaction vessel.

The seal made by the plug 222 when it is inserted into the vessel 221 can be characterized as a hybrid seal, having characteristics of both a radial seal (such as an O-ring) and a face-to-face seal (where a seal is simply pressed against a surface).

The plug receiving portion 251 of the locking region may extend upwards from the sealing portion 252 to form a roughly cylindrical segment coaxial with the reservoir region and with the sealing portion 252. The segment may taper outward towards the top for easy mold release. The purpose of the plug receiving portion 251 is to connect the sealing portion 252 to the latching features and to retain the plug body portion of the vessel plug 222. The distance between the portion of the vessel plug 222 that engages the latching portion 250 and the vessel plug's elastomeric seal determines the length of the plug receiving portion 251; the plug receiving portion 251 can be long enough to allow the vessel plug to engage into the locked position with sufficient compression of the elastomeric seal to adequately seal the reaction vessel 221. The plug receiving portion 221 couples at its top to the latching portion.

The latching portion 250 cooperates with engagement features on the vessel plug 222 to lock and retain the vessel plug 222 to the vessel base 246. The latching portion 250 may extend outward and upward from near the top of the plug receiving portion 251 as a base flange connecting to a substantially cylindrical side wall. The side wall may extend slightly below the base flange. Vertical cuts may divide the cylindrical side wall into two or more sections to increase radial flexibility. In some embodiments, three vertical cuts divide the cylindrical side wall into three symmetrical sections. Each section may include a circumferentially disposed medial portion flanked by symmetrical lateral portions. Each medial portion may include a latching feature 246(a)' projecting inward from the cylindrical side wall. The upper surface of the latching feature 246(a)' can slope downward towards the part center to allow the vessel plug 222, as it enters, to deflect the cylindrical side wall outward. The lower surface of the latching feature 246(a)' is substantially perpendicular to the axis of the vessel base 246. Once the engagement feature (corresponding to the vessel third plug portion 222(c)) of the vessel plug 222 descends below the lower surface of the latching feature 246(a), the cylindrical side wall recovers by snapping back towards the centerline. This snap back action traps the engagement feature of the vessel plug 222 beneath the lower surface of each latching feature 246(a)'. In an alternative embodiment, the cylindrical side wall of the latching portion 250 is not divided by vertical cuts, and a circumferential ridge extends medially to form an annular latching feature. In a second alternative embodiment, the cylindrical side wall of the latching portion 250 is divided into a plurality of symmetrical sections, each section having a latching feature 246(a)' that is continuous with the upper rim of the cylindrical side wall and that extends both medially and towards the vessel base 246. These latching features 246(a)' are deflected outwards as the vessel plug descends through the latching portion, and recover by snapping back towards the center line as the vessel plug descends below the lower surface of the latching feature. This snap back action traps the engagement feature of the vessel plug 222 beneath the lower surfaces of the latching features 246(a)'.

Relief openings can pierce the flange connecting the side wall to the plug receiving portion 261. The relief openings underlie each latching feature 246(a)' to prevent undercuts in the vessel base and avoid more complex mold operations. The remainder of the flange connects to the side wall and may continue as the lateral portions of the side wall sections. These lateral portions provide stiffness to produce the snap back action that engages the vessel base 246 to the vessel plug 222.

In some embodiments, the upper opening of the latching portion 250 includes an inward and downward facing chamfer contiguous with the upper surface of the latching feature. This chamfer helps to center the vessel plug 222.

The vessel plug 222 closes and seals to the vessel base to retain reaction vessel contents. This seal may be resistant to pressures of up to 50 pounds per square inch. Retention is desirable both to prevent evaporative loss that might alter concentrations during amplification and to prevent amplified nucleic acid from contaminating other assays. In an embodiment, the vessel plug 222 includes an elastomeric seal and a plug body that supports the elastomeric seal. In an alternative embodiment, the sealing surface of the reaction vessel base 246 incorporates an elastomeric O-ring and the seal is formed by closure of the vessel plug 222 against this O-ring. In another embodiment, the sealing surface of the reaction vessel base 246 and the vessel plug 222 have a friction fit on insertion of the vessel plug 222, the friction fit forming a seal. In another embodiment, the reaction vessel base 246 and the vessel plug 222 incorporate collapsible seal regions that form a seal on insertion of the vessel plug 222 into the reaction vessel base 246. Vessel plugs 222 may be at least partly opaque to exclude interfering light during processing.

In some embodiments, the plug body is electrically conductive. This has the benefit of supporting measurements by a sensing circuit, such as a liquid sensor. Such a sensing circuit may be associated with a pipettor that is used to transport a vessel plug 222, advantageously providing a means to verify acquisition of the vessel plug 222 or signal loss during transport. A preferred method of producing electrical conductivity in the plug body is admixture of a base polymer with a conductive material such as carbon or metallic particles.

For some embodiments, the elastomeric seal can be a thermoplastic elastomer with hardness of 30-40 durometer (Shore) A. In other embodiments, the hardness can be 20-50 (Shore) A, or about 30 (Shore) A. Elastomers deform sufficiently to form a tight seal with the vessel base. Thermoplastic elastomers are advantageous because of their compatibility with plastics injection molding processes.

The vessel plugs 222 can be formed in any suitable manner. In some embodiments, the forming process for vessel plugs is two-part plastics injection molding. The process overmolds the elastomeric seal about the pre-formed plug body. The polymer for the elastomeric seal can be injected into the same mold while the polymer for the plug body is still in place and warm, allowing the two polymers to flow into each other and for chemical bonds that hold the elastomeric seal firmly in place without adhesive. This has the advantage of producing high quality parts at relatively low expense. In some embodiments, the molding process forms the plug body of a carbon-loaded polypropylene such as RTP 199 X 106053A produced by RTP Company of Winona, Minn. The preferred material for the elastomeric seal is Dynaflex™ G7930-1001 produced by PolyOne Corporation of McHenry, Ill.

In some embodiments, the elastomeric seal may be substantially cylindrical with a chamfered lower end. The upper end may extend into a retaining aperture at the bottom of the plug body, such that the upper end infiltrates into the retaining aperture, capturing the elastomeric seal to the plug body. In some embodiments, the retaining aperture is counterbored with the larger diameter distal from the bulk of the elastomeric seal so that the elastomer may expand into the counterbore for better retention. Alternatively, the manufacturing process may form the elastomeric seal as a separate piece from the plug body and may bond the elastomeric seal to the plug body through another method such as a friction fit or an adhesive.

The elastomeric seal can be large enough to provide adequate compression without bottoming on the sealing portion of vessel base 246. The hardness and dimensions can cooperate to allow the elastomeric seal to the sealing portion with reasonable sealing force. In some embodiments, the elastomeric seal diameter is small enough so that, when compressed by engagement of the vessel plug to the vessel base, it conforms to the sealing portion without contacting the internal wall of the plug receiving portion. This advantageously concentrates sealing force to the sealing portion of vessel base and distributes sealing force evenly to prevent leaks. In some embodiments, the sealing force is about 44 newtons (about 9.9 lbs) and produces a pressure on the sealing surface of about 300 (about 43.5 pounds per square inch) to about 1000 kPa (145.0 pounds per square inch).

The vessel plug 222 has functions of supporting the elastomeric seal, engaging with the latching features 246($a$)' of the vessel base 246, transmitting the engagement forces from the latching features 246($a$)' to the elastomeric seal, mating to a pipettor mandrel for handling, and indicating successful mating. The vessel plug 222 may comprise a substantially cylindrical tube supporting the elastomeric seal at the tube's bottom. A portion of the vessel plug 222 may extend above the top of the reaction vessel 221 when it is engaged, in order to ensure that seating forces applied by the compression head 1342 of the slidable lid 1315 (see FIG. 16($i$)) are transmitted through the vessel plug and further securing the elastomeric seal during thermal cycling. In some embodiments, two or more vertical plug slots split the plug body for a fraction of the plug body length to provide radial flexibility. The tube terminates at the top end in one or more engagement features. The engagement features may correspond to parts of a vessel plug third portion 222($c$). As shown in FIG. 5($c$), the vessel plug third portion 222($c$) may be coupled to a vessel plug first portion 222($a$), and a vessel plug second portion 222($b$). The first, second, and third vessel plug portions 222($a$), 222($b$), 222($c$) may all be integrally formed with respect to each other.

The engagement features engage the latching features 246($a$)' on the vessel base 246 to seat the vessel plug 222 to the vessel base 246. Once seated, in some embodiments, the system does not remove the vessel plug 222, nor is the plug 222 designed to be removable by a user. The intent is to join the parts together and seal the reservoir region for at least as long as the parts remain in the system and as long as the parts remain anywhere within the laboratory. This advantageously prevents escape of any amplified nucleic acids that might otherwise contaminate assays or samples. In some embodiments, the engagement features are segments of a locking flange extending outward from the top end of the plug body. The height of the locking flange is slightly less than the gap distance of the vessel base 246 between the upper surface of the base flange and the lower surface of the latching feature. The locking flange thus fits within the gap distance. Compliance of the parts, particularly the compliance of the elastomeric seal, may take up variations within the component production tolerances.

The plug body may also include a circular locating wall 222($g$) extending upward from the upper surface of the locking flange with outer diameter complementary to the inner diameter of the latching features 246($a$)' of the vessel base 246. The locating wall advantageously limits relative motion of the vessel plug and the vessel base to maintain the seal. Two or more vertical flange slots may segment the locking flange and the locating wall. These flange slots continue as the plug slots that segment a portion of the plug body and provide flexibility to the part. The vessel plug 222 may also include a counterbored aperture as described above.

The engagement features lock to the complementary latching features 246($a$)' on the vessel base 246 and dispose the elastomeric seal in sealing contact with the vessel base sealing surface. As noted above, the engagement features may correspond to parts of a vessel plug third portion 222($c$). Compliance of the elastomeric seal pushes the vessel plug upwards so that the upper surface of the locking flange on the vessel plug 222 contacts the lower surface of the latching feature on the vessel base 246. The efficacy of the sealing contact depends on cooperation of several dimensions and material properties, but a wide variety of dimensions may still achieve acceptable sealing contact. Some dimensions may change together without affecting the seal. For example, a longer plug body matched with a longer plug receiving portion would have only minor effect on the seal efficacy. Similarly, a softer elastomeric seal might compensate for a longer plug body or a stiffer body plug material might work with a shorter plug body. In some embodiments, interaction with other parts at least partly determines the length of the plug body, and this length in turn may determine the size of the plug receiving portion. Commercial availability of useful thermoplastic elastomers at least partly determines the elastomeric seal hardness. The primary determinant of the dimensions and material property combination is that the combination provides the required sealing efficacy.

The plug body interior can accept and grip a pipettor mandrel to allow the system to move the vessel plug or the closed reaction vessel. The plug body inside diameter may be slightly smaller than the mandrel outside diameter, but the plug slots permit the plug body to flex and expand radially as the mandrel enters. The plug body length, material stiffness, and plug slot length cooperate to open the plug body with reasonable downward force of the mandrel and to provide adequate gripping strength. The restoring force of the flexed plug body serves to grip the mandrel. Additional geometry within the plug body may serve to enhance gripping. In some embodiments, four hemispherical protrusions of the tube wall material into the lumen of the plug body help to grip the pipettor mandrel. These protrusions advantageously concentrate the restoring force to produce a high pressure contact with the mandrel. High pressure contact increases the friction between mandrel and plug body to better retain the plug body on the mandrel. The plug 222 may be made of conductive plastic, allowing the plug to be detected by the pipettor with a suitable sensing circuit, such as a liquid sensor. Alternatively a pipettor may detect the presence of a vessel plug 222 using a pressure sensor that measures pressure within the pipettor, generating a pressure profile that is characteristic of the presence of a vessel plug 222 on the pipette mandrel. In some embodiments both a liquid sensor and a pressure sensor are used to detect the presence of a vessel plug 222 on a pipettor.

FIG. 5(*d*) shows a perspective view of a reaction vessel 221 according to another embodiment of the invention. The configuration of the reaction vessel 221 shown in FIG. 5(*d*) is generally similar to the configuration of the reaction vessel shown in FIGS. 5(*a*)-5(*c*). In the embodiment shown in FIG. 5(*d*), the plug 222 now has a rim that extends up over the edge of the vessel base 246 when inserted. This ensures that when the slidable lid of a thermal cycler module is closed, it presses down on the plug 222, securing it tightly. The upper surface of the plug 222 may extend any suitable distance (e.g., at least about 1 mm) above the top surface of the vessel base 245 when the plug 222 is inserted into the vessel base 245.

Alternative reaction vessel embodiments include a vessel that is made of a flexible material that conforms to the shape of the heating block, rather than a pliant material that only bends slightly. In yet other embodiments, the vessel can have a non-circular cross-section, having configurations that are wedge shaped, rectangular, or polygonal.

The above-described reaction vessel can be used in a process for determining a nucleic acid in a sample using a system including a preparation location and a thermal cycler module. The process can include providing in the preparation location a vessel plug with a handling feature and a vessel base configured to lockably engage with the vessel plug; pipetting an amplification reagent to the vessel base with a pipette tip held on a mandrel; pipetting the nucleic acid to the vessel base; lifting the vessel plug using the mandrel to grip the handling feature; engaging the vessel plug to the vessel base; and moving the engaged vessel plug and vessel base to the thermal cycler module. Each of the features of this process is described in further detail above and below. This and other processes described herein can provide for efficient processing of nucleic acids, since a pipette mandrel can be used to perform multiple functions.

F. Millitip

Embodiments of the invention can also include the use of millitips.

Figure 6C:
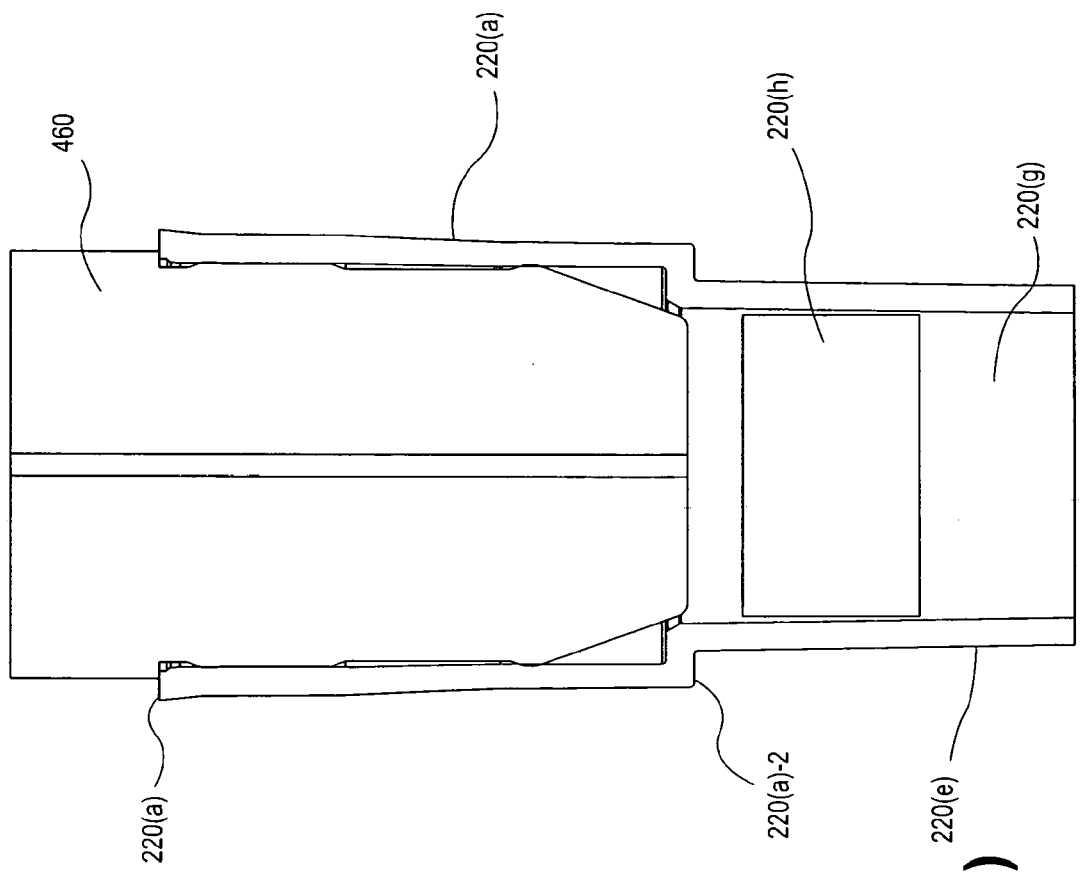
FIG. 6(c) shows a portion of a millitip secured to a pipettor mandrel.

FIG. 6(*a*) shows a millitip according to an embodiment of the invention. FIG. 6(*b*) shows a mounting aperture of a millitip. FIG. 6(*c*) shows a millitip on a mandrel.

In embodiments of the invention, a millitip 220 can be a relatively large capacity pipette tip carried within each assay cartridge and used during the isolation phase. Multiple processes within the system may use the millitip, but the system can use each millitip for transfers involving a single assay cartridge. In some cases, each millitip is only used for transfers involving a single assay cartridge. This reduces the possibility of inter-sample contamination. In some embodiments, the millitip has a capacity of at least one milliliter and tapers to a pipetting orifice. Millitips may couple to pipettors through a compliant coupling taper that supports repeated remove and replace operations. Length of the millitip may be sufficient to reach the depth of a 100 mm tube or other sample containers used on the system when mounted on a suitable pipette mandrel. Millitips may incorporate barrier and venting features. Preferred materials are electrically conductive non-reactive polymers.

As shown in FIGS. 6(*a*)-6(*c*), the millitip 220 can be a generally conical hollow body open at both ends with axial symmetry. The central lumen opens into a pipetting orifice 220(*b*) at the millitip apex and into a mounting aperture 220(*f*) at the millitip base. The mounting aperture 220(*f*) couples to a pipettor mandrel during use; pipetted fluids enter and leave through the pipetting orifice 220(*b*).

In some embodiments, the walls forming the millitip 220 are thin and tapered; the walls may be about 0.8 mm thick near the base and about 0.5 mm thick at the apex. The wall thickness can be sufficient to give the millitip 220 mechanical strength sufficient for penetrating barrier films on containers, or to open valves (e.g., a "duckbill" valve of a covered tube). The conical body may taper in several segments. Segmented tapering advantageously permits a narrow pipetting orifice to couple to a large capacity pipette tip. The large capacity pipette tip supports single step transfer of reagents, saving time and improving transfer precision. The narrow pipetting orifice supports good transfer precision, which directly improves assay precision. The intermediate tapers permit both high capacity and good precision in a pipette tip of practical length.

In some embodiments, a coupling taper 220(*a*) extends from the mounting aperture 220(*f*) to a lower diametral step forming a seating surface 220(*a*)-2. In other embodiments, the seating surface can be ribs or other protrusions that extend slightly from the end of the tip. The millitip 220 continues below the seating surface as an upper taper that extends for the majority of the part length. A lower taper 220(*c*) forms the apical end of part that in some embodiments terminates in a 1.3 mm diameter flat annulus surrounding a 0.8 mm pipetting orifice. The annulus is disposed perpendicular to the long axis of the millitip 220. A middle taper 220(*d*) connects the lower taper 220(*c*) and upper taper 220(*e*). The millitip walls can be of constant thickness (about 0.8 mm) through the entire part, except for the lower taper 220(*c*) and the mounting aperture 220(*f*). Walls of the lower taper 220(*c*) may thin out towards the apex. The interior taper angles defining the lumen may increase in steps towards the apex. The angles can be about 0.8 degrees in the coupling taper, about 2.8 degrees in the upper taper 220(*e*), about 3.2 degrees in the middle taper, and about 6.0 degrees in the lower taper 220(*c*) (all measured with respect to the millitip axis).

The coupling taper 220(*a*) may be a compliant taper with a smooth interior surface and without supporting ribs. The absence of ribs increases compliance and contributes to a smooth inner surface in plastic injection molded parts by eliminating sink marks associated with variable thickness sections. Thinner walls (about 0.45 mm) contribute to increased compliancy in the coupling taper. Compliancy in the coupling taper 220(*a*) has the benefit of allowing a millitip to elastically deform with minimal resistance when coupling to a pipetting mandrel. Elastic deformation advantageously permits recovery to near the original shape, permitting the system to load and unload the millitip from several different pipettor mandrels while preserving a fluid tight seal on each use.

In some embodiments, the coupling taper 220(*a*) may abruptly change diameter at the top of the upper taper forming a seating surface perpendicular to the axis of the millitip 220. This seating surface may rest on a complementary surface in the assay cartridge and support the millitip 220 at a controlled height and within a controlled locus. In some embodiments, interaction of the millitip 220 at the height of the seating surface and the assay cartridge control the location sufficiently to permit lead in features on the descending pipettor mandrel to align the millitip 220 with the mandrel during millitip pickup. In some embodiments, the seating surface forms a flat annulus about 0.7 mm wide surrounding a 7 mm core.

The open end of the coupling taper 220(*a*) forming the mounting aperture ends in a stopping annulus 220(*a*)-1 disposed perpendicularly to the axis of the millitip 220. The stopping annulus may interact with features on a pipettor mandrel to provide a fixed relationship between the height of the mandrel and the height of the millitip 220. This advantageously locates the pipetting orifice with respect to the controlled height of the pipettor to more precisely aspirate, dispense, and mix liquids.

Millitips may incorporate an aerosol barrier 220(*h*). In some embodiments, the upper taper 220(*e*) section of the millitip 220 includes an abrupt internal diametral decrease slightly below the seating surface (with the millitip oriented in the normal operating position with the pipetting orifice at the bottom). This diametral decrease forms a step that may retain a self-supporting porous substrate as an aerosol barrier. The aerosol barrier reduces the likelihood of contamination during pipetting by preventing any aerosols or splashes escaping the top of the millitip 220.

Millitips can incorporate venting features. Venting features may serve to equalize pressure in a reagent well as a millitip aspirates or dispense the contents of a reagent well through a compliant barrier seal. Since such a barrier film may effectively seal around a millitip, the pipetting operation may change the pressure in the reagent well. A change in reagent well pressure may affect pipetting precision or generate aerosols that are a potential source of contamination. Venting features advantageously maintain a patent air flow path through the barrier film while the millitip is in the well. This patent air flow path allows more rapid pressure equalization across the barrier film, which reduces the effect of barrier film interference with pipetting precision. Improved pipetting precision may directly improve assay precision. In some embodiments, venting features include abrupt deviations from the millitip's otherwise smooth conical outside wall. Such deviations can extend in the vertical direction so as to at least overlap the location of the barrier film during pipetting. Venting features may include sharp corners on the outside diameter, protruding ribs, incised channels, or similar features. In addition, the exterior of the millitip pipette orifice may be an annulus, the plane of which is at right angles to the central axis of the millitip. Such a configuration prevents a tight seal from forming when the lower terminus of the millitip is in contact with the bottom of an angled well, such as the reaction well of the assay cartridge, thus improving pipetting accuracy.

In some embodiments, millitips are electrically conductive. This has the benefits of dispelling the effects of static electricity and supporting measurements by a sensing circuit, such as a liquid sensor, as described in more detail below. Static electricity may cause lightweight parts without a discharge path to accumulate charge causing unfavorable interactions with other structures. For example, a pipette tip that acquires a charge (as by sliding engagement with a pipettor mandrel) may repel other charged pipette tips to such an extent that charged tips are displaced from known locations. The displaced tips may become unavailable for use and may interfere with other mechanisms. A preferred method of producing electrical conductivity in millitips is admixture of the base polymer with a conductive material such as carbon or metallic particles.

It is also noted that measurements by a sensing circuit associated with a pipette mandrel can be used to indicate successful attachment of the conductive tip to the mandrel, and detachment of the conductive tip from the mandrel. It can also permit liquid sensing via the mandrel through the conductive pipette tip, and provide an indication of the fill level of a conductive pipette tip that is carrying liquid. A sensing circuit is described in further detail below.

The preferred forming process for millitips is plastics injection molding. This has the advantage of producing high quality parts at low expense. In some embodiments, the molding process forms each millitip of a carbon-loaded polypropylene such as RTP 199 X 106053A produced by RTP Company of Winona, Minn.

G. Cartridge Loading Unit

Figure 7B:
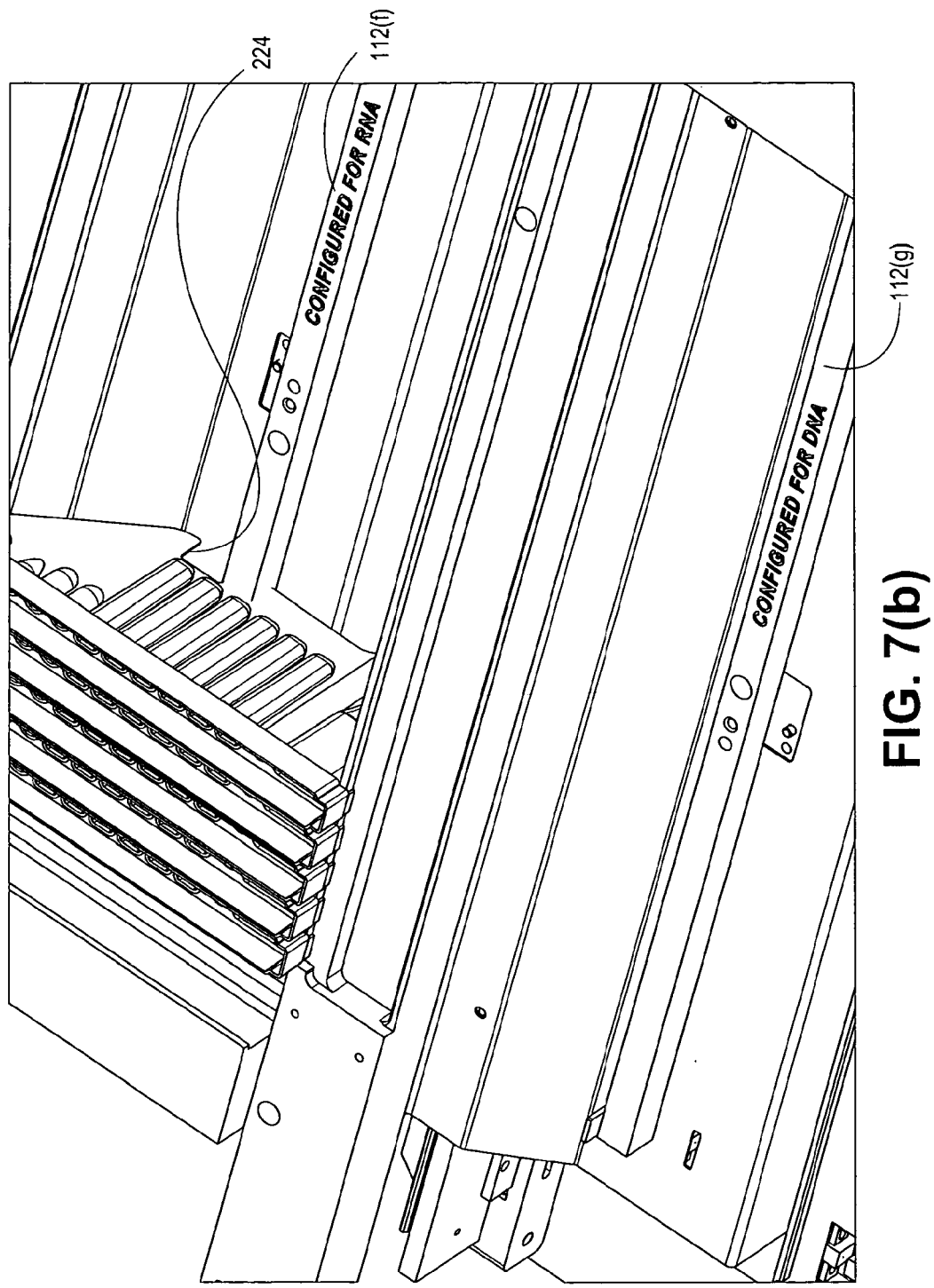
FIG. 7(b) shows a partial top perspective view of a cartridge loading unit.
Figure 7C:
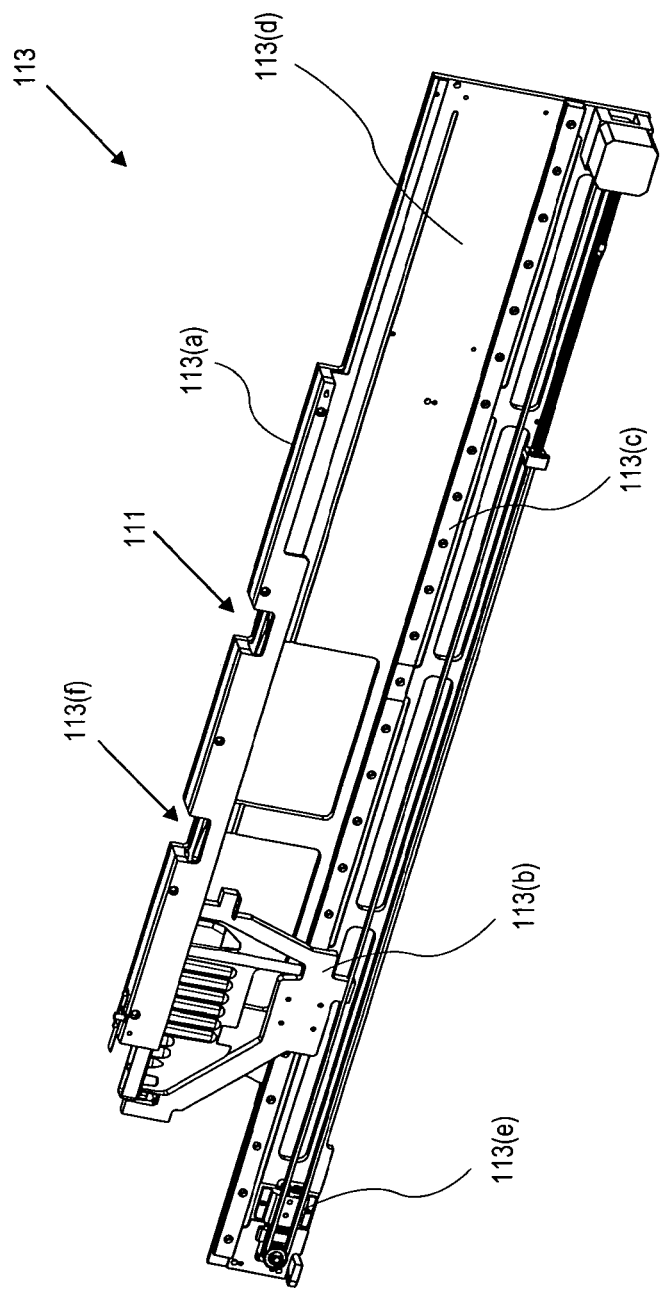
FIG. 7(c) shows a perspective view of a cartridge loading unit presentation lane.

FIG. 7(*a*) shows a top perspective view of an assay cartridge loading unit.

FIG. 7(*b*) shows a partial top perspective view of an assay cartridge loading unit.

FIG. 7(*c*) shows a perspective view of an assay cartridge presentation lane of an assay cartridge loading unit.

The assay cartridge loading unit 112 serves as an area for loading and temporary storage of assay cartridges 200 on the system. In operation, the operator may load fresh assay cartridges 200 into the system at the cartridge loading unit 112, also called the CLU 112, without interrupting normal instrument operation. After loading, the CLU 112 may read identifying indicia, such as a barcode, that are attached to the loaded assay cartridges. The assay cartridge 200 may then be transported to allow addition of sample from the sample pipettor 700 and processing by an XYZ transport device (described in further detail below). The CLU 112 may then transfer the assay cartridge 200 to the transfer shuttle 898 (shown in FIG. 14) for further processing.

As shown in FIG. 7(*a*), the CLU 112 can include two subassemblies: an onload module 119 and a presentation lane 113. In some embodiments, the CLU 112 can have a movable gate (not shown) that can selectively prevent cartridges from moving from an onload lane of the onload module 119 to the presentation lane 113. This gate can be pneumatically actuated. An access door (not shown) can also be provided to provide other access to the CLU 112. Power to the onload lane motors of the CLU can be cut when the access door is opened, as a safety feature.

These two subassemblies may be separate until assembled onto the main system. The onload module 119 may be coupled to and oriented perpendicular to the presentation lane 113. The presentation lane may be an example of a loading lane. Assay cartridges 200 can be loaded into the onload module 119. In one embodiment, the onload module 119 can include a storage location comprising a cavity configured to hold assay cartridge 200. This cavity may be embodied as the interior space of a cartridge lane. In some embodiments, the storage location comprises two onload cartridge lanes (112(*b*) and 112(*c*)) that hold one or more assay cartridges each, an interlocked cover 112(*a*) (which may be a hinged or slidable cover), a touch pad for operator interaction, and a barcode reader (not shown). Although the storage location comprises two cartridge lanes in this embodiment, in other embodiments, the storage location may comprise only one, or even three or more cartridge lanes. In embodiments of the invention, the sliding cover of the CLU is locked unless the onload lanes are idle and the movable gate is closed to prevent the operator from accidentally forcing assay cartridges into the presentation lane while loading. Embodiments of the invention can also prevent jamming.

Each lane can include a CLU baseplate 118 for supporting and aligning components of the cartridge loading unit 112, CLU rails 122 that the assay cartridges rest upon, a loading transport such as a pusher 112(*d*) mounted to a linear rail, and sensors that detect the presence of the assay cartridges 200. These sensors may be optical, electrical, magnetic, or electromagnetic sensors. Although the loading transport in this embodiment is a pusher, in other embodiments, the loading transport could be a device that pulls the assay cartridges towards the cartridge presentation lane.

The pushers 112(*d*) can be driven by a stepper motor and belt in a manner similar to the previously described pusher plate 617 of the sample presentation unit 110, and may have a home position within the onload module 119. The stepper motor may have an encoder. The system can determine the number of assay cartridges loaded by packing the cartridges using the pusher and using the encoder position. Any suitable type of encoder may be used In one embodiment, the onload module 119 may be temperature controlled. Temperature control of the onload module 119 may be achieved by the inclusion of thin film heaters, infrared emitters, thermoelectric devices, a flow of heated or refrigerated air through the unit, or other means. Temperature control devices may be incorporated into or affixed to a portion of the CLU baseplate 118 that is adjacent to the onload lanes (112(*b*) and 112(*c*)). Different portions of the CLU may be maintained at different temperatures. Although two onload lanes 112(*b*), 112(*c*) are shown, it is understood that embodiments of the invention may include any suitable number of onload lanes.

The onload module 119 can also include a cover sensor and latch. The latch locks the cover 112(*a*) and is unlocked when the pusher 112(*d*) moves past a designated position. Alternatively, the latch may be moved to the locked and unlocked position using a linear actuator, pneumatic cylinder, or solenoid. In one embodiment, as a safety feature when the cover (112(*a*)) is opened the cartridge sensors lose power.

In operation, the user may load assay cartridges 200 into the CLU (112) as follows:
(a) The user signals their intention to add assay cartridges 200 to the CLU 112 by pressing a "load" button (physical or virtual).
(b) The system waits for the onload lanes to become idle.
(c) The movable gate between the onload and presentation lanes closes.
(d) The CLU pushers 112(*d*) move to their home positions.
(e) The CLU pusher 112(*d*) in the front cartridge lane 112(*c*) moves to a designated Open Cover position to unlock the cover 112(*a*).
(f) The user opens the cover 112(*a*), adds assay cartridges 200 to one or more cartridge lanes (112(*b*) and 112(*c*)), and closes the cover 112(*a*).
(g) CLU pusher 112(*d*) in the front cartridge lane 112(*c*) returns to the home position to re-lock the cover 112(*a*).
(h) The pusher (112(*d*)) moves to the assay cartridges 200 forward until they stall against the movable gate.

In some embodiments, each lane (112(*b*) and 112(*c*)) of the cartridge loading unit 112 can hold up to 50 assay cartridges 200. In other embodiments, more the number of assay cartridges held by each lane can be more or less than 50. In some embodiments assay cartridges can be loaded into a cartridge lane by using a magazine of cartridges, rather than individually.

As shown in FIG. 7(*b*) each cartridge lane (112(*b*) and 112(*c*)) can be configured to hold specific types of assay cartridges 200. In one embodiment, one type of assay cartridge 200 is used for DNA isolation and a second type of assay cartridge 200 is used for RNA isolation. This configuration can be added or changed by a user. For example, if the operator generally studies only DNA samples, both cartridge lanes (112(*b*) and 112(*c*)) can be configured for DNA assay cartridges 200. Configuration can be performed by attaching an identification bar 112(*f*) to the cartridge lane (112(*b*) and 112(*c*)) at one of two locations. For example, attaching the identification bar 112(*f*) towards the front of the system may configure that cartridge lane (112(*b*) or 112(*c*)) for RNA assay cartridges; attaching the identification bar 112(*f*) towards the back of the system may configure that cartridge lane (112(*b*) or 112(*c*)) for DNA assay cartridges. Alternatively, cartridge lanes (112(*b*) and 112(*c*)) may be configured without an identification bar 112(*f*) or with identification bars 112(*f*) at both positions in order to designate additional assay cartridge types. In some embodiments, identification bars 112(*f*) can have a square cross-section, however other configurations, including asymmetric cross-sections, are possible. There may also be a sensor under each identification bar 112(*f*) position for each cartridge lane (112(*b*) and 112(*c*)) that can detect the specified configuration. Each identification bar 112(*f*) can also include indicia to alert the operator to the configuration.

Although identification bars are described in detail, it is understood that embodiments of the invention are not limited to the use of identification bars and that any suitable cartridge identification device can be used. For example, instead of identification bars, each cartridge could have an RF ID tag (or other identification device) that could be detected by a sensor in each cartridge lane 112(*b*), 112(*c*). Such identification mechanism may be mechanical in nature, or may use some electrical, optical, or magnetic mode of operation.

As shown in FIG. 4(*a*)-1 an assay cartridge 200 can be designed to have a keying feature 224, which may be placed at different locations on the vertical web 226 or other suitable locations of the assay cartridge 200 to interface with the identification bar 112(*f*) and designate different assay cartridge 200 types. When an assay cartridge 200 is placed in a correctly configured cartridge lane (112(*b*) and 112(*c*)) of the CLU 112 the identification bar 112(*f*) enters this keying feature. Failure of an assay cartridge 200 to seat properly within the cartridge lane (112(*b*) and 112(*c*))) may alert the operator to the use of an incorrect assay cartridge. Other assay cartridge 200 types may be designated by incorporating a keying feature 224 that includes a wide notch that accommodates multiple identification bars 112(*f*) within a cartridge lane (112(*b*) and 112(*c*)). Assay cartridges 200 may also be designed without a keying feature, for occupation of cartridge lane (112(*b*) and 112(*c*)) configured without an identification bar 112(*f*).

The use of the above-described keying features and identification bar has a number of advantages. Because the keying features and identification bar are visible to the user, the user cannot make a mistake by putting the wrong cartridge in the wrong cartridge lane. Further, if an assay cartridge is placed in the wrong position, then it may not be possible to close the cover of the CLU. Embodiments of the invention thus reduce the chance of operator error.

As seen in FIG. 7(*a*), the CLU presentation lane 113 may be placed adjacent to the onload module 119. An embodiment of the CLU presentation lane 113 is shown in more detail in FIG. 7(*c*). The presentation lane 113 may include a presentation carriage 113(*b*) that moves along a CLU presentation rail 113(*c*), a CLU presentation guide 113(*a*) that provides accurate location of the assay cartridge 200 in the X and Z direction, and a CLU presentation vertical support 113(d) that is coupled to and provides support for the aforementioned structures. The CLU presentation carriage 113(b) may be driven by a stepper motor and timing belt in a manner similar to that used by the presentation carriage of the sample presentation unit 110. In one embodiment, the CLU presentation lane 113 accepts an assay cartridge 200 from either of the two cartridge lane (112(b) and 112(c)) and then transports the assay cartridge 200 into the system for processing. The cartridge presentation lane 113 may be in the motion path of the sample pipettor 700. In such an embodiment, the cartridge presentation lane 113 may include an orifice or gap 111 (shown also in FIG. 7(a)) in the presentation guide 113(a) through which the millitip pipettor 704 of the sample pipettor 700 can access the assay cartridge 200. Another gap 113(f) may also be present in the presentation guide 113(a) to allow access to an XYZ transport device. The CLU presentation lane 113 may include multiple interface points with an external device, such as the XYZ gantry 130, in order to address scheduling needs and reduce contamination issues. In some embodiments, the system may have cartridge presentation lanes arranged at both ends of the onload lanes.

A drive assembly 113(e) may be coupled to the vertical support 113(a). It can be used to drive the cartridge carriage 113(b) along the CLU presentation lane 113. It may include components such as a drive pulley, a spring tensioner, and a drive belt.

In some embodiments, the presentation lane 113 may be temperature controlled. Temperature control of the presentation lane 113 be may be achieved by the inclusion of thin film heaters, infrared emitters, thermoelectric devices, a flow of heated air through the unit, or other means. Such devices may be attached to the CLU presentation vertical support 113(d). Alternatively, the CLU presentation guide 113(a) may include one or more skirts that are proximate to the assay cartridge 200 and permit incorporation of temperature control devices by similar means. The presentation lane 113 may also include a device for measuring the temperature of the reagent pack. Suitable temperature sensing devices include infrared temperature sensors.

Embodiments of the invention may include other variations. For example, although two onload lanes are shown in the embodiments that are described above, other embodiments of the invention may include one to three or more onload lanes for different cartridge types. Further, other embodiments of the invention may comprise a dedicated bypass lane or a loading position for a "one off" cartridge. For example, if the system is normally only loaded with DNA cartridges and there is an unanticipated need to run an RNA assay; a single RNA cartridge could be loaded into a bypass onload lane (or other separate, designated position) rather than having to unload and re-key one of the onload lanes. In yet another embodiment, there could be a dedicated STAT (short turnaround time) position or lane for an assay cartridge designated for use with a STAT sample. In still another embodiment of the invention, the cartridge loading unit may hold assay cartridges 200 in a radial or circular arrangement such as, for example, supported by a turntable.

Yet other embodiments of the invention can relate to the use of a nonspecific onload lane holding mixed cartridge types, where the system utilizes a pick-and-place device to select and transfer individual cartridges into the presentation lane. A vision system can also be used to distinguish different assay cartridge types.

Other functional features may be included in the CLU. For example, it can be desirable to incorporate a mixing device into the CLU to suspend cartridge contents. For example, an orbital mixer or ultrasonic mixer could be used in some embodiments of the invention.

H. Reagent Storage Unit

Figure 8A:
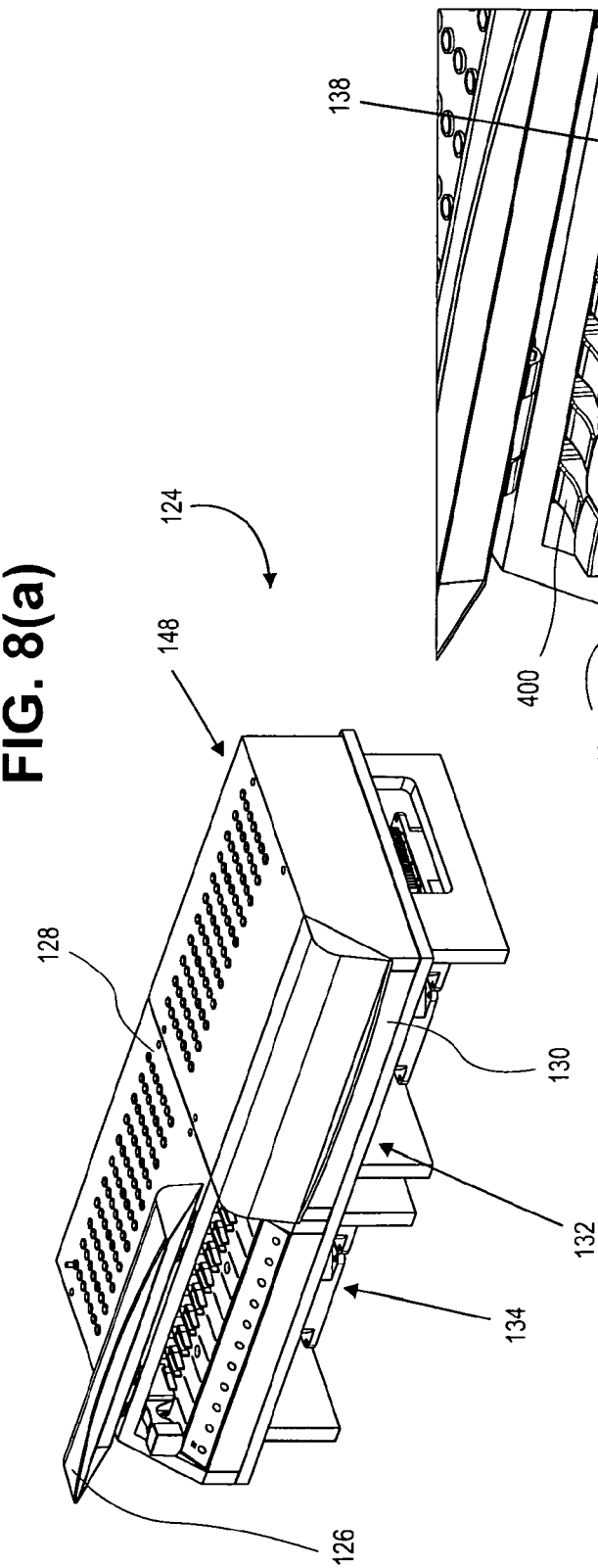
FIG. 8(a) shows a front perspective view of a reagent storage unit according to an embodiment of the invention.

FIG. 8(a) shows a top perspective view of a reagent storage unit

Figure 8B:
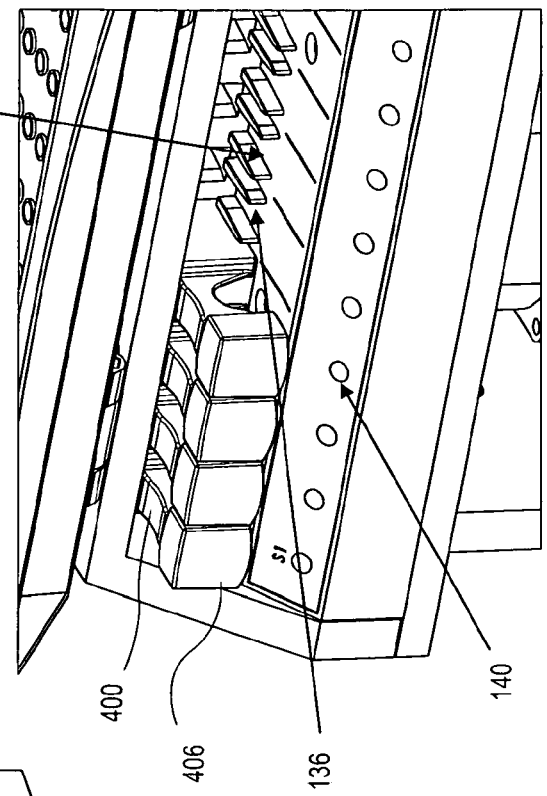
FIG. 8(b) shows a front perspective view of a portion of the reagent storage unit.

FIG. 8(b) shows an enlarged view of the front of a reagent storage unit

Figure 8C:
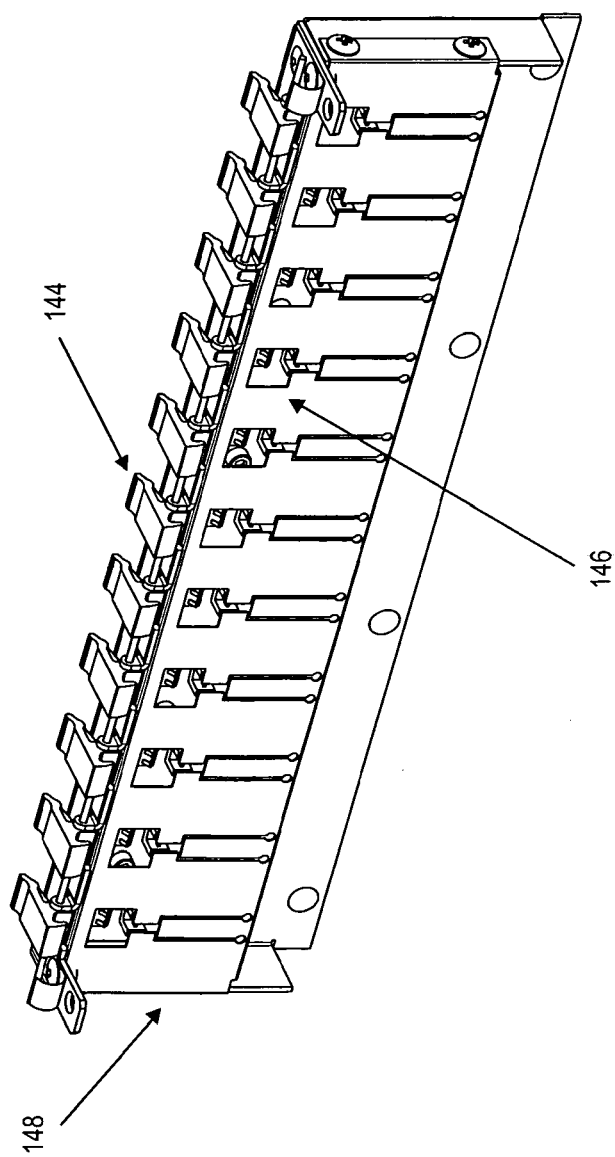
FIG. 8(c) shows an interior of a distal wall 148 of a reagent storage unit.
Figure 8E:
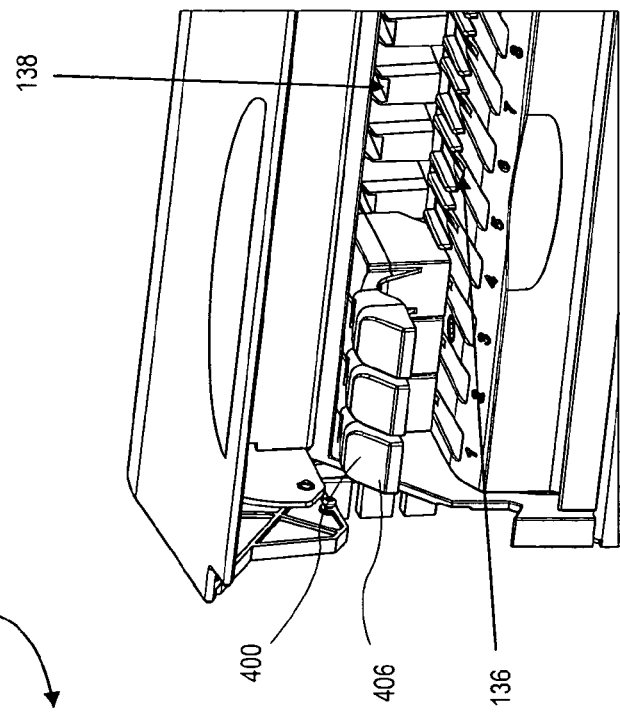
FIG. 8(e) shows a portion of a front perspective view of a reagent storage unit according to another embodiment of the invention.
Figure 8D:
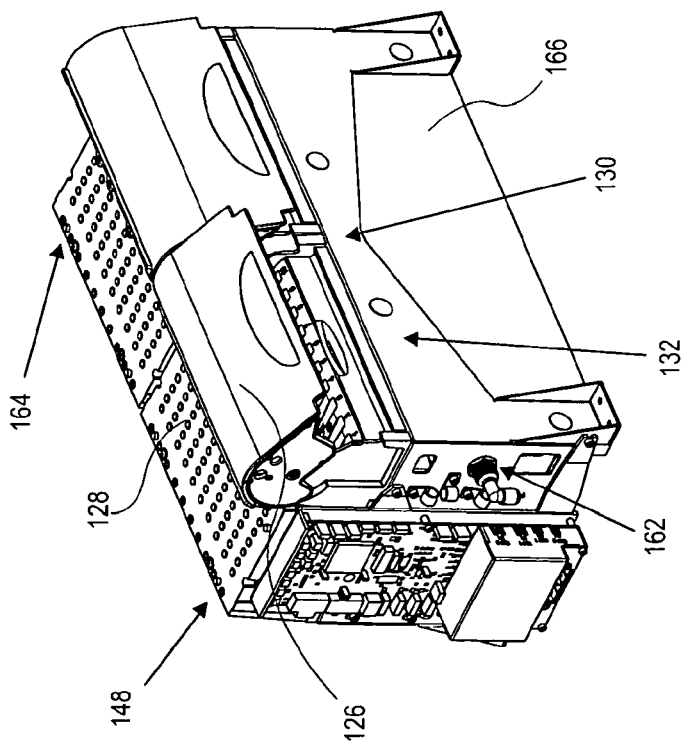
FIG. 8(d) shows a front perspective view of a reagent storage unit according to another embodiment of the invention.
Figure 8F:
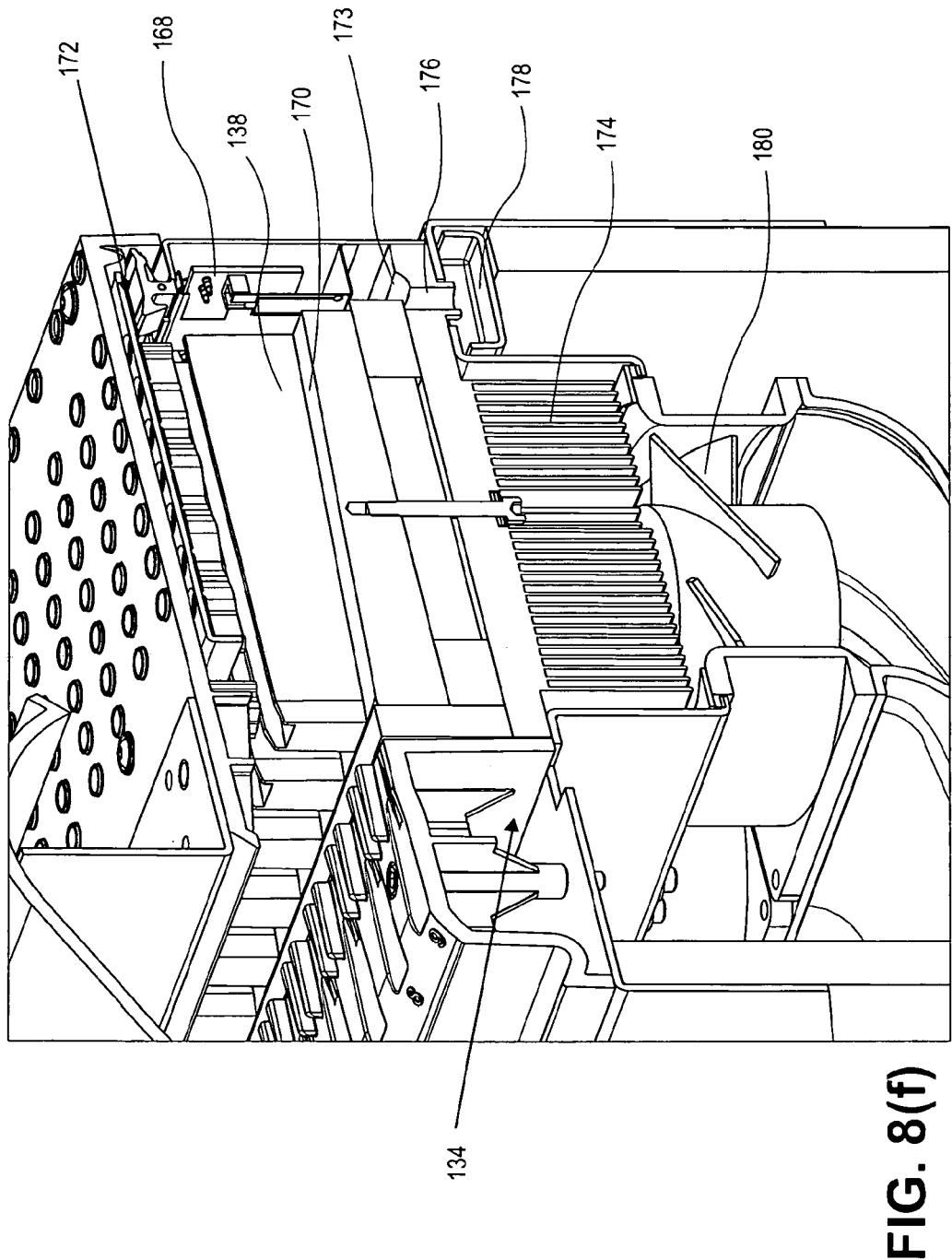
FIG. 8(f) shows a side, perspective, cross-sectional view of a reagent storage unit.
Figure 8G:
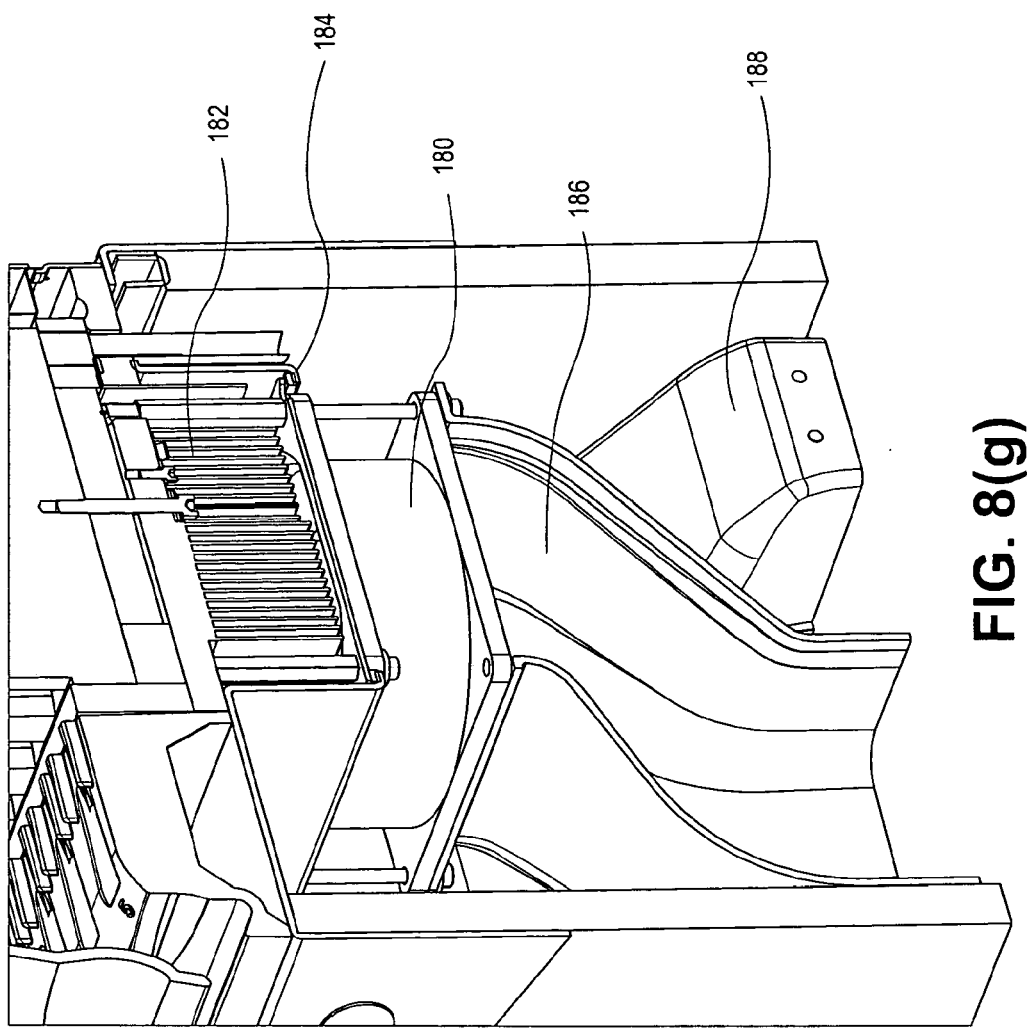
FIG. 8(g) another side, perspective, cross-sectional view of a reagent storage unit.
Figure 8H:
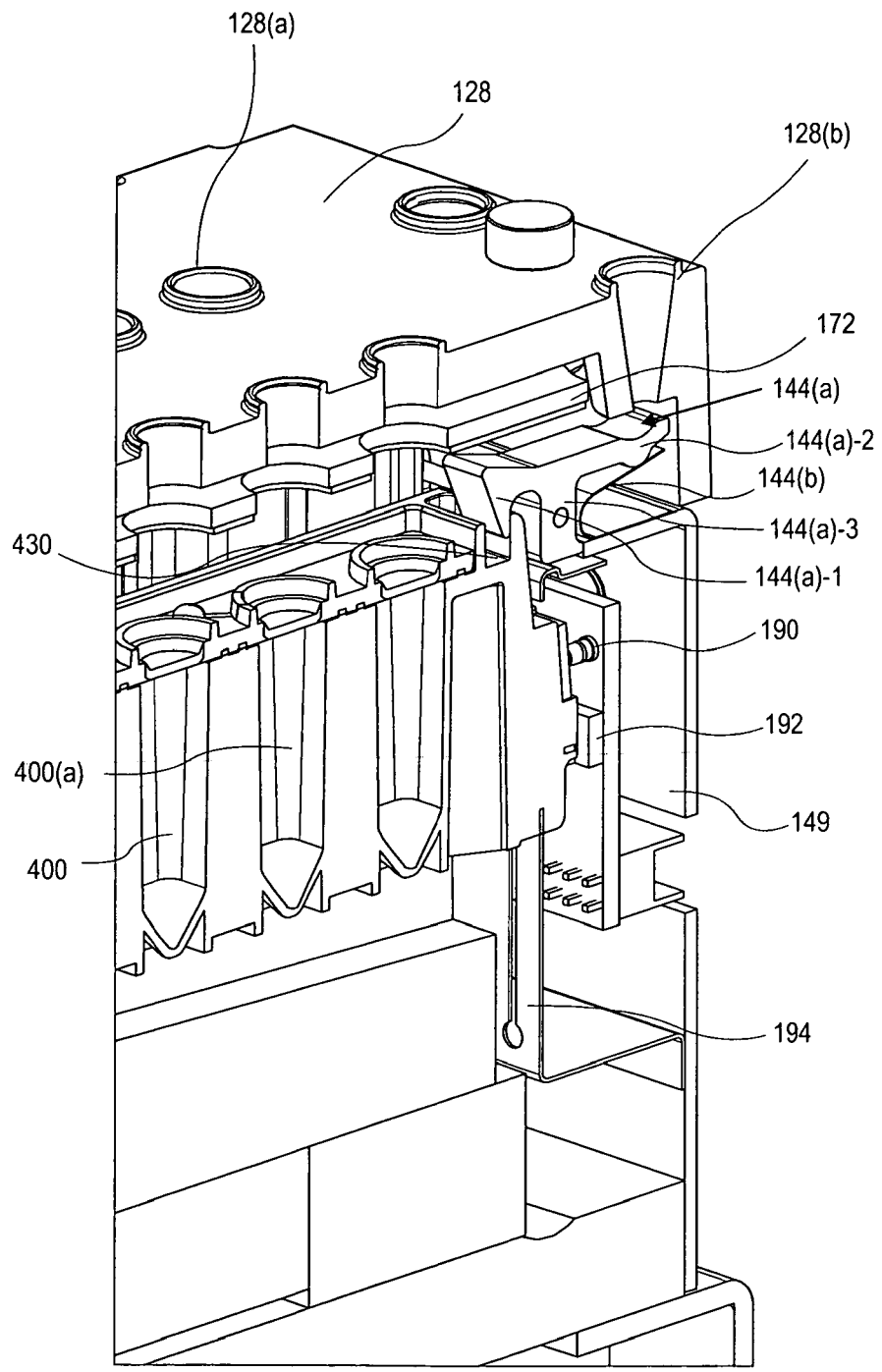
FIG. 8(h) shows a perspective, cross-sectional view showing a rear portion of a reagent storage unit.
Figure 8I:
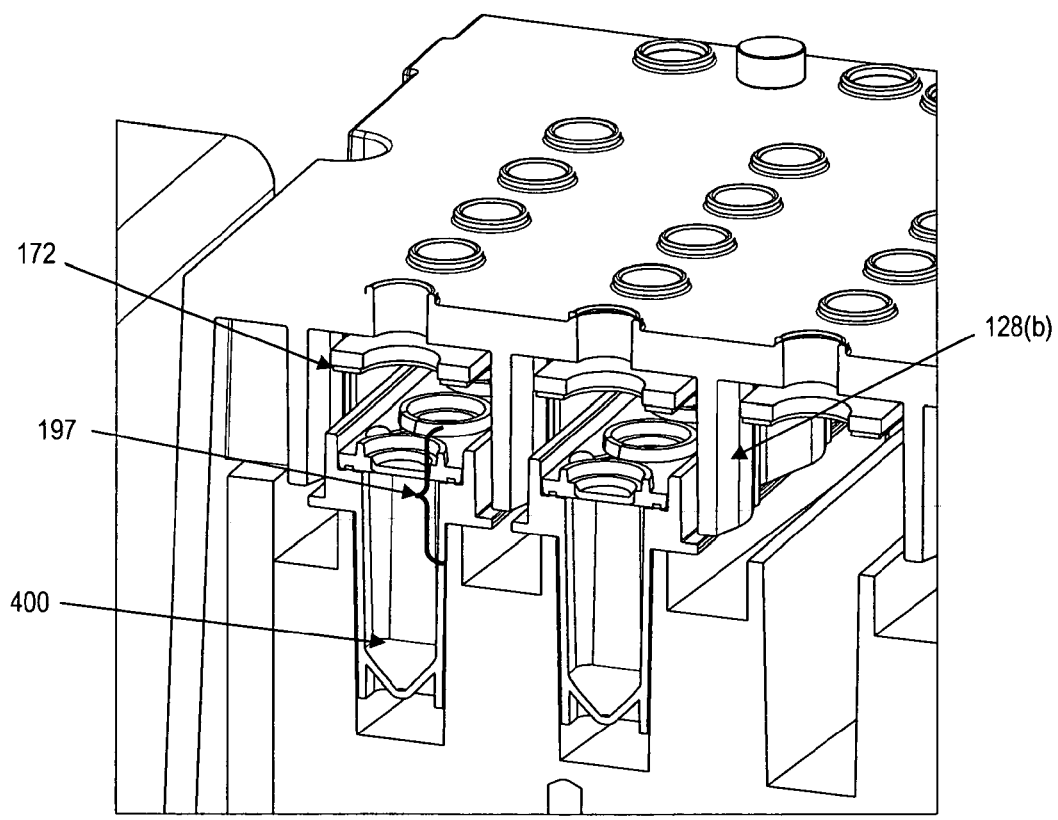
FIG. 8(i) shows a portion of a reagent storage unit cover as it interfaces with a containment feature of a reagent pack 400.

FIG. 8(c) shows an interior wall of a reagent storage unit

The reagent storage unit 124, or RSU, may be used as a repository for reagent packs 400 on the system. The reagent storage unit 124 can facilitate on-system storage of reagent packs 400, advantageously improving the stability of reagents on the system and reducing the need to store reagents in a separate device when the system is not in use. The RSU may have a pressure sensor (not shown) for sensing ambient air pressure.

In one embodiment of the invention, the reagent storage unit 124 has a baseplate 132, a proximal wall 130 of a body disposed on the baseplate 132, a distal wall 148 opposite the proximal wall 130, and a cover 128. The baseplate 132, distal wall 148, and the proximal wall 130 may define a cavity. The cover may include a dampening spring to control the rate of opening. The interior surface of the reagent storage unit 124 may incorporate guide features 136 that align the assay reagent packs on insertion.

The unit may be temperature controlled in order to maintain the integrity of the reagents. Different areas of the reagent storage unit 124 may be maintained at different temperatures. Temperature control may be provided by one or more thermal electric units 134 that are in thermal communication with the baseplate 132 of the reagent storage unit 124. Other means of providing temperature control include the use of channels within the baseplate 132 that conduct fluids, direction of chilled gases into the interior of the reagent storage unit 124 or against a surface in thermal contact with the unit, and positioning a mechanical refrigeration unit in thermal contact with the reagent storage unit 124. Such temperature control devices may further incorporate heat exchangers and fans or similar devices in order more efficiently remove heat from the reagent storage unit 124. Other features to maintain reagent integrity during storage, such as mixing devices to keep reagent pack 400 contents mixed and in suspension, may be incorporated into the reagent storage unit 124. Such mixing devices include rockers, orbital mixers, and ultrasonic devices.

The cover 128 of the reagent storage unit 124 may include one or more access doors 126, as shown in FIG. 8(a). These can be opened in order to add or remove reagent packs and closed during normal operation. In one embodiment, the access door 126 of the reagent storage unit 124 is constructed in one or more sections that are attached to cover 128 by a hinge. Alternatively, the access door 126 may move along a track incorporated into the reagent storage unit 124. This door 126 serves to reduce contamination, control evaporation, and to help control the temperature within the reagent storage unit 124. In some embodiments, the access doors 126 can be opaque to protect light sensitive reagents.

As shown in FIG. 8(b) the proximal wall 130 of the reagent storage unit 124 may also include one or more status indicators 140 that indicate the condition of assay reagent packs held within the unit. These status indicators 140 may indicate the presence or absence of an assay reagent pack at a particular location within the reagent storage unit 124, indicate that an assay reagent pack 400 needs to be replaced, or otherwise provide the user with cues to the operation of the unit. In one embodiment, the status indicators 140 are color-encoded LEDs; alternative embodiments include but are not limited to incandescent lamps, an LCD display, or other suitable visual indicators. In another embodiment, the reagent storage unit 124 may incorporate audible alarms to indicate the status of reagent packs 400 stored therein. In yet another embodiment, the reagent storage unit 124 may provide information to the system controller related to the status of reagent packs 400 stored therein. In yet another embodiment, the status indicators 140 may be replaced with user notifications on the system monitor or on a remote device (e.g., a mobile device).

The distal wall 148 may include mechanisms that secure the reagent packs within the reagent storage unit 124 and means for addressing read/write memory devices incorporated into the reagent packs 400, as shown in FIG. 8(*c*). The interior of the distal wall 148 of the reagent storage unit 124 can include one or more latch assemblies 144 for securing the reagent pack 400, which may include a mechanical latch. The RSU latch assembly 144 may be similar in design to the rack clasp 554 of the microtip storage unit 120 shown in FIG. 13(*d*). In one embodiment, upon contact with the reagent pack 400, the latch assembly 144 is biased against it, and pressure is provided by a pliant member such as a spring. The spring may also act as a ground path for other components of the reagent storage unit 124, such as a thermal electric unit 134. The reagent pack 400 can be released from this latch assembly 144 when pressure is applied to the latching mechanism by the XYZ gantry pipettor, using a disposable microtip 542. In an alternative embodiment, the distal wall may include apertures positioned such that addition of a new reagent pack 400 to a position occupied by a spent reagent pack pushes the spent reagent pack through the aperture associated with that storage position. In such an embodiment, the spent reagent pack would be directed to a waste container.

In one embodiment, the distal wall 148 of the reagent storage unit 124 may also include a reagent pack reader 146, which includes a device for interrogating addressable memory units 426 incorporated into the assay reagent packs 400, as shown in FIG. 9(*c*). Addressable memory units 426 may include RFID chips, contact memory devices such as 1-Wire devices™ (registered trademark of Maxim Integrated Products, Inc. of Sunnyvale, Calif.) devices, and iButton™ (registered trademark of Maxim Integrated Products, Inc. of Sunnyvale, Calif.) devices. These may store information related to specific lots of reagent, information related to the cartridge to the memory unit is attached, or both. The distal wall 148 of the reagent storage unit 124 may also include devices for detecting the presence of an assay reagent pack 400, including but not limited to a Hall effect sensor, an optical sensor, or a gravimetric sensor.

Reduced temperatures within the reagent unit can lead to the formation of condensation on the interior surface of the cover 128, particularly in humid environments. Since this condensation may be a source of contamination should it fall into a reagent pack 400, the reagent storage unit cover 128 may be in thermal contact with one or more heating devices. Such heating devices warm the cover 128, advantageously preventing the buildup of condensation without overwhelming the capacity of cooling devices that are in thermal contact with the baseplate 132. Suitable heating devices may include resistance heaters, thin film heaters, and infrared emitters. The interior temperature of the reagent storage unit 124 may be maintained through the use of one or more temperature sensors that form part of a temperature feedback loop.

In one embodiment, the reagent storage unit cover 128 also includes holes, piercings, channels, or similar entry means for a pipetting device to access the contents of assay reagent packs 400 held within the reagent storage unit 124 without the need for opening the unit and exposing its contents to the environment. Such openings may also be provided in order for the XYZ gantry to release a latch assembly 144 that secures a reagent pack 400 within the RSU 124, as noted above. In some embodiments, the reagent storage unit cover 128 is protected by a set of actuated doors, which cover the piercings or other entry means when the reagent storage unit 124 is not being accessed.

FIG. 8(*d*) shows a front perspective view of a reagent storage unit according to another embodiment of the invention. FIG. 8(*e*) shows a portion of a front perspective view of a reagent storage unit according to another embodiment of the invention. In FIGS. 8(*d*) and 8(*e*), the RSU cover 128, the RSU distal wall 148, the access door 126, the baseplate 132, the cold plate 138, the guide feature 136, and the proximal wall 130 in the reagent storage unit 124, as well as the reagent pack 400 and the reagent pack handle 406, are described above, and the descriptions above are incorporated herein.

FIG. 8(*d*) additionally shows an acoustic noise barrier 166 at a front of the reagent storage unit 124, and alignment pins 164 at a rear of the reagent storage unit 124. The acoustic noise barrier 166 can comprise any suitable sound insulating material (e.g., a noise reducing foam), to reduce the noise generated by internal components (e.g., a fan) of the reagent storage unit 124.

FIG. 8(*f*) shows a side, perspective, cross-sectional view of a reagent storage unit. FIG. 8(*g*) another side, perspective, cross-sectional view of a reagent storage unit. As shown therein, the reagent storage unit 124 can have a heat source at a top region of the reagent storage unit 124, and a cold source at a bottom region. As shown in FIG. 8(*f*), the top can include a heater 172, which can serve to reduce condensation that may be a source of contamination. It can use any suitable heat device including an electrical heating coil, heating coils with hot fluids passing through them, and one or more thin film heaters The reagent storage unit 124 can include a tapered floor 170 that serves to guide condensate away from the unit, and can be operatively coupled to a finned heat sink 174 and a fan 180. The fan 180 may be controlled by a controller (e.g., on a data board 168) that utilizes data provided by sensors to modulate fan speed and thereby minimize noise, and it may be coupled to an intake manifold 186 (shown in FIG. 8(*g*)), and an exhaust manifold 188. Such sensors may monitor ambient temperature, ambient humidity, and internal temperature of the reagent storage unit 124. A seal 184 can prevent mixing of ingoing and outgoing air. Referring again to FIG. 8(*f*), a condensate trough 173, a condensate port 176, and a condensate tray 178 may be used to remove condensate from the tapered floor 170 of the cold plate 130.

In embodiments of the invention, an algorithm can utilize information on ambient air pressure, ambient temperature, and heat sink temperature to control fan speed. This can advantageously reduce noise and power consumption. The logic for the algorithm may reside in a memory unit (e.g., a memory chip) on a data board 168 in the reagent storage unit 124 or remote from it.

FIG. 8(*h*) shows a perspective, cross-sectional view showing a rear portion of a reagent storage unit. As shown, the previously described latch assembly 144 may comprise a latch 144(*a*), which can be biased into a forward position by a latch spring 144(*b*). The latch spring 144(*b*) could be a flexible strip of metal, a torsion spring, or other biasing element. FIG. 8(*h*) also shows a pack pressure sensor 192, as well as an electrical contact 190. These elements can sense the presence of the reagent pack 400. The electrical contact 190 can also be used to read information from a memory element attached to the reagent pack 400.

FIG. 8(*h*) also shows a first aperture 128(*a*) and a second aperture 128(*b*) in the cover 128. The first aperture 128(*a*) is disposed above a well 400(*a*) of the reagent pack 400. A pipettor (not shown) can access a reagent in the reagent well 400(*a*).

The second aperture 128(*b*) provides access to one end of the latch 144(*a*), so that a probe (such as a pipette tip) can be inserted into the second aperture 128(*b*) and can provide downward force, thereby causing a rear releasing feature 144(*a*)-2 of the latch 144(*a*) to move down while the front fastener 144(*a*)-1 of the latch 144(*a*) pivots up. A pivot portion 144(*a*)-3 is between the fastener 144(*a*)-1 and the releasing feature 144(*a*)-2. Once this happens, the latch 144(*a*) disengages from the latch pocket 430 (which may be an example of a mating feature) of the reagent pack 400. The reagent pack 400 is pushed outward (ejected) and toward the front of the reagent storage unit 124 by the spring ejection plate 194 secured to a rear wall 149 of the reagent storage unit 124. This advantageously distinguishes the reagent pack 400 to be removed from the reagent storage unit, simplifying this task for the user. The sprint ejection plate 194 could be any other suitable resilient member (e.g., a spring).

Thus, one embodiment of the invention is directed to a method comprising aligning a probe with an aperture in a storage unit. The storage unit could be a reagent storage unit. Then, the method includes inserting the probe through an aperture in the storage unit and pushing a latch as the probe is inserted through the aperture, thereby causing the latch to disengage from a latch pocket of a consumable pack held within the storage unit. The consumable pack may be a reagent pack or a pack of pipette tips, etc. Such embodiments advantageously use a probe (e.g., a pipette) that may have other uses including pipetting or moving components within the system.

In an alternative embodiment, a latch 144(*a*) could be pivoted out of the latch pocket 430 of a reagent pack 400 by applying pressure using a linear actuator. Such linear actuators can include a solenoid, motor drive, hydraulic or pneumatic ram, or other suitable actuator.

In some embodiments, as shown above, the reagent pack further comprises a second well, and the cover further includes a third aperture, and the third aperture of the cover aligns over the second well thereby providing the pipettor access to the second well. The first, the second, and the third apertures are arranged linearly in such embodiments (e.g., as shown in FIG. 8(*h*), the apertures in the cover 128 above the reagent wells including reagent well 400(*a*) and the releasing feature 144(*a*)-2 are aligned in a linear fashion).

FIG. 8(*i*) shows a portion of a reagent storage unit cover as it interfaces with a containment feature 197 of a reagent pack 400. Both sides of the reagent pack 400 may include L-shaped (or other shaped) containment features that can conform to an internal cover wall 128(*b*). As shown, there can be multiple parallel walls 128(*b*) expending downward from a major horizontal portion of the cover 128. These features can help to ensure that the reagent pack 400 is property situated in its corresponding slot in the reagent storage unit 124.

As an alternative to reagent storage units that hold the reagent pack in a fixed position, other embodiments include a reagent storage unit in which reagent packs are stored in a temperature controlled storage unit, such as a refrigerator, and moved to a reagent pipetting area as needed. In still another embodiment of the invention, the reagent storage unit may hold reagent packs 400 in a radial or circular arrangement such as, for example, supported by a turntable. In still another embodiment of the invention, the reagent storage unit may hold reagent packs 400 in a radial or circular arrangement such as, for example, supported by a turntable. In such an embodiment, the reagent packs 400 may be stored in a rotary carrier that spins on its central axis to present a specific reagent pack to a pipetting device. Alternatively, reagent packs 400 may be stored in fixed locations and accessed by transfer devices with multiple degrees of freedom. Transfer devices for such an embodiment include an XYZ manipulator or articulated arm with a suitable gripping or support feature.

I. Reagent Pack

FIG. 9(*a*) shows a top perspective view of a portion of a reagent pack

FIG. 9(*b*) shows a cutaway view of a reagent pack

FIG. 9(*c*) shows an exploded view of a reagent pack

FIG. 9(*d*) shows a barrier lid of a reagent pack

FIG. 9(*e*) shows an end portion of a reagent pack

The system may store reagents in the form of a reagent pack 400. In some embodiments, as shown in FIG. 9(*a*), a reagent pack 400 can be a multi-use consumable that contains reagents useful for performing an assay type multiple times. The reagent pack 400 may store sufficient reagents to support the performance of 20 to 100 individual assays of a specified type. In one embodiment, the reagent pack 400 stores sufficient reagent to support the performance of 50 (or more or less than this) individual assays of a specified type. The system dedicates each reagent pack to a single assay type and requires only a single reagent pack 400, in combination with an assay cartridge 200, to supply all reagents needed for an assay. In some embodiments, reagent packs 400 store reagents used for multiple assay types. Reagents stored in the reagent pack 400 may be stable at ambient temperatures. Alternatively, reagents stored in the reagent pack 400 may use refrigerated storage for stability.

The system design can allocate reagent storage between reagent packs 400 and assay cartridges 200, based on assay specificity and storage condition needs. In some embodiments, reagents stored in assay cartridges 200 can be determined by specimen type. For example, a DNA assay cartridge can store reagents related to DNA extraction and purification regardless of whether the system uses that assay cartridge to perform a *Chlamydia trachomatis* ("CT") and *Neisseria gonorrhoeae* ("NG") assay or a cytomegalovirus ("CMV") assay. In one embodiment, reagent packs 400 store reagents that are specific for a particular analyte. In another embodiment, reagent packs 400 store reagents that require refrigerated storage. In yet another embodiment, reagent packs 400 store both reagents that are specific for a particular analyte and reagents that require refrigerated storage. Examples include but are not limited to: (1) a CMV reagent pack storing amplification primers specific for a CMV assay, (2) a reagent pack storing achromopeptidase or proteinase K enzymes that are used for multiple assay types and require refrigerated storage, and (3) a reagent pack storing both (a) amplification primers for a *CT* and *NG* assay and (b) achromopeptidase or proteinase K enzymes that are used for multiple assay types. Other types of reagents may be used in other embodiments of the invention. Materials may be transferred between reagent receptacles (408, 414) of a given reagent pack 400 while it is stored in the reagent storage unit 124. In some embodiments materials may be transferred between reagent receptacles (408, 414) of different reagent packs 400 while the reagent packs are stored in the reagent storage unit 124.

As shown in FIG. 9(*a*), the reagent pack 400 can include a generally rectangular elongated body formed to include multiple reagent receptacles including one or more large reagent receptacles 408, and one or more relatively smaller reagent receptacles 414, as well as features to facilitate handling and automation. The large and small receptacles 408, 414 are aligned in a linear array in this embodiment.

In some embodiments, the reagent pack 400 may be manufactured by injection molding. Alternatively, the reagent pack 400 may be manufactured by assembling individual reagent receptacles 408, 414. In such an embodiment individual reagent receptacles 408, 414 may be joined using adhesives, by welding, or by fixing to a framework.

The reagent pack can have a proximal end 450 and a distal end 404 at opposite termini of the elongated body. The orientation of the reagent receptacles defines the top and bottom of the reagent pack; reagent receptacles are open at the top and closed on the bottom and sides. The reagent pack 400 may be opaque to protect photosensitive reagents from light. In one embodiment, the reagent pack 400 is made from a carbon-filled plastic, which may be conductive or have antistatic properties.

In some embodiments, the reagent receptacles (408, 414) align in a single row (or be in a linear array) along the reagent pack long axis. This advantageously provides for compact storage, and additionally allows heat transfer surfaces to flank two sides of each reagent receptacle during storage. This two-sided proximity helps maintain reagents at the desired storage temperature, improving reagent stability and helping to assure reagent quality. Reagent receptacles 408, 414 can be open top containers of generally rectangular cross-section, oriented parallel to the major axis of the reagent pack 400. This arrangement produces good thermal contact with fixed heat transfer surfaces when a user slides the reagent packs into the reagent storage unit 124.

Reagent receptacles 408, 414 may be defined by relatively thin walls to allow for rapid heat exchange. A vertical wall 447 may separate adjacent reagent receptacles 408, 414. In one embodiment, individual reagent receptacles 408, 414 do not share walls with other reagent receptacles 408, 414. Separate walls advantageously prevent fluid creep between adjacent reagent receptacles 408, 414 reducing the possibility of reagent contamination. The reagent receptacle walls may extend below the bottoms to form standing features 444 that terminate at a common height and support the reagent pack on flat working surfaces.

Reagent receptacles 408, 414 may taper towards the bottom for easier molding. As shown in FIG. 9(b), the bottom of each reagent receptacle 408, 414 may also angle downwards centrally to minimize dead volume during pipetting. In some embodiments, the bottom portion 446 of each receptacle has an inverse pyramidal configuration.

A reagent pack 400 according to an embodiment of the invention may accommodate sufficient volumes of reagents for multiple instances of an assay. In some embodiments, each reagent pack 400 includes reagents for about 20 to about 100 instances of an assay and in some cases about 50 instances. In some embodiments a reagent pack 400 may supplied with empty or partially filled reagent receptacles (408, 414), to which reagents are subsequently transferred from bulk containers, such as bottles. Individual reagent receptacles may differ in dimension to accommodate the requirements of an assay type. Factors that can determine the size of a reagent receptacle include the number of uses desired for the reagent pack type, concentration dependent stability issues with reagent components, and the need to minimize the volume of the final reaction mixture. As noted above, in some embodiments, each reagent pack can include a large reagent receptacle 408 and a plurality of small reagent receptacles 414. In one embodiment a reagent pack 400 has six or more small reagent receptacles 414. Each reagent receptacle 408, 414 can be large enough to accommodate a microtip 542 used to remove a volume of reagent for use in an assay. In a preferred embodiment, large reagent receptacles 408 have the capacity to store about 3.0 mL of fluid and small reagent receptacles 414 have the capacity to store about 1.2 mL of fluid. Each reagent receptacle 408, 414 can includes additional capacity to maintain at least a 7 mm headspace 452 between the liquid surface of a reagent 448 and a barrier lid 418 that overlies the reagent receptacle 408, 414 when filled with the reagent 448. The headspace 452 (which may be filled with air) may serve to insulate the stored reagent from heat applied to the top of the reagent pack 400 when held within the reagent storage unit 124.

Figure 9A:
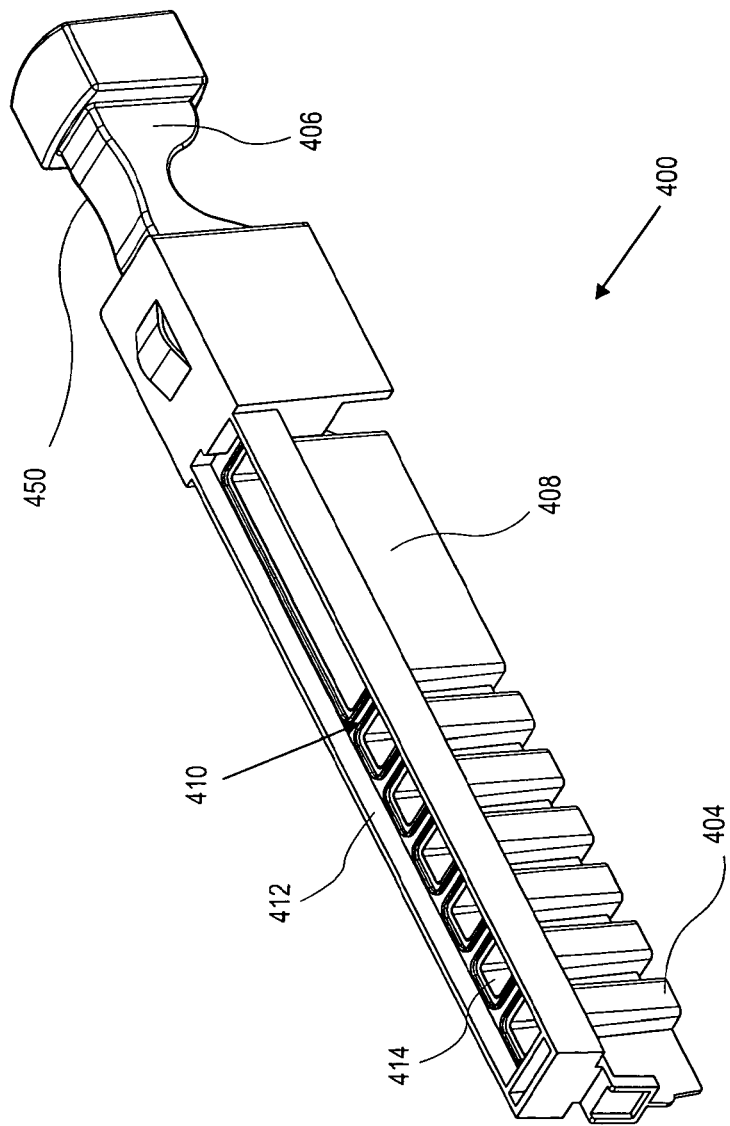
FIG. 9(a) shows a top perspective view of a portion of a reagent pack.
Figure 9B:
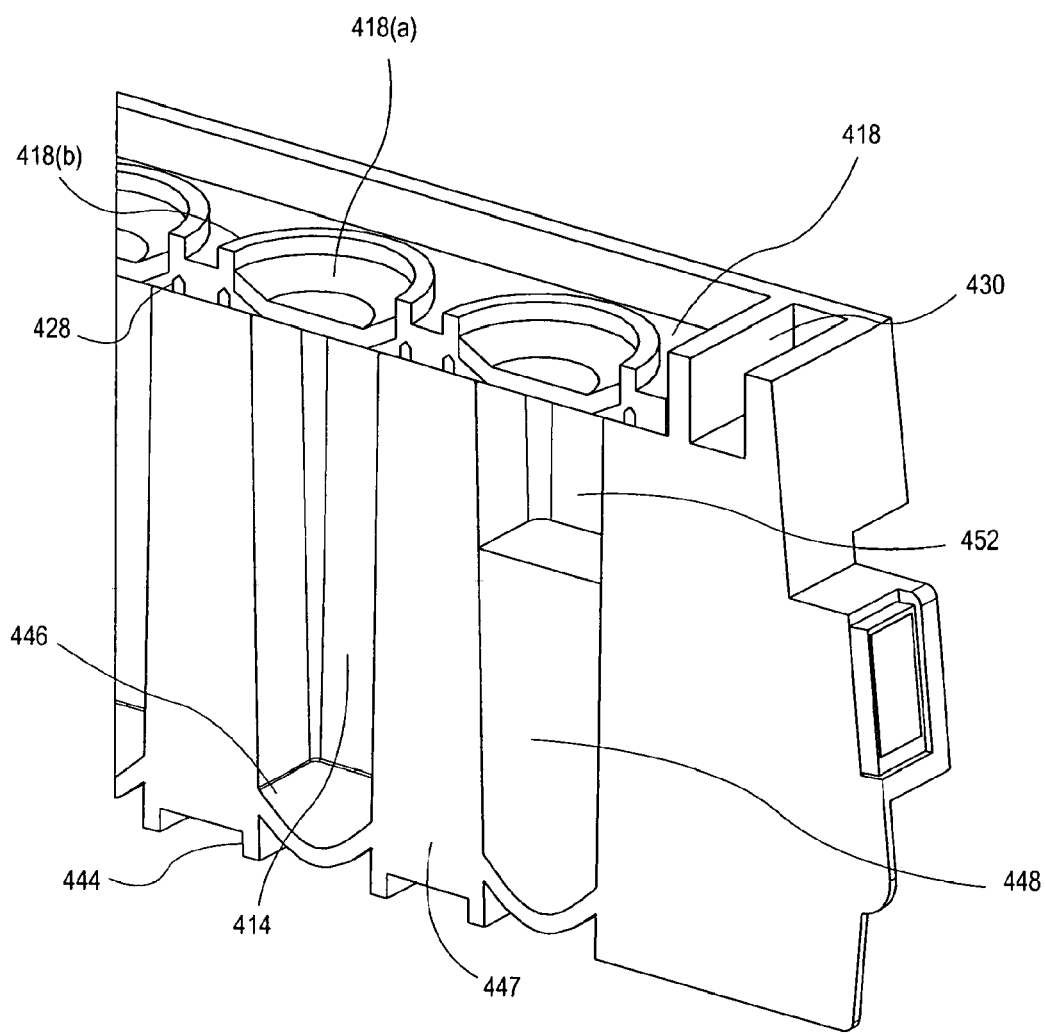
FIG. 9(b) shows an exploded view of a reagent pack according to an embodiment of the invention.
Figure 9C:
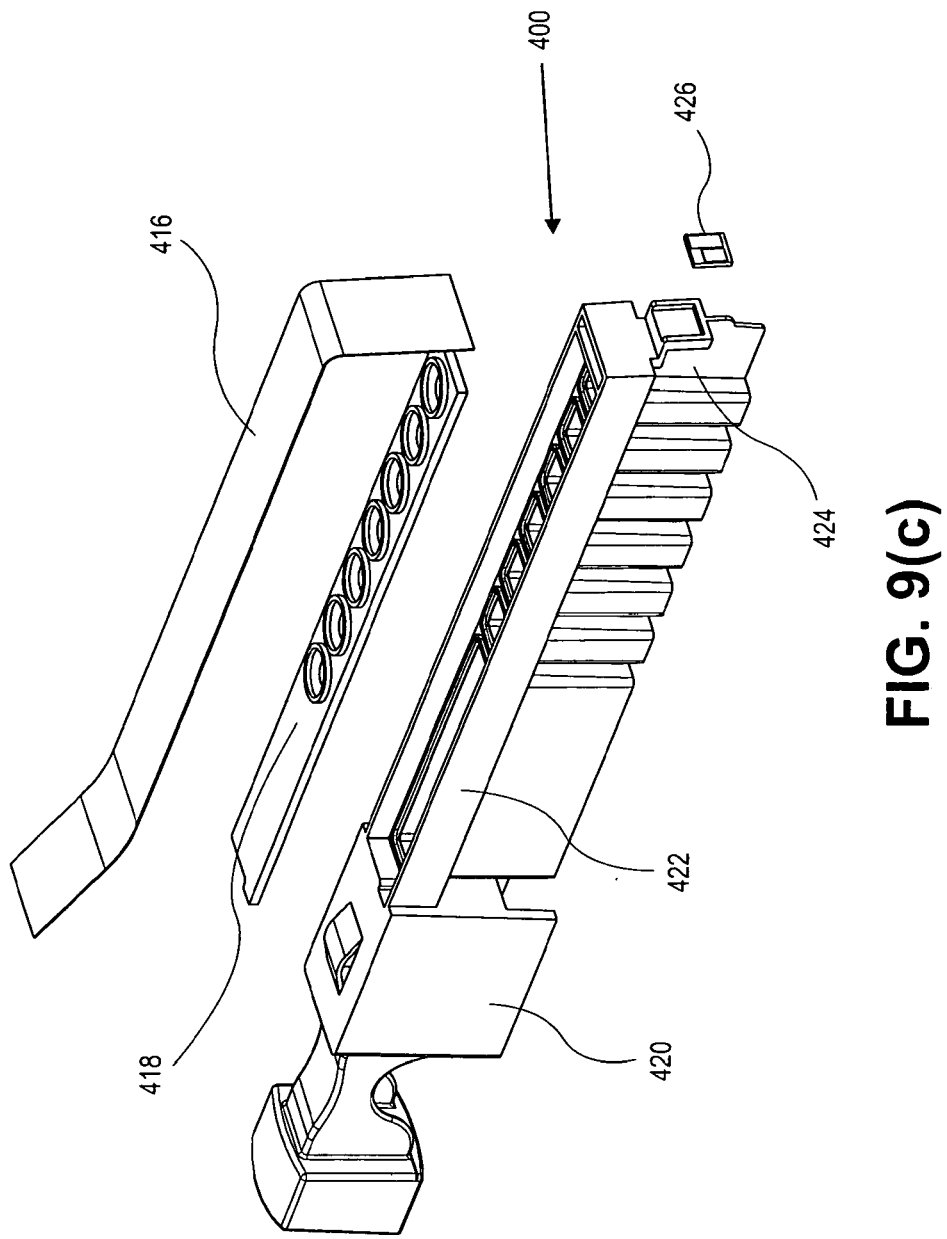
FIG. 9(c) shows an end portion of a reagent pack.

As shown in FIGS. 9(a) and 9(c), the reagent pack 400 may include features to facilitate handling and automation, including a containment section 412 (which includes the receptacles 408, 414), a gripping handle 406, a barrier lid 418, a storage cover 416, an electronic memory 426, labeling, features to engage the reagent storage unit 124, and selected reagents. In some embodiments, the body of the reagent back 400 may be made by a manufacturing process that includes injection molding.

A reagent pack 400 according to an embodiment of the invention may include a containment section 412. The containment section 412 may be defined at least in part by containment walls 422 defining parts of the sides of the reagent pack 400. The containment walls 422 may also be adjacent to or coincide with the distal end 404 and the proximal end 450, and may surround the upper openings of the reagent receptacles 408, 414. Further, a containment floor 410 may also connect the containment wall 422 to the openings of each reagent receptacle. In one embodiment, the containment floor 410 is a horizontal web that is contiguous with both the openings of the reagent receptacles 408, 414 and the containment walls 422. The containment section 412 can serve to prevent contamination through containment of drips or spills of liquids that may occur during processing or handling. A centrally disposed vertical web may connect reagent receptacle walls below the containment floor to add rigidity. The walls that define each reagent receptacle 408, 414 may extend vertically as rims above the containment floor 410 to prevent the incursion of fluids dripped or spilled in the containment region into the reagent receptacles 408, 414. In some embodiments, these rims may also be energy directors 428 (see FIGS. 9(b) and 9(e)) used during the attachment of closures, such as the barrier lid 418, to one or more reagent receptacles 408, 414. These rims may also support leak testing of the sealed reagent receptacles 408, 414 during reagent pack 400 manufacturing.

The barrier lid 418 may individually seal the reagent receptacles to protect the reagents from environmental factors and to prevent reagent cross-contamination. The barrier lid 418 can be a single part spanning all of the reagent receptacle openings 408, 414. Alternatively, the barrier lid 418 may be a series of individual sealing members that cover individual reagent receptacle 408, 414 openings. In another embodiment, the barrier lid 418 may be a combination of a single part that spans multiple reagent receptacle 408, 414 openings and individual sealing members that cover individual reagent receptacle 408, 414 openings or an individual sealing member that covers a single reagent receptacle 408, 414. In yet another embodiment, the barrier lid 418 may be a multilayer composite of polymer foils and a formed polymer support. The polymer support may confer rigidity to the barrier lid 418, may provide features to align the barrier lid 418 with the reagent receptacles 408, 414, and may provide further isolation features, such as raised lips 418(b) around each reagent receptacle location in the barrier lid, as shown in FIG. 9(d).

Such raised lips 418(b) can help keep the user's fingers from touching and contaminating the portion of the barrier lid 418 immediately atop the reagent receptacles 408, 414. In some embodiments, the barrier lid 418 includes at least one compliant elastomeric component that permits the barrier lid 418 to at least partially reseal after piercing. The compliant elastomeric component may be in the form of a strip of preformed caps 418(a) joined by gates and runners (see FIG. 9(d)).

Figure 9D:
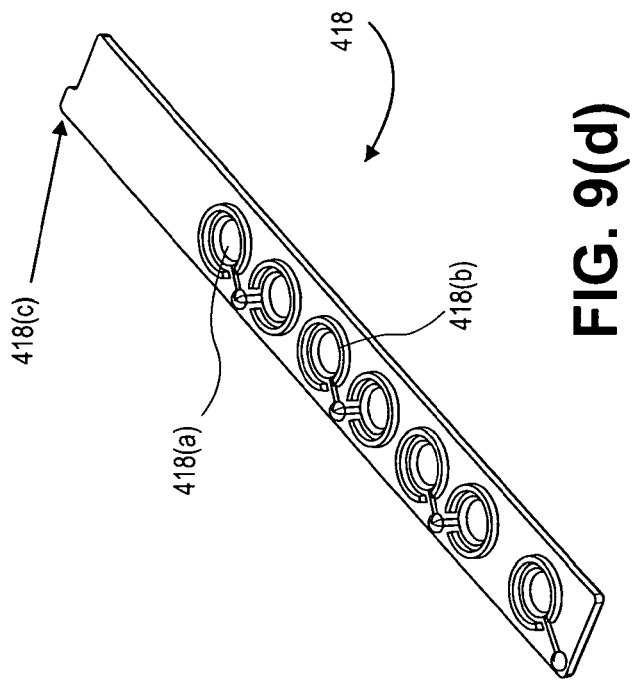
FIG. 9(d) shows a top perspective view of a barrier lid.

FIG. 9(d) shows that the barrier lid 418 can include an orientation tab 418(c) projecting asymmetrically from one end prevent the lid from being placed on the reagent pack in the wrong orientation during manufacturing. In one embodiment, the manufacturing process is over-molding of the formed polymer support to the elastomeric component. Suitable materials for the polymer support include polypropylene, such as natural PURELL X50109 manufactured by LyondellBasell Industries of Rotterdam, The Netherlands. Other suitable materials for the polymer support include, but are not limited to, polyethylene, nylon, polystyrene, and other polymers with suitable stiffness. Suitable materials for the elastomeric component may be a thermoplastic elastomer such as DYNAFLEX® G7930, GLS grade 7930-1001-00 manufactured by GLS Corporation of McHenry, Ill. Other suitable materials for the elastomeric component of the barrier lid 418 include, but are not limited to, silicone elastomer, latex, and natural rubber.

In operation, a pipette tip (not shown) pierces a barrier lid 418 (e.g., a preformed cap 418(a) of the barrier lid 418) to access a reagent receptacle's 408, 414 contents. The manufacturing process may pre-score the barrier lid 418 so that tearing during piercing occurs in predictable locations. In some embodiments, the manufacturing process laser welds the barrier lid 418 to the rims of each reagent well 408, 414. Alternatively, the manufacturing process may use other suitable processes attachment methods to fix the barrier lid 418 to the reagent receptacles 408, 414, including but not limited to heat sealing, ultrasonic welding, induction welding, or adhesive bonding.

Reagents packs may include a storage cover 416 designed to protect reagent pack contents during shipping, off-system storage, or handling, as shown in FIG. 9(c). The storage cover 416 may be a single use "tear-off" cover loosely affixed to the upper surface of the containment walls 422. In some embodiments, the storage cover is a replaceable cover that is held in place by friction or by an interference "snap fit" to the containment walls 422. This advantageously allows a user to replace the storage cover if the reagent pack 400 is removed from the system. The storage cover 416 may include identifying or instructional labeling.

FIG. 9(a) additionally shows that the gripping handle 406 may extend from the proximal end 450 of the reagent pack 400 to simplify insertion and removal from the system. Placement of the gripping handle 406 at one end advantageously allows a user to slide the reagent pack 400 into the reagent storage unit 124 through a relatively small opening, reducing temperature fluctuations in the reagent storage unit 124 during insertion. Further, the end placement helps keep user hands, a possible source of nucleic acid contamination, distant from the reagents. The gripping handle may include an extension along the reagent pack axis with a recess along the lower surface to serve as a finger hold. In one embodiment, this extension is hollow, which advantageously reduces the weight of the reagent pack 400. The design of the gripping handle 406, coupled with the low weight of the reagent pack 400, permits the user to securely grip the reagent pack 400. The gripping handle 406 may include a label surface that remains visible when the reagent pack 400 is installed in the reagent storage unit 124. This label location permits a user to identify individual reagent packs by simple inspection without disrupting system operation.

In some embodiments, an isolation portion 420, shown in FIG. 9(c), further separates the gripping handle from reagent receptacles (408, 414) within the reagent pack 400. The isolation portion 420 may be an extended hollow segment with a top wall and parallel side walls, with the side walls arranged parallel to the axis of the reagent pack. The isolation portion 420 can serve to separate the gripping handle 406 from the reagent receptacles (408, 414) to reduce the likelihood of reagent contamination from user handling The isolation portion may be from 0.5 inches to 1.5 inches in length. In one embodiment, the isolation portion is about 1 inch in length. The isolation portion 420 may also serve to stabilize the reagent pack 400 when it is placed on a flat surface. The isolation portion may be from 0.5 inches to 1.5 inches in length. In one embodiment the isolation portion is about 1 inch in length. The isolation portion 420 may also serve to stabilize the reagent pack 400 when it is placed on a flat surface. A secondary purpose may be to provide surfaces to support reagent pack labeling.

The reagent pack 400 may also include electronic memory 426 to store information related to the reagent pack 400 and to transfer information about the reagent pack 400 to and from the system, as shown in FIG. 9(c). The electronic memory 426 may communicate by electrical contact or wirelessly. In some embodiments, the electronic memory 426 is a contact memory device utilizing the 1-Wire® protocol manufactured by Maxim Integrated Products, Inc. of Sunnyvale, Calif. In other embodiments, the electronic memory 426 may be an RFID device, an iButton (registered trademark of Maxim Integrated Products, Inc. of Sunnyvale, Calif.) device, or another electronic memory device of suitable dimensions. The electronic memory may be mounted anywhere on the reagent pack. In one embodiment, the electronic memory 426 is affixed to a locating feature 432, shown in FIG. 9(e) near the distal end 404 of the reagent pack 400. Upon loading into the reagent storage unit 124, the recess may be disposed proximate to a reagent pack reader 146 (FIG. 8(c)) that provides power and information. The memory device 426 may include information entered during reagent pack 400 manufacturing and information transferred during use. Information stored in the memory device 426 entered during manufacturing may include: assay type, reagent cartridge serial number, lot number, and reagent expiration, and information related to the stability of the contents of the reagent pack once it has been accessed by the system. Information entered during manufacturing may also be encoded in a one dimensional barcode, a two dimensional barcode, or through similar labeling. Information transferred during use may include: the date that the reagent pack was first loaded onto the system, the amount of time the reagent pack has been stored on the system, the number of tests run from the reagent pack, and the number of tests remaining in the reagent pack, and a history of which individual systems that the reagent pack has been loaded onto. In some embodiments, the system writes new information to the electronic memory 426 after each access of the reagent pack 400 and reads information whenever a user loads a reagent pack.

Figure 9E:
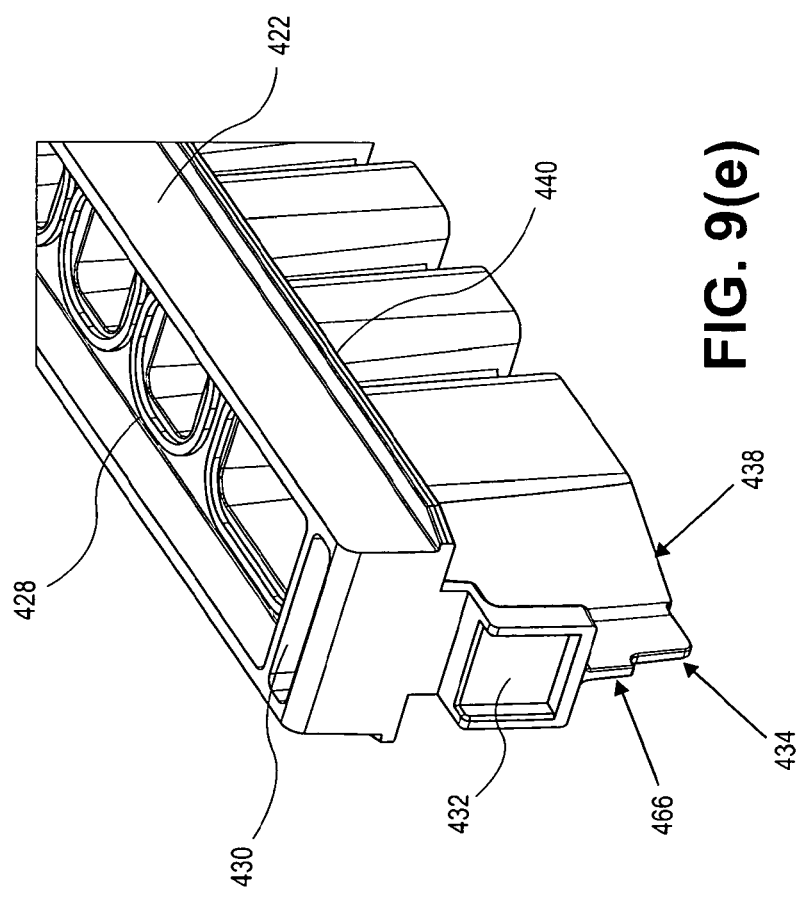
FIG. 9(e) shows a cross-sectional view of an end of a reagent pack.

FIG. 9(e) shows that the reagent pack 400 may include features to engage the reagent storage unit 124 including tapered lead-in features 438 to guide the reagent pack during insertion, a pack shoulder 440 to support the reagent pack within the reagent storage unit 124, a latch pocket 430 to lock the reagent pack into the reagent storage unit 124, a spring engager 434 to help eject the reagent pack once the system releases the reagent pack 400 from the reagent storage unit 124, and a sensor flag 466 to indicate the presence of a reagent pack 400 in a reagent slot.

Lead-in features 438 may extend from the side walls of the reagent receptacle closest to the distal end of the reagent pack 404. In one embodiment, the lead-in features 438 are extensions of the side walls that angle toward the midline of the reagent pack, forming a taper that aids the user in centering the reagent pack during insertion into the reagent storage unit 124 reagent storage unit 124.

The containment floor 410 of the reagent pack may extend beyond the side containment walls 422 as a pack shoulder 440. In some embodiments, the pack shoulder 440 is a controlled surface. The pack shoulder 440 may extend laterally approximately 1-2 mm from either side of the containment walls 422 and can serve to locate the reagent pack 400 vertically within the reagent storage unit 124 reagent storage unit 124. The lower surface of the pack shoulder 440 may support the reagent pack 440 on the RSU cold plate 138 in the reagent storage unit 124 (see FIG. 8(b)). This advantageously reduces the effect of tolerance stack-up by locating the reagent pack 400 with respect to the RSU cold plate 138 based on a controlled surface. The upper surface of the pack shoulder 440 secures the reagent pack 400 during pipetting operations, when the compliant portion of the barrier lid 418 may grip an ascending microtip 542. An end of the pack shoulder 440 may also include tapered lead-in features.

As described in more detail above, the system may secure reagent packs 400 within the reagent storage unit 124 using a spring-loaded latch assembly 144 (see FIG. 8(c)). The reagent pack 400 can include a mating feature, such as a latch pocket 430 that is complementary to a latching portion of the RSU latch assembly 144. As shown in FIG. 9(e) the latch pocket 430 may be an open rectangular cavity near the distal end 404 of the reagent pack 400. In one embodiment, a portion of the containment wall 422 surrounds the latch pocket; a front portion of the containment wall joined to extended side portions of the containment wall can define a rectangular opening perpendicular to the axis of the reagent pack, defining a latch pocket 430 that is complementary to the latching portion of the RSU latch assembly 144. The latch pocket 430 may be covered by the storage cover 416 prior to use, preventing the user from successfully loading a reagent pack 400 onto the system without first removing the storage cover 416.

As described in more detail above, the system may eject released reagent packs. FIG. 9(e) shows an extension of the vertical wall 424 at the distal end of the reagent pack 404 that can act as a spring engager 434 which interacts with an ejection spring. In one embodiment, the spring engager 434 is located proximate to the lower surface of the reagent pack near the midline. The upper portion of this extension of the vertical wall may also incorporate a sensor flag 46 that interacts with a reagent pack sensor within the reagent storage unit 124 to indicate the presence of a reagent pack within the reagent storage unit 124.

There can also be a number of other alternative embodiments of the invention. For example, common reagents used in all assays or sample processes could be held outside of the reagent packs in bulk bottles, or reagent packs could be single use.

J. Processing Lanes

Figure 10A:
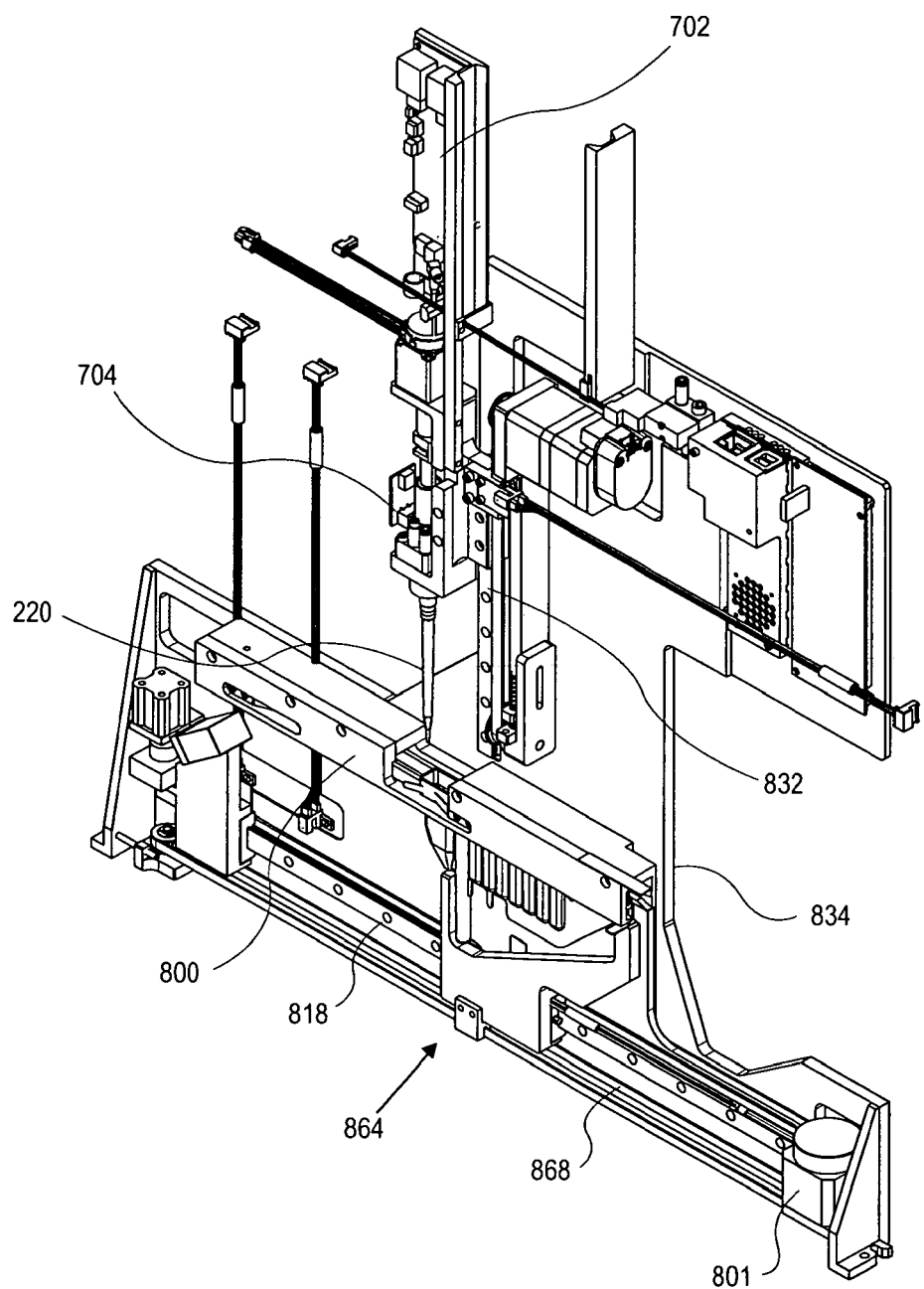
FIGS. 10(a) and 10(b) disclose an assay cartridge in processing lane.

FIG. 10(a) shows a perspective view of a processing lane with an engaged assay cartridge.

Figure 10B:
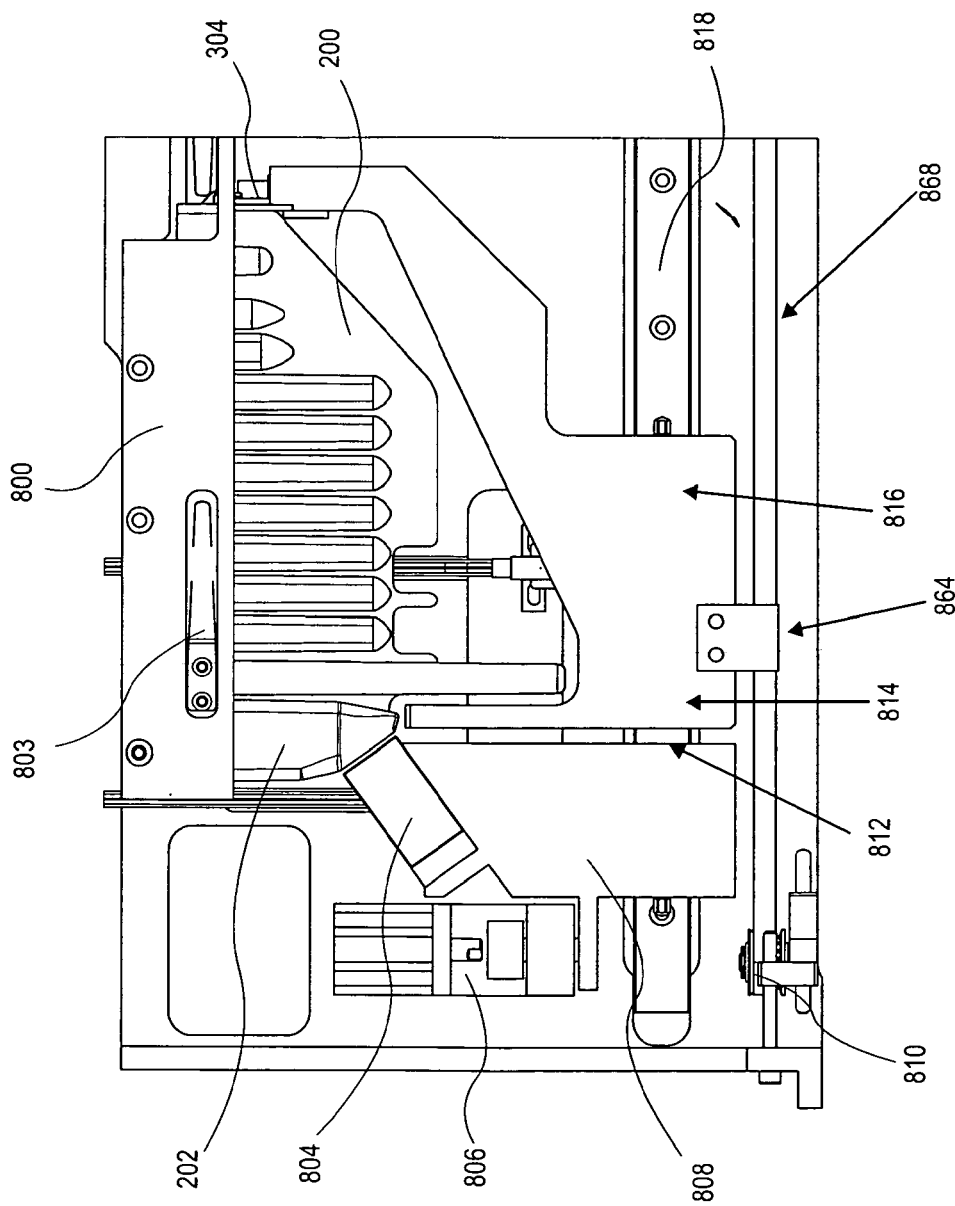

FIG. 10(b) shows a side view of a processing lane with an engaged assay cartridge.

Figure 10C:
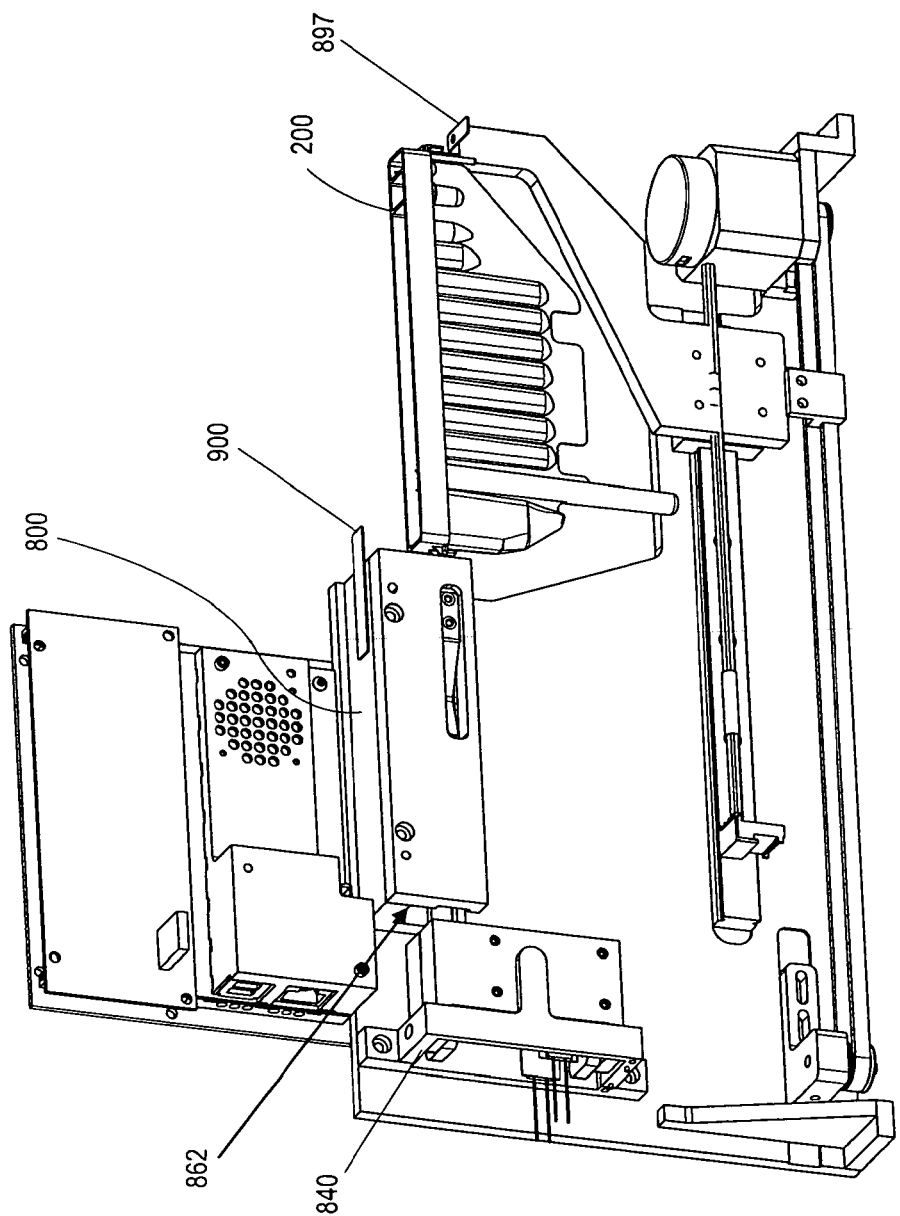
FIG. 10(c) discloses an assay cartridge in a heating lane.

FIG. 10(c) shows a perspective view of a processing lane that has thermal control with an engaged assay cartridge.

Figure 10E:
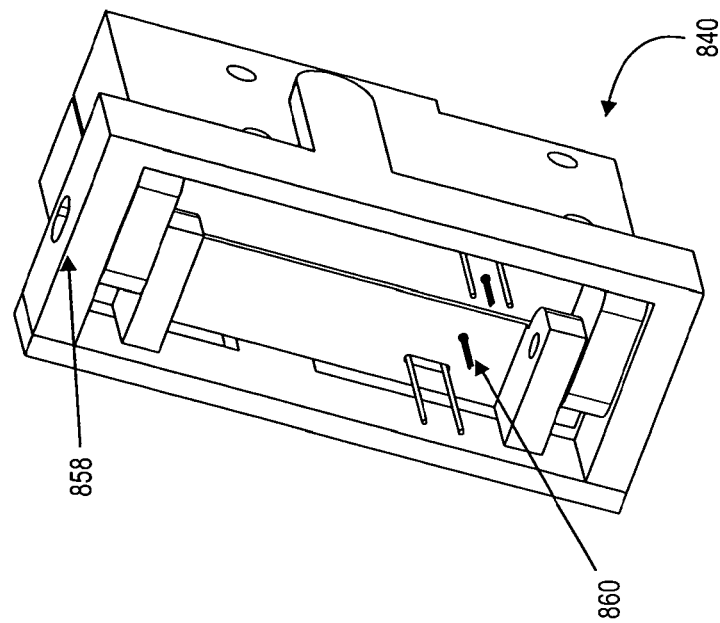
FIGS. 10(d) and 10(e) show perspective view of a processing lane heater.
Figure 10D:
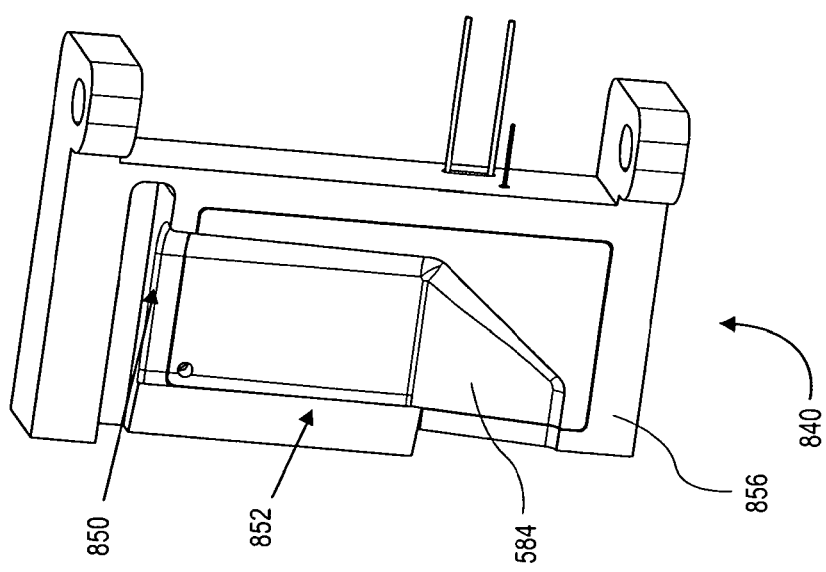

FIGS. 10(d) and 10(e) show different perspective views of an embodiment of a processing lane heater.

Figure 11:
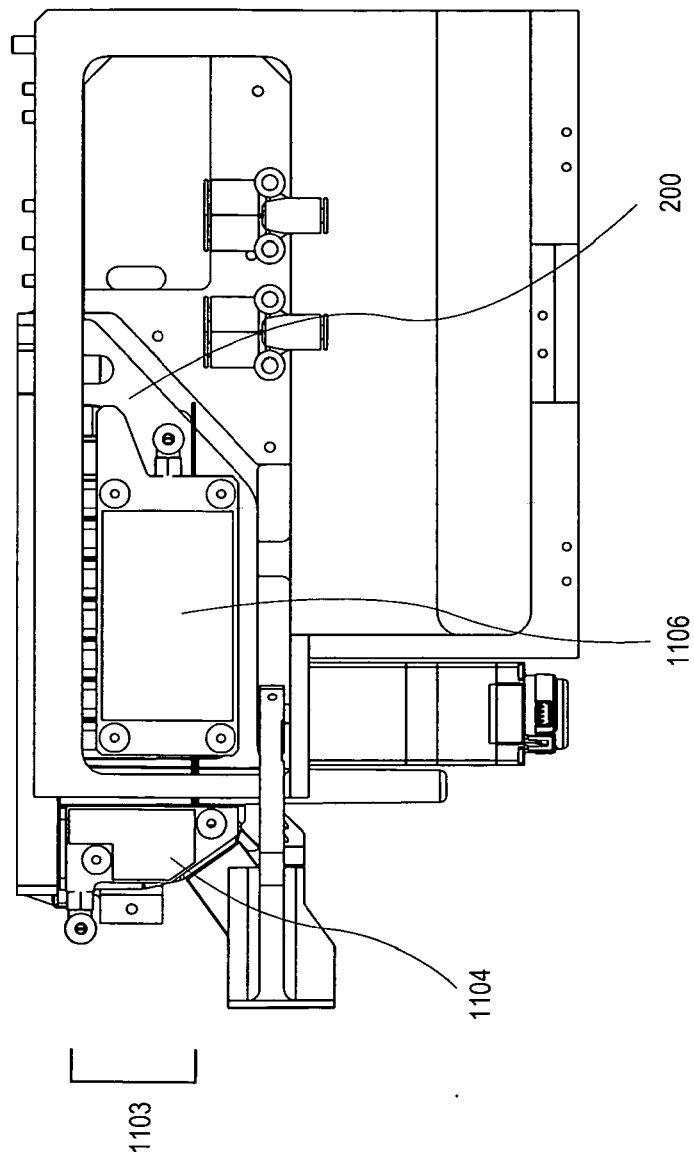
FIG. 11 shows a side view of another lane heater embodiment.

FIG. 11 shows a side, cross-sectional view of a processing lane of a processing lane heater according to an alternative embodiment of the invention.

The assay cartridges 200 described above are processed by the system in one or more processing areas, which incorporate mechanisms for performing specific steps necessary for processing a patient sample. Such mechanisms may include fluid transfer devices suited to a volume of about 1 mL, or fluid transfer devices suited to a volume of 100 μL to 200 μL, or even down to 10 μL or less, temperature control devices, magnetic devices, and devices for performing other necessary functions. A processing area may include one or more of these devices. These processing areas may include one or more lanes that process the assay cartridge 200 in a linear fashion. In some embodiments lanes that process the assay cartridge 200 may be arranged in a radial or circular fashion. In other embodiments, processing areas may include rotating carousels, areas where the assay cartridge is immobile and accessed by processing mechanisms on a gantry system or articulated arm, or other configurations that permit access to the assay cartridge by processing mechanisms in a controlled manner.

Referring again to FIG. 1(b), FIG. 1(b) shows an embodiment of the system that includes a number of processing lanes 116 for processing assay cartridges 200. The system may include a first, second, third, etc. processing lanes configured to process a sample in an assay cartridge 200. It can also include a transfer shuttle 50, which moves assay cartridges 200 between the processing lanes 116.

In some embodiments, a controller 94 directs operations of the processing lanes 116 and the transfer shuttle 50. In one embodiment, the controller can store and execute one or more protocols for directing assay cartridges 200 through a series of specified processing lanes 116 in a specified order using the transfer shuttle 50. For example, the controller 94 may be configured to execute a first protocol and a second protocol. In one embodiment, the controller 94, in executing the first protocol, directs the transfer shuttle 50 to move an assay cartridge 200 from a first processing lane (e.g., a cartridge loading lane) to a second processing lane (e.g., a heating lane). In executing the second protocol, the controller may direct the transfer shuttle 50 to move an assay cartridge 200 from the first processing lane (e.g., the cartridge loading lane) to a third processing lane (e.g., a wash lane) without moving the assay cartridge to the second processing lane (e.g., the heating lane). Thus, in embodiments of the invention, cartridges can be transferred between adjacent or non-adjacent lanes in any suitable manner. Non-limiting examples of first, second, and third processing lanes can be selected from the group consisting of a heating lane configured to warm an assay cartridge, an amplification preparation lane, a temperature stabilization heating lane configured to maintain the temperature of an assay cartridge, an elution lane, and a wash lane.

In other embodiments of the invention, the system includes a first processing lane configured to perform operations on a sample in an assay cartridge 200, a transfer shuttle 50 to move assay cartridges into and out from the first processing lane, and a controller 771 to direct operation of the system. The controller 94 may be configured to control operations in the first processing lane and the transfer shuttle 50. Such a controller may be configured to execute a first protocol and a second protocol. The controller, in executing the first protocol, directs the transfer shuttle to move a first assay cartridge 200 into the first processing lane. After a fixed interval, the controller directs the transfer shuttle 50 to move the first assay cartridge 200 out of the first processing lane. Within the fixed interval, the controller directs the first processing lane to execute a first sequence of operations. The controller, in executing the second protocol, directs the transfer shuttle 50 to move a second assay cartridge 200 into the first processing lane. After the fixed interval, the controller 94 directs the transfer shuttle 50 to move the second assay cartridge out of the first processing lane and directs the first processing lane to execute a second sequence of operations. This sequence of operations of the first protocol may be different from the sequence of operations of the second protocol.

Flexibility in both the routing of assay cartridges 200 between individual processing lanes 116 and in the operations performed within a given processing lane gives the system a high degree of operational adaptability.

The system can include processing lanes 116 that perform the operational steps needed for nucleic acid extraction and purification from a biological or patient sample. Each processing lane 116 can accommodate an assay cartridge 200. When the system uses a linearly arranged assay cartridge 200 each processing lane may extend linearly relative to the long axis of the assay cartridge. Such processing lanes 116 may mirror the dimensions of the assay cartridge 200, reducing the need to orient the assay cartridge and permitting the system to package multiple processing lanes in a space-efficient parallel manner. In some embodiments, the system includes processing lanes that are physically arranged in an order approximating their order of use in at least some protocols. This advantageously minimizes the distance and time the system needs to transfer assay cartridges between processing lanes. Alternatively, the system may include processing lanes with similar functions grouped together. This advantageously minimizes the time spent performing repetitive functions, such as, for example, washing.

As show in FIG. 1(b) the system may include different types of processing lanes that support functions appropriate to different processing steps. In some embodiments, the system includes multiple replicates of some lane types, allowing processing of multiple assay cartridges 200 in parallel. Examples of processing lane types include a cartridge loading lane 116(f), a transfer lane 50, a heated temperature stabilization lane 116(j), a wash lane 116(a) and 116(b), an elution lane 116(e), an amplification preparation lane 116(g), and a waste lane 116(c). In some embodiments, the system includes 13 processing lanes in the following sequence:

| LANE POSITION | LANE TYPE |
|---|---|
| 1 | AMPLIFICATION PREPARATION LANE |
| 2 | CARTRIDGE LOADING LANE |
| 3 | ELUTION LANE |
| 4 | WASTE LANE |
| 5 | HEATED TEMPERATURE STABILIZATION LANE |
| 6 | AMBIENT TEMPERATURE STABILIZATION LANE |
| 7 | AMBIENT TEMPERATURE STABILIZATION LANE |
| 8 | WASH LANE |
| 9 | WASH LANE |
| 10 | WASH LANE |
| 11 | WASH LANE |
| 12 | WASH LANE |
| 13 | WASH LANE |

The first lane position can be near the center of the instrument, with successive lanes numbered toward the right side of the system as viewed from the front. Successive lane positions may be disposed adjacent the preceding lane position. Alternatively, the system may incorporate one or more processing lanes that individually incorporate all of the processing tools needed to perform every processing step.

Figure 20A:
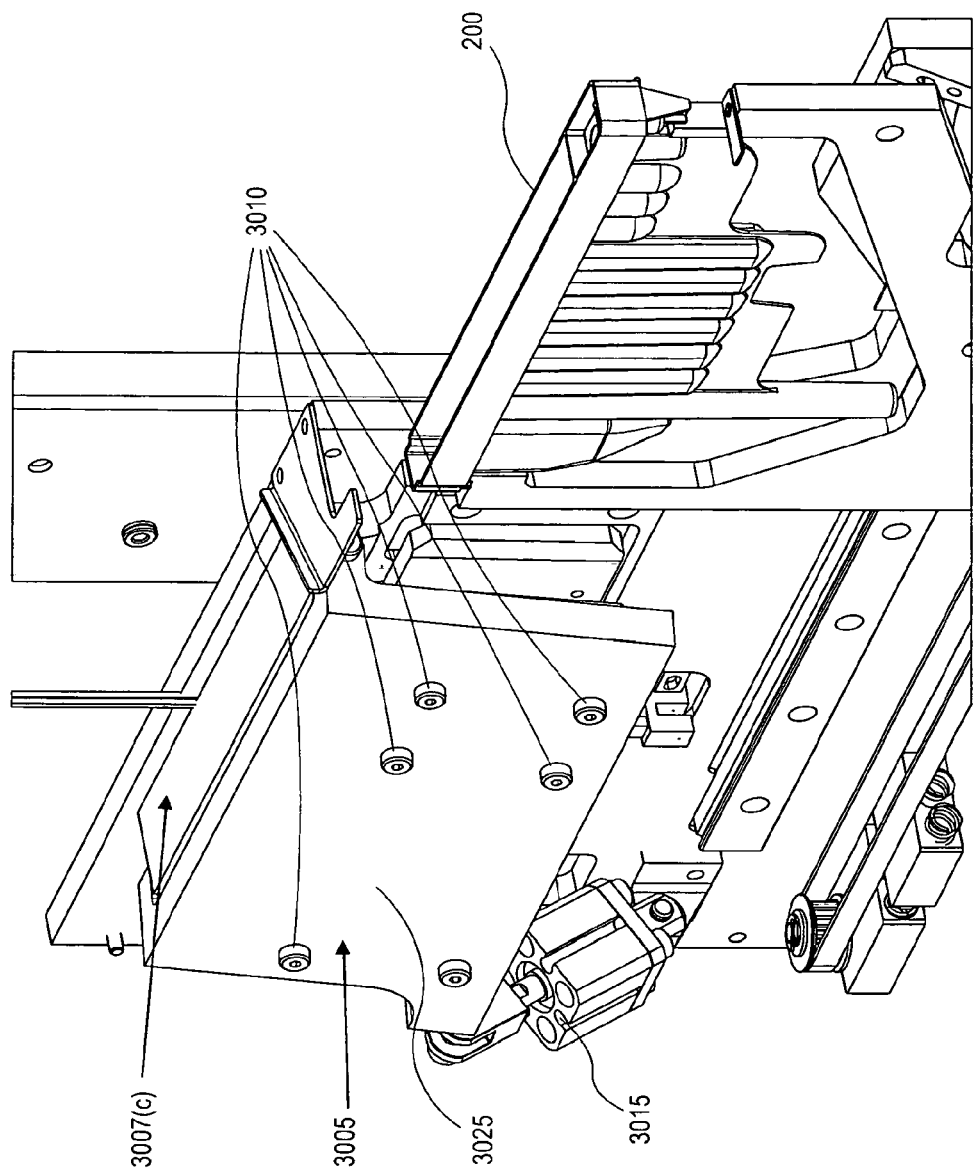
FIG. 20(a) shows an embodiment of a cartridge heater.
Figure 20B:
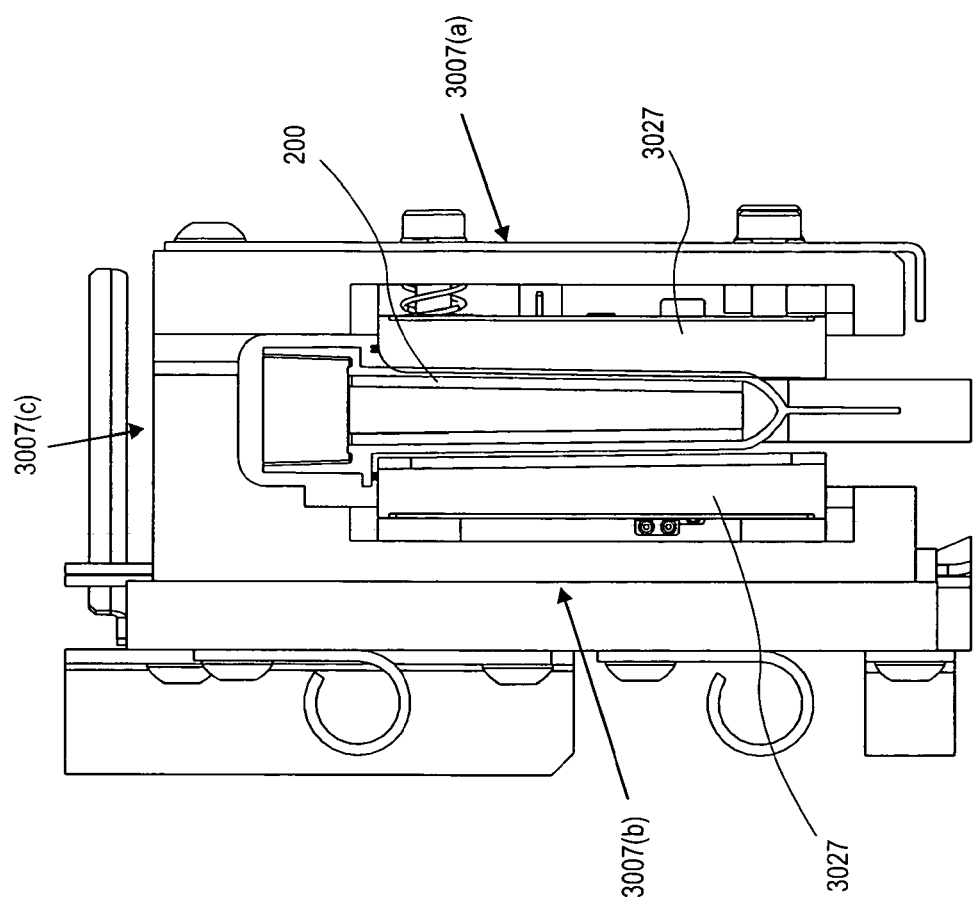
FIG. 20(b) shows a section of an embodiment of a cartridge heater.
Figure 20C:
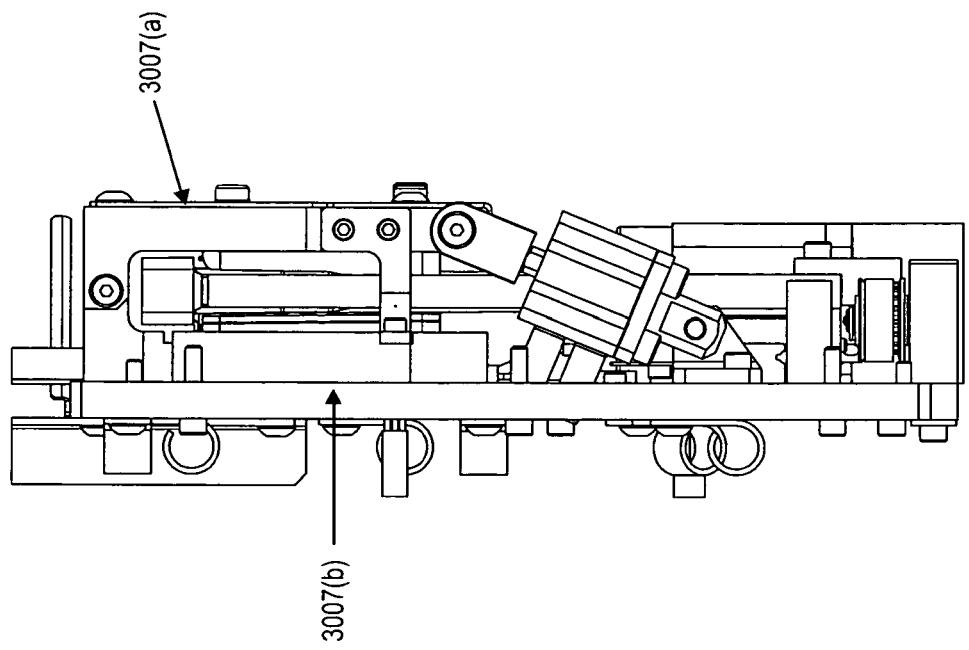
FIG. 20(c) shows an embodiment of a cartridge heater in an open position.
Figure 20D:
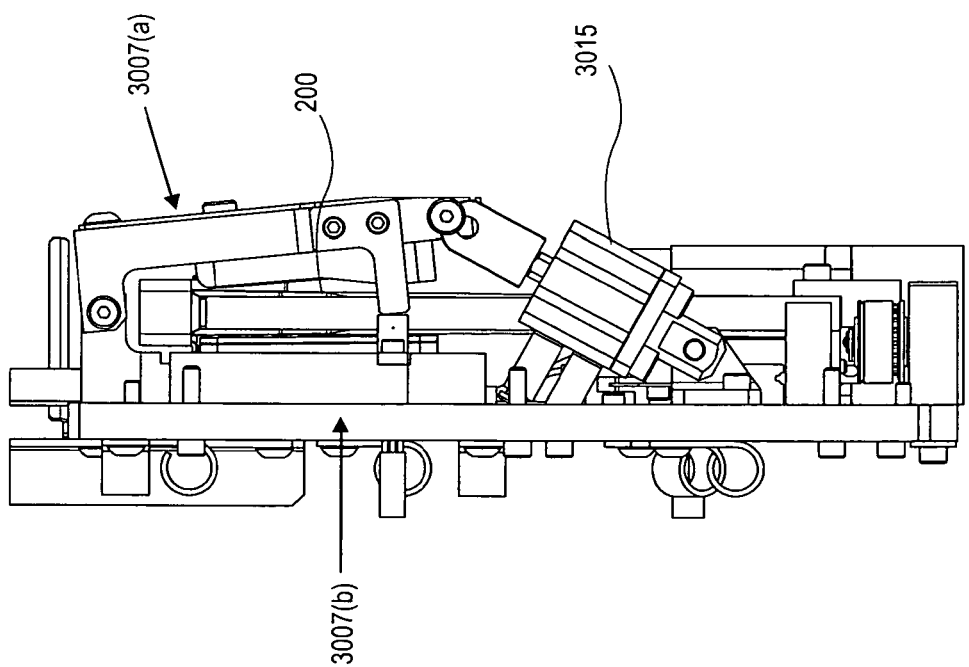
FIG. 20(d) shows an embodiment of a cartridge heater in a closed position.
Figure 20E:
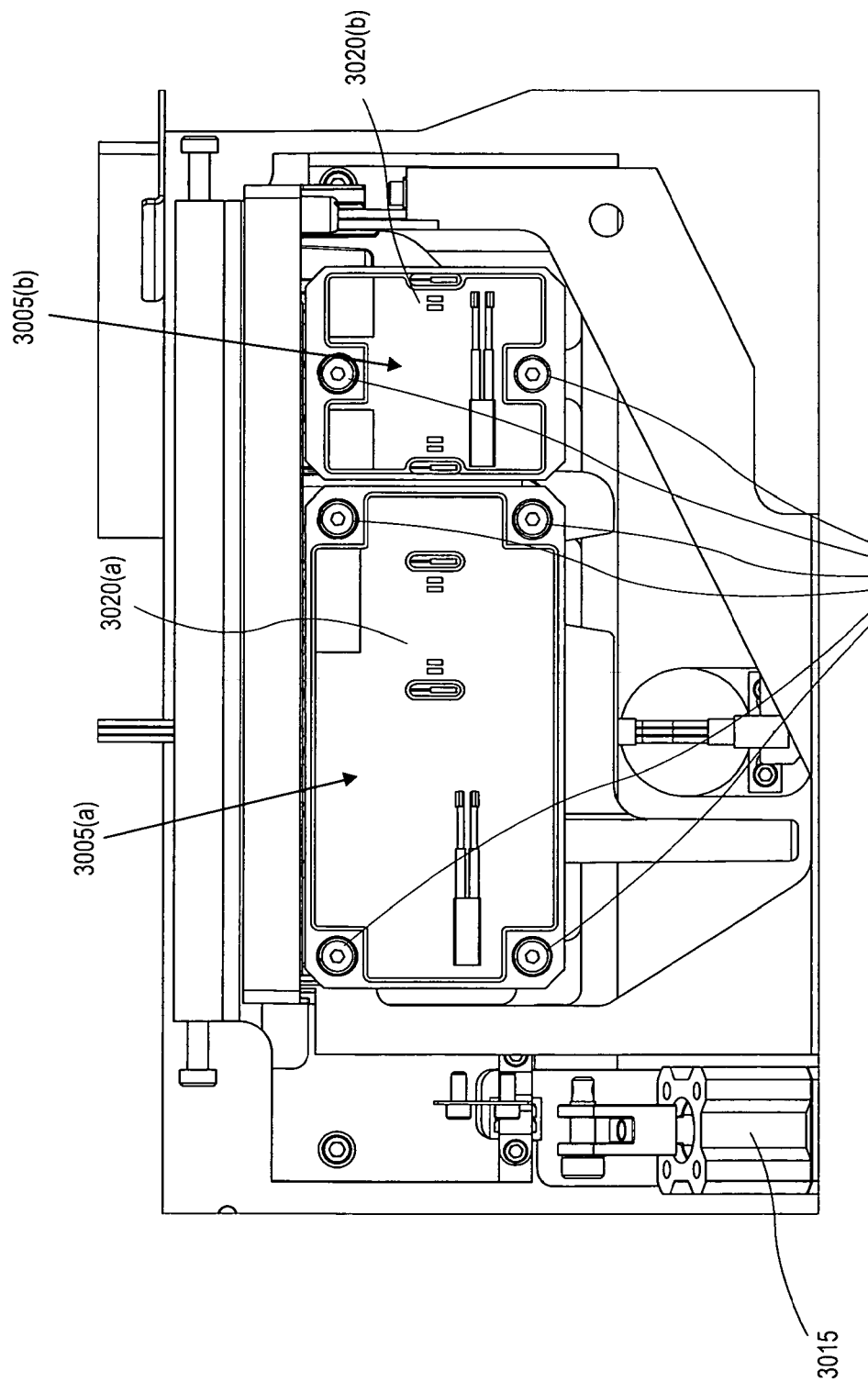
FIG. 20(e) shows a section of an embodiment of a cartridge heater.
Figure 20F:
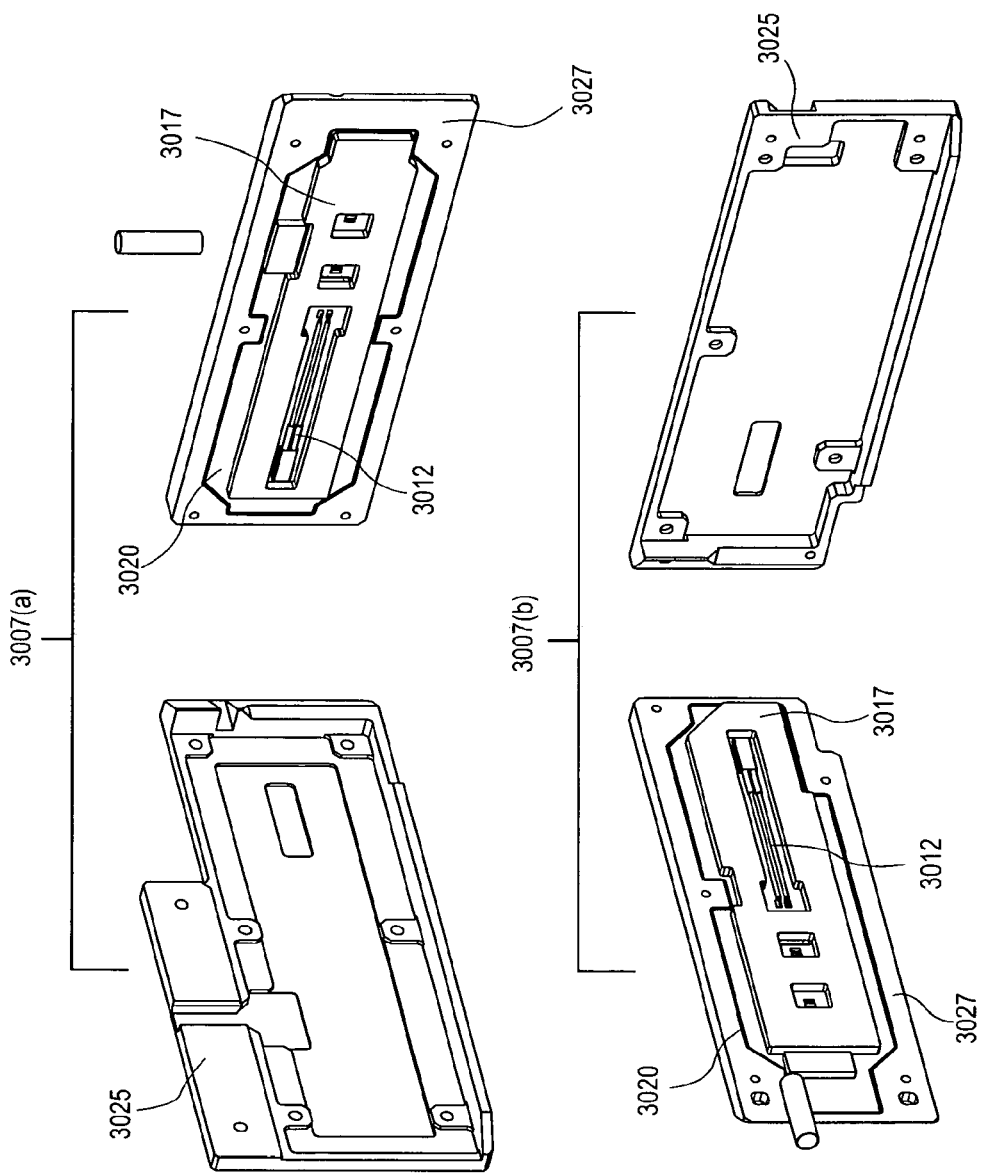
FIG. 20(f) shows components of a cartridge heater.
Figure 20G:
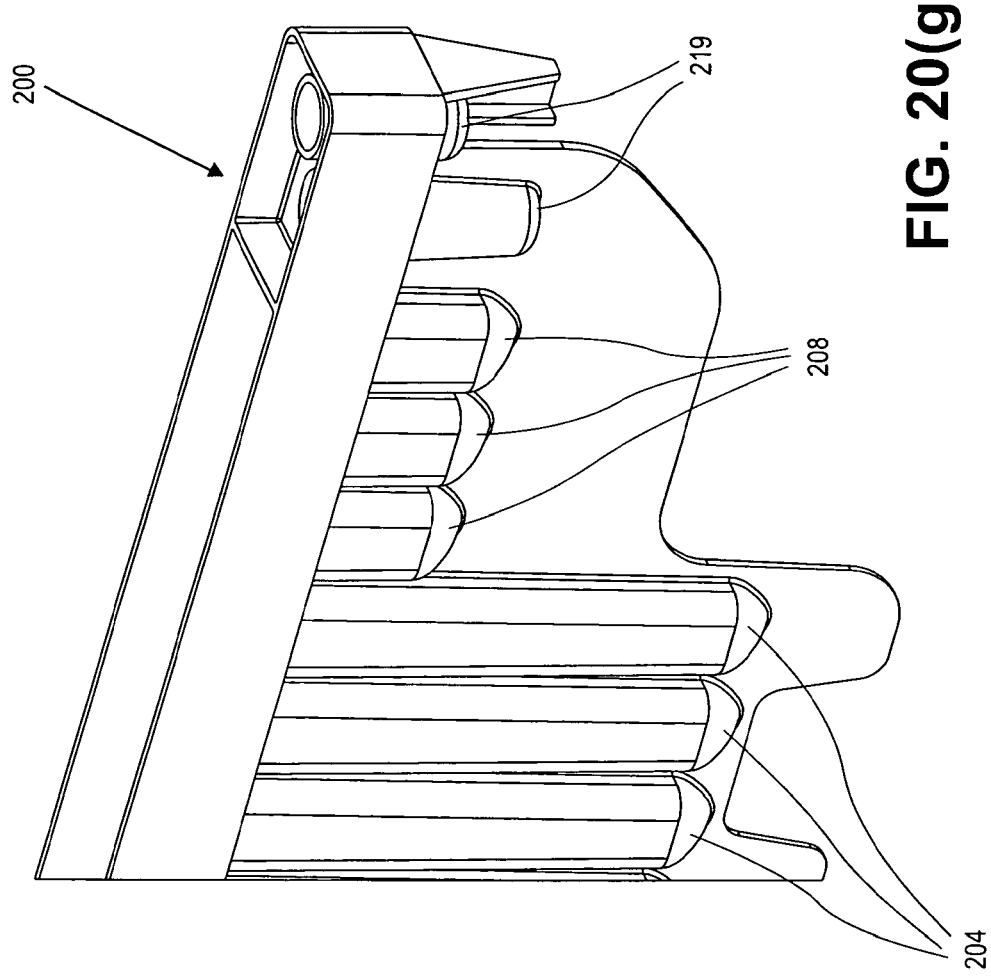
FIG. 20(g) shows an embodiment of an assay cartridge that may be used with a cartridge heater.
Figure 20H:
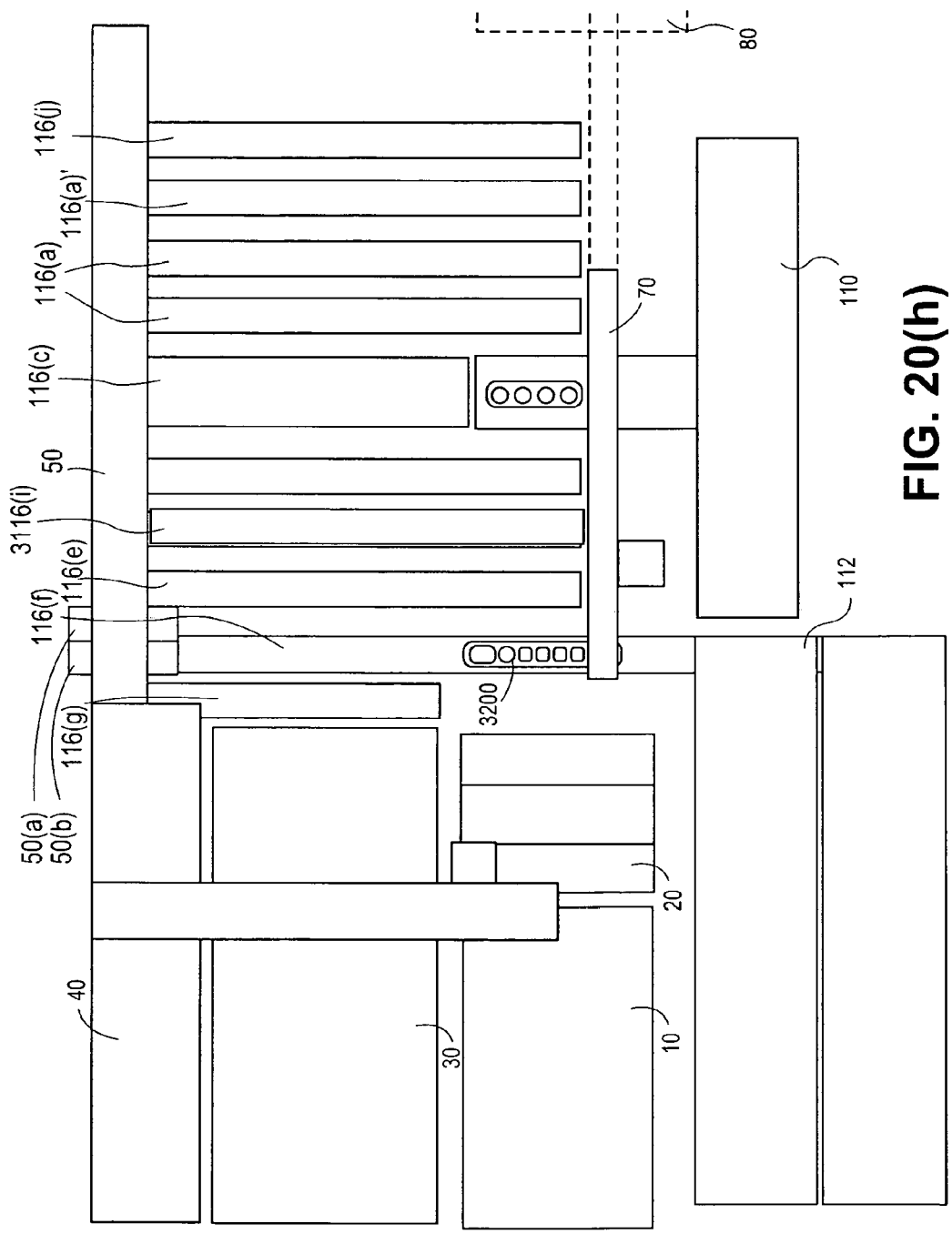
FIG. 20(h) shows a top plan view of a layout of the components of an instrument according to an embodiment of the invention.
Figure 20I:
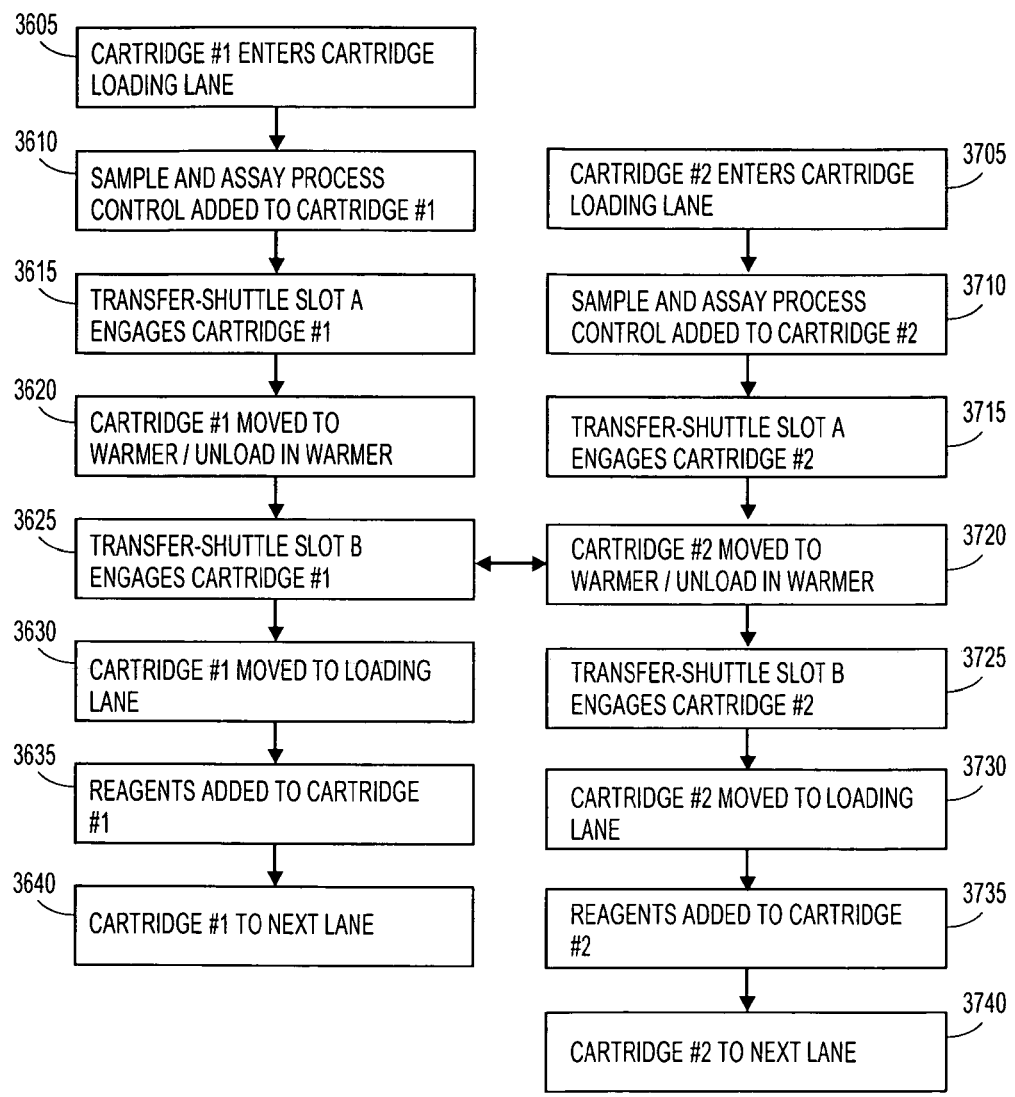
FIG. 20(i) shows an embodiment of a cartridge-swapping process.

Another embodiment of a system with different types of processing lanes configured to perform different steps is shown in FIG. 20(h). In this embodiment, the system includes a cartridge warming lane, which serves to rapidly bring the temperature of the cartridge and its contents to the temperature required for consistent sample processing. In such an embodiment, the system may have 10 processing lanes, some of which are replicates, in the following sequence:

| LANE POSITION | LANE TYPE |
|---|---|
| 1 | AMPLIFICATION PREPARATION LANE |
| 2 | CARTRIDGE LOADING LANE |
| 3 | ELUTION LANE |
| 4 | CARTRIDGE WARMING LANE |
| 5 | WASH LANE (SMALL MAGNET) |
| 6 | WASTE LANE |
| 7 | WASH LANE (LARGE MAGNET) |
| 8 | WASH LANE (LARGE MAGNET) |
| 9 | WASH LANE (LARGE MAGNET) |
| 10 | TEMPERATURE STABILIZATION LANE WITH PIPETTE PUMP |

Embodiments of the invention may use one or more of the above described lanes, in any suitable combination.

Figure 14A:
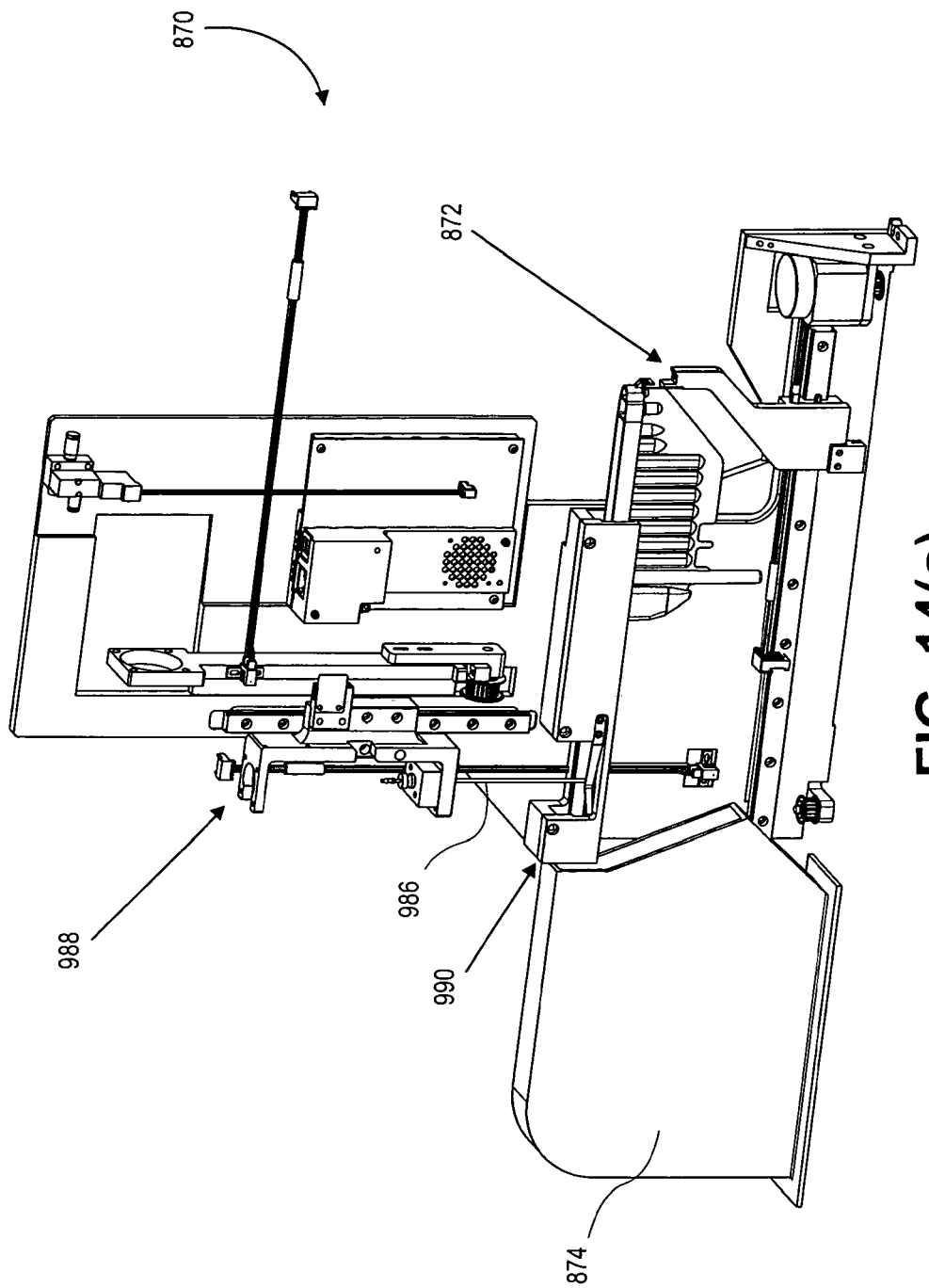
FIG. 14(a) shows components in a waste lane.
Figure 14B:
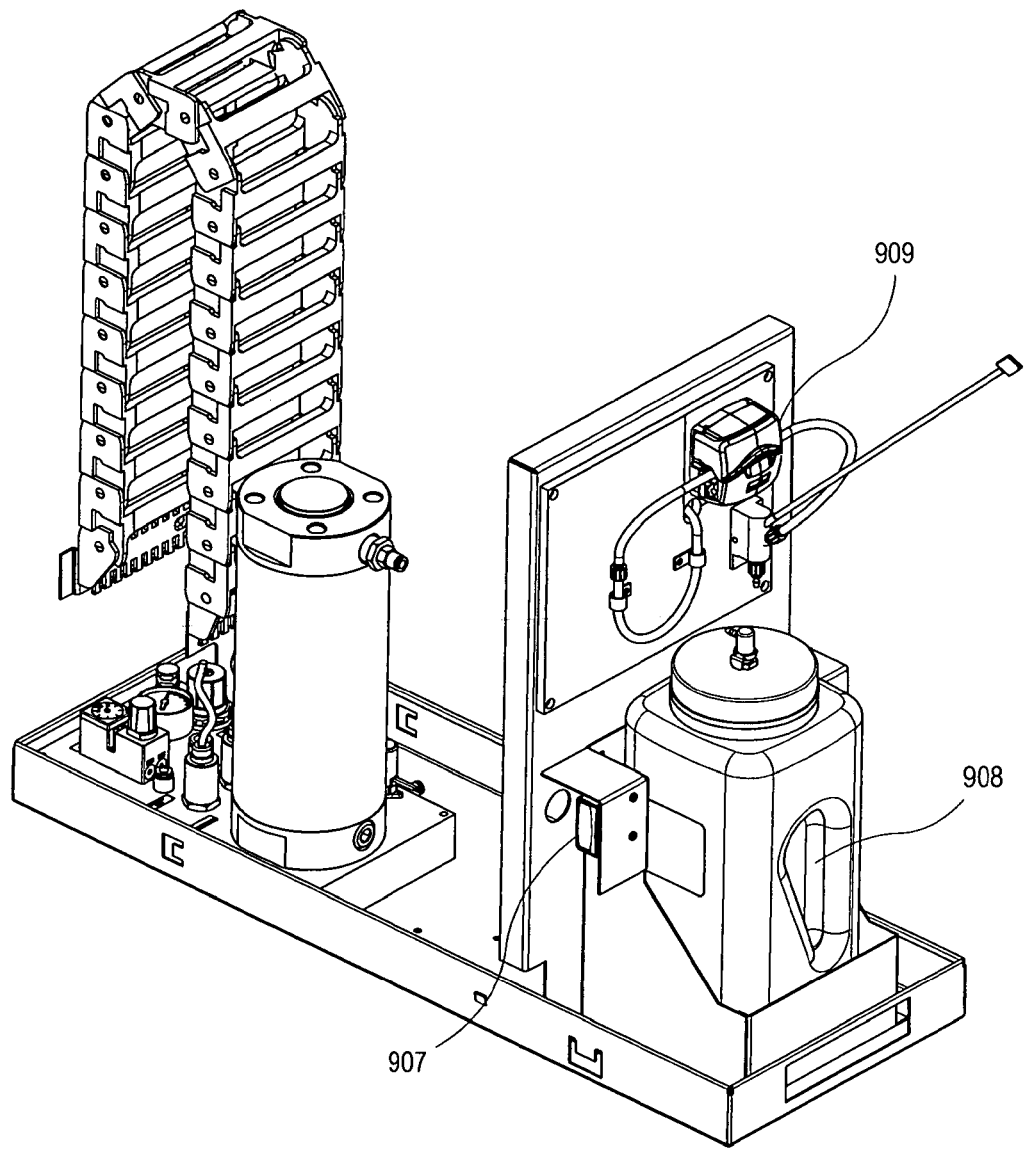
FIG. 14(b) shows a hydropneumatic assembly.
Figure 14C:
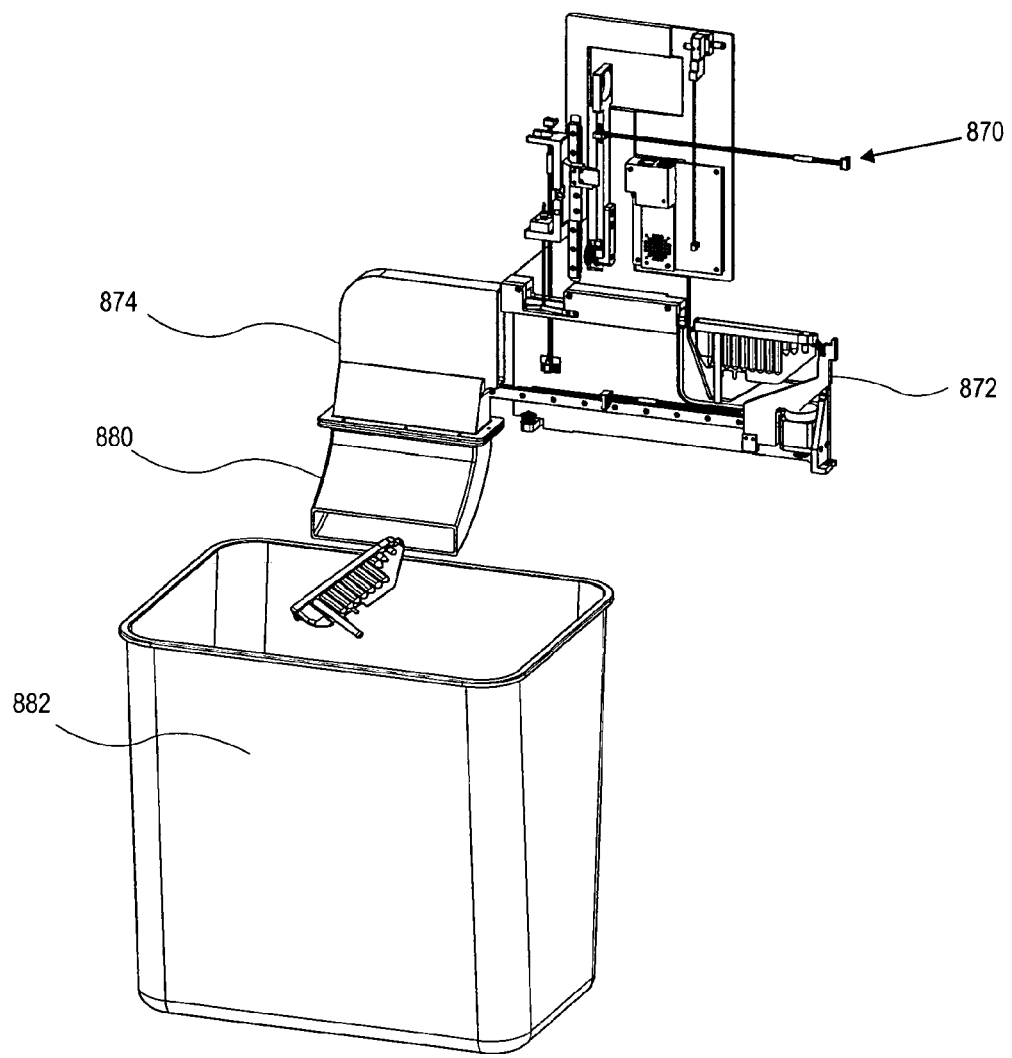
FIG. 14(c) shows a perspective view of a waste lane.
Figure 14D:
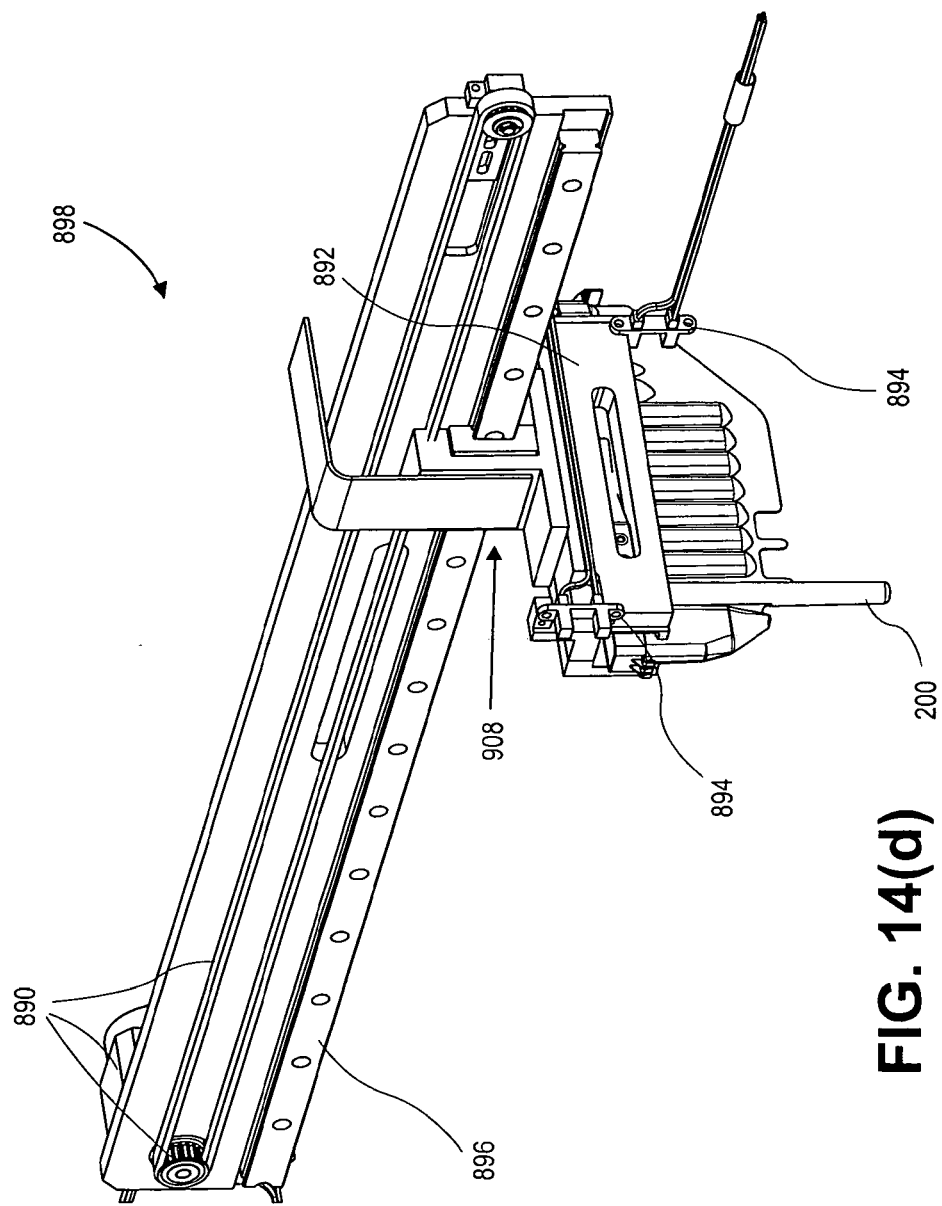
FIG. 14(d) shows a perspective view of a transfer shuttle.
Figure 14F:
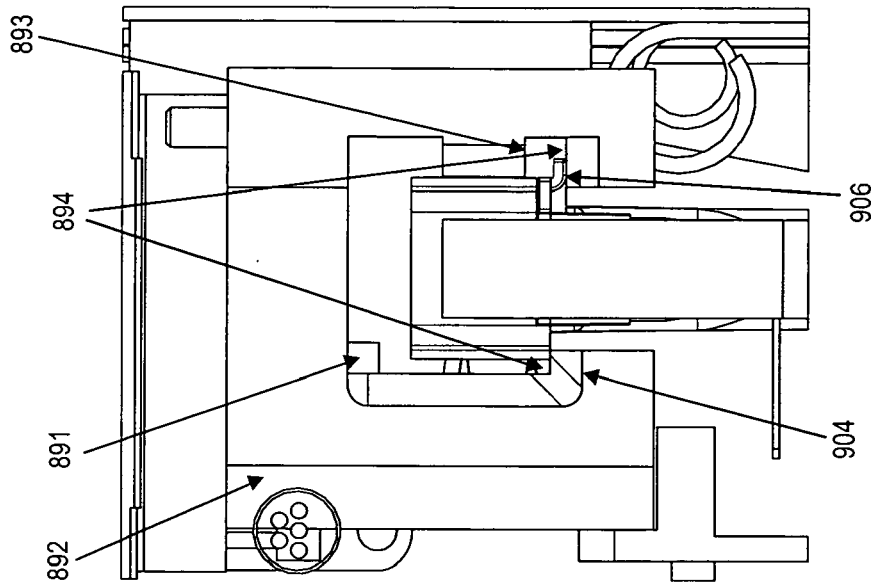
FIG. 14(f) shows a front view of a processing lane.
Figure 14E:
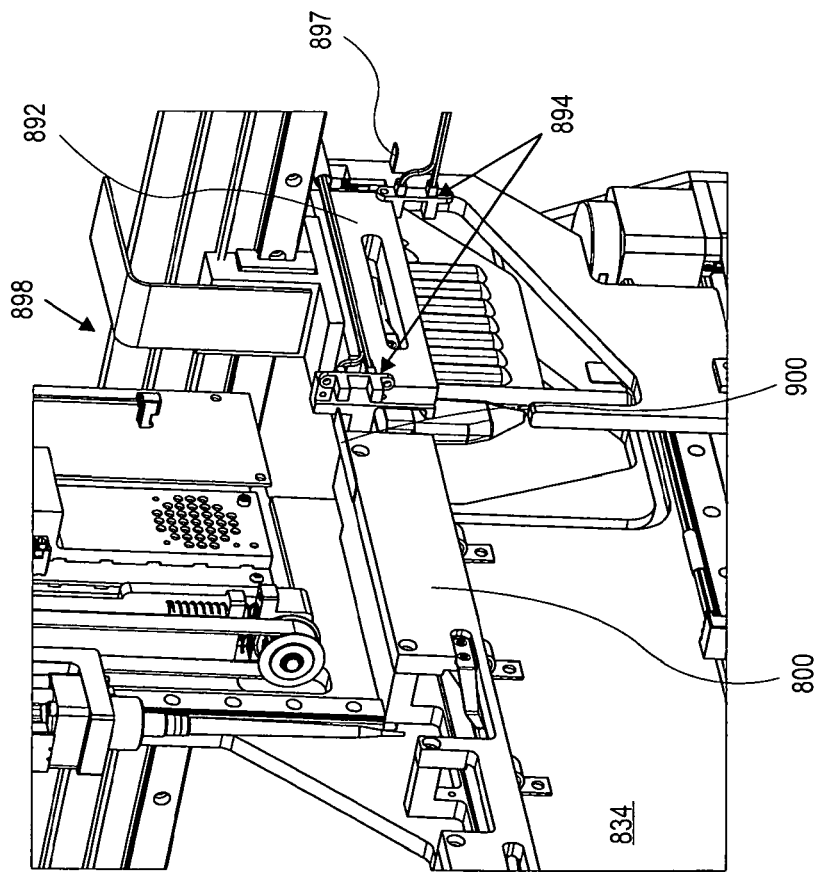
FIG. 14(e) shows a close up perspective view of a transfer shuttle.

Referring to FIGS. 10(a)-10(c), a processing lane may include a lane support 834 to retain processing lane components, a cartridge guide 800 to support and guide an assay cartridge 200, a cartridge carriage 816 to move an assay cartridge 200 along a lane motion path within the processing lane, and a transfer position to interact with the transport shuttle 898 (shown in FIG. 14(e)).

Figure 20K:
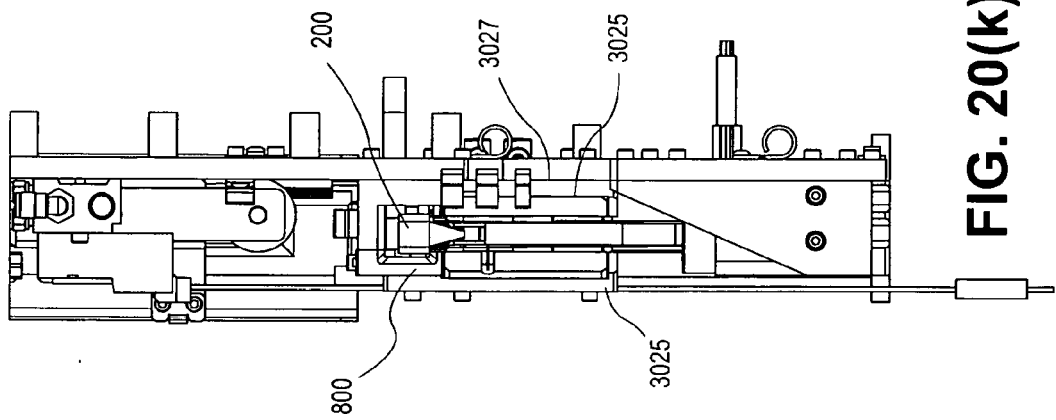
FIG. 20(k) shows a section of an embodiment of a lane with a lane heater.
Figure 20J:
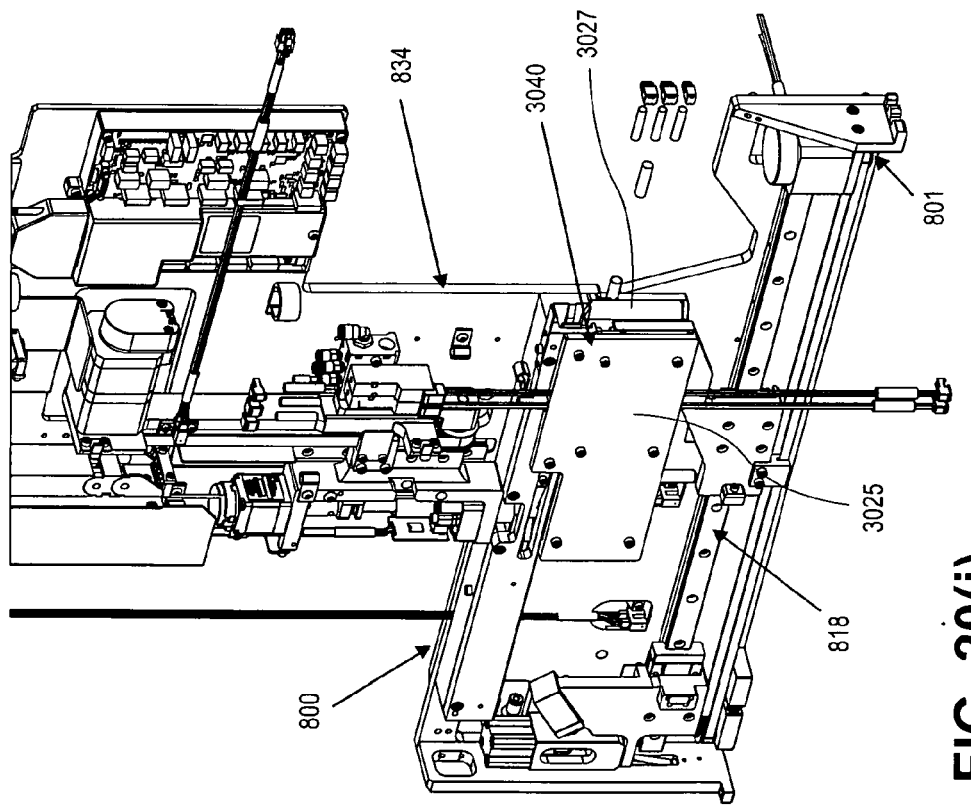
FIG. 20(j) shows an embodiment of a lane with a lane heater.

The lane support 834 (see FIG. 20(j)) provides attachment points and holds processing lane components in relationship to one another. In some embodiments, the lane support forms a vertical wall disposed generally parallel to the axis of an assay cartridge 200 in the processing lane 116. The configuration of the lane support 834 may be different in different processing lanes 116, conforming to the shape of other processing lane components. The lane support 834 may include mounting locations for at least some of these components.

The cartridge guide 800 supports an assay cartridge 200 while in a processing lane. Its purpose can be to retain the assay cartridge 200 during movement. It may also serve to consistently locate the assay cartridge 200 for interaction with processing tools. In some embodiments, the cartridge guide 800 supports a controlled surface that is part of the assay cartridge 200. In one embodiment, the controlled surface of the assay cartridge 200 is the bottom surface of the horizontal web 228 as discussed above. The cartridge guide 800 may support the assay cartridge 200 by providing a running surface within a guide channel 862 (see FIG. 10(c)), such a guide channel having a cross-section that is approximately complementary to the cross-section of at least portion of the assay cartridge 200.

In some embodiments, the cross-section of the guide channel 862 is slightly larger than the nominal size of an assay cartridge 200 in order to reduce friction, prevent jamming, or both. In some embodiments, the guide channel 862 of the cartridge guide 800 is the approximate shape of an inverted "U", fixed to the lane support with the open portion of the U facing downwards. Such an inverted U-shape includes a closed top wall, closed side walls depending at about right angles from the top wall, and an open bottom wall connected at about a right angle to the side walls. The open bottom wall may include two horizontal wall segments separated by a gap, with each segment connected to one of the side walls. This gap forms a channel opening. The various assay cartridge compartments and its vertical web may project through the channel opening.

FIG. 14(f) shows the inside of a shuttle channel 892 and the features therein may be similar to those in the guide channel 862. The upper aspect of the bottom wall forms a running surface. The assay cartridge rides upon the running surface, which may support the assay cartridge horizontal web 228 on one side and the bottom surface of a cartridge flange 906 on the other side. Since the running surface supports assay cartridge features that may be at two different heights, the two horizontal wall segments may also be at different heights.

As shown in FIG. 14(f), an indexing wall 893 can be placed below the top rim of the assay cartridge 200 to minimize contamination by fluid transfer. The cartridge guide 800 can cover the assay cartridge wherever possible to minimize contamination. The cartridge guide 800 can have a secondary anti-rotation feature 891 to prevent upwards rotation of the assay cartridge during pipetting operation.

In some embodiments, the cartridge guide 800 includes a retention recess formed within the interior of the U-shaped guide channel 862 as shown in FIG. 10(c). An external view of the cartridge guide 800 is also shown in FIG. 14(e). The retention recess extends along one wall of the U-shaped channel and is roughly complementary in shape to the cartridge flange 906. The retention recess can act to constrain vertical movement of the assay cartridge 200 during pipetting operations. As discussed above, such vertical movement may occur due to friction between a pipette tip and a barrier film 205; such movement adversely affects the accuracy of pipetting operations and may lead to spillage with subsequent contamination of the system.

The cartridge guide 800 may extend along less than the entire motion path of a processing lane. In a preferred embodiment, the cartridge guide 800 does not reach into the transfer position. In other embodiments, such as the waste lane shown in FIG. 14(a), the cartridge guide does not extend into other operative locations. The transfer shuttle 50 may perform the cartridge guide 800 function when an assay cartridge 200 is in the transfer position as described in more detail below. The cartridge guide 800 may terminate adjacent certain operative locations, such as lane heaters 840 (FIG. 10(c)) and 1104 (FIG. 11), where intimate contact between a portion of the assay cartridge 200 and the operative location is desirable for operation. The extended length of the linear-style assay cartridge allows the cartridge guide 800 to support the assay cartridge 200 when only a portion of the assay cartridge is engaged within the cartridge guide.

The cartridge guide 800 may include index springs to press the assay cartridge 200 against an internal aspect of one of the side walls of the guide channel 862 in order to better control lateral position of the assay cartridge. Index springs may be strips of a relatively stiff but elastic material, such as spring steel, mounted to a cartridge guide 862 side wall. In some embodiments, the index springs mount in openings within the cartridge guide 862 side wall.

Any of the walls of the guide channel 800 may include openings or piercings in one or more locations. In some embodiments openings in the guide channel top wall, give processing tools access to assay cartridge 200 compartments. Other openings, such as those described above for index spring mounting, may serve other functions.

A cartridge pusher (which may be an example of a loading transport) may be used to position an assay cartridge in any of several operative positions within a processing lane. The cartridge pusher can include a cartridge carriage 816 to engage the assay cartridge 200, a carriage track 818 to guide the motion of the cartridge carriage, and a carriage drive (not shown) to move the cartridge carriage along the carriage track.

In one embodiment, the cartridge carriage 816 engages a controlled surface of an assay cartridge 200 to move the assay cartridge within the cartridge guide 800. The cartridge carriage 816 may also unload the assay cartridge from the transfer shuttle 898 (see FIG. 14(d)), and return it. In some embodiments, the controlled surface utilized by the cartridge carriage 816 is a vertically disposed edge of the vertical web 226 at the distal end of the assay cartridge 200. A support tab feature 218 may be provided on the distal end of the assay cartridge, depending from the assay cartridge a small distance distal to the aforementioned controlled surface and thereby defining a gap. The cartridge carriage 816 can include a propelling feature 304 (see FIGS. 4(d) and 10(b)) that fits within this gap. In this configuration, movement of the cartridge carriage 816 toward the proximal end of the assay cartridge 200 drives the propelling feature 304 against the controlled surface. Alternatively, movement of the cartridge carriage 816 away from the proximal end of the assay cartridge 200 drives against the propelling feature 304 against the proximal aspect of the support tab 218.

In some embodiments, the cartridge carriage 816 positions an assay cartridge 200 at an operative location by driving from a single direction, by driving the propelling feature 304 against the controlled surface. This has the benefit of compensating for backlash in the lane motion path and of reducing the effect of tolerance stack up in the assay cartridge; improving the system's ability to position the assay cartridge 200 within a processing lane 116 consistently.

In some embodiments, the cartridge carriage 816 may engage an assay cartridge 200 using support tabs 218 near both ends. In other embodiments, the cartridge carriage 816 may engage an assay cartridge 200 using a support tab 218 located near only one end. This embodiment advantageously permits the use of processing lanes 116 that include tools which operate on the external surface of the assay cartridge 200. Such an arrangement can minimize interference between processing lane tools and the cartridge carriage 816. For example, a waste lane 116(c) or a processing lane incorporating a lane heater 116(j) may engage an assay cartridge from only one end.

The cartridge carriage 816 may connect to the carriage track 818 through a moving connection such as a track bearing. In some embodiments, the cartridge carriage 816 includes a magnetically responsive strike plate 814 at its proximal end to couple to a magnet trolley 808, as described in greater detail below. In at least some processing lanes, the cartridge carriage 816 may include a microtip holder to store one or more microtips 542. The microtip holder can be a shelf that extends from the cartridge carriage 816, and includes at least one microtip holding feature. In some embodiments, this microtip holding feature is a hole or piercing through the shelf. The microtip holder may be disposed on the lane motion path so that the cartridge pusher may position a microtip 542 (see FIG. 13(f)) under a pipettor in a processing lane. Towards that end the microtip holder may located near the distal terminus of the cartridge carriage 816. Alternatively, microtip holding features may be placed at other positions within a processing lane in which they are accessible by a suitable pipettor. Such locations include but are not limited to the cartridge guide 800 and portions of the lane support 834.

The cartridge carriage 816 can also serve as a grounding plane to improve the accuracy of a liquid sensor. Portions of the cartridge carriage 816 may be extended to come into close proximity to the wells of the assay cartridge 200. In embodiments of the invention, liquid sensors can be capacitance based; in such embodiments, bringing a metal object close to the bottom of a liquid filled well may provide a greater change in capacitance that would be observed with liquid alone. A sensing circuit that can include liquid sensing capability is described in further detail below.

The cartridge carriage 816 may be disposed beneath the cartridge guide 800 to engage and drive from the underside of an assay cartridge 200. This arrangement facilitates processing of the assay cartridge 200 using processing tools located above the cartridge. The cartridge guide 800 and cartridge carriage 816 both need access to the assay cartridge. While some embodiments include a cartridge guide 800 that is generally disposed above an assay cartridge 200 and a cartridge carriage 816 that is disposed below an assay cartridge, this is merely one of a number of arrangements that may accomplish a similar result. In alternative embodiments, the system may include a cartridge guide 800 that is disposed below an assay cartridge 200 and a cartridge carriage 816 that is disposed above the assay cartridge, a cartridge guide and a cartridge carriage that oppose each other on either side of an assay cartridge, a cartridge guide and a cartridge carriage in an intercalated arrangement, or some combination of these. An arrangement in which the cartridge carriage 816 is disposed beneath the cartridge guide 800 to engage and drive an assay cartridge 200 from the underside advantageously limits the width of processing lanes 116, subsequently decreasing the distance between processing lanes and decreasing the size of an assembly of processing lanes. In arrangements where a large number of processing lanes 116 are present in response to a need for high system throughput, for example, a small decrease in processing lane width can produce a considerable reduction in system size. Further, since some processing tools, such as pipettors, require access to the assay cartridge 200 from above the disposition of the cartridge carriage 816 beneath the cartridge guide 800 avoids potential interference with processing tools.

In some embodiments, in at least some processing lanes 116, the assay cartridge does not rest fully on the cartridge carriage 816 during movement. In such embodiments, the cartridge guide 800 supports the assay cartridge 200 and the cartridge carriage 816 provides motive force to move it along the motion path. Such an arrangement can simplify release of the assay cartridge 200 from a processing lane configured in this fashion, for example, for transfer to a waste container following use.

A carriage track 818 may be used to guide the motion of the cartridge carriage 816 and, in some processing lanes, may guide motion of other components such as magnet trolleys 808. In some embodiments, the carriage track 818 attaches to the lane support 834, oriented parallel to the direction of and extending along at least a portion of the motion path within the processing lane. The carriage track 818 can link to moving components such as the cartridge carriage 816 through complementary bearings. In some embodiments, the carriage track 816 is a linear guide rail and the bearings may be caged ball bearing blocks, caged roller bearing blocks, or equivalent devices.

The carriage drive may move the cartridge carriage 816 along the carriage track 818 by any of a number of drive methods such as a lead screw and nut, a linear motor, or a pneumatic actuator. In some embodiments, the system uses a drive motor 801 attached to the lane support 834 near one end of the carriage track 818 and coupled to a drive pulley. An idler pulley 810 may be attached to the lane support 834 near the opposing end of the carriage track 818, by an attachment that allows adjustment of the separation distance between idler pulley 810 and drive pulley. In such an embodiment, a timing belt 868 may connect the drive pulley to the idler pulley and connect to the cartridge carriage 864 via a coupling device 864. Rotation of the motor 800 drives the timing belt 868, resulting in movement the cartridge carriage 816 along the carriage track 818.

Specific types of processing lanes, including transfer lanes 116(*h*), heating lanes 116(*j*), and wash lanes 116(*b*) may include a millitip pipettor assembly 704. This serves to transfer fluids among compartments of the assay cartridge 200 while in the processing lane. This millitip pipettor assembly 704 can include a millitip pipettor that is similar to the millitip pipettor used for transferring samples, as described above. The millitip pipettor assembly may include a liquid sensor, a pressure sensor for sensing pressure within the millitip pipettor, or both types of sensors. In some embodiments, the millitip pipettor assembly 704 is disposed above the cartridge guide 800 at a fixed position along the lane motion path. Thus, in some embodiments of the invention, the cartridge guide can be positioned to align an assay cartridge with a first pipettor such as a millitip pipettor (or alternatively or additionally, a second pipettor such as a microtip pipettor). The guide channel 862 top wall may include a piercing at the fixed position to allow the millitip pipettor to access the assay cartridge. Alternatively, the guide channel may be discontinuous, having a gap at a fixed position to allow the millitip pipettor access to the assay cartridge 200. Other components of the millitip pipettor assembly 704 may include a lane elevator 832 that serves to raise and lower the millitip pipettor with respect to the cartridge guide 800, a millitip mandrel to engage a millitip 220 from the assay cartridge, a millitip aspirator to drive pipetting action, a millitip ejector to disengage a millitip 220 from a mandrel after use, a liquid sensor 702 to detect fluids, millitips, and alignment features. A description of each of these other components of a millitip pipettor assembly is provided in more detail below.

Some processing lanes 116 may include a microtip pipettor assembly to transfer fluids among compartments of the assay cartridge in the processing lane. The microtip pipettor assembly may include a liquid sensor, a pressure sensor for sensing pressure within the microtip pipettor, or both types of sensors. In some embodiments, the microtip pipettor assembly is substantially similar to the millitip pipettor assembly 704 and disposed in the same fashion. However, the microtip pipettor assembly includes a microtip pipettor 1142 similar to that utilized on the XYZ transport device 1100 described below. Features of the microtip pipettor may be substantially similar to those of the millitip pipettor 704 used for aspiration of samples. The microtip pipettor assembly can include a lane elevator, a fluid level sensor, a microtip mandrel for engaging a microtip 542, a microtip aspirator to drive pipetting action, and a microtip ejector to release microtips from the microtip pipettor assembly. In some embodiments, the microtip pipettor assembly can access microtips 542 held in a microtip holder on the cartridge carriage 816, and may return microtips 542 to the cartridge carriage after use. A microtip pipettor assembly may be used to transfer a reaction vessel plug 222 to a reaction vessel base 246. In such an embodiment, the microtip pipettor assembly may also remove a plugged reaction vessel from the assay cartridge, and transport a plugged reaction vessel between different areas of the system. Processing lanes 116 that incorporate a microtip pipettor assembly may include an elution lane 116(e) or other processing lanes where transfer of small volumes of liquid is necessary.

In an alternative embodiment, processing lanes 116 may incorporate dual resolution pipette pumps, which are capable of accurate aspiration and dispensing of a wide range of volumes. In some embodiments, pipetting functions may be provided by a gantry system that supports one or more pipettor carriages, similar to the pipettor carriage 712 of the sample pipettor 700 that positions a pipettor over a processing lane when needed.

FIG. 10(b) shows an example of a processing lane 116 that includes a magnetic separation mechanism that incorporates a separation magnet 804 to selectively apply a magnetic field to the contents of a well of the assay cartridge 200, permitting the system to remove liquid contents without removing a magnetically responsive solid or particulate phase. Examples of such processing lanes can include an ambient temperature lane 116(h), a wash lane 116(b), an elution lane 116(e), or other processing lane where manipulation of a magnetically responsive solid or particulate phase is needed. The applied magnetic field draws the magnetically responsive solid or particulate phase to an internal surface of the assay cartridge 200 near the region where the magnetic field 804 is applied. In some embodiments, this region is within the culvert 211 at the lower proximal aspect of the reaction well 202. This permits a pipettor to enter the reaction well 202 and withdraw liquid contents at a point distant from the culvert 211, at the point of greatest reaction well depth. This relative positioning of a pipettor and the separation magnet 804 advantageously permits the removal of a large a fraction of the fluid held in the reaction well with minimal risk of unintended aspiration of the magnetically responsive solid or particulate phase. Removing a large fraction of fluid is beneficial because residual fluid degrades wash efficacy. Retention of a significant portion of residual fluid within a well may require the use of additional processing steps in order to sufficiently reduce contamination. This in turn requires additional processing time and the consumption of additional reagents. Separation magnets 804 of different processing lanes 116 may be of different shapes and sizes, advantageously permitting the system to generate "pellets" of magnetically responsive solid or particulate phase materials with different sizes and geometries when the field of the separation magnet is applied to an assay cartridge 200, advantageously allowing optimization of pellet dimensions for specific processing steps. A separation magnet may include a backing device that helps shape and focus the magnetic field. Such backing devices can be made with magnetic stainless steel.

Some embodiments of the invention can be directed to a system comprising a slidable cartridge carriage configured to engage an assay cartridge, the cartridge carriage engaging a carriage track. It can also include a slidable magnet trolley, the slidable magnet trolley engaging the carriage track and comprising a separation magnet, and a reversible coupling device (e.g., a magnet) configured to reversibly couple slidable cartridge carriage and the slidable magnet trolley. In an alternative embodiment, a magnet may be brought into proximity to an assay cartridge using a pivoting mechanism that rotates the magnet into position. In another embodiment a magnet may be moved vertically to be brought into proximity to an assay cartridge. In such an embodiment, the magnet may be coupled to a vertically mounted linear actuator, a rail system, or other suitable vertical transport.

Illustratively, in some embodiments, each processing lane 116 that incorporates a separation magnet 804 includes a movable magnet trolley 808 disposed to travel parallel to, or along the carriage track 818. An embodiment of a magnet trolley is shown in FIG. 10(b). By disposing the magnet trolley 808 at different distances from the assay cartridge 200, the system may selectively apply a magnetic field to the contents of the assay cartridge. The magnet trolley 808 may be placed at an end of the processing lane that gives it access to the reaction well 202 of an assay cartridge 200 held within that processing lane. Alternatively, the system may selectively apply magnetic fields using a controllable electromagnet proximate the reaction well. In another embodiment, the system may selectively apply magnetic fields by moving a magnetic shield between a magnetic field source and the assay cartridge.

In one embodiment, the magnet trolley 808 uses movement of the same carriage drive used to move the cartridge carriage 816 to apply a magnetic field to the assay cartridge 200. Alternatively, the system may move the magnet trolley independently of the carriage drive. In some embodiments, the magnet trolley 808 includes a secondary latching magnet 812 that couples the magnet trolley 808 to the cartridge carriage 816. The latching magnet 812 is an example of a reversible coupling. Other suitable reversible couplings may include mechanical devices such as latches that can be mechanically actuated.

In operation, the system moves the cartridge carriage 816 to a first position adjacent the magnet trolley 808, activates a latching mechanism, and then withdraws the cartridge carriage to the next operative location with the magnet trolley in tow. In order to disengage the magnet trolley 808, the cartridge carriage 816 may be moved to a second position that aligns the magnet trolley with a locking mechanism that, when activated, prevents the magnet trolley from moving. Subsequently, moving the cartridge carriage 816 releases the latching magnet 812 and removes the assay cartridge 200 from the field of the separation magnet 804. The first position and the second position may be substantially identical in some embodiments.

In some embodiments, the latching mechanism includes a latching magnet 812 and a magnetically responsive strike plate 814. One of the latching magnet 812 and the strike plate 814 may disposed on the magnet trolley 808 and the other on the cartridge carriage 816. In some embodiments, the latching magnet 812 is disposed on the magnet trolley 808 to reduce the influence of the magnetic field from the latching magnet on the assay cartridge 200 contents. Alternatively, the cartridge carriage or a portion thereof may be composed of a magnetically responsive material. In some embodiments, the locking mechanism may include a locking actuator 806, positioned on the lane support 834 so that it can be aligned with the magnet trolley 808. Such a locking actuator 806 may be activated to fix the magnet trolley 808 to the lane support 834 or deactivated to permit the magnet trolley to move with the cartridge carriage 816.

In one embodiment of the operation of the magnetic separation mechanism, the magnet trolley 808 may normally reside in a home position near one terminus of the carriage track 818. The cartridge pusher may position the cartridge carriage 816 adjacent the magnet trolley 808, allowing the latching magnet 812 to engage the strike plate 814 and thereby attaching the magnet trolley 808 to the cartridge carriage 816. When attached to the cartridge carriage 816, the magnet trolley 808 may align the separation magnet 804 immediately adjacent the reaction well 202, thereby applying a magnetic field to the reaction well contents. The separation may be held at an angle that is complementary to that of a wall of the reaction well. Subsequent motion by the cartridge pusher moves the cartridge carriage 816 and the attached magnet trolley 808 as a substantially single unit, maintaining proximity of the separation magnet 804 to the assay cartridge 200 during subsequent processing steps. Such processing steps may include the removal of liquid from a well of the assay cartridge 200 or dispensing of fluid into a well of the assay cartridge.

To detach the magnet trolley 808, the cartridge pusher positions the cartridge carriage 816 such that the magnet trolley returns to its home position. The locking actuator 806 may then be activated to engage a feature that prevents the magnet trolley 808 from moving. The cartridge pusher then moves the cartridge carriage 816 away from the home position. By arranging the locking actuator 806 to exert a greater force on the magnet trolley 808 than that of the latching magnet 812 on the strike plate 814, the motion causes the cartridge carriage 816 to separate from the magnet trolley. In some embodiments, the locking actuator 806 is a linear actuator such as a pneumatic cylinder or solenoid disposed on the lane support 834. The feature that engages the locking actuator 806 can be a hole or piercing in the magnet trolley 808 disposed to align with the locking actuator when the magnet trolley is in its home position.

A consequence of this arrangement of the magnet trolley 808 and cartridge carriage 816 is that the separation magnet 804 can only approach the assay cartridge 200 at the reaction well 202. This advantageously prevents unwanted interactions between the separation magnet and other assay cartridge compartments, in particular reagent wells utilized for storage of magnetically responsive solid phase or microparticles.

As noted above, different processing lanes 116 may utilize separation magnets 804 with different dimensions. Magnets may be found in temperature stabilization lanes, wash lanes, elution lanes, PCR prep lanes, transfer lanes, etc. For example, ambient temperature lanes 116(*h*), wash lanes 116 (*a*), and elution lanes 116(*e*) may use a relatively large separation magnet 804. A large separation magnet 804 may apply a stronger magnetic field to more rapidly collect magnetically responsive solid phase or microparticles dispersed throughout a liquid volume, thus reducing time required for processing. A large separation magnet 804 may apply a magnetic field to collect magnetically responsive solid phase or microparticles from the reaction well contents onto a relatively a large area of the reaction well 202 inner surface. This large area advantageously disperses the magnetically responsive solid phase or microparticles, reducing the opportunities for interaction between them so that subsequent resuspension of the magnetically responsive solid phase or microparticles may be less vigorous and more complete. This in turn reduces the time required for processing and reduces the chances of contamination resulting from fluids that might remain trapped within clumps of aggregated material.

Other processing lanes 116, such as certain wash lanes 116(*b*), may use a relatively small separation magnet 804. A small separation magnet 804 concentrates the magnetic field on a relatively small area of surface of the assay cartridge. In some embodiments, the small area may overlap the area of the reaction well 202 that is affected by a large separation magnet 804 and is disposed close to the bottom of the reaction well. A small separation magnet 804 advantageously supports processing steps where it is desirable to collect magnetically responsive microparticles in a small area. Such processing steps include resuspension of the magnetically responsive solid phase or microparticles in a relatively small volume of fluid. For example, elution of nucleic acids from the magnetically responsive solid phase or microparticles using a very small volume of fluid allows the system to effectively concentrate the resulting eluted nucleic acid as described below. Processing in a wash lane 116(*b*) may precede elution in many protocols so that the relatively small eluent volume may more readily re-suspend the collected microparticles.

Processing lanes 116 may also include features used to confirm the alignment of various lane components. Such features may include alignment flags. In FIG. 10(*c*), a first alignment flag 900 attached to the cartridge guide 800 and a second alignment flag 897 attached to the attached to the cartridge carriage 816 are shown. These alignment flags are described in further detail below.

Consistent processing of samples can necessitate control of the temperature of assay cartridge 200 contents during processing. To accomplish this, processing lane 116 may include a heating assembly, for example, a lane heater, of varying configuration. With reference to FIGS. 10(*d*)-11, some processing lanes 116 may include a lane heater 840, 1103 that heats at least a portion of the assay cartridge 200. The lane heater 840, 1103 may heat the reaction well 202, as shown in FIGS. 4(*a*) and 10(*b*), wells used for storing assay reagents 204, 208, 209, or a combination of these, as shown in FIG. 10(*d*). This advantageously permits the performance of specific processing steps at elevated temperatures, if desired, and may allow pre-heating of reagents prior to addition to the reaction well 202 in order to tightly control reaction temperature. In some embodiments, the reaction well 202 and the large reagent wells 204 are heated. The lane heater 840, 1103 may be disposed at the proximal end of the lane motion path and configured so that the cartridge carriage 816 can drive the assay cartridge 200 into the lane heater 840, 1103. In one embodiment, the lane heater 840 or a portion thereof may be of floating clamshell construction, with two independent sides configured to fit snugly around an end of the assay cartridge 200, and an open end to permit entry of the assay cartridge. The lane heater 840, 1103 may have an open top 850 to accommodate the reaction well 202. In some embodiments, the two independent sides each contain a heat block 854 to provide heat, at least one temperature sensor 860 to control the heater temperature, an insulated cover 856 on the external aspect to contain heat, and a spring to couple the independent sides against the assay cartridge 200. The two heat blocks 854 may couple to one another in a pivoting connection 858 at the end opposite the open end 852. The cavity between the heat blocks 854 may be slightly narrower than the width of the reaction well 202 so that the spring drives the two heat blocks 854 into tighter thermal contact with the assay cartridge 200 walls.

In an embodiment shown in FIG. 11, the lane heater 1103 has two heating devices 1104 and 1106, with one heating device 1104 that applies heat to the reaction well 202 and a second heating device 1106 that applies heat to reagent storage wells 204 of an inserted assay cartridge 200. The heating devices 1104 and 1106 may be configured so that the heating surfaces do not contact the assay cartridge but are in close proximity, providing heat via radiation and convection. Alternatively, the reaction well heating device 1104 may be configured similarly to the lane heater 840 shown in FIG. 10(*c*), which contacts the exterior wall of the reaction well 202 and is described in detail below. These heating devices may act in concert or be controlled independently.

The lane heater 840 may mount to the lane support 834 by a floating connection so that slight misalignment or flexure of the assay cartridge 200 does not impede insertion into the lane heater. The tapered shape of the reaction well 202, which may be mirrored by an internal contour of the lane heater 840, further serves to guide insertion. The cartridge guide 800 terminates distal to the lane heater 840 so as not to interfere with insertion.

In some embodiments, in operation, the cartridge pusher moves the cartridge carriage 816 towards the lane heater 840 so that the leading edge of the reaction well 202 engages the corresponding taper in the heat block 854. As the reaction well enters further, the side walls of the reaction well 202 engage the internal walls of the heat block 854, enlarging the cavity by pivoting the heat blocks about their connection point 858. The heat block 854 position adjusts to press inward on the external walls of the reaction 202 when the assay cartridge 200 is completely inserted. The lane heater 840, 1102 may maintain temperature by any of a number of methods, but the temperature may be maintained by controlling the heaters with a PID loop connected to the temperature sensors 860. The cartridge pusher may disengage the assay cartridge 200 from the lane heater 840 by simply repositioning the cartridge carriage 816 in the distal direction.

The efficiency of an instrument process may be affected by the temperature of the testing environment. The testing environment may impact both the temperature of the contents of the assay cartridge 200 (held in storage prior to use) and the temperature of the samples being processed. For example, the efficiency or reproducibility of chemistry processes may be negatively impacted if the samples that are being processed are too cold. Heaters may be integrated into lane designs that require access to assay cartridge 200 contents (as discussed above), but while such heaters may be adequate to maintain the temperature of an assay cartridge, they may not be sufficient to bring assay cartridge contents from ambient to processing temperature within a single pitch interval. Thus, in some embodiments of the invention, an instrument or process disclosed herein further includes one or more direct and dedicated heating components or steps for this purpose. For example, an instrument may include one or both of a cartridge heater coupled to an assay cartridge to raise the temperature of an assay cartridge and its contents and one or more lane heaters integrated into processing lanes to maintain the temperature of an assay cartridge and its contents.

An instrument disclosed herein may include one or more cartridge heaters, configured to transfer heat to an assay cartridge 200, thereby transferring heat to a sample and other liquid components contained in an assay cartridge. The cartridge heater may be under active control, such that heat applied to an assay cartridge is controlled by a controller running computer software. For example, the controller may access a protocol specifying, for one, some or all assay cartridges: a desired sample or reagent temperature or temperature range, a desired sample or reagent temperature profile (e.g., that the sample be warmed from a first temperature to a second temperature over a given period of time or during a certain processing stage), or an output of a cartridge heater, advantageously allowing the system to perform a broad range of temperature dependent processes. For example, a protocol may require that a first step be performed at an elevated temperature, for example the lysis of gram positive bacteria, that is incompatible with processes performed at other steps. Such protocols may perform the first step in a first processing lane and the second step in a second processing lane. In one embodiment of such a protocol a first step may be performed at 60° C. to 80° C. and a second step at 30° C. to 50° C. In another embodiment of such a protocol a first step may be performed at 65° C. to 75° C. and a second step at 35° C. to 45° C. In still another embodiment of such a protocol a first step may be performed at about 70° C. and a second step at about 37° C. If a protocol requires a certain temperature, the controller, using the computer software, may determine a voltage or a voltage temporal profile to be provided to one or more cartridge heaters. Such a determination may be based, e.g., upon measured temperatures of an assay cartridge or sample or reagents therein, physical characteristics of an assay cartridge (e.g., a size, shape or material), a specific heat of a reagent or sample, a starting temperature of a reagent or sample, and/or an ambient temperature.

FIG. 20(*a*) shows an embodiment of a cartridge heater 3005. The cartridge heater may be an example of a heating assembly. The cartridge heater 3005 may be configured to apply heat to one or more sides of an assay cartridge 200. The cartridge heater 3005 may comprise a front wall 3007(*a*) and a back wall 3007(*b*), as shown in FIG. 20(*b*). The front wall 3007(*a*) may be positioned adjacent to a first side of the assay cartridge 200, and the back wall 3007(*b*) may be positioned adjacent to a second side of the assay cartridge 200 opposite the first side. The first and second walls 3007(*a*) and 3007(*b*) may be connected, e.g., by a top wall 3007(*c*). As shown in FIG. 20(*a*), the top wall may include a hinge that permits the front wall 3007(*a*) to pivot relative to the heater back wall 3007(*b*). The cartridge heater 3005 may also include mount elements 3010 in FIG. 20(*a*), which include spring mounts that can be seen protruding through the wall 3007(*a*) of the heater in FIG. 20(*b*). These serve to press the right hand interior heater component 3027 against the outer wall of the assay cartridge 200, and therefore to press the assay cartridge 200 against the left hand interior heater component.

The cartridge heater 3005 may be moved between open and closed positions by heater actuator 3015, as shown in FIGS. 20(*c*) and 20(*d*). The heater actuator 3015 may be a linear actuator. The cartridge heater's back wall 3007(*b*) may be substantially fixed in position. The instrument may determine that a cartridge 200 has been moved into a heating position between the front and back walls 3007(*a*) and 3007(*b*). For example, the controller may sense the assay cartridge 200 (e.g., via an optical detector or a movement detector) or it may receive a signal indicating the cartridge's new presence. The controller may determine whether the cartridge heater 3005 is in an open position or a closed position (e.g., using a sensor). The front wall 3007(*a*) is further from the cartridge 200 and the back wall 3007(*b*) in the open position as compared to the closed position. If the cartridge heater 3005 is in an open position, the heater actuator 3015 may move a portion of the cartridge heater 3005 (e.g., the front wall 3007(*a*)) to a closed position closer to the assay cartridge heater. In some instances, the front surface 3007(*a*) is in contact with the assay cartridge in a closed position but not in an open position.

FIGS. 20(*c*) and 20(*d*) show an embodiment in which the actuator 3015 moves the front wall 3007(*a*) angularly to reduce an angle between the front and back walls 3007(*a*) and 3007(*b*). Thus, the front wall 3007(*a*) moves closer towards the lane's center and clamps onto the cartridge 200. The heater 3005 may then be in close thermal contact with the assay cartridge 200 and heat the assay cartridge 200 using both the front and back walls 3007(*a*) and 3007(*b*). Since the walls 3007(*a*), 3007(*b*) can be in physical contact with the assay cartridge 200, heat can be quickly transferred to liquids in the cartridge 200 by thermal conduction. In some embodiments, the actuator 3015 moves the front wall 3007(*a*) horizontally and/or vertically.

FIG. 20(*e*) shows a section of an embodiment of a cartridge heater 3005. As shown, the cartridge heater 3005 may include a plurality of heater zones. The heater zones may correspond to different portions of an assay cartridge 200. For example, the cartridge heater 3005 may include a first heater zone 3005(*a*) configured to heat large reagent wells 204 and a second heater zone 3005(*b*) configured to heat medium reagent wells 209 of the assay cartridge 200. By including different zones, samples and reagents deposited into different wells of a cartridge can be raised to different temperatures. Additionally, the zones may permit the wells to be raised to the same temperature (e.g., by accounting for well shapes and/or relative locations of wells within the cartridge). A zone may be configured to provide substantially uniform heat throughout the zone, to provide varying heat across the zone (e.g., to apply more heat to outer zone portions than middle portions), or to provide heat in discrete regions.

The cartridge heater 3005 may comprise a plurality of heating elements 3020. Each heating element 3020 may be sized and position to heat one or more wells in the cartridge 3200. Each heating element 3020 may be under separate control, such that it can produce independent heating output.

FIG. 20(*f*) shows components of a cartridge heater 3005. As described above, the cartridge heater 200 may include a front wall 3007*a* and a back wall 3007*b*. Each wall may include a heater casing 3025. The heater casing 3025 may partly encapsulate an interior heater component 3027. The interior heater component 3027 may be connected to a heater casing 3025 using one or more connectors 3010, as shown in FIG. 20(*e*). The interior heater component 3027 may include one or more heating elements 3020. The casing 3025 may prevent heat from the heating elements 3020 from escaping in a direction not in the direction of the cartridge 200. It may also reflect heat to improve the efficiency of the cartridge heater 3005.

The heating elements 3020 may be partly covered by an insulator 3017, such as a foam insulator. The insulator 3017 may comprise holes, in which may reside a thermal cut off element 3012 (see below). The holes can provide access for other system components or to allow heat produced by the heating elements 3020 to be disbursed primarily in discrete and targeted locations. One or both of the interior heater components may include one or more thermistors (not shown). The thermistors may monitor the temperature of the interior heater component 3027, and an output of the heating element 3020 may be adjusted based on the monitored temperature. The thermal cut off element 3012 can be a temperature sensitive switch that acts as a local safety feature by stopping power to the heating element should the temperature exceed a pre-set limit.

FIG. 20(*g*) shows a portion of an embodiment of an assay cartridge 200 that may be used with the cartridge heater 3005. The assay cartridge 200 includes large reagent wells 204 and medium reagent wells 208 but no small reagent wells. The assay cartridge also includes reaction vessel component holders 219. The wells 204 and 208 may have a cross-section with a substantially flat and vertical side along the long side of the assay cartridge 200. For example, the wells 3204 and 3208 may have a substantially rectangular cross-section. This may increase the surface area facing the cartridge heater 3005 and thereby increase heating efficiency. The interior heater components 3027 may be configured to contact a flat external surface of the large and medium reagent wells 204 and 208. In some instances, the reaction vessel component holders 219 do not include a side that is substantially flat and vertical. Thus, there may be nominal clearance between the reaction vessel component holders 219 and the cartridge heater 3005 during heating.

All wells corresponding to a particular heating zone may have a substantially similar size, shape and/or heater-adjacent surface profiles. This may allow the wells to be evenly heated by a uniform heat output by a heating zone. For example, an assay cartridge 200 may include a plurality of large reagent wells 204, and a cartridge heater 3005 may include a first heating zone 3005*a* with an area and position complementary to a side-surface area of a large-well portion of the cartridge 200. The first heating zone can be juxtaposed with the reaction well in the assay cartridge in some embodiments. Similarly, an assay cartridge 200 may include a plurality of medium reagent wells 208, and a cartridge heater 3005 may include a second heating zone 3005*b* with an area and position complementary to a side-surface area of a medium-well portion of the cartridge 200. The second heating zone can be juxtaposed with a reagent well in the assay cartridge.

The cartridge heater 3005 in FIGS. 20(*a*) and 20(*b*) is in a relatively fixed position within an instrument, only moving relatively small distances towards and away from the center of a lane. In some embodiments, a cartridge heater 3005 moves along with an assay cartridge 200 as the assay cartridge 200 progresses through different lanes and processing stages. For example, a cartridge heater 3005 may be positioned on a top surface of the assay cartridge 200 after samples and/or reagents have been added to the wells.

FIG. 20(*h*) shows a top plan view of a layout of the components of an instrument according to an embodiment of the invention, with some components removed clarify the basic structural and functional modules. Many of the instrument's lanes, units and components parallel those in above-described embodiments and like numerals can refer to like features. Thus, above-described details of similar components may also pertain to the lanes, units and components depicted in FIG. 20(*h*).

The layout shown in FIG. 20(*h*) includes a cartridge warming lane 3116(*i*). In this lane, one or more assay cartridges 200 may be warmed by one or more cartridge heaters 3005, as described above. The heating lane 3116(*i*) may include a pump to transfer fluids (e.g., samples) from one well to another.

In some embodiments, one or more lane heaters 3040 (distinct from the cartridge heater 3005) are integrated into one or more processing lanes and cartridge loading lanes. Lane heaters 3040 may be configured to primarily maintain a temperature of an assay cartridge and/or its contents and/or to regulate the temperature within a small range relative to the cartridge heater's range of regulation. Thus, a cartridge heater 3005, which may contact or be very close to a large surface area of the assay cartridge 200, may quickly and reliably initially heat the assay cartridge 200. Lane heaters 3040, which may be positioned further from the assay cartridge 200, may then be tasked with temperature regulation within a smaller range of temperatures. In some instances, a cartridge heater 3005 is configured to heat an assay cartridge 200 primarily by conduction, while a lane heater 3040 is configured to heat an assay cartridge 200 primarily by convection and/or radiation. Thus, the cartridge heater 3005 may heat the assay cartridge 200 faster, more efficiently and more reliably than a lane heater 3040 can. Despite the structural and efficiency advantages of using a cartridge heater 3005, in other embodiments, an instrument includes only lane heaters 3040 and no cartridge heater 3050.

Lane heaters 3040 may be included in one, more or all of the lanes (e.g., shown in FIG. 1(*b*) or FIG. 20(*g*)). In some embodiments, elution lane 116(*e*), wash lanes 50, 116(*a*) and 116(*a*)', and temperature stabilization lane 116(*j*) include a lane heater 3040. Lane heaters 3040 may be structurally the same or similar across lanes. In some instances, lane heaters 3040 differ across lanes, e.g., based on prior, current or subsequent processing. For example, the size, number of position of a lane heater's heating elements 3020 may vary depending on which wells are likely to have contents in the lane. Such heating-element specificity may reduce system noise and improve system power efficiency.

FIGS. 20(j) and 20(k) show embodiments of an instrument with a lane heater 3040. The lane heater 3040 may comprise structural parts and/or characteristics similar to or the same as those described with respect to the cartridge heater 3005. As shown in FIG. 20(j), the lane heater 3040 may be positioned substantially under the cartridge guide 800, such that the interior heater components 3027 may heat the wells of the assay cartridge 200. In some embodiments, interior heater component 3027 is fixed and positioned to straddle the sides of the cartridge 200. Therefore, unlike the cartridge heater 3005, the lane heater 3040—in some instances—may not include an actuator 3015 to move one of the lane heater's walls. Rather than clamping onto an assay cartridge 200, the lane heater 3040 may be positioned and configured to be near the sides of the assay cartridge 200. In some embodiments, the lane heater 3040 is not in direct contact with the assay cartridge 200 (i.e., a gap exists between the interior heater components 3027 and the cartridge 200).

Though the heat transfer to the assay cartridge 200 may be less efficient, this configuration eliminates the need to have a moving heater part, thereby reducing potential mechanical difficulties, space requirements and processing time. Thus, an assay cartridge 200 may move along the cartridge guide 800 down the lane until it is positioned between walls of the lane heater 3040. The lane heater 3040 may adjust or maintain the assay cartridge's temperature to or within a desired range while or before the appropriate processing is occurring.

In some embodiments, the above-described cartridge heater 3005 and/or lane heater 3040 may be configured to cool a cartridge and/or its contents. For example, the heating elements 3005 may be replaced with cooling elements that may cool a nearby or in-contact cartridge 200 using cycled chilled fluid and/or thermoelectric cooling While the above describes several heater designs based on resistance heaters, other embodiments may incorporate alternative heating methods to accomplish the same ends. Such heating methods include infrared heaters, convection or forced air heaters, Peltier devices, and flexible heaters that conform to the surface of the assay cartridge 200. Alternatively, liquids may be heated within pipette tips prior to being dispensed.

Processing lanes 116 may provide access for processing tools on the system that are external to the processing lanes so that they may operate on assay cartridges 200. For example, as shown in FIG. 1(b) the cartridge loading lane 116(f) may receive assay cartridges 200 from the cartridge loading unit 112 and may present the received assay cartridge to the sample pipettor 70 for addition of sample, and to the XYZ pipettor on the XYZ transport device 40 for addition of reagents from reagent packs 400. The elution lane 116(e) may exchange microtips 542 with the XYZ pipettor on the XYZ transport device 40. The amplification preparation lane 116 (g) may present the assay cartridge 200 to the XYZ pipettor on the XYZ transport device 40 for transfer of materials between compartments, for addition of reagents from reagent packs 400, for plugging of reaction vessels 221, and for removal of reaction vessels. The waste lane 116(c) may transfer liquid contents of the assay cartridge 200 to liquid waste storage 94 and may move the expended assay cartridge to solid waste storage 92 as shown in FIG. 1(d).

Processing lanes 116 may perform any available operation on an assay cartridge 200 present in the processing lane during a fixed or specified operational interval, or "pitch". An operation is available if the processing lane 116 has access to processing tools needed for the operation. Some operations, such as simply storing an assay cartridge 200 during an extended reaction, require no processing tools. Others, such as transfer of materials between compartments of an assay cartridge 200, may need access to processing tools that may be resident in the processing lane 116. Still other operations, such as transfer of reagents from outside of the assay cartridge 200, may require access to processing tools external to the processing lane 116. Since such external processing tools may be otherwise engaged such operations may introduce constraints on the flexibility of processing lane operation scheduling; a processing lane 116 has access to an external processing tool only while that tool is not being utilized for other tasks. In some embodiments, different types of processing lanes 116 may have access to processing tools as described below.

The cartridge loading lane 116(f) may have access to the cartridge loading unit 112, to the sample pipettor 70, to the XYZ pipettor on the XYZ transport device 40, and to the transfer shuttle 50. Available functions of the cartridge loading lane 116(f) can include loading assay cartridges 200 from the cartridge loading unit 112 and presenting those cartridges for resuspension of solid phase, microparticle or lyophilized reagents, fluid addition, piercing of the barrier film 205, and mixing by the sample pipettor 70 and the XYZ pipettor on the XYZ transport device 40. Either the sample pipettor 70 or the XYZ pipetter on the XYZ transport device 40 may transfer a fluid to, from, or within an assay cartridge 200 in the cartridge loading lane 116(f). The cartridge loading lane 116(f) may share an extended cartridge pusher with the cartridge loading unit 112. At the intersection of the sample pipettor 70 motion path, the cartridge guide 800 in the cartridge loading lane 116(f) may have an opening or gap to admit the sample pipettor 70. At a position accessible to the XYZ pipettor on the XYZ transport device 40, the cartridge guide 800 in the cartridge loading lane 116(f) may have an opening or gap to admit the XYZ pipettor.

A high temperature stabilization lane 116(j) may have access to a lane heater (840, 1103), to a millitip pipettor 704, and to the transfer shuttle 50. Available functions of a temperature stabilization lane include heating assay cartridge 200 contents, microparticle or solid phase resuspension, mixing, and transfer of materials among compartments of an assay cartridge.

A low temperature stabilization lane 116(h), which may provide heat at a lower temperature than the high temperature stabilization lane 116(j), may have access to a millitip pipettor 704, to a separation magnet 804, and to the transfer shuttle 50. Available functions of a low temperature stabilization lane (e.g., an ambient temperature lane) 116(h) include re-suspension of microparticles or solid phase reagents, mixing, and transfer of materials among compartments of an assay cartridge 200. Additionally, the low temperature stabilization lane (e.g., an ambient temperature lane) 116(h) may apply a magnetic field to the assay cartridge 200 to facilitate separation and washing of magnetically responsive solid phases or microparticles.

A wash lane 116(b) may have access to a millitip pipettor 704, to a separation magnet 804, and to the transfer shuttle 50. The separation magnet 804 of a wash lane 116(b) may be smaller than the separation magnet of a low temperature stabilization lane 116(h). Available functions of the wash lane 116(b) include re-suspension of microparticles or solid phase reagents, mixing, and transfer of materials among compartments of an assay cartridge 200. Additionally, the wash lane may apply a magnetic field to the reaction well to facilitate separation and washing of magnetic microparticles. Wash lanes in general may include large or small magnets.

Figure 15A:
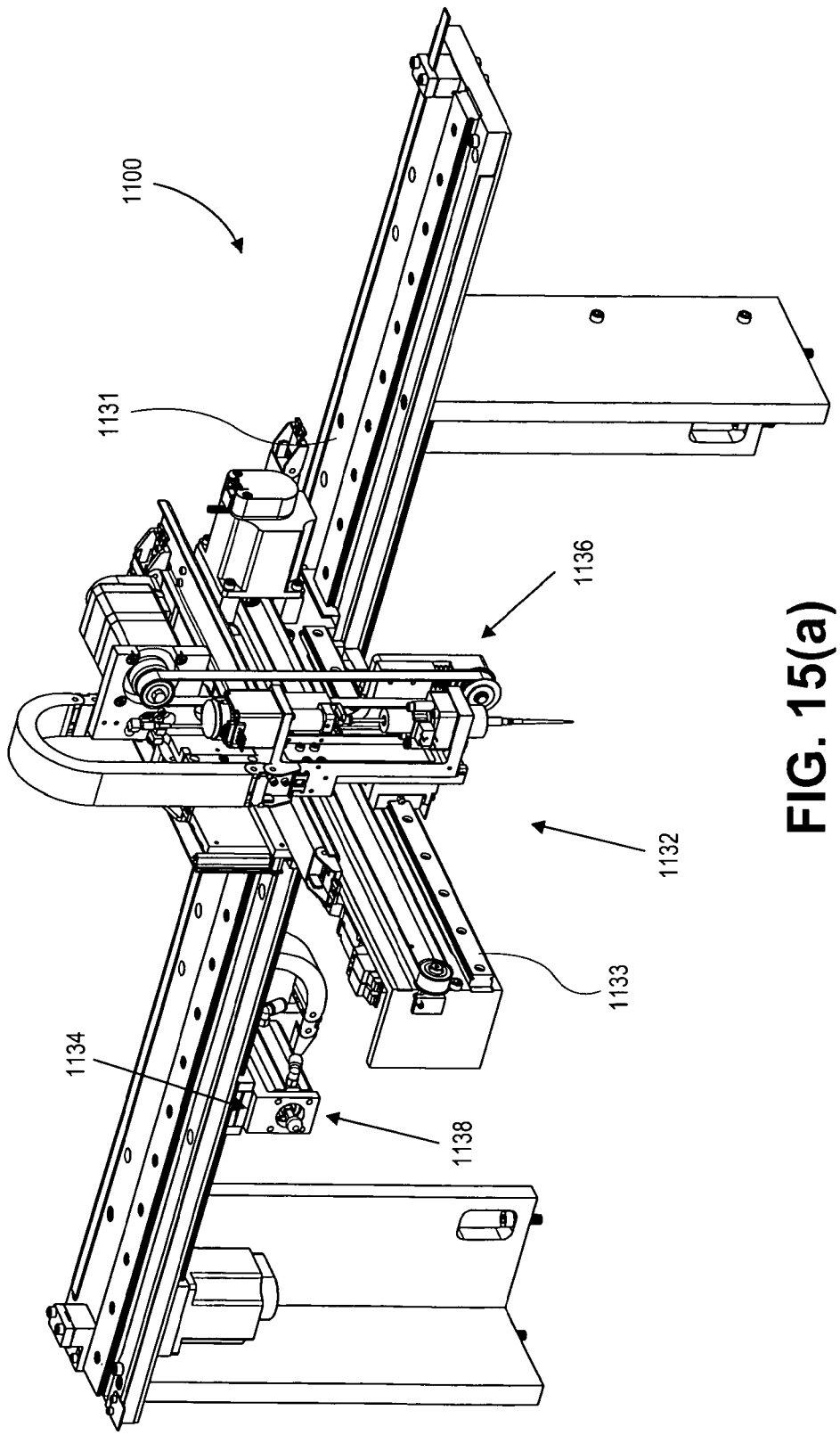
FIG. 15(a) shows an XYZ transport device.
Figure 15B:
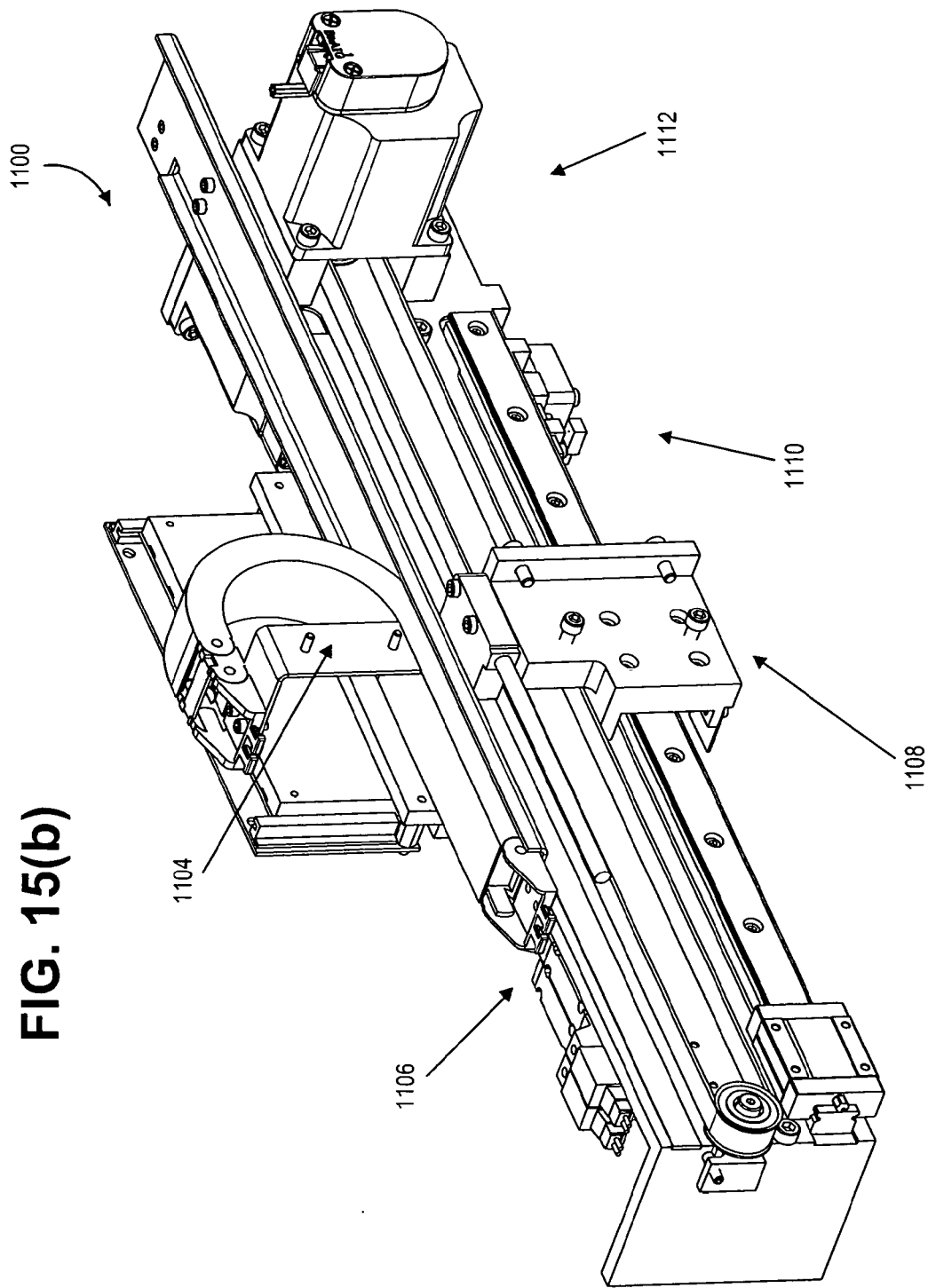
FIG. 15(b) shows an XYZ transport device Y axis arm.
Figure 15C:
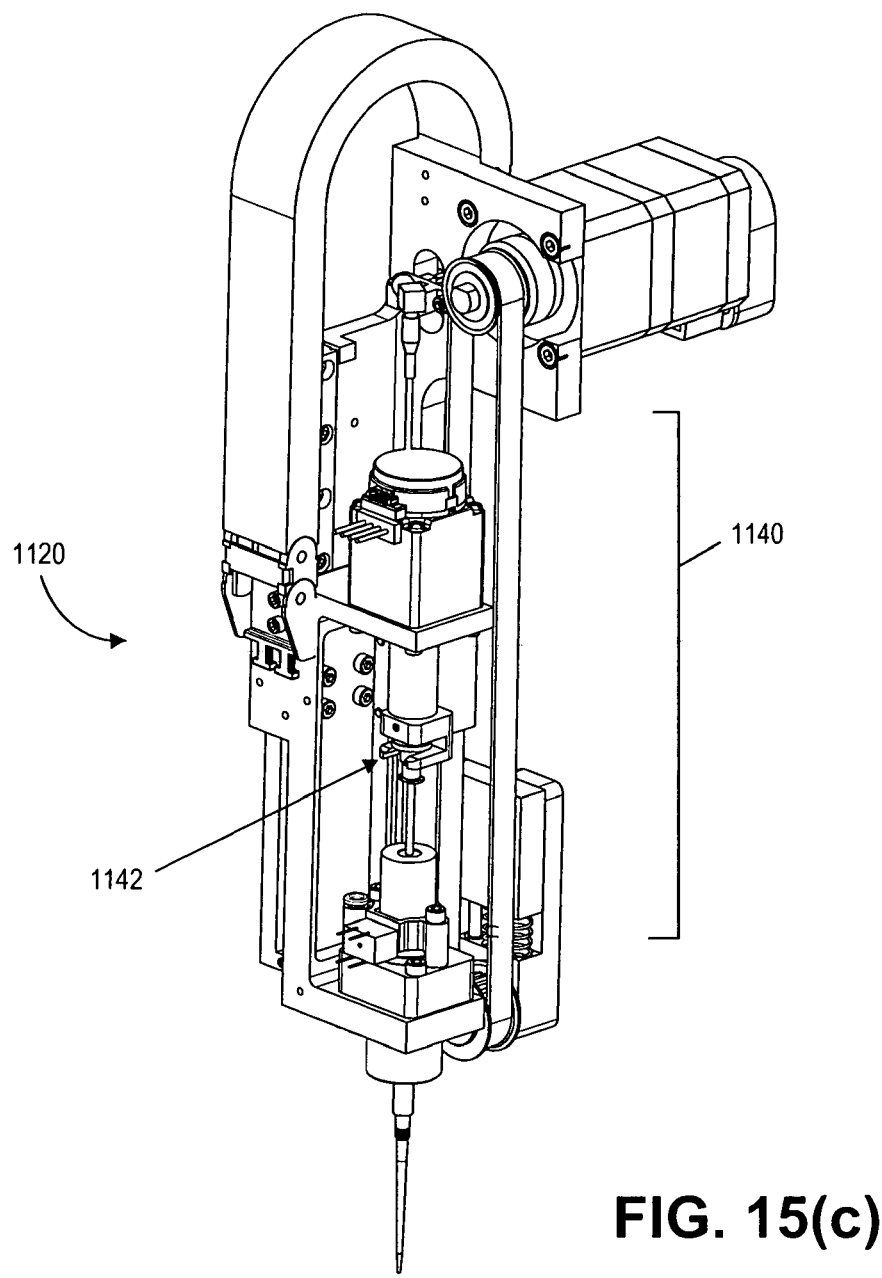
FIG. 15(c) shows a Z axis elevator for the XYZ transport device.

An elution lane 116(e) may have access to a microtip pipettor 1142 similar to that utilized by the XYZ transport device 1100 of FIGS. 15(a)-15(c), to a separation magnet 804, to an XYZ pipettor on an XYZ transport device 40, and to a transfer shuttle 50. It can also dispose of microtips within used wells of the assay cartridge. Available functions of the elution lane include re-suspension of microparticles, mixing, and transfer of materials among compartments of an assay cartridge. Additionally, an elution lane 116(e) may apply a magnetic field to the assay cartridge 200 to facilitate collection of suspended magnetically responsive solid phases or microparticles. The elution lane 116(e) can also have the capability to pick up, drop off, and seat the vessel plug 222 to close the reaction vessel 221. Because it provides access to the XYZ pipettor 40, the elution lane 116(e) may transfer materials between the assay cartridge 200 and the reagent storage unit 124 and transfer materials between the assay cartridge and any of the thermal cycler modules 1300 (see FIG. 16(a)). The elution lane 116(e) can have a source of and disposal method for microtips 542. In some embodiments, microtips are disposed of by ejection into a well of an assay cartridge 200. In other embodiments, the XYZ pipettor on the XYZ transport device 40, which has access to both source and disposal site for microtips 542, delivers one or more microtips 542 to the elution lane. After the microtip pipettor in the elution lane uses the microtips 542, the XYZ pipettor on the XYZ transport device 40 may pick up and then discard the expended microtips 542.

An amplification preparation lane 116(g) may have access to the XYZ pipettor of the XYZ transport device 40 and the transfer shuttle 50. Available functions of the amplification preparation lane 116(g) may include re-suspension of microparticles or solid phases, mixing, and transfer of materials among compartments of an assay cartridge 200, transfer of materials between the assay cartridge and the reagent storage unit 124, and transfer of materials between the assay cartridge and any of the thermal cycler modules 1300. Additionally, the XYZ pipettor of the XYZ transport device 40 may pick up, drop off, and seat the vessel plug 222 to close the reaction vessel 221 and to transport the reaction vessel. The cartridge guide 800 of the amplification preparation lane may have an opening or gap at a location within the reach of the XYZ pipettor of the XYZ transport device 40 in order to admit the XYZ pipettor. The amplification preparation lane 116(g) may have a vessel detection sensor, which can sense the conductive plug of a sealed reaction vessel. Such a vessel detection sensor may utilize a liquid level sensing circuit to detect the presence of a conductive plug. Alternatively, the vessel detection sensor may utilize a pressure sensor that monitors the internal pressure of the pipette pump. As another alternative, the vessel detection sensor may utilize both a liquid level sensing circuit and a pressure sensor to detect the presence of a sealed reaction vessel on a pipette mandrel. The amplification preparation lane 116(g) can also have a connection to the waste chute—utilized to collect microtips and used (i.e. after thermal cycling) reaction vessels. The XYZ gantry can utilize a "soft eject" routine that slowly eases these items off of the pipette mandrel so that they drop in a controlled manner.

The waste lane 116(c) can includes access to an aspiration probe 986, to a solid waste ejector 874, and to a transfer shuttle 50 as shown in FIGS. 14(a) and 14(c). Available functions of the waste lane 116(c) include draining liquids from assay cartridge 200 compartments and disposal of assay cartridges.

Subject to the conflict constraints on the use of external tools, and to the timing constraints of the pitch interval and transfer windows as discussed below, a processing lane may perform any available operation in any sequence. A first protocol and a second protocol may specify that the same operations are performed in a given processing lane 116, or the first protocol may specify operations in a given lane that differ from those specified by a second protocol. This processing lane concept provides capabilities for flexible protocol execution by a combination of this selectable operation sequence within a processing lane and by the ability to route an assay cartridge through selectable sequence of processing lanes.

Other embodiments of the invention can include a number of other features, in addition to or as alternatives to the features described above. For example, embodiments of the invention may one or more multifunctional lanes, each lane capable of performing all sample processing steps on an inserted cartridge. Such a processing lane may include a thermal cycler module.

K. Microtips

FIG. 12(a) shows a side, cross-sectional view of a pipettor mandrel 460 engaged with a collar 490(a) of a microtip 490. FIG. 12(b) shows a perspective view of the microtip 490 shown in FIG. 12(a).

In embodiments of the invention, a microtip 490 can be a relatively small-capacity pipette tip, e.g., having a capacity no greater than about 100 or 200 μL. The microtip 490 may be used for one or more the uses described above with respect to millitip 220, such as for use during the isolation phase.

The microtip 490 may share any or all of the physical characteristics described above with respect to millitip 220. For example, the microtip 490 may taper to a pipetting orifice and may couple to a pipettor through a compliant coupling taper supporting remove-and-replace operations. A length of the microtip 490 may be sufficient to reach the depth of a 100 mm tube or other sample containers used on the system when mounted on a suitable pipette mandrel. In some embodiments, the length of the microtip 490 is about 30-80 mm, e.g., about 50 mm.

As shown in FIGS. 12(a) and 12(b), the microtip 490 can include a mounting aperture that couples to a pipettor mandrel 460 during use. The microtip 490 may be tapered, e.g., in a plurality of segments. Thus, a coupling taper 490(a) may extend from a mounting aperture to a lower diametral step forming a seating surface 490(a)-2. As with the millitip 220, the microtip 490 may include an upper taper 490(e), a middle taper 490(d), and a lower taper 490(c). These taper segments may have one or more described above with respect to the millitips' respective segments. In some embodiments, for the microtip 490, the middle taper 490(d) (not the upper taper 490(e)) extends for the majority of the part length, as shown in FIG. 12(b). In some embodiments, the coupling taper 490(a) extends about 5-15 mm (e.g., about 7.5 mm) from the top of the microtip, the upper taper 490(e) extends about 5-15 mm (e.g., about 7.2 mm) from the end of the coupling taper, the middle taper 490(d) extends about 15-45 mm (e.g., about 28.8 mm) from the end of the upper taper, and the lower taper 490(c) extends about 3-10 mm (e.g., about 6.3 mm) from the end of the middle taper.

The lower taper 490(c) may form the apical end of part that in terminates in an annulus (e.g., a flat annulus with a diameter of about 0.5 mm to about 1 mm) surrounding a pipetting orifice (e.g., with a diameter of about 0.1 mm to about 0.5 mm). In some embodiments, the diameter of the annulus is about 0.8 mm and the diameter of the orifice is about 0.3 mm.

As with the millitip 220, the coupling taper 490(a) of the microtip 490 may be a compliant taper with a smooth interior surface and without supporting ribs. Walls of the coupling taper 490(a) may have a thickness of about 0.1-1.0 mm (e.g., about 0.5 mm).

As with the millitip 220, the microtip's coupling taper 490(a) may abruptly change diameter at the top of the upper taper forming a seating surface perpendicular to the axis of the microtip 490. The seating surface may form a flat annulus having a width of about 0.05-0.5 mm (e.g., about 0.10 mm) surrounding a core having a having a diameter of about 1 mm-5 mm (e.g., about 3 mm).

The open end of the coupling taper 490(a) forming the mounting aperture may end in a stopping annulus, as described above for the millitip 220. The microtip 490 may include an aerosol barrier and/or an abrupt internal diametral decrease in the upper taper 490(a), as described above with respect to the millitip 220.

Figures 1, 12C:
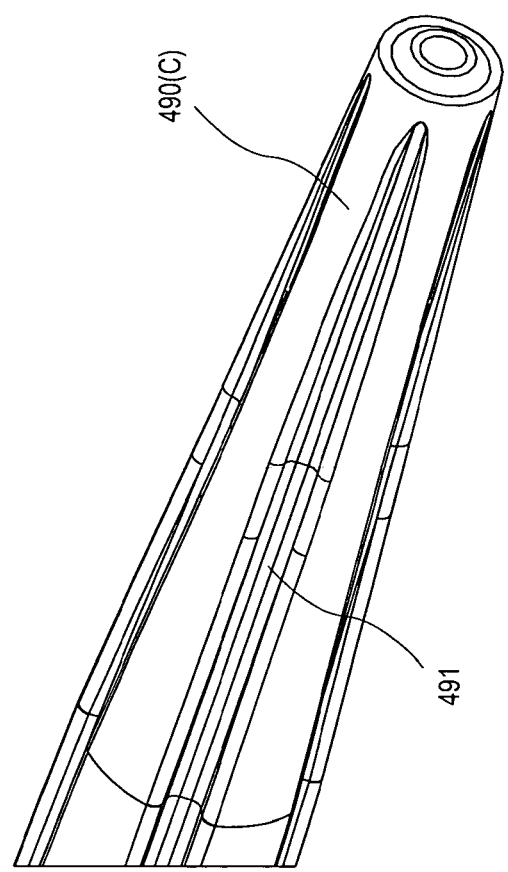

As shown in FIG. 12(c)-1, the microtip may also include one or more venting features 491 at a lower taper 490(c). FIG. 12(c)-2 shows a side view of a portion of the lower taper 490(c). The dimensions shown in FIG. 12(c)-2 are in inches, but the dimensions can vary in other embodiments. In embodiments of the invention, the venting features may comprise abrupt deviations from the microtip's otherwise smooth outside wall. The deviations may extend in the vertical direction along a major axis of the microtip, and may include sharp corners on the outside diameter, protruding ribs, incised channels, or similar features. In addition, the exterior of the microtip pipette orifice may be an annulus, the plane of which is at right angles to the central axis of the microtip. In some embodiments, one or more ventilation features or channels do not extend to the distal tip of the microtip. For example, a ventilation channel may end between about 0.1-0.5 mm (e.g., about 0.25 mm) from the end of the tip.

The microtip 490 may comprise one or more materials (e.g., an admixture of a base polymer with a conductive material) or properties (being electrically conductive) as described above with respect to the millitip 220. The microtip 490 may be manufactured using a forming process as described above with respect to the millitip's formation.

L. Microtip Storage

Figure 13B:
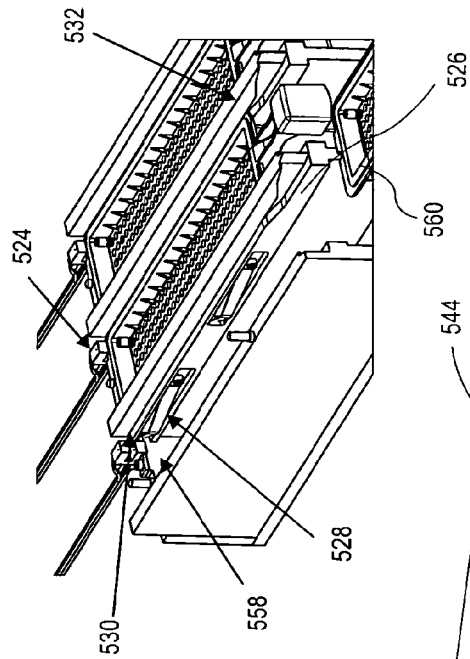
FIG. 13(b) shows a portion of a microtip storage unit.
Figure 13A:
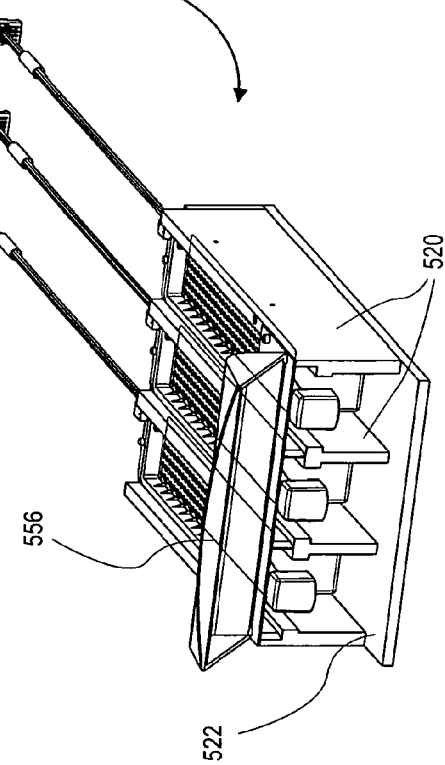
FIG. 13(a) shows a microtip storage unit.

FIG. 13(a) shows a front perspective view of a microtip storage unit according to an embodiment of the invention, with an access cover in an open configuration.

FIG. 13(b) shows a portion of a microtip storage unit according to an embodiment of the invention.

Figure 13F:
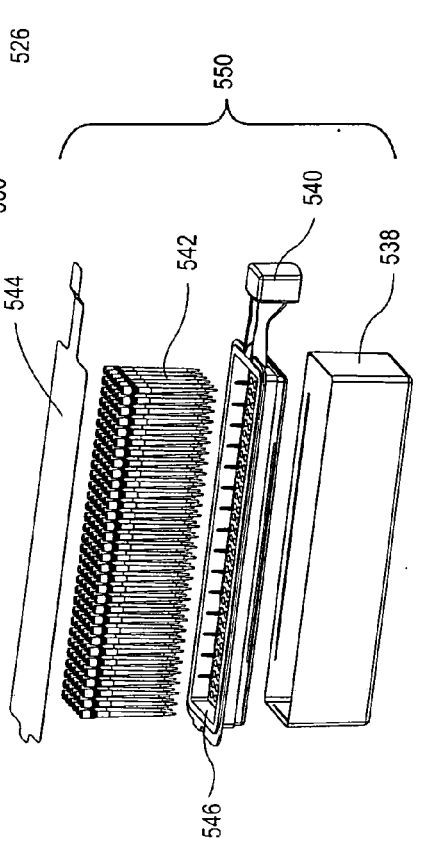
FIG. 13(f) shows a rack clasp in a microtip storage unit.
Figure 13C:
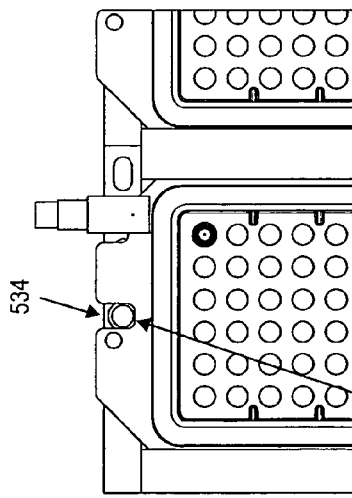
FIG. 13(c) shows a plan view of a portion of a microtip storage unit.

FIG. 13(c) shows a top plan view of a portion of a microtip storage unit.

FIG. 13(d) shows a rack clasp in a microtip storage unit according to an embodiment of the invention.

FIG. 13(e) shows a perspective view of a microtip rack according to an embodiment of the invention.

FIG. 13(f) shows an exploded view of a microtip rack according to an embodiment of the invention.

As shown in FIG. 13(f), microtips 542 may be provided in the form of a plurality of tips held in a microtip rack 550. Microtip racks 550 may, in turn, be stored on the system in a microtip storage unit 120. In some embodiments, the microtip rack 550 and the microtip storage unit 120 have structural similarities to the reagent pack 400 and the reagent storage unit 124 (see FIG. 9(a)-9(e) and FIG. 8(a)-8(c), respectively).

Referring to FIG. 13(a), the microtip storage unit 120 may include a platform accommodating one or more microtip racks 550. Storage of multiple microtip racks 550 advantageously permits replacement of spent microtip racks 550 without interrupting system operations. In one embodiment, the microtip storage unit 120 accommodates up to four microtip racks 550. This advantageously allows the system to use all of the microtips 542 in a single microtip rack 550 without concern that insufficient microtips 542 will remain for assays in progress. The microtip storage unit 120 may include a conductive path between system ground and any loaded microtip racks 550. This advantageously dissipates static charges that might otherwise accumulate and displace microtips 542 from the microtip racks 550. To support this function, at least a portion of the microtip rack 550 may be made of a conductive or antistatic plastic. Such conductive or antistatic plastics include carbon-filled polypropylene, polyacetylene, polypurrole, polyaniline, and polymers mixed or treated with antistatic agents such as aliphatic amines, aliphatic amides, quaternary ammonium salts, phosphoric acid esters, polyols, polyol esters, PEDOT:PSS, and polyaniline nanofibers.

Each rack 550 may hold any suitable number of microtips. In some embodiments, each rack may hold a 6×20 array of microtips. The racks may hold more or less microtips in other embodiments of the invention. In some embodiments, microtips held in a microtip rack 550 may be nested within one another.

As shown in FIG. 13(a) and FIG. 13(b), in some embodiments, the microtip storage unit 120 can include three or more (e.g., four or more) parallel slots defined by slot walls 520, a rear wall 558, a finger guide 532, and an access cover 556. Each of the parallel slots accommodates a microtip rack 550. A dampening spring may be added to the access cover 556 to control the movement of the access cover 556.

The microtip storage unit may also include a base plate 522 perpendicular to and connecting the parallel slot walls 520 and the rear wall 558. Each slot may include rack guides 530 extending from the slot walls 520 to support the lower aspect of the microtip rack flange 560. Rack guides 530 on either side may thus support each microtip rack 550. One or more bias springs 528 (or other type of biasing element) on one side of each slot may force the microtip rack 550 against the opposite slot wall 520 to stabilize the microtip rack 550 and assure positional accuracy. The front edge of the rack guides may include lead-in features 526 that serve to direct microtip racks 550 to compensate for misalignments during the loading process. An exterior wall of the microtip storage unit may serve as a mounting point for a waste chute leading to a waste disposal area.

Referring to FIG. 13(c), the rear wall 558 may include a centering pin 534 that engages a centering slot 536 on the microtip rack 550 upon insertion. This centering pin 534 can serve to fix the location of the microtip rack 550 within the microtip storage unit. 120. The microtip storage unit 120 may further secure each loaded microtip rack in place using a spring-loaded rack clasp 554 (FIG. 13(d)), which is similar to the RSU latch assembly as shown in FIG. 8(c). In some embodiments, the rack clasp 554 pivots on a clasp pivot 570 and may engage a complementary clasp recess 552 in the microtip rack 550 (FIG. 13(e)). The rear wall 558 may also include an ejection spring (or other biasing element) so that the microtip rack 550 can be ejected when the clasp 554 does not secure the microtip rack 550.

A single latch pivot 570 may extend across the rear wall 558 to mount a plurality of rack latches 554 within the microtip storage unit 120. The rack latch 554 may operate in substantially identical fashion to the reagent storage unit 124, seating within a mating feature, such as latch recess 552, upon loading the microtip rack 550 and holding the microtip rack 550 in place until released. The microtip rack 550 may be released from the microtip storage unit 120 by the application of downwards pressure on the rack latch tab 568, which causes the rack latch 554 to rotate around the axis defined by the latch pivot 570 thereby withdrawing the rack latch 554 from the clasp recess 552 of the microtip rack 550. In one embodiment, the downwards pressure is supplied by the XYZ elevator 1120 (shown in FIG. 15(*c*)), as applied through a microtip 542. As described for the reagent storage unit 124 above, the rear wall of the microtip storage unit 120 may include apertures that align with the stored microtip racks 550, which would permit spent microtip racks to be displaced out through the rear of the microtip storage unit upon loading of a new microtip rack into the same slot.

The microtip storage unit 120 may include sensors that detect the presence of microtip racks 550. Suitable sensors include but are not limited to Hall effect sensors, optical sensors, or gravimetric sensors, and may be affixed to the rear wall 558 of the microtip storage unit 120. In one embodiment, the sensor is an optical sensor, such as the Opto slot sensor, from Optek of Carrollton, Tex. Alternatively, the system may detect the presence of a microtip rack 550 by confirming successful loading of a microtip 542 to an XYZ pipettor (e.g., element 1136 shown in FIG. 15(*a*)).

As shown in FIG. 13(*b*), a finger guide 532 may extend across the upper aspect of the front portion of the microtip storage unit 120. This can act as a guide and as a physical limit during the loading process. In one embodiment, in order to load a microtip rack 550 into the microtip storage unit 120, the user slides a microtip rack 550 into a parallel slot by aligning the distal end 566 of the microtip rack 550 above the rack guide 530 but below the finger guide 532. As shown in FIG. 13(*a*), an access cover 556 may shield the front portion of the microtip storage unit 120. In one embodiment, the access cover 556 can be affixed to the finger guide 532 with hinges, to allow opening for user loading and unloading of microtip racks 550. The access cover 556 may include a set of indicators associated with each slot that inform the user of the status of loaded microtip racks 550. In some embodiments, these indicators are a set of LEDs, the color of which indicates the presence and status of loaded microtip racks. In other embodiments, the status of the loaded microtip racks 550 can be indicated on a system display as part of the system's user interface. Alternative embodiments include but are not limited to incandescent lamps, an LCD display, or other suitable visual indicators In some embodiments, an XYZ pipettor may be accessible to the microtip storage unit 120. In some embodiments, the microtip storage unit 120 resides near the front of the system to permit an operator to easily load and unload microtip racks.

In a preferred embodiment microtips, 542 stored in the microtip storage unit 120 are held in microtip racks 550. FIG. 13(*e*) shows a microtip rack 550 that has a proximal end 562 and a distal end 566. The proximal end 562 may include a handle assembly 564, which provides the user with a gripping point for insertion and removal of the rack. The distal end 566 may include a clasp recess 552, which interfaces with the rack clasp 554 of the microtip storage unit 120 on insertion of the microtip rack 550. The microtip rack 550 may also include a barcode, RFID chip, one wire device, or other devices that convey information related to the microtip rack 550 to the system. Each microtip rack 550 holds a plurality of microtips 542. In one embodiment, a microtip rack 550 holds 161 microtips 542 in a 7×23 matrix. A microtip rack 550 may be formed by snapping components together (e.g., as in FIG. 13(*f*)), or they may be friction fit, welded, or glued together.

In order to dissipate static charges accumulated on the microtips 542, portions the microtip rack 550 that contact the microtips 542, may be constructed of a conductive or antistatic materials, at least in part. Such conductive or antistatic plastics include carbon-filled polypropylene, polyacetylene, polypurrole, polyaniline, and polymers mixed or treated with antistatic agents such as aliphatic amines, aliphatic amides, quaternary ammonium salts, phosphoric acid esters, polyols, polyol esters, PEDOT:PSS, and polyaniline nanofibers. In some embodiment only tip support 546 is made from conductive or antistatic materials. The rack base 538 of the microtip rack 550 is designed enclose the microtips 542 in order to prevent contamination. In one embodiment, the rack base 538 includes a clasp recess 552 to secure the microtip rack 550 within the microtip storage unit 120. The rack base 538 may also be made of conductive or antistatic materials. The relationship between the microtip support 546, microtips 542, and microtip rack base 538 is also shown in the exploded view of the microtip rack 550 shown in FIG. 13(*f*). Microtips 542 may be further protected from contamination by placement of a rack cover 544 over the microtips 542. The rack cover 544 is attached to the microtip rack 550; in one embodiment, the rack cover 544 is affixed to the upper periphery of the microtip rack 550 using an adhesive. The rack cover 544 may be composed of multiple layers, and may be held in place using adhesive.

A microtip rack 550 may serve to store items other than microtips. Such items include reaction vessel bases 246, reaction vessel plugs 222, sealed reaction vessels awaiting further processing, and testing devices for use in characterizing thermal cycler performance. In some embodiments microtips may be returned to the microtip rack 550 after use, for re-use or eventual disposal.

M. Waste Processing: Waste Processing Lane

FIG. 14(*a*) shows a perspective view of a waste processing lane according to an embodiment of the invention.

FIG. 14(*b*) shows a perspective view of a liquid waste storage assembly according to an embodiment of the invention.

FIG. 14 (*c*) shows a perspective view of a waste processing lane in association with a solid waste container according to an embodiment of the invention.

Following processing of a sample, it may be desirable for the system to have a device for discarding the used assay cartridge 200 and its contents, along with other consumables, in a manner that minimizes the risk of contamination and that assures the safety of the user. As explained above, with reference to FIG. 1(*b*), at least one of the processing lanes 116 can be used for disposal of used assay cartridges 200 following processing of the sample. The waste lane 116(*c*) has access to or includes tools for the disposal of both solid and liquid waste.

FIG. 14(*a*) shows an embodiment a waste lane 870 that includes access to an aspiration probe 986, to a solid waste garage 874, and to a waste cartridge carriage 872. Functions of a waste lane 870 can include removal of liquids from assay cartridges 200 and disposal of assay cartridges 200. Alternatively, a waste lane 870 may dispose of assay cartridges 200 without prior removal of waste fluids.

As shown in FIG. 14(*a*), a waste lane 870 may include an aspiration probe 986 that removes accessible liquid waste from an assay cartridge 200. In some embodiments an aspiration probe 986 is disposed above a waste cartridge guide 990 at a fixed position along the lane motion path. The aspiration probe 986 may be mounted on a probe elevator 988 that facilitates vertical movement of the aspiration probe 986. The upper wall of the waste cartridge guide 990 can include an opening or gap at the fixed position that is in alignment with a probe elevator 988 to allow the aspiration probe 986 access to the assay cartridge 200.

Some components of the waste lane 870 may be located within the processing area of the system while others may be located elsewhere on the system, both for design convenience and to minimize the risk of contamination. For example, the risk of contamination from waste materials is reduced by placing a waste container in a compartment that is at least partially isolated from the portion of the system dedicated to sample processing and analysis.

In an embodiment shown in FIG. 14(b), components of a waste lane 870 include a peristaltic pump 909, a liquid waste container 908, and a fill sensor 907. These are functionally part of the waste lane, but as shown in FIG. 1(d), these may be stored in an enclosed cabinet in the base of the system.

In operation, the aspiration probe 986 enters and drains the assay cartridge 200 of waste or residual liquids. The aspiration probe 986 can include a hollow tube that is fluidically connected to a peristaltic pump 909, which provides suction. Alternatively, suction may provided via connection to a negative pressure source, such as a vacuum pump. In some embodiments, the hollow tube of the aspiration probe is spring loaded. This arrangement impels the aspiration probe 986 downward until the hollow tube either reaches a pre-set vertical stop or collides with the bottom of an assay cartridge 200 compartment, assuring that all fluid contents are removed while minimizing damage to the aspiration probe 986. In some embodiments, the hollow tube of the aspiration probe 986 is conductive and in communication with a liquid level sensing circuit. This permits the system to verify that the aspiration probe has contacted liquid waste and to verify its successful removal. In an alternative embodiment, the waste lane 870 may include a millitip pipettor 704, and utilize a millitip 220 to transfer waste fluids from an assay cartridge 200.

As shown in FIG. 14(b), the peristaltic pump 909 can drive draining action by transferring fluid through the aspiration probe 986 into a liquid waste container 908. In some embodiments, the liquid waste container 908 may be connected to the aspiration probe 986 and include a connection to a source of negative pressure, thereby avoiding the use of an active pumping mechanism. The liquid waste container 908 serves to stores waste fluids and connects by tubing to the peristaltic pump 909. In some embodiments, the liquid waste container 908 includes a fill sensor 907 that monitors the level of liquid stored therein. This fill sensor 907 may be any of a number of sensor types, including a float valve, a scale to monitor the weight of the liquid waste container 908, or a capacitive sensor. In one embodiment, the fill sensor 907 is a through-beam optical sensor. Alternatively, the system may estimate the fill level of the liquid waste container 908 by aggregating the known fill volume of each assay cartridge 200 compartment that has been drained. The peristaltic pump 909 and liquid waste container 908 are functionally part of the waste lane 870 but may reside outside the waste lane. In an alternative embodiment liquid waste may be transferred from the assay cartridge 200 to an external drain, avoiding the need to store liquid waste on the system.

In one embodiment, the waste lane 870 functions by moving the spent assay cartridge 200 so that the aspiration probe 986 drains successive compartments of the assay cartridge 200, transferring the drained fluids to a liquid waste container 908. The waste cartridge carriage 816 in the waste lane 870 may advance to move a compartment to a position under the aspiration probe 986 and causes the probe elevator 988 to lower the aspiration probe into the compartment. The probe elevator 988 lowers the aspiration probe 986 into a compartment to a depth sufficient to reach the bottom of the deepest compartment. Spring-loading may stop the aspiration probe 986 at the compartment bottom irrespective of the actual depth. This advantageously accommodates tolerance stack up that may contribute uncertainties related to compartment depth. Alternatively, the probe elevator 988 may selectively lower the aspiration probe 986 to depths appropriate for specific compartments. As the probe elevator 988 lowers the aspiration probe 986, the system may monitor a liquid level sensor to determine the fill level of the compartment, and activate a peristaltic pump 909 or other negative pressure source to begin draining once the aspiration probe contacts fluid. Once the aspiration probe assembly 870 drains a compartment, the liquid level sensor may confirm the efficacy of the draining process by sensing the decreased fill level. After draining, the probe elevator 988 raises the aspiration probe 986 and the cartridge carriage 816 advances to reposition assay cartridge 200 so that the aspiration probe is aligned with the next compartment.

As shown in FIG. 14(c), a waste lane 870 can include a solid waste ejector, which serves to dispose of the assay cartridge 200. The solid waste ejector is aligned with the waste cartridge guide 800 and may be disposed at the proximal end of the waste cartridge guide. The solid waste ejector accepts an assay cartridge 200 from the cartridge guide 800 and stores it for operator removal. Components of the solid waste ejector may include a waste garage 874 to accept and temporarily accommodate an expended assay cartridge during ejection, a waste chute 880 to direct the expended assay cartridge so as to avoid jamming, and a solid waste container 882 to retain the expended assay cartridges. In some embodiments, the waste garage 874 and the waste chute 880 may be combined in a single component. The solid waste container 882 can be functionally part of the waste lane 116(c), but may reside outside the waste lane. As shown in FIG. 1(d) solid waste 92 may be stored in a waste cabinet beneath the system. The system may incorporate features that reduce the probability of or minimize the impact of inadvertent release of contaminants. The waste cabinet may include ultraviolet light sources, In one embodiment, the waste cabinet is maintained at negative pressure, with incoming air, outgoing air, or both passing through HEPA filters. Such a HEPA filter may be mounted in a manifold that directs air flow to or from different parts of the system through different regions of a single filter. Air pressure may be monitored on both sides of such a HEPA filter to determine if the HEPA filter needs to be changed. In some embodiments, the solid waste container may be disposable. In other embodiments, the solid waste container may be reusable and used in conjunction with a disposable liner. In order to help ensure containment of solid waste the system may include a bin sensor that monitors the current capacity of the waste bin, allowing the system to notify the user when the waste bin requires emptying. In some embodiments, the system includes a waste bin sensor that allows the system to notify a user of failure to replace the waste bin in the waste cabinet after emptying.

The waste garage 874 may be an elongated hollow body, which is open at the end facing the cartridge guide 800 and which is open at the bottom where it couples to the waste chute 880. In some embodiments, the waste garage 874 and the waste chute 880 can be combined into a single part that is removable for easy cleaning. In some embodiments, the waste cartridge carriage 872 moves the assay cartridge 200 into the waste garage 874 as the waste lane 870 drains successive assay cartridge compartments. Once an assay cartridge 200 is fully within the waste garage 874, the waste cartridge guide 990 no longer provides support; as a result the assay cartridge 200 falls through the open bottom into the connected waste chute 880. In other embodiments, the assay cartridge 200 is moved into the waste garage 874 without removal of waste liquid from some or all of the assay cartridge 200 compartments, effectively combining liquid and solid waste disposal functions and simplifying the operation of the system.

The waste chute 880 may be a hollow body forming a channel large enough to accommodate an assay cartridge 200. The walls of the waste chute 880 may turn so that the channel changes direction from substantially vertical to an angle downward of and lateral to the direction of the waste lane 870 motion path. The angled section directs assay cartridges 200 dropping through the waste chute 880 laterally into the solid waste container 882 disposed below. This reduces undesirable stacking of expended assay cartridges 200 within the solid waste container 882, as assay cartridges so directed are less likely to nest vertically with one another. This advantageously prevents assay cartridges 200 from blocking the waste chute when the waste container is only partially full. The waste chute 880 may include a door that, when closed, provides a barrier between the solid waste container 882 and the waste lane 870 in order to further isolate contaminated waste.

Since an assay cartridge drops vertically once it leaves the cartridge guide 800, the waste cartridge carriage 816 of the waste lane 870 may not manipulate the assay cartridge from the normal controlled surface. As noted above, in other processing lanes the propelling feature 303 of the cartridge carriage 816 lies within a gap defined by a controlled surface 248 and a support tab 218 of the assay cartridge 200. In the waste lane 870 this arrangement may present a risk of snagging as the assay cartridge 200 drops. In a preferred embodiment, this is prevented by having the cartridge carriage 816 push the assay cartridge 200 from the distal surface of the support tab 218. In this arrangement the cartridge carriage 816 does not have the capacity to retract an assay cartridge 200 once it is within the waste lane 116(c), and can only advance it. This advantageously reduces the chances of contamination or system malfunction due to inadvertent reintroduction of a used assay cartridge 200 into the processing lanes 116 or transfer shuttle 898. The system may further reduce the possibility of snagging by providing sufficient room within the cartridge guide 800 so that a drained assay cartridge does not fully enter the garage. Processing of the next assay cartridge 200 in succession may then push the previous drained assay cartridge fully into the waste garage 874 and down to the waste chute 880.

In some embodiments, the system has one or more accessory waste chutes that direct solid waste to the solid waste container 882. One of the accessory waste chutes may be accessible by the sample pipettor assembly 700, and may include a passive stripping device for removal of the film piercer 268 following piercing of the protective film overlying the assay cartridge 200. This passive stripping device can be a rigid, bifurcate assembly that arches vertically, with the central gap aligned with the travel path of the sample pipettor assembly 700. In such an arrangement, simple lateral movement of the sample pipettor assembly 700 allows the passive stripping device to engage the film piercer 268 and gently release it from the pipette mandrel 728. This advantageously permits controlled release of the film piercer, which may have a sharp edge, into an accessory waste chute. An accessory waste chute may be accessible by the XYZ pipettor 1142. In such an embodiment, the XYZ pipettor 1142 can be used to dispose of used microtips 542 and used reaction vessels 221.

N. Transfer Shuttle

FIG. 14(d) shows a perspective view of a transfer shuttle according to an embodiment of the invention.

FIG. 14(e) shows a transfer shuttle aligned with a processing lane.

Processing of assay cartridges 200 across multiple processing lanes 116 can include a mechanism for transfer of the assay cartridge between lanes. As shown in FIG. 1(c), in some embodiments, assay cartridges 200 are transferred between processing lanes 116 using the transfer shuttle 118 at a transfer position. Some processing lanes, such as the cartridge loading lane 116(f), may only use the transfer position to unload an assay cartridge 200. Other processing lanes, such as the waste lane 116(c), may use the transfer position only to load or accept an assay cartridge 200. Other processing lanes, such as an amplification preparation lane (116g), an elution lane (116e), and a wash lane (116b) may both load and unload assay cartridges 200 at the transfer position. In some embodiments, the transfer position of a specific processing lane 116 is proximate to the intersection of the transfer shuttle 118 motion path with the lane motion path of that processing lane. The transfer shuttle 118 may be moved between lanes by any suitable means, including, for example, a gantry system, an overhead crane, a conveyer belt, or a track with drive wheels.

The transfer shuttle 118 moves assay cartridges 200 among processing lanes 116, as discussed above. In an embodiment shown in FIG. 14(d), the transfer shuttle 898 may include a shuttle gantry 908 and a shuttle channel 892. The shuttle gantry 908 supports the shuttle channel 892 and moves it among the processing lanes. The shuttle channel 892 may include alignment sensors 894 for detecting alignment flags 900 on the cartridge guides 816 of the processing lanes, ensuring proper alignment between the shuttle channel and each cartridge guide. Similar alignment flags 897 may also be positioned on the cartridge carriage 816 of a processing lane 116. In some embodiments, the alignment sensors 894 are optical sensors. Alternatively, alignment sensors may be placed on the cartridge guides 816 of the processing lanes 116 and alignment flags positioned on the shuttle channel 892.

The shuttle gantry 908 can be a single-axis linear transport disposed perpendicularly to the lane motion path of the processing lanes 116. In some embodiments, the shuttle gantry 908 includes a linear transport including a shuttle track 896 that is attached to the shuttle gantry extends in the direction of travel. The shuttle track 896 may extend the full length of the desired travel, and incorporate a shuttle drive 890. A variety of drive systems may be suitable for this purpose, including lead screw and nut, a linear motor, or a pneumatic actuator. In some embodiments, the shuttle drive 890 includes an idler pulley that is attached to the shuttle track 896 near one end of travel and a fixed motor connected to a drive pulley that is attached to the shuttle track near the opposite end of travel. A timing belt may extend between the idler pulley and the drive pulley, and connect to the shuttle gantry 908. The distance between the drive pulley and the idler pulley may be adjustable to simplify installation of the timing belt and to permit adjustment of the tension for optimal performance. The shuttle gantry 908 may include a track bearing configured to rest on a portion of the shuttle track 896. In this configuration, rotation of the motor drives the timing belt through the drive pulley and moves the shuttle channel 892 to various positions along the shuttle track 896. Alternatively, the transfer shuttle 898 may be any structure capable of reaching each of the processing lanes such as a rotary transport, a guided track transport, an elevator, an XYZ Cartesian transport, or an articulated arm.

The shuttle channel 892 may be a section of U-shaped channel similar to a portion of the guide channel 862 of a cartridge guide 800. As with the cartridge guide 800, the interior aspect of the lower wall of the shuttle channel 892 may support an assay cartridge horizontal web 228 on one side and the bottom surface of a cartridge flange 906 on other side. The opening or gap in the lower wall allows the wells and vertical web 226 of an assay cartridge 200 to extend below the shuttle channel 892. A linear spring may serve to align and retain an assay cartridge 200 within the shuttle channel 892. In some embodiments, as shown in FIG. 14(e), the shuttle channel 892 includes tapering or angled lead-in features 904. Such lead-in features 904 may serve to compensate for minor misalignments between the shuttle channel 892 and the guide channel 862 of a processing lane 116, thereby preventing damage to the assay cartridge 200 during transfer and reducing the frequency of system failures due to misaligned assay cartridges.

In one example of how the transfer shuttle 898 can function, the shuttle gantry 908 positions the shuttle channel 892 at the transfer position in a first processing lane. The cartridge carriage 816 of the first processing lane then moves to the transfer position to place the assay cartridge 200 in the shuttle channel 892. The shuttle gantry 908 then repositions the shuttle channel 892 at the transfer point of a second processing lane. The cartridge carriage 816 of the second processing lane then moves the assay cartridge from the shuttle channel 892 into the guide channel 862 of the second lane. The cartridge carriage of the second processing lane may move to the transfer position prior to the arrival of the shuttle channel in order to simplify transfer of the assay cartridge 200. During transfer the system may control the transfer velocity of the transfer shuttle 898 in order to reduce splashing of the contents of the assay cartridge 200.

In another example of how the transfer shuttle 898 can function, a transfer shuttle having more than one shuttle channel positions a first shuttle channel at a transfer position of a first processing lane. The cartridge carriage of the first processing lane then transfers a first assay cartridge to a first shuttle channel of the transfer shuttle. The shuttle gantry then repositions the transfer shuttle, aligning a second shuttle channel of the transfer shuttle with the transfer position of a second processing lane. The cartridge carriage of the second processing lane transfers a second assay cartridge to the second shuttle channel of the transfer shuttle. The shuttle gantry then repositions the transfer shuttle to align the first shuttle channel with the transfer position of the second processing lane. The cartridge carriage of the second processing lane then retrieves the first assay cartridge from the first shuttle channel of the transfer shuttle for processing within the second processing lane. The shuttle gantry then repositions the transfer shuttle to transfer the second assay cartridge to another processing lane, which may be the first processing lane. This operation may be referred to as a cartridge switch. A cartridge switch may occur within a single operational pitch, which is described in greater detail below. In some embodiments, the first processing lane is the cartridge presentation lane. In some embodiments, the second processing lane is a warming lane.

Figure 14G:
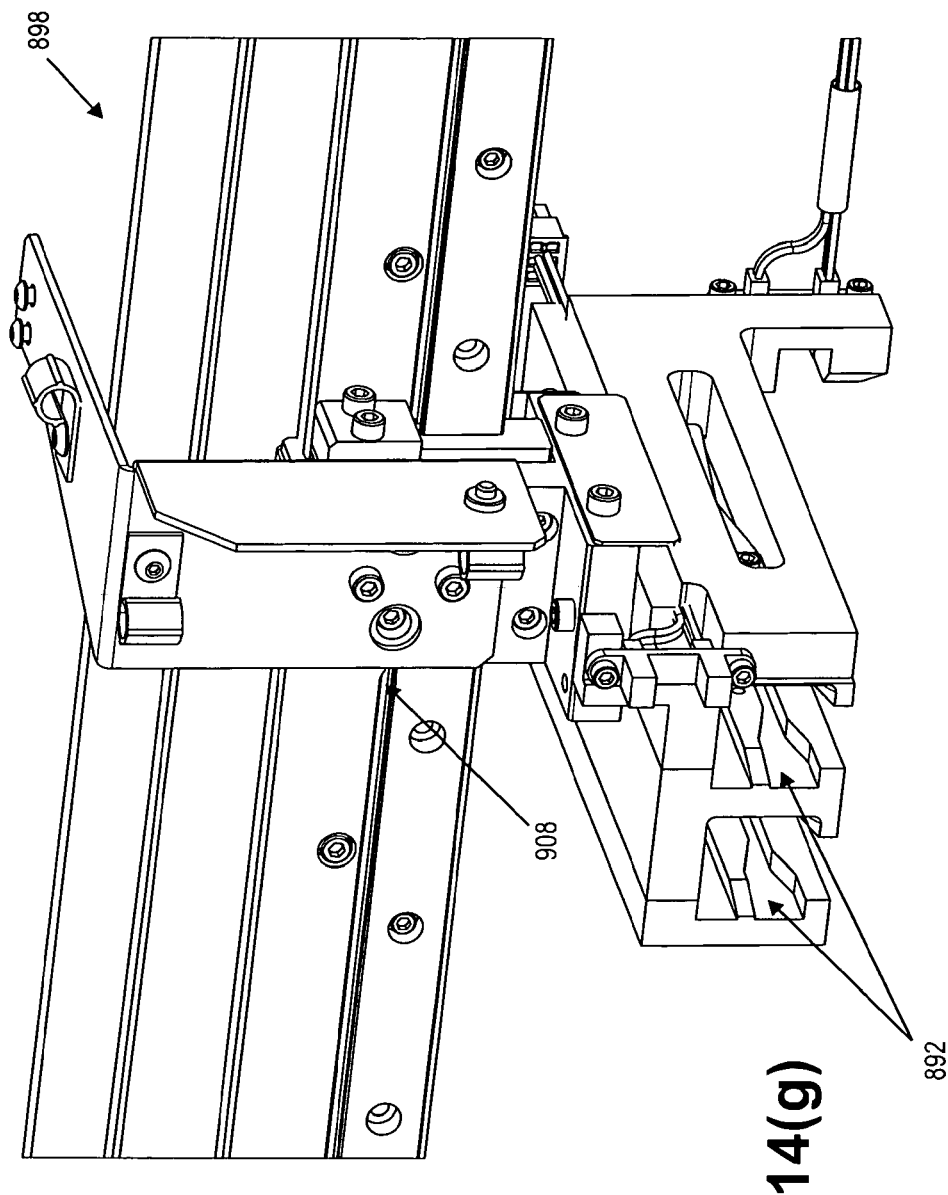
FIG. 14(g) shows another transfer shuttle according to another embodiment of the invention.

FIG. 14(g) shows another transfer shuttle 898 according to one embodiment of the invention. In this embodiment, two shuttle channels 892 may be coupled to a shuttle gantry 908, so that two cartridges can be transported simultaneously. In yet other embodiments, three or more shuttle channels may be present in the transfer shuttle. This embodiment is advantageous, as it can increase productivity as more assay cartridges can be transferred.

O. XYZ Transport Device

FIG. 15(a) shows a perspective view of an XYZ axis transport device according to an embodiment of the invention.

FIG. 15(b) shows a perspective view of a portion of a Y axis transport device.

FIG. 15(c) shows a Z axis elevator for the XYZ axis transport device.

Figure 15D:
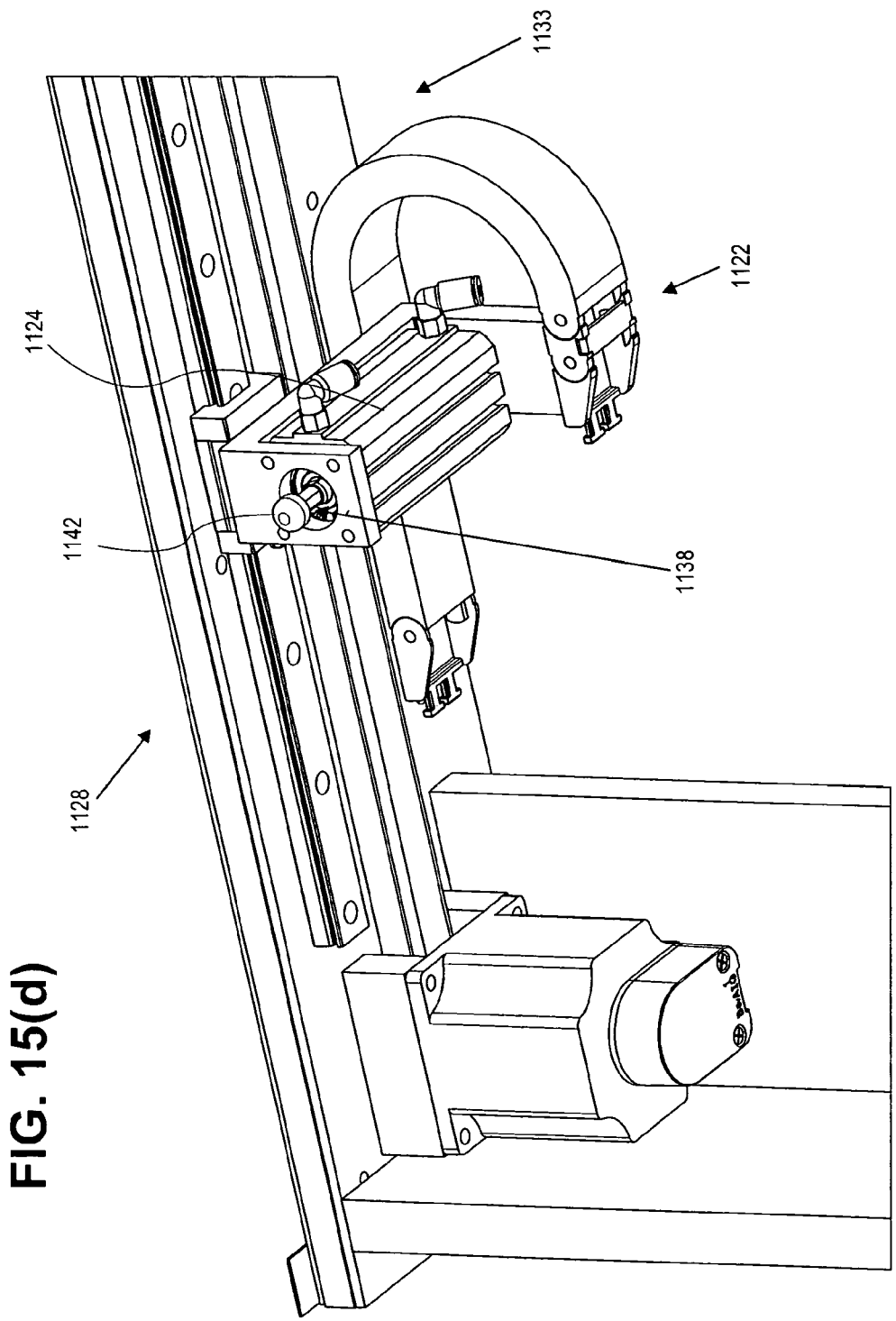
FIG. 15(d) shows an X' axis.

FIG. 15(d) shows an X' axis transport device.

As shown in FIG. 1(c), an XYZ transport device 40 is positioned to access both sample processing and sample analysis portions of the system. According to a more specific embodiment of the invention shown in FIG. 15(a), an XYZ transport device 1100 can comprise a number of independent motion systems. The first may be an XYZ axis transport apparatus 1132. In one embodiment, the XYZ axis transport apparatus 1132 can associated with (e.g., coupled to) a pipetting arm 1136. The XYZ axis transport apparatus 1132 can move in an X direction, a Y direction, or a Z direction. A second independent motion system may be an X' axis transport device 1134. In one embodiment, the X' axis transport device 1134 is associated with a slide-lock manipulator 1138 that is used to access thermal cyclers 1300. Another independent motion system may include an X-axis transport element 1133. It may include a linear track, as well as a drive device for causing the XYZ axis transport apparatus 1132 to move in an X direction. Yet another independent motion system may include a Y-axis transport element 1131. It may include a linear track, as well as a drive device for causing the X-axis transport element 1133 to move in a Y direction.

The pipetting arm 1136 may move along both X and Y axes along the major planes of the system, and (as shown in FIG. 15(c)) may include a pump carriage 1140 that can move vertically in the Z axis. The pump carriage 1140 may include a microtip pipettor 1142 similar to those utilized in some processing lanes 116 of the system. This pipettor 1142 can be used to load and shuck microtips 542, pipette reagents between the reagent storage unit 124 and processing lanes 116, place plugs 222 in the base of reaction vessels 221, and transfer PCR reaction vessels 221 to and from the thermal cycler cell garage 1200. The XYZ transport can include devices that facilitate processing of reaction vessels, including mixing devices capable of releasing air bubbles trapped against the interior of a reaction vessel. Such devices include orbital mixers, ultrasonic devices, and devices that spin the reaction vessel. In some embodiments, the XYZ transport may include multiple pump carriages, carrying pipette pumps of with different effective volume ranges.

Alternative embodiments of the system may utilize a dedicated device for the transfer of reaction vessels, reaction vessel plugs, and microtips. Such dedicated devices may include a gripper configured for "pick and place" of items such as reaction vessels, reaction vessel plugs, and microtips, The XYZ transport device 1100 may also include positional encoders and a linear encoder reader 1104 that provide positional information and feedback to a controller, as shown in FIG. 15(b). Examples of such encoders include magnetic linear encoders that may be incorporated into gantries and other supporting structures and encoders that are incorporated directly into drive motors 1112, such as optical rotary encoders.

To further refine movement and orientation on the system, the pipettor 1142 may include a sensing circuit that signals proximity to and contact with objects or fluids, either through the pipettor 1142 or an extension of the pipettor such as a disposable microtip 542. Such a sensing circuit is described in further detail below, and can be responsive to conductive objects or fluids. Other possible sensing mechanisms include optical, acoustic, and radio frequency sensors. Examples of conductive objects include conductive pipette tips, conductive plugs 222 for PCR reaction vessels, and conductive surfaces on the system itself. This sensing circuit can provide confirmation of the presence of a conductive pipette tip 542, plug 222, or plugged PCR reaction vessel 221 on the pipettor, and allows the use of known conductive features on the system for calibration of the position of the XYZ transport device 1100.

FIG. 15(b) also shows air valves 1106 for controlling air flow to pneumatic systems, a home sensor 1110 for indicating a home position for the pipetting arm 1136, as well as a carriage mount for the pipetting arm 1136.

The XYZ transport device 1100 may include additional independent motion systems that may include positional encoders, such as an X' axis transport device 1134 as described above and as shown in FIGS. 15(a) and 15(d). Such independent motion systems may include a slide lock manipulator 1138, which moves along an X' axis can be used to manipulate a slidable cover or door that lies within its motion path. In one embodiment, the sliding cover is a slidable lid of a thermal cycler module (see FIGS. 16(j)-16(m)).

A system according to an embodiment of the invention may comprise a linear track, a pipetting arm coupled to the linear track, and an actuator coupled to the linear track and configured to extend away from the linear track and retract towards the linear track. In one embodiment, the actuator can move independently of the pipetting arm along an X' axis. In accordance embodiments of the invention, the X' axis can be parallel with the long axis of the thermal cycler module garage. FIG. 15(d) shows an embodiment where the slide lock manipulator 1138 includes a linear actuator 1124 that terminates in a gripping feature 1142. FIG. 15(d) also shows an X'-axis motor with a rotary encoder, a rail 1128, and a conduit cover 1122 (e.g., for covering wires and other conduits). In an alternative embodiment, the actuator is a slide lock manipulator that moves in concert with the pipetting arm and is coupled to the same motion mechanism.

A pneumatic cylinder can cause the actuator 1124 to extend and retract away from and towards the X-axis transport element 1133. The pneumatic cylinder may extend in any axis that is suitable for its function. In one embodiment, the pneumatic cylinder extends along the Y axis. In the embodiment described above, this gripping feature 1142 may be in the form of a cylinder, and may reversibly engage the slidable lid of a thermal cycler module (or other analytical unit). In such an embodiment, the XYZ transport can include sensors that determine the position of such a slidable lid. Movement of the linear actuator 1124 results allows the system to move the slidable lid, thereby opening or closing the thermal cycler module. The linear actuator 1124 can be a pneumatic cylinder, although other mechanisms that provide linear movement such as hydraulic cylinders, linear stepper motors, worm gear drives, timing belt and pulley assemblies, and solenoids may also be used.

The gripping feature 1142 may be an expanded section of the terminus of the linear actuator 1124, the expanded section having sufficient radius and thin enough section to engage a complementary feature on the slidable lid of the thermal cycler module. In one embodiment, the X' axis transport device 1134 moves the slide lock manipulator 1138 into a position adjacent to the thermal cycler module. The slide lock manipulator 1138 then extends the linear actuator 1124 to engage the slidable lid with the gripping feature 1142. The gripping feature 1142 may be released from the slidable lid by reversing this operation. The gripping feature 1124 can have an approximately circular cross-section, with a rounded edge and a thickness that increases towards the center, however other geometries, including polyhedrons, spheroids, conical sections, and combinations of the shapes are possible. Alternatively the gripping feature 1124 may incorporate two or more extensions that either passively or actively engage a feature on the slidable lid.

The slide lock manipulator can be used in other embodiments of the invention. For example, the slide lock manipulator can be used in a method comprising: acquiring a reaction vessel (e.g., reaction vessel 221 in FIG. 5(c)) with a pipetting arm (e.g., pipetting arm 1136 in FIG. 15(a)), opening the analytical unit (e.g., the thermal cycler module 1300 in FIG. 16(b)) with a slide lock manipulator (e.g., 1138 in FIG. 15(a)), aligning the pipetting arm with the analytical unit, and releasing the reaction vessel from the pipetting arm. Thus, the particular XYZ transport device 1100 shown in FIG. 15(a).

P. Sensor System

As noted above, the system can include a sensor system. In some subassemblies, a secondary controller may be associated with a sensor system that includes a sensing circuit that provides feedback to the system. In one embodiment, a subassembly that is associated with a sensor system is a pipetting device. A sensor system according to an embodiment of the invention may comprise a mandrel (e.g., element 4110 in FIG. 15(e)), which may form part of a pipetting device, and a sensing circuit configured to determine a characteristic of an extension element on the mandrel. The sensing circuit comprises one or more sensor channels, coupled to a processor (e.g., controller 4600 in FIG. 15(e)) configured to determine the characteristic of the extension element based on the error signal. The sensing circuit may comprise a phase-locked loop (also known as a PLL), a plurality of sense channels, a processor or controller, and other components.

Figure 15E:
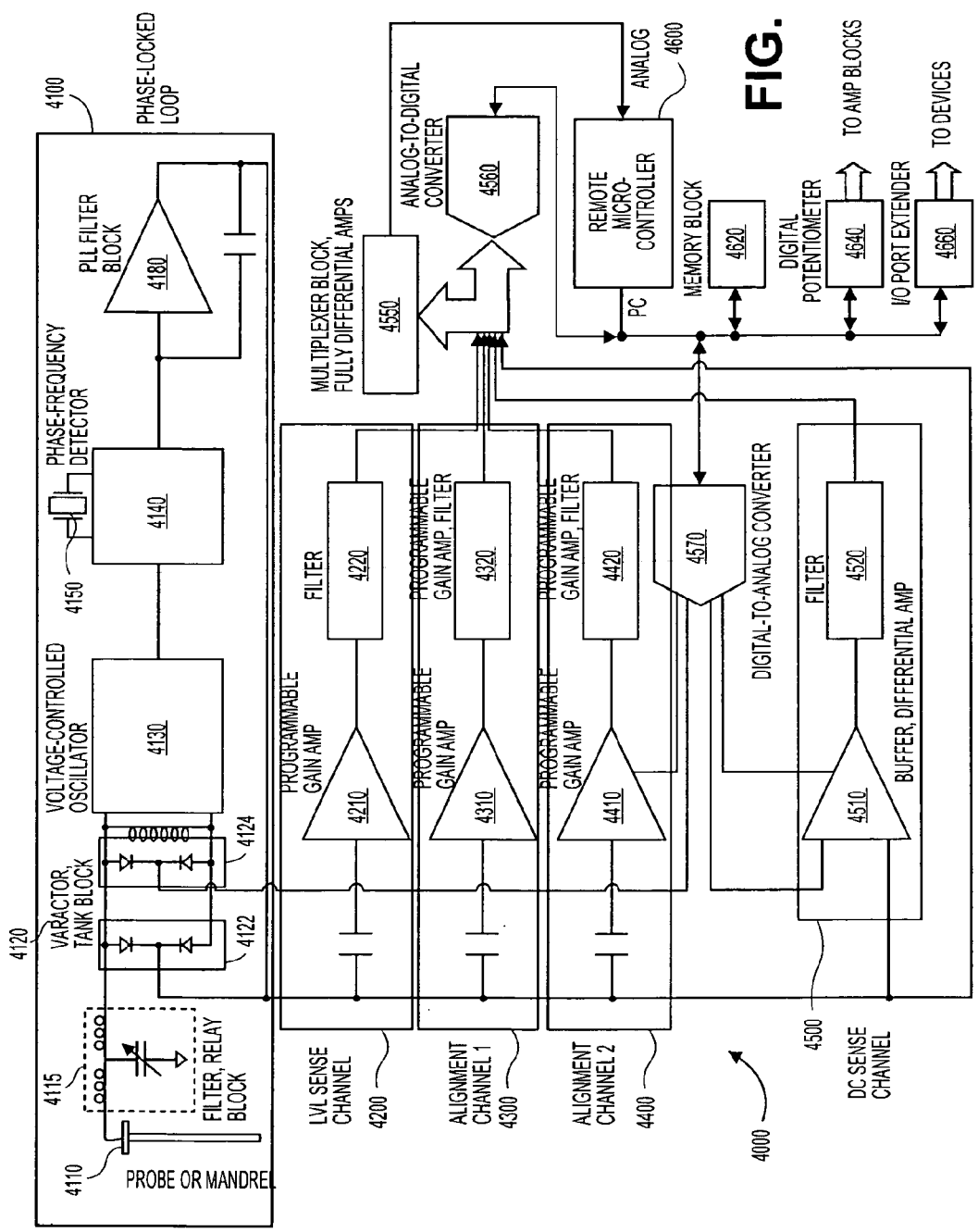
FIG. 15(e) shows a sensor system according to an embodiment of the invention.

An exemplary sensing system comprising a sensing circuit (e.g., a liquid level sensing circuit) is shown in FIG. 15(e). The sensing circuit according to an embodiment of the invention provides a signal that indicates when a portion of the subassembly contacts or approaches a discontinuity in permittivity, conductivity or a source of electromagnetic (electrostatic) induction. One example of a detectable discontinuity in permittivity is an air-liquid interface; for this reason, such a sensing circuit may be referred to as a liquid sensor. An example of a detectable discontinuity in conductivity includes a good conductor physically attaching to a material with higher resistivity. Examples of detectable sources of electromagnetic induction include any conductive, charge holding elements in relatively close proximity to the portion of the subassembly under discussion. These discontinuities in permittivity, conductivity or sources of mutual capacitance, either individually or combined, modify the amount of capacitance "seen" by the circuit which results in a detectable modulation or change in the signal. For example, a detectable modulation or change can be indicated as a PLL "error" signal.

In some embodiments, the sensing circuit can be a liquid level sending circuit as described in Radio Frequency Liquid Sensor, or RFLS. One example of an RFLS is found in U.S. Pat. No. 4,912,976, which is herein incorporated by reference in its entirety, for all purposes. It describes a capacitance-based liquid sensing circuit that includes a reactive element that forms part of a tuned circuit in a voltage-controlled oscillator. The current embodiment incorporates a related capacitance-based liquid sensing circuit that includes a distributed reactive element that forms part of a tuned circuit in a voltage-controlled oscillator. The reactive element can be coarsely modeled as a combination of capacitance, resistance and inductance including a dielectric and terminal conductors. The reactive element need not be continuously self-contained or localized, but can change according to the application. The properties of the reactive element can be altered (and consequently detected) by effecting change to any of the basic constituents, e.g., changes to the dielectric, to terminal conductors or to the mutual capacitance environment.

Changes in the local environment surrounding one terminal of the reactive element amount to a change in the reactive element's dielectric. When the permittivity of the dielectric changes, the capacitance sensed by the circuit can be altered resulting in a change in frequency. This change in frequency can be detected by comparison to a fixed frequency reference. Such a change indicates that one of the terminals of the reactive element has, for example, encountered a liquid.

In some embodiments, one of the reactive element terminals is a liquid handling probe that forms part of the RFLS circuit. Alternatively, one terminal of the reactive element may be altered adding a conductive extension of the subassembly that is discarded after use. Examples of disposable conductive extension elements include, but are not limited to, millitips and microtips. In such an embodiment, the sensing circuit can provide a signal that indicates the successful attachment, and subsequent release, of a conductive millitip (220 of FIG. 6), microtip (490 of FIG. 12(b)), film piercer (262 in FIG. 4(e)), or reaction vessel plug (222 of FIG. 5) to the pipette mandrel. The sensing circuit can also be configured to detect different volumes of liquid in a pipette tip attached to a mandrel as well as to provide information regarding the type of liquid.

As an example of changing the mutual capacitance environment, another embodiment of the liquid level sensing circuit can be used to detect the approach of a pipette mandrel (which forms one of the reactive element terminals) to one or more conductive targets (which can form other reactive element terminals) that are placed within the path of the pipettor. This approach can be a patterned series of movements that comprise a search for a conductive target in 3-dimensional space that is initiated once the pipette mandrel is brought into proximity to the conductive target. Such information, when combined with information regarding the position of associated stepper motors, can be used for automating alignment of the pipettor within the system. The conductive targets may be fortuitously located system components or conductive targets incorporated into the system for this purpose. Conductive targets can include projections that extend from a system component. Examples of projecting conductive targets include substantially planar tabs and cylindrical pins. Alternatively, a conductive target can be a hole or gap in an otherwise continuous conductive surface. Any discontinuity or array of discontinuities in a conductive element can be used for detection purposes. The detected modulated signal can be used to measure alignment, proximity, contact, speed, acceleration, direction and vibration in addition to other parameters. This can be useful in characterizing a range of mechanical performance specifications.

FIG. 15(e) is a simplified block diagram of a sensor system 4000, according to one embodiment of the present invention. The sensor system 4000 may be incorporated into or associated with the pipetting arm 1136 shown in FIG. 15(a). The sensor system 4000 may be configured to perform multiple functions including liquid level detections, basic instrument alignment functions, pipette tip (or other device detection; as described above) detections and detections of discontinuities in permittivity, conductivity, and sources of electromagnetic (electrostatic) induction. The sensor system 4000 includes a phase-locked loop based sensor ("PLL sensor" or "sensing circuit") 4100, a level sense channel 4200, a first alignment channel 4300, a second alignment channel 4400, a direct current ("DC") sense channel 4500, a multiplexor ("mux") 4550, an analog-to-digital converter (ADC) 4560, a digital-to-analog converter (DAC) 4570, a processor 4600, a memory block 4620, a digital potentiometer 4640, and an input-output ("I/O") port extender 4660, all operatively and/or electrically coupled together. The PLL sensor 4100 includes a reactive element 4110, a filter and relay block 4115, an inductive-capacitive-resistive ("LCR") tank circuit 4120, a voltage-controlled oscillator ("VCO") 4130, a phase-frequency detector ("PFD") 4140, a reference oscillator 4150, and a filter 4160. The tank circuit 4120 includes a first set of varactors 4124 and a second set of varactors 4122. The first set of varactors 4124 are connected to the VCO 4130 and the reactive element 4110 through the filter and relay block 4115. The midpoint of the first set of varactors is connected to the processor 3600 through the DAC 4570.

The sensor system 4000 may further comprise a plurality of sense channels. For example, the sensor system 4000 may comprise a level sense channel 4200, which includes an amplifier circuit 4210 and a filter 4220. It may also include a first alignment channel 4300, which includes an amplifier circuit 4310 and a filter 4320, and a second alignment channel 4400, which includes an amplifier circuit 4410 and a buffer 4420. It may further include a DC sense channel 4500, which includes an amplifier circuit 4510 and a filter 4520.

The reactive element 4110 may comprise a pipette mandrel, or a pipette mandrel in combination with an extension element such as a pipette tip, piercer, pipette tip with liquid, etc. The reactive element 4110 may be configured to sense changes in the surrounding dielectric and sense changes due to electromagnetic induction. Furthermore, the sensor system 4000 may be configured to determine a characteristic of an extension element of the pipettor mandrel. For example, the reactive element 4110 may include an extension element such as a film piercer or a reaction vessel, each with different electrical properties, and the sensor system 4000 can determine if the extension element is present or has changed in any way. Other reactive elements 4110 and extension elements may be used and would be known and appreciated by one of ordinary skill in the art with the benefit of this disclosure. In certain embodiments, the reactive element 4110 (e.g., mandrel) can have a resistance, a reactance (e.g., capacitive reactance or inductive reactance), or a combination of both (e.g., an impedance).

The PFD 4140 is a multistate phase-frequency detector configured for phase-locked loop applications where a minimum phase and frequency difference between a reference and a VCO is achieved when the loop is locked. The PFD 4140 is further configured to compare the frequency of the VCO 4130 to the frequency of the reference oscillator 4150 (i.e., a fixed oscillator) and generate a corresponding difference voltage or error signal. The error signal is proportional in magnitude and direction to the difference between the VCO and reference output frequencies. As further described below, the PLL error signal (from PLL sensor 4100) can be used as the source of all measurement channels (e.g., level sense channel 4200) in the sensor system 4000. The error signal generated by PFD 4140 can be fed back to the VCO 4130 through the filter 4160, where the VCO 4130 adjusts its operating frequency until it matches the frequency of the reference oscillator 4150. In this "locked" condition, the error voltage is relatively constant (non-changing) and is continuously monitored by the processor 4600. In one embodiment, the filter 4160 is an active filter to provide for a wide range of VCO 4130 tuning voltages. In some embodiments, the operating frequency of the VCO 4130 or the reference oscillator may be multiplied or divided. In another embodiment, the VCO 4130 operating frequency is a function of the tank circuit 4120, the filter relay block 4115, and the reactive element 4110.

The LCR tank circuit 4120 controls the frequency of the VCO 4130 and includes the reactive element 4110. This reactive element may be distributed; in one example such a distributed reactive element includes filter block 4115. When the reactive element 4110 experiences a change in capacitance, the frequency of the LCR tank circuit 4120 also changes. A change in any element of the LCR tank circuit 4120 (i.e., capacitance, resistance, or inductance) causes a change in the frequency of the VCO 4130, thus changing the PLL error voltage monitored by the processor 4600. Changes in the capacitance of the LCR tank circuit 4120 may be caused by a number of events including pipette tips touching liquid, mandrels passing in close proximity to conductive targets, and the placement of a pipette tip on a mandrel. The LCR tank circuit 4120 includes two sets of varactors, which function as voltage controlled capacitors. The first set of varactors 4124 is configured to adjust the sensitivity of the system 4000. The sensitivity is changed by making adjustments to the operating point of the sensor system 4000. The sensitivity adjustment is performed by altering the point of interplay between the first and second sets of varactors, thereby providing for very sensitive responses for very small changes in capacitance as well as smaller responses for large changes in capacitance. For example, biasing 4124 at a high capacitance, forces 4122 to a low capacitance due to the PLL locked condition. Any required change in the capacitance 4122 due to the operation of the PLL requires a relatively high voltage due to the position of the operating point. This results in enhanced sensitivity. Likewise, biasing 4124 at a low capacitance, forces 4122 to a high capacitance. Any required change in the capacitance 4122 due to the operation of the PLL requires a relatively low voltage due to the position of the operating point. This results in decreased sensitivity. The first set of varactors 4124 is configured to exploit the shape of the varactor characteristic curves to improve sensor performance for a wide range of applications. The operation and exploitation of varactor characteristic curves to improve the sensitivity of the sensor 4000 would be known and appreciated by one of ordinary skill in the art with the benefit of this disclosure. The second set of varactors 4122 is configured to provide a variable voltage input to adjust the VCO 4130 output frequency. In an alternative embodiment, the PLL sensor 4100 is configured to compare the phase of the VCO 4130 with the phase of the reference oscillator 4150 to generate a corresponding difference voltage. Such phase comparisons may be made using a voltage phase detector. In one embodiment, the VCO 4130 is configured to operate at a nominal frequency of 6 MHz. In another embodiment, the reference oscillator 4150 is a crystal oscillator. Further embodiments may include different configurations of the phase/frequency detector, the loop filter, the charge pump (combined with the loop filter) and the tank circuit, including additional active or passive devices, which would be appreciated by one of ordinary skill in the art with the benefit of this disclosure The filter and relay block 4115 is configured to filter out both radiated and received radio-frequency ("RE") energy, according to an embodiment of the invention. The filter can be tuned to calibrate the response of the sensor 4000. Filter and relay block 4115 further includes a relay configured to both remove any potential charge on the mandrel and provide a transient startup pulse to the PLL loop if needed.

The filter 4160 is configured as a multi-pole filter or integrator with a charge pump function, according to an embodiment of the invention. The filter 4160 is configured to receive the output of the PFD 4140 and generate a DC error signal proportional to the difference between the reference oscillator 4150 frequency and the VCO 4130 frequency. The steady-state DC error level is fed back to the VCO varactors to maintain a minimum phase and frequency difference with respect to the reference oscillator output frequency.

The level sense channel 4200 is configured to respond to small PLL error transients that are induced when a pipette tip enters or exits a liquid, according to an embodiment of the invention. The PLL error signal can be AC-coupled to the programmable gain, single-supply amplifier circuit 4210 and through filter 4220. The PLL error signal may be characterized as an AC-coupled phase-locked loop error voltage, which may be an example of a first error signal or second error signal. In an embodiment of the invention, the amplifier can be in a non-inverting configuration.

In other embodiments, the filter 4220 may be a multiple-stage Sallen-Key low-pass filter. The output of the level sense channel 4200 is directed to both a fully differential analog interface (e.g., mux 4550) connected to a remote microcontroller (e.g., processor 4600) ADC and to a local ADC 4560. The time constant of this signal chain allows the sensor system 4000 to respond to transient entry and exit liquid level sense events encountered by a conductive pipette tip attached to a conductive mandrel (i.e., reactive element 4110). On entry and exit events, the output signal of level sense channel 4200 is configured to produce a positive or negative signal (relative to mid-supply), respectively. In one embodiment, the level sense channel 4200 output signal is sent to the processor 4600 for further processing by way of the mux 4550 and/or the ADC 4560. The processor 4600 is configured to determine, for example, whether the reactive element 4110 (e.g. a pipette tip) enters or exits a liquid based on the electrical characteristics of the level sense channel 4200 output signal. To illustrate, the PLL error signal operates at a nominal value when the pipette tip (e.g., reactive element 4110) is not making contact to other objects or mediums. In other words, the PLL error signal can be a substantially constant voltage when the pipette tip is not touching anything. As described above, a positive signal excursion (e.g., positive voltage "spike") occurs when the pipette comes into contact with a liquid. The magnitude of the spike depends on the various electrical characteristics of the liquid. The level sense channel 4200 is configured to detect the positive or negative voltage spike and thus determine that the pipette has made contact with the liquid. There are a variety of ways that the level sense channel 4200 can detect a positive or negative voltage spike. In one embodiment, the level sense channel 4200 compares the magnitude of the voltage spike (i.e., contact with a liquid) to the magnitude of the nominal voltage (i.e., no contact) and measures the difference voltage. The nominal voltage can be referred to as a reference voltage. In another embodiment, the level sense channel 4200 may offset the positive reference voltage slightly higher than the nominal value to filter out any small positive voltage spikes that may occur due to noise on the channel. Similarly, the level sense channel 4200 may offset the negative reference voltage slightly lower than the nominal value to filter out any small negative voltage spikes due to noise on the channel. In some embodiments, the sensor system 400 can store the reference values (i.e., reference voltages, offset reference voltages, etc.) in memory block 4620. Other output signal configurations may be used and would be known and appreciated by one of ordinary skill in the art with the benefit of this disclosure.

In certain embodiments, the level sense channel 4200 can also detect a fill level of an extension element (e.g., a pipette tip). For example, certain extension elements can hold a certain volume of a liquid. The electrical characteristics of the extension element will change depending on how much liquid is present inside the extension element. To illustrate, an extension element with no liquid inside may have a certain reactance which may yield a certain PLL error voltage. An extension element filled with a liquid may have a different reactance and thus a different PLL error voltage. The level sense channel 4200 is configured to measure and quantify the difference between the two voltages (including the other detectable water levels and error voltages in between). It should be noted that this type of measurement is different from detecting an initial contact with a liquid. As described above, when the extension element comes into initial contact with a liquid, the level sense channel 4200 measures a voltage spike in the PLL error voltage relative to a nominal value. In contrast, the level sense channel 4200 is measuring the change in the nominal value as the amount of water in the extension element changes. For example, slowly adding a liquid to the extension element would cause the PLL error signal (i.e., the nominal value) to slowly increase or decrease depending on the electrical characteristics of the liquid. Quantifying and/or calibrating the level sense channel 4200 to accurately measure a fill level of an extension element based on the changing PLL error signal would be understood by those of ordinary skill in the art with the benefit of this disclosure. In other embodiments, DC sense channel 4500 may detect the fill level of an extension element (e.g., a pipette tip) as described in more detail below.

The first alignment channel 4300 is configured to optimize the sensor system 4000 response to instrument alignment targets, according to an embodiment of the invention. The amplifier circuit 4310 includes an AC-coupled, single supply, dual stage amplifier with programmable gains. More specifically, the dual stage amplifier includes a high-gain and low-gain section followed by a filter 4320. The first alignment channel 4300 is configured to receive an AC coupled phase-locked loop error voltage, which may be an example of a first error signal or second error signal. In one embodiment, the filter 4220 performs a simple low-pass function. The output of the first alignment channel 4300 is directed to both a fully differential analog interface (e.g., mux 4550) connected to a remote microcontroller (e.g., processor 4600) analog-to-digital converter ("ADC") and to a local ADC 4560. The time constant of the signal chain allows the sensor system 4000 to respond to higher-frequency transient alignment events as sensed by the motion of a conductive mandrel (e.g., reactive element 4110) in close proximity to a conductive target. In one non-limiting example, the output signal of the first alignment channel 4300 produces a negative going response when a mandrel (i.e., reactive element 4110) approaches a conductive target, and a positive going response when the mandrel moves away from the target. In one embodiment, the output signal of the first alignment channel 4300 is sent to the processor 4600 for further processing by way of the mux 4550 and/or the ADC 4560. The processor 4600 is configured, in one non-limiting example, to optimize the sensor system 4000 response to instrument alignment targets based on the electrical characteristics of the first alignment channel 4400 output signal. In some embodiments, the amplifier circuit 4310 may comprise one or more amplifier stage and may or may not include the filter 4320. In one embodiment, the amplifier gain is set by the programmable digital potentiometer 4640.

The second alignment channel 4400 is configured to optimize the sensor system 4000 response to instrument alignment targets, according to an embodiment of the invention. The amplifier circuit 4410 includes an AC-coupled, single supply, dual stage amplifier with programmable gains. More specifically, the dual stage amplifier includes a high-gain and low-gain section followed by a filter 4420. In one embodiment, the filter 4420 performs a simple low-pass function. The output of the second alignment channel 4400 is directed to both a fully differential analog interface (e.g., mux 4550) connected to a remote microcontroller (e.g., processor 4600) ADC and to a local ADC 4560. The second alignment channel 4400 also includes a programmable offset function. The time constant of this signal chain allows the sensor system 4000 to respond to lower-frequency transient alignment events as sensed by the motion of a conductive mandrel (e.g., reactive element 4110) in close proximity to a conductive target. In one non-limiting example, the channel 4400 produces a negative going response when a mandrel (i.e., reactive element 4110) approaches a conductive target, and a positive going response when the mandrel moves away from the target. In one embodiment, the output signal of the second alignment channel 4400 is sent to the processor 4600 for further processing by way of the mux 4550 and/or the ADC 4560. The processor 4600 is configured, in one non-limiting example, to optimize the sensor system 4000 response to instrument alignment targets based on the electrical characteristics of the second alignment channel 4400 output signal. In some embodiments, the amplifier circuit 4410 may comprise one or more amplifier stage and may or may not include the filter 4420. In one embodiment, the amplifier gain is set by the programmable digital potentiometer 4640. The gain of the second alignment channel 4400 may differ from the gain of the first alignment channel 4300. In another embodiment, the second alignment channel does not include the filter 4420. The gains of each alignment channel are typically adapted for different targeting applications.

The DC sense channel 4500 is configured to sense liquids, targets, tips and some environmental conditions, according to an embodiment of the invention. The channel 4500 is further configured to evaluate and track the performance of the sensor system 4000 as it interacts with a plurality of stimuli (e.g., liquid, solid, and gaseous environments, changes in permittivity, etc.). The DC sense channel 4500 includes an amplifier circuit 4510 that comprises a DC-coupled, single-supply, fully-differential amplifier configured to compare the PLL error signal to a programmable reference bias voltage and to amplify the difference, according to one embodiment of the invention. The resulting difference signal passes through a filter 4520. The DC sense channel 4500 is configured to receive a DC coupled phase-locked loop error voltage, which may be an example of a first error signal or second error signal. In one embodiment, the filter 4520 is a low-pass filter. The output of the DC sense channel 4500 is directed to both a fully differential analog interface (e.g., mux 4550) connected to a remote microcontroller (e.g., processor 4600) ADC and to a local ADC 4560. The time constant of the signal chain allows the sensor system 4000 to respond to both transient events and steady-state conditions as sensed by the motion or static condition of a conductive mandrel or probe (e.g., reactive element 4110). Furthermore, the DC sense channel 4500 produces a continuous DC output signal allowing it to sense effects which are semi-persistent such as tips installed on a mandrel, the fill level of an extension element such as a pipette tip, etc. For example, mandrel tips may alter the electrical properties of the reactive element 4110 thereby causing a shift in the DC channel output voltage. A DC reference bias voltage may be programmed to compensate for such semi-persistent changes in the PLL error signal. In one embodiment, the output signal of the DC sense channel 4500 is sent to the processor 4600 for further processing by way of the mux 4550 and/or the ADC 4560. The processor 4600 is configured, in one non-limiting example, to sense liquids, targets, tips, and environmental conditions based on the electrical characteristics of the DC sense channel 4500 output signal. To illustrate, an extension element on the mandrel with no liquid inside may have a certain reactance which may yield a certain PLL error voltage. DAC 4570 may apply a DC reference bias voltage to compensate for the reactance of the extension element. Upon filling, an extension element filled with a liquid may have a different reactance and thus a different PLL error voltage. The DC sense channel 4500 is configured to measure and quantify the difference between the two voltages (the reference bias voltage compensating for the PLL error voltage attributable to the extension element alone and the PLL error voltage attributable to the extension element including the filling liquid). In some embodiments, this may include comparing the output of DC sense channel 4500 to one or more stored reference values established by a calibration procedure. Quantifying and/or calibrating the DC sense channel 4500 to accurately measure a fill level of an extension element based on the PLL error signal would be understood by those of ordinary skill in the art with the benefit of this disclosure. Alternatively, other amplifier and filter configurations may be used and would be known to one of ordinary skill in the art with the benefit of this disclosure.

The DAC 4570 is configured to adjust sensor sensitivity, alignment channel offset, DC channel offset, and DC channel reference. In one embodiment, the DAC 4570 is a 4-channel device. The local ADC 4560 is an 8-channel device positioned on the sensor board (not shown) configured to sample the sensor signals from the various channels previously discussed (e.g., first alignment channel 4300). The ADC 4560 includes additional functionality to generate interrupts based on sensed events to an associated microcontroller or computer, such as processor 4600.

The mux 4550 can comprise two multiplexors configured to direct various sensor signals (e.g., from the first or second alignment channels) to one of two analog differential buffers. These analog channels are connected remotely (off of the PCB) to the ADC of the microcontroller (processor 4600).

The processor 4600 handles system communications and signal processing tasks associated with the sensor system 4000 (e.g., implementing pipetting functions). Furthermore, the processor 4600 provides the interface to the sensor system 4000 for communication and data management tasks, and the processor 4600 can be a remote or local microcontroller. The processor 4600 may be configured to receive analog outputs (e.g., from the level sense channel 4200) through the MUX 4550 or from the digital output from the ADC 4560. The processor 4600 is further configured to digitize analog signals and provide additional control functions to the various channels including the second alignment channel 4400 and DC sense channel 4500, as shown in FIG. 15(*e*). In an embodiment, the processor 4600 resides within a same module as the sensor board (not shown).

In one embodiment, the processor 4600 is configured to communicate with the memory block 4620, digital potentiometer 4640, and I/O port extender 4660. The memory block 4620 is configured as local memory for data storage. The digital potentiometer 4640 is configured to adjust measurement channel gains, as described above. The I/O port extender 4660 is configured to apply control to the multiplexers, relay block, and phase-frequency detector (connection not shown).

There are a number of advantages to embodiments of the invention including the use of a PLL circuit for detecting an impedance of a probe. As described above, the impedance of the reactive element 4110 (e.g. the probe), and by extension the impedance measured at the tank circuit 4120, determines the operating frequency of the VCO 4130. An impedance describes a measure of opposition to alternating current (AC) which comprises a measurement of the relative amplitude and phase of the voltage (V) and current (I). An impedance typically has a complex element which can be described as a resistance (R) plus a reactance (X). The reactance may be, for example, a capacitive or inductive reactance. Typically, in order to measure the impedance of the probe, an AC signal source, a source voltage measurement, and a current measurement is needed. The current measurement can be transformed into a secondary voltage measurement (through I-V conversion) where the resulting measurements may be expressed in vector coordinates (magnitude and phase). As such, the PLL sensor 4100 provides a convenient structure well suited to perform impedance measurements because it can be configured to automatically align the phase and perform a single voltage measurement to indicate, with high accuracy, any changes to the complex impedance (R+iX) as required by the sensor system 4000.

Embodiments of the invention can incorporate several features that can result in successful utilization of the distributed reactive element in sensing discontinuities in permittivity, conductivity or sources of electromagnetic induction.

1. The sensing circuits can use both AC and DC modes of operation which enable detection of both transient and steady-state signals. The AC mode is useful when looking only for change or transient events in the presence of noise such as when entering or exiting a liquid. The DC mode is useful when continuous tracking of conditions is needed. This can occur for example, when the mandrel is tracked to determine if it touches or attaches (to varying degrees) to any conductive element. These modes can be applicable over different sensor sensitivities. For example, the DC mode is useful in quantizing environmental effects at high sensitivity while at low sensitivity, the DC mode is useful for tip detection.
2. The sensing circuits can incorporate methods for adjusting sensitivity without adjusting gain. This allows accommodation of a very wide range of sensing applications with the same hardware while providing enhanced noise performance. It also allows the hardware to perform outside its normal expected range of application thus extending its usefulness. This is done through voltage dependent capacitance. The voltage dependence of the spacing between charges on the two sides of a pn junction can be used to facilitate sensitivity adjustments.
3. The realization of one terminal of the reactive element incorporates shielding in such a way as to enhance noise performance. This imposes specific lengths on the antenna connection between the sensor and the mandrel.
4. The inclusion of an electrical switch device in this embodiment allows several additional functions, including discharge of the pipette mandrel and a mechanism for reliable startup of the phased locked loop.

Q. Thermal Cycler Modules

As noted above, PCR or "Polymerase Chain Reaction" refers to a method used to amplify DNA through repeated cycles of enzymatic replication followed by denaturation of the DNA duplex and formation of new DNA duplexes. Denaturation and renaturation of the DNA duplex may be performed by altering the temperature of the DNA amplification reaction mixture. Real time PCR refers to a PCR process in which a signal that is related to the amount of amplified DNA in the reaction is monitored during the amplification process. This signal is often fluorescence; however, other detection methods are possible. In an exemplary embodiment, a PCR subsystem takes a prepared and sealed reaction vessel and performs a complete real-time polymerase chain reaction analysis, thermal cycling the sample multiple times and reporting the intensity of emitted fluorescent light at each cycle.

The PCR subsystem can comprise several subsystems including an optical excitation subsystem, an optical detection subsystem, a PCR reaction vessel including plug, one or more thermal cycler modules 1300 and a thermal cycler garage 1200. The PCR subsystem can be supported by a transport device such as an XYZ transport device.

In embodiments of the invention, a thermal cycle can refer to one complete amplification cycle, in which a sample moves through a time versus temperature profile, also known as a temperature profile, that includes: heating the sample to a DNA duplex denaturing temperature, cooling the sample to a DNA annealing temperature, and exciting the sample with an excitation source while monitoring the emitted fluorescence. A typical DNA denaturing temperature can be about 90° C. to 95° C. A typical DNA annealing temperature can be about 60° C. to 70° C. A typical DNA polymerization temperature can be about 68° C. The time required to transition between these temperatures is referred to as a temperature ramping time. Ideally, each thermal cycle will amplify a target sequence of nucleic acid by a factor of two. In practice, however, amplification efficiency is often less than 100%

The system may comprise one or more analytical units. In some embodiments, the analytical units may comprise thermal cycler modules. For example one or more thermal cycler modules can be housed in a hardware structure called a thermal cycler garage, which provides power, communication, and chassis mounts for each. The thermal cycler garage may house about 20 thermal cycler modules, although the number can vary depending on the throughput requirements of the system.

A reaction vessel can refer to a plastic consumable containing RNA or DNA from a patient sample, target sequence specific primers and probes, a "master mix" that includes nucleotide monomers and enzymes necessary for synthesis of new DNA strands, and process control materials. Small fluid volumes facilitate rapid heat transfer, so the total liquid volume contained in the reaction vessel is minimal A typical volume can be 40 µL to 50 µL.

In general, the thermal cycler module can: (1) accept a prepared and sealed reaction vessel with sample and reagents, (2) press the vessel into a temperature controlled thermal block, (3) rapidly cycle the block and associated sample through a defined temperature profile, (4) expose the sample to one or more excitation light sources at the appropriate portion of the temperature cycle, and (5) accommodate the optical collection path of emitted fluorescence to be sent to the detector.

As shown in further detail below, a thermal cycler module for performing real time PCR within a PCR reaction vessel can comprise a thermal block with a receptacle for receiving a PCR reaction vessel. A slidable lid can overlap with the thermal block and can have an open position and a closed position, the slidable lid moving longitudinally between the open and closed positions. It may also include an excitation optics assembly, the excitation optics assembly located beneath the thermal block. It may further include an emission optics assembly, which can be located adjacent to the thermal block. The locations of these assemblies can be reversed in some embodiments.

FIG. 16(*a*) shows a side, perspective view of a thermal cycler module 1300. The thermal cycler module 1300 comprises an enclosure 1312 in the form of a rectangular box-like structure. The rectangular, box-like structure can allow a large number of thermal cycler modules to be placed in a relatively small area. Although the thermal cycler module 1300 is in the form of a box-like structure, it can be in any other suitable shape or configuration.

An excitation optics assembly 1304 is used to provide excitation radiation to a sample in the thermal cycler module 1300. The emissions optics assembly 1302 is used to receive and transmit emissions radiation from the sample in the thermal cycler module 1300. Both the excitation optics assembly 1312 and the emissions optics assembly 1302 are mechanically and operationally coupled to the enclosure 1312.

FIG. 16(*b*) shows a side, cross-sectional view of a thermal cycler module. The enclosure 1312 of the thermal cycler module 1300 may include an enclosure recess 1312(*a*), which may be cooperatively configured to receive a slidable lid 1315. The slidable lid 1315 may comprise a body 1315(*a*), which may define a cavity 1341. A biasing element 1344 such as a spring may be attached to an upper portion of the body 1315(*a*). A compression head 1342 may be coupled to the biasing element 1344, and may be perpendicularly oriented with respect to the orientation of the biasing element 1344. As will be explained in further detail below, the compression head 1342 can push down on a reaction vessel 221 so that it is in good thermal contact with a thermal block assembly 1311 comprising a thermal block. An electronics and blower assembly 1313 in the thermal cycler module 1300 can heat and cool the thermal block in the thermal block assembly 1311, thereby heating and cooling the sample in the reaction vessel 221. When a sample in the reaction vessel 221 is undergoing thermal cycling, light from the excitation optics assembly 1304 can provide light to a sample in the reaction vessel 221. Light emitted from the sample in the reaction vessel 221 can exit the thermal cycler module 1300 through the emissions optics assembly 1302.

FIG. 16(*c*) shows a garage 1200 with a plurality of thermal cycler modules 1300. The garage 1200 may comprise a number of linear garage rail structures 1200(*a*), and adjacent pairs of these garage rail structures 1200(*a*) may define a garage port 1200(*b*). The rail structures 1200(*a*) may be in the form of inverted "T" shaped beams, which may engage side recesses in the thermal cycler module 1300. The garage 1200 may hold one, two, three, four, or five or more thermal cycler modules 1300. The number of thermal cycler modules 1300 on the system can be optimized to address throughput needs. In one embodiment, the thermal cycler garage 1200 contains 20 thermal cycler modules 1300. They may be aligned with each other, and may form a compact array. In another embodiment, the thermal cycler garage may hold thermal cycler modules 1300 in a radial or circular arrangement. The thermal cycler modules 1300 may rest on a base 1202, which may have a number of slots 1204 formed in it. The slots allow optical cables of excitation optics assemblies 1304 to pass through.

As noted, the thermal cycler garage 1200 provides power, communications, and chassis mounts that secure the thermal cycler modules 1300 (e.g., PCR cells) within the system. The number of thermal cycler modules 1300 housed in the thermal cycler garage 1200 can be a function of the throughput requirements for the system. In one embodiment, the thermal cycler garage 1200 houses about 20 thermal cycler modules. The thermal cycler garage 1200 may also incorporate indicators (not shown in FIG. 16(*c*)), such as LEDs, that indicate the status of individual thermal cycler modules 1300. These indicators may provide the user with visual cues, for example color, that signify the current temperature or portion of the temperature profile within the thermal cycler modules 1200. Power and communications are provided by one or more printed circuit boards.

Figure 16A:
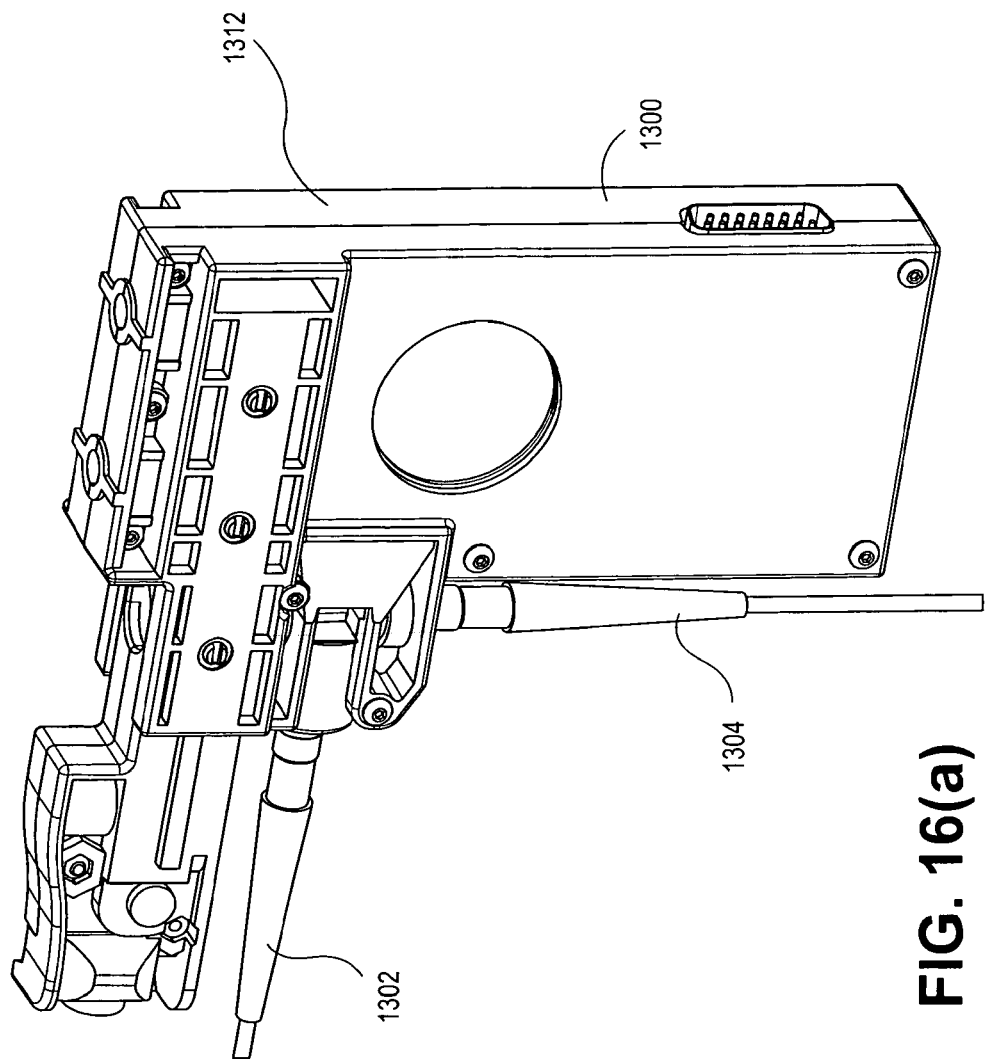
FIG. 16(a) shows a side, perspective view of a thermal cycler module.
Figure 16B:
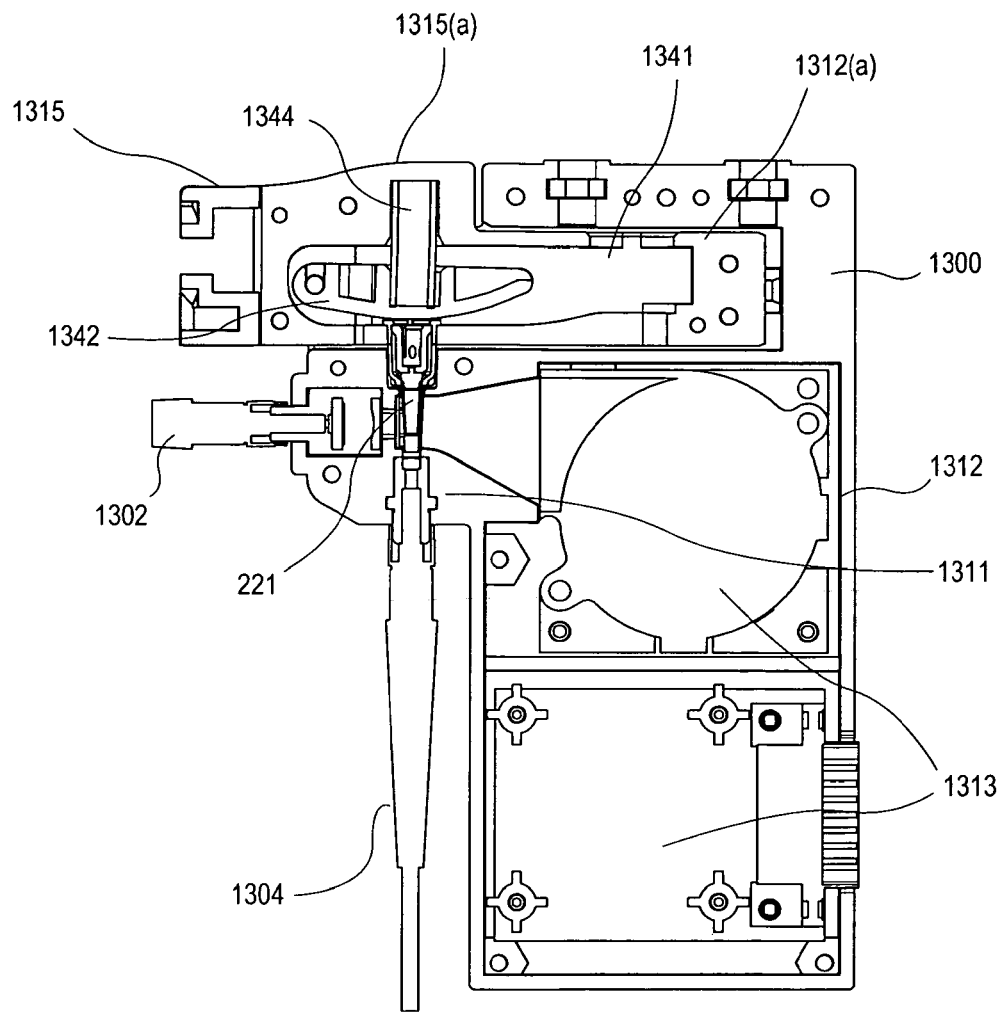
FIG. 16(b) shows a side, cross-sectional view of a thermal cycler module.

Referring to FIG. 16(b), the thermal cycler module 1300 may also include slidable lid 1315 that is normally closed during thermal cycling, but opens to provide access to a thermal block of a thermal block assembly 1311. In one embodiment, the slidable lid 1315 can be a slide-lock lid that slides at the top of the thermal cycler module 1300, moving parallel to the plane of the system. The motion of a slidable lid 1315 can be utilized to perform accessory operations other than closing the thermal cycler module 1300. Such operation include seating of the reaction vessel 221 within the receptacle of the thermal block assembly 1311, releasing the thermal cycler module 1300 from the receptacle of thermal block assembly 1311, manipulating an optical shutter mechanism that reduces the amount of ambient light entering the detection optics when the sliding lid is open, and providing a fluorescent target that can be utilized for alignment of the system's optical subsystem.

Figure 16C:
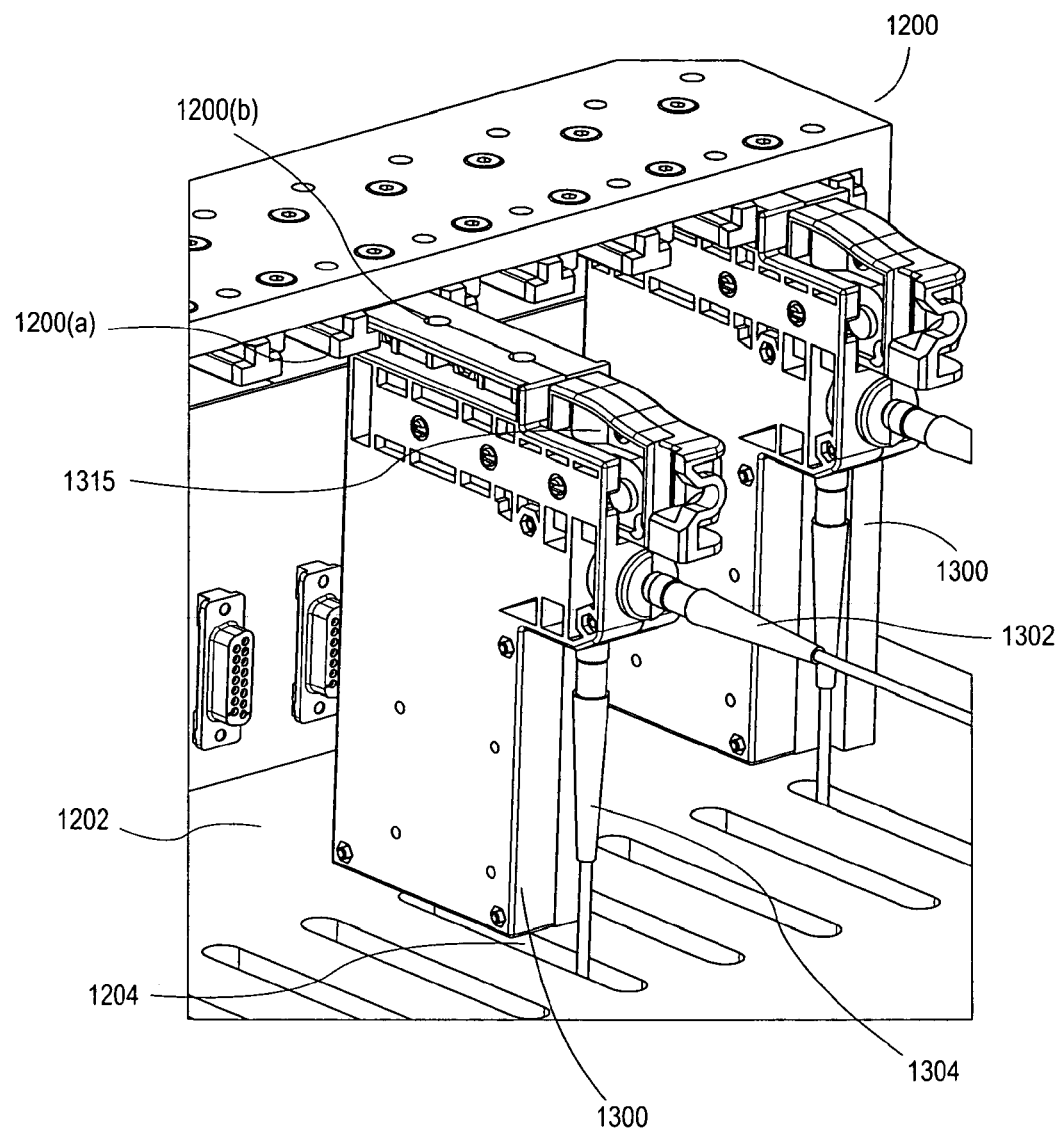
FIG. 16(c) shows a garage with a plurality of thermal cycling cells.
Figure 16D:
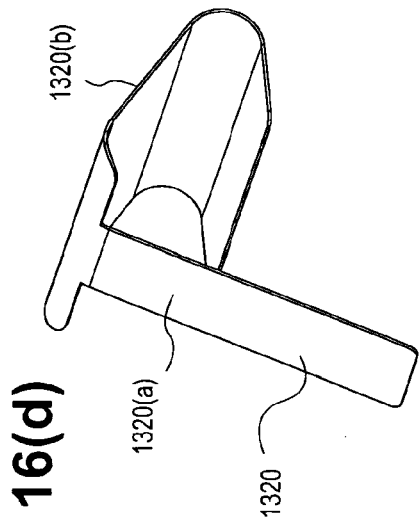
FIG. 16(d) shows a thermal cycling shutter.

FIG. 16(d) shows an optical shutter, which may alternatively be referred to as a shutter element 1320 that may be incorporated into a slidable lid 1315. It includes a narrow first portion 1320(a), and a wider second portion 1320(b) that is integrally formed with the first portion 1320(a). The narrower first portion 1320(a) is at a middle part of one end of the wider second portion 1320(b). The thermal cycler shutter element 1320 may be made of any suitable material (e.g., metal, plastic, etc.) that may flex and may have resiliency.

Figure 16G:
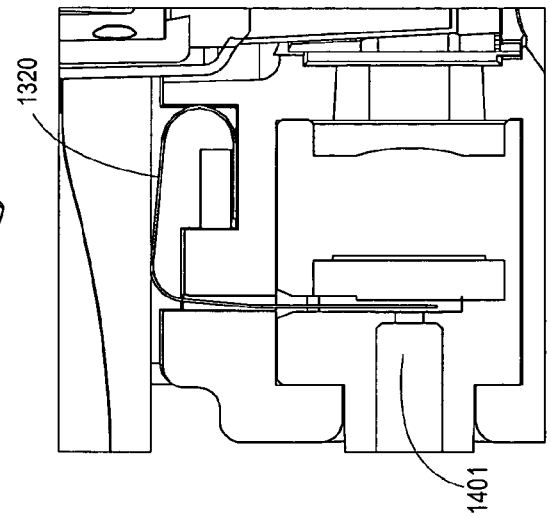
FIG. 16(g) shows an internal side view of a portion of a thermal cycler module with the shutter in a closed position, while the corresponding slidable lid is in an open position.
Figure 16F:
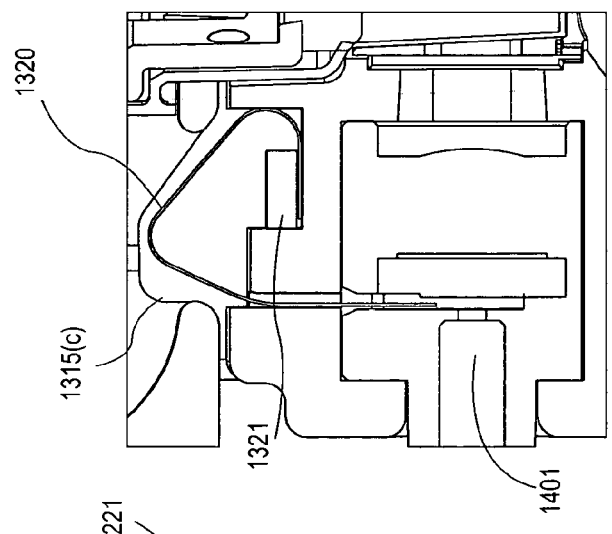
FIG. 16(f) shows an internal side view of a portion of a thermal cycler module with the shutter in an open position while a corresponding slidable lid is in a closed position.
Figure 16E:
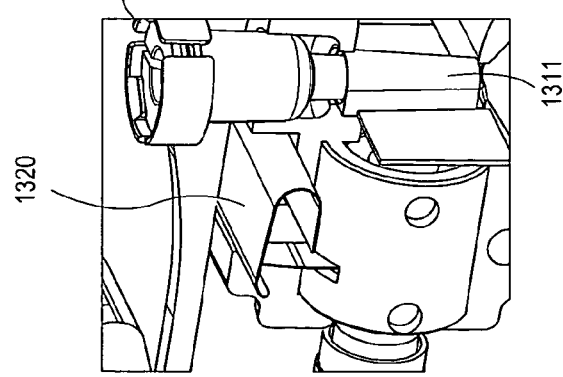
FIG. 16(e) shows a perspective view of a portion of a thermal cycler module with the shutter in a closed position

FIG. 16(e) shows a perspective view of a portion of a thermal cycler module with the shutter element 1320 in a closed position. The first portion 1320(a) of the shutter element 1320 can be positioned between a pair of optical elements, and can be near a thermal block assembly 1311.

FIG. 16(f) shows an internal side view of a portion of a thermal cycler module with the shutter element 1320 in a closed position while a corresponding slidable lid 1315 is in an open position. The slidable lid is an example of a movable lid. Other types of movable lids, can move, but need not slide. As shown, the slidable lid 1315 may have an internal recess 1315(c), which may receive the second portion 1320(b) of the shutter element 1320. A securing element 1321 in the thermal cycler module 1300 may secure an end of the second portion 1320(b). As a result, the narrower first portion 1320(a) lifts up, light can pass from the sample in the reaction vessel 221 to the light emission light pipe 1401.

FIG. 16(g) shows an internal side view of a portion of a thermal cycler module with the shutter element 1320 in a closed position, while the corresponding slidable lid is in an open position. As shown, a bottom surface of the slidable lid 1315 pushes down on the second portion 1320(b) of the shutter element 1320 so that the first portion 1320(a) is pushed downward. The first portion 1320(a) thereafter blocks any light from entering the emission light pipe 1401. This configuration advantageously prevents stray light from entering the downstream optical detection system (not shown) when the thermal cycler module is open and not in use In other embodiments, the shutter element 1320 prevents stray light from entering the downstream optical detection system when the thermal block assembly is exposed, rather than when the thermal cycler module 1300 is not in use. For instance, an open thermal cycler module 1300 may be in use to temporarily hold a reaction vessel 221 in order to accommodate scheduling of the XYZ pipettor elsewhere on the system.

FIG. 16(h)-1 shows a partial internal perspective view of internal components of a slidable lid 1315. FIG. 16(h)-2 shows a side, perspective view of the slidable lid 1315. The slidable lid 1315 may include a body 1315(a), which may define an elongated aperture 1341 (one half of which is shown in FIG. 16(h)-1). The elongated aperture 1341 may house a biasing element 1344, which is coupled to a compression head 1342. An aperture 1340 for receiving a reaction vessel (not shown) is at a top portion of the slidable lid 1315. The aperture 1340 allows the reaction vessel to pass though the slidable lid 1315.

Figures 1, 16I:
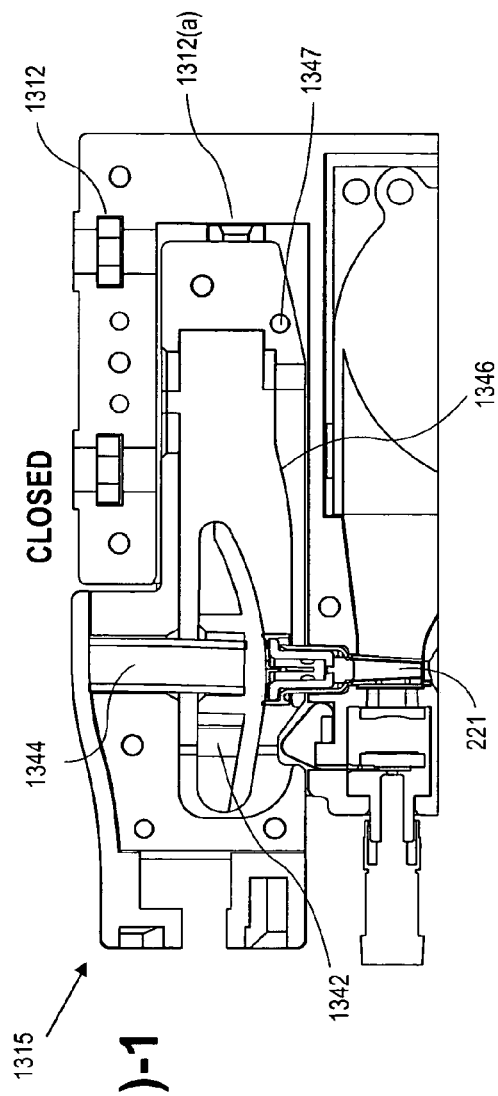
Figures 2, 16I:
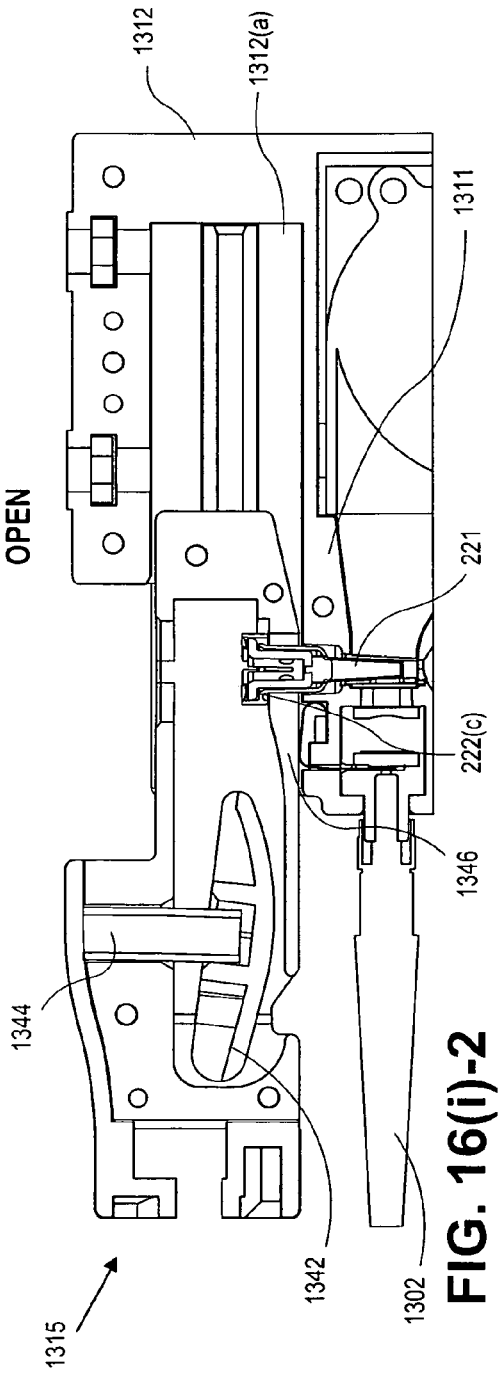

FIG. 16(i)-1 shows a side, cross-sectional view of a slidable lid 1315 in a thermal cycler module, where the slidable lid 1315 is in a closed position. As shown, a forward portion of the slidable lid 1315 fits into the enclosure recess 1312(a) of the thermal cycler module enclosure 1312. The compression head 1342, impelled by a biasing element 1344, pushes down on the reaction vessel 221 thereby forcing it into a heat block and providing good thermal contact with the heat block. In one embodiment, the compression head 1342 is brought into contact with the reaction vessel 221 when the slidable lid 1315 is closed.

FIG. 16(i)-2 shows a side, cross-sectional view of a slidable lid 1315 in a thermal cycler module, wherein the slidable lid 1315 is in an open position. To move the slidable lid 1315 to an option position, it is withdrawn from the enclosure recess 1312(a). As it is withdrawn, the compression head 1342 is no longer in contact with the reaction vessel 221, and downward pressure is no longer applied. Further, as the slidable lid 1315 is withdrawn, an upwardly tapered ridge pushes up on a wider vessel plug third portion 222(c) so that it is pushed upward thereby disengaging the reaction vessel 221 from the thermal block of the thermal block assembly 1311. Because the reaction vessel 221 may pushed down in intimate contact with the thermal block for an extended time, it can be difficult to remove from the thermal block after thermal cycling. The design shown in FIG. 16(i)-2 advantageously and efficiently provides for automatic separation of the reaction vessel 221 from the thermal block.

Figure 16K:
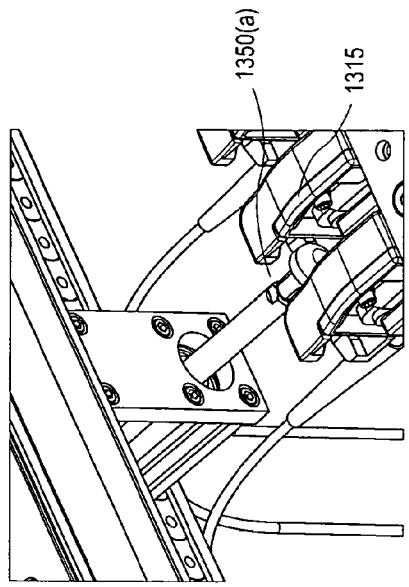
FIGS. 16(j)-16(m) show a gripping feature that is configured to manipulate a slidable lid.
Figure 16M:
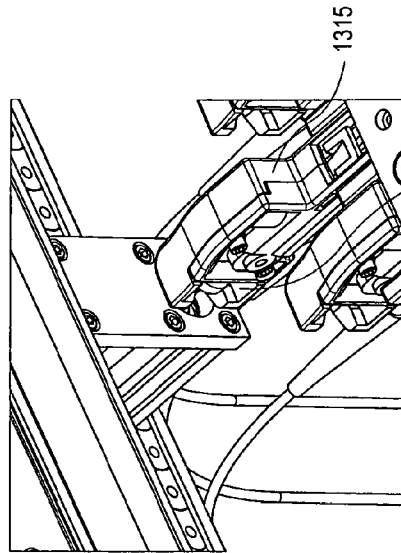
Figure 16J:
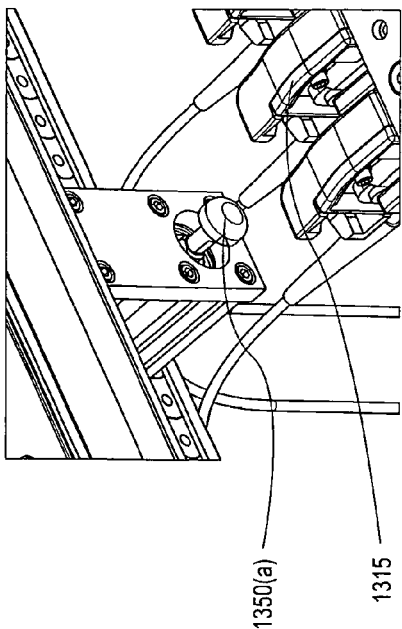
Figure 16L:
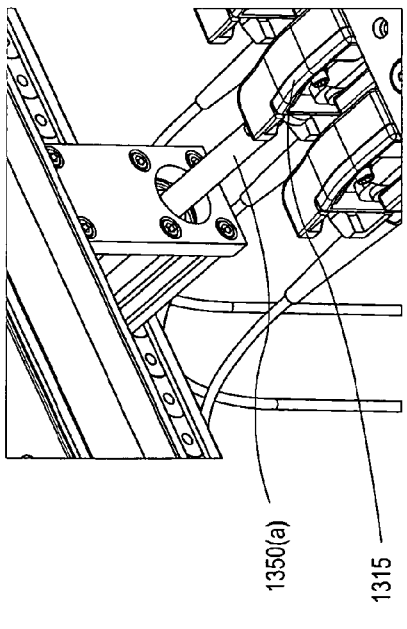

The system may utilize an actuator with a gripping feature to open and close the slidable lid 1315. FIGS. 16(j)-16(k) show a gripping feature that is configured to manipulate a slidable lid. The gripping feature 1350(a) may be part of an XYZ gantry in some embodiments of the invention, as described above. As shown in these Figures, a gripping feature 1350(a) can be in a retracted position in FIG. 16(j). In FIG. 16(k), the gripping feature 1350(a) is in an extended position and is manipulated so that it is in between two thermal cycler modules. It then moves laterally to engage an end portion of the slidable lid 1315. As shown in FIG. 16(l) and 16(m), after it engages the end portion of the slidable lid 1315, it can retract and can also pull the slidable lid 1315, thereby separating the slidable lid 1315 from the previously described enclosure in the thermal cycler assembly.

Figure 16N:
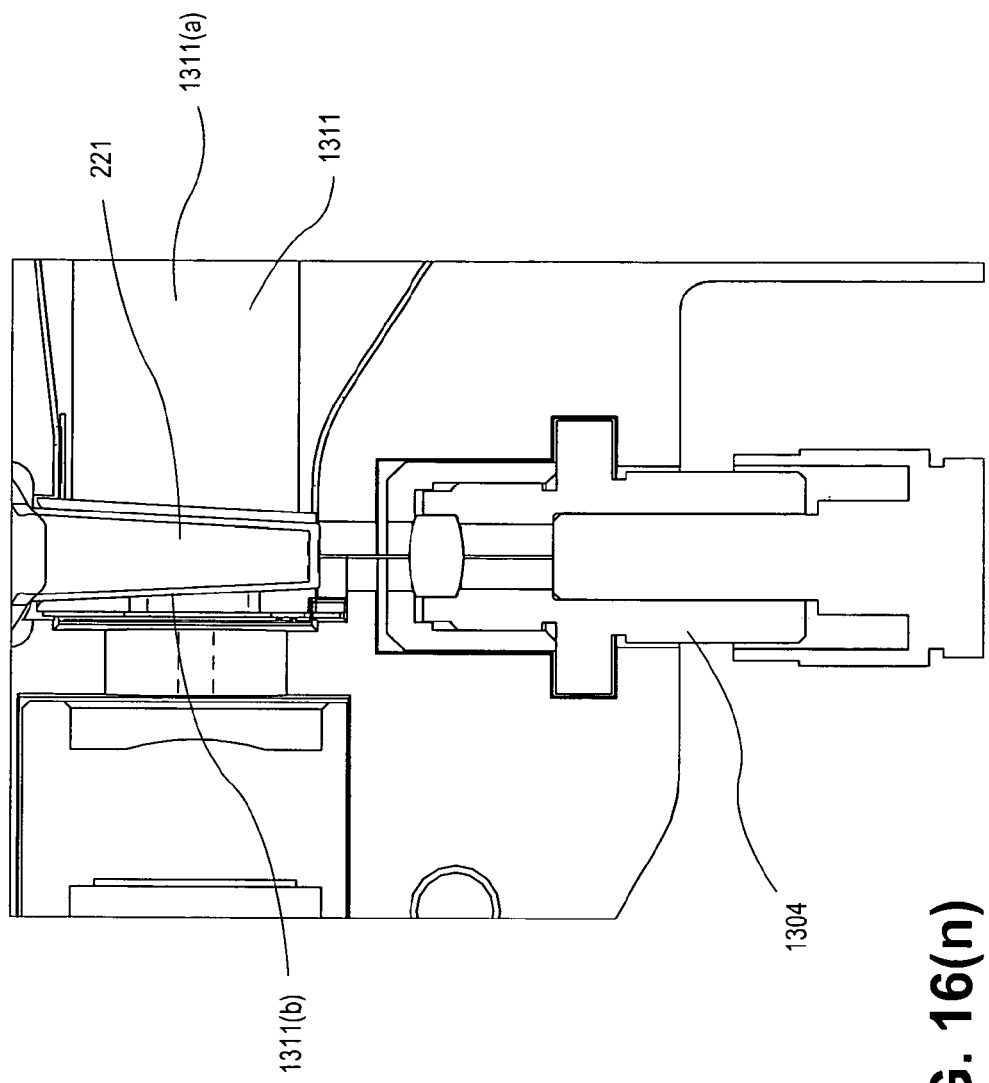
FIG. 16(n) shows a side, cross-sectional view of an excitation optics assembly, in position beneath a thermal block.
Figure 16Q:
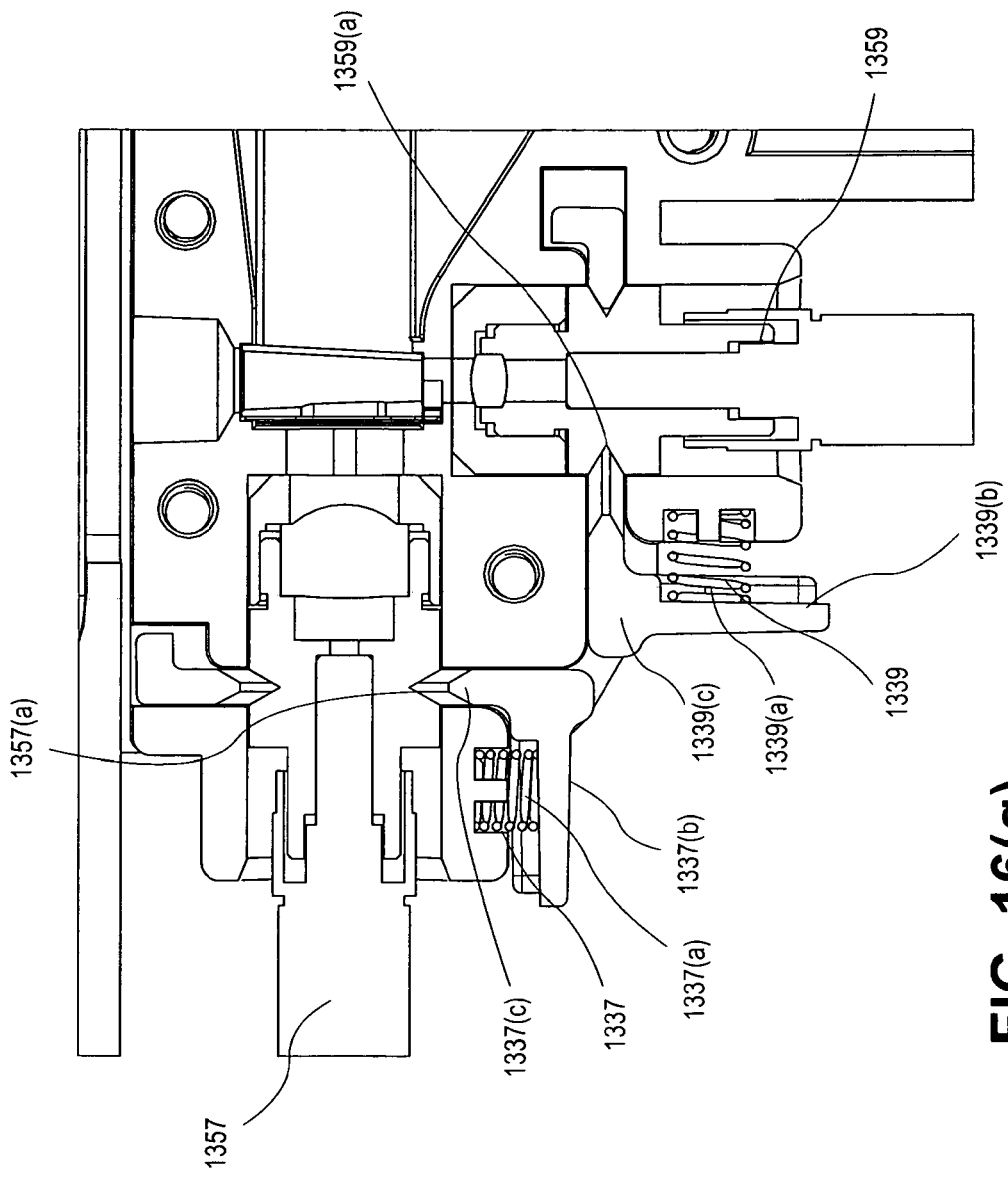
FIG. 16(q) shows a side, cross-sectional view of emission and excitation optics spring latches, as they can hold emission and excitation optics assemblies.

FIG. 16(n) shows a side, cross-sectional view of an excitation optics assembly, in position beneath a thermal block 1311(a) in a thermal block assembly 1311. The thermal block 1311(a) may also define a thermal block receptacle, which may contain and be cooperatively structured with the reaction vessel 221. An excitation optics assembly may be located beneath the reaction vessel 221.

More detailed descriptions of operation follow with reference to FIGS. 16(a)-16(n). One accessory operation of the slidable lid 1315 can be seating a reaction vessel 221 within a receptacle in a thermal block assembly 1311 of a thermal cycler module 1300. Thermal transfer is facilitated by close contact between the thermal block assembly 1311 and the surface of the reaction vessel 221. The conical shape of the receptacle of the thermal block assembly 1311 can provide the desired contact when a downwards vertical force is applied to an inserted reaction vessel 221.

This downward force can be provided by a slidable lid 1315 that comprises a biasing element 1344. The biasing element 1344 can overlap with the thermal block assembly 1311. It may comprise a segment of resilient tubing, a spring, a pneumatic cylinder, or other suitable device. In one embodiment, the biasing element 1344 can be interposed between a curved force director in the form of a compression head 1342, and the inner surface of the top of the slidable lid 1315. As shown in FIG. 16(*i*), the compression head 1342 and the biasing element 1344 can be positioned within the slidable lid 1315 so that the apex of the force director is oriented towards the thermal block and is positioned over the receptacle 221 of the thermal block when the slidable lid 1315 is in the closed position. In this configuration, the compression head 1342 is impelled upwards as the slidable lid 1315 closes if a reaction vessel 221 is engaged in the receptacle of the thermal block assembly 1311. Resistance from the biasing element 1344 asserts a downwards force against the top of the vessel plug 222 that impels the reaction vessel 221 into the receptacle of the thermal block assembly 1311, firmly seating both the vessel plug 222 in the reaction vessel base 248 and the reaction vessel 221 in the thermal block 1331, and holding the reaction vessel 221 in place during thermal cycling. The amount of force directed against the reaction vessel 221 can be five or more pounds, preferably around 12 pounds.

The downwards force may be applied by other mechanisms. The slidable lid 1315 may include an inclined plane that increases in thickness longitudinally, oriented such that the inclined plane contacts and applies force to the reaction vessel 221 as the slidable lid is closed. The slidable lid 1315 can house a segment of linear spring, positioned to contact and apply a downwards force against the reaction vessel 221. In another embodiment, the slidable lid 1315 can incorporate a linear actuator, positioned to align with the reaction vessel 221 when the slidable lid 1315 is closed.

Firm seating of a reaction vessel 221 within the receptacle of the thermal block assembly 1311 is desirable for optimal heat transfer. However, this practice can lead to difficulty in removal of a reaction vessel 221 after thermal cycling. The motion of the slidable lid 1315 can be utilized to ensure that an inserted reaction vessel 221 can be released from the thermal block assembly 1311 for transfer elsewhere on the system. The reaction vessel 221 may, for example, be retrieved using the pipettor assembly of the XYZ transport device.

As shown in FIG. 16(*i*)-1, in one embodiment, a slidable lid 1315 includes a lid base plate that lies immediately above the thermal block assembly 1311. The lid base plate 1347 can comprises an elongated aperture 1341, the elongated aperture 1341 comprising a proximal terminus, a distal terminus, and parallel edges extending between the proximal terminus and the distal terminus. The distal terminus of the elongated aperture 1341 can be aligned with the receptacle of the thermal block assembly 1311 when the slidable lid 1315 is in the closed position. The thickness of the lateral edges of the elongated aperture 1341 can increase progressively from the distal terminus to the proximal terminus of the elongated aperture 1341 to form a tapered ridge 1346 that can engage a top portion of a reaction vessel 221 that is seated in the receptacle of the thermal block assembly 1311. The lid base plate 1347 can be oriented such that this tapered ridge engages and provides an upwards impetus to the inserted reaction vessel 221 as the slidable lid 1315 moves from the closed to the open position. This impetus is sufficient to loosen the reaction vessel 221 within the receptacle of the thermal block assembly 1311 following thermal cycling, allowing the pipettor assembly of the XYZ transport device to engage and remove the reaction vessel 221 from the thermal cycler cell 1300. A hole 1351 can be provided in the slidable lid 1315, so that an XYZ transport device can retrieve the reaction vessel 221.

As shown in FIGS. 16(*f*) and 16(*g*), the slidable lid 1315, when closed, can serve to block exterior light that might interfere with detection from entering the thermal cycler module 1300. When multiple thermal cycler modules 1300 are used there is the further possibility of exterior light entering through the detection optics of an open thermal cycler module 1300 interfering with measurements being made in adjacent, closed thermal cycler modules 1300. In one embodiment, the thermal cycler module 1300 may further comprise a shutter element 1320, which may be a spring shutter. The shutter element 1320 being positioned in proximity to the detection optics assembly of the thermal cycler module 1300. The shutter element 1320 is responsive to movement of the slidable lid 1315 and may be resilient. Movement of the slidable lid 1315 to the open position can displace the shutter element 1320 so that it extends into the detection optics assembly, blocking at least a portion of the ambient light from entering the detector. Movement of the slidable lid 1315 to the closed position can subsequently allow the shutter element 1320 to retract from the detection optics assembly, permitting measurement of fluorescence from the reaction vessel 221 during thermal cycling.

The slidable lid 1315 can have additional accessory functions that are independent of its movement. The slidable lid 1315 may include a fluorescent target that can be utilized to calibrate the optical subassembly of the system, as portions of it may be within range of the emission and detection optics when there is no reaction vessel 221 engaged in the receptacle of the thermal block assembly 1311. The fluorescent target can be a curved force director such as a compression head 1342 comprised of a suitable fluorescent material. Alternatively, the entire slidable lid 1315 may comprise a fluorescent material in order to simplify the manufacturing process. Suitable fluorescent materials include fluorescent polymers and structural materials with fluorescent coatings. Also, the slidable lid 1315 may also comprise a heater in some embodiments. Such a heater can be used to prevent condensation from forming within a reaction vessel 221 that is engaged in the receptacle of the thermal block assembly 1311.

FIG. 16(*o*) shows a side perspective view of a thermal block assembly. FIG. 16(*p*) shows a top, perspective view of a thermal block assembly 1311. As shown therein, the thermal block assembly 1311 can include a thermal block 1311(*a*), a thin film heater 1319 attached to the thermal block 1311(*a*), and a lateral aperture 1362. The thermal block 1311(*a*) may define a receptacle 1311(*b*) for a reaction vessel (not shown). The lateral aperture 1362 may allow light to pass from a sample to detection optics downstream of the reaction vessel in the thermal block 1311(*a*). Temperature sensing elements 1364 may be associated with the thermal block 1311(*a*). These can be used to measure the temperature of the thermal block or of a reaction vessel held therein. The temperature of the reaction vessel or its contents may be determined directly or derived from the temperature of the thermal block. Temperature sensing elements include thermistors and thermal imaging devices.

In embodiments of the invention, the thermal block 1311(*a*) may comprise any suitable characteristics that support rapid thermal cycling of a reaction vessel. For example, it may comprise a substantially planar thermal mass for transferring thermal energy, and a receptacle for forming a thermal contact surface with a vessel. The receptacle can comprise a frustum of a conical shape and having an upper opening and a lower opening, the receptacle being affixed to the front surface of the thermal mass. The thermal block may be composed of a highly thermally conductive material such as copper, copper alloy, aluminum, aluminum alloy, magnesium, gold, silver, or beryllium. The thermal block may have a thermal conductivity of about 100 W/mK or greater and a specific heat of about 0.30 kJ/kgK or less. In some embodiments, the thermal block has a thickness between about 0.015 inches and about 0.04 inches. It may also have a plurality of heat transfer fins. The thermal block can also comprise a heating element that provides the heat that is transferred to the reaction vessel. The heating element can be a thin film heater affixed to the back surface of the planar thermal mass, although other heat sources such as resistance heaters, thermoelectric devices, infrared emitters, streams of heated fluid, or heated fluid contained within channels that are in thermal contact with the thermal block may also be used. The thermal block may also include one or more temperature sensors that are used in conjunction with a controller to control the temperature of the thermal block by, for instance, a PID loop. These temperature sensors may be imbedded in the thermal block. The thermal block may comprise an optical aperture, where the optical aperture is positioned to permit optical communication through the planar thermal mass to the interior of the receptacle. This aperture can serve as an optical window for the detection optics.

The receptacle of the thermal block 1311(*a*) may also have any suitable characteristics necessary to secure the reaction vessel and ensure good thermal contact with it. For example, in some embodiments, the walls of the conical receptacle 1311(*b*) have an angle of about 1 degree to about 10 degrees, an angle of about 4 degrees to about 8 degrees, or an angle of about 6 degrees. The decreasing internal radius of the receptacle ensures that as the reaction vessel that is pressed into the receptacle of the thermal block the exterior of the reaction vessel is brought into intimate contact with the interior of the receptacle. The receptacle of the thermal block 1311(*a*) may also have an upper opening and a lower opening. The upper opening allows for insertion of the reaction vessel. The lower opening allows for reaction vessels to fit tightly within the receptacle 1311(*b*) despite variation in the length of the vessel that can be a consequence of the manufacturing process. The lower opening may also act as an optical window for the excitation optics. The thermal cycler module 1300 can include containment features, such as O-ring seals or containment vessels that encompass all or part of the thermal block, to reduce the risk of contamination from reaction vessels held in the receptacle 1311(*b*).

The thermal cycler module 1300 may also include any suitable optical components. Excitation optics may include an optical fiber in optical communication with a light source and a lens that directs light emitted from a terminus of the excitation optical fiber into a reaction vessel engaged in the receptacle of the thermal block. Alternatively, excitation light may be provided by a light source that is incorporated into the thermal cycler module and is in optical communication with a reaction vessel engaged in the receptacle of thermal block without an intervening optical fiber. Suitable light sources include but are not restricted to lasers, LEDs, and other high output light sources. LEDs used for excitation may emit an essentially single wavelength or emit multiple wavelengths in order to simulate white light. Multiple single color LEDs may be used to provide excitation light at different frequencies. Detection optics may include an optical fiber that is in optical communication with a detector located elsewhere on the system and a lens that directs light emitted from a reaction vessel engaged in the receptacle of the thermal block into a terminus of the detection optical fiber. Detection optical fibers from multiple thermal cycler modules may be directed to a single detector. Alternatively, detection optical fibers may be associated with individual detectors associated with specific thermal cycler modules. In another embodiment, the detector may be mounted within the housing of the thermal cycler module and placed in optical communication with a reaction vessel engaged in the receptacle of the thermal block without an intervening optical fiber. Suitable detectors include, but are not limited to 1D CCDs, 2D CCDs, photomultiplier tubes, photodiodes, avalanche photodiodes, and silicon photomultipliers. Detectors may also include interference filters, diffraction gratings, or similar devices for separation of emitted light into discrete wavelengths. Detection optics may also include a shutter mechanism that blocks light from entering the detector when the interior of the thermal cycler module is exposed.

Embodiments of the invention may also include optical casings for excitation and emission optics assemblies. These optical casings serve to protect lenses, optical filters, and waveguides associated with the excitation and emission optics. The optical casing may also include features that facilitate mounting and alignment of the excitation and emission optics in the thermal cycler. An optical casing can have a circumferential groove in the outer surface. Such a circumferential groove permits an optical casing to be held in place with a latching mechanism incorporated into the thermal cycler. In one embodiment, the latching mechanism is a spring-loaded latch. In such an embodiment, the user can press the spring loaded latch of the thermal cycler to remove or install an optical casing. The optical casing may be rotationally symmetrical, so that they are not orientation specific. In one embodiment, the excitation optical casing is a cylindrical body that incorporates lenses, optical filters, and waveguides associated with the excitation optics, having a circumferential groove that interfaces with a latching mechanism of the thermal cycler, and the emission optical casing is a cylindrical body that incorporates lenses, optical filters, and waveguides associated with the emission optics, having a circumferential groove that interfaces with a latching mechanism of the thermal cycler. Use of such optical casings simplifies replacement of optical components and permit cleaning of the lenses without disassembly of the thermal cycle.

FIG. 16(*q*) shows a thermal cycler spring latch that holds an emission optics assembly 1357 in the thermal cycler module, as well as an excitation optics assembly 1359 that is held in place with an excitation spring latch 1339. The spring latches 1337, 1339 can be compressed, thereby removing any biasing force against the emission and excitation optics assemblies 1357, 1359 and allowing them to be easily removed by a user.

More specifically, the spring latches 1337, 1339 may each comprise a base 1337(*b*), 1339(*b*) that is integrally formed with a head 1337(*c*), 1339(*c*). A biasing element 1337(*a*), 1339(*a*) such as a spring may push against the base 1337(*b*), 1339(*b*) to bias the head 1337(*c*), 1339(*c*) into a groove (or other type of recess) 1357(*a*), 1359(*a*) in the emission or excitation optics assembly 1357, 1359. To remove the optics assemblies 1357, 1359, a user may simply press down on the bases 1337(*b*), 1339(*b*) thereby withdrawing the heads 1337 (*c*), 1339(*c*) from the grooves 1357(*a*), 1359(*a*), so that they are disengaged from the thermal cycler module 1300.

The thermal cycler module 1300 may also include one or more addressable memory units, where the addressable memory unit stores information (e.g., optical alignment information) that is specific for the thermal cycler module. The memory units can be I2C memory blocks, each of which with a capacity of about 32 kbits. Individual memory blocks can have different functions. For example, one memory block may be write protected memory used to store the serial number and manufacturing test data specific for that thermal cycler module, where a different memory block may have read/write memory that is used to store thermal cycler module calibration information, temperature overshoot and undershoot information, and information related to the number of performance cycles of various components within that thermal cycler module. Typical performance cycles may be the number of heater cycles, the number of blower cycles, and the total number of thermal cycles completed.

There are also a number of alternative configurations of the thermal block assembly. In one embodiment, a thermal block assembly holds the reaction vessel near a heating device at one end and has an extended cooling "tail" region (with or without fins) for use in conjunction with a blower for cooling. In another embodiment, the thermal block assembly could hold the reaction vessels at one terminus and have an extended tail with a thin film heater on one side and cooling fins on the other side, with a blower to direct cooling air to the non-heated side. Other embodiments can include a cylindrical thermal block, with a central cavity to hold the reaction vessel, a helical arrangement of cooling fins on the outer surface, and a helical resistive heater nestled against the surface of the cylinder that is exposed between the cooling fins. In yet another embodiment, the thermal block may be replaced by an array of resistive heating wires that surround the reaction vessel, heating it primarily by radiation and convection.

While blowers directing a stream of air may be used for cooling a thermal block, in other embodiments of the invention, cooling can be provided by a heat pipe that is integrated into the thermal block assembly and is in thermal communication with a large heat sink and fan assembly located elsewhere on the system. Other embodiments of the invention may include the use of a relatively large thermal mass that is moved (via pneumatic cylinder, rotary motor, solenoid, linear actuator, mechanical linkage, or other suitable means) into physical contact with the thermal block to provide rapid cooling. Other embodiments of the invention can include forced/pressurized air stream could be used in place of a blower for cooling.

R. Thermal Cycler Module Control

Figure 17A:
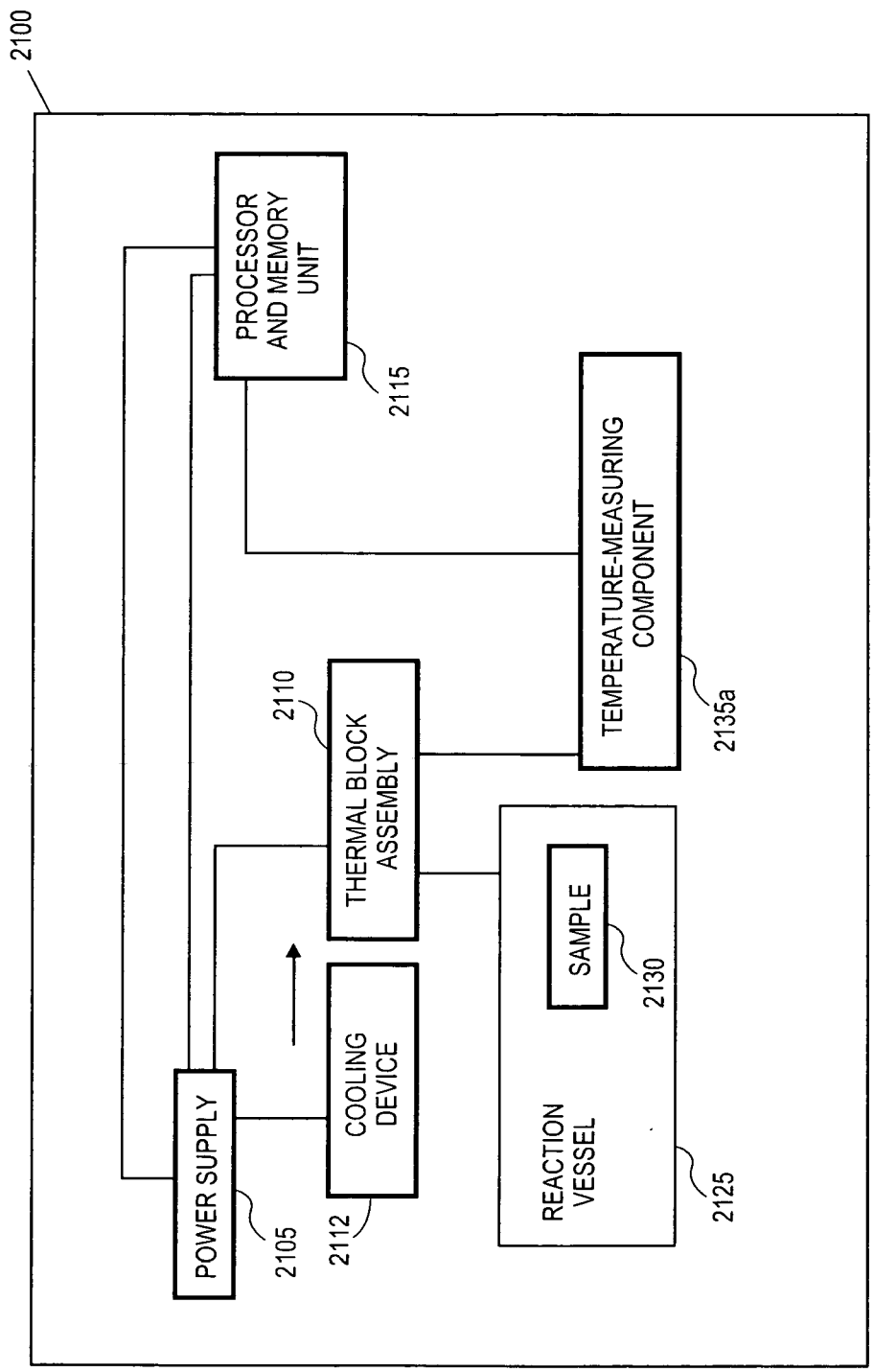
FIG. 17(a) shows a block diagram of some components in a thermal cycler module.

FIG. 17(a) shows a schematic block diagram illustrating some components of a thermal cycler module 2100 according to an embodiment of the invention. Thermal cycler module 2100 may include a power supply 2105. In some embodiments, a power supply is external to the thermal cycler module 2100.

Power supply 2105 is connected to thermal block assembly 2110. Thermal block assembly 2110 may include components (e.g., a heater) that may provide heat. A cooling device 2112, such as a fan, may also be coupled to the power supply 2105. An exemplary thermal block assembly 1311 has been described in connection with FIG. 16(b). Thermal block assembly 2110 and/or the cooling device 2112 may operate in a binary fashion (being either on or off/heating or cooling) or in a continuous fashion, whereby different applied voltages result in different degrees of effective heating and cooling.

Voltage output by power supply 2105 may be at least partly controlled by a voltage signal received from, e.g., an internal processor and internal memory 2115 and/or an external source (e.g., the signal being transmitted via wireless receiver 2120). In one embodiment, the internal memory includes pre-determined (e.g., testing) voltage signals, which may be transmitted to power supply 2105. In one embodiment, a voltage signal is received from an external source (e.g., an external computer system). In one embodiment, an initial signal (e.g., a voltage signal or a temperature signal) is received from a source (e.g., by from temperature measuring component 2135a), and a processor in the processor and memory unit 2115 converts the initial received signal into a new voltage signal, which is then sent to power supply 2105. The frequency at which temperature data is gathered may be optimized for thermal cycling requirements. A temperature measuring component 2135a may obtain measurements at intervals ranging from 100 milliseconds to 500 milliseconds. In one embodiment, the temperature measuring component 2135a obtains measurements at intervals of about 200 milliseconds.

Thermal block assembly 2110 may be connected to reaction vessel 2125, e.g., to heat and cool the vessel upon receiving a voltage from power supply 2105. A sample 2130 may be placed within reaction vessel 2125.

Thermal cycler module 2100 may include one or more temperature-measurement components 2135(a) (e.g., a thermistor). Temperature-measuring components 2135(a) may measure a temperature, e.g., within reaction vessel 2125 and/or thermal block assembly 2110, to produce a time-dependent temperature signal. Temperature-measurement components 2135(a) may send measured temperature signals to the processor and memory unit 2115. In some embodiments a temperature measurement component may send data to an external source, for use in characterizing the thermal cycler module 2100.

In some embodiments of the invention, the processor and memory unit 2115 may comprise one or more microprocessors, coupled to one or more memory devices (e.g., computer readable media). These devices may be on the same circuit board, or may be distant from each other, but operatively coupled to each other. The memory unit may store algorithms for processing samples, as well as calibration information. The calibration information may include values specific for the individual thermal cycler module or may include values common to all of the thermal cycler modules. Calibration information can include factors for calculating the temperature of the interior of the PCR vessel from the temperature of the thermal block.

Figure 17B:
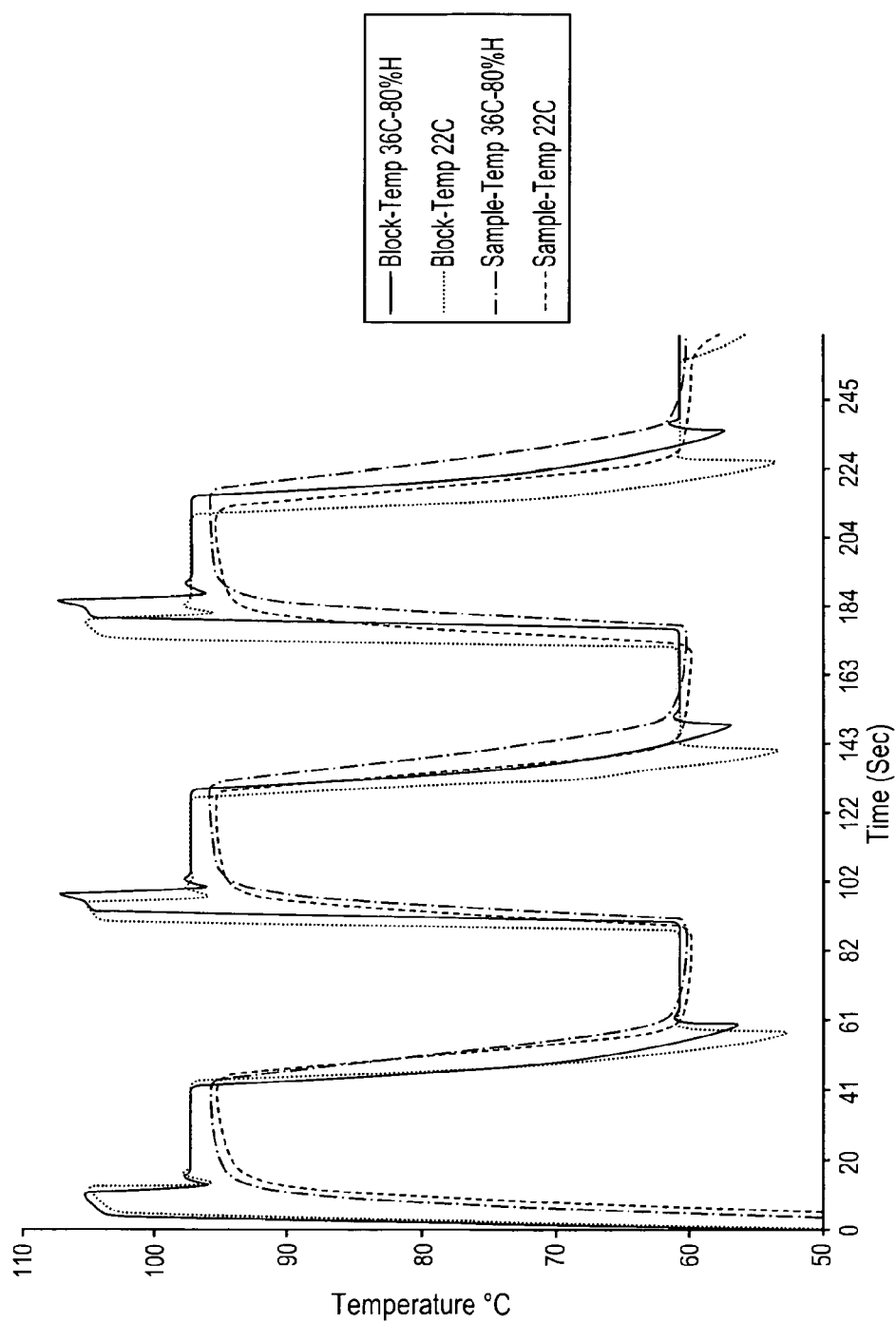
FIG. 17(b) shows a graph of temperature signals vs. time from different thermal cyclers.

Each thermal cycler module (e.g., within a thermal cycler garage) may be influenced by various environmental or hardware factors affecting the precise temperature profile that it will exhibit in response to a defined voltage. One factor that may influence a thermal cycler module's temperature is the ambient temperature. FIG. 17(b), for example, shows temperature measurements of a heat block and a sample, in response to an applied voltage signal, when the ambient temperature was either 36° C. or 22° C. At the lower ambient temperature, the sample and block temperature ramping times were faster, leading to faster cycle times. Within a garage, the ambient temperature of a thermal cycler may be affected by its relative location. For example, thermal cyclers positioned close to a perimeter of the garage may sit at a lower ambient temperature as compared to more centrally located thermal cyclers. Thus, thermal cycles in a garage may gradually experience phase shifts relative to each other.

Another factor that may influence a thermal cycler module's temperature profile is the thermal cycler module's hardware components. For example, slight variations within each cycler's thermal block assembly (e.g., including a fan and a heater) may cause variable temperature profiles across cyclers. FIG. 17(b) shows temperature profiles of a thermal block and a sample for two different cyclers. Though the cyclers include the same hardware components, minor differences in the hardware may account for the observed difference in ramping and cycle times.

The temperature-profile variation among thermal cyclers may lead to inconsistent rates of DNA amplification across the cyclers. Thus, DNA amplification may be inconsistent across days (e.g., based on variability of a garage-surrounding temperature) and even across cyclers within a single amplification session. Additionally, the phase shifts caused by variable temperature profiles may make it difficult to obtain reliable fluorescent measurements of amplification. In embodiments of the invention, since a reaction vessel may be assigned to any thermal cycler, variation in performance between different thermal cyclers may contribute to overall variation in assay performance. This negatively impacts system precision and, potentially, both the ultimate sensitivity of an assay and the accuracy of the final reported results.

In one embodiment, control of thermal cycler performance is achieved using a PID (proportional integral derivative controller) control loop. The thermal block is fitted with thermistors that give temperature information. A typical thermal cycle may shift the temperature of the thermal block between about 70° C. and about 95° C. To achieve a thermal block temperature of 70° C., a fixed voltage is applied until that temperature is achieved. Temperature is then maintained using a PID control loop and temperature data from the thermal block. To raise the temperature of the thermal block to 95° C., a fixed voltage is again applied until the desired temperature was reached. Similarly, to reduce the temperature a fixed voltage may be applied to a blower that directs air over the thermal block. The air supplied to this blower may be at ambient temperature or may be chilled. Other cooling methods, such as the use of a directed stream of pressurized air, flow of a cooling fluid through channels in the thermal block, and the use of Peltier cooling devices in thermal contact with the thermal block may also be used. Since it is desirable to minimize cycle times voltages may be selected that minimize heating and cooling times generating the fastest possible temperature ramping rates achievable by each thermal cycler.

Figure 17C:
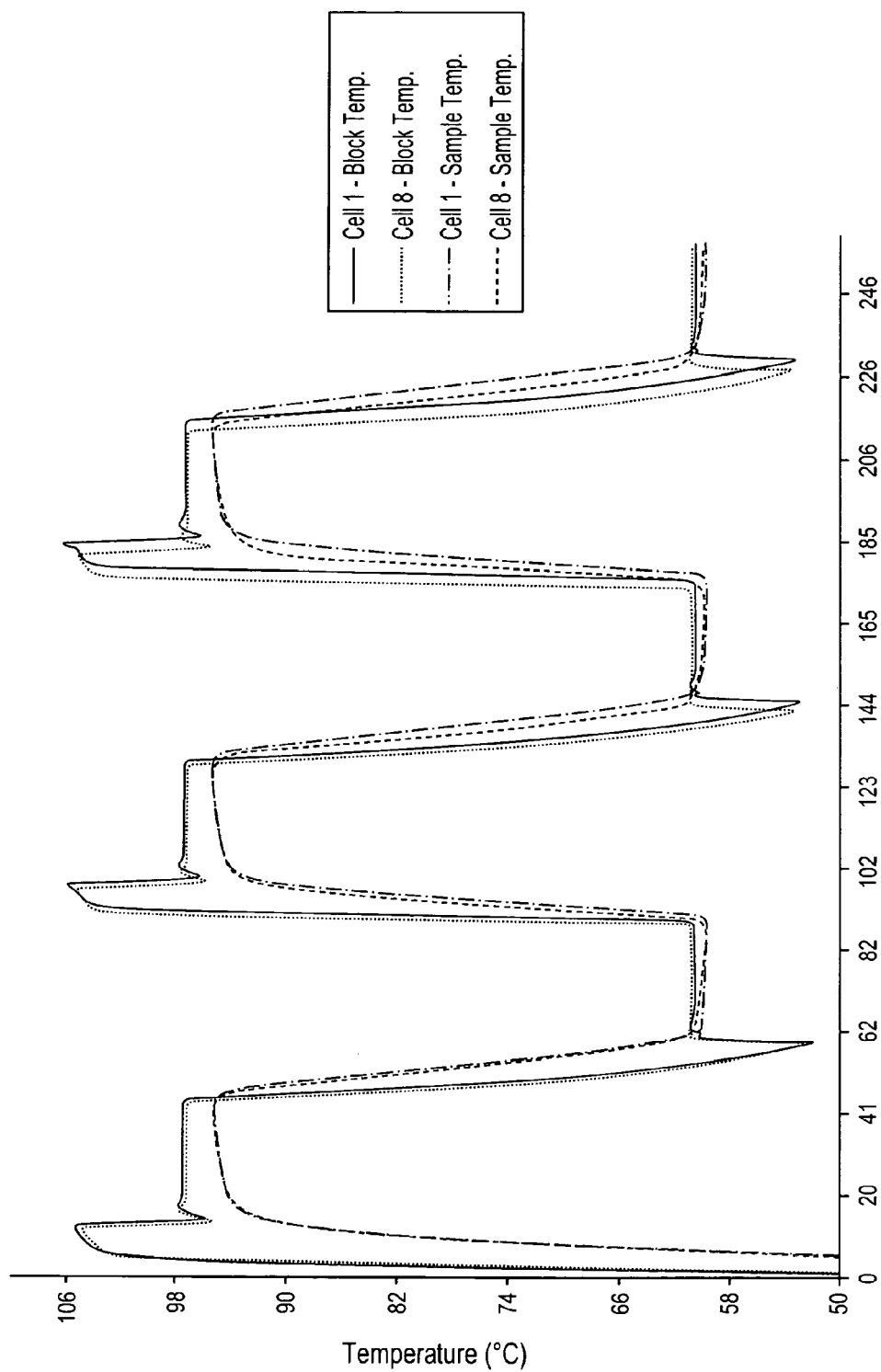
FIG. 17(c) shows another graph of temperature signals vs. time for different thermal cyclers.

In another embodiment of the invention, an algorithm, which can be stored in the memory unit of the processor and memory unit 2115, can be used to produce identical temperature versus time profiles across all thermal cycler modules. Such an algorithm compensates for sources of variation in the temperature ramping rates of different thermal cyclers. Such an algorithm may also compensate for different environmental conditions. Sources of variation can include ambient temperature (FIG. 17(b)), thermal block performance, and blower performance (hardware variation; FIG. 17(c)).

Figure 17D:
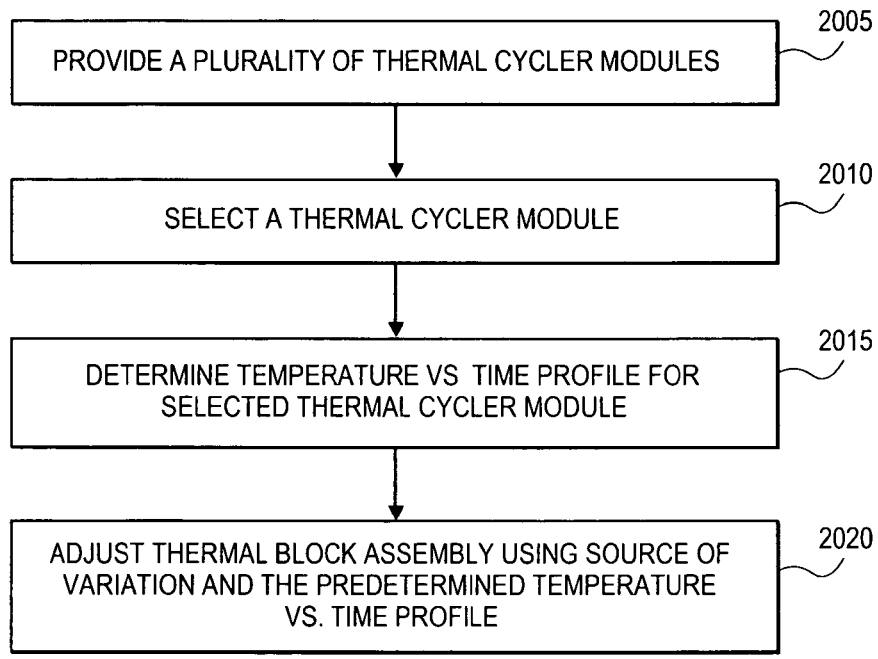
FIG. 17(d) shows a flowchart illustrating a method according to an embodiment of the invention.

FIG. 17(d) shows a flowchart illustrating a method according to an embodiment of the invention. In the method, a plurality of thermal cycler modules may be provided as described above (block 2005). The plurality of thermal cycler modules may be 2, 3, 5, 6, or 7 or more.

Then, a thermal cycler module may be selected (block 2010). The selected thermal cycler module may be one of many thermal cycler modules. The other thermal cycler modules that are not selected may form a set of thermal cycler modules. A set of thermal cycler modules may comprise 1, 2, or 3 or more thermal cycler modules.

The thermal cycler module may be selected in any suitable manner. It can be selected as the least responsive thermal cycler module in the array of thermal cycler modules. For example, the selected thermal cycler module may be the slowest ramping thermal cycler module in the array of thermal cycler modules. It may correspond to a longest cycle time or the slowest heat transfer of a thermal cycler module. In other embodiments, the temperature vs. time profile does not need to be based on the least responsive thermal cycler module, but can be based on the performance of a different type of thermal cycler performance characteristic. Regardless of how the temperature vs. time profile is created, these embodiments of the invention can address both overshoot and individual thermal cycler performance issues.

After the thermal cycler module is selected, a temperature vs. time profile is created for the selected thermal cycler module profile (block 2015). It can then be stored in a memory unit (e.g., a computer readable medium such as a memory chip) in the processor and memory unit 2115.

After the temperature vs. time profile for the selected thermal cycler is created, the thermal block assembly of each thermal cycler module in the array can be adjusted using a source of variation (e.g., ambient temperature) and the predetermined temperature vs. time profile (block 2020). This can be done by obtaining the predetermined temperature vs. time profile associated with a selected thermal cycler module in an array of thermal cycler modules. The array of thermal cycler modules can comprise the selected thermal cycler module and a set of thermal cycler modules. A processor in the processor and memory unit 2115 then controls the thermal cycler modules in the set of thermal cycler modules so that their performance matches the predetermined temperature vs. time profile. Each of the thermal cycler modules in the set of thermal cycler modules can be controlled using a source of variation between the thermal cycler modules in the array.

Illustratively, the least responsive thermal cycler module that gives acceptable performance in a plurality of thermal cycler modules can be selected. A temperature vs. time profile can then be created using the selected thermal cycler module. An algorithm is then created, and is used to control the thermal block assembly 2110 (and hence the heat provided by to the reaction vessel) as well as the cooling device 2112. The algorithm uses the selected temperature vs. time profile, and information about a source of variation such as the ambient temperature of the thermal cycler module to determine how to control the thermal block assembly 2112 and the cooling device 2112. The following equation can be used in the algorithm:

$$dB/dt = h_a + k(Ta - B(t)), \qquad (1)$$

where $dB/dt$ = change in thermal block temperature in degrees per second;

Ta = ambient temperature (° C.);

$h_a$ = thin film heater output at ambient temperature (° C./second);

k = rate of heat transfer; and

B(t) = the temperature of the thermal block at a given time t.

If B(t) is not measured directly, one can integrate and solve for B(t) to get the temperature of the thermal block at any given time t:

$$B(t) = (B(0) - (h_a/k) - Ta)e^{kt} + (h_a/k) + Ta,$$

where

B(0) = starting block temperature at time=0.

The processor in the processor and memory unit 2115 can control the thin film heater output ($h_a$) by applying modulated pulses of voltage to the thermal block assembly 2110, and can control the rate of heat transfer (k) in a similar fashion using the cooling device 2112 (e.g., blower, a fan, or cooling fluid). Alternate methods for modulating heater and fan output are also possible in embodiments of the invention.

In equation (1) above, dB/dt at a given time can be determined from the predetermined time vs. temperature profile of the selected thermal cycler module, and the ambient temperature of the thermal cycler module, Ta, can be measured by a temperature measuring component (e.g., a thermistor). The variables $h_a$ and k can be controlled independently, and both can be varied simultaneously (i.e. the heater and the blower can be used in combination) to satisfy equation (1).

Figure 17E:
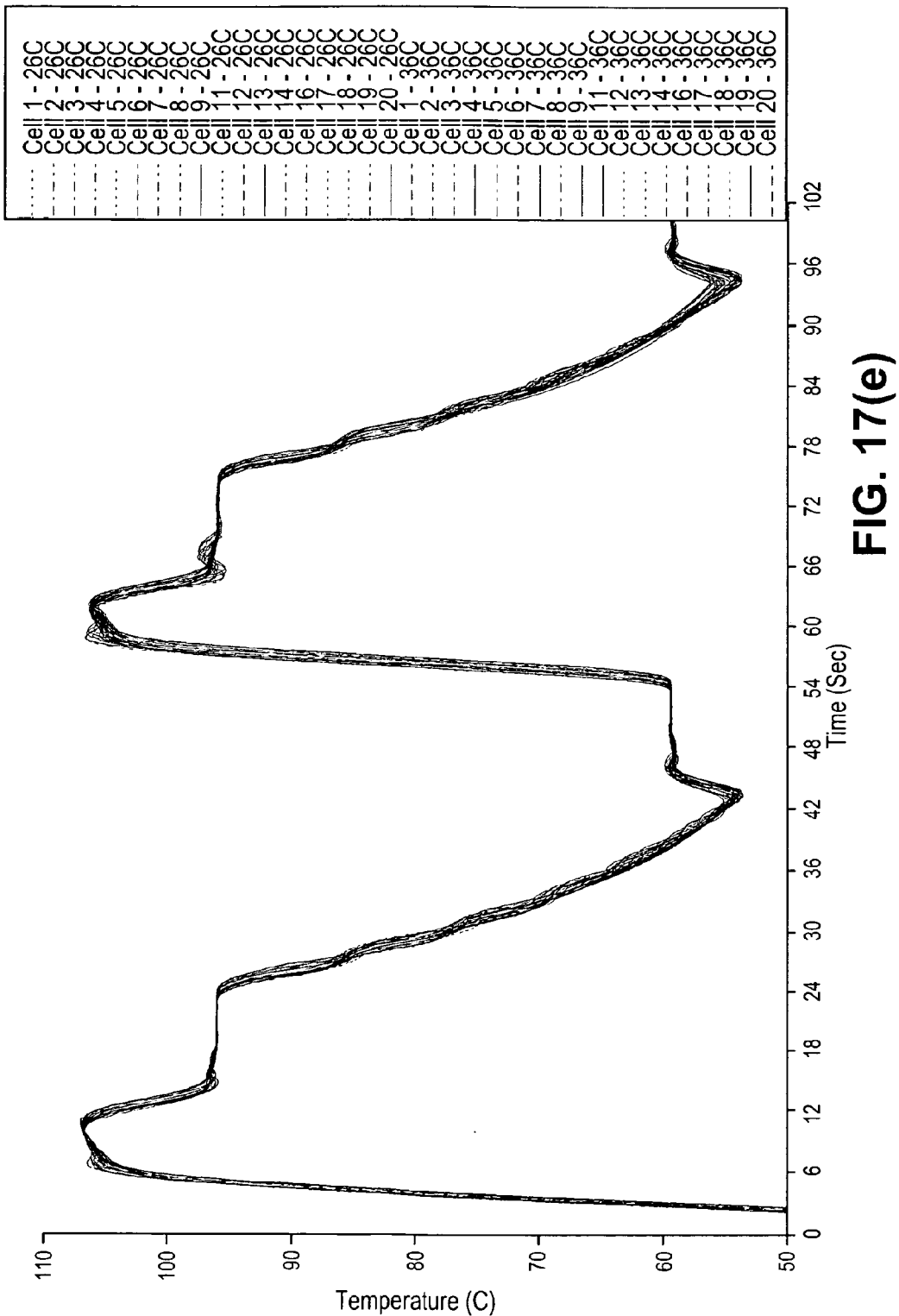
FIG. 17(e) shows an example of temperature signals produced in response to calibrated voltage signals.

FIG. 17(e) shows an example of block temperature measurements from 20 independent thermal cycler modules that were programmed using the above-described algorithm. As shown in FIG. 17(e), the thermal cycler modules in the array of thermal cycler modules perform consistently. This can be advantageously done without significant hardware modifications or requiring narrow product specifications. Use of consistent thermal profiles among all thermal cyclers on the system advantageously reduces variation in the PCR process due to hardware differences and environmental factors. Use of consistent thermal profiles also produces identical thermal cycling times in every thermal cycler on the system, permitting an accurate estimate of when thermal cycling will be complete for a given sample and simplifying resource scheduling.

Q. Optics Systems

Embodiments of the invention can also include an excitation and detection subsystem (herein called detection subsystem). The detection subsystem can be responsible for exciting the dyes in the assay and quantifying the fluorescence emitted at each PCR cycle. Both excitation and emission can occur over a range of wavelengths. Light used to excite the fluorescent dyes can, for example, range from 400 nm to 800 nm. The detector used to measure light emitted from the dyes can, for example, be sensitive to light ranging from 400 nm to 800 nm. The detection subsystem includes hardware and software components from the light source(s) through to the detection on the CCD camera. This includes all the optical components with each thermal cycler module, the fiber optics routing from each thermal cycler module and the spectrophotometer mounted under the PCR base plate. The dynamic range of the detection subsystem can allow for the detection of amplified PCR products over at least 3 thermal cycles that are within the linear detectable range of the amplification curve or having a range of fluorescence intensity of 2 orders of magnitude. The detection subsystem can detect a plurality of emitted wavelengths from the reaction vessel and to perform the detection asynchronously across multiple reaction vessels. In one embodiment up to 7 different dyes can be detected asynchronously among up to 20 different reaction vessels.

The detection subsystem comprises at least the following components: an excitation light source, an assembly or assemblies for directing excitation light to the reaction vessels, an assembly or assemblies for directing light emitted by fluorescence occurring within the reaction vessels to a detector, and one or more detectors for measuring the emitted light. The excitation light source can be one or more lasers that are optically coupled to an excitation fiber optic assembly. In some embodiments, light from two lasers (for example a 640 nm laser and a 532 nm laser) is passed through line filters to remove light that is outside of the nominal wavelength range. The beams can be made collinear (or slightly non-collinear). Beams can be made collinear by a variety of optical devices, including a beam splitter. In another embodiment, the excitation laser beams are not made collinear in order to avoid crosstalk between them. The excitation laser beams can be directed to individual excitation optical fibers using mirrors mounted in a two axis galvanometer. Each excitation optical fiber would then direct the excitation light to an individual thermal cycler module. In one embodiment, an assembly of 20 excitation optical fibers would be used to supply excitation light to each of 20 thermal cycler modules. Additional optical fibers that are utilized for other purposes may be present in the assembly of excitation optical fibers; such uses can include optical alignment. The excitation optical fibers can be held in an ordered array, with a two axis galvanometer directing light to the input end of each excitation optical fiber as needed. In addition, the two axis galvanometer may direct excitation light to a neutral position where it does not enter an optical fiber. Alternatively, an optical switch may be used to direct light from an excitation source to the optical fibers. A variety of optical fibers are suitable for this use. In one embodiment, the excitation optical fibers are about 200 μm in diameter, and may be bundled in a 4×5 array. In some embodiments, excitation and emission optical fiber bundles can include 22 (or more) fibers. Excitation optical fibers carrying the excitation light terminate in the excitation optics assembly of the thermal cycler module, which is described above.

Although lasers are the preferred light sources in embodiments of the invention, embodiments of the invention may include other light sources including, but not limited to, tunable lasers, individual single wavelength LEDs, assemblies of single wavelength LEDs, and multi-wavelength LEDs, white LEDs with a multibandpass filter, and an assembly of single wavelength LEDs and a multibandpass filter. Excitation light sources may be incorporated into the excitation optics assemblies.

Light emitted from the reaction vessel as a result of exposure to the excitation light is collected by the emission optics assembly of the thermal cycler module, which is described above. In one embodiment, this directs the emitted light to the input end of an emission optical fiber, which subsequently directs emitted light to a detector. In order to improve coupling efficiency the emission optics assembly may focus the emitted light over an area that is smaller than that of the input end of the emission optical fiber. For example, the emitted light may be focused as a 200 μm spot on an emission optical fiber input end having an area of 800 μm. An emission optical fiber may taper to a smaller diameter beginning from the input end in order to improve coupling efficiency. Other features, including lenses integrated into the input end of an emission optical fiber, can be used to increase coupling efficiency. Suitable lens configurations include ball or spherical lenses, aspherical lenses, and graded index lenses.

The detector can be a spectrometer. The spectrometer may be a multi-channel or an imaging spectrometer, which can permit simultaneous reading of multiple optical fibers and reduce the need for switching. The spectrometer can include a multi-bandpass filter between the output terminus of the emission optical fibers and the detector to selectively remove excitation wavelengths. If a single detector is used the emission optical fibers may be arranged in a bundle at the input of the detector. Such a multi-channel spectrometer may use a CCD for detection of emitted light. For example, 20 emission optical fibers from individual thermal cycler modules can be arranged in a 2×10 bundle at the input of a detector. In an alternative embodiment, the detector may be a single photodiode, photomultiplier, channel photomultiplier, or similar device equipped with an appropriate optical filter. Such an appropriate optical filter can be a set of optical filters or a tunable filter.

If a single detector is used the detection system may be able to support asynchronous measurement of fluorescence from each of the thermal cycler modules. One way to accomplish this is to use a spectrometer that has an integration time that is short when compared to the point in the thermal cycle where the read event is to occur. For example, to read during a phase of the thermal cycle that lasts approximately 15 seconds, a spectrometer capable of making an accurate measurement within 50 msec is desirable. The annealing phase of the thermal cycle, which typically takes place at around 60° C., may be used to take advantage of improved dye fluorescence characteristics at lower temperatures. Excitation light can be directed to the input end of a specific excitation fiber for the required integration time using mirrors mounted in a two axis galvanometer, then directed to another position. If a CCD-based detector is used the CCD may be cleared between each read event. The CCD may be activated prior to directing the excitation light to the appropriate excitation optical fiber and kept active following switching of the excitation light to a different position in order to facilitate this. The read event can be triggered by monitoring the temperature of the thermal block of the thermal cycler module to ensure that the contents of the PCR reaction vessel are at the desired temperature. In one embodiment, the read event can be triggered within a defined portion of a temperature versus time profile that is applied to a thermal cycler, as described above.

As the throughput of a system increases the complexity of scheduling appropriate read times on a single detector for multiple analytical units, such as thermal cyclers, that work in parallel also increases. The workflow for the system, which is described in detail below, may advantageously simplify this task by preparing samples for reading in a serial fashion. This ensures that each sample enters the analytical portion of the system at a different time point, greatly reducing the probability that a significant number of samples will require that a read event be performed within the same time interval.

Figure 18A:
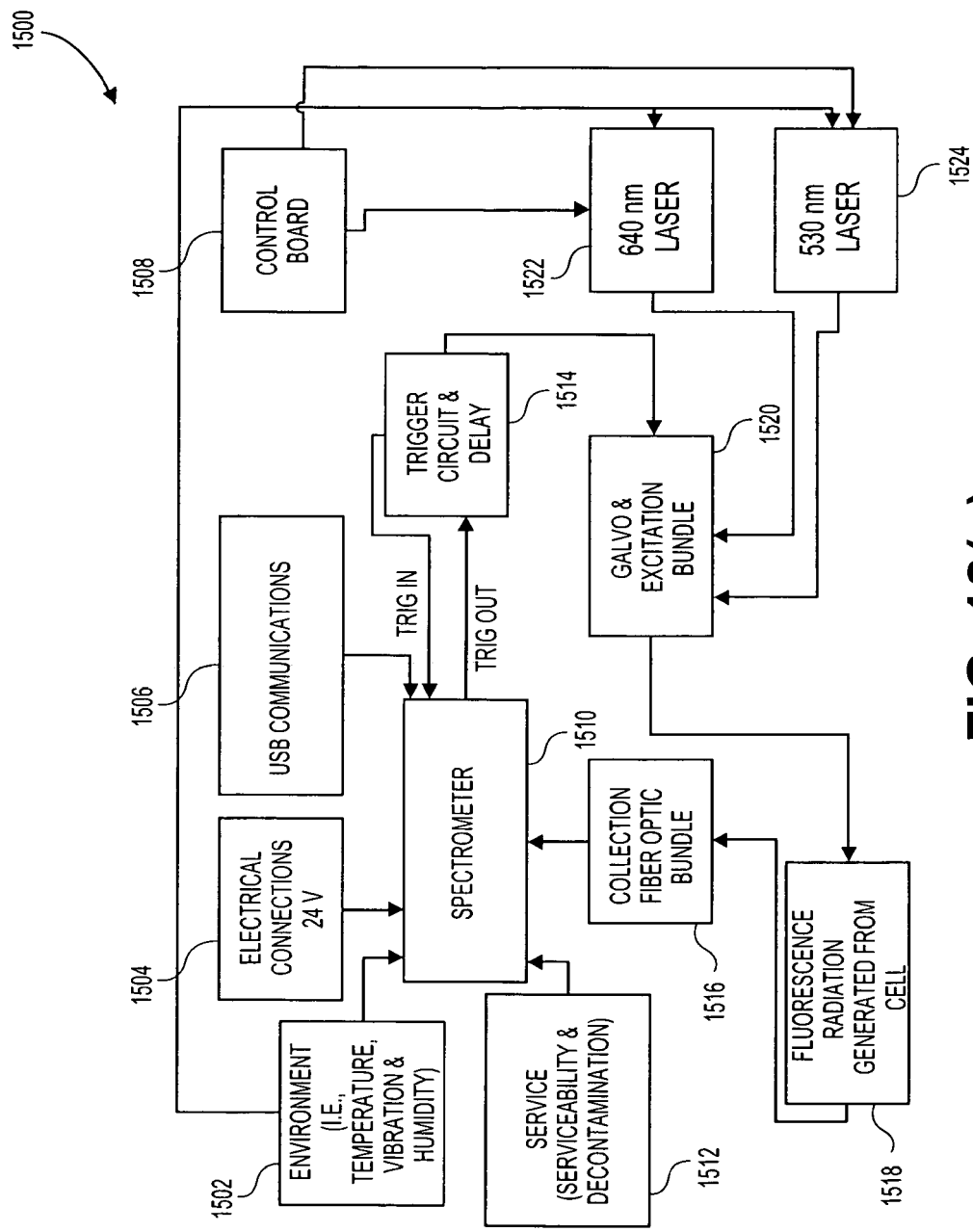
FIG. 18(a) shows a detection optics block diagram.

FIG. 18(a) shows a detection optics functional block diagram. FIG. 18(a) shows a plurality of light sources comprising a first light source 1522 and a second light source 1524, which can provide light to a two-axis galvanometer and excitation bundle 1520. A control board 1508 can provide control signals to the first light source 1522 and the second light source 1524. In one embodiment, the first light source 1522 may comprise a 640 nm laser, while the second light source 1524 may comprise a 530 nm laser. However, the first and second light sources 1522, 1524 can provide light of any suitable wavelengths.

The two-axis galvanometer and excitation bundle 1520 can receive light from the first and second light sources 1522, 1524, and can be controlled by a trigger circuit and delay 1514. Light is provided to one or more reaction vessels as the light passes through the thermal block. Block 1518 depicts excitation and the subsequent emission of fluorescence generated from one or more reaction vessels.

Fluorescence radiation from the reaction vessels in block 1518 may be captured by a collection fiber optic bundle 1516, which may pass the radiation to a spectrometer 1510. In addition to the collection fiber optic bundle 1516, access to the spectrometer may also be supplied for maintenance and decontamination of the spectrometer 1512, environmental controls that maintain the spectrometer within acceptable operating conditions 1502, electrical power 1504, and communications with the system 1506. The trigger and circuit delay 1514 may be in operative communication with the spectrometer 1510.

Figure 18B:
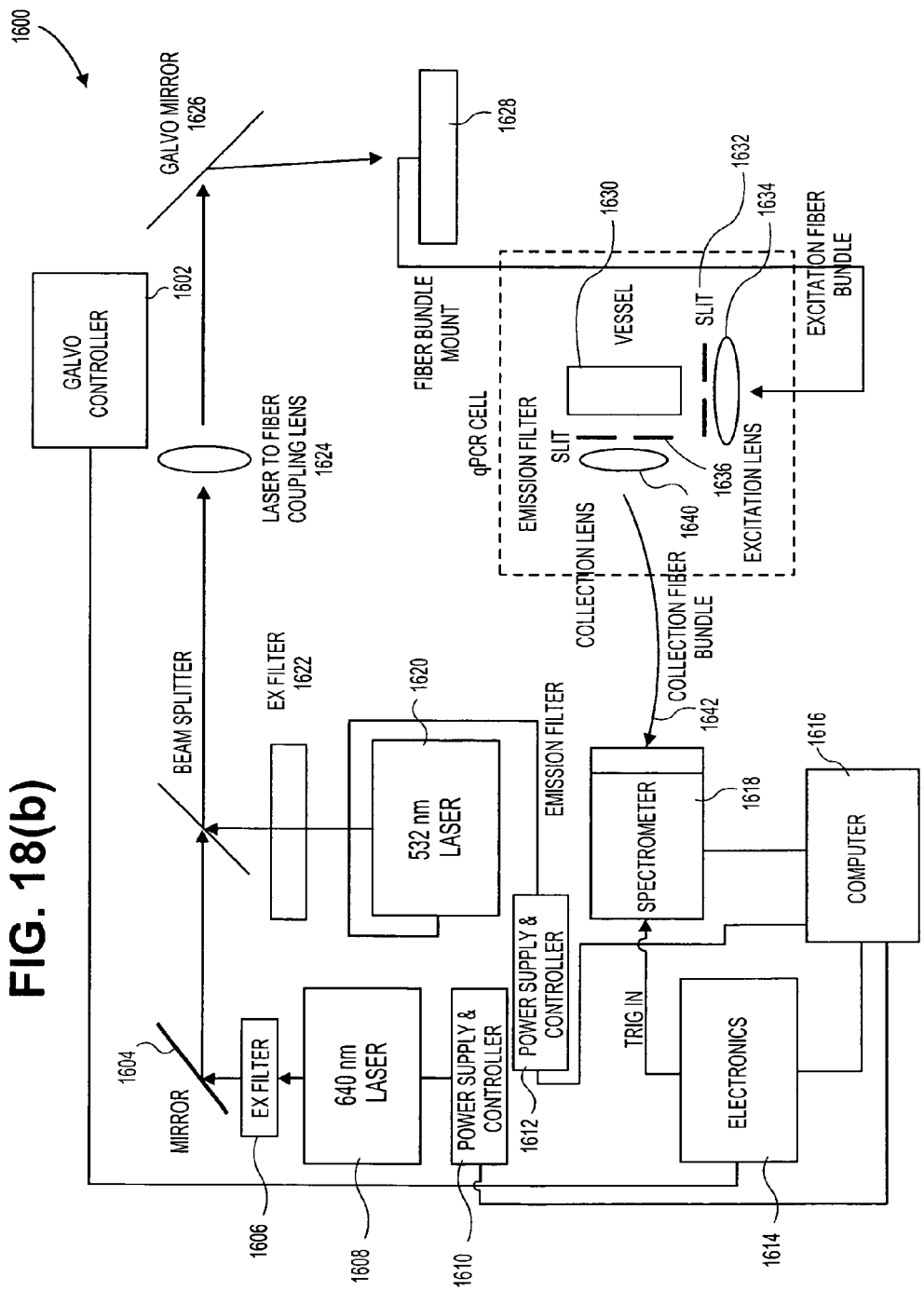
FIG. 18(b) shows a detection optics light path.

FIG. 18(b) shows a more detailed diagram of an optics detection system according to an embodiment of the invention. The system comprises a computer 1616, which can provide control signals to first and second power supply and controllers 1610, 1612. The first power supply and controller 1610 can supply power to a first light source 1606, while the second power supply and controller 1612 may provide power to a second light source 1620. Light from the first light source 1608 may pass through an excitation filter 1606 and may be reflected by an aluminum front surface coated mirror. Light from the second light source 1620 may be reflected using a beam splitter. The light beams from the first and second light sources 1608, 1620 can then be collinear and can be focused by a planoconvex lens 1624, reflected by a two-axis galvanometer mirror 1626, and directed into an excitation fiber bundle 1644 connected to a fiber bundle mount 1620. In other embodiments, the light beams need not be collinear and may be angled to prevent cross-talk between them. Galiliean telescopes can be used for collimation of the output of both light sources (e.g., lasers) and to reduce spot size for coupling to excitation fibers. Further, initial alignment of the light sources (e.g., lasers) can be performed manually, aligning the beams to a target holes via coarse adjusters prior to performing automated calibration of the galvometric mirror.

In some embodiment, the excitation fiber bundle can comprise twenty (or twenty two) 200 µm core diameter fibers (CeramOptec, p/n Optran WF, NA=0.12) arranged in 5×4 array with 0.425 mm spacing between the fibers (CeramOptec, p/n RSSLSMA20/20XWF200/220P12/BPGS+BPVC/1.5M/BC).

Exemplary fiber bundle specifications are as follows:

20 CeramOptec optical fibers (part number WF200/220/245P12, available from CeramOptec of East Longmeadow, Minn.) with the following specifications:
 a. Pure fused silica core diameter: 200 µm±2%
 b. Dopped silica clad: 220 µm±2%
 c. Polyimide coating: 245 µm±2%
 d. Low OH version
 e. Numerical aperture: 0.12±0.02

Light from the excitation fiber bundle can then pass to an excitation lens 1634 and to a reaction vessel 1630 containing a sample via a first slit 1632. Fluorescent radiation from the sample in the reaction vessel 1630 can then pass through a second slit 1636. Once the emission radiation passes through the second slit 1636, it is focused by a collection lens 1640 and to a collection fiber bundle 1642. The collection fiber bundle 1642 is coupled to a spectrometer 1618, which receives the fluorescent radiation. Suitable control electronics 1614 may be coupled to the computer 1616 and the spectrometer 1618.

Figure 18C:
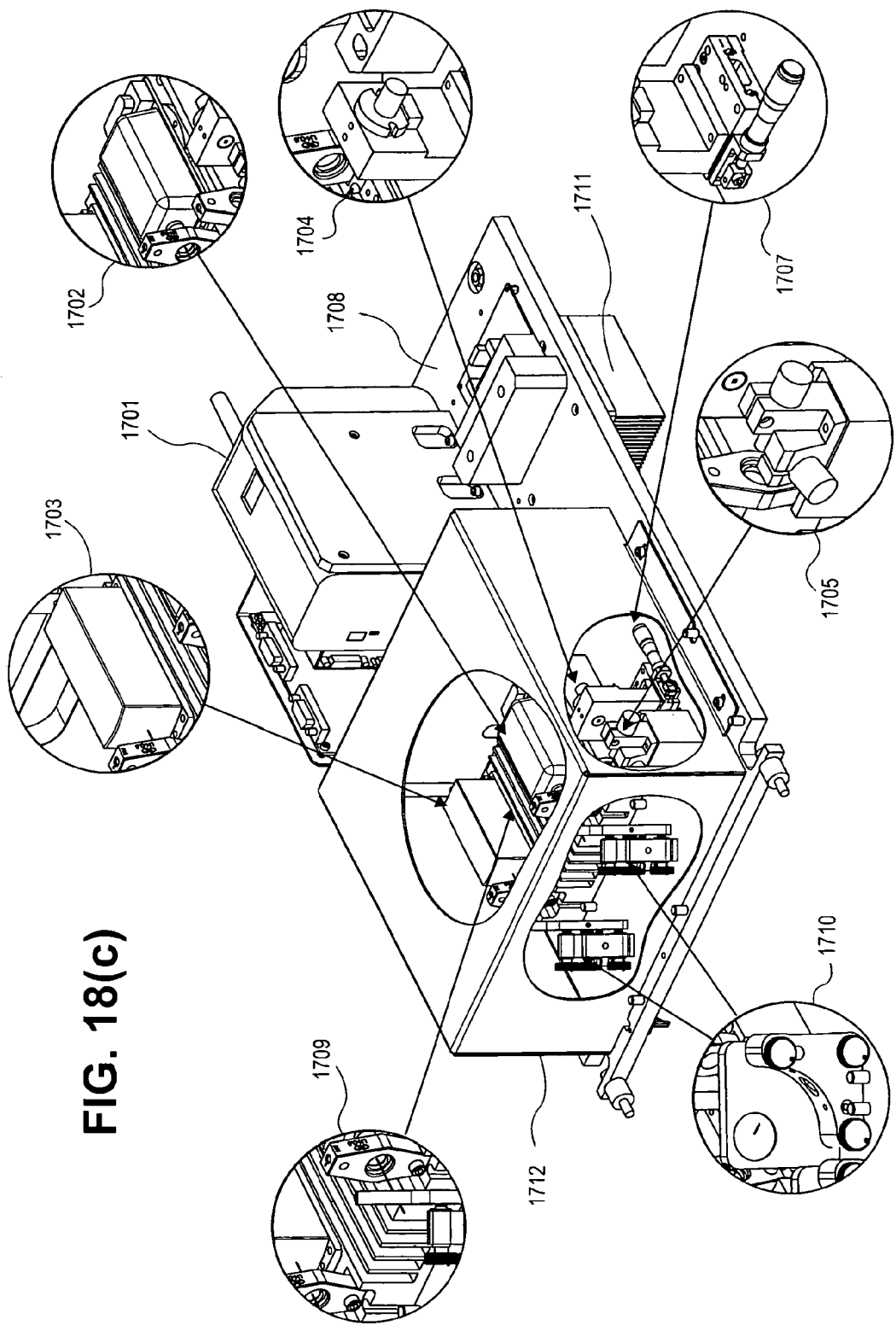
FIG. 18(c) shows a detection optics assembly.

FIG. 18(c) shows a perspective view of a detection optics assembly according to an embodiment of the invention. FIG. 18(c) shows a detector in the form of a spectrophotometer 1701 with a 2D array mounted on a plate 1708. A first light source 1703 in the form of a 640 nm laser, a second light source in the form of a 532 nm laser 1702, mount optics 1710, and a galvanometer 1705 are also mounted on the plate 1708. Various finned heat sinks 1709, 1711 may also be mounted on the plate 1708. An enclosure 1712 in the form of a cover can cover at least the first light source 1703, the second light source 1702, the mount optics 1710, and the galvanometer 1705. An excitation fiber bundle 1704 can be in operative communication with the first and second light sources 1701, 1702.

In one embodiment, the detection optics assembly is supplied as a discrete, essentially closed unit in order to facilitate field replacement and service. Such a detection optics assembly can include alignment targets in the form of holes that extend through the casing of the unit, correct alignment of the light sources encased therein indicated by observation of light transmitted through an alignment target hole. A detection optics assembly may include coarse adjustment devices that extend through the casing of the unit to permit alignment without the necessity of opening the unit. In some embodiments a final alignment of the light sources is performed in an automated fashion using a galvanometer mirror.

As noted above, embodiments of the invention can use galvanometers. Alignment can be an issue with 2D galvanometer systems. Embodiments of the invention provide each thermal cycler module with a fluorescent target that can be observed by the system's detection optics when the reaction vessel is not in the thermal block. In some embodiments, this is a discrete device shaped like a reaction vessel that is either fluorescent or contains fluorescent materials. This is placed in the thermal block of a thermal cycler module for the purpose of aligning the optics for that module, and can be removed before the thermal cycler module is used for PCR. In other embodiments, all or part of the slidable lid are fluorescent, emitting brightly enough to reflect some light off of the interior walls of the receptacle and into the collection optics. The opaque plug of the reaction vessel blocks light to and from the slidable lid during PCR. This provides a fluorescent target that sends light down the emission fiber associated with a particular thermal cycler module when the 2D galvanometer is lined up properly. To align the optics with a specific thermal cycler, the galvanometer scans the beam across the excitation fibers while recording the position of the galvanometer. When the system identifies the position that gives maximum intensity from the collection fiber corresponding to the specific thermal cycler module, it records it as the calibrated position for that thermal cycler. The reason this is desirable is because, while the use of the galvanometer lets one use a centralized light source and switch back and forth among the different thermal cyclers very quickly, alignment has to be close to optimal to get good performance. Having an automatable alignment mechanism in place reduces maintenance (manual alignment of 20+ fibers is labor intensive) and provides consistent performance over time.

A similar process may be performed following alignment and prior to performing thermal cycling in order to assure that the optical path to a thermal cycler is not blocked. A significant reduction intensity of the light observed by the detector in the absence of a reaction vessel, relative to that observed in a prior alignment observation, could indicate an interruption in the optical path associated with a thermal cycler. The controller may then take actions such as selecting a different thermal cycler for the determination that is in process and notifying the user of a possible fault condition.

Other embodiments of the invention may utilize a single detector for thermal cycler. Such a detector may be an individual spectrometer that is in communication with each thermal cycler. In another embodiment, the detector could be a photodiode, photomultiplier, channel photomultiplier, or similar device associated with each thermal cycler.

S. System Operations and Sample Handling

Many different processing embodiments have been described above, and are described in further detail below.

One embodiment of the invention is directed to a method comprising loading a sample into a system, and loading an assay cartridge into a preparation location. The assay cartridge includes a reaction well and a compartment. A reaction vessel is in the compartment. The method also includes extracting the nucleic acid in the reaction well, transferring the extracted nucleic acid from the reaction well to the reaction vessel, moving the reaction vessel to the thermal cycler module, and detecting the nucleic acid in the thermal cycler module. These and other steps are described in further detail below.

Figure 19:
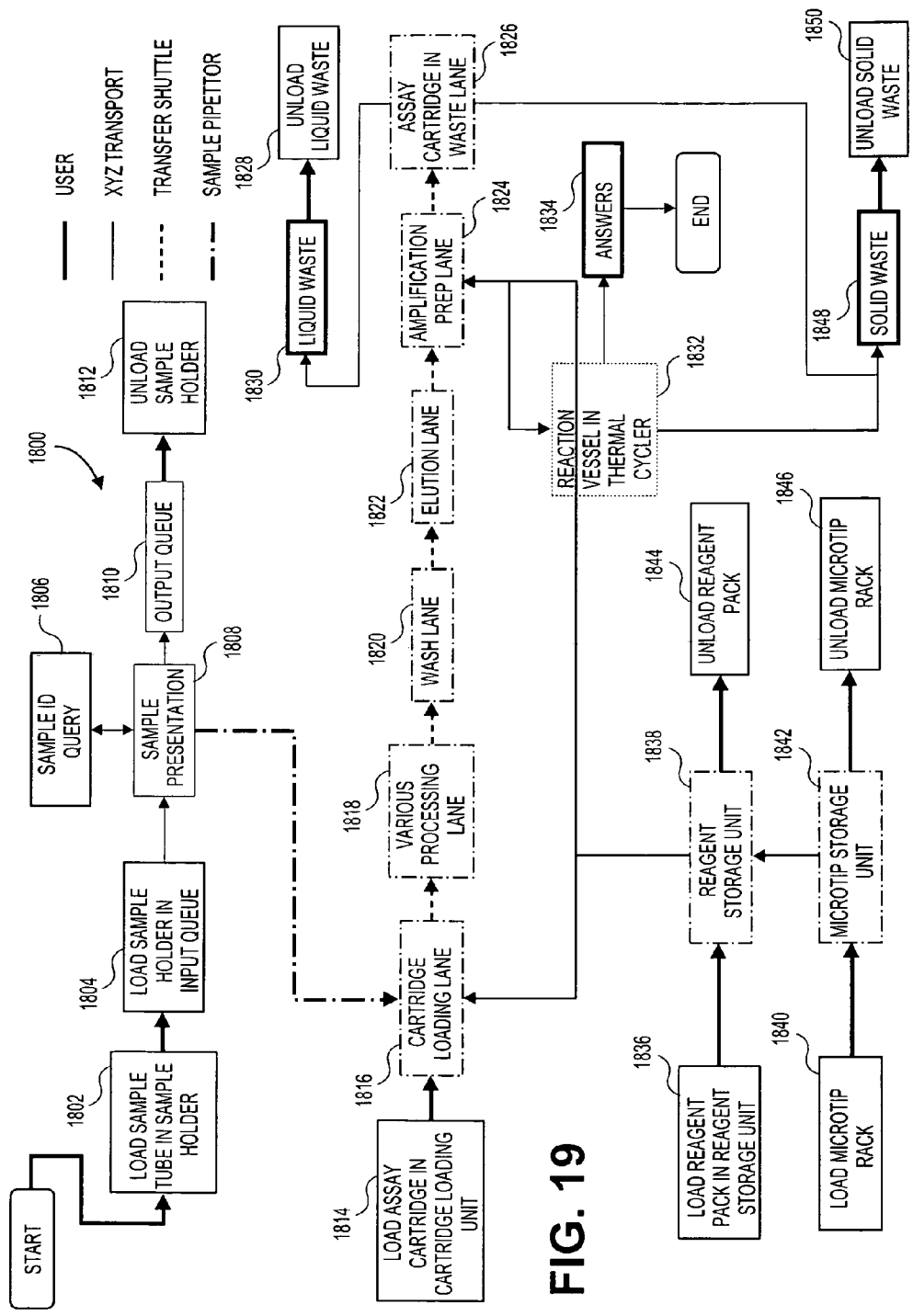
FIG. 19 shows a process flow diagram illustrated methods according to embodiments of the invention.

FIG. 19 shows a flowchart processing methods according to embodiments of the invention.

The system according to an embodiment of the invention can be designed to function in a conventional clinical laboratory environment and require minimal user intervention. FIG. 19 shows an embodiment where normal user interaction with the system is limited to loading of samples for analysis 1804, removing remaining samples once they are processed by the system 1812, replenishing consumables (1814, 1836, 1840), and removing waste (1828, 1850). In another embodiment, the system is used in conjunction with an automated laboratory system, and the normal user interaction with the system is limited to replenishment of consumables and removal of waste. Other user interactions that are not shown include periodic maintenance. This advantageously places a minimal burden placed on the user, in terms of both hands on time and training, which in turn facilitates integration of the system into the workflow of a conventional clinical laboratory.

A typical workflow for analysis of a sample by the system can be described with reference to the flowchart shown in FIG. 19, with periodic reference to previously described system components.

Analysis begins by loading a sample onto the system 1802. Samples are generally provided in sample tubes, and may be whole blood, serum, plasma, saliva, urine, cerebrospinal fluid, suspensions of fecal material, swabs taken from wounds or other body surfaces, or other clinically relevant fluids or suspensions. Swabs samples can be provided as tubes containing at least a portion of the swab, with the sample collection portion of the swab immersed in liquid. Sample tubes may have indicia that provide identification of individual tubes. Such indicia may be machine readable, and include one and two dimensional barcodes.

In some embodiments, sample tubes are loaded onto the system by placing them in a sample holder (block 1802), which can provide support for one or more sample tubes while providing features that facilitate handling. An exemplary sample holder 616 can be found in FIG. 2(*a*). The sample holder 616 may have indicia that provide identification of an individual sample holder 616. Such indicia may be machine readable, and include one and two dimensional barcodes.

Once a sample tube has been placed in a sample holder 616, it is loaded onto the system by placing the sample holder 616 into an input queue (block 1804). FIG. 1(*c*) shows an embodiment where the input queue 628 is located in a sample presentation unit 110. Various embodiments and features of a sample presentation unit 110 are detailed above. The sample tube progresses through the input queue 628 until it reaches a sample presentation area, where it is identified (block 1806) and brought into the sample processing workflow. In some embodiments, the sample presentation area is a portion of the sample presentation unit 110 and is accessible to a sample pipettor 70. For example, in some embodiments, the sample presentation area may include the presentation track 624 shown in FIG. 2(*a*). Samples may be identified based on the indicia of individual sample tubes, and by their position on an identified sample holder 616. In some embodiments, the user may manually designate a specific sample via a keyboard 104, as shown in FIG. 1(*c*), or by other suitable means. Identification of individual samples permits association of the sample with a specific patient, which in turn provides the system with information regarding the tests to be performed on the sample. Identification of individual samples also allows the system to associate results from those tests with an individual patient.

At the sample presentation area, in a sample presentation process (block 1808), a portion or aliquot of the sample may be taken from the sample tube for analysis by the system. For example, referring to FIG. 4(a)-1, aliquots may be removed from the sample tube using the millitip 220 provided with the assay cartridge 200, and then transferred into a reaction well in the assay cartridge 200. This millitip 220 may be returned to the assay cartridge 200 following aliquot transfer for later use.

The system may take one or multiple aliquots from a single sample tube in order to support the performance of multiple tests. When multiple aliquots are taken, the system may first determine the level of fluid in the sample tube, calculate the volumes required for testing as appropriate for the specified tests, and alert the user if the volume of the sample is insufficient to complete all tests. Under such circumstances, the system may optimize the order in which aliquots are removed in order to perform as many tests as possible, or may remove aliquots based on a test priority. Alternatively, performance of multiple tests may require loading of individual sample tubes for each test.

Once aliquot removal from the sample tube is complete, the sample is moved to an output queue 640 (block 1810). If the sample is held in a sample holder, transfer to the output queue 640 may be delayed until aliquots are taken from all sample tubes in the holder. The output queue 640 may be located on a portion of the sample presentation unit 110 (see FIG. 2(a)), which is described in detail above. Once samples are in the output queue 640, they may be removed from the system (block 1812). The user may then choose to store the sample tube for possible retesting of remaining sample or may simply discard the sample tube. Sample may be stored in a sample holder or removed from the holder for more space efficient storage.

As described above, sample aliquots are processed by the system using consumables. This reduces the probability of contamination due to carryover. In a preferred embodiment, referring to FIG. 4(a)-1, initial sample processing is performed in a disposable assay cartridge 200. These are supplied to the system by the user, who may place them in a cartridge loading unit for temporary storage 1814 prior to use by the system. An exemplary cartridge loading unit 112 is shown in FIG. 1(c). The user may place assay cartridges 200 in a cartridge loading unit 112 individually, or they may simultaneously place multiple assay cartridges 200 in the cartridge loading unit 112. In one embodiment, the linear arrangement of the assay cartridge 200 simplifies the simultaneous grasping of multiple units, and assay cartridges may be supplied in packaging with spacing that facilitates this. As noted above, different types of assay cartridge 200 may be utilized. Under these circumstances, different types of assay cartridges 200 may be placed in different areas of the cartridge loading unit 112 for selective introduction into the system workflow as they are needed. In the embodiment shown in FIG. 7(a), different types of assay cartridges 200 may be loaded into separate lanes (112(b) and 112(c)). Alternatively, different assay cartridge types may carry indicia signifying the cartridge type and may be loaded at any available location in a cartridge loading unit 112 or equivalent structure. Use of different types of assay cartridges supports the use of different processing protocols, which in turn allows the system to both process a broader range of sample types and to perform a greater variety of assays than could be supported by a single type of assay cartridge.

In some embodiments, an assay cartridge 200 is transferred from a cartridge loading unit 112 prior to receiving the sample aliquot. As shown in FIG. 1(b), the assay cartridge 200 can be transferred from the cartridge loading unit 112 by moving the assay cartridge to the cartridge loading lane 116(f). Once in the cartridge loading lane 116(f), the assay cartridge 200 may be brought into a position where the sample pipettor 70 can transfer the sample aliquot (block 1816).

In an embodiment of the invention, and referring to FIG. 4(a)-1, the assay cartridge 200 can be supplied with a protective barrier film 205 overlying the reagent wells 204, 208, 209. This film 205 can be removed or pierced to gain access to the contents of the reagent wells 204, 208, 209. In one embodiment, the system utilizes a piercing element end 266 (a) of a film piercer 262, shown in FIG. 4(f), to pierce the film overlying the reagent wells 204, 208, 209. This film piercer 262 may be conveniently supplied as part of the assay cartridge 200. Film piercing may take place while the cartridge is in the sample aliquot transfer location, utilizing the sample pipettor 70 to manipulate the film piercer 262. The film piercer 262 may be used prior to transfer of the sample aliquot to the assay cartridge 200, followed by disposal of the film piercer 262. The film piercer 262 may have a cutting edge that slices through the film covering the reagent wells 204, 208, 209 with minimal resistance, thereby avoiding the aerosolization of the well contents and subsequent contamination issues. In an alternative embodiment, the system may utilize the millitip 220 supplied on the assay cartridge 200 to pierce the film covering the reagent wells 204, 208, 209, and supply reagents to the reaction well in the assay cartridge.

The assay cartridge 200 can also receive reagents from other sources, which may be stored in a reagent storage unit 124 of the system as shown in FIG. 1(b), while in the cartridge loading lane. Such sources may include bulk bottles. In some embodiments, this is accomplished using the XYZ transport device 130. FIG. 9(a) illustrates an embodiment in which such reagents are stored in a disposable multiuse reagent pack 400. As noted above, the reagent pack 400 contains liquid reagents required for the performance of a specific assay. Examples of materials transferred to an assay cartridge 200 from a reagent pack 400 at this point in the process may include, but are not limited to, process control materials that can indicate successful extraction of nucleic acids, enzymes that support lysis of bacteria, and magnetically responsive microparticle suspensions. In some embodiments, materials from the reagent packs are added to the assay cartridge after the sample aliquot has been added. In other embodiments, materials from the reagent pack 400 can be added to the assay cartridge 200 before the sample aliquot is added. In yet another embodiment, some materials from the reagent pack 400 are added to the assay cartridge 200 (e.g., to the reaction well) before the sample aliquot is added while others are added afterwards.

As noted above, the reagent pack 400 can be a consumable item. Reagent packs 400 may added to the system by the user via loading (block 1836) into a reagent storage unit 124. An exemplary reagent storage unit 124 is shown in more detail in FIGS. 8(a)-8(c). In operation, a user may request that the instrument provide a loading opportunity. In preparing for the loading opportunity, the system may release selected reagent packs 400 from the reagent storage unit 10 by releasing the latch assemblies 144 associated with the selected reagent packs. During the loading opportunity, a user may open the RSU access door 126 and view status indicators 140 associated with each loaded reagent pack 400. The user may remove any released reagent packs 400 and insert any new reagent packs 400. The instrument verifies the changes by reading the electronic memory associated with each loaded reagent pack 426. The reagent pack 400 may hold sufficient reagent for a number of assays, and may be accessed multiple times while stored within the reagent storage unit 124. During the reaction storage unit operation (block 1838), the system may monitor fluid levels within the reagent pack 400 using a fluid level sensing circuit in order to determine when the reagent pack is exhausted. Alternatively, the system may aggregate data related to the usage of a reagent pack 400 and relate that data to known fill volumes in order to determine when a reagent pack is exhausted. The system may notify the user of exhausted or soon to be exhausted reagent packs so that they can be replaced without impacting workflow (block 1844). In some embodiments, the user may remove a reagent pack on request for off-board storage.

Following addition of a sample aliquot and any necessary reagents from the reagent pack 400, the assay cartridge 200 is transferred to a processing area (block 1818). Referring additionally to FIGS. 1(*b*) and 4(*a*)-1, the assay cartridge 200 is moved from the cartridge transfer lane 116(*f*) to the transfer shuttle 50. The transfer shuttle 50 shuttle moves the assay cartridge 200 through a series of the processing lanes 116 as directed by the protocol associated with the aliquoted sample. A protocol may designate the repeated use of a specific processing lane at different times as the protocol progresses. The system may subject assay cartridges to different processing protocols to extract and purify nucleic acids. For example, the system can treat DNA assay cartridges differently from RNA assay cartridges to reflect the physical-chemistry requirements of the different purification procedures. Further, the system may also use different protocols for samples that use the same type of assay cartridge. For example, DNA extraction from gram positive bacteria may require a different collection of steps to lyse the more robust walls of the bacteria than the steps required for other DNA isolation. The system may, for example, apply heat to a DNA assay cartridge applied to extraction and purification of DNA from gram positive bacteria. This heating step produces an extended elevated temperature that aids in lysis of the gram positive bacterial cell walls.

The system benefits from applying different protocols by savings in time and by avoidance of incompatible conditions. Different protocols save time by skipping unneeded steps. For example, extraction and purification of DNA from gram positive bacteria requires a period of heating that is not required for DNA from other sources. While applying a heating step to such sample may not be harmful, by deleting the heating step the system can process DNA from these other samples more rapidly. This flexibility in processing reduces time to result compared to the alternative of subjecting all samples to the same timeline. Without use of different protocols the slowest method required by any individual assay would necessarily dictate system processing time.

Applying different protocols may avoid incompatible conditions in situations where the conditions for one extraction and purification process are irreconcilable with those of another. A system might adapt a single processing protocol and avoid some incompatibilities, such as that due to the gram positive bacteria heating step mentioned above, by, for example, simply placing an assay cartridge in the appropriate processing lane without activating the heater. Similarly, false reagent transfers (i.e. performed without reagent pickup or delivery) or transfers of inert reagents could possibly allow a common processing protocol for all samples. Such adaptive methods, however, still limit the performance of a single processing protocol system performance to that of the most restrictive method. Further, a common processing protocol may simply not be possible when mere delay causes the incompatibility. Time delay alone may be problematic, for example, when a protocol depends on the action of an enzyme and the length of time controls the extent of enzymatic action. Applying different processing protocols avoids this processing bottleneck and retains flexibility to apply new or updated methods.

The system applies multiple protocols by routing each assay cartridge through a series of processing lanes 116. Each processing lane 116 acts on the assay cartridge 200 to perform a subset of the total processing steps in a protocol. Any given protocol may route assay cartridges 200 through some or all of the processing lanes 116. Different protocols may use some of the same processing lanes 116. In one embodiment, each instance of a protocol routes the assay cartridge 200 associated with that instance through the same sequence of processing lanes 116 on the same relative timeline.

Each processing lane 116 may accommodate only one assay cartridge 200 at a time. This advantageously simplifies system design by allowing use of a single mechanism for transferring assay cartridges 200 between processing lanes 116 and increases processing flexibility by eliminating resource conflicts within a processing lane.

Each instance of a protocol may use a consistent pathway and consistent timing. In this embodiment, for a given protocol each specific processing step uses a designated mechanism in a designated location at a designated time relative to the start of that instance of the protocol. For example, one version of the DNA gram positive isolation and purification protocol requires a transfer of diluent to the reaction well following addition of magnetically responsive microparticles. In this protocol, the transfer can always occur in processing lane 2, always using the processing lane 2 pipettor 244 seconds after the start of sample aliquoting. This practice advantageously reduces assay variation by assuring that each assay receives the same treatment by the same mechanisms. Replicates of a single mechanism, even though products of the same design using the same manufacturing process, may not perform identically. Each replicate suffers variations caused by deviations within manufacturing tolerances, local nonuniformities in operating environment, wear and operating history, and from other sources beyond reasonable enumeration.

In one embodiment, the system avoids much of the effect of non-identical mechanism performance by always using a designated mechanism for each particular step in each protocol. This design reduces the need to tightly match mechanism performance across different operative locations. For example, the processing lane 2 pipettor may transfer a different actual amount than does the processing lane 3 pipettor with the same nominal transfer volume. Processing lane 2 may have a slightly higher temperature in the vicinity of its pipettor than does processing lane 3. But because each instance of a protocol uses the same pipettor for a particular operation, the differences contribute an overall bias or systematic error rather than a random error. Such systematic variations may be corrected through calibration, but random variations associated with different mechanisms are much more difficult to correct. The system thus gains the benefits of improved assay precision without the expense and complexity of tightly matched components.

Assay precision may also be improved by reducing the impact of ambient temperature on sample processing operations. In one embodiment, this is achieved by routing all assay cartridges through a processing lane that incorporates an assay cartridge heater as an initial process step. Bringing the assay cartridge and its contents to a controlled temperature prior to the performance of temperature-sensitive processing steps improves the consistency of the results of such steps as ambient temperatures fluctuate. The temperature of the assay cartridge and its contents may be maintained subsequently by the use of assay cartridge warmers in other processing lanes.

The system may retain each assay cartridge 200 within a particular processing lane 116 for a fixed duration. This duration may be the same for any assay cartridge 200 in any processing lane 116 regardless of the protocol. This assures consistent timing for all steps in the protocol. Flexible lane-based processing ideally requires transfer of an assay cartridge from any lane to any other lane. In practice, some transfers may never occur. For example, assay cartridges 200 generally enter the amplification preparation lane 116(*g*) as shown in FIG. 1(*b*) only near the end of the process, and assay cartridges 200 that enter the waste lane 116(*c*) may only proceed to the solid waste disposable.

In some embodiments, the system transfers assay cartridges 200 between processing lanes 116 using a single transfer shuttle 50 in a random access arrangement that permits the transfer of an assay cartridge 200 from any processing lane to any other processing lane. The transfer shuttle 50 interacts only with the source and destination lane without interfering with any other lane. In one embodiment, the transfer shuttle 50 may transfer only one assay cartridge 200 at a time. In this context transfer between lanes includes unloading of an assay cartridge 200 from one identified lane and subsequent loading of the assay cartridge 200 into another identified lane. Transfer among processing lanes 116 is a broader term that includes transfer between identified processing lanes 116 and also includes the general process of unloading and loading without limitation to particular processing lanes 116. The transfer shuttle 50 may have multiple positions for carrying assay cartridges. In one embodiment, the transfer shuttle 50 includes two or more cartridge slots 50(*a*), 50(*b*). This arrangement permits the exchange of one assay cartridge 200 for another within a processing lane in a single step. This arrangement may allow cartridges to be switched between different lanes within a single operational, or pitch, interval, as described below. Two or more of such switching steps may be combined to exchange assay cartridges 200 between processing lanes.

FIG. 20(*h*) shows a top plan view of a system with two cartridge slots 50(*a*) and 50(*b*) that can be used for switching assay cartridges 200 between different processing lanes 116. The embodiment of the instrument in FIG. 20(*h*) includes many other lanes discussed in more detail above. The number and precise configurations and properties of wash lanes 116 (*a*) and 116(*a*)' (and 116(*b*), which is not shown in FIG. 20(*g*)) and temperature stabilization lanes 116(*j*) (and 116(*h*), which is not shown in FIG. 20(*g*)) may vary based on design and biological objectives.

FIG. 20(*i*) shows an embodiment of a cartridge-switching process. At block 3605, a first cartridge enters a cartridge loading lane 116(*f*). At block 3610, one or more samples and assay process controls are loaded into the first cartridge, which may be performed in one or more steps. The assay process controls may include a process control composition used to assess whether later-performed extraction and purification steps were properly performed. If a control was not sufficiently amplified, it may be concluded that the samples in the assay cartridge did not undergo proper processing.

At block 3615, a first slot ("Slot A") 50*a* of the transfer shuttle 50 engages the first cartridge. At block 3620, the first cartridge is moved by the transfer shuttle 50 to the heating lane 3116(*i*) and it is unloaded in the lane. The first cartridge may be warmed for a warming interval, e.g., between about 10-300 seconds, such as about 53 seconds. The first cartridge may be heated to a temperature of about 35-45° C. (e.g., the target temperature is 35° C. plus or minus 3° C.). One or more of the first cartridge, contents of the first cartridge's medium wells, contents of the first cartridge's large wells, and contents of the first cartridge's reaction vessel component holders may be heated to one or more desired temperatures.

As shown on the right hand side of FIG. 20(*i*), a second cartridge can be undergoing a similar set of steps, except that it is behind in time. That is, steps 3705, 3710, and 3715 are similar to steps 3605, 3610, and 3615.

At block 3625, a second slot ("Slot B") 50*b* of the transfer shuttle 50 engages the warmed first assay cartridge, followed immediately by unloading of the second assay cartridge in Slot A into the heating lane 3116(*i*). This substantially simultaneous transfer of assay cartridges into the out of Slots A and B improves the speed of processing, as compared to the case where there is only one slot in the transfer shuttle.

At block 3630, the first cartridge is moved by the transfer shuttle 50 back to the loading lane 116(*f*). At block 3635, reagents are added to the first cartridge in the loading lane 116(*f*). At block 3640, the first cartridge continues to the next lane in a processing recipe. Blocks 3725, 3730, 3735, and 3740 are similar to blocks 3625, 3630, 3635, and 3640.

As illustrated above, the multiple cartridge slots 50*a*, 50*b* in the transfer shuttle 50 may allow for multiple cartridges 200 to be swapped within a single lane, or even between adjacent lanes.

In other embodiments, the slots of the transfer shuttle may permit two cartridges to be simultaneously loaded or heated, but not overlapping within each other in the loading lane 116(*f*) or the heating lane 3116(*i*). Thus, a cartridge heater may be at least partly loaded and heated within a single pitch (e.g., about 100-200 s). While the time between other processing steps may be approximately the duration of one pitch, both heating and partial or full loading may be occurring within the same time interval. This may improve the temporal efficiency of the instrument. Additionally, by using a two-slot transfer shuttle, a single motor may control the movement of both assay cartridges.

In some embodiments, protocols may diverge further from pipeline architecture. That is, some protocols including relatively rapid processing may start later but finish earlier than other protocols including less rapid processing. This has the benefit of providing further flexibility to support rapid protocols without significant constraint by slower protocols.

The capability for later started assay cartridges to "pass" earlier started assay cartridges is available through the flexible capacity of the transfer shuttle. The transfer shuttle 50, as described above, may transfer an assay cartridge 200 from any source lane to any destination lane; it is not limited to transfers between adjacent lanes. Since transfer windows are staggered, the system may, for example, launch a first protocol routing a first assay cartridge in successive pitches to each of lanes 1-13 in succession. The system may then launch a second assay cartridge in lane 1 after the first assay cartridge transfers from lane 1 to lane 2. The second assay cartridge may in the next pitch interval transfer from lane 1 to lane 13 where it would complete its processing. Long distance transfers of this type may occur in what would otherwise be transfer shuttle idle time. Thus, in such embodiments, later started assay cartridges may finish processing before some earlier started assay cartridges. This advantageously allows rapid processing of selected specimens.

In some embodiments, protocols may include conditional branches. That is, the system can process an assay cartridge 200 in a manner where further processing includes a first set of steps if a condition is fulfilled and a second set of step if a condition is not fulfilled. For example, the system might transfer an assay cartridge 200 to a waste lane 116(*c*) if some essential component were missing. In some embodiments, the system might repeat a wash step if washing were determined to be inadequate.

Conditions may include anomaly sensing, efficacy sensing, external input, or a variety of other conditions limited only by the value of altering a protocol on the occurrence of the condition.

Anomaly sensing can include detection of anomalous events such as failure to detect pick up of a millitip 220, microtip 490, reaction vessel plug 222, or reaction vessel 221. Other examples of anomalous events include detection of pressure that does not match an expected profile or value during pipetting and detection of reagent or sample fill volumes outside of expected bounds.

Efficacy testing can include any test of an intermediate result during processing. For example, the system may assess wash efficacy by measuring the amount of residual fluid after washing using the liquid level sensor to determine the height of fluid in the reaction well 202. Other exemplary efficacy tests include measurement of assay cartridge temperature after exposure to a lane heater 1103 and determination of magnetically responsive solid phase dispersal prior to transfer from the reagent well or after resuspension in the reaction well. The later may be measured by optical or magnetic measurement of compartment contents.

External input can include operator input such as correction of a mistakenly entered sample type or sample dilution factor.

Any yet unprocessed portion of a protocol may be subject to a branch. Branches may be limited to activities within a pitch or may span activities between pitches. Branches may alter transfers between lanes and may combine some or all of these variations. Protocols can include multiple conditional branches.

In some embodiments, conditional branches may be limited to aborting a protocol in progress if a fatal condition is met. For example, if the system detected that no millitip 220 is present in an assay cartridge, processing of that cartridge may be aborted immediately or at the next available transfer window. Rather than further processing an assay cartridge 200 where no test result could be determined, the system might use the transfer shuttle to move that assay cartridge to the waste lane directly. A replacement assay cartridge could then be launched during the next available pitch interval to start the protocol anew.

In other embodiments, anomalies may occur that are not fatal to further processing. For example if the system failed to detect a resuspension buffer in a compartment of an assay cartridge 200, the system might alter the processing protocol to provide that resuspension buffer from another compartment containing a reserve supply. Similarly, processing may continue using resuspension buffer from another source such as a different assay cartridge 200, a reagent pack 400, or a bulk supply bottle.

In some cases, such as when reserve stocks of reagents are drawn from a reagent pack 400, the system might route an assay cartridge 200 to another processing lane 116 to provide the reserve reagent. Depending on lane availability and the tolerance of the protocol to delay, rerouting of an assay cartridge may occur either within a pitch interval or at a normal pitch interval transition. Some protocols may be tolerant of delay in some operations. For example, some protocols may tolerate delays after washing of solid phase but before resuspension of the solid phase. This gives an opportunity to resume processing after a delay to obtain resuspension buffer from another source. This advantageously avoids loss of expended reagents, sample, and time when results are not at risk.

In some embodiments, protocols may include loops. Loops are processing activity where an assay cartridge 200 returns to a processing lane 116 used during an early pitch in a later pitch. One example of a loop is the process for routing an assay cartridge 200 from a cartridge loading lane 116(*f*) to a different processing lane, then returning it to the cartridge loading lane 116(*f*), as described above. In another example of a protocol that includes a loop a given assay cartridge 200 may be routed to a processing lane X at pitch N and returned to processing lane X at a pitch N+Z, where Z is a positive number. In some embodiments, protocols may include multiple returns one or more processing lanes. Loops may include conditional branches including conditional branches that terminate or extend loops. The protocol flexibility provided by branching and looping beneficially allows a large variety of processing, including processing developed after the system is deployed. This assures that the system will keep current in its processing capability as new assay types are developed.

In alternative embodiments a pipeline design could advance all assay cartridges within a protocol by aligning involved lanes and displacing assay cartridges to adjacently aligned lanes. A pipeline style design may transfer assay cartridges 200 singly or in groups. Another alternative could utilize multiple parallel shuttles attached to a common transport. The common transport may displace the parallel shuttles by one or lane increments. This alternative allows selective transfer of individual assay cartridges between adjacent lanes, and mass transfer of each assay cartridge to its neighboring lane.

In the preferred random access design shown in FIG. 1(*b*), the transfer shuttle 50 transfers assay cartridges 200 in a time-staggered fashion in order to avoid conflicts. For any particular lane used in a protocol, the transfer shuttle loads successive assay cartridges at fixed intervals. The interval may be the same irrespective of the processing lanes involved. This interval, also called the pitch interval, may be of any length, but is at least equal to the product of the time required for the transfer shuttle 50 to perform a transfer operation and the maximum number of processing lanes 116 used in an extraction and purification protocol. The time within a pitch interval may be subdivided in order to schedule the performance of multiple operations upon an assay cartridge within a single pitch interval. For example, an assay cartridge 200 may undergo multiple fluid transfers while held in a processing lane 116 during a single pitch interval. As noted above, in some circumstances a pitch interval may be divided between two assay cartridges 200 using a switching operation. The use of time-staggered transfer with a fixed pitch interval advantageously allows a single transfer shuttle to complete all transfers while maintaining a consistent residence time for an assay cartridge in each processing lane. The use of a fixed pitch interval also advantageously simplifies scheduling of multiple processes that are being performed simultaneously within the system. The use of time-staggered transfer implies that operations on different assay cartridges in different processing lanes may overlap in time. Some operations may proceed within one processing lane in the same time interval that the transfer shuttle 50 uses to transfer a different assay cartridge from a second processing lane to a third processing lane.

In one embodiment, the pitch interval is 150 seconds. The length of this pitch interval may be greater than the product of the time required for the transfer shuttle 50 to perform a transfer operation and the maximum number of processing lanes 116 used in an extraction and purification protocol. In such an embodiment, the transfer shuttle may be idle at least part of the time.

The system may reserve fixed transfer windows for each possible transfer shuttle 50 operation. The preferred length of a transfer window is approximately five seconds. If an assay cartridge 200 were present in a processing lane 116, the transfer shuttle 50 would transfer it to the next processing lane in the protocol during the window associated with that pair of processing lanes. For example, a transfer of an assay cartridge 200 from the elution lane 116(e) to the amplification preparation lane 116(g) may occur in a transfer window beginning 100 seconds after pitch start. If, however, no assay cartridge 200 were present in the elution lane 116(e) during a particular pitch, the transfer shuttle 50 would be idle during the transfer window. Depending on the distribution of assay cartridges in the processing lanes, the transfer shuttle may be active during each transfer window, during some of the transfer windows, or during none of the transfer windows. The last occurs only if no assay cartridges are in process.

The dedication of transfer windows within a pitch interval to pairs of lanes may require that the destination lane for each transfer be vacant before the transfer window occurs. Each processing lane 116, except the first and last processing lanes in a protocol, may need two transfer windows. The first transfer window allows transfer of an assay cartridge 200, if one were present, out of the processing lane to a successor lane. The second transfer window allows transfer of an assay cartridge 200, if one were present, into the processing lane from a predecessor lane. A consequence of this "empty before filling" requirement is that the system dedicates the earliest transfer window in a pitch interval to the last processing lane pair in a protocol. This creates a "hole" in the next to last processing lane. To account for this the system may assign subsequent transfer windows in reverse order of the processing lane usage, so that the hole propagates through processing lanes in successive transfer windows until it reaches the first lane in the protocol. The next transfer window may then occur in the following pitch interval. In an alternative embodiment, the use of a transfer shuttle 50 with multiple positions for assay cartridges 200 may allow the transfer shuttle to act as temporary storage for assay cartridges being transferred, permitting assay cartridge switching between processing lanes as described above. Such a switching operation may take place within a single pitch interval.

As noted above, different protocols may route assay cartridges 200 through different sequences of processing lanes. The system may transfer assay cartridges among processing lanes despite a difference in processing lane sequence between protocols by fixing the transfer windows for transfers that are common to all protocols, by sharing transfer windows among processing lane pairs, by delaying the start of an instance of a protocol for one or more pitches to avoid timing conflicts, and by allocating multiple transfer windows to conflicting processing lane pairs.

Some transfers may be common to all protocols. For example, assay cartridge 200 disposal in the waste lane 116 (c) may always follow amplification mixture preparation in the amplification preparation lane 116(g). Amplification mixture preparation in the amplification preparation lane 116(g) may, in turn, always follow nucleic acid elution in the elution lane 116(e), which may always follow a small magnet wash in the wash lane 116(b). Transfers among these lanes need not present any special timing problems; the system may use fixed transfer windows for such transfers. The system may also use fixed transfer windows when transferring assay cartridges among lanes used only by a single protocol. Transfers among these lanes present no timing conflicts.

The system may share a fixed transfer window when a common source lane transfers to two or more different destination lanes. This need not present a timing conflict, as the system may transfer an assay cartridge 200 in the source lane to only one of these destination lanes at a given point in the protocol. The source lane can maintain a single transfer window to unload; the destination lanes may share this single fixed transfer window to receive an assay cartridge from the source lane.

The system may also share a fixed transfer window when a common destination lane receives transfers from more than one source lane. This can generate a timing conflict. In one embodiment, the destination lane maintains a fixed transfer window to avoid shifts in timing that might propagate to subsequent transfers and create further conflicts. Since the destination lane may receive only one transfer, the system may schedule protocol instances so that only one of the source lanes contains an assay cartridge. This may require that the system look ahead to determine a possible conflict and delay the start of an instance of a protocol for one or more pitch intervals to avoid the conflict.

The system may allocate multiple transfer windows when a protocol inserts the use of one or more non-common processing lanes between lanes that are common to another protocol. These inserted lanes require at least one pitch interval, but the subsequent return to the common lanes requires preservation of the common lane transfer windows in order to minimize timing conflicts. Providing more than one transfer window allows the system to select among transfer windows to minimize conflicts. The system may shift the transfer from the last common lane before the insert to the later transfer window. The system may return to the common lane timing when the assay cartridge returns to the common lanes. For example, the RNA protocol may insert a non-common step by transferring the assay cartridge 200 sequentially through processing lanes 8, 9, and 10. DNA protocols may not use lane 9, but rather move the assay cartridge 200 directly from lane 8 to lane 10. In this instance the system may include two transfer windows to move assay cartridges out of lane 8. The first window begins at 110 seconds after pitch start. The second transfer window begins at 115 seconds after pitch start. The RNA protocol uses the later transfer window to move the assay cartridge from lane 8 to lane 9 at 115 seconds after pitch start. The DNA protocols use the earlier transfer window. Every protocol transfers an assay cartridge into lane 10 at the transfer window beginning 110 seconds after pitch start. The multiple transfer windows for lane 8 produce a dead period in the lane 8 pitch interval for the DNA protocols. During this dead period, lane 8 sits empty. The dead period does not upset processing timing because it is consistent for each instance of the DNA protocols.

As discussed above, a switch between protocols may cause a timing conflict that the system may resolve by delaying a protocol start for one or more pitch intervals. Such a delay may reduce system throughput. The system minimizes the number of such delays by scheduling assays so as to minimize any delays. In some embodiments, the system starts all pending assays that use the same protocol before starting any pending assays that use a different protocol.

Within a pitch interval, and subject only to the timing of transfer windows, a protocol may use a processing lane to perform any operations of which the lane is capable. These operations may be in any sequence and may be of any duration. The system may perform two or more consecutive sets of processing steps in a single processing lane over multiple pitch intervals without transferring the assay cartridge 200. The system thus provides two levels of protocol flexibility: first, a protocol may selectively route assay cartridges among processing lanes; and second, a protocol may freely select operations within a processing lane. First and second assay cartridges may be used to process samples according to first and second protocols, wherein the first and second protocols may be different.

As noted above, while the system may transfer an assay cartridge 200 between any two processing lanes 116 in order to accommodate a variety of sample types and assay chemistries, the general workflow of the isolation process may be similar. This provides that certain general steps may occur in the same sequence. Nucleic acid extraction and isolation methods are known and described, e.g., in Merel et al. (1996) *Clinical Chemistry* 42:1285-6; Ausubel et al. *Current Protocols in Molecular Biology* (2003 ed.), Sambrook et al. *Molecular Cloning* ($3^{rd}$ ed); Bailey et al. (2003) *J. Assoc. Lab. Automation* 8:113-20. The process generally includes steps of sample treatment, binding of the nucleic acids in the sample to a solid or suspended particulate phase, separation of the bound nucleic acids from unbound components of the sample, washing the solid or suspended particulate phase, and elution or release of the nucleic acid back into solution. The purpose of these steps is to release nucleic acids from cells, nuclei, or sample matrix, to reduce or eliminate components that may interfere with nucleic acid amplification or detection, and to adjust the concentration of nucleic acids relative to the concentration in the original sample. Variations of the described process and other nucleic acid isolation protocols are also within the scope of the invention. Variations may include changes in the volumes of materials transferred, in the conditions of chemical processing steps, in the sequence of operations, in the number of wash steps, and other changes.

In one embodiment, the system extracts and purifies nucleic acids by mixing magnetically responsive microparticles with an aliquot of sample and reagents under environmental conditions that favor binding of nucleic acids to the solid phase. When extraction and purification are performed in a cartridge such as the one shown in FIG. 4(*a*)-1, reagents transferred from the reagent wells 204, 208, 209 to the reaction well 202 of the assay cartridge 200 in early steps of the protocol may provide conditions that favor binding of the target nucleic acid sequence to the magnetically responsive microparticles. Reagents may be arranged in the wells of the assay cartridge 200 in an order that reflects their use, so that droplets that accidentally fall during reagent delivery operations only land in previously emptied wells.

Once the nucleic acids bind to the solid phase the system may transfer the cartridge to wash lanes, such as 116(*a*) and 116(*b*) of FIG. 1(*b*), to remove unbound material by applying a magnetic field to the reaction mixture; magnetic microparticles respond to the applied magnetic field by moving within the reaction mixture, thereby segregating the solid phase from the bulk liquid. The system can then remove the bulk liquid by aspiration, leaving behind the solid phase. An embodiment of a processing lane that includes such a magnetic separator is shown in FIG. 10(*b*) and described in more detail above. In subsequent steps, the system may wash the solid phase by adding a wash liquid, re-suspending solid phase to form a suspension in the wash liquid, and again segregating the solid phase followed by aspiration of the liquid portion of the reaction mixture while leaving behind the solid phase. This wash step may be repeated several times, and may involve the use of one or wash liquids. In some embodiments, expended wash liquids are returned to previously emptied wells of the assay cartridge 200 for eventual disposal. When washing (block 1820) is complete, the system may transfer the cartridge to an elution lane 116(*e*) and add an eluent, which releases the nucleic acid from the solid phase and back into solution within the eluent volume (block 1822). The system may complete the nucleic acid extraction and purification process by transferring the cartridge to an amplification preparation lane 116(*g*) and again segregating the solid phase through application of a magnetic field, followed by aspiration of the eluent volume and transfer of the eluent volume containing the isolated nucleic acid to a reaction vessel for further processing (block 1824). In an alternative embodiment, the system may transfer reagents required for amplification to a reaction vessel prior to transfer of the eluent volume containing the isolated nucleic acid to the reaction vessel.

The solid phase can be a magnetically responsive solid phase. Under these circumstances, an applied magnetic field can act as a controllable switch to selectively anchor a magnetically responsive solid phase. If the solid phase is a suspension of magnetically responsive microparticles these may form a distinctive "pellet" against a desired location on the interior wall of a container on application of a magnetic field. The location, shape, and size of this pellet can be controlled by controlling the distribution and intensity of the magnetic field, advantageously permitting the system to generate pellets of solid phase at different locations within a container, and with desirable characteristics for avoiding nonspecific aggregation of the particles and for resuspension on removal of the magnetic field. This advantageously simplifies automation because the system may simply apply a magnetic field either by disposing the magnetically responsive solid phase in proximity to magnetic materials or by activating an electromagnet.

Although a magnetically responsive solid phase is preferred, other solid phases may also be suitable. For example, the system may manipulate the solid phase by settling under gravity or centrifugation, by filtration, by size exclusion chromatography, by optical tweezers, by electrophoresis, by dielectrophoresis, by flow cytometry based sorting, by mechanical obstruction such as the use of solid phases too large to fit within a pipette during separation, or by any of a number of other methods.

The magnetically responsive solid phase is preferably a suspension of magnetically responsive microparticles. They advantageously simplify automation as the system may transfer a measured amount of solid phase by simple pipetting, which is a well-established and repeatable process. Pipetting has the further benefit of commonality with other liquid reagent transfers. That is, the system needs no additional devices to transfer the solid phase. A suspension of magnetically responsive microparticles has the further advantage of improving assay speed and precision by providing a more uniform interaction between solid phase and solvated components of the liquid reaction mixture. A dispersed suspension of microparticles reduces the time required for nucleic acid isolation by minimizing diffusion distances between reactants. This dispersion also improves uniformity by providing each element of the liquid reaction mixture with approximately equal access to the solid phase as each other liquid element. This improved reaction uniformity directly enhances assay reproducibility, and hence precision. Magnetically responsive microparticles are known in the art and are commercially available. Microparticles for nucleic acid binding can be functionalized with various species that will attract and bind nucleic acids, including, but not limited to, nucleic acid sequences, proteins, dyes, hydrophilic groups, hydrophobic groups, and charged groups.

Processing a sample in this fashion provides the opportunity to concentrate the isolated target nucleic acid in a reduced volume. The system may adjust nucleic acid concentration by isolating nucleic acids from relatively large sample volumes and eluting the isolated nucleic acids from the solid or suspended particulate phase in a relatively small volume. This has beneficial effects of reducing assay time, increasing assay sensitivity, and improving assay precision. In some embodiments, the volume of sample initially transferred is about 1 mL and the volume of eluent added is about 40 µL. In some embodiments, the volume of eluent transferred to the amplification vessel is smaller than the volume of eluent added, in order to account for dead volume in the reaction vessel and minimize the chances of inadvertent transfer of solid phase to the reaction vessel. In some embodiments, the volume of eluent transferred is about 25 µL.

Adjusting nucleic acid concentration can advantageously reduce assay time by reducing the volume of subsequent reactions. PCR is dependent on cycling the reaction volume through a series of temperature changes. Small amplification reaction volumes permit reduced thermal pathlengths, leading to more rapid thermal equilibration of the entire reaction volume and hence reduced temperature cycle time. Higher concentrations of target nucleic acids within the amplification reaction volume can also reduce the number of amplification cycles required for detection, as the growth curve that characterizes successful PCR amplification will become evident earlier in the process.

As discussed above, a short thermal pathlength allows rapid thermal equilibration of a reaction volume. This in turn enables rapid temperature changes during amplification reactions. Thermal cycling-based amplification methods typically cycle amplification reaction mixtures through a number of target temperatures, each target temperature supporting one or more phases of the amplification reaction. A typical PCR amplification may require 50 or more of these temperature cycles. Rapid temperature changes reduce the time required for each cycle of amplification. This reduced cycle time is especially desirable as even small time savings accumulate rapidly over multiple amplification cycles, thus reducing the overall time required to produce answers.

Adjusting nucleic acid concentration can increase assay sensitivity by keeping the number of amplification cycles within a reproducible range. Exponential nucleic acid amplification, such as PCR, is subject to noise and to nonspecific amplification that may produce an erroneous signal if the reaction is allowed to continue for a large number of cycles, even in the absence of the target nucleic acid. As a result, attempting to improve the sensitivity of a PCR-based assay by simply extending the number of amplification cycles soon encounters a limiting condition. By including a higher concentration of target sequences in the initial amplification mixture, a signal that is attributable to target amplification can appear in earlier cycles, thus avoiding erroneous results from spurious amplification events. The higher target sequence concentration attainable by adjusting the nucleic acid concentration increases confidence that signals observed reflect the actual presence of target sequences rather than spurious events. Since assay sensitivity depends, at least in part, on distinguishing target-based specific signal from non-target spurious signals, higher initial target sequence concentrations improve overall assay sensitivity.

Adjusting nucleic acid concentration also improves assay precision by reducing the effect of sampling error. Amplification based assays permit the detection of extremely low concentrations of target sequence. Some target nucleic acid sequences may be present at such low concentrations that individual aliquots taken from the same sample may have significant variations in the number of target sequences present. This variation establishes an irreducible minimum of imprecision in determination of the target concentration in the aliquot. For example, where each milliliter of sample contains 1000 copies of a target nucleic acid sequence, 5 µL, aliquots of such a sample would contain, on average, five copies. Basic statistics show, however, that less than 18% of individual 5 µL aliquots would contain this average number of copies. About 3% of 5 µL aliquots would contain at least ten copies; tests on these aliquots would overestimate target sequence concentration by a factor of two or more. A small fraction of 5 µL aliquots would contain no target nucleic acid sequences at all, so that mere detection of the presence of the sequence would be impossible. One way to reduce the effect of sampling error is to increase the volume of the sample aliquot. However, this would necessarily increase the final reaction volume. For the reasons noted above, this is undesirable. Adjusting nucleic acid concentration allows use of a large initial source sample aliquot, the nucleic acids of which are released by sample processing into a smaller test aliquot to increase the number of target nucleic acid sequence copies in the amplification mixture, while retaining the time savings and other benefits of small amplification volumes.

As noted above, the system may accomplish the goal of adjusting nucleic acid concentration by isolating nucleic acids using a solid phase. This solid phase may be a particulate or microparticulate phase that can remain in fluid suspension for a time, which advantageously simplifies handling and improves reaction kinetics. Solid phase processing permits separation and exchange of liquid components of a reaction mixture while retaining specific reactants, such as nucleic acids, that are bound to the solid phase. This binding may be physical or chemical, but the separation process is mechanical. Solid phase processing is beneficial because its mechanical separation process is readily automatable, and can provide a cleaner separation than the precipitation or liquid/liquid phase separations of conventional chemical processes.

Although solid phase processing is preferred, other methods of adjusting nucleic acid concentration may also be suitable. For example, the system may precipitate nucleic acids and separate the precipitate from the remaining supernatant by filtration or centrifugation. Alternatively, the system may extract nucleic acids by differential solubility in organic and aqueous phases or by separating the nucleic acids from other constituents by electrophoresis, column chromatography, or by any of a number of other methods. In order to utilize this method to concentrate isolated nucleic acids, the system can have the capacity to accurately dispense both large and small volumes.

Accordingly, the system may include both large volume pipettors that utilize millitips 220 provided in the assay cartridge 200 (as shown in FIG. 4(*a*)-1) and small volume pipettors that utilize microtips 542 that are incorporated into the processing lanes 116 or have access to them. Microtips 542 may be supplied in microtip racks 550, as shown in FIG. 13(*f*), that are loaded onto the system by the user 1840. In an embodiment shown in FIG. 1(*c*) the system includes a microtip storage unit 120 for this purpose. A detailed description of a preferred embodiment of a microtip storage unit is found above and in FIGS. 13(*a*), 13(*b*), and 13(*c*). The system may automatically deposits expended microtips 542 into solid waste, such as the solid waste container 92 shown in FIG. 1(*d*), but users may need to unload empty microtip racks 550. Alternatively, the system may dispose of used mictrotips within the wells of an assay cartridge 200. The multiple slots within the microtip storage unit 120 allow the system to use all microtips 542 within a microtip rack 550 without concern of running out of microtips 542; microtip racks 550 in other slots provide a reserve capacity.

Users may unload empty microtip racks 550 once the system has used all microtips 542 in a microtip rack 550. In operation, a user may request that the instrument provide a loading opportunity. In preparing for a loading opportunity, the system may release empty microtip racks 550 from the microtip storage unit 20 by releasing the rack clasp 554 associated with the selected microtip racks 550. During a loading opportunity, a user may open the access cover 556 and view indicator lamps associated with each loaded microtip rack 550. The user may remove any released microtip rack 550 and insert any new microtip racks 550. In some embodiments, users may not reload microtip racks previously unloaded back onto the system. This advantageously limits the possibility of contamination from user handling of exposed microtips.

Following isolation of the target nucleic acid, at least a portion of the elution volume containing the target nucleic acid is transferred to a reaction vessel 221 that may be provided on the assay cartridge 200, as shown in FIG. 4(a)-1. In some embodiments this takes place in an amplification preparation lane, such as 116(g) of FIG. 1(b), which may also be accessible to the XYZ transport device 40. Other materials useful for the amplification reaction may also be added to the reaction vessel 221. In some embodiments, these amplification materials are transferred to the reaction vessel 221 prior to the transfer of the elution volume to the reaction vessel 221. Such materials may include, but are not limited to polymerases required for nucleic acid replication, target-specific primer sequences, target-specific probe sequences, nucleotide triphosphates, and other materials that support the amplification reaction. These materials may be stored in the reagent storage module 10 and transferred using the XYZ transport device 40. Following the addition of processed sample and all necessary reagents the reaction vessel 221 may be closed using a plug 222. This plug 222 can be provided on the assay cartridge 200, and may include a handling feature 222(f) that allows it to be manipulated by the XYZ transport device 40. Insertion of the plug 222 into the reaction vessel 221 may seal the reaction vessel for the remainder of its time on the system.

After sealing, the reaction vessel 221 proceeds to the amplification and detection portion of the system (block 1832). Amplification phase processing centers on the reaction vessel 221 and the thermal cyclers. Processing in the amplification phase may be mechanically simple compared to the isolation phase. Once the amplification preparation lane 116 (g) mixes the isolated nucleic acid with amplification reagents in the reaction vessel, the system may seal the reaction vessel 221 and transport it to an available thermal cycler module. In a preferred embodiment, the system has multiple thermal cycler modules, which may be arranged in a garage 1200 as shown in FIG. 16(c). The performance of these thermal cycler modules 1300 may be matched, so that the path of the reaction vessel after leaving the processing lanes 116 may lead to any one of the thermal cycler modules 1300. The system may then lock the vessel into the thermal cycler module 1300 and begin the process of thermal cycling and monitoring (block 1832). The thermal cycling and monitoring continues until the earlier of signal detection or a pre-set number of thermal cycles without signal detection.

In some embodiments, particularly those associated with reverse transcription of isolate RNA sequences, the thermal cycler may heat the amplification vessel to a fixed temperature prior to initiating amplification by, for example, thermal cycling.

In some embodiments, the system monitors the progress of the amplification by illuminating the reaction vessel 221 with excitation light at selected points within each thermal cycle. The instrument may select these points based on the part of the thermal cycle and on the measured temperature in the amplification vessel. In some embodiments, the system measures the signal during the same portion of each thermal cycle, but the timing within the portion may vary so that the amplification vessel has a measured temperature equal to a preselected temperature at the time of measurement. This has the benefit of reducing variations in measurement that might otherwise contribute to assay imprecision. In another embodiment, the system measures the signal within a defined portion of a defined temperature versus time profile that the thermal cycler is directed to follow. This has the benefit of providing consistent thermal cycling times, thereby simplifying scheduling. The system may combine measurements from multiple thermal cycles to assign one or more values to the measured reaction (block 1834). Numerous methods of combining measurements are known in the art.

After removal of the sealed reaction vessel 221 the expended assay cartridge may be transferred to waste. In one embodiment, shown in FIG. 1(b), the transfer shuttle 50 moves the expended cartridge 1826 to a waste lane 116(c). As noted above, the waste lane 116(c) may be configured so that once an assay cartridge 200 is placed within it the assay cartridge 200 cannot be returned to the transfer shuttle 50. An embodiment of such a waste lane is shown in FIGS. 14(a), 14(b), and 14(c). The waste lane may be supplied with an aspiration probe 986 to remove remaining fluid contents of the cartridge to liquid waste 1830. The emptied assay cartridge 200 may then be discarded (block 1848) to the solid waste container 882. In some embodiments, the expended assay cartridge 200 is simply transferred to the solid waste container 882 along with any residual liquids it may contain.

After completion of thermal cycling, the system may release the reaction vessel 221 from the thermal cycler, and the XYZ transport device 40 may transfer (block 1850) the expended reaction vessel 221 to the solid waste container 882, thereby ending the processing of a specific sample. In some embodiments, the expended reaction vessel is disposed of by transferring it to a dedicated wasted container, which may be designed to avoid damage to the expended reaction vessel. In other embodiments, the expended reaction vessel is removed from the system by transferring it to an unloading rack, where it may be retrieved by the user for further analysis.

EXAMPLES

Each of the examples below summarizes the processing steps in a protocol. The processing steps include extraction and isolation of nucleic acids, set up of the amplification mixture, transfer of the amplification mixture to a thermal cycler, amplification and detection, and waste disposal.

Example 1

Gram Positive DNA: Group B Streptococcus Assay

| Pitch | Lane/Device | Operations |
|---|---|---|
| 1 | CLU Presentation Lane | Transfer sample aliquot to assay cartridge reaction well<br>Transfer process controls from reagent pack to assay cartridge reaction well (XYZ gantry) |

-continued

| Pitch | Lane/Device | Operations |
|---|---|---|
| 2 | 70° C. Processing Lane | Transfer enzyme from reagent pack to assay cartridge reaction well (XYZ gantry) Mix contents of assay cartridge reaction well Transfer assay cartridge to shuttle Retrieve assay cartridge from shuttle Temperature stabilize at 70° C. (90 seconds) Mix paramagnetic particles in assay cartridge reagent well Transfer buffer and paramagnetic particles from assay cartridge reagent wells to assay cartridge reaction well Transfer assay cartridge to shuttle |
| 3 | Wash Lane 1 (Large Magnet) | Retrieve assay cartridge from shuttle Mix contents of assay cartridge reaction well Apply magnet Aspirate liquid from assay cartridge reaction well Transfer assay cartridge to shuttle |
| 4 | Wash Lane 2 (Large Magnet) | Retrieve assay cartridge from shuttle Transfer wash buffer 1 from assay cartridge reagent well to assay cartridge reaction well Mix contents of assay cartridge reaction well Apply magnet Aspirate liquid from assay cartridge reaction well Transfer assay cartridge to shuttle |
| 5 | Wash Lane 3 (Large Magnet) | Retrieve assay cartridge from shuttle Transfer wash buffer 2 from assay cartridge reagent well to assay cartridge reaction well Mix contents of assay cartridge reaction well Apply magnet Aspirate liquid from assay cartridge reaction well Transfer assay cartridge to shuttle |
| 6 | Wash Lane 4 (Small Magnet) | Retrieve assay cartridge from shuttle Transfer wash buffer 3 from assay cartridge reagent well to assay cartridge reaction well Mix contents of assay cartridge reaction well Apply magnet Aspirate liquid from assay cartridge reaction well Transfer assay cartridge to shuttle |
| 7 | Elution Lane (Large Magnet) | Retrieve assay cartridge from shuttle Transfer elution buffer from assay cartridge reagent well to assay cartridge reaction well Mix contents of assay cartridge reaction well Apply magnet Transfer liquid from assay cartridge reaction well to reaction vessel Transfer assay cartridge to shuttle |
| 8 | PCR Preparation Lane | Retrieve assay cartridge from shuttle Transfer PCR reagents from reagent pack to reaction vessel (XYZ gantry) Transfer plug to reaction vessel and seal Transfer sealed reaction vessel to thermal cycler (XYZ Gantry) Transfer assay cartridge to shuttle |
| 9 | Waste Lane | Retrieve assay cartridge from shuttle Transfer assay cartridge to waste |
| 9 to N | Thermal Cycler | Amplify and monitor contents of reaction vessel |

To incorporate the use of the Cartridge Warming Lane, the processing of a series of assay cartridges is interleaved. Within a given pitch (X), at about 50 seconds after moving into the CLU presentation lane and receiving a sample aliquot, the assay cartridge (N) is moved to one of the two positions of the transfer shuttle. The shuttle moves to the Cartridge Warming Lane and retrieves the previous assay cartridge (N−1) in the series from the cartridge heater into the remaining open position, then transfers the current assay cartridge (N) to the cartridge heater. The previous assay cartridge (N−1) is then returned to the CLU presentation lane by the 60 second mark of the pitch (X) for further processing through the end of pitch (X), after which it moves on to the next lane in the protocol designated for assay cartridge (N−1) at the start of pitch (X+1). This leaves the transfer shuttle empty. A third assay cartridge (N+1) is moved to the CLU presentation lane at the start of pitch (X+1), receives a sample aliquot, and is moved to the transfer shuttle at about 50 seconds after the start of the pitch (X+1). The assay cartridge (N) is returned to the CLU presentation lane at the 60 second mark of the subsequent pitch (X+1) for further processing after it is switched in the Cartridge Warming Lane for the next assay cartridge (N+1) in the series, and so on.

Example 2

DNA: CT-NG Assay

| Pitch | Lane/Device | Operations |
|---|---|---|
| 1 | CLU Presentation Lane | Transfer sample aliquot to assay cartridge reaction well Transfer process controls from reagent pack to assay cartridge reaction well (XYZ gantry) Transfer dilution buffer from assay cartridge reagent well to assay cartridge reaction well Transfer digestion buffer from assay cartridge reagent well to assay cartridge reaction well Transfer enzyme from reagent pack to assay cartridge reaction well Mix contents of assay cartridge reaction well Transfer assay cartridge to shuttle |
| 2 | 37° C. Processing Lane | Retrieve assay cartridge from shuttle Mix binding buffer and paramagnetic particles in assay cartridge reagent wells Transfer binding buffer and paramagnetic particles from assay cartridge reagent wells to assay cartridge reaction well Mix contents of assay cartridge reaction well Transfer assay cartridge to shuttle |
| 3 | Wash Lane 1 (Large Magnet) | Retrieve assay cartridge from shuttle Apply magnet Aspirate liquid from assay cartridge reaction well Transfer assay cartridge to shuttle |
| 4 | Wash Lane 2 (Large Magnet) | Retrieve assay cartridge from shuttle Mix wash buffer 1 in assay cartridge reagent well Transfer wash buffer 1 from assay cartridge reagent well to assay cartridge reaction well Mix contents of assay cartridge reaction well Apply magnet Aspirate liquid from assay cartridge reaction well Transfer assay cartridge to shuttle |
| 5 | Wash Lane 3 (Large Magnet) | Retrieve assay cartridge from shuttle Mix wash buffer 2 in assay cartridge reagent well Transfer wash buffer 2 from assay cartridge reagent well to assay cartridge reaction well Mix contents of assay cartridge reaction well Apply magnet Aspirate liquid from assay cartridge reaction well Transfer assay cartridge to shuttle |
| 6 | Wash Lane 4 (Small Magnet) | Retrieve assay cartridge from shuttle Mix wash buffer 3 in assay cartridge reagent well Transfer wash buffer 3 |

| Pitch | Lane/Device | Operations |
|---|---|---|
| 7 | Elution Lane (Large Magnet) | from assay cartridge reagent well to assay cartridge reaction well<br>Mix contents of assay cartridge reaction well<br>Apply magnet<br>Aspirate liquid from assay cartridge reaction well<br>Transfer assay cartridge to shuttle<br>Retrieve assay cartridge from shuttle<br>Mix elution buffer in assay cartridge reagent well<br>Transfer elution buffer from assay cartridge reagent well to assay cartridge reaction well<br>Mix contents of assay cartridge reaction well<br>Apply magnet<br>Transfer liquid from assay cartridge reaction well to reaction vessel<br>Transfer assay cartridge to shuttle |
| 8 | PCR Preparation Lane | Retrieve assay cartridge from shuttle<br>Transfer PCR reagents from reagent pack to reaction vessel (XYZ gantry)<br>Transfer plug to reaction vessel and seal<br>Transfer sealed reaction vessel to thermal cycler (XYZ Gantry)<br>Transfer assay cartridge to shuttle |
| 9 | Waste Lane | Retrieve assay cartridge from shuttle<br>Transfer assay cartridge to waste |
| 9 to N | Thermal Cycler | Amplify and monitor contents of reaction vessel |
| N + 1 | XYZ Gantry | Transfer reaction vessel to waste |

To incorporate the use of the Cartridge Warming Lane, the processing of a series of assay cartridges is interleaved. Within a given pitch (X), at about 50 seconds after moving into the CLU presentation lane and receiving a sample aliquot, the assay cartridge (N) is moved to one of the two positions of the transfer shuttle. The shuttle moves to the Cartridge Warming Lane and retrieves the previous assay cartridge (N−1) in the series from the cartridge heater into the remaining open position, then transfers the current assay cartridge (N) to the cartridge heater. The previous assay cartridge (N−1) is then returned to the CLU presentation lane by the 60 second mark of the pitch (X) for further processing through the end of pitch (X), after which it moves on to the next lane in the protocol designated for assay cartridge (N−1) at the start of pitch (X+1). This leaves the transfer shuttle empty. A third assay cartridge (N+1) is moved to the CLU presentation lane at the start of pitch (X+1), receives a sample aliquot, and is moved to the transfer shuttle at about 50 seconds after the start of the pitch (X+1). The assay cartridge (N) is returned to the CLU presentation lane at the 60 second mark of the subsequent pitch (X+1) for further processing after it is switched in the Cartridge Warming Lane for the next assay cartridge (N+1) in the series, and so on.

Example 3

RNA: Hepatitis C Virus Assay

| Pitch | Lane/Device | Operations |
|---|---|---|
| 1 | CLU Presentation Lane | Transfer sample aliquot to assay cartridge reaction well<br>Transfer process controls from reagent pack to assay cartridge reaction well (XYZ gantry) |
| | | Transfer dilution buffer from assay cartridge reagent well to assay cartridge reaction well<br>Transfer digestion buffer from assay cartridge reagent well to assay cartridge reaction well<br>Transfer enzyme from reagent pack to assay cartridge reaction well<br>Mix contents of assay cartridge reaction well<br>Transfer assay cartridge to shuttle |
| 2 | 70° C. Processing Lane | Retrieve assay cartridge from shuttle<br>Mix binding buffer and paramagnetic particles in assay cartridge reagent well<br>Transfer binding buffer and paramagnetic particles from assay cartridge reagent wells to assay cartridge reaction well<br>Mix contents of assay cartridge reaction well<br>Transfer assay cartridge to shuttle |
| 3 | Wash Lane 1 (Large Magnet) | Retrieve assay cartridge from shuttle<br>Apply magnet<br>Aspirate liquid from assay cartridge reaction well<br>Transfer assay cartridge to shuttle |
| 4 | Wash Lane 2 (Large Magnet) | Retrieve assay cartridge from shuttle<br>Mix wash buffer 1 in assay cartridge reagent well<br>Transfer wash buffer 1 from assay cartridge reagent well to assay cartridge reaction well<br>Mix contents of assay cartridge reaction well<br>Apply magnet<br>Aspirate liquid from assay cartridge reaction well<br>Transfer assay cartridge to shuttle |
| 5 | Wash Lane 3 (Large Magnet) | Retrieve assay cartridge from shuttle<br>Mix wash buffer 2 in assay cartridge reagent well<br>Transfer wash buffer 2 from assay cartridge reagent well to assay cartridge reaction well<br>Mix contents of assay cartridge reaction well<br>Apply magnet<br>Aspirate liquid from assay cartridge reaction well<br>Transfer assay cartridge to shuttle |
| 6 | Wash Lane 4 (Small Magnet) | Retrieve assay cartridge from shuttle<br>Mix wash buffer 3 in assay cartridge reagent well Transfer wash buffer 3 from assay cartridge reagent well to assay cartridge reaction well<br>Mix contents of assay cartridge reaction well<br>Apply magnet<br>Aspirate liquid from assay cartridge reaction well<br>Transfer assay cartridge to shuttle |
| 7 | Elution Lane (Large Magnet) | Retrieve assay cartridge from shuttle<br>Mix elution buffer in assay cartridge reagent well<br>Transfer elution buffer from assay cartridge reagent well to assay cartridge reaction well<br>Mix contents of assay cartridge reaction well<br>Apply magnet<br>Transfer liquid from assay cartridge reaction well to reaction vessel<br>Transfer assay cartridge to shuttle |
| 8 | PCR Preparation Lane | Retrieve assay cartridge from shuttle<br>Transfer PCR reagents from reagent pack to reaction vessel (XYZ gantry)<br>Transfer plug to reaction vessel and seal |

| Pitch | Lane/Device | Operations |
|---|---|---|
| | | Transfer sealed reaction vessel to thermal cycler (XYZ Gantry) |
| | | Transfer assay cartridge to shuttle |
| 9 | Waste Lane | Retrieve assay cartridge from shuttle |
| | | Transfer assay cartridge to waste |
| 9 to N | Thermal Cycler | Fixed temperature for reverse transcription |
| | | Amplify and monitor contents of reaction vessel |
| N + 1 | XYZ Gantry | Transfer reaction vessel to waste |

To incorporate the use of the Cartridge Warming Lane, the processing of a series of assay cartridges is interleaved. Within a given pitch (X), at about 50 seconds after moving into the CLU presentation lane and receiving a sample aliquot, the assay cartridge (N) is moved to one of the two positions of the transfer shuttle. The shuttle moves to the Cartridge Warming Lane and retrieves the previous assay cartridge (N−1) in the series from the cartridge heater into the remaining open position, then transfers the current assay cartridge (N) to the cartridge heater. The previous assay cartridge (N−1) is then returned to the CLU presentation lane by the 60 second mark of the pitch (X) for further processing through the end of pitch (X), after which it moves on to the next lane in the protocol designated for assay cartridge (N−1) at the start of pitch (X+1). This leaves the transfer shuttle empty. A third assay cartridge (N+1) is moved to the CLU presentation lane at the start of pitch (X+1), receives a sample aliquot, and is moved to the transfer shuttle at about 50 seconds after the start of the pitch (X+1). The assay cartridge (N) is returned to the CLU presentation lane at the 60 second mark of the subsequent pitch (X+1) for further processing after it is switched in the Cartridge Warming Lane for the next assay cartridge (N+1) in the series, and so on.

U. System Control Architecture

Control and coordination of the activities of the subsystems described above is provided by one or more computers. In one embodiment of the invention, control of the system is distributed between a primary controller and a plurality of secondary controllers. The primary controller may include one or more computers, which provide a user interface and transmit primary commands to secondary controllers. Each subsystem may incorporate a secondary controller that receives commands from the primary controller. Examples of secondary controllers include compact motion control cards, also known as a cMCCs, and cMCC-derived control cards. A secondary controller is configured to receive a primary command from a system computer, and then processes the primary command to generate a series of secondary commands that are transmitted to effectors incorporated into the subsystem in order to achieve the primary command. Examples of primary commands received from the primary controller include, but are not limited to, designation of a position of a system component or temperature of a system component. Examples of secondary commands generated by a secondary controller include, but are not limited to, speed of rotation in a specific motor, duration of rotation in a specific motor, and voltage applied to a temperature controlling element. Examples of effectors acted upon by the secondary controller include rotary stepper motors, linear stepper motors, resistive heating elements, and thermoelectric cooling elements. In addition, a secondary controller may monitor feedback from the subsystem, and utilize that feedback to generate corrective secondary commands as necessary. Examples of feedback provided to a secondary controller include, but are not limited to, information related to actual position of a subsystem component or to actual temperature of a subsystem component. Secondary controllers may also be used to perform analog to digital data conversion.

Tasks such as continuous generation of secondary commands, subsequent monitoring and correction of operations, and analog to digital data conversion are tasks that require real time, high frequency processing. This system architecture advantageously permits the use of secondary controllers with specialized microprocessors, for example cMCCs and cMCC-derived control cards that are optimized for repetitive, high frequency tasks. Secondary controllers can also utilize system on a chip, or SOC, cards that combine control and analog data conversion functions. Control cards used in secondary controller may incorporate an onboard bus that permits expansion of the functions of the secondary controller. Such an expansion of function could include additional inputs and/or outputs to and from the control card, respectively. Another example of expanded function is to provide communication with an additional, tertiary control card. The use of a primary controller with connections to secondary controllers advantageously permits accurate and rapid control of subsystem functions while allowing the use of a general purpose computer as a primary controller to provide functions such as data storage and a familiar interface for the user.

As noted above, secondary controllers may receive data related to the performance of their associated subsystems. This data may serve as feedback, used to generate corrective secondary commands Data received by the secondary controllers may also be transferred to the primary controller. This data can include data from position encoders, homing sensors, automated alignment procedures, current supplied to heating elements, temperatures achieved by heating elements, temperature profiles from thermal cyclers, and number of duty cycles for specific components. Such data can be used to determine if a subsystem or subsystem component shows evidence of deteriorating performance. If such a determination is made the system may notify the user in advance of the failure of a subsystem or subsystem component, permitting the user to perform maintenance or schedule service on the system prior to experiencing an actual system malfunction. This advantageously reduces system downtime.

In some embodiments secondary controllers incorporate safety features, including shutdown commands for motors, solenoids, or heaters. A primary controller may cascade a global shutdown command throughout the secondary controllers of the system. Alternatively, a global shutdown command may originate with or be communicated between secondary controllers.

In some subassemblies, the secondary controller may be associated with a sensing circuit that provides feedback to the system. As described above, the sensing circuit can provide a signal that indicates when a portion of the subassembly contacts or approaches a liquid or a surface. In some embodiments this sensing circuit is a capacitance-based liquid sensing circuit as described above, which may include a reactive element that forms part of a tuned circuit in a voltage-controlled oscillator. In some embodiments, the reactive element is a liquid handling probe that forms part of the liquid sensing circuit. Alternatively, the reactive element may be a conductive extension of the subassembly that is discarded after use. Examples of disposable conductive extensions include, but are not limited to, millitips and microtips.

Figures 2, 12C:
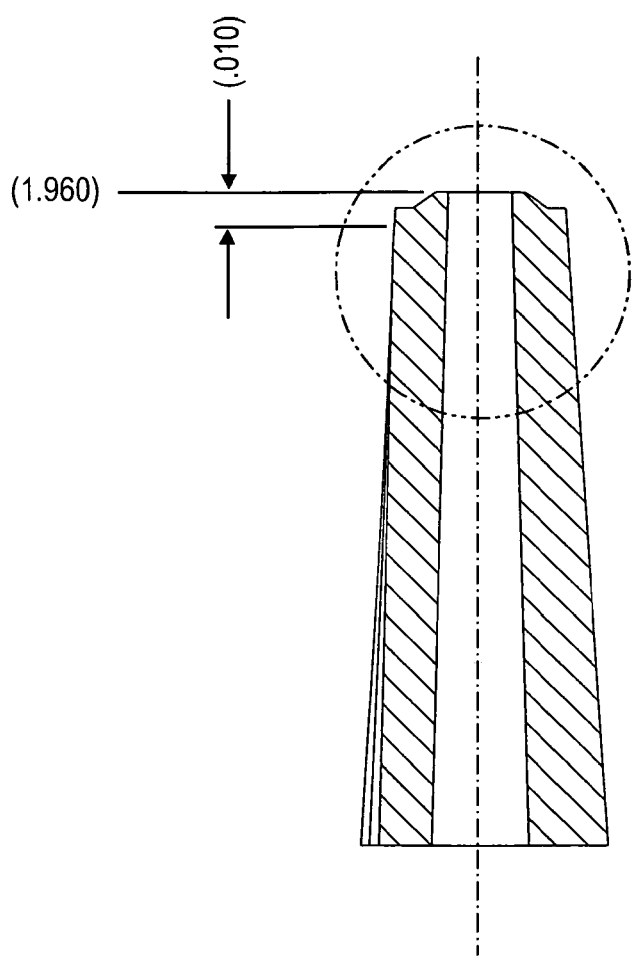

A sensing circuit may also be used to detect contact with or proximity to conductive surfaces. In one embodiment, the sensing circuit can be used to detect the successful attachment of conductive items to a pipette mandrel that forms part of the circuit. In such an embodiment, the sensing circuit can provide a signal that indicates the successful attachment, and subsequent release, of a conductive millitip (220 of FIG. 6), microtip (490 of FIG. 12(*b*)), or reaction vessel plug (222 of FIG. 5) to the pipette mandrel.

In another embodiment, the sensing circuit can be used to detect the approach of a pipette mandrel which forms part of the circuit to one or more conductive targets that are placed within the path of the pipettor. This approach can be a patterned series of movements that comprise a search for a conductive target that is initiated once the pipette mandrel is brought into proximity to the conductive target. Such information, when combined with information regarding the position of an associated stepper motor, can be used for automating alignment of the pipettor within the system. The conductive targets may be fortuitously located system components or conductive targets incorporated into the system for this purpose. Conductive targets can include projections that extend from a system component. Examples of projecting conductive targets include substantially planar tabs and cylindrical pins. Alternatively, a conductive target can be a hole or gap in an otherwise continuous conductive surface The primary controller may be connected to a secondary controller by a network connection. This connection may convey information or may provide both information and power to the secondary controller. In one embodiment, the connection is provided by a Controller Area Network bus, also known as a CAN bus, a digital serial bus that is commonly used in industrial environments. Alternatively, the network connection between the system primary controller and a secondary controller can be a Universal Serial Bus, RS-485, Ethernet, or HSSI connection. Such network connections may also be used to provide communication between secondary controllers. Wireless connections, such as Zigbee, Firewire, or Bluetooth may also be used to provide communication between a primary controller and a secondary controller, or between secondary controllers. Such communication between secondary controllers facilitates synchronization of tasks throughout the system.

In one embodiment, most of the subsystems of the system can incorporate a secondary controller. Subsystems that incorporate a secondary controller may include, as shown in FIG. 1(*b*), individual processing lanes of the sample processing lane assembly 116, the cartridge transfer shuttle 50, the cartridge loading unit 112, the sample presentation unit 110, the XYZ transport device 40, the sample pipettor assembly 70, the reagent storage module 10, and the thermal cycler garage 30. In some embodiments, the secondary controller directs the activities of the subassembly into which it is incorporated. Alternatively, a secondary controller may direct the activities of the assembly with which it is incorporated and one or more other subassemblies. For example, a secondary controller incorporated into the thermal cycler garage 30 may control activity within the thermal cycler subassembly and additionally control activities within the optical subsystem (FIG. 18(*c*)). In some embodiments a subassembly may incorporate more than one secondary controller, each of which directs the activities of different portions of the subassembly. For example, the thermal cycler garage (30 of FIG. 1(*b*)) may incorporate two secondary controllers, each responsible for the control of a portion of the plurality of thermal cyclers housed within the thermal cycler garage. In other embodiments multiple secondary controllers may be used to control a single function.

Figure 21:
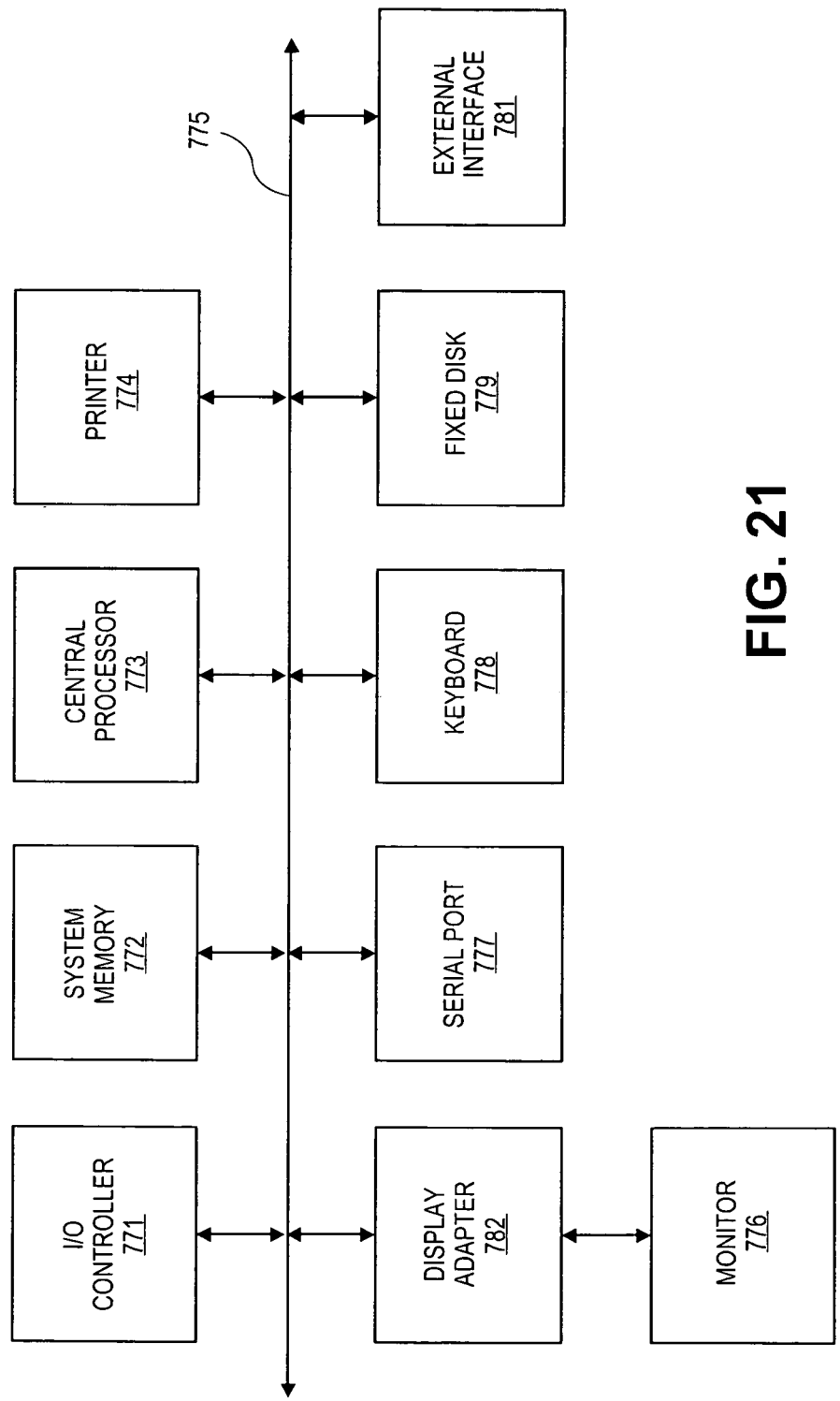
FIG. 21 shows a diagram illustrating parts of a general purpose computer apparatus.

In addition to systems required for sample, consumable, and fluid handling the system may operate one or more computer apparatuses to facilitate the functions described herein. Any of the elements in FIG. 21 may use any suitable number of subsystems to facilitate the functions described herein. The subsystems shown in FIG. 20 are interconnected via a system bus 775. Additional subsystems such as a printer 774, keyboard 778, fixed disk 779 (or other memory comprising computer readable media), monitor 776, which is coupled to display adapter 782, and others are shown. Peripherals and input/output (I/O) devices, which couple to I/O controller 771, can be connected to the computer system by any number of means known in the art, such as serial port 777. For example, serial port 777 or external interface 781 can be used to connect the computer apparatus to a wide area network such as the Internet, a mouse input device, or a scanner. The interconnection via system bus allows the central processor 773 to communicate with each subsystem and to control the execution of instructions from system memory 772 or the fixed disk 779, as well as the exchange of information between subsystems. The system memory 772 and/or the fixed disk 779 may embody a computer readable medium.

The previous description provides exemplary embodiments only, and is not intended to limit the scope, applicability, or configuration of the disclosure. Rather, the previous description of the exemplary embodiments will provide those skilled in the art with an enabling description for implementing one or more exemplary embodiments. It is understood that various changes may be made in the function and arrangement of elements without departing from the spirit and scope of the invention. Several embodiments were described herein, and while various features are ascribed to different embodiments, it should be appreciated that the features described with respect to one embodiment may be incorporated within other embodiments as well. By the same token, however, no single feature or features of any described embodiment should be considered essential to every embodiment of the invention, as other embodiments of the invention may omit such features.

Specific details are given in the previous description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have also included additional steps or operations not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

While detailed descriptions of one or more embodiments have been give above, various alternatives, modifications, and equivalents will be apparent to those skilled in the art without varying from the spirit of the invention. Moreover, except where clearly inappropriate or otherwise expressly noted, it should be assumed that the features, devices, and/or components of different embodiments may be substituted and/or combined. Thus, the above description should not be taken as limiting the scope of the invention. Lastly, one or more elements of one or more embodiments may be combined with one or more elements of one or more other embodiments without departing from the scope if the invention. For example, any suitable elements of an assay cartridge can be combined with any suitable elements of the various processing lanes in any suitable manner, without departing from the spirit and scope of the invention.

The invention claimed is:

1. A method for operating thermal cycler modules, the method comprising:
obtaining a predetermined temperature vs. time profile of a sample in a selected thermal cycler module in an array of thermal cycler modules, the array of thermal cycler modules comprising the selected thermal cycler module and a set of thermal cycler modules; and
controlling, by a processor, all of the thermal cycler modules in the array of thermal cycler modules so that temperature vs. time profiles for samples in the thermal cycler modules in the array match the predetermined temperature vs. time profile, each of the thermal cycler modules in the array of thermal cycler modules being controlled in response to a source of variation between the thermal cycler modules in the array.

2. The method of claim 1 wherein the source of variation comprises an ambient temperature of the thermal cycler module, or a physical characteristic of the thermal cycler module.

3. The method of claim 1 wherein controlling the thermal cycler modules comprises, for each module, adjusting $h_a$, which is a thin film heater output at an ambient temperature (° C/second) and k, which is a rate of heat transfer, using the following equation:

$$dB/dt = h_a + k(Ta - B(t)), \text{where}$$

dB/dt=change in block temp in degrees per second,
Ta=ambient temperature (° C.),
$h_a$=thin film heater output at ambient temperature (° C./second),
k=rate of heat transfer, and
B(t)=the temperature of the thermal block at a given time t.

4. The method of claim 3 wherein $B(t)=(B(0)-(h_a/k)-Ta)e^{kt}+(h_a/k)+Ta$, where B(0)=starting block temperature at time=0.

5. The method of claim 3 wherein k is adjusted using a blower.

6. A method of driving a first thermal cycler module in a predetermined thermal profile (B(t)), the first thermal cycler module including a thermal block, a heater thermally coupled to the thermal block, and a blower to direct air to the thermal block, the method comprising:
determining a rate of change of the thermal block temperature with respect to time (dB/dt) as a function of heater output ($h_a$), of blower heat transfer (k), and of ambient temperature (Ta);
measuring the thermal block temperature;
measuring the ambient temperature at the first thermal cycler module; and
adjusting, by a processor, one of the heater output and the blower heat transfer according to a modeled relationship of:

$$dB/dt = h_a + k(Ta - B(t)).$$

7. The method of claim 6 wherein the step of adjusting one of the heater output and the blower heat transfer includes adjusting the heater output and the blower heat transfer.

8. The method of claim 7 wherein the first thermal cycler module includes the processor and a memory, the processor sensing the thermal block temperature and the ambient temperature, and the memory including a representation of the predetermined thermal profile and a representation of the modeled relationship.

9. The method of claim 8 wherein the processor controls the blower heat transfer by adjusting the power supplied to the blower.

10. The method of claim 9 wherein the same predetermined thermal profile is determined through evaluation of the rate of change of the thermal block temperature with respect to time as a function of heater output, of blower heat transfer, and of ambient temperature of a plurality of thermal cycler modules and selection of a thermal profile achievable by each of the plurality of thermal cycler modules as the predetermined profile.

11. The method of claim 10 wherein the response of the first thermal cycler module matches the response of a second thermal cycler module.

12. The method of claim 11 wherein first thermal cycler module is disposed adjacent the second thermal cycler module.

13. The method of claim 1 wherein the thermal cycler module comprises a blower to cool the sample and a thin film heater to heat the sample.

14. The method of claim 1 wherein the selected thermal cycler module comprises a thermal block holding a reaction vessel containing the sample, and wherein the method further comprises, prior to obtaining the predetermined temperature vs. time profile:
performing a thermal cycling process on the sample in the reaction vessel using the selected thermal cycler module.

15. The method of claim 14 wherein the thermal cycling process cycles the temperature of the thermal block between about 70° C. and about 95° C.

16. A system comprising:
an array of thermal cycler modules;
a processor; and
a computer readable medium coupled to the processor, the computer readable medium comprising code, executable by the processor, to implement a method comprising obtaining a predetermined temperature vs. time profile of a sample in a selected thermal cycler module in the array of thermal cycler modules, the array of thermal cycler modules comprising the selected thermal cycler module and a set of thermal cycler modules, and
controlling all of the thermal cycler modules in the array of thermal cycler modules so that temperature vs. time profiles for samples in the thermal cycler modules in the array match the predetermined temperature vs. time profile, each of the thermal cycler modules in the array of thermal cycler modules being controlled in response to a source of variation between the thermal cycler modules in the array.

17. The system of claim 16 wherein controlling the thermal cycler modules comprises, for each module, adjusting $h_a$, which is a thin film heater output at an ambient temperature (° C./second) and k, which is a rate of heat transfer, using the following equation:

$$dB/dt = h_a + k(Ta - B(t)), \text{where}$$

dB/dt=change in block temp in degrees per second,
Ta=ambient temperature (° C.),
$h_a$=thin film heater output at ambient temperature (° C./second),
k=rate of heat transfer, and
B(t)=the temperature of the thermal block at a given time t.

18. The system of claim 16 wherein each of the thermal cycler modules in the array of thermal cycler modules comprises a blower and a heater.

19. A system comprising:
a thermal cycler module comprising a thermal block, a heater thermally coupled to the thermal block, and a blower to direct air to the thermal block;
a processor; and
a computer readable medium, the computer readable medium comprising code, executable by the processor, to implement a method comprising determining a rate of change of the thermal block temperature with respect to time (dB/dt) as a function of heater output ($h_a$), of blower heat transfer (k), and of ambient temperature (Ta),
measuring the thermal block temperature,
measuring the ambient temperature at the first thermal cycler module, and
adjusting one of the heater output and the blower heat transfer according to a modeled relationship of:

$$dB/dt = h_a + k(Ta - B(t)).$$

20. The system of claim 19 wherein the step of adjusting one of the heater output and the blower heat transfer includes adjusting the heater output and the blower heat transfer.

21. A method comprising:
obtaining a predetermined temperature ramping time; and
controlling, by a processor, thermal cycler modules in a set of thermal cycler modules so that the temperature ramping time for each thermal cycler module in the set of thermal cycler modules match the predetermined temperature ramping time, each of the thermal cycler modules in the set of thermal cycler modules being controlled in response to a source of variation between the thermal cycler modules in the set.

22. The method of claim 21 wherein the thermal cycler modules comprise heaters, and wherein the processor controls the heaters in the thermal cycler modules during controlling.

23. A system comprising:
an array of thermal cycler modules including a set of thermal cycler modules;
a processor; and
a computer readable medium coupled to the processor, the computer readable medium comprising code, executable by the processor for implementing a method comprising
obtaining a predetermined temperature ramping time, and
controlling the thermal cycler modules in the set of thermal cycler modules so that the temperature ramping time for each thermal cycler module in the set matches the predetermined temperature ramping time, each of the thermal cycler modules in the set of thermal cycler modules being controlled in response to a source of variation between the thermal cycler modules in the set.

24. The system of claim 23 wherein the thermal cycler modules comprise heaters, and wherein the processor controls the heaters in the thermal cycler modules during controlling.

* * * * *